US012747210B2

(12) United States Patent
Esteban

(10) Patent No.: US 12,747,210 B2
(45) **Date of Patent: *Sep. 29, 2026**

(54) ORGANIC MOLECULES FOR USE IN LIGHT-EMITTING DEVICES

(71) Applicant: Samsung Display Co., Ltd., Yongin-si (KR)

(72) Inventor: Alhama Arjona Esteban, Stuttgart (DE)

(73) Assignee: Samsung Display Co., Ltd., Yongin-si (KR)

( * ) Notice: Subject to any disclaimer, the term of this patent is extended or adjusted under 35 U.S.C. 154(b) by 1111 days.

This patent is subject to a terminal disclaimer.

(21) Appl. No.: 17/812,980

(22) Filed: Jul. 15, 2022

(65) Prior Publication Data

US 2022/0388960 A1 Dec. 8, 2022

Related U.S. Application Data

(63) Continuation-in-part of application No. 16/603,725, filed as application No. PCT/EP2018/059494 on Apr. 13, 2018, now Pat. No. 11,393,984.

(30) Foreign Application Priority Data

| | | | |
|---|---|---|---|
| Apr. 13, 2017 | (DE) | ..................... | 10 2017 108 055.4 |
| Jun. 6, 2017 | (DE) | ..................... | 10 2017 112 434.9 |
| Sep. 21, 2017 | (DE) | ..................... | 10 2017 121 930.7 |

(51) Int. Cl.
*C07D 211/82* (2006.01)
*C07C 15/28* (2006.01)
(Continued)

(52) U.S. Cl.
CPC ............ *C07D 211/82* (2013.01); *C07C 15/28* (2013.01); *C07C 15/30* (2013.01); *C07C 15/38* (2013.01);
(Continued)

(58) Field of Classification Search
None
See application file for complete search history.

(56) References Cited

U.S. PATENT DOCUMENTS 11,393,984 B2 * 7/2022 Esteban ............... C07D 519/00
2014/0117329 A1 5/2014 Lee et al.
(Continued)

FOREIGN PATENT DOCUMENTS

EP 1 486 550 A1 12/2004
EP 1 829 871 A1 9/2007
(Continued)

OTHER PUBLICATIONS

International Search Report for corresponding International Application No. PCT/EP2018/059494, dated Jul. 19, 2018.

*Primary Examiner* — Jay Yang
(74) *Attorney, Agent, or Firm* — Womble Bond Dickinson (US) LLP

(57) ABSTRACT

An organic compound is disclosed comprising:
a first chemical moiety with a structure of formula I Formula I (Continued)

10 and two second chemical moieties, independently from another with a structure of formula II, Formula II

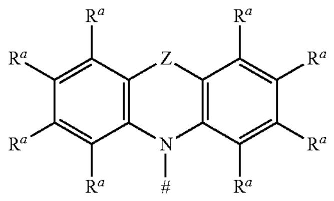

wherein the first chemical moiety is linked to each of the two second chemical moieties via a single bond.

20 Claims, 9 Drawing Sheets

(51) Int. Cl.

| | |
|---|---|
| ***C07C 15/30*** | (2006.01) |
| ***C07C 15/38*** | (2006.01) |
| ***C07C 209/82*** | (2006.01) |
| ***C07D 307/91*** | (2006.01) |
| ***C07D 333/76*** | (2006.01) |
| ***C07D 401/12*** | (2006.01) |
| ***C07D 401/14*** | (2006.01) |
| ***C07D 403/10*** | (2006.01) |
| ***C07D 403/14*** | (2006.01) |
| ***C07D 405/12*** | (2006.01) |
| ***C07D 409/12*** | (2006.01) |
| ***C07D 409/14*** | (2006.01) |
| ***C07D 487/04*** | (2006.01) |
| ***C07D 491/048*** | (2006.01) |
| ***C07D 493/04*** | (2006.01) |
| ***C07D 495/04*** | (2006.01) |
| ***C07D 519/00*** | (2006.01) |
| ***C07F 3/00*** | (2006.01) |
| ***H01L 51/00*** | (2006.01) |
| ***H10K 50/11*** | (2023.01) |
| ***H10K 50/125*** | (2023.01) |
| ***H10K 85/30*** | (2023.01) |
| ***H10K 85/60*** | (2023.01) |
| *H10K 101/40* | (2023.01) |
| *H10K 102/00* | (2023.01) |

(52) U.S. Cl.

CPC .......... *C07C 209/82* (2013.01); *C07D 307/91* (2013.01); *C07D 333/76* (2013.01); *C07D 401/12* (2013.01); *C07D 401/14* (2013.01); *C07D 403/10* (2013.01); *C07D 403/14* (2013.01); *C07D 405/12* (2013.01); *C07D 409/12* (2013.01); *C07D 409/14* (2013.01); *C07D 487/04* (2013.01); *C07D 491/048* (2013.01); *C07D 493/04* (2013.01); *C07D 495/04* (2013.01); *C07D 519/00* (2013.01); *C07F 3/006* (2013.01); *H10K 50/11* (2023.02); *H10K 50/125* (2023.02); *H10K 85/30* (2023.02); *H10K 85/615* (2023.02); *H10K 85/622* (2023.02); *H10K 85/631* (2023.02); *H10K 85/652* (2023.02); *H10K 85/654* (2023.02); *H10K 85/657* (2023.02); *H10K 85/6572* (2023.02); *H10K 85/6574* (2023.02); *H10K 85/6576* (2023.02); *C07B 2200/05* (2013.01); *H10K 2101/40* (2023.02); *H10K 2102/351* (2023.02)

(56) References Cited

U.S. PATENT DOCUMENTS

2016/0126474 A1* 5/2016 Kim .................... H10K 85/626
548/440
2017/0025620 A1 1/2017 Jeon et al.

FOREIGN PATENT DOCUMENTS

| | | | |
|---|---|---|---|
| EP | 2 272 828 | A1 | 1/2011 |
| KR | 10-2017-0011875 | A | 2/2017 |
| WO | WO 2008/127057 | A1 | 10/2008 |
| WO | WO 2009/057978 | A2 | 5/2009 |

* cited by examiner

ORGANIC MOLECULES FOR USE IN LIGHT-EMITTING DEVICES

CROSS REFERENCE TO RELATED APPLICATIONS

This application is a continuation-in-part of U.S. patent application Ser. No. 16/603,725, filed Oct. 8, 2019, which claims priority under 35 U.S.C. § 371 to International Application No. PCT/EP2018/059494, filed Apr. 13, 2018, which claims priority to German Patent Application No. 10 2017 108 055.4 filed Apr. 13, 2017, and German Patent Application No. 10 2017 112 434.9 filed Jun. 6, 2017 and German Patent Application No. 10 2017 121 930.7 filed Sep. 21, 2017 the disclosures of which are incorporated by reference herein in their entireties.

FIELD OF INVENTION

The invention relates to organic molecules and their use in light-emitting devices.

BRIEF DESCRIPTION OF THE DRAWINGS

Exemplary embodiments of the present invention will be described below in more detail, with reference to the accompanying drawings, of which.

DETAILED DESCRIPTION OF EXEMPLARY EMBODIMENTS OF THE INVENTION

Figure 1:
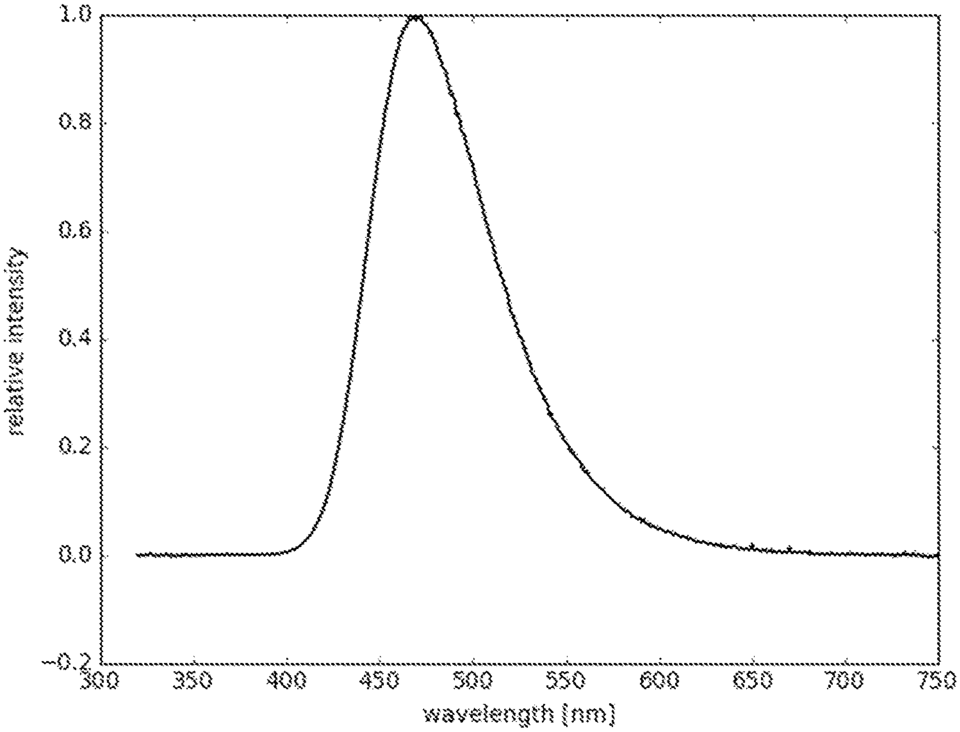
FIG. 1 is an emission spectrum of example 1 (10%) by weight) in PMMA.

Exemplary embodiments of the invention, will now be discussed in further detail. This invention may, however, be embodied in many different forms and should not be construed as limited to the embodiments set forth herein.

The object of the present invention is to provide molecules which are suitable for use in light-emitting devices.

This object is achieved by the invention which provides a new class of organic molecules.

According to the invention the organic molecules are purely organic molecules, i.e. they do not contain any metal ions in contrast to metal complexes known for use in light-emitting devices.

According to the present invention, the organic molecules exhibit emission maxima in the blue, sky-blue or green spectral range. The organic molecules exhibit in particular emission maxima between 420 nm and 520 nm, preferably between 440 nm and 495 nm, more preferably between 450 nm and 470 nm. The photoluminescence quantum yields of the organic molecules according to the invention are, in particular, 20% or more. The molecules according to the invention exhibit in particular thermally activated delayed fluorescence (TADF). The use of the molecules according to the invention in a light-emitting device, for example an organic light-emitting diode (OLED), leads to higher efficiencies of the device. Corresponding OLEDs have a higher stability than OLEDs with known emitter materials and comparable color.

The organic light-emitting molecules of the invention comprise or consist of a first chemical moiety comprising or consisting of a structure of Formula I,

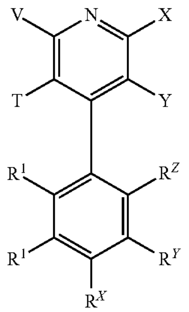

Formula I and two second chemical moieties, each independently from another comprising or consisting of a structure of Formula II,

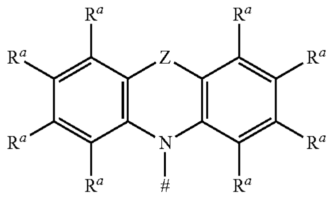

Formula II wherein the first chemical moiety is linked to each of the two second chemical moieties via a single bond.

T is the binding site of a single bond linking the first chemical moiety to one of the two second chemical moieties or is $R^2$.

V is $R^2$.

X is the binding site of a single bond linking the first chemical moiety to one of the two second chemical moieties or is $R^2$.

Y is the binding site of a single bond linking the first chemical moiety to one of the two second chemical moieties or is $R^2$ # represents the binding site of a single bond linking the first chemical moiety to one of the two second chemical moieties.

Z is at each occurrence independently from another selected from the group consisting of a direct bond, $CR^3R^4$, $C{=}CR^3R^4$, $C{=}O$, $C{=}NR^3$, $NR^3$, O, $SiR^3R^4$, S, S(O) and $S(O)_2$.

$R^X$ is selected from the group consisting of CN and $R^1$;
$R^Y$ is selected from the group consisting of CN and $R^1$;
$R^Z$ is selected from the group consisting of CN and $R^1$;
$R^1$ is at each occurrence independently from another selected from the group consisting of
hydrogen,
deuterium,
$C_1$-$C_5$-alkyl,
wherein one or more hydrogen atoms are optionally substituted by deuterium;
$C_2$-$C_8$-alkenyl,
wherein one or more hydrogen atoms are optionally substituted by deuterium;
$C_2$-$C_8$-alkynyl,
wherein one or more hydrogen atoms are optionally substituted by deuterium; and
$C_6$-$C_{18}$-aryl,
which is optionally substituted with one or more substituents $R^6$.
$R^2$ is at each occurrence independently from another selected from the group consisting of hydrogen,
deuterium,
$C_1$-$C_5$-alkyl,
wherein one or more hydrogen atoms are optionally substituted by deuterium;
$C_2$-$C_8$-alkenyl,
wherein one or more hydrogen atoms are optionally substituted by deuterium;
$C_2$-$C_8$-alkynyl,
wherein one or more hydrogen atoms are optionally substituted by deuterium; and
$C_6$-$C_{18}$-aryl,
which is optionally substituted with one or more substituents $R^6$.
$R^P$ is at each occurrence independently from another selected from the group consisting of hydrogen,
deuterium,
$C_1$-$C_5$-alkyl,
wherein one or more hydrogen atoms are optionally substituted by deuterium;
$C_2$-$C_5$-alkenyl,
wherein one or more hydrogen atoms are optionally substituted by deuterium;
$C_2$-$C_5$-alkynyl,
wherein one or more hydrogen atoms are optionally substituted by deuterium; and
$C_6$-$C_{18}$-aryl,
which is optionally substituted with one or more substituents $R^6$.
$R^a$, $R^3$ and $R^4$ is at each occurrence independently from another selected from the group consisting of hydrogen, deuterium, $N(R^5)_2$, $OR^5$, $Si(R^5)_3$, $B(OR^5)_2$, $OSO_2R^5$, $CF_3$, CN, F, Br, I,
$C_1$-$C_{40}$-alkyl,
which is optionally substituted with one or more substituents $R^5$ and
wherein one or more non-adjacent $CH_2$-groups are optionally substituted by $R^5C{=}CR^5$, $C{\equiv}C$, $Si(R^5)_2$, $Ge(R^5)_2$, $Sn(R^5)_2$, $C{=}O$, $C{=}S$, $C{=}Se$, $C{=}NR^5$, $P({=}O)(R^5)$, SO, $SO_2$, $NR^5$, O, S or $CONR^5$;
$C_1$-$C_{40}$-alkoxy,
which is optionally substituted with one or more substituents $R^5$ and
wherein one or more non-adjacent $CH_2$-groups are optionally substituted by $R^5C{=}CR^5$, $C{\equiv}C$, $Si(R^5)_2$, $Ge(R^5)_2$, $Sn(R^5)_2$, $C{=}O$, $C{=}S$, $C{=}Se$, $C{=}NR^5$, $P({=}O)(R^5)$, SO, $SO_2$, $NR^5$, O, S or $CONR^5$;
$C_2$-$C_{40}$-thioalkoxy,
which is optionally substituted with one or more substituents $R^5$ and
wherein one or more non-adjacent $CH_2$-groups are optionally substituted by $R^5C{=}CR^5$, $C{\equiv}C$, $Si(R^5)_2$, $Ge(R^5)_2$, $Sn(R^5)_2$, $C{=}O$, $C{=}S$, $C{=}Se$, $C{=}NR^5$, $P({=}O)(R^5)$, SO, $SO_2$, $NR^5$, O, S or $CONR^5$;
$C_2$-$C_{40}$-alkenyl,
which is optionally substituted with one or more substituents $R^5$ and wherein one or more non-adjacent $CH_2$-groups are optionally substituted by $R^5C{=}CR^5$, $C{\equiv}C$, $Si(R^5)_2$, $Ge(R^5)_2$, $Sn(R^5)_2$, $C{=}O$, $C{=}S$, $C{=}Se$, $C{=}NR^5$, $P({=}O)(R^5)$, SO, $SO_2$, $NR^5$, O, S or $CONR^5$;
$C_2$-$C_{40}$-alkynyl,
which is optionally substituted with one or more substituents $R^5$ and
wherein one or more non-adjacent $CH_2$-groups are optionally substituted by $R^5C{=}CR^5$, $C{\equiv}C$, $Si(R^5)_2$, $Ge(R^5)_2$, $Sn(R^5)_2$, $C{=}O$, $C{=}S$, $C{=}Se$, $C{=}NR^5$, $P({=}O)(R^5)$, SO, $SO_2$, $NR^5$, O, S or $CONR^5$;
$C_6$-$C_{60}$-aryl,
which is optionally substituted with one or more substituents $R^5$; and
$C_3$-$C_{57}$-heteroaryl,
which is optionally substituted with one or more substituents $R^5$.
$R^5$ is at each occurrence independently from another selected from the group consisting of hydrogen, deuterium, $N(R^6)_2$, $OR^6$, $i(R^6)_3$, $(OR^6)_2$, $SO_2R^6$, $CF_3$, CN, F, Br, I, $C_1$-$C_{40}$-alkyl,
which is optionally substituted with one or more substituents $R^6$ and
wherein one or more non-adjacent $CH_2$-groups are optionally substituted by $R^6C{=}CR^6$, $C{\equiv}C$, $Si(R^6)_2$, $Ge(R^6)_2$, $Sn(R^6)_2$, $C{=}O$, $C{=}S$, $C{=}Se$, $C{=}NR^6$, $P({=}O)(R^6)$, SO, $SO_2$, $NR^6$, O, S or $CONR^6$;
$C_1$-$C_{40}$-alkoxy,
which is optionally substituted with one or more substituents $R^6$ and
wherein one or more non-adjacent $CH_2$-groups are optionally substituted by $R^6C{=}CR^6$, $C{\equiv}C$, $Si(R^6)_2$, $Ge(R^6)_2$, $Sn(R^6)_2$, $C{=}O$, $C{=}S$, $C{=}Se$, $C{=}NR^6$, $P({=}O)(R^6)$, SO, $SO_2$, $NR^6$, O, S or $CONR^6$;
$C_1$-$C_{40}$-thioalkoxy,
which is optionally substituted with one or more substituents $R^6$ and
wherein one or more non-adjacent $CH_2$-groups are optionally substituted by $R^6C{=}CR^6$, $C{\equiv}C$, $Si(R^6)_2$, $Ge(R^6)_2$, $Sn(R^6)_2$, $C{=}O$, $C{=}S$, $C{=}Se$, $C{=}NR^6$, $P({=}O)(R^6)$, SO, $SO_2$, $NR^6$, O, S or $CONR^6$;
$C_2$-$C_{40}$-alkenyl,
which is optionally substituted with one or more substituents $R^6$ and
wherein one or more non-adjacent $CH_2$-groups are optionally substituted by $R^6C{=}CR^6$, $C{\equiv}C$, $Si(R^6)_2$, $Ge(R^6)_2$, $Sn(R^6)_2$, $C{=}O$, $C{=}S$, $C{=}Se$, $C{=}NR^6$, $P({=}O)(R^6)$, SO, $SO_2$, $NR^6$, O, S or $CONR^6$;
$C_2$-$C_{40}$-alkynyl,
which is optionally substituted with one or more substituents $R^6$ and
wherein one or more non-adjacent $CH_2$-groups are optionally substituted by $R^6C{=}CR^6$, $C{\equiv}C$, $Si(R^6)_2$, $Ge(R^6)_2$, $Sn(R^6)_2$, $C{=}O$, $C{=}S$, $C{=}Se$, $C{=}NR^6$, $P({=}O)(R^6)$, SO, $SO_2$, $NR^6$, O, S or $CONR^6$;

$C_6$-$C_{60}$-aryl, which is optionally substituted with one or more substituents $R^6$; and $C_3$-$C_{57}$-heteroaryl, which is optionally substituted with one or more substituents $R^6$.

$R^6$ is at each occurrence independently from another selected from the group consisting of hydrogen, deuterium, OPh, $CF_3$, CN, F, $C_1$-$C_5$-alkyl, wherein optionally one or more hydrogen atoms are independently from each other substituted by deuterium, CN, $CF_3$, or F;

$C_1$-$C_5$-alkoxy, wherein optionally one or more hydrogen atoms are independently from each other substituted by deuterium, CN, $CF_3$, or F;

$C_1$-$C_5$-thioalkoxy, wherein optionally one or more hydrogen atoms are independently from each other substituted by deuterium, CN, $CF_3$, or F;

$C_2$-$C_5$-alkenyl, wherein optionally one or more hydrogen atoms are independently from each other substituted by deuterium, CN, $CF_3$, or F;

$C_2$-$C_5$-alkynyl, wherein optionally one or more hydrogen atoms are independently from each other substituted by deuterium, CN, $CF_3$, or F;

$C_6$-$C_{18}$-aryl, which is optionally substituted with one or more $C_1$-$C_5$-alkyl substituents;

$C_3$-$C_{17}$-heteroaryl, which is optionally substituted with one or more $C_1$-$C_5$-alkyl substituents;

$N(C_6$-$C_{15}$-aryl$)_2$, $N(C_3$-$C_{17}$-heteroaryl$)_2$; and $N(C_3$-$C_{17}$-heteroaryl$)(C_6$-$C_{18}$-aryl$)$.

The substituents $R^a$, $R^3$, $R^4$ or $R^5$ independently from each other can optionally form a mono- or polycyclic, aliphatic, aromatic and/or benzo-fused ring system with one or more substituents $R^a$, $R^3$, $R^4$ or $R^5$.

According to the invention exactly one substituent selected from the group consisting of $R^X$, $R^Y$ and $R^Z$ is CN, and exactly two substituents selected from the group consisting of T, X and Y represent the binding sites of a single bond linking the first chemical moiety and one of the two second chemical moieties.

In one embodiment, the organic light-emitting molecules according to the invention comprises or consist of a first chemical moiety comprising or consisting of a structure of Formula Ia:

Formula Ia

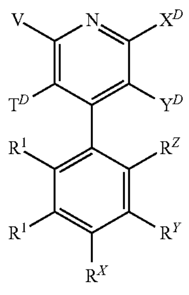

wherein $R^1$, $R^X$, $R^Y$, $R^Z$ and V are defined as above;

$T^D$ is the binding site of a single bond linking the first chemical moiety to one of the two second chemical moieties;

$X^D$ is the binding site of a single bond linking the first chemical moiety to one of the two second chemical moieties;

$Y^D$ is $R^2$ and wherein apart from that the above-mentioned definitions apply.

In one embodiment, $R^1$, $R^2$ and $R^P$ is at each occurrence independently from another selected from the group consisting of hydrogen (H), methyl and phenyl.

In a further embodiment of the invention, the two second chemical moieties each at each occurrence independently from another comprise or consist of a structure of Formula IIa:

Formula IIa

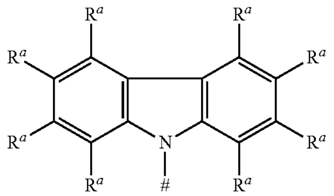

wherein # and $R^a$ are defined as above.

In a further embodiment of the invention, the two second chemical moieties each at each occurrence independently from another comprise or consist of a structure of Formula IIb, a structure of Formula IIb-2, a structure of Formula IIb-3 or a structure of Formula IIb-4:

Formula IIb

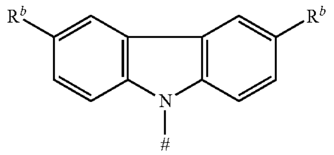

Formula IIb-2

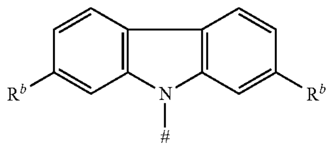

Formula IIb-3

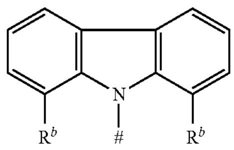

Formula IIb-4

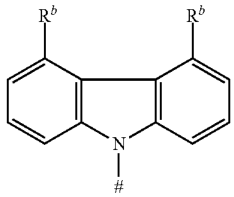

wherein $R^b$ is at each occurrence independently from another selected from the group consisting of hydrogen, deuterium, $N(R^5)_2$, $OR^5$, $Si(R^5)_3$, $B(OR^5)_2$, $OSO_2R^5$, $CF_3$,

CN,

F,

Br,

I, $C_1$-$C_{40}$-alkyl, which is optionally substituted with one or more substituents $R^5$ and wherein one or more non-adjacent $CH_2$-groups are optionally substituted by $R^5C{=}CR^5$, C≡C, $Si(R^5)_2$, $Ge(R^5)_2$, $Sn(R^5)_2$, C=O, C=S, C=Se, $C{=}NR^5$, $P({=}O)(R^5)$, SO, $SO_2$, $NR^5$, O, S or $CONR^5$;

$C_1$-$C_{40}$-alkoxy, which is optionally substituted with one or more substituents $R^5$ and wherein one or more non-adjacent $CH_2$-groups are optionally substituted by $R^5C{=}CR^5$, C≡C, $Si(R^5)_2$, $Ge(R^5)_2$, $Sn(R^5)_2$, C=O, C=S, C=Se, $C{=}NR^5$, $P({=}O)(R^5)$, SO, $SO_2$, $NR^5$, O, S or $CONR^5$;

$C_1$-$C_{40}$-thioalkoxy, which is optionally substituted with one or more substituents $R^5$ and wherein one or more non-adjacent $CH_2$-groups are optionally substituted by $R^5C{=}CR^5$, C≡C, $Si(R^5)_2$, $Ge(R^5)_2$, $Sn(R^5)_2$, C=O, C=S, C=Se, $C{=}NR^5$, $P({=}O)(R^5)$, SO, $SO_2$, $NR^5$, O, S or $CONR^5$;

$C_2$-$C_{40}$-alkenyl, which is optionally substituted with one or more substituents $R^5$ and wherein one or more non-adjacent $CH_2$-groups are optionally substituted by $R^5C{=}CR^5$, C≡C, $Si(R^5)_2$, $Ge(R^5)_2$, $Sn(R^5)_2$, C=O, C=S, C=Se, $C{=}NR^5$, $P({=}O)(R^5)$, SO, $SO_2$, $NR^5$, O, S or $CONR^5$;

$C_2$-$C_{40}$-alkynyl, which is optionally substituted with one or more substituents $R^5$ and wherein one or more non-adjacent $CH_2$-groups are optionally substituted by $R^5C{=}CR^5$, C≡C, $Si(R^5)_2$, $Ge(R^5)_2$, $Sn(R^5)_2$, C=O, C=S, C=Se, $C{=}NR^5$, $P({=}O)(R^5)$, SO, $SO_2$, $NR^5$, O, S or $CONR^5$;

$C_6$-$C_{60}$-aryl, which is optionally substituted with one or more substituents $R^5$; and $C_3$-$C_{57}$-heteroaryl, which is optionally substituted with one or more substituents $R^5$.

Apart from that the aforementioned definitions apply.

In one additional embodiment of the invention, the two second chemical moieties each at each occurrence independently from another comprise or consist of a structure of Formula Ic, a structure of Formula IIc-2, a structure of Formula IIc-3 or a structure of Formula IIc-4:

Formula IIc

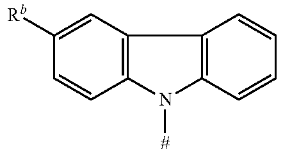

Formula IIc-2

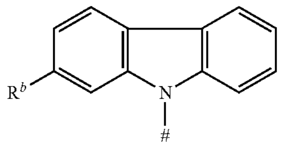

Formula IIc-3

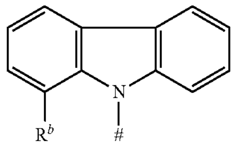

Formula IIc-4

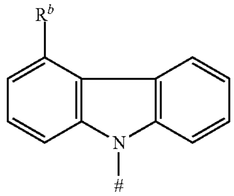

wherein the aforementioned definitions apply.

In a further embodiment of the invention, $R^b$ is at each occurrence independently from another selected from the group consisting of Me, $^i$Pr, $^t$Bu

CN, $CF_3$,

Ph, which is optionally substituted with one or more substituents independently from each other selected from the group consisting of Me, $^i$Pr, $^t$Bu, CN, $CF_3$, and Ph, pyridinyl, which is optionally substituted with one or more substituents independently from each other selected from the group consisting of Me, $^i$Pr, $^t$Bu, CN, $CF_3$, and Ph, carbazolyl, which is optionally substituted with one or more substituents independently from each other selected from the group consisting of Me, $^i$Pr, $^t$Bu, CN, $CF_3$, and Ph, triazinyl, which is optionally substituted with one or more substituents independently from each other selected from the group consisting of Me, $^i$Pr, $^t$Bu, CN, $CF_3$, and Ph, and $N(Ph)_2$.

In the following exemplary embodiments of the second chemical moiety are shown:

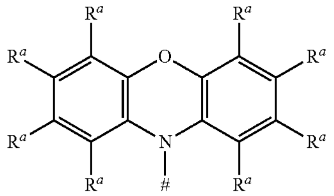

-continued
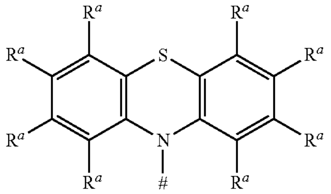
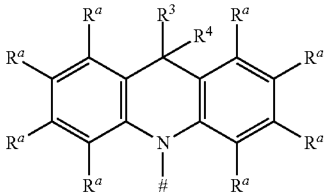
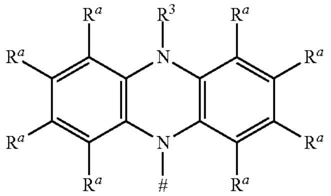
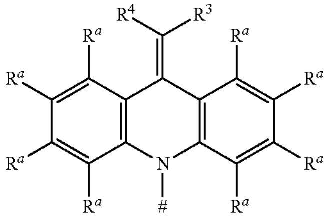
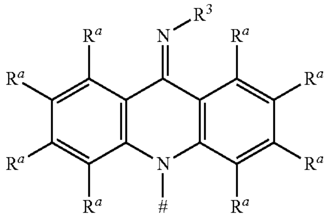
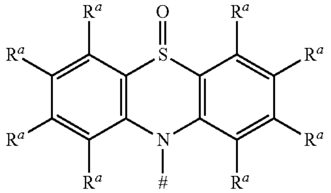
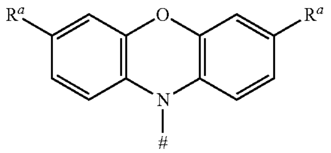
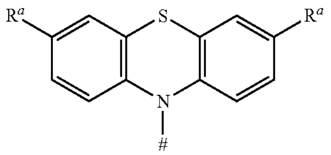
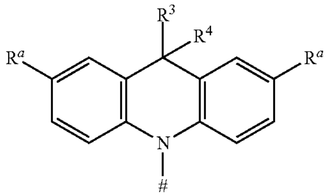
-continued
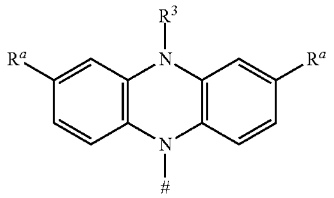
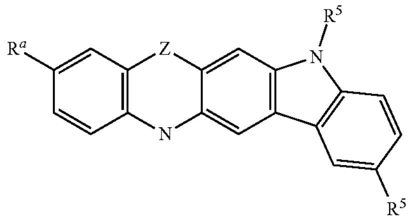
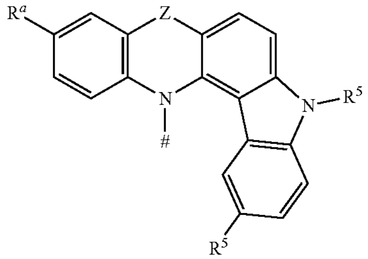
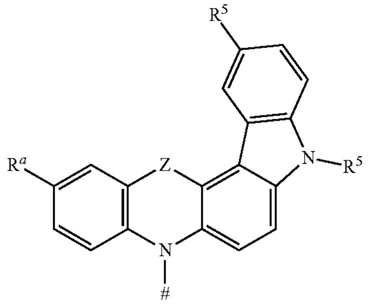
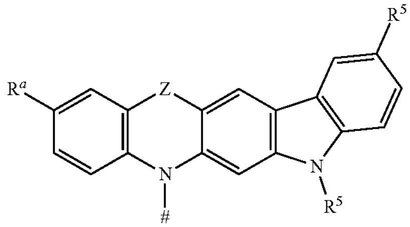
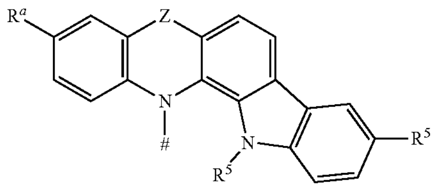
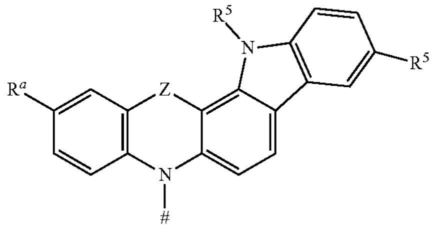

-continued
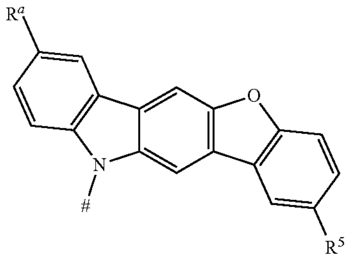
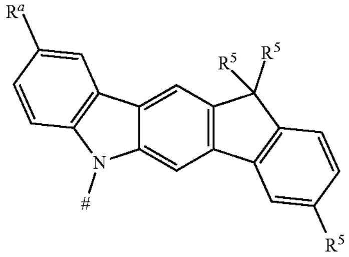
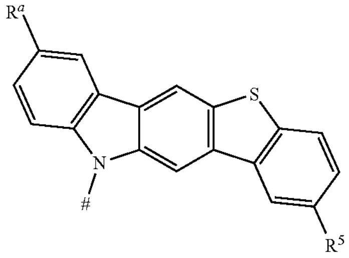
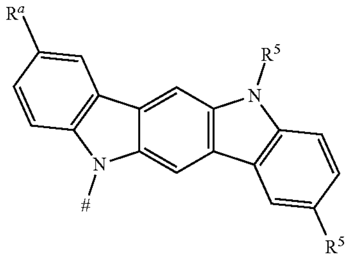
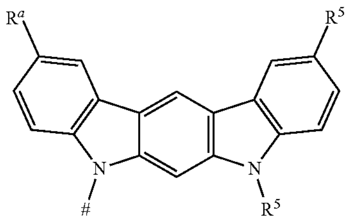
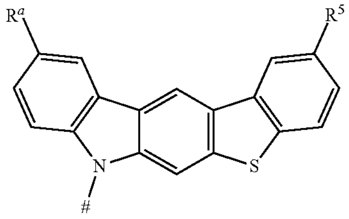
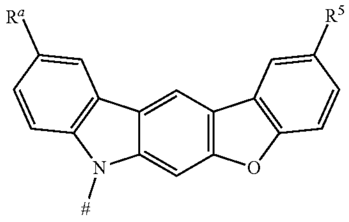
-continued
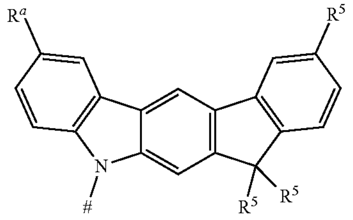
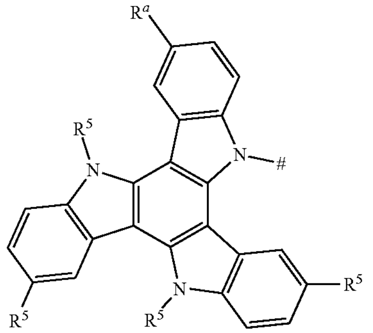
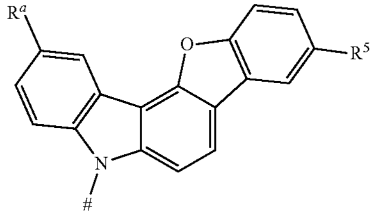
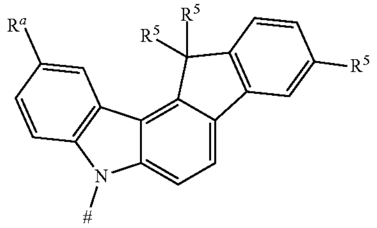
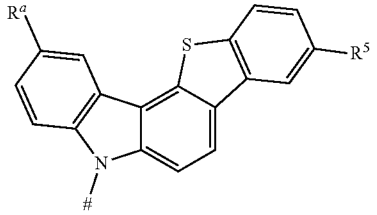
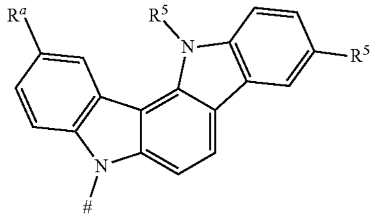
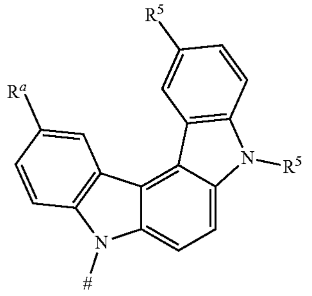

-continued
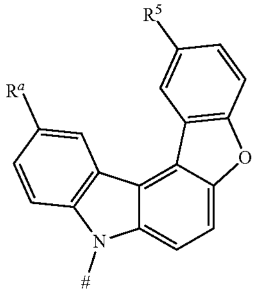
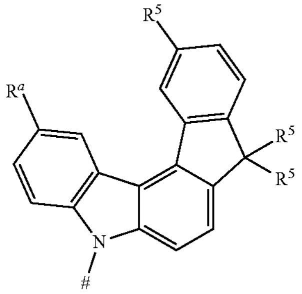
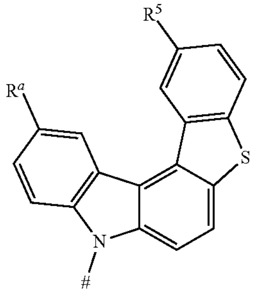
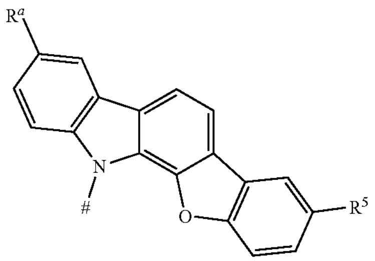
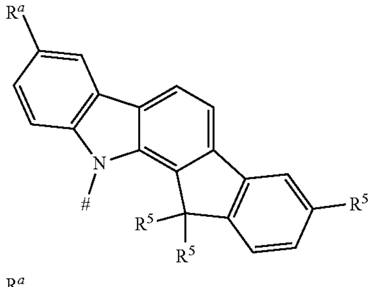
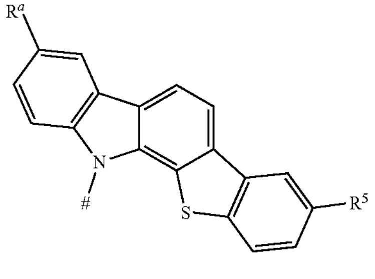
-continued
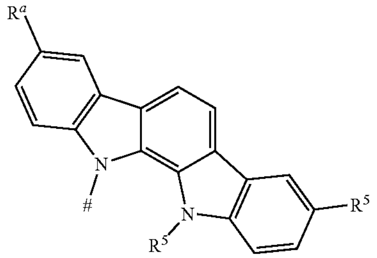
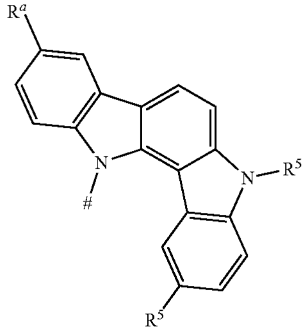
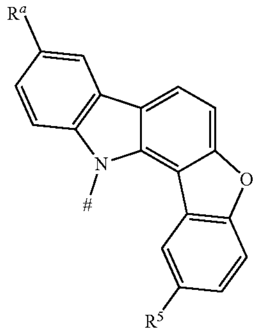
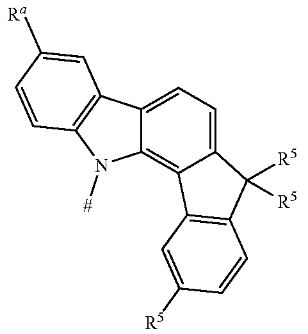
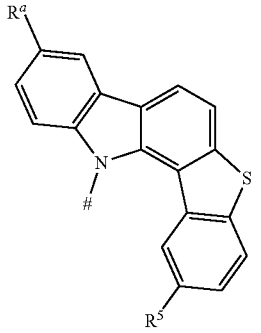
wherein for #, Z, $R^a$, $R^3$, $R^4$ and $R^5$ the aforementioned definitions apply.
In one embodiment, $R^a$ and $R^5$ is at each occurrence independently from another selected from the group consisting of hydrogen (H), methyl (Me), i-propyl ($CH(CH_3)_2$) ($^i$Pr), t-butyl ($^t$Bu), phenyl (Ph), CN, $CF_3$, and diphenylamine ($NPh_2$).

In one embodiment of the invention, the organic molecules comprise or consist of a structure of Formula III:

Formula III

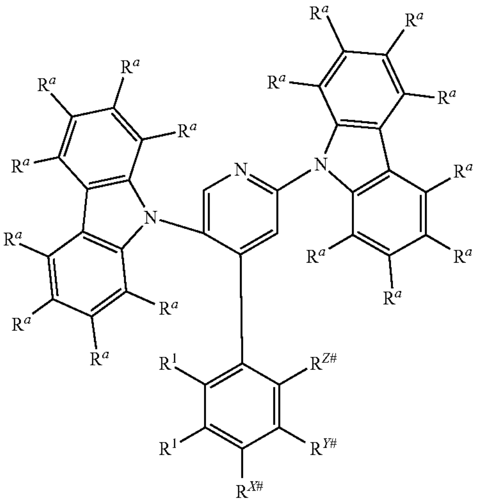

wherein the aforementioned definitions apply, $R^{X\#}$, $R^{Y\#}$ and $R^{Z\#}$ is independently from each other selected from the group consisting of CN and $R^P$, and wherein exactly one substituent selected from the group consisting of $R^{X\#}$, $R^{Y\#}$ and $R^{Z\#}$ is CN.

In a preferred embodiment of the invention, $R^{X\#}$ is CN.

In a further embodiment of the invention, the organic molecules comprise or consist of a structure selected from the group of Formula IIIa-1, Formula IIIa-2, and Formula IIIa-3:

Formula IIIa-1

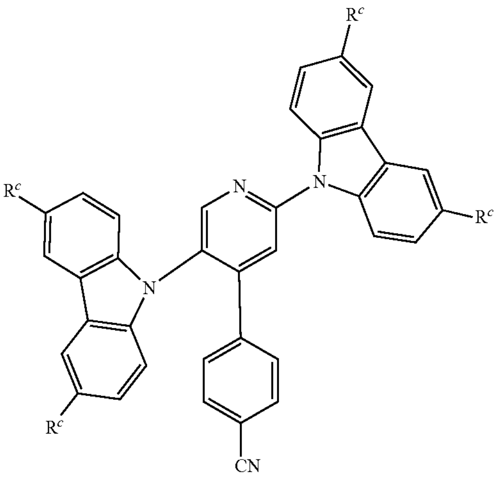

-continued

Formula IIIa-2

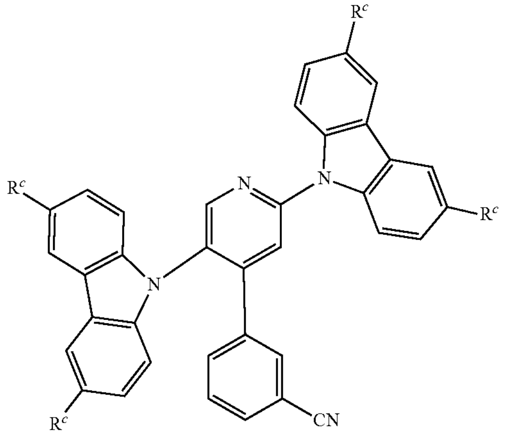

Formula IIIa-3

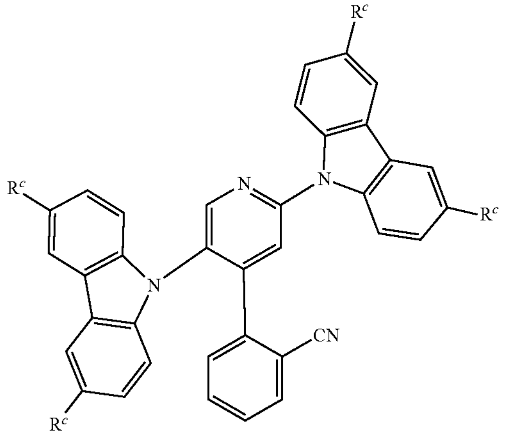

wherein $R^c$ is at each occurrence independently from another selected from the group consisting of Me, $^i$Pr, $^t$Bu Ph, which is optionally substituted with one or more substituents independently from each other selected from the group consisting of Me, $^i$Pr, $^t$Bu, CN, $CF_3$, and Ph, pyridinyl, which is optionally substituted with one or more substituents independently from each other selected from the group consisting of Me, $^i$Pr, $^t$Bu, CN, $CF_3$, and Ph, pyrimidinyl, which is optionally substituted with one or more substituents independently from each other selected from the group consisting of Me, $^i$Pr, $^t$Bu, CN, $CF_3$, and Ph, carbazolyl, which is optionally substituted with one or more substituents independently from each other selected from the group consisting of Me, $^i$Pr, $^t$Bu, CN, $CF_3$, and Ph, triazinyl, which is optionally substituted with one or more substituents independently from each other selected from the group consisting of Me, $^i$Pr, $^t$Bu, CN, $CF_3$, and Ph, and $N(Ph)_2$.

In a preferred embodiment of the invention, the organic molecules comprise or consist of a structure of Formula IIIa-1.

In a further embodiment of the invention, the organic molecules comprise or consist of a structure selected from the group of Formula IIIb-1 Formula IIIb-2 and Formula IIIb-3:

Formula IIIb-1

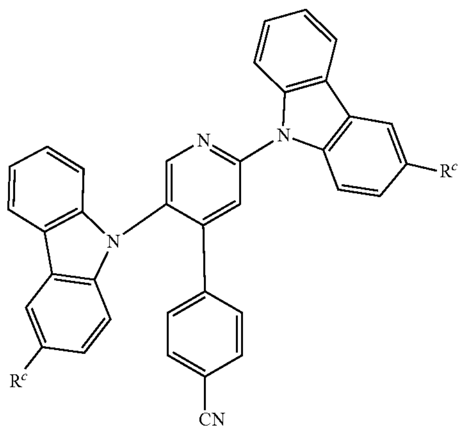

Formula IIIb-2

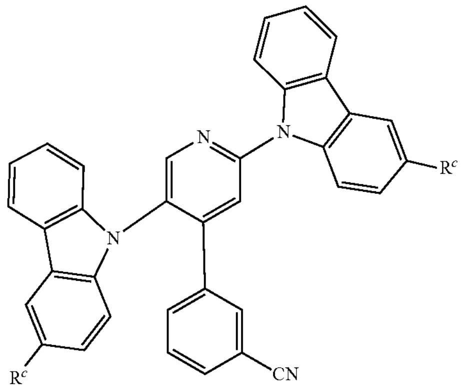

Formula IIIb-3

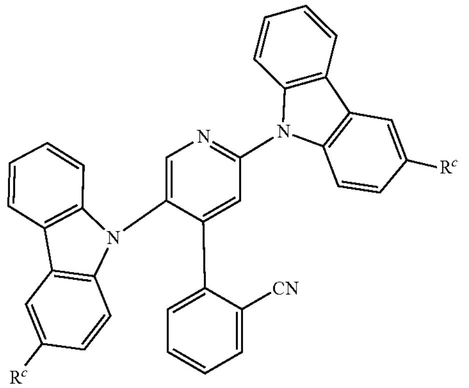

wherein the aforementioned definitions apply.

In a preferred embodiment of the invention, the organic molecules comprise or consist of a structure of Formula IIIb-1.

In a further embodiment of the invention, the organic molecules comprise or consist of a structure selected from the group of Formula IIIc-1, Formula IIIc-2, and Formula IIIc-3:

Formula IIIc-1

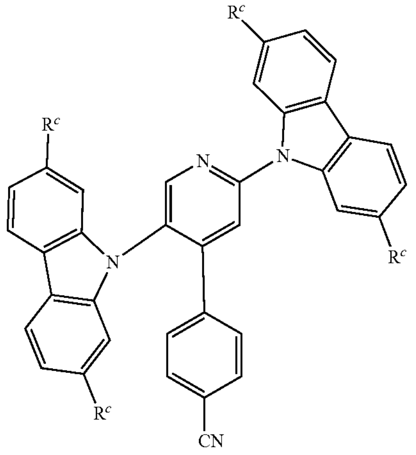

Formula IIIc-2

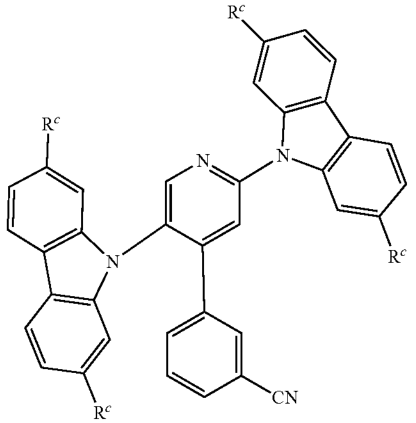

Formula IIIc-3

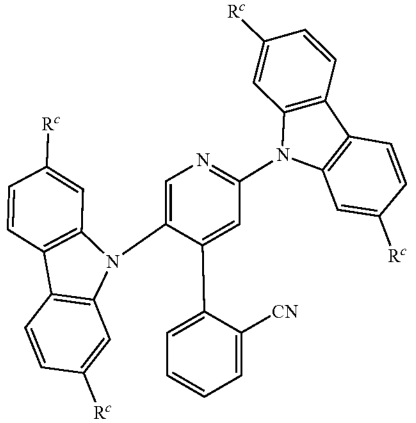

wherein the aforementioned definitions apply.

In a preferred embodiment of the invention, the organic molecules comprise or consist of a structure of Formula IIIc-1.

In a further embodiment of the invention, the organic molecules comprise or consist of a structure selected from the group of Formula IIId-1, Formula IIId-2, and Formula IIId-3:

Formula IIId-1

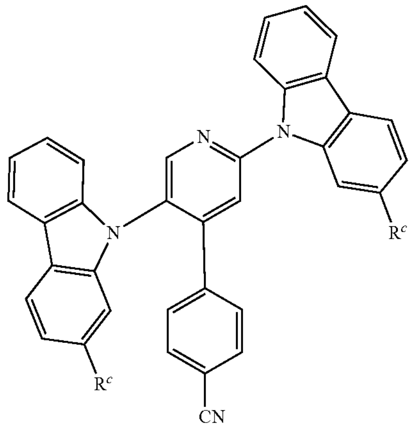

Formula IIId-2

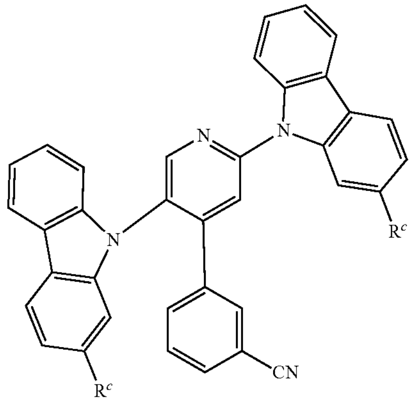

Formula IIId-3

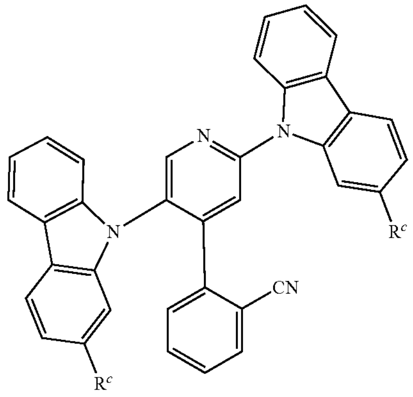

wherein the aforementioned definitions apply.

In a preferred embodiment of the invention, the organic molecules comprise or consist of a structure of Formula IIId-1.

In a further embodiment of the invention, the organic molecules comprise or consist of a structure selected from the group of Formula IIIe-1, Formula IIIe-2, and Formula IIIe-3:

Formula IIIe-1

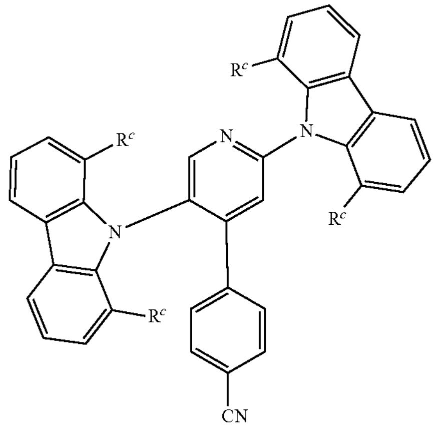

Formula IIIe-2

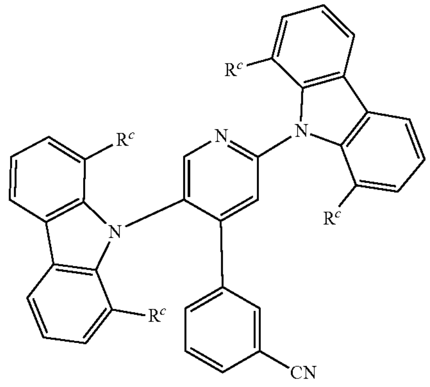

Formula IIIe-3

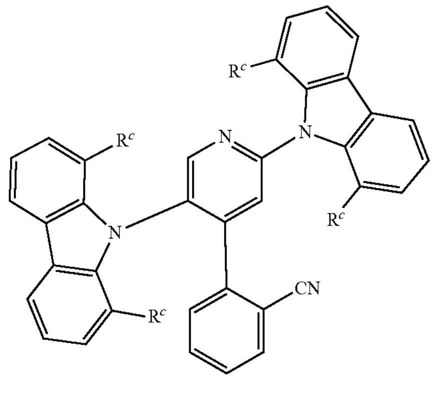

wherein the aforementioned definitions apply.

In a preferred embodiment of the invention, the organic molecules comprise or consist of a structure of Formula IIIe-1.

In a further embodiment of the invention, the organic molecules comprise or consist of a structure selected from the group of Formula IIIf-1, Formula IIIf-2, and Formula IIIf-3:

Formula IIIf-1

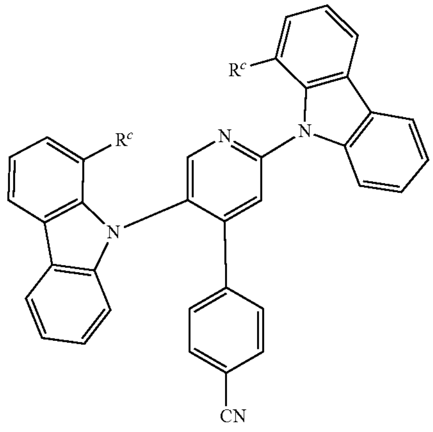

Formula IIIf-2

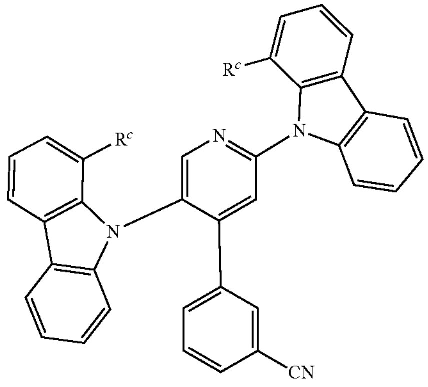

Formula IIIf-3

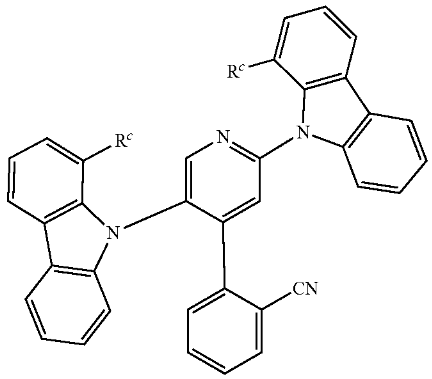

wherein the aforementioned definitions apply.

In a preferred embodiment of the invention, the organic molecules comprise or consist of a structure of Formula IIIf-1.

In a further embodiment of the invention, the organic molecules comprise or consist of a structure selected from the group of Formula IIIg-1, Formula IIIg-2, and Formula IIIg-3:

Formula IIIg-1

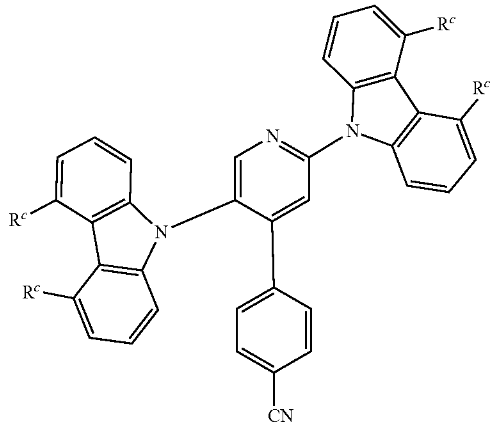

Formula IIIg-2

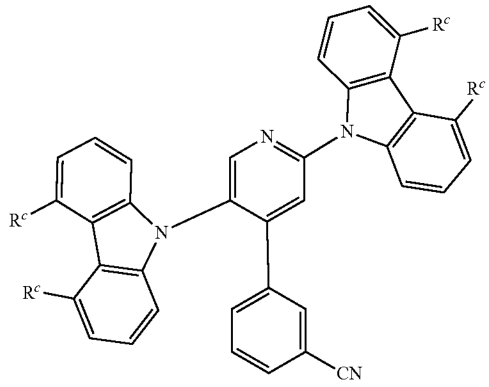

Formula IIIg-3

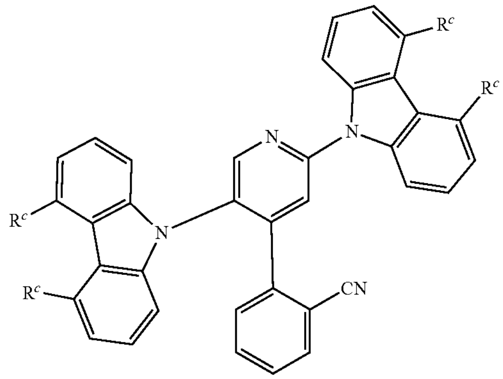

wherein the aforementioned definitions apply.

In a preferred embodiment of the invention, the organic molecules comprise or consist of a structure of Formula IIIg-1.

In a further embodiment of the invention, the organic molecules comprise or consist of a structure selected from the group of Formula IIIh-1, Formula IIIh-2, and Formula IIIh-3:

Formula IIIh-1

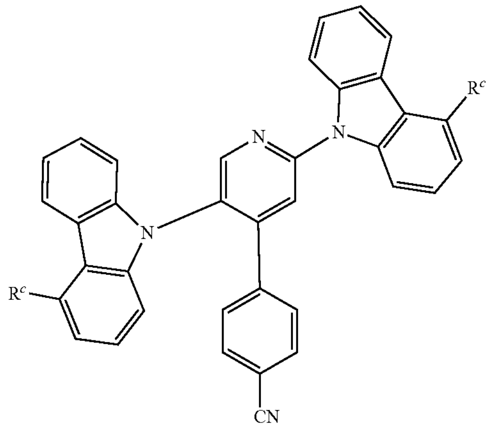

Formula IIIh-2

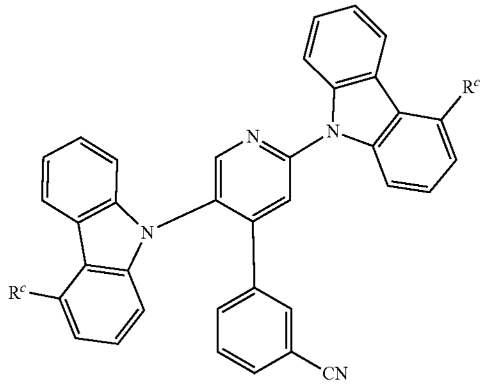

Formula IIIh-3

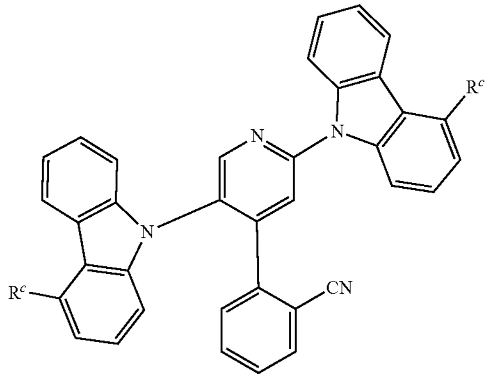

wherein the aforementioned definitions apply.

In a preferred embodiment of the invention, the organic molecules comprise or consist of a structure of Formula IIIh-1.

In one embodiment of the invention, the organic molecules comprise or consist of a structure of Formula IV:

Formula III

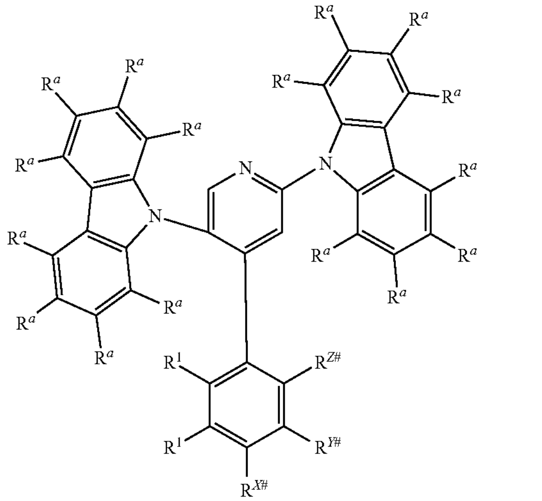

wherein the aforementioned definitions apply and wherein exactly one substituent selected from the group consisting of $R^{X\#}$, $R^{Y\#}$ and $R^{Z\#}$ is CN.

In a preferred embodiment of the invention, $R^{X\#}$ is CN.

In a further embodiment of the invention, the organic molecules comprise or consist of a structure selected from the group of Formula IVa-1, Formula IVa-2 and Formula IVa-3:

Formula IVa-1

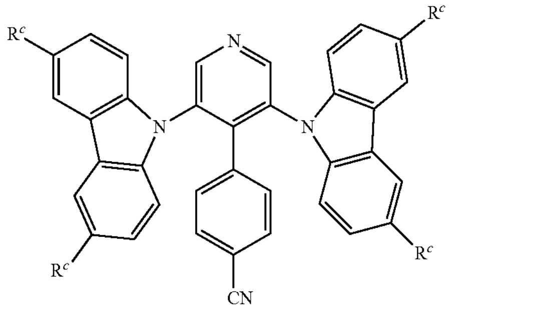

Formula IVa-2

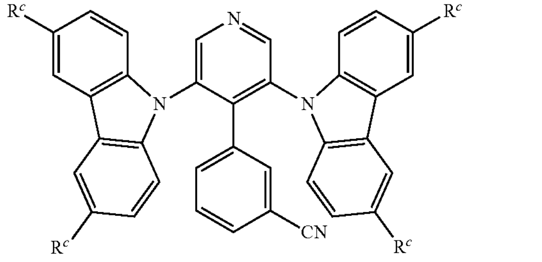

-continued

Formula IVa-3

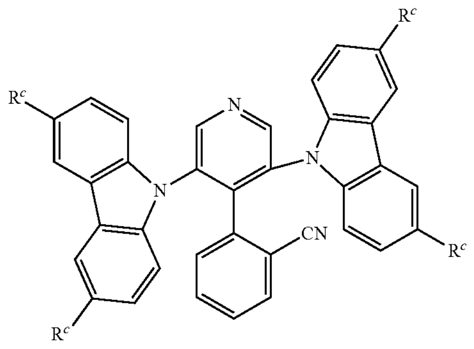

Formula IVa-1 Formula IVa-2 Formula IVa-3 wherein the aforementioned definitions apply.

In a preferred embodiment of the invention, the organic molecules comprise or consist of a structure of Formula IVa-1.

In a further embodiment of the invention, the organic molecules comprise or consist of a structure selected from the group of Formula IVb-1, Formula IVb-2, and Formula IVb-3:

Formula IVb-1

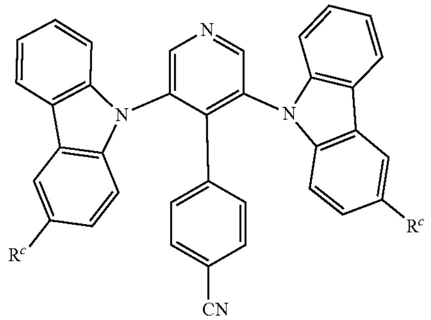

Formula IVb-2

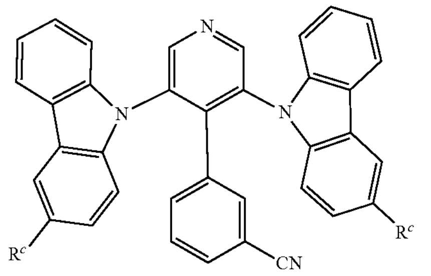

-continued

Formula IVb-3

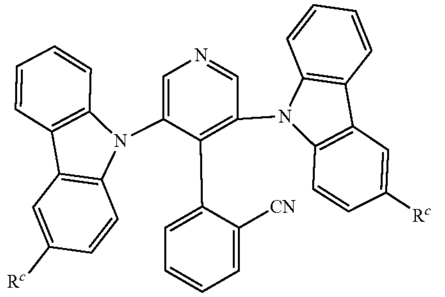

wherein the aforementioned definitions apply.

In a preferred embodiment of the invention, the organic molecules comprise or consist of a structure of Formula IVb-1.

In a further embodiment of the invention, the organic molecules comprise or consist of a structure selected from the group of Formula IVc-1, Formula IVc-2, and Formula IVc-3:

Formula IVc-1

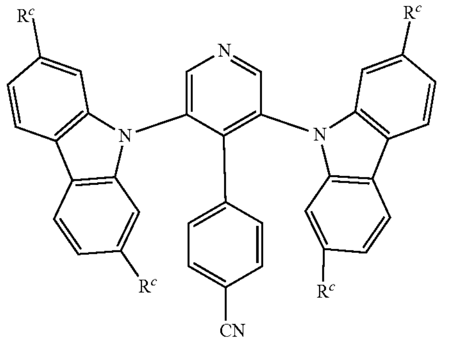

Formula IVc-2

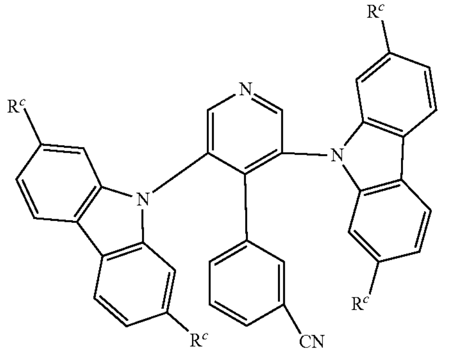

-continued

Formula IVc-3

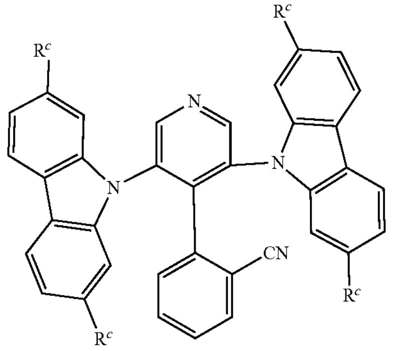

wherein the aforementioned definitions apply.

In a preferred embodiment of the invention, the organic molecules comprise or consist of a structure of Formula IVc-1.

In a further embodiment of the invention, the organic molecules comprise or consist of a structure selected from the group of Formula IVd-1, Formula IVd-2, and Formula IVd-3:

Formula IVd-1

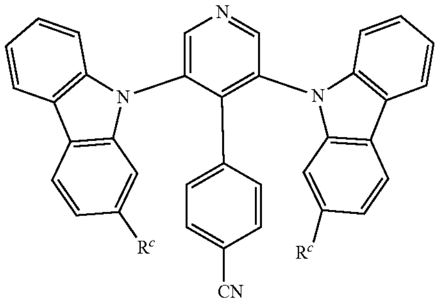

Formula IVd-2

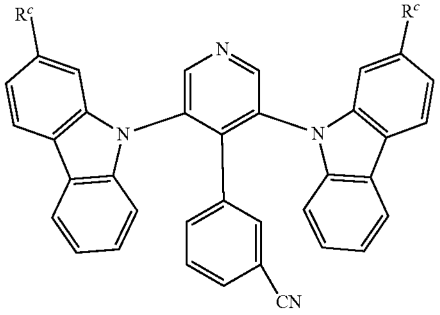

Formula IVd-3

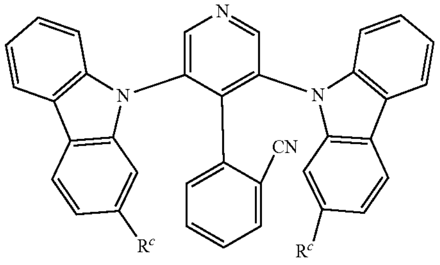

wherein the aforementioned definitions apply.

In a preferred embodiment of the invention, the organic molecules comprise or consist of a structure of Formula IVd-1.

In a further embodiment of the invention, the organic molecules comprise or consist of a structure selected from the group of Formula IVe-1, Formula IVe-2, an Formula IVe-3:

Formula IVe-1

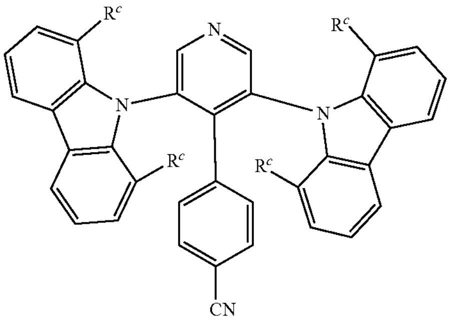

Formula IVe-2

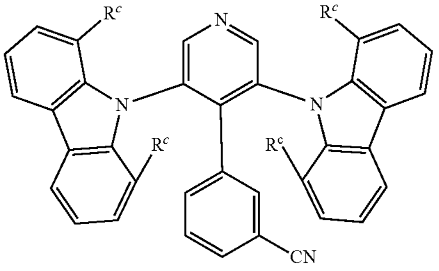

Formula IVe-3

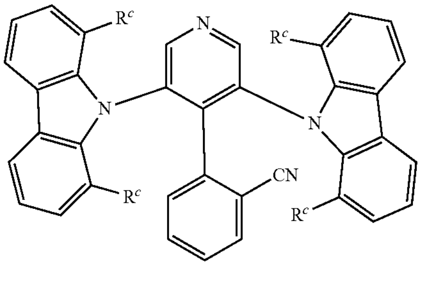

wherein the aforementioned definitions apply.

In a preferred embodiment of the invention, the organic molecules comprise or consist of a structure of Formula IVe-1.

In a further embodiment of the invention, the organic molecules comprise or consist of a structure selected from the group of Formula IVf-1, Formula IVf-2, and Formula IVf-3:

Formula IVf-1

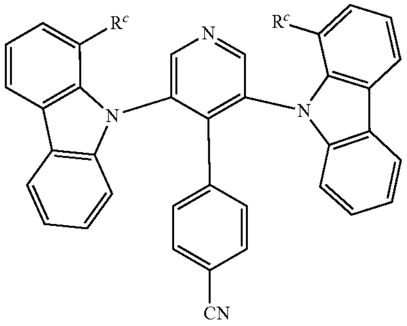

Formula IVf-2

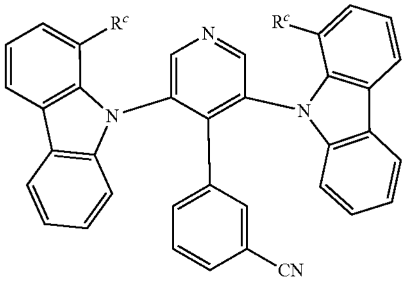

Formula IVf-3

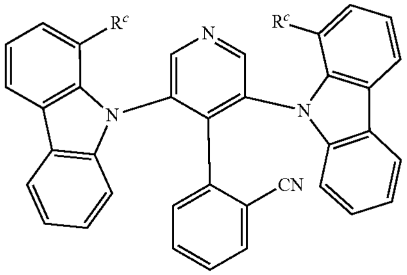

wherein the aforementioned definitions apply.

In a preferred embodiment of the invention, the organic molecules comprise or consist of a structure of Formula IVf-1.

In a further embodiment of the invention, the organic molecules comprise or consist of a structure selected from the group of Formula IVg-1, Formula IVg-2, and Formula IVg-3:

Formula IVg-1

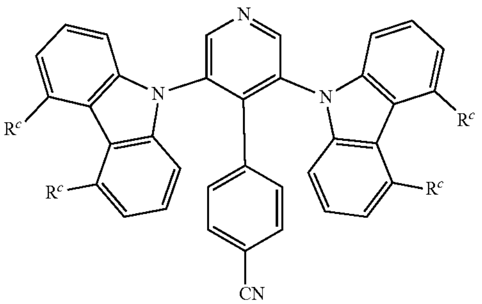

-continued

Formula IVg-2

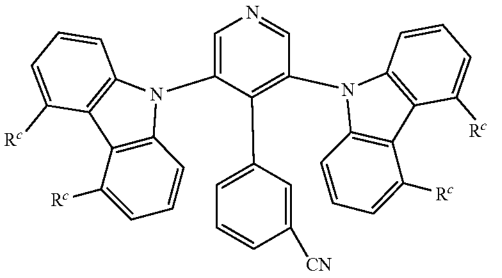

Formula IVg-3

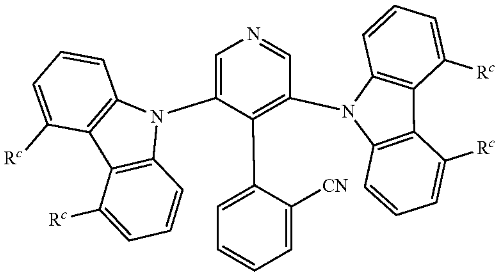

wherein the aforementioned definitions apply.

In a preferred embodiment of the invention, the organic molecules comprise or consist of a structure of Formula IVg-1.

In a further embodiment of the invention, the organic molecules comprise or consist of a structure selected from the group of Formula IVh-1, Formula IVh-2, and Formula IVh-3:

Formula IVh-1

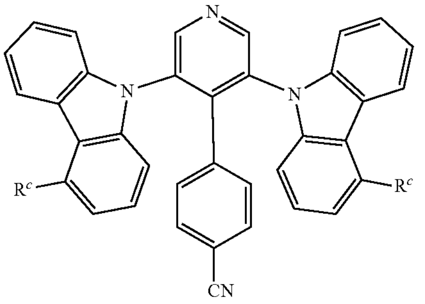

Formula IVh-2

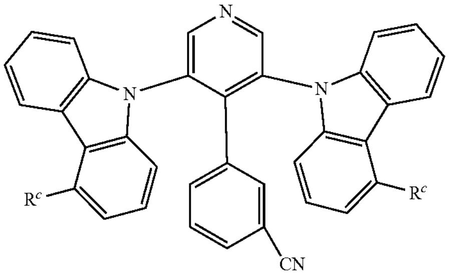

-continued

Formula IVh-3

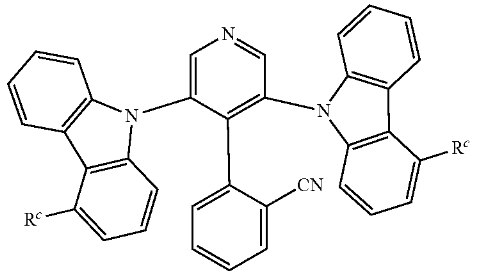

wherein the aforementioned definitions apply.

In a preferred embodiment of the invention, the organic molecules comprise or consist of a structure of Formula IVh-1.

In one embodiment of the invention, the organic molecules comprise or consist of a structure of Formula V:

Formula V

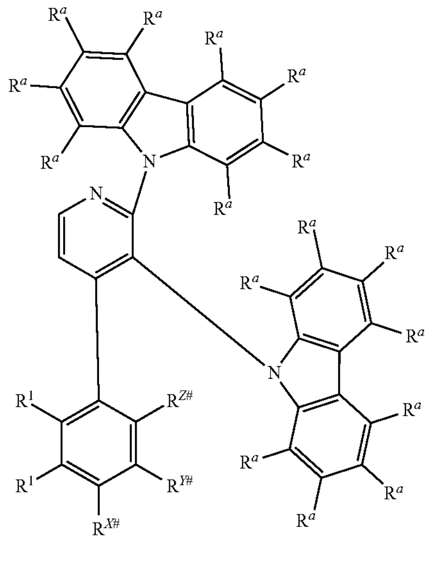

wherein the aforementioned definitions apply and wherein exactly one substituent selected from the group consisting of $R^{X\#}$, $R^{Y\#}$ and $R^{Z\#}$ is CN.

In a preferred embodiment of the invention, $R^{X\#}$ is CN.

In a further embodiment of the invention, the organic molecules comprise or consist of a structure selected from the group of Formula Va-1, Formula Va-2 and Formula Va-3:

Formula Va-1

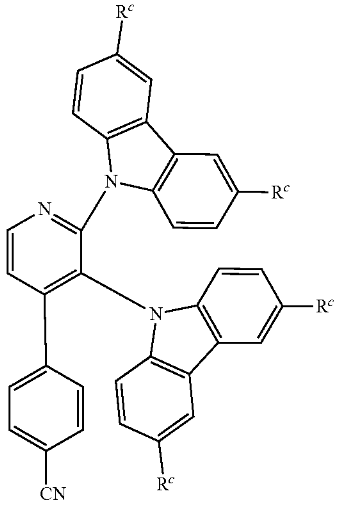

Formula Va-2

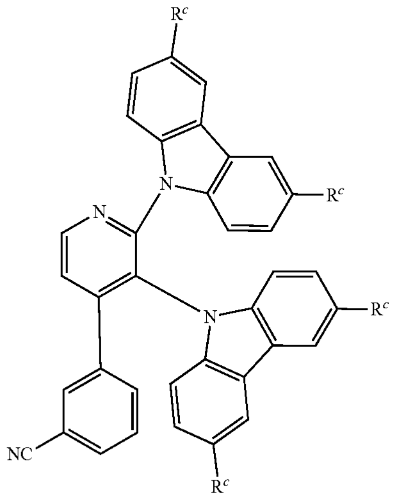

Formula Va-3

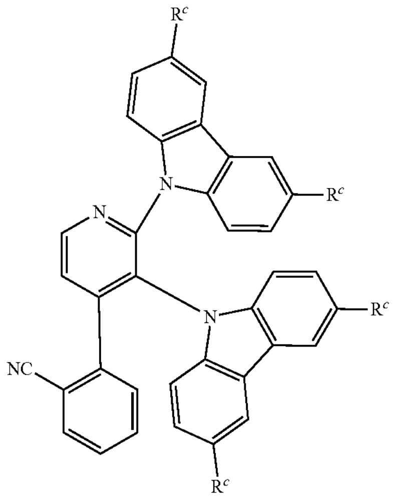

wherein the aforementioned definitions apply.

In a preferred embodiment of the invention, the organic molecules comprise or consist of a structure of Formula Va-1.

In a further embodiment of the invention, the organic molecules comprise or consist of a structure selected from the group of Formula Vb-1, Formula Vb-2, and Formula Vb-3:

Formula Vb-1

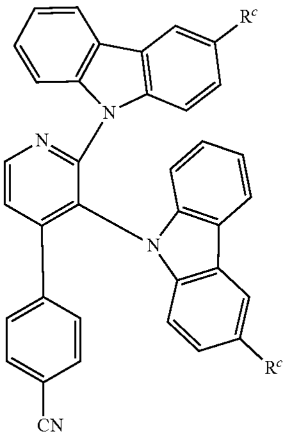

Formula Vb-2

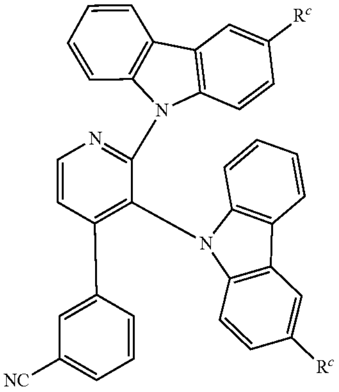

Formula Vb-3

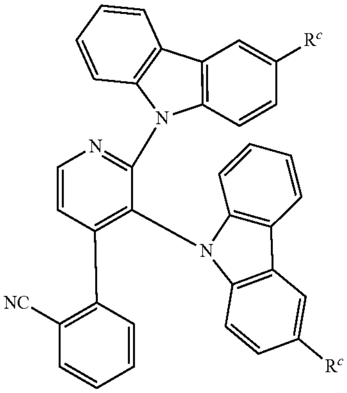

wherein the aforementioned definitions apply.

In a preferred embodiment of the invention, the organic molecules comprise or consist of a structure of Formula Vb-1.

In a further embodiment of the invention, the organic molecules comprise or consist of a structure selected from the group of Formula Vc-1, Formula Vc-2, and Formula Vc-3:

Formula Vc-1

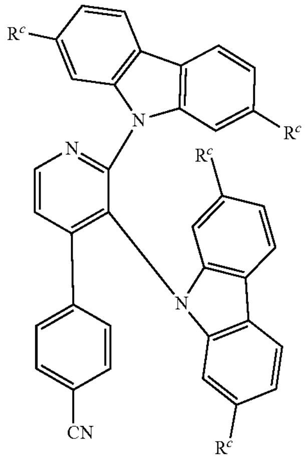

Formula Vc-2

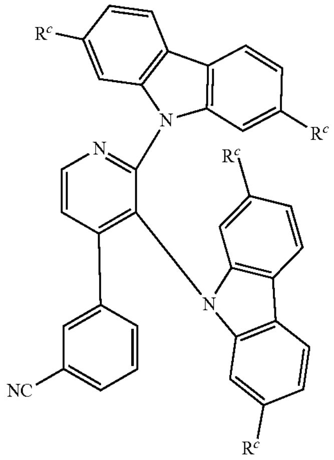

Formula Vc-3

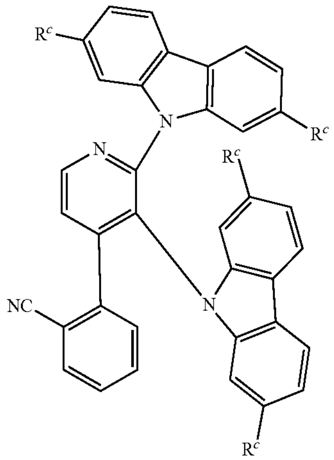

wherein the aforementioned definitions apply.

In a preferred embodiment of the invention, the organic molecules comprise or consist of a structure of Formula Vc-1.

In a further embodiment of the invention, the organic molecules comprise or consist of a structure selected from the group of Formula Vd-1, Formula Vd-2, and Formula Vd-3:

Formula Vd-1

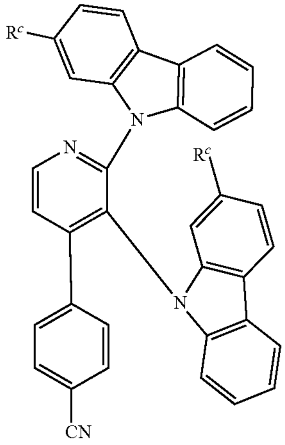

Formula Vd-2

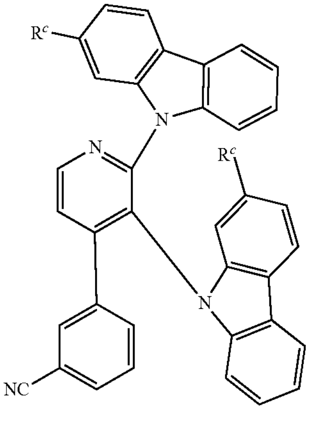

Formula Vd-3

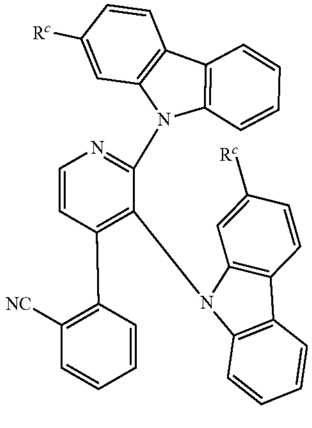

wherein the aforementioned definitions apply.

In a preferred embodiment of the invention, the organic molecules comprise or consist of a structure of Formula Vd-1.

In a further embodiment of the invention, the organic molecules comprise or consist of a structure selected from the group of Formula Ve-1, Formula Ve-2, and Formula Ve-3:

Formula Ve-1

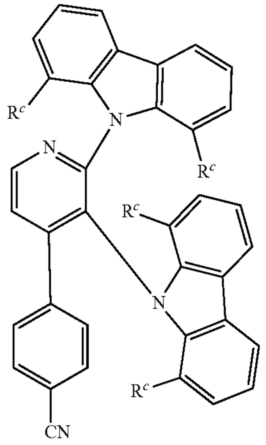

Formula Ve-2

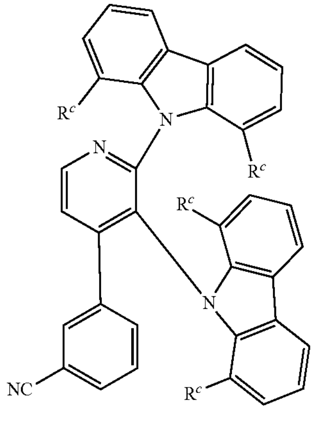

Formula Ve-3

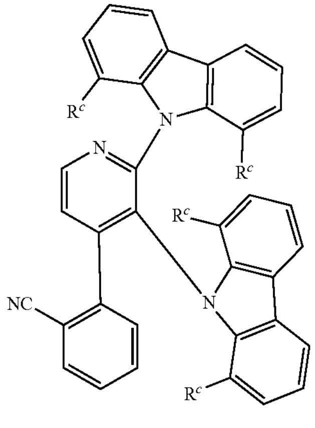

wherein the aforementioned definitions apply.

In a preferred embodiment of the invention, the organic molecules comprise or consist of a structure of Formula Ve-1.

In a further embodiment of the invention, the organic molecules comprise or consist of a structure selected from the group of Formula Vf-1, Formula Vf-2, and Formula Vf-3:

Formula Vf-1

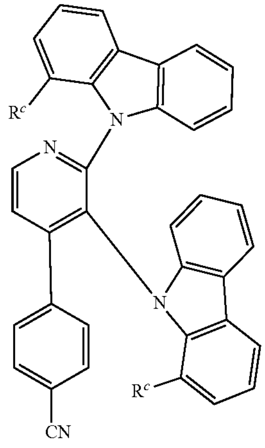

Formula Vf-2

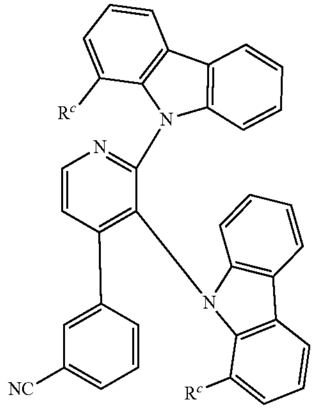

Formula Vf-3

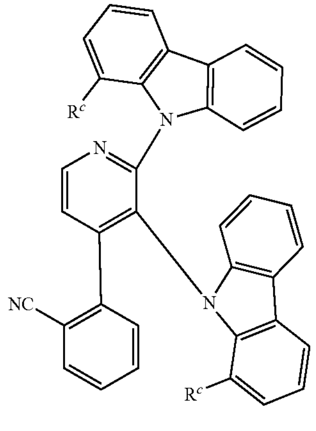

wherein the aforementioned definitions apply.

In a preferred embodiment of the invention, the organic molecules comprise or consist of a structure of Formula Vf-1.

In a further embodiment of the invention, the organic molecules comprise or consist of a structure selected from the group of Formula IVg-1, Formula IVg-2, and Formula IVg-3

Formula Ve-1

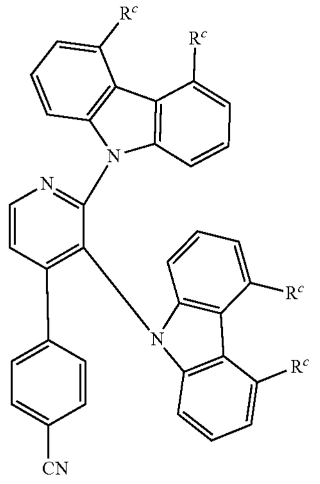

Formula Ve-2

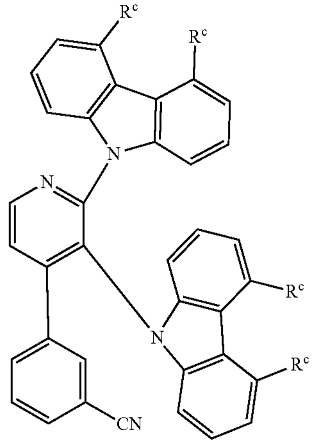

Formula Ve-3

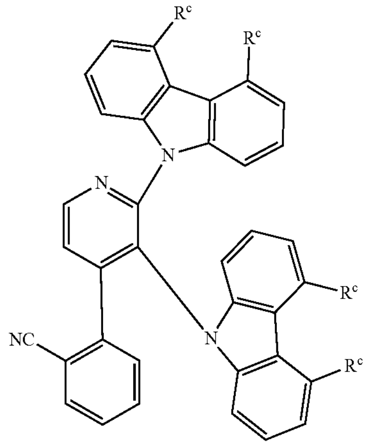

wherein the aforementioned definitions apply.

In a preferred embodiment of the invention, the organic molecules comprise or consist of a structure of Formula Vg-1.

In a further embodiment of the invention, the organic molecules comprise or consist of a structure selected from the group of Formula Vh-1, Formula Vh-2, and Formula Vh-3:

Formula Vh-1

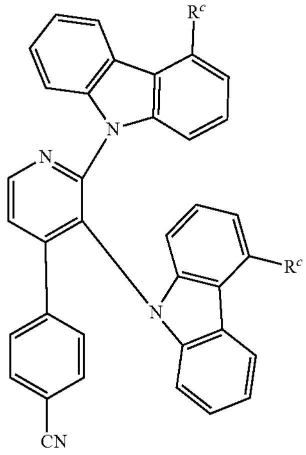

Formula Vh-2

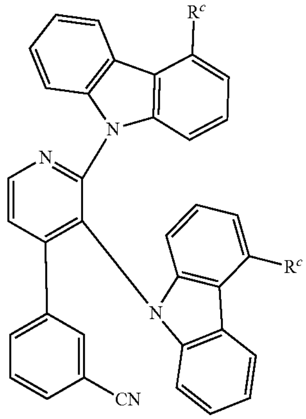

Formula Vh-3

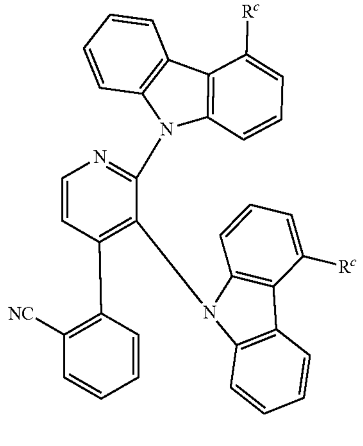

wherein the aforementioned definitions apply.

In a preferred embodiment of the invention, the organic molecules comprise or consist of a structure of Formula Vh-1.

In one embodiment of the invention $R^c$ is at each occurrence independently from another selected from the group consisting of Me, $^{i}$Pr, $^{t}$Bu Ph, which is optionally substituted with one or more substituents independently from each other selected from the group consisting of Me, $^{i}$Pr, $^{t}$Bu, CN, $CF_3$ and Ph; and triazinyl, which is optionally substituted with one or more substituents independently from each other selected from the group consisting of Me, $^{i}$Pr, $^{t}$Bu, CN, $CF_3$ and Ph.

As used throughout the present application, the terms "aryl" and "aromatic" may be understood in the broadest sense as any mono-, bi- or polycyclic aromatic moieties. Accordingly, an aryl group contains 6 to 60 aromatic ring atoms, and a heteroaryl group contains 5 to 60 aromatic ring atoms, of which at least one is a heteroatom. Notwithstanding, throughout the application the number of aromatic ring atoms may be given as subscripted number in the definition of certain substituents. In particular, the heteroaromatic ring includes one to three heteroatoms. Again, the terms "heteroaryl" and "heteroaromatic" may be understood in the broadest sense as any mono-, bi- or polycyclic heteroaromatic moieties that include at least one heteroatom. The heteroatoms may at each occurrence be the same or different and be individually selected from the group consisting of N, O and S. Accordingly, the term "arylene" refers to a divalent substituent that bears two binding sites to other molecular structures and thereby serving as a linker structure. In case, a group in the exemplary embodiments is defined differently from the definitions given here, for example, the number of aromatic ring atoms or number of heteroatoms differs from the given definition, the definition in the exemplary embodiments is to be applied. According to the invention, a condensed (annulated) aromatic or heteroaromatic polycycle is built of two or more single aromatic or heteroaromatic cycles, which formed the polycycle via a condensation reaction.

In particular, as used throughout the present application the term aryl group or heteroaryl group comprises groups which can be bound via any position of the aromatic or heteroaromatic group, derived from benzene, naphthaline, anthracene, phenanthrene, pyrene, dihydropyrene, chrysene, perylene, fluoranthene, benzanthracene, benzphenanthrene, tetracene, pentacene, benzpyrene, furan, benzofuran, isobenzofuran, dibenzofuran, thiophene, benzothiophene, isobenzothiophene, dibenzothiophene; pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthoimidazole, phenanthroimidazole, pyridoimidazole, pyrazinoimidazole, quinoxalinoimidazole, oxazole, benzoxazole, napthooxazole, anthroxazol, phenanthroxazol, isoxazole, 1,2-thiazole, 1,3-thiazole, benzothiazole, pyridazine, benzopyridazine, pyrimidine, benzopyrimidine, 1,3,5-triazine, quinoxaline, pyrazine, phenazine, naphthyridine, carboline, benzocarboline, phenanthroline, 1,2,3-triazole, 1,2,4-triazole, benzotriazole, 1,2,3-oxadiazole, 1,2,4-oxadiazole, 1,2,5-oxadiazole, 1,2,3,4-tetrazine, purine, pteridine, indolizine and benzothiadiazole or combinations of the abovementioned groups.

As used throughout the present application the term cyclic group may be understood in the broadest sense as any mono-, bi- or polycyclic moieties.

As used throughout the present application the term biphenyl as a substituent may be understood in the broadest sense as ortho-biphenyl, meta-biphenyl, or para-biphenyl, wherein ortho, meta and para is defined in regard to the binding site to another chemical moiety.

As used throughout the present application the term alkyl group may be understood in the broadest sense as any linear, branched, or cyclic alkyl substituent. In particular, the term alkyl comprises the substituents methyl (Me), ethyl (Et), n-propyl ($^n$Pr), i-propyl ($^i$Pr), cyclopropyl, n-butyl ($^n$Bu), i-butyl ($^i$Bu), s-butyl ($^s$Bu), t-butyl ($^t$Bu), cyclobutyl, 2-methylbutyl, n-pentyl, s-pentyl, t-pentyl, 2-pentyl, neo-pentyl, cyclopentyl, n-hexyl, s-hexyl, t-hexyl, 2-hexyl, 3-hexyl, neo-hexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2,2,2]octyl, 2-bicyclo[2,2,2]-octyl, 2-(2,6-dimethyl)octyl, 3-(3,7-dimethyl)octyl, adamantyl, 2,2,2-trifluorethyl, 1,1-dimethyl-n-hex-1-yl, 1,1-dimethyl-n-hept-1-yl, 1,1-dimethyl-n-oct-1-yl, 1,1-dimethyl-n-dec-1-yl, 1,1-dimethyl-n-dodec-1-yl, 1,1-dimethyl-n-tetradec-1-yl, 1,1-dimethyl-n-hexadec-1-yl, 1,1-dimethyl-n-octadec-1-yl, 1,1-diethyl-n-hex-1-yl, 1,1-diethyl-n-hept-1-yl, 1,1-diethyl-n-oct-1-yl, 1,1-diethyl-n-dec-1-yl, 1,1-diethyl-n-dodec-1-yl, 1,1-diethyl-n-tetradec-1-yl, 1,1-diethyln-n-hexadec-1-yl, 1,1-diethyl-n-octadec-1-yl, 1-(n-propyl)-cyclohex-1-yl, 1-(n-butyl)-cyclohex-1-yl, 1-(n-hexyl)-cyclohex-1-yl, 1-(n-octyl)-cyclohex-1-yl and 1-(n-decyl)-cyclohex-1-yl.

As used throughout the present application the term alkenyl comprises linear, branched, and cyclic alkenyl substituents. The term alkenyl group exemplarily comprises the substituents ethenyl, propenyl, butenyl, pentenyl, cyclopentenyl, hexenyl, cyclohexenyl, heptenyl, cycloheptenyl, octenyl, cyclooctenyl or cyclooctadienyl.

As used throughout the present application the term alkynyl comprises linear, branched, and cyclic alkynyl substituents. The term alkynyl group exemplarily comprises ethynyl, propynyl, butynyl, pentynyl, hexynyl, heptynyl or octynyl.

As used throughout the present application the term alkoxy comprises linear, branched, and cyclic alkoxy substituents. The term alkoxy group exemplarily comprises methoxy, ethoxy, n-propoxy, i-propoxy, n-butoxy, i-butoxy, s-butoxy, t-butoxy and 2-methylbutoxy.

As used throughout the present application the term thioalkoxy comprises linear, branched, and cyclic thioalkoxy substituents, in which the O of the exemplarily alkoxy groups is replaced by S.

As used throughout the present application, the terms "halogen" and "halo" may be understood in the broadest sense as being preferably fluorine, chlorine, bromine or iodine.

Whenever hydrogen (H) is mentioned herein, it could also be replaced by deuterium at each occurrence.

It is understood that when a molecular fragment is described as being a substituent or otherwise attached to another moiety, its name may be written as if it were a fragment (e.g. naphtyl, dibenzofuryl) or as if it were the whole molecule (e.g. naphthalene, dibenzofuran). As used herein, these different ways of designating a substituent or attached fragment are considered to be equivalent.

In one embodiment, the organic molecules according to the invention have an excited state lifetime of not more than 150 μs, of not more than 100 μs, in particular of not more than 50 μs, more preferably of not more than 10 μs or not more than 7 μs in a film of poly(methyl methacrylate) (PMMA) with 10% by weight of organic molecule at room temperature.

In one embodiment of the invention, the organic molecules according to the invention represent thermally-activated delayed fluorescence (TADF) materials, which exhibit a $\Delta E_{ST}$ value, which corresponds to the energy difference between the first excited singlet state (S1) and the first excited triplet state (T1), of less than 5000 $cm^{-1}$, preferably less than 3000 $cm^{-1}$, more preferably less than 1500 $cm^{-1}$, even more preferably less than 1000 $cm^{-1}$ or even less than 500 $cm^{-1}$.

In a further embodiment of the invention, the organic molecules according to the invention have an emission peak in the visible or nearest ultraviolet range, i.e., in the range of a wavelength of from 380 to 800 nm, with a full width at half maximum of less than 0.50 eV, preferably less than 0.48 eV, more preferably less than 0.45 eV, even more preferably less than 0.43 eV or even less than 0.40 eV in a film of poly(methyl methacrylate) (PMMA) with 10% by weight of organic molecule at room temperature.

In a further embodiment of the invention, the organic molecules according to the invention have a "blue material index" (BMI), calculated by dividing the photoluminescence quantum yield (PLQY) in % by the CIEy color coordinate of the emitted light, of more than 150, in particular more than 200, preferably more than 250, more preferably of more than 300 or even more than 500.

Orbital and excited state energies can be determined either by means of experimental methods or by calculations employing quantum-chemical methods, in particular density functional theory calculations. The energy of the highest occupied molecular orbital $E^{HOMO}$ is determined by methods known to the person skilled in the art from cyclic voltammetry measurements with an accuracy of 0.1 eV. The energy of the lowest unoccupied molecular orbital $E^{LUMO}$ is calculated as $E^{HOMO}+E^{gap}$, wherein $E^{gap}$ is determined as follows: For host compounds, the onset of the emission spectrum of a film with 10% by weight of host in poly (methyl methacrylate) (PMMA) is used as $E^{gap}$, unless stated otherwise. For emitter molecules, $E^{gap}$ is determined as the energy at which the excitation and emission spectra of a film with 10% by weight of emitter in PMMA cross.

The energy of the first excited triplet state T1 is determined from the onset of the emission spectrum at low temperature, typically at 77 K. For host compounds, where the first excited singlet state and the lowest triplet state are energetically separated by >0.4 eV, the phosphorescence is usually visible in a steady-state spectrum in 2-Me-THF. The triplet energy can thus be determined as the onset of the phosphorescence spectrum. For TADF emitter materials, the energy of the first excited triplet state T1 is determined from the onset of the delayed emission spectrum at 77 K, if not otherwise stated measured in a film of PMMA with 10% by weight of emitter materials. Both for host and emitter materials, the energy of the first excited singlet state S1 is determined from the onset of the emission spectrum, if not otherwise stated measured in a film of PMMA with 10% by weight of host or emitter materials.

The onset of an emission spectrum is determined by computing the intersection of the tangent to the emission spectrum with the x-axis. The tangent to the emission spectrum is set at the high-energy side of the emission band and at the point at half maximum of the maximum intensity of the emission spectrum.

A further aspect of the invention relates to a process for preparing organic molecules (with an optional subsequent reaction) according to the invention, wherein a with two $R^2$ substituted 4-chloro-difluoro-pyridine is used as a reactant:

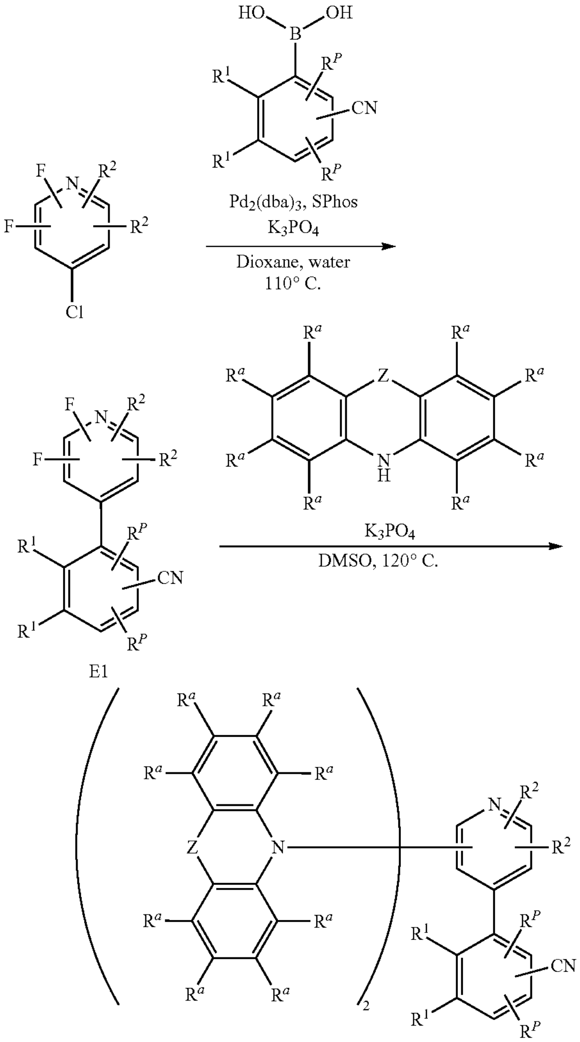

E1

According to the invention, in the reaction for the synthesis of E1 a boronic acid ester can be used instead of a boronic acid.

For the reaction of a nitrogen heterocycle in a nucleophilic aromatic substitution with an aryl halide, preferably an aryl fluoride, typical conditions include the use of a base, such as tribasic potassium phosphate or sodium hydride, for example, in an aprotic polar solvent, such as dimethyl sulfoxide (DMSO) or N,N-dimethylformamide (DMF), for example.

An alternative synthesis route comprises the introduction of a nitrogen heterocycle via copper- or palladium-catalyzed coupling to an aryl halide or aryl pseudohalide, preferably an aryl bromide, an aryl iodide, aryl triflate or an aryl tosylate.

A further aspect of the invention relates to the use of an organic molecule according to the invention as a luminescent emitter or as an absorber, and/or as host material and/or as electron transport material, and/or as hole injection material, and/or as hole blocking material in a light-emitting device.

The organic light-emitting device may be understood in the broadest sense as any device based on organic materials that is suitable for emitting light in the visible or nearest ultraviolet (UV) range, i.e., in the range of a wavelength of from 380 to 800 nm. More preferably, organic light-emitting device may be able to emit light in the visible range, i.e., of from 400 to 800 nm.

In the context of such use, the light-emitting device is more particularly selected from the group consisting of:

light-emitting device (i.e., organic light-emitting diodes; OLEDs), light-emitting electrochemical cells, OLED sensors, especially in gas and vapour sensors not hermetically externally shielded, organic diodes, organic solar cells, organic transistors, organic field-effect transistors, organic lasers and down-conversion elements.

In a preferred embodiment in the context of such use, the organic light-emitting device is a device selected from the group consisting of an organic light emitting diode (OLED), a light emitting electrochemical cell (LEC), and a light-emitting transistor.

In the case of the use, the fraction of the organic molecule according to the invention in the emission layer in a light-emitting device, more particularly in OLEDs, is 1% to 99% by weight, more particularly 5% to 80% by weight. In an alternative embodiment, the proportion of the organic molecule in the emission layer is 100% by weight.

In one embodiment, the emission layer comprises not only the organic molecules according to the invention but also a host material whose triplet (T1) and singlet (S1) energy levels are energetically higher than the triplet (T1) and singlet (S1) energy levels of the organic molecule.

A further aspect of the invention relates to a composition comprising or consisting of:

(a) at least one organic molecule according to the invention, in particular in the form of an emitter and/or a host, and (b) one or more emitter and/or host materials, which differ from the organic molecule according to the invention and (c) optional one or more dyes and/or one or more solvents.

In one embodiment, the emission layer comprises (or (essentially) consists of) a composition comprising or consisting of:

(a) at least one organic molecule according to the invention, in particular in the form of an emitter and/or a host, and (b) one or more emitter and/or host materials, which differ from the organic molecule according to the invention and (c) optional one or more dyes and/or one or more solvents.

Particularly preferably the emission layer EML comprises (or (essentially) consists of) a composition comprising or consisting of:

(i) 1-50% by weight, preferably 5-40% by weight, in particular 10-30% by weight, of one or more organic molecules according to the invention E;

(ii) 5-99% by weight, preferably 30-94.9% by weight, in particular 40-89% by weight, of at least one host compound H; and (iii) optionally 0-94% by weight, preferably 0.1-65% by weight, in particular 1-50% by weight, of at least one further host compound D with a structure differing from the structure of the molecules according to the invention; and (iv) optionally 0-94% by weight, preferably 0-65% by weight, in particular 0-50% by weight, of a solvent; and (v) optionally 0-30% by weight, in particular 0-20% by weight, preferably 0-5% by weight, of at least one further emitter molecule F with a structure differing from the structure of the molecules according to the invention.

Preferably, energy can be transferred from the host compound H to the one or more organic molecules according to the invention E, in particular transferred from the first excited triplet state T1(H) of the host compound H to the first excited triplet state T1(E) of the one or more organic molecules according to the invention E and/or from the first excited singlet state S1 (H) of the host compound H to the first excited singlet state S1(E) of the one or more organic molecules according to the invention E.

In a further embodiment, the emission layer EML comprises (or (essentially) consists of) a composition comprising or consisting of:

(i) 1-50% by weight, preferably 5-40% by weight, in particular 10-30% by weight, of one organic molecule according to the invention E;

(ii) 5-99% by weight, preferably 30-94.9% by weight, in particular 40-89% by weight, of one host compound H; and (iii) optionally 0-94% by weight, preferably 0.1-65% by weight, in particular 1-50% by weight, of at least one further host compound D with a structure differing from the structure of the molecules according to the invention; and (iv) optionally 0-94% by weight, preferably 0-65% by weight, in particular 0-50% by weight, of a solvent; and (v) optionally 0-30% by weight, in particular 0-20% by weight, preferably 0-5% by weight, of at least one further emitter molecule F with a structure differing from the structure of the molecules according to the invention.

In one embodiment, the host compound H has a highest occupied molecular orbital HOMO(H) having an energy $E^{HOMO}(H)$ in the range of from −5 to −6.5 eV and the at least one further host compound D has a highest occupied molecular orbital HOMO(D) having an energy $E^{HOMO}(D)$ wherein $E^{HOMO}(H)>E^{HOMO}(D)$.

In a further embodiment, the host compound H has a lowest unoccupied molecular orbital LUMO(H) having an energy $E^{LUMO}(H)$ and the at least one further host compound D has a lowest unoccupied molecular orbital LUMO(D) having an energy $E^{LUMO}(D)$, wherein $E^{LUMO}(H)>E^{LUMO}(D)$.

In one embodiment, the host compound H has a highest occupied molecular orbital HOMO(H) having an energy $E^{HOMO}(H)$ and a lowest unoccupied molecular orbital LUMO(H) having an energy $E^{LUMO}(H)$, and the at least one further host compound D has a highest occupied molecular orbital HOMO(D) having an energy $E^{HOMO}(D)$ and a lowest unoccupied molecular orbital LUMO(D) having an energy $E^{LUMO}(D)$ the organic molecule according to the invention E has a highest occupied molecular orbital HOMO(E) having an energy $E^{HOMO}(E)$ and a lowest unoccupied molecular orbital LUMO(E) having an energy $E^{LUMO}(E)$, wherein $E^{HOMO}(H)>E^{HOMO}(D)$ and the difference between the energy level of the highest occupied molecular orbital HOMO(E) of the organic molecule according to the invention E ($E^{HOMO}(E)$) and the energy level of the highest occupied molecular orbital HOMO(H) of the host compound H ($E^{HOMO}(H)$) is between −0.5 eV and 0.5 eV, more preferably between −0.3 eV and 0.3 eV, even more preferably between −0.2 eV and 0.2 eV or even between −0.1 eV and 0.1 eV; and $E^{LUMO}(H)>E^{LUMO}(D)$ and the difference between the energy level of the lowest unoccupied molecular orbital LUMO(E) of the organic molecule according to the invention E ($E^{LUMO}(E)$) and the lowest unoccupied molecular orbital LUMO(D) of the at least one further host compound D ($E^{LUMO}(D)$) is between −0.5 eV and 0.5 eV, more preferably between −0.3 eV and 0.3 eV, even more preferably between −0.2 eV and 0.2 eV or even between −0.1 eV and 0.1 eV.

In a further aspect, the invention relates to a light-emitting device comprising an organic molecule or a composition of the type described here, more particularly in the form of a device selected from the group consisting of organic light-emitting diode (OLED), light-emitting electrochemical cell, OLED sensor, more particularly gas and vapour sensors not hermetically externally shielded, organic diode, organic solar cell, organic transistor, organic field-effect transistor, organic laser and down-conversion element.

In a preferred embodiment, the organic light-emitting device is a device selected from the group consisting of an organic light emitting diode (OLED), a light emitting electrochemical cell (LEC), and a light-emitting transistor.

In one embodiment of the light-emitting device of the invention, an interlayer of the light-emitting device may include the organic molecule according to the invention E.

In one embodiment of the light-emitting device of the invention, an emission layer EML of the light-emitting device may include the organic molecule according to the invention E.

In one embodiment of the light-emitting device of the invention, the organic molecule according to the invention E is used as emission material in a emission layer EML.

In one embodiment of the light-emitting device of the invention, the organic molecule according to the invention E is used as host material in a emission layer EML.

In one embodiment of the light-emitting device of the invention the emission layer EML consists of the composition according to the invention described here.

Exemplarily, when the organic light-emitting device is an OLED, it may exhibit the following layer structure:

1. substrate
2. first electrode
3. hole injection layer, HIL
4. hole transport layer, HTL
5. electron blocking layer, EBL
6. emission layer, EML
7. hole blocking layer, HBL
8. electron transport layer, ETL
9. electron injection layer, EIL
10. second electrode, wherein the OLED comprises each layer only optionally, different layers may be merged and the OLED may comprise more than one layer of each layer type defined above.

Furthermore, the organic light-emitting device may optionally comprise one or more protective layers protecting the device from damaging exposure to harmful species in the environment including, exemplarily moisture, vapor and/or gases.

In one embodiment of the invention, the organic light-emitting device is an OLED, which exhibits the following inverted layer structure:

1. substrate
2. second electrode
3. electron injection layer, EIL 4. electron transport layer, ETL
5. hole blocking layer, HBL
6. emission layer, B
7. electron blocking layer, EBL
8. hole transport layer, HTL
9. hole injection layer, HIL
10. first electrode Wherein the OLED with an inverted layer structure comprises each layer only optionally, different layers may be merged and the OLED may comprise more than one layer of each layer types defined above.

In one embodiment of the invention, the organic light-emitting device is an OLED, which may exhibit stacked architecture. In this architecture, contrary to the typical arrangement, where the OLEDs are placed side by side, the individual units are stacked on top of each other. Blended light may be generated with OLEDs exhibiting a stacked architecture, in particular white light may be generated by stacking blue, green and red OLEDs. Furthermore, the OLED exhibiting a stacked architecture may optionally comprise a charge generation layer (CGL), which is typically located between two OLED subunits and typically consists of a n-doped and p-doped layer with the n-doped layer of one CGL being typically located closer to the first electrode.

In one embodiment of the invention, the organic light-emitting device is an OLED, which comprises two or more emission layers between anode and cathode. In particular, this so-called tandem OLED comprises three emission layers, wherein one emission layer emits red light, one emission layer emits green light and one emission layer emits blue light, and optionally may comprise further layers such as charge generation layers, blocking or transporting layers between the individual emission layers. In a further embodiment, the emission layers are adjacently stacked. In a further embodiment, the tandem OLED comprises a charge generation layer between each two emission layers. In addition, adjacent emission layers or emission layers separated by a charge generation layer may be merged.

The wording "(interlayer and/or capping layer) includes an organic molecule" as used herein may be understood as "(interlayer and/or capping layer) may include one kind of organic molecule represented by Formula I or two different kinds of organic molecules, each represented by Formula I."

For example, the interlayer and/or capping layer may include Example 1 only as the organic molecule. In this regard, Example 1 may be present in the emission layer of the light-emitting device. In one or more embodiments, the interlayer may include, as the organic molecule, Example 1 and Example 2. In this regard, Example 1 and Example 2 may be present in the same layer (for example, both Example 1 and Example 2 may be present in the emission layer), or may be present in different layers (for example, Example 1 may be present in the emission layer, and Example 2 may be present in the electron transport region).

The term "interlayer" as used herein refers to a single layer and/or all of a plurality of layers between the first electrode and the second electrode of the light-emitting device.

Another aspect of the present disclosure provides an electronic apparatus including the light-emitting device. The electronic apparatus may further include a thin-film transistor. For example, the electronic apparatus may further include a thin-film transistor including a source electrode and a drain electrode, wherein the first electrode of the light-emitting device may be electrically connected to the source electrode or the drain electrode. In an embodiment, the electronic apparatus may further include a color filter, a color conversion layer, a touch screen layer, a polarizing layer, or any combination thereof. The electronic apparatus may be the same as described herein.

The substrate may be formed by any material or composition of materials. Most frequently, glass slides are used as substrates. Alternatively, thin metal layers (e.g., copper, gold, silver or aluminum films) or plastic films or slides may be used. This may allow a higher degree of flexibility. The first electrode is mostly composed of materials allowing to obtain an (essentially) transparent film. As at least one of both electrodes should be (essentially) transparent in order to allow light emission from the OLED, either the first electrode or the second electrode is transparent. Preferably, the first electrode comprises a large content or even consists of transparent conductive oxides (TCOs). Such first electrode may exemplarily comprise indium tin oxide, aluminum zinc oxide, fluorine doped tin oxide, indium zinc oxide, PbO, SnO, zirconium oxide, molybdenum oxide, vanadium oxide, wolfram oxide, graphite, doped Si, doped Ge, doped GaAs, doped polyaniline, doped polypyrrol and/or doped polythiophene.

Figure 4:
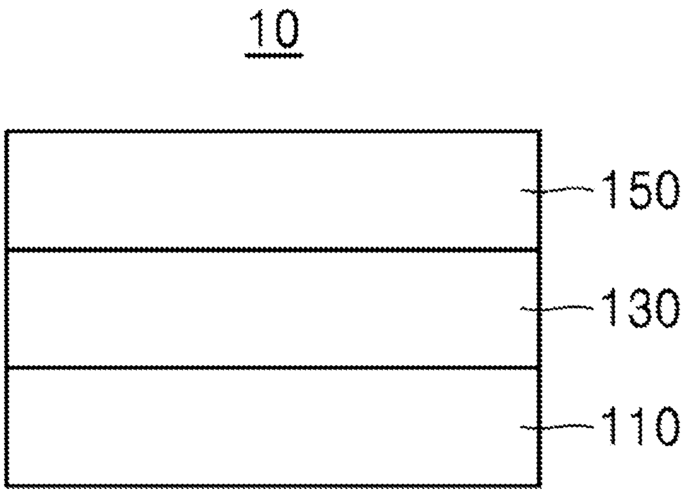
FIG. 4 is a schematic cross-sectional view of a light-emitting device 10 according to an embodiment.

FIG. 4 is a schematic cross-sectional view of a light-emitting device 10 according to an embodiment. The light-emitting device 10 includes a first electrode 110, an interlayer 130, and a second electrode 150.

Hereinafter, the structure of the light-emitting device 10 according to an embodiment and a method of manufacturing the light-emitting device 10 will be described with reference to FIG. 4.

[First Electrode 110]

In FIG. 4, a substrate may be additionally arranged under the first electrode 110 or on the second electrode 150. In an embodiment, as the substrate, a glass substrate or a plastic substrate may be used. In one or more embodiments, the substrate may be a flexible substrate, and for example, may include plastics with excellent heat resistance and durability, such as polyimide, polyethylene terephthalate (PET), polycarbonate, polyethylene napthalate, polyarylate (PAR), polyetherimide, or any combination thereof.

The first electrode 110 may be formed by, for example, depositing or sputtering a material for forming the first electrode 110 on the substrate. When the first electrode 110 is an anode, a material for forming the first electrode 110 may be a high-work function material that facilitates injection of holes.

The first electrode 110 may be a reflective electrode, a semi-transmissive electrode, or a transmissive electrode. In an embodiment, when the first electrode 110 is a transmissive electrode, a material for forming the first electrode 110 may include indium tin oxide (ITO), indium zinc oxide (IZO), tin oxide ($SnO_2$), zinc oxide (ZnO), or any combination thereof. In one or more embodiments, when the first electrode 110 is a semi-transmissive electrode or a reflective electrode, a material for forming the first electrode 110 may include magnesium (Mg), silver (Ag), aluminum (Al), aluminum-lithium (Al—Li), calcium (Ca), magnesium-indium (Mg—In), magnesium-silver (Mg—Ag), or any combination thereof.

The first electrode 110 may have a single layer structure consisting of a single layer or a multi-layer structure including a plurality of layers. For example, the first electrode 110 may have a three-layer structure of ITO/Ag/ITO.

Particularly preferably, the first electrode 110 (essentially) consists of indium tin oxide (ITO) (e.g., $(InO_3)0.9(SnO_2)0.1$). The roughness of the first electrode 110 caused by the transparent conductive oxides (TCOs) may be compensated by using a hole injection layer (HIL). Further, the HIL may facilitate the injection of quasi charge carriers (i.e., holes) in that the transport of the quasi charge carriers from the TCO to the hole transport layer (HTL) is facilitated. The hole injection layer (HIL) may comprise poly-3,4-ethylendioxy thiophene (PEDOT), polystyrene sulfonate (PSS), $MoO_2$, $V_2O_5$, CuPC or CuI, in particular a mixture of PEDOT and PSS. The hole injection layer (HIL) may also prevent the diffusion of metals from the first electrode 110 into the hole transport layer (HTL). The HIL may exemplarily comprise PEDOT:PSS (poly-3,4-ethylendioxy thiophene:polystyrene sulfonate), PEDOT (poly-3,4-ethylendioxy thiophene), mMTDATA (4,4',4''-tris[phenyl(m-tolyl)amino]triphenylamine), Spiro-TAD (2,2',7,7'-tetrakis(n,n-diphenylamino)-9,9'-spirobifluorene), DNTPD (N1,N1'-(biphenyl-4,4'-diyl)bis(N1-phenyl-N4,N4-di-m-tolylbenzene-1,4-diamine), NPB (N,N'-nis-(1-naphthalenyl)-N,N'-bis-phenyl-(1,1'-biphenyl)-4,4'-diamine), NPNPB (N,N'-diphenyl-N,N'-di-[4-(N,N-diphenyl-amino)phenyl]benzidine), MeO-TPD (N,N,N',N'-tetrakis(4-methoxyphenyl)benzidine), HAT-CN (1,4,5,8,9,11-hexaazatriphenylen-hexacarbonitrile) and/or Spiro-NPD (N,N'-diphenyl-N,N'-bis-(1-naphthyl)-9,9'-spirobifluorene-2,7-diamine).

[Interlayer 130]

The interlayer 130 is arranged on the first electrode 110. The interlayer 130 may include an emission layer.

The interlayer 130 may further include a hole transport region arranged between the first electrode 110 and the emission layer, and an electron transport region arranged between the emission layer and the second electrode 150.

In an embodiment, the interlayer 130 may further include, in addition to various organic materials, a metal-containing compound such as an organometallic compound, an inorganic material such as quantum dots, and the like.

In one or more embodiments, the interlayer 130 may include, i) two or more emitting units sequentially stacked between the first electrode 110 and the second electrode 150, and ii) a charge generation layer between the two or more emitting units. When the interlayer 130 includes the two or more emitting units and the charge generation layer, the light-emitting device 10 may be a tandem light-emitting device.

[Hole Transport Region in Interlayer 130]

The hole transport region may have: i) a single layer structure consisting of a single layer consisting of a single material, ii) a single layer structure consisting of a single layer consisting of multiple materials that are different from each other, or iii) a multi-layer structure including multiple layers including different materials.

The hole transport region may include a hole injection layer, a hole transport layer, an emission auxiliary layer, an electron blocking layer, or any combination thereof.

For example, the hole transport region may have a multi-layer structure including a hole injection layer/hole transport layer structure, a hole injection layer/hole transport layer/emission auxiliary layer structure, a hole injection layer/emission auxiliary layer structure, a hole transport layer/emission auxiliary layer structure, or a hole injection layer/hole transport layer/electron blocking layer structure, wherein constituent layers of each structure are stacked sequentially from the first electrode 110.

The hole transport region may include a compound represented by Formula 201, a compound represented by Formula 202, or any combination thereof:

Formula 201

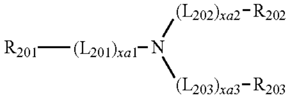

Formula 202

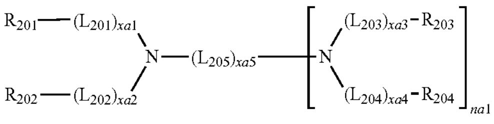

wherein, in Formulae 201 and 202, $L_{201}$ to $L_{204}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $L_{205}$ may be *—O—*', *—S—*', *—N($Q_{201}$)-*', a $C_1$-$C_{20}$ alkylene group unsubstituted or substituted with at least one $R_{10a}$, a $C_2$-$C_{20}$ alkenylene group unsubstituted or substituted with at least one $R_{10a}$, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$, xa1 to xa4 may each independently be an integer from 0 to 5, xa5 may be an integer from 1 to 10, $R_{201}$ to $R_{204}$ and $Q_{201}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $R_{201}$ and $R_{202}$ may optionally be bonded to each other via a single bond, a $C_1$-$C_5$ alkylene group unsubstituted or substituted with at least one $R_{10a}$, or a $C_2$-$C_5$ alkenylene group unsubstituted or substituted with at least one $R_{10a}$, to form a $C_8$-$C_{60}$ polycyclic group (for example, a carbazole group, etc.) unsubstituted or substituted with at least one $R_{10a}$ (for example, Compound HT16, etc.), $R_{203}$ and $R_{204}$ may optionally be bonded to each other via a single bond, a $C_1$-$C_5$ alkylene group unsubstituted or substituted with at least one $R_{10a}$, or a $C_2$-$C_5$ alkenylene group unsubstituted or substituted with at least one $R_{10a}$, to form a $C_8$-$C_{60}$ polycyclic group unsubstituted or substituted with at least one $R_{10a}$, and na1 may be an integer from 1 to 4.

For example, each of Formulae 201 and 202 may include at least one of groups represented by Formulae CY201 to CY217:

CY201

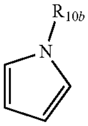

CY202

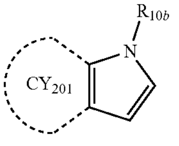

-continued

CY203

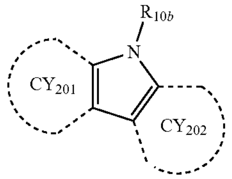

CY204

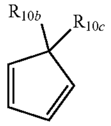

CY205

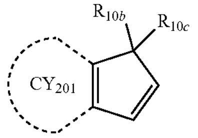

CY206

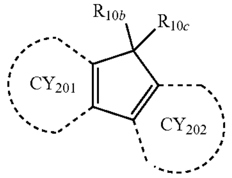

CY207

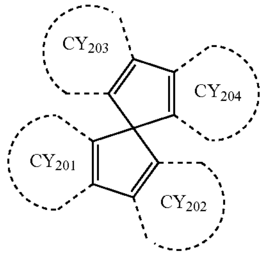

CY208

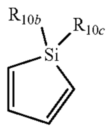

CY209

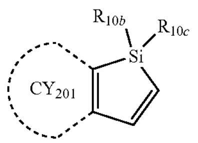

CY210

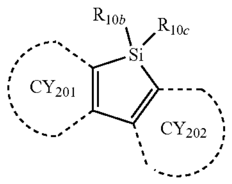

-continued

CY211

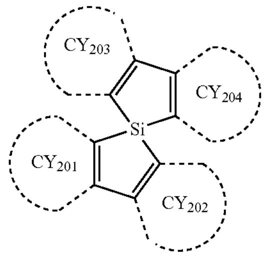

CY212

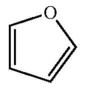

CY213

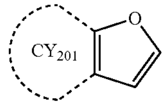

CY214

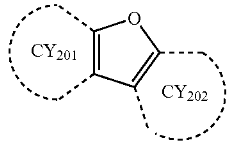

CY215

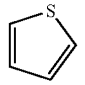

CY216

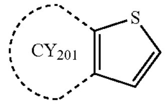

CY217

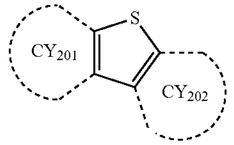

wherein, in Formulae CY201 to CY217, $R_{10b}$ and $R_{10c}$ may each be the same as described in connection with $R_{10a}$, ring $CY_{201}$ to ring $CY_{204}$ may each independently be a $C_3$-$C_{20}$ carbocyclic group or a $C_1$-$C_{20}$ heterocyclic group, and at least one hydrogen in Formulae CY201 to CY217 may be unsubstituted or substituted with $R_{10a}$.

In an embodiment, in Formulae CY201 to CY217, ring $CY_{201}$ to ring $CY_{204}$ may each independently be a benzene group, a naphthalene group, a phenanthrene group, or an anthracene group.

In one or more embodiments, each of Formulae 201 and 202 may include at least one of the groups represented by Formulae CY201 to CY203.

In one or more embodiments, Formula 201 may include at least one of the groups represented by Formulae CY201 to CY203 and at least one of the groups represented by Formulae CY204 to CY217.

In one or more embodiments, in Formula 201, xa1 may be 1, $R_{201}$ may be one of the groups represented by Formulae CY201 to CY203, xa2 may be 0, and $R_{202}$ may be one of the groups represented by Formulae CY204 to CY207.

In one or more embodiments, each of Formulae 201 and 202 may not include the groups represented by Formulae CY201 to CY203.

In one or more embodiments, each of Formulae 201 and 202 may not include the groups represented by Formulae CY201 to CY203, and may include at least one of the groups represented by Formulae CY204 to CY217.

In one or more embodiments, each of Formulae 201 and 202 may not include the groups represented by Formulae CY201 to CY217.

For example, the hole transport region may include one of Compounds HT1 to HT46, m-MTDATA, TDATA, 2-TNATA, NPB(NPD), β-NPB, TPD, Spiro-TPD, Spiro-NPB, methylated NPB, TAPC, HMTPD, 4,4',4"-tris(N-carbazolyl)triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), polyaniline/poly(4-styrenesulfonate) (PANI/PSS), or any combination thereof:

HT1

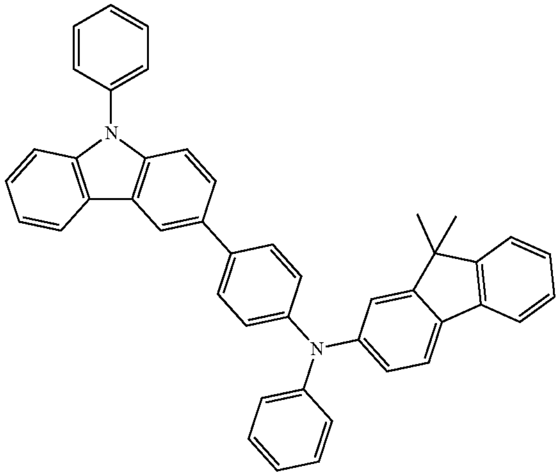

HT2

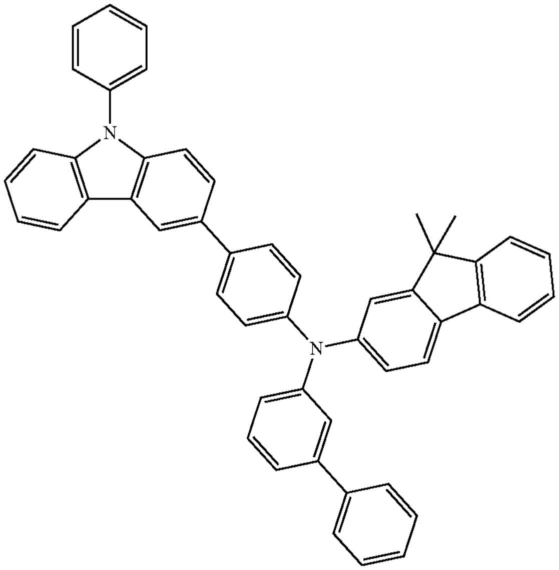

HT3

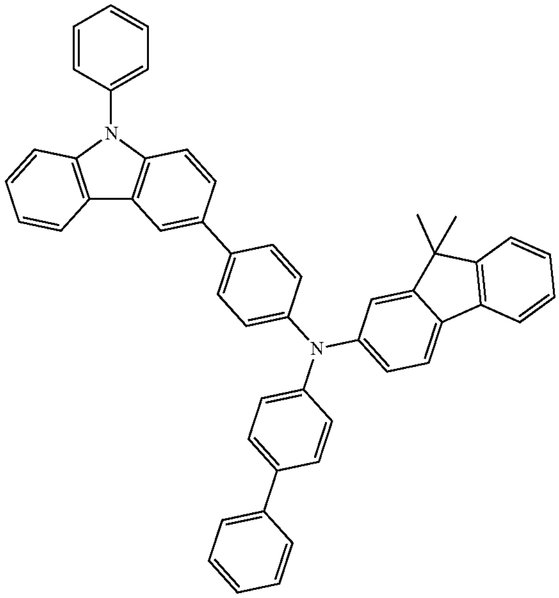

HT4

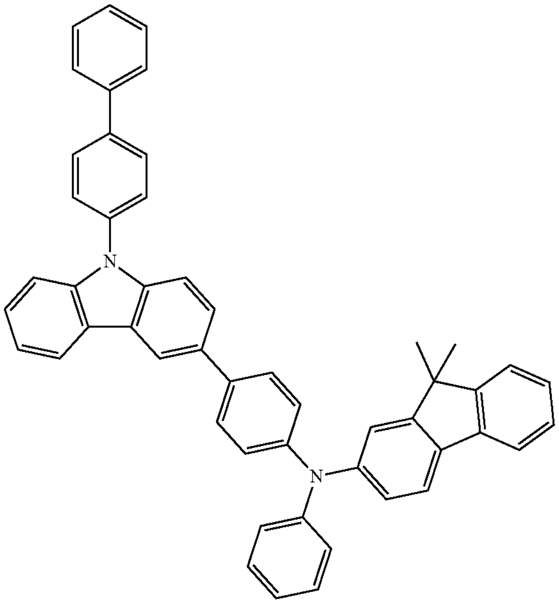

-continued
HT5
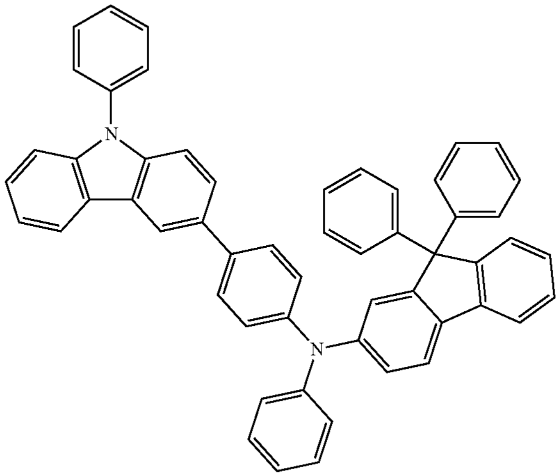
HT6
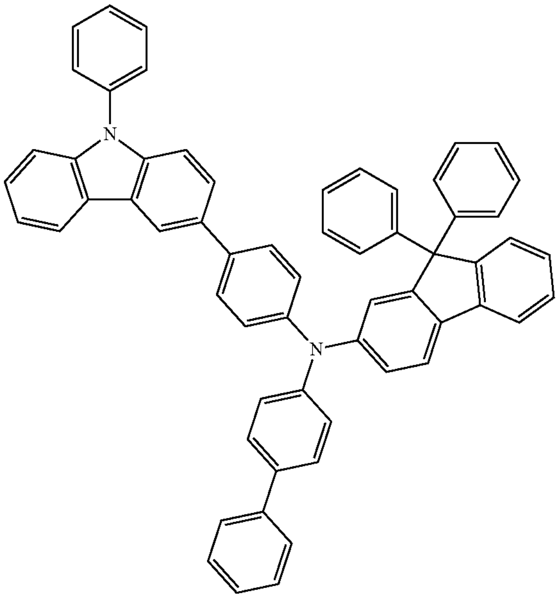
HT7
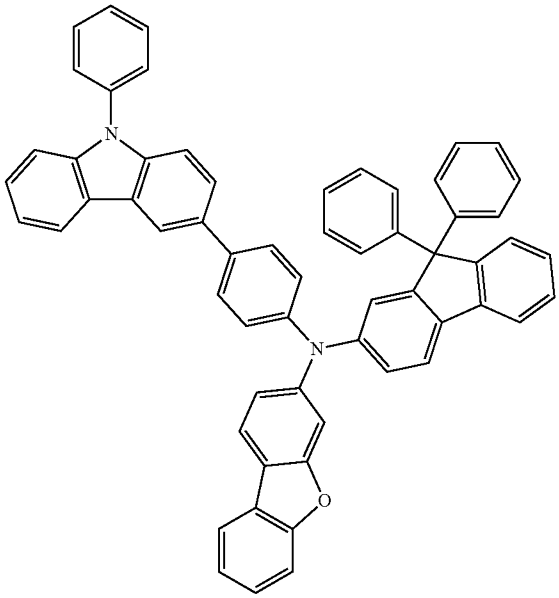
HT8
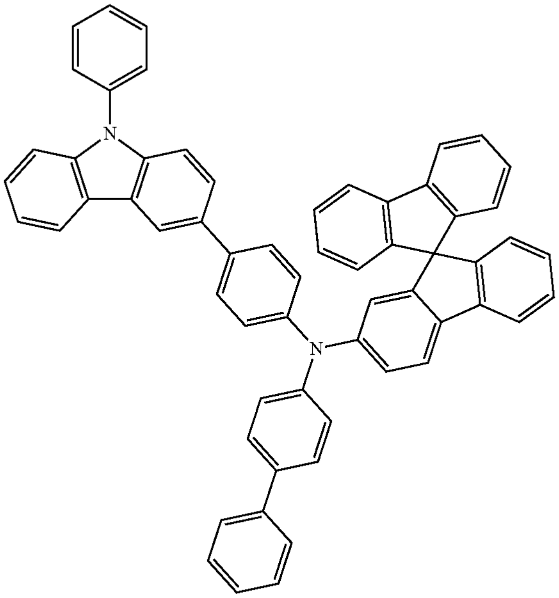

-continued
HT9
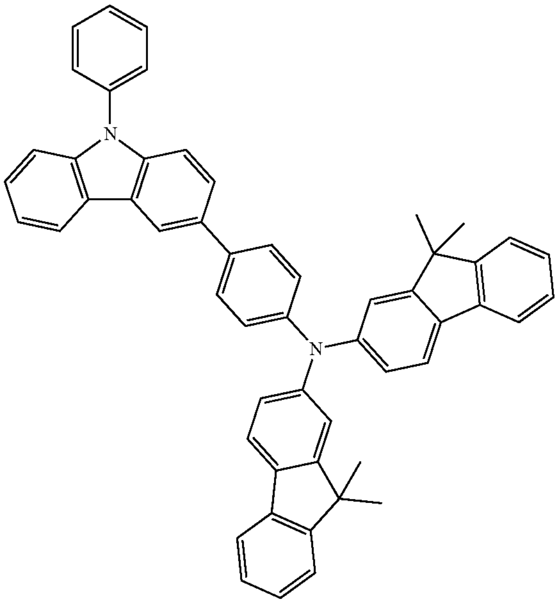
HT10
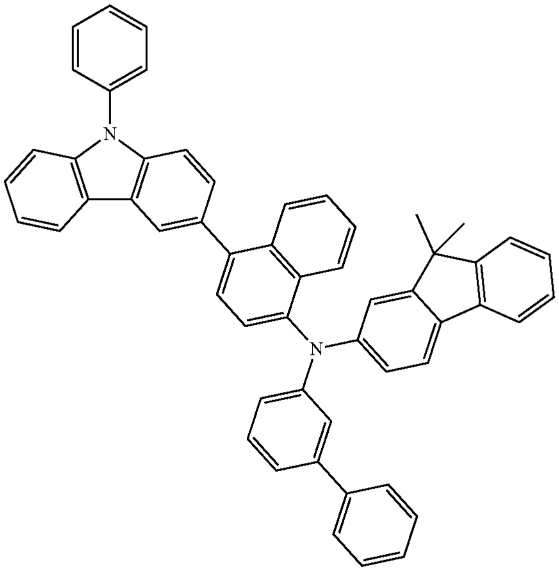
HT11
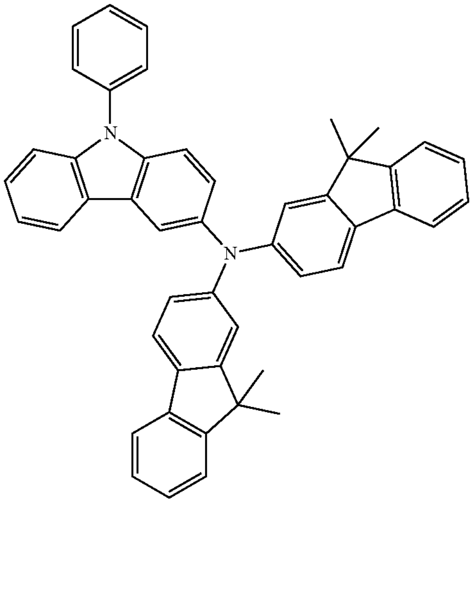
HT12
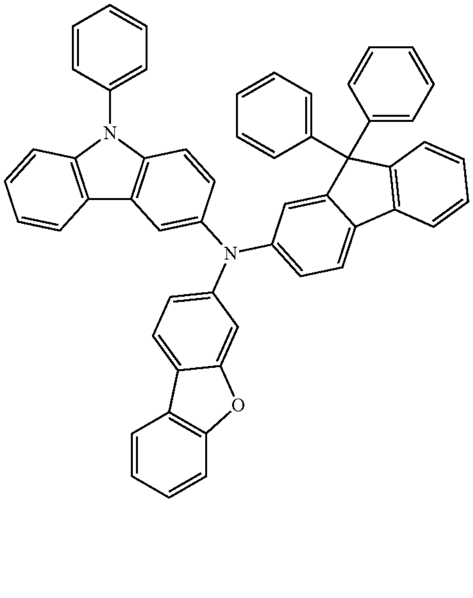

-continued
HT13
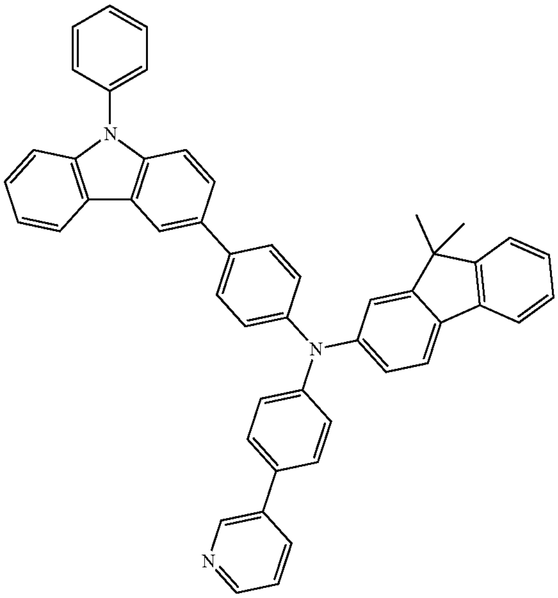
HT14
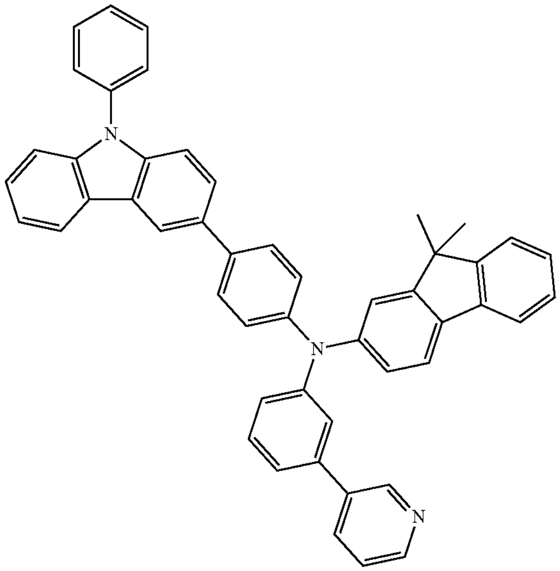
HT15
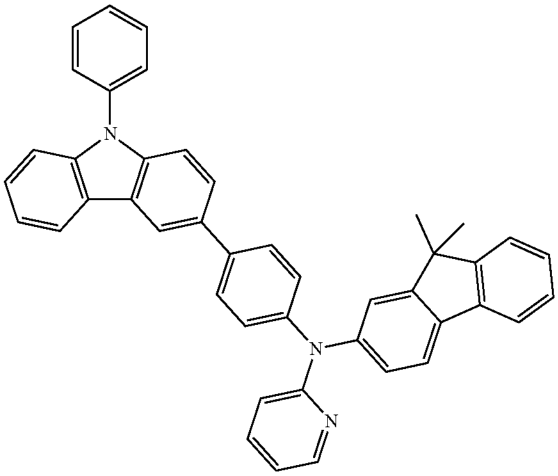
HT16
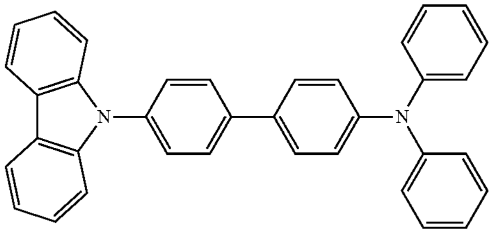
HT17
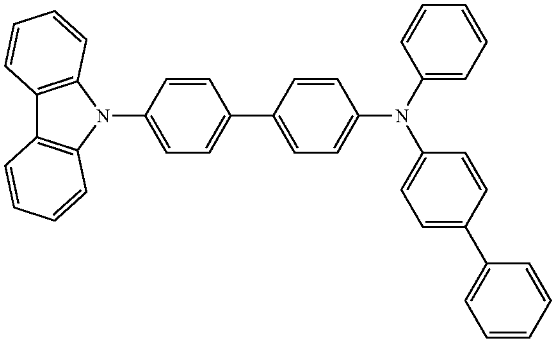
HT18
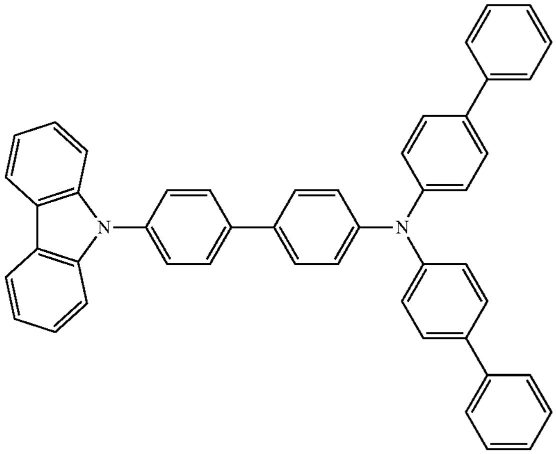

-continued
HT19
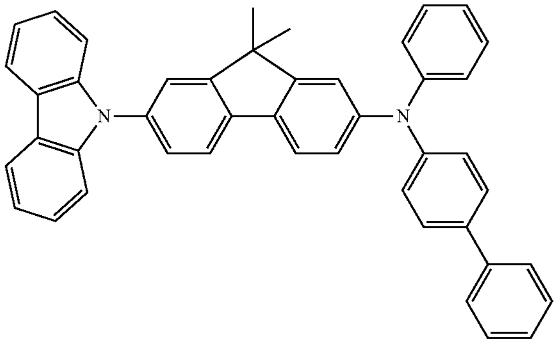
HT20
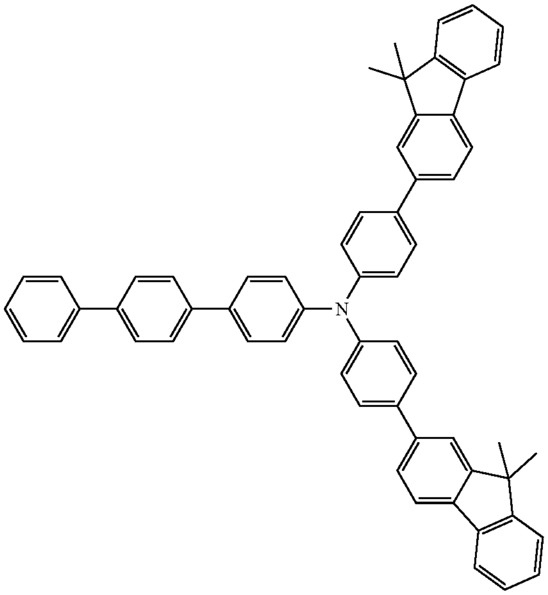
HT21
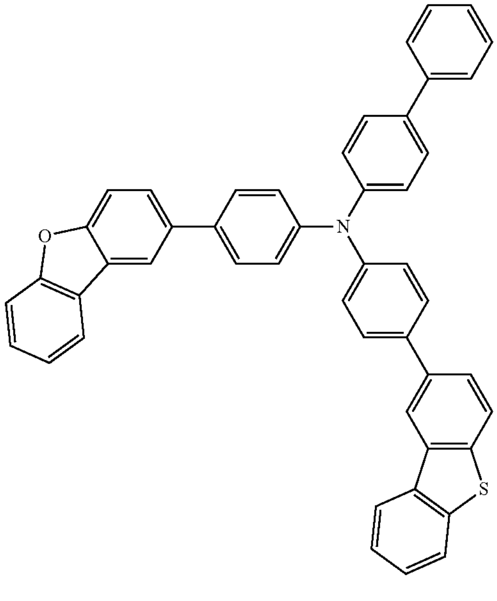
HT22
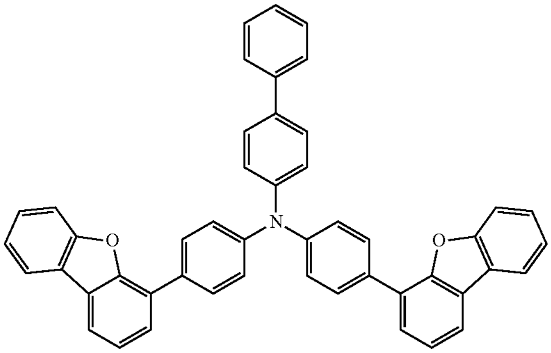

-continued
HT23
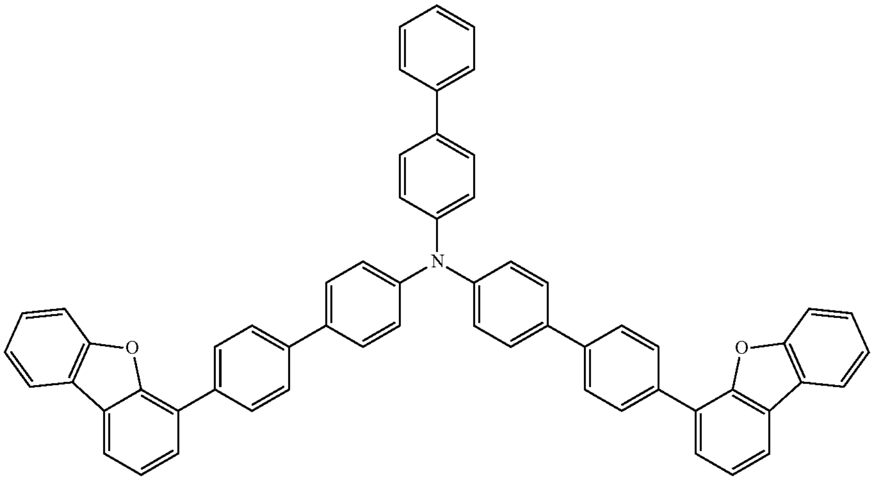
HT24
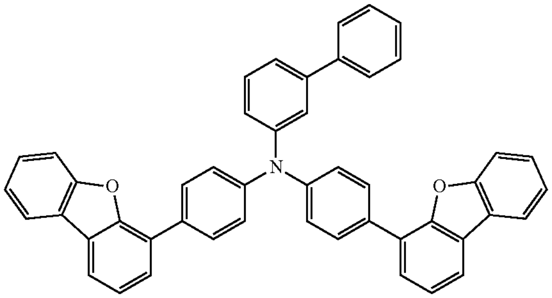
HT25
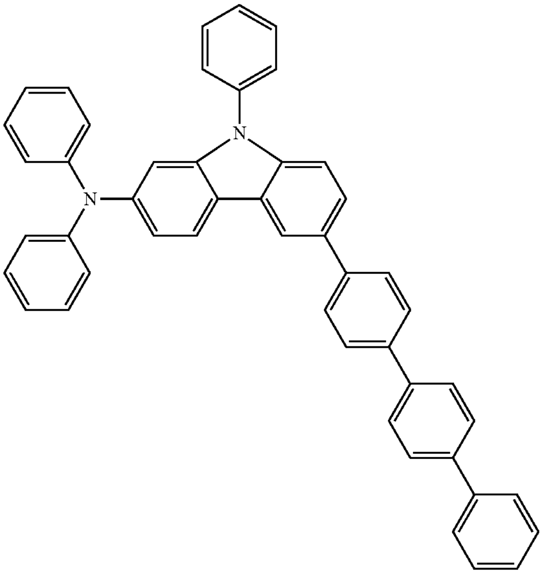
HT26
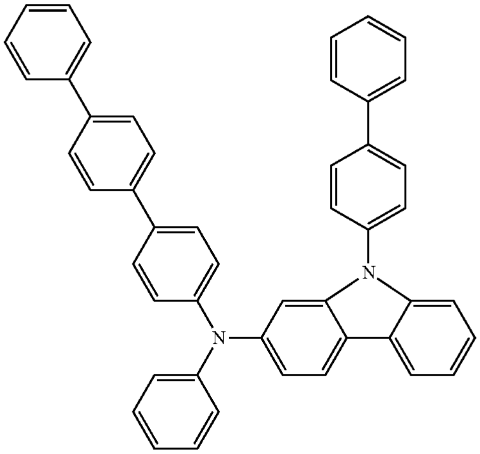
HT27
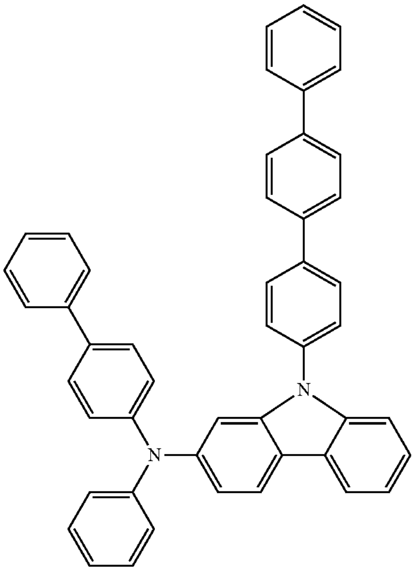

-continued
HT28
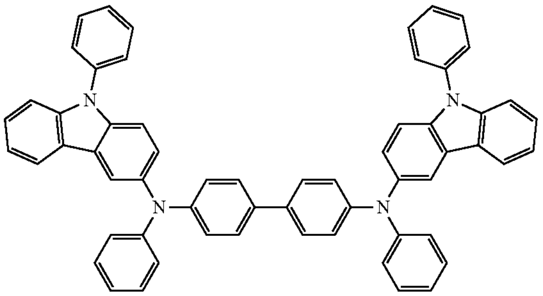
HT29
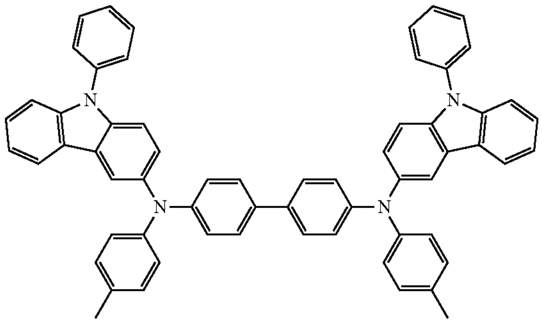
HT30
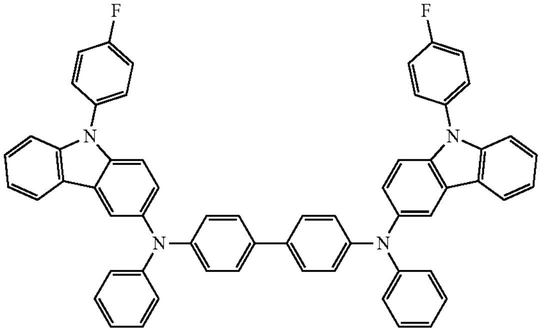
HT31
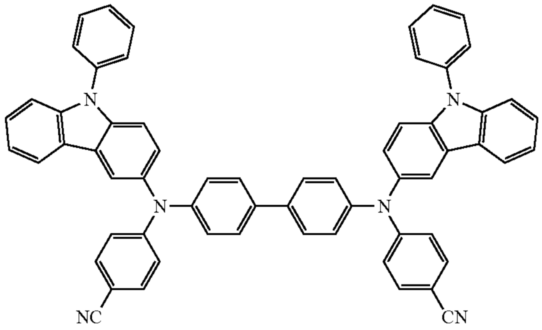
HT32
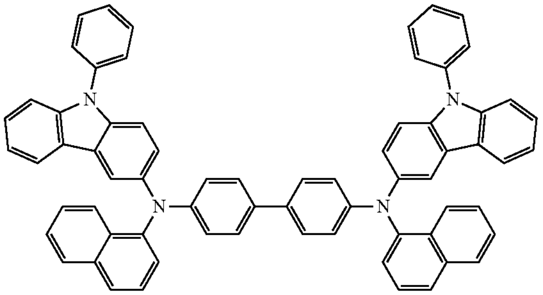
HT33
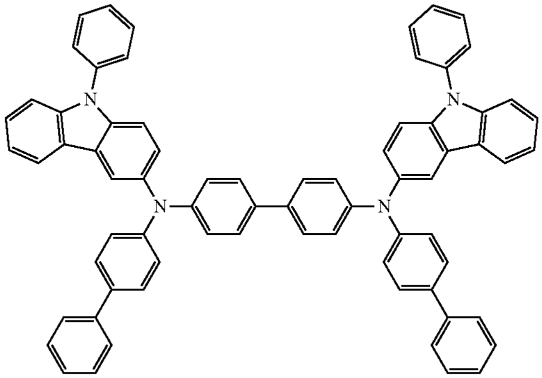
HT34
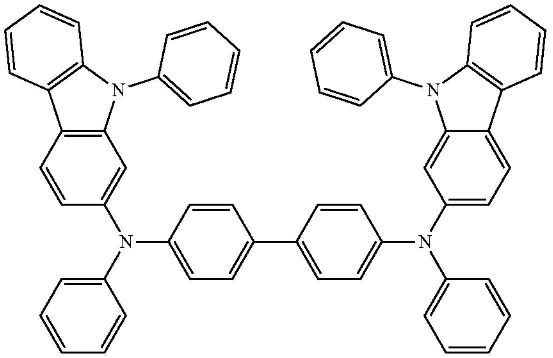
HT35
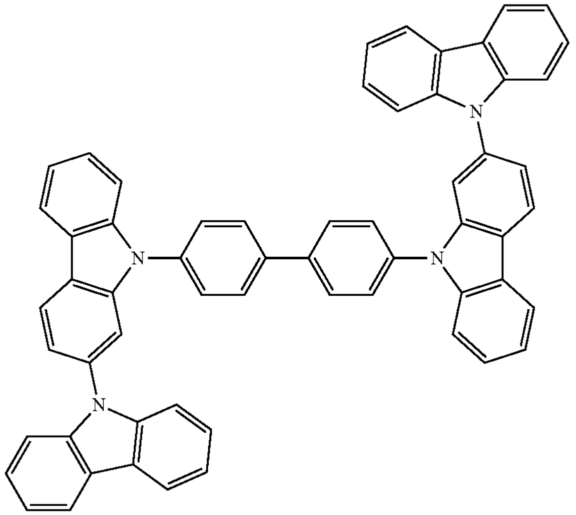

-continued
HT36
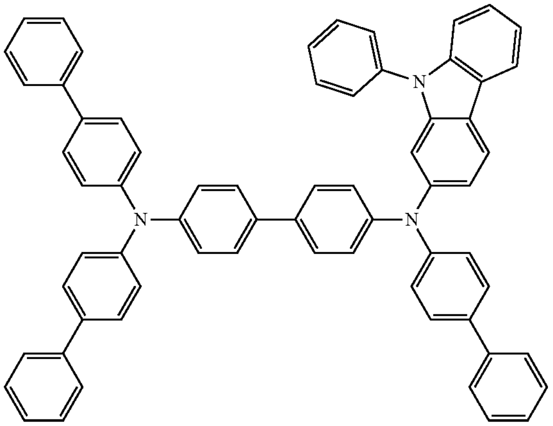
HT37
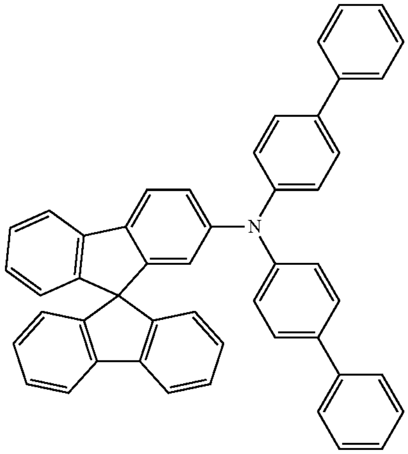
HT38
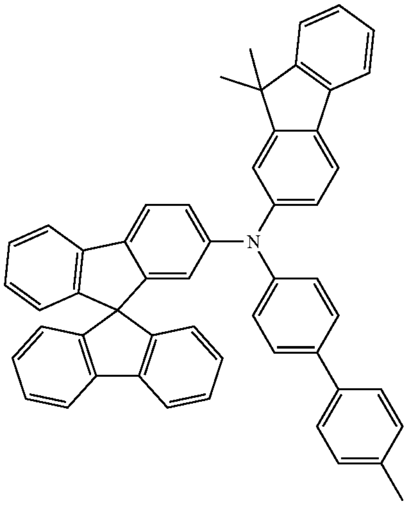
HT39
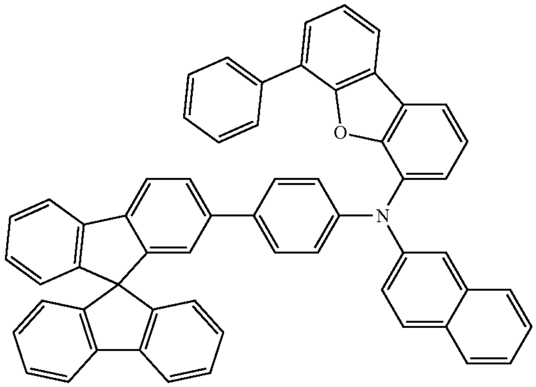
HT40
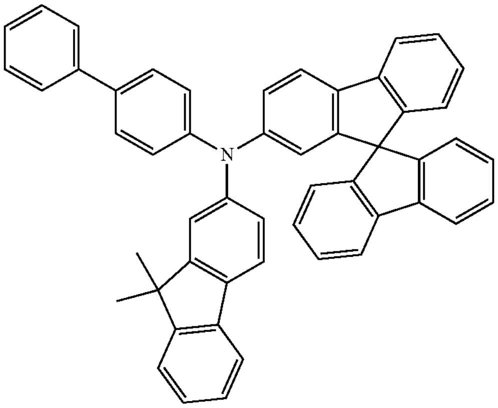
HT41
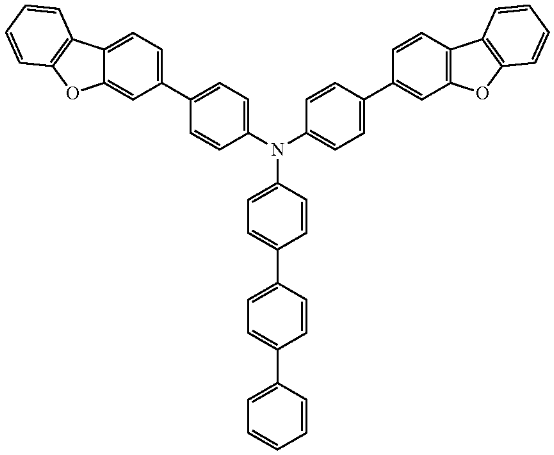

-continued
HT42
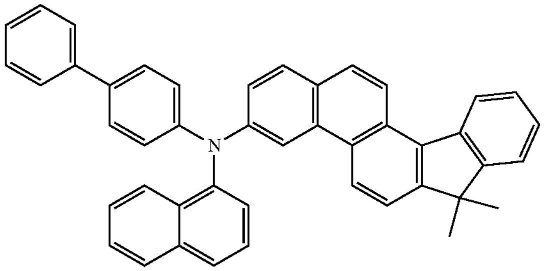
HT43
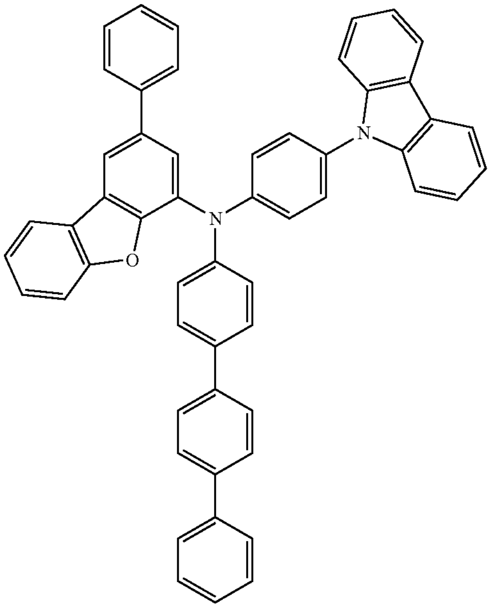
HT44
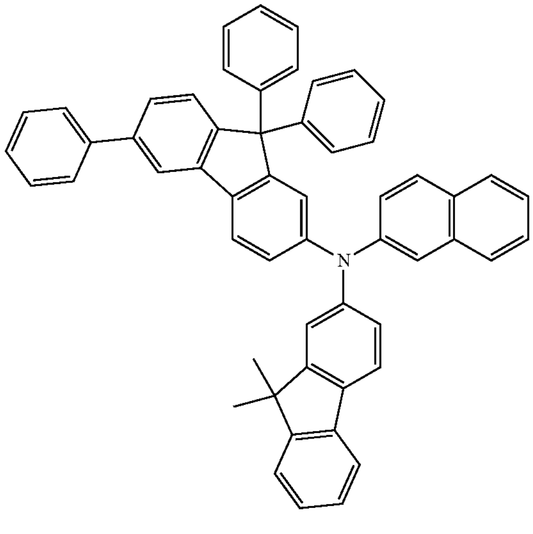
HT45
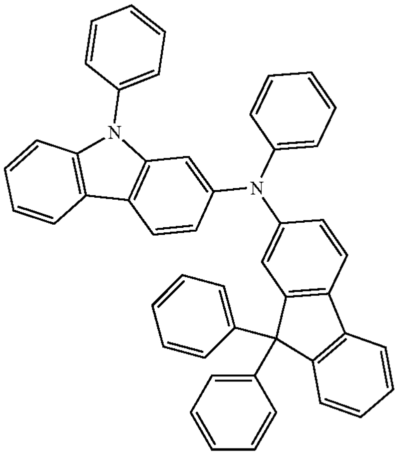

-continued
HT46
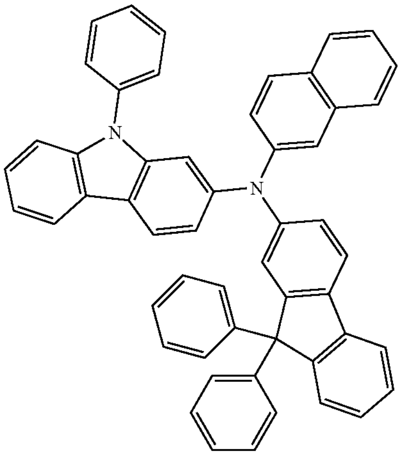
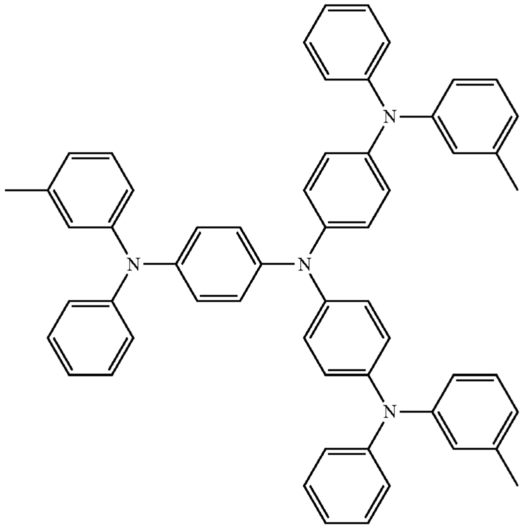
m-MTDATA
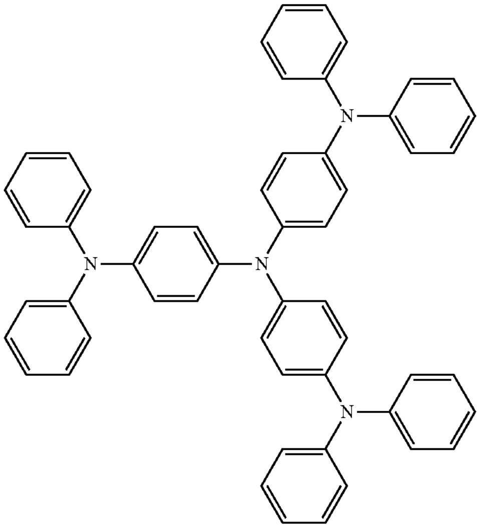
TDATA
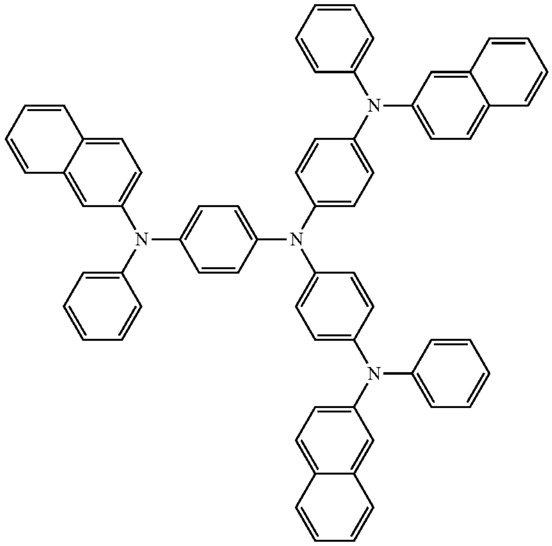
2-TNATA
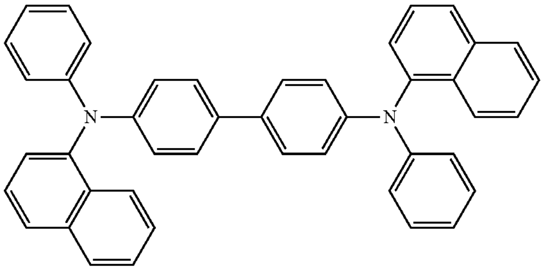
NPB
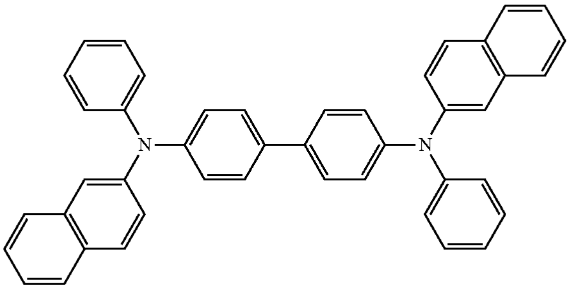
β-NPB -continued

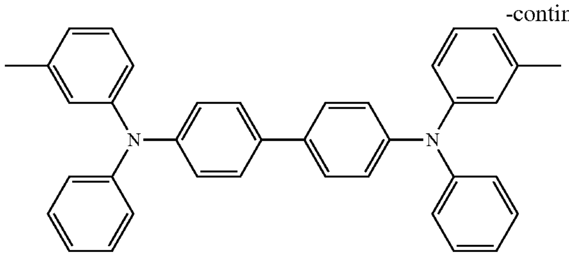

TPD

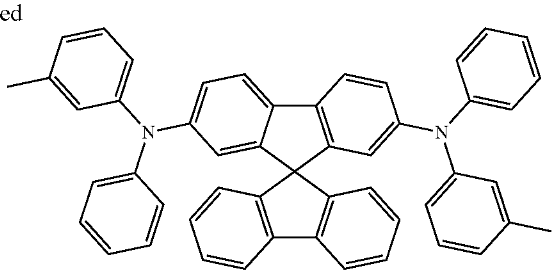

Spiro-TPD

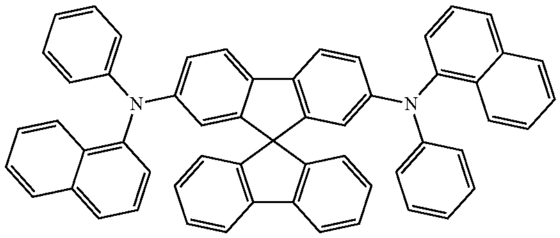

Spiro-NPB

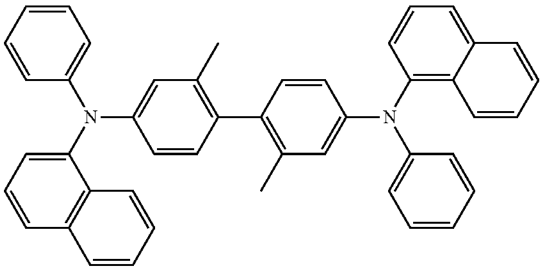

methylated-NPB

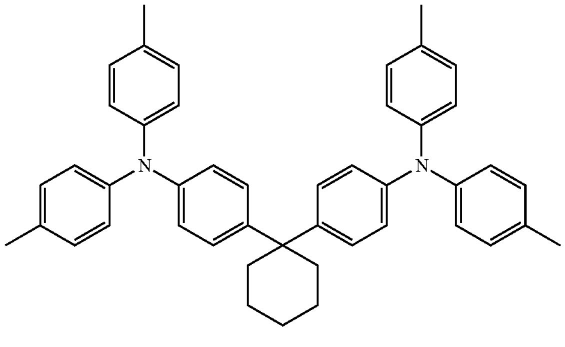

TAPC

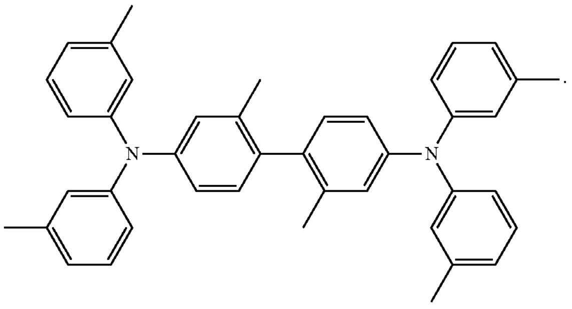

HMTPD

A thickness of the hole transport region may be in a range of about 50 Å to about 10,000 Å, for example, about 100 Å to about 4,000 Å. When the hole transport region includes a hole injection layer, a hole transport layer, or any combination thereof, a thickness of the hole injection layer may be in a range of about 100 Å to about 9,000 Å, for example, about 100 Å to about 1,000 Å, and a thickness of the hole transport layer may be in a range of about 50 Å to about 2,000 Å, for example, about 100 Å to about 1,500 Å. When the thicknesses of the hole transport region, the hole injection layer, and the hole transport layer are within these ranges, satisfactory hole transporting characteristics may be obtained without a substantial increase in driving voltage.

Adjacent to the first electrode or hole injection layer (HIL) typically a hole transport layer (HTL) is located. Herein, any hole transport compound may be used. Exemplarily, electron-rich heteroaromatic compounds such as triarylamines and/or carbazoles may be used as hole transport compound. The HTL may decrease the energy barrier between the first electrode and the emission layer EML. The hole transport layer (HTL) may also be an electron blocking layer (EBL). Preferably, hole transport compounds bear comparably high energy levels of their triplet states T1. Exemplarily the hole transport layer (HTL) may comprise a star-shaped heterocycle such as tris(4-carbazoyl-9-ylphenyl) amine (TCTA), poly-TPD (poly(4-butylphenyl-diphenyl-amine)), [alpha]-NPD (poly(4-butylphenyl-diphenyl-amine)), TAPC (4,4'-cyclohexyliden-bis[N,N-bis(4-methylphenyl)benzenamine]), 2-TNATA (4,4',4"-tris[2-naphthyl(phenyl)amino]triphenylamine), Spiro-TAD, DNTPD, NPB, NPNPB, MeO-TPD, HAT-CN and/or TrisPcz (9,9'-diphenyl-6-(9-phenyl-9H-carbazol-3-yl)-9H,9'H-3,3'-bicarbazole). In addition, the HTL may comprise a p-doped layer, which may be composed of an inorganic or organic dopant in an organic hole-transporting matrix. Transition metal oxides such as vanadium oxide, molybdenum oxide or tungsten oxide may exemplarily be used as inorganic dopant. Tetrafluorotetracyanoquinodimethane ($F_4$-TCNQ), copper-pentafluorobenzoate (Cu(I)pFBz) or transition metal complexes may exemplarily be used as organic dopant.

The emission auxiliary layer may increase light-emission efficiency by compensating for an optical resonance distance according to the wavelength of light emitted by the emission layer, and the electron blocking layer may block the leakage of electrons from the emission layer to the hole transport region. Materials that may be included in the hole transport region may be included in the auxiliary layer and the electron blocking layer EBL.

The EBL may exemplarily comprise mCP (1,3-bis(carbazol-9-yl)benzene), TCTA, 2-TNATA, mCBP (3,3-di(9H-carbazol-9-yl)biphenyl), tris-Pcz, CzSi (9-(4-tert-Butylphenyl)-3,6-bis(triphenylsilyl)-9H-carbazole), and/or DCB (N,N'-dicarbazolyl-1,4-dimethylbenzene).

[p-Dopant]

The hole transport region may further include, in addition to these materials, a charge-generation material for the improvement of conductive properties. The charge-generation material may be uniformly or non-uniformly dispersed in the hole transport region (for example, in the form of a single layer consisting of a charge-generation material).

The charge-generation material may be, for example, a p-dopant.

For example, the p-dopant may have a lowest unoccupied molecular orbital (LUMO) energy level of equal to or less than about −3.5 eV.

In an embodiment, the p-dopant may include a quinone derivative, a cyano group-containing compound, a compound including element EL1 and element EL2, or any combination thereof. Examples of the quinone derivative are TCNQ, F4-TCNQ, and the like.

Examples of the cyano group-containing compound are HAT-CN, a compound represented by Formula 221, and the like:

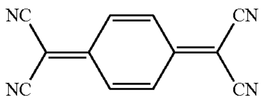

TCNQ

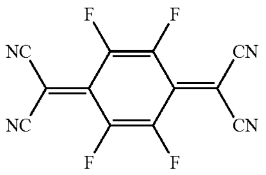

F4-TCNQ

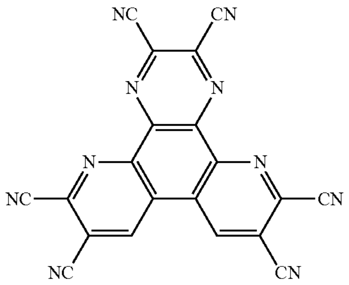

HAT-CN

Formula 221

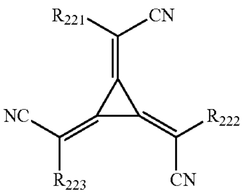

wherein, in Formula 221, $R_{221}$ to $R_{223}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, and at least one of $R_{221}$ to $R_{223}$ may each independently be a $C_3$-$C_{60}$ carbocyclic group or a $C_1$-$C_{60}$ heterocyclic group, each substituted with: a cyano group; —F; —Cl; —Br; —I; a $C_1$-$C_{20}$ alkyl group substituted with a cyano group, —F, —Cl, —Br, —I, or any combination thereof; or any combination thereof.

In the compound including element EL1 and element EL2, element EL1 may be metal, metalloid, or any combination thereof, and element EL2 may be non-metal, metalloid, or any combination thereof.

Examples of the metal are an alkali metal (for example, lithium (Li), sodium (Na), potassium (K), rubidium (Rb), cesium (Cs), etc.); alkaline earth metal (for example, beryllium (Be), magnesium (Mg), calcium (Ca), strontium (Sr), barium (Ba), etc.); transition metal (for example, titanium (Ti), zirconium (Zr), hafnium (Hf), vanadium (V), niobium (Nb), tantalum (Ta), chromium (Cr), molybdenum (Mo), tungsten (W), manganese (Mn), technetium (Tc), rhenium (Re), iron (Fe), ruthenium (Ru), osmium (Os), cobalt (Co), rhodium (Rh), iridium (Ir), nickel (Ni), palladium (Pd), platinum (Pt), copper (Cu), silver (Ag), gold (Au), etc.); post-transition metal (for example, zinc (Zn), indium (In), tin (Sn), etc.); lanthanide metal (for example, lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), lutetium (Lu), etc.); and the like.

Examples of the metalloid are silicon (Si), antimony (Sb), tellurium (Te), and the like.

Examples of the non-metal are oxygen (O), halogen (for example, F, Cl, Br, I, etc.), and the like.

Examples of the compound including element EL1 and element EL2 are metal oxide, metal halide (for example, metal fluoride, metal chloride, metal bromide, metal iodide, etc.), metalloid halide (for example, metalloid fluoride, metalloid chloride, metalloid bromide, metalloid iodide, etc.), metal telluride, or any combination thereof.

Examples of the metal oxide are tungsten oxide (for example, WO, $W_2O_3$, $WO_2$, $WO_3$, $W_2O_5$, etc.), vanadium oxide (for example, VO, $V_2O_3$, $VO_2$, $V_2O_5$, etc.), molybdenum oxide (MoO, $Mo_2O_3$, $MoO_2$, $MoO_3$, $Mo_2O_5$, etc.), rhenium oxide (for example, $ReO_3$, etc.), and the like.

Examples of the metal halide are alkali metal halide, alkaline earth metal halide, transition metal halide, post-transition metal halide, lanthanide metal halide, and the like.

Examples of the alkali metal halide are LiF, NaF, KF, RbF, CsF, LiCl, NaCl, KCl, RbCl, CsCl, LiBr, NaBr, KBr, RbBr, CsBr, LiI, NaI, KI, RbI, CsI, and the like.

Examples of the alkaline earth metal halide are $BeF_2$, $MgF_2$, $CaF_2$, $SrF_2$, $BaF_2$, $BeCl_2$, $MgCl_2$, $CaCl_2$), $SrCl_2$, $BaCl_2$, $BeBr_2$, $MgBr_2$, $CaBr_2$, $SrBr_2$, $BaBr_2$, $BeI_2$, $Mg_2$, $CaI_2$, $SrI_2$, $BaI_2$, and the like.

Examples of the transition metal halide are titanium halide (for example, $TiF_4$, $TiCl_4$, $TiBr_4$, $TiI_4$, etc.), zirconium halide (for example, $ZrF_4$, $ZrCl_4$, $ZrBr_4$, $ZrI_4$, etc.), hafnium halide (for example, $HfF_4$, $HfCl_4$, $HfBr_4$, $HfI_4$, etc.), vanadium halide (for example, $VF_3$, $VCl_3$, $VBr_3$, $VI_3$, etc.), niobium halide (for example, $NbF_3$, $NbCl_3$, $NbBr_3$, $NbI_3$, etc.), tantalum halide (for example, $TaF_3$, $TaCl_3$, $TaBr_3$, $TaI_3$, etc.), chromium halide (for example, $CrF_3$, $CrCl_3$, $CrBr_3$, $CrI_3$, etc.), molybdenum halide (for example, $MoF_3$, $MoCl_3$, $MoBr_3$, $MoI_3$, etc.), tungsten halide (for example, $WF_3$, $WCl_3$, $WBr_3$, $WI_3$, etc.), manganese halide (for example, $MnF_2$, $MnCl_2$, $MnBr_2$, $MnI_2$, etc.), technetium halide (for example, $TcF_2$, $TcCl_2$, $TcBr_2$, $TcI_2$, etc.), rhenium halide (for example, $ReF_2$, $ReCl_2$, $ReBr_2$, $ReI_2$, etc.), iron halide (for example, $FeF_2$, $FeCl_2$, $FeBr_2$, $FeI_2$, etc.), ruthenium halide (for example, $RuF_2$, $RuCl_2$, $RuBr_2$, $RuI_2$, etc.), osmium halide (for example, $OsF_2$, $OsCl_2$, $OsBr_2$, $OsI_2$, etc.), cobalt halide (for example, $CoF_2$, $CoCl_2$, $CoBr_2$, $CoI_2$, etc.), rhodium halide (for example, $RhF_2$, $RhCl_2$, $RhBr_2$, $RhI_2$, etc.), iridium halide (for example, $IrF_2$, $IrCl_2$, $IrBr_2$, $IrI_2$, etc.), nickel halide (for example, $NiF_2$, $NiCl_2$, $NiBr_2$, $NiI_2$, etc.), palladium halide (for example, $PdF_2$, $PdCl_2$, $PdBr_2$, $PdI_2$, etc.), platinum halide (for example, $PtF_2$, $PtC_2$, $PtBr_2$, $PtI_2$, etc.), copper halide (for example, CuF, CuCl, CuBr, CuI, etc.), silver halide (for example, AgF, AgCl, AgBr, AgI, etc.), gold halide (for example, AuF, AuCl, AuBr, AuI, etc.), and the like.

Examples of the post-transition metal halide are zinc halide (for example, $ZnF_2$, $ZnCl_2$, $ZnBr_2$, $ZnI_2$, etc.), indium halide (for example, $InI_3$, etc.), tin halide (for example, $SnI_2$, etc.), and the like.

Examples of the lanthanide metal halide are YbF, $YbF_2$, $YbF_3$, $SmF_3$, YbCl, $YbCl_2$, $YbCl_3$ $SmCl_3$, YbBr, $YbBr_2$, $YbBr_3$ $SmBr_3$, YbI, $YbI_2$, $YbI_3$, $SmI_3$, and the like.

Examples of the metalloid halide are antimony halide (for example, $SbCl_5$, etc.) and the like. Examples of the metal telluride are alkali metal telluride (for example, $Li_2Te$, a $na_2Te$, $K_2Te$, $Rb_2Te$, $Cs_2Te$, etc.), alkaline earth metal telluride (for example, BeTe, MgTe, CaTe, SrTe, BaTe, etc.), transition metal telluride (for example, $TiTe_2$, $ZrTe_2$, $HfTe_2$, $V_2Te_3$, $Nb_2Te_3$, $Ta_2Te_3$, $Cr_2Te_3$, $Mo_2Te_3$, $W_2Te_3$, MnTe, TcTe, ReTe, FeTe, RuTe, OsTe, CoTe, RhTe, IrTe, NiTe, PdTe, PtTe, $Cu_2Te$, CuTe, $Ag_2Te$, AgTe, $Au_2Te$, etc.), post-transition metal telluride (for example, ZnTe, etc.), lanthanide metal telluride (for example, LaTe, CeTe, PrTe, NdTe, PmTe, EuTe, GdTe, TbTe, DyTe, HoTe, ErTe, TmTe, YbTe, LuTe, etc.), and the like.

[Emission Layer in Interlayer 130]

When the light-emitting device 10 is a full-color light-emitting device, the emission layer may be patterned into a red emission layer, a green emission layer, and/or a blue emission layer, according to a sub-pixel. In an embodiment, the emission layer may have a stacked structure of two or more layers of a red emission layer, a green emission layer, and a blue emission layer, in which the two or more layers contact each other or are separated from each other to emit white light. In one or more embodiments, the emission layer may include two or more materials of a red light-emitting material, a green light-emitting material, and a blue light-emitting material, in which the two or more materials are mixed with each other in a single layer to emit white light.

The emission layer may include a host and a dopant. The dopant may include a phosphorescent dopant, a fluorescent dopant, or any combination thereof.

In the emission layer, an amount of the dopant may be in a range of about 0.01 part by weight to about 15 parts by weight based on 100 parts by weight of the host.

In one or more embodiments, the emission layer may include a quantum dot.

In one or more embodiments, the emission layer may include a delayed fluorescence material.

The delayed fluorescence material may act as a host or a dopant in the emission layer.

A thickness of the emission layer may be in a range of about 100 Å to about 1,000 Å, for example, about 200 Å to about 600 Å. When the thickness of the emission layer is within these ranges, excellent luminescence characteristics may be obtained without a substantial increase in driving voltage.

Adjacent to the hole transport layer (HTL), typically, the emission layer EML is located. The emission layer EML comprises at least one light emitting molecule. Particularly, the EML comprises at least one light emitting molecule according to the invention E. In one embodiment, the emission layer comprises only the organic molecules according to the invention E. Typically, the EML additionally comprises one or more host materials H. Exemplarily, the host material H is selected from CBP (4,4'-Bis-(N-carbazolyl)-biphenyl), mCP, mCBP Sif87 (dibenzo[b,d]thiophen-2-yltriphenylsilane), CzSi, Sif88 (dibenzo[b,d]thiophen-2-yl)diphenylsilane), DPEPO (bis[2-(diphenylphosphino)phenyl] ether oxide), 9-[3-(dibenzofuran-2-yl)phenyl]-9H-carbazole, 9-[3-(dibenzofuran-2-yl)phenyl]-9H-carbazole, 9-[3-(dibenzothiophen-2-yl)phenyl]-9H-carbazole, 9-[3,5-bis(2-dibenzofuranyl)phenyl]-9H-carbazole, 9-[3,5-bis(2-dibenzothiophenyl)phenyl]-9H-carbazole, T2T (2,4,6-tris(biphenyl-3-yl)-1,3,5-triazine), T3T (2,4,6-tris(triphenyl-3-yl)-1,3,5-triazine) and/or TST (2,4,6-tris(9,9'-spirobifluorene-2-yl)-1,3,5-triazine). The host material H typically should be selected to exhibit first triplet (T1) and first singlet (S1) energy levels, which are energetically higher than the first triplet (T1) and first singlet (S1) energy levels of the organic molecule.

In one embodiment of the invention, the EML comprises a so-called mixed-host system with at least one hole-dominant host and one electron-dominant host. In a particular embodiment, the EML comprises exactly one light emitting molecule according to the invention E and a mixed-host system comprising T2T as electron-dominant host and a host selected from CBP, mCP, mCBP, 9-[3-(dibenzofuran-2-yl)phenyl]-9H-carbazole, 9-[3-(dibenzofuran-2-yl)phenyl]-9H-carbazole, 9-[3-(dibenzothiophen-2-yl)phenyl]-9H-carbazole, 9-[3,5-bis(2-dibenzofuranyl)phenyl]-9H-carbazole and 9-[3,5-bis(2-dibenzothiophenyl)phenyl]-9H-carbazole as hole-dominant host. In a further embodiment the EML comprises 50-80% by weight, preferably 60-75% by weight of a host selected from CBP, mCP, mCBP, 9-[3-(dibenzofuran-2-yl)phenyl]-9H-carbazole, 9-[3-(dibenzofuran-2-yl)phenyl]-9H-carbazole, 9-[3-(dibenzothiophen-2-yl)phenyl]-9H-carbazole, 9-[3,5-bis(2-dibenzofuranyl)phenyl]-9H-carbazole and 9-[3,5-bis(2-dibenzothiophenyl)phenyl]-9H-carbazole; 10-45% by weight, preferably 15-30% by weight of T2T and 5-40% by weight, preferably 10-30% by weight of light emitting molecule according to the invention.

In order to modify the emission spectrum and/or the absorption spectrum of the emission layer EML further, the emission layer EML may further comprise one or more further emitter molecules F. Such an emitter molecule F may be any emitter molecule known in the art. Preferably such an emitter molecule F is a molecule with a structure differing from the structure of the molecules according to the invention E. The emitter molecule F may optionally be a TADF emitter. Alternatively, the emitter molecule F may optionally be a fluorescent and/or phosphorescent dopant which is able to shift the emission spectrum and/or the absorption spectrum of the emission layer EML. Exemplarily, the triplet and/or singlet excitons may be transferred from the emitter molecule according to the invention E to the emitter molecule F before relaxing to the ground state S0 by emitting light typically red-shifted in comparison to the light emitted by emitter molecule E. Optionally, the emitter molecule F may also provoke two-photon effects (i.e., the absorption of two photons of half the energy of the absorption maximum).

Optionally, an organic light-emitting device (e.g., an OLED) may exemplarily be an essentially white organic light-emitting device. Exemplarily such white organic light-emitting device may comprise at least one (deep) blue emitter molecule and one or more emitter molecules emitting green and/or red light. Then, there may also optionally be energy transmittance between two or more molecules as described above.

As used herein, if not defined more specifically in the particular context, the designation of the colors of emitted and/or absorbed light is as follows:

violet: wavelength range of >380-420 nm;
deep blue: wavelength range of >420-480 nm;
sky blue: wavelength range of >480-500 nm;
green: wavelength range of >500-560 nm;
yellow: wavelength range of >560-580 nm;
orange: wavelength range of >580-620 nm;
red: wavelength range of >620-800 nm.

With respect to emitter molecules, such colors refer to the emission maximum. Therefore, exemplarily, a deep blue emitter has an emission maximum in the range of from >420 to 480 nm, a sky blue emitter has an emission maximum in the range of from >480 to 500 nm, a green emitter has an emission maximum in a range of from >500 to 560 nm, a red emitter has an emission maximum in a range of from >620 to 800 nm.

substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, —$Si(Q_{301})(Q_{302})(Q_{303})$, —$N(Q_{301})(Q_{302})$, —$B(Q_{301})(Q_{302})$, —$C(=O)(Q_{301})$, —$S(=O)_2(Q_{301})$, or —$P(=O)(Q_{301})(Q_{302})$, xb21 may be an integer from 1 to 5, and $Q_{301}$ to $Q_{303}$ may each be the same as described in connection with $Q_1$.

For example, when xb11 in Formula 301 is 2 or more, two or more of $Ar_{301}$ may be bonded to each other via a single bond.

In one or more embodiments, the host may include a compound represented by Formula 301-1, a compound represented by Formula 301-2, or any combination thereof:

Formula 301-1

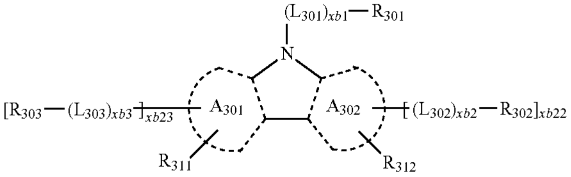

Formulas 301-2

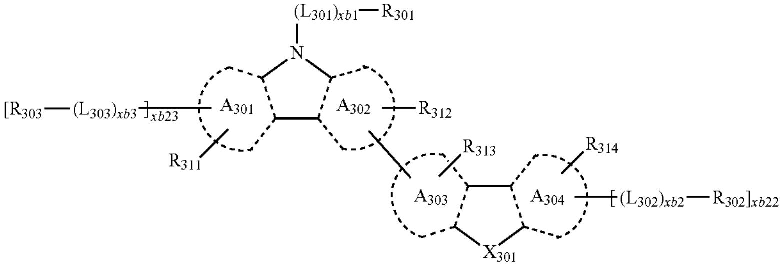

A deep blue emitter may preferably have an emission maximum of below 480 nm, more preferably below 470 nm, even more preferably below 465 nm or even below 460 nm. It will typically be above 420 nm, preferably above 430 nm, more preferably above 440 nm or even above 450 nm.

[Host]

The interlayer 130 may further include one or more hosts.

The host may further include a compound represented by Formula 301:

Formula 301

$$[Ar_{301}]_{xb11}\text{-}[(L_{301})_{xb1}\text{-}R_{301}]_{xb21}$$

wherein, in Formula 301

$Ar_{301}$ and $L_{301}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, xb11 may be 1, 2, or 3, xb1 may be an integer from 0 to 5, $R_{301}$ may be hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or wherein, in Formulae 301-1 and 301-2, rings $A_{301}$ to $A_{304}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $X_{301}$ may be O, S, N-$[(L_{304})_{xb4}$-$R_{304}]$, $C(R_{304})(R_{305})$, or $Si(R_{304})(R_{305})$, xb22 and xb23 may each independently be 0, 1, or 2, $L_{301}$, xb1, and $R_{301}$ may each be the same as described herein, $L_{302}$ to $L_{304}$ may each independently be the same as described in connection with $L_{301}$, xb2 to xb4 may each independently be the same as described in connection with xb1, and $R_{302}$ to $R_{305}$ and $R_{311}$ to $R_{314}$ may each be the same as described in connection with $R_{301}$.

In one or more embodiments, the host may include an alkali earth metal complex, a post-transition metal complex, or any combination thereof. In an embodiment, the host may include a Be complex (for example, Compound H55), an Mg complex, a Zn complex, or any combination thereof.

In one or more embodiments, the host may include: one of Compounds H1 to H128; 9,10-di(2-naphthyl)anthracene (ADN); 2-methyl-9,10-bis(naphthalen-2-yl)anthracene (MADN); 9,10-di-(2-naphthyl)-2-t-butyl-anthracene (TBADN); 4,4'-bis(N-carbazolyl)-1,1'-biphenyl (CBP); 1,3-di-9-carbazolylbenzene (mCP); 1,3,5-tri(carbazol-9-yl)benzene (TCP); or any combination thereof:
H1
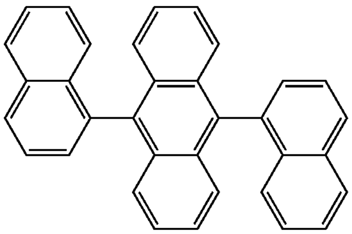
H2
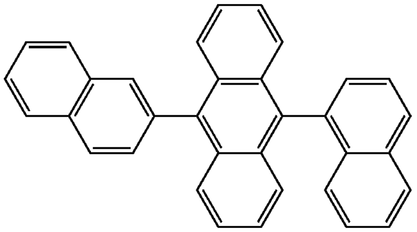
H3
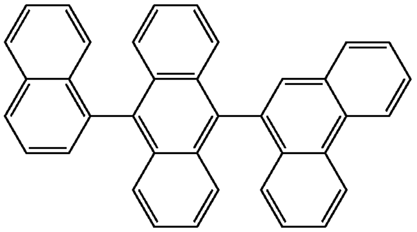
H4
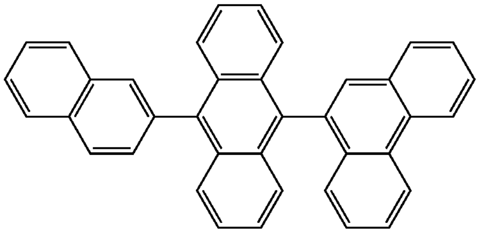
H5
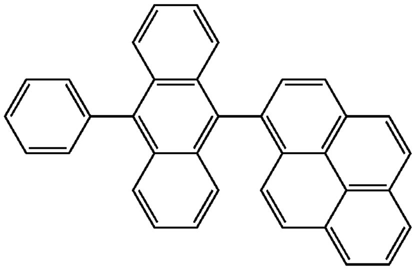
H6
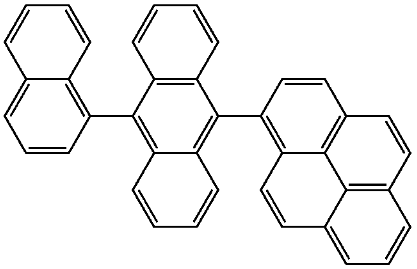
-continued
H7
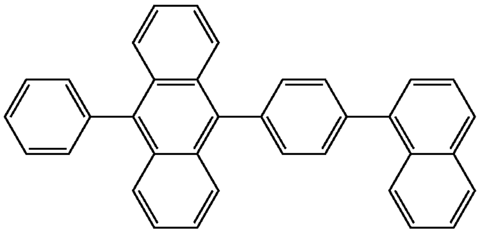
H8
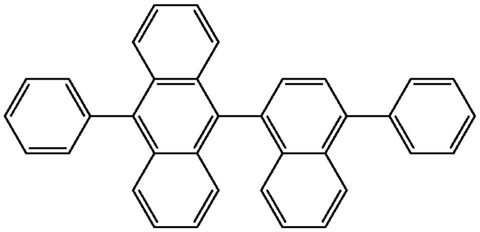
H9
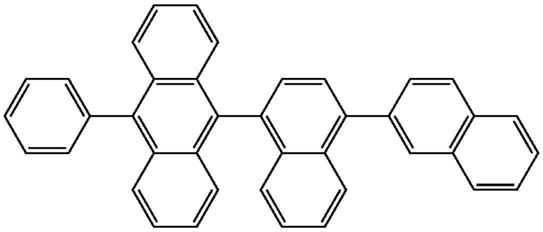
H10
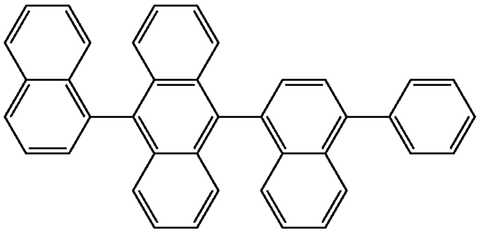
H11
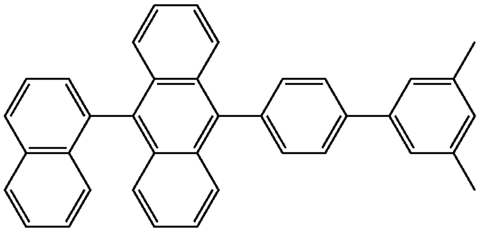
H12
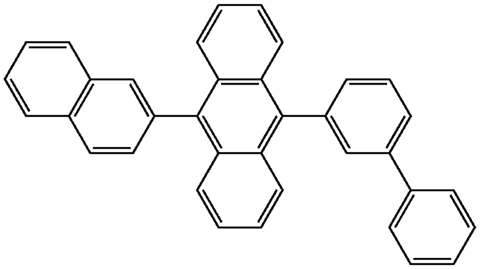

-continued
H13
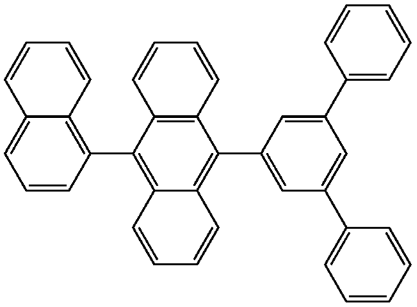
H14
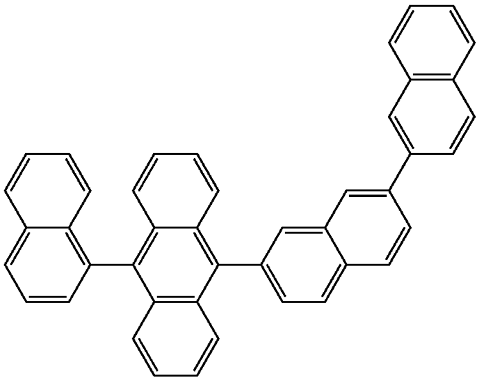
H15
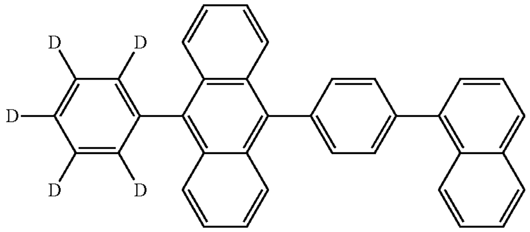
H16
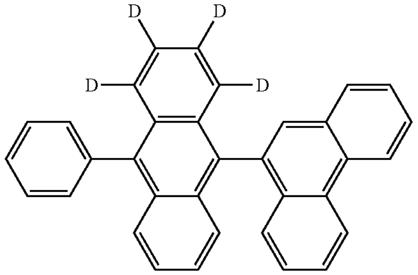
H17
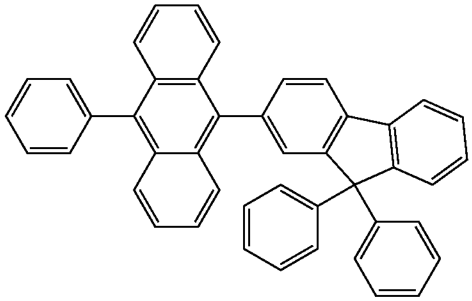
-continued
H18
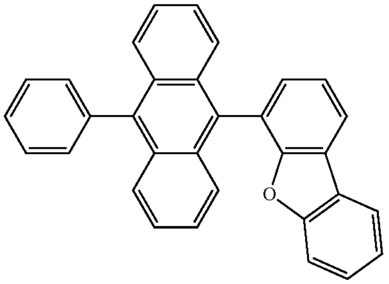
H19
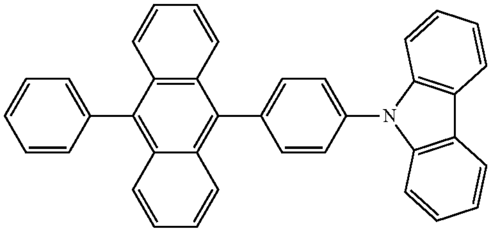
H20
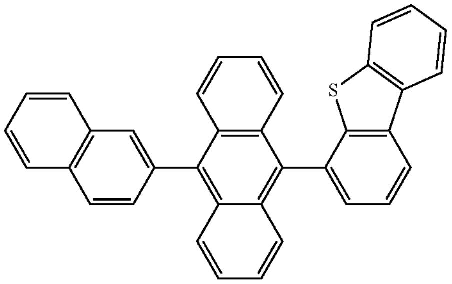
H21
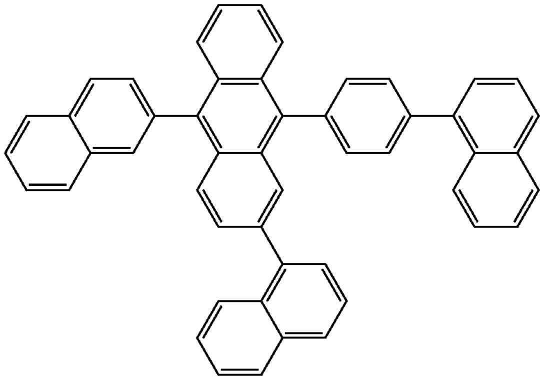
H22
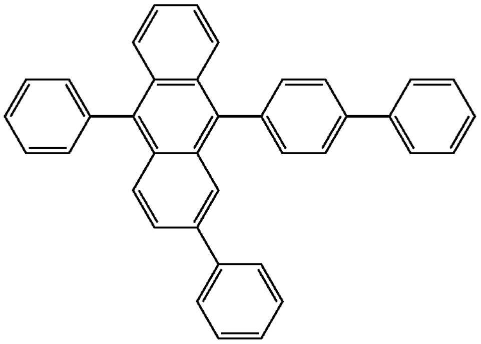

-continued
H23
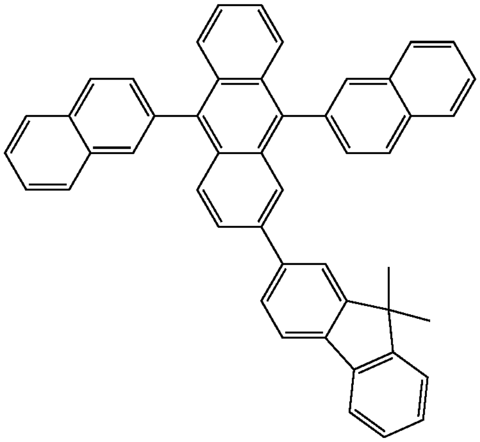
H24
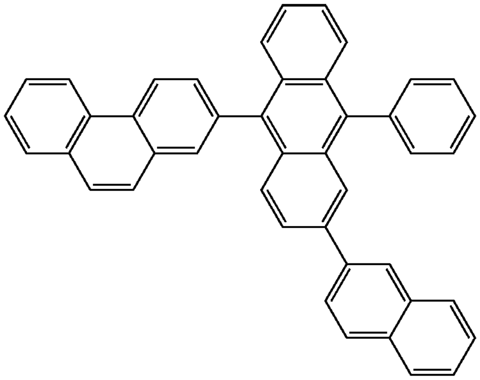
H25
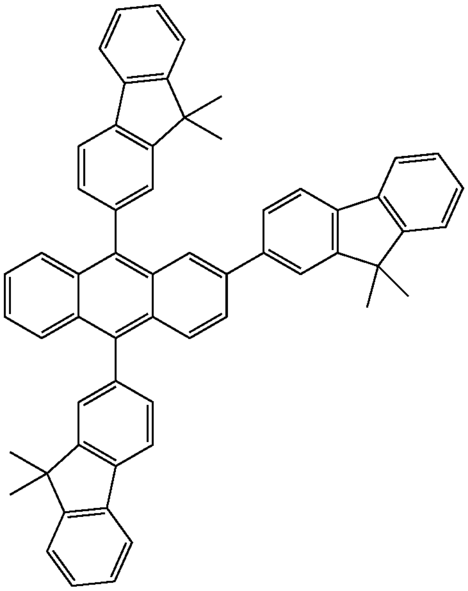
-continued
H26
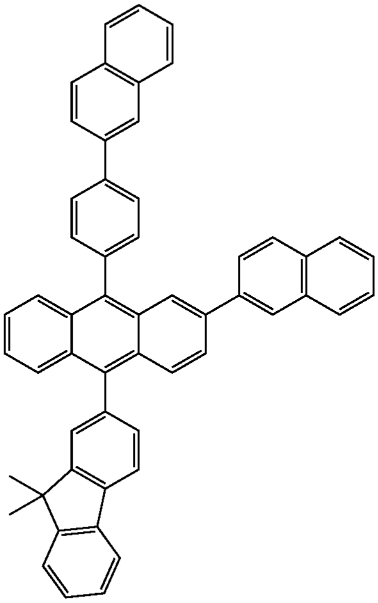
H27
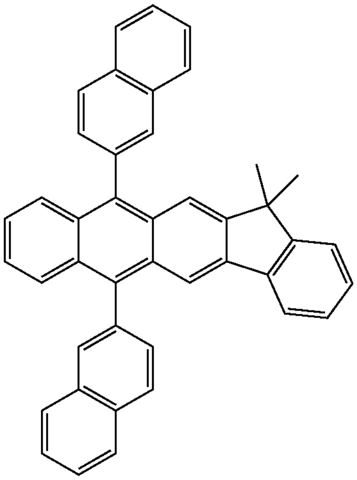
H28
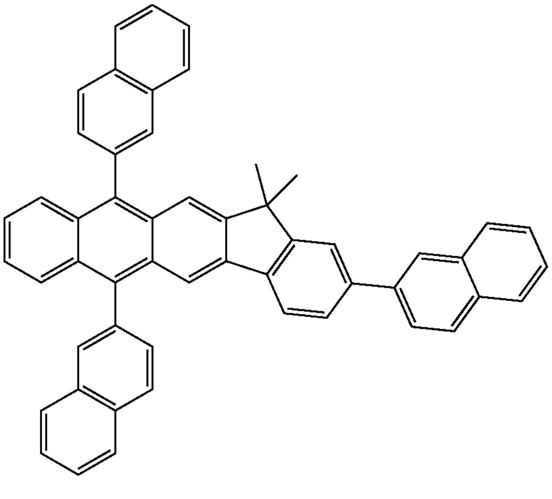

-continued
H29
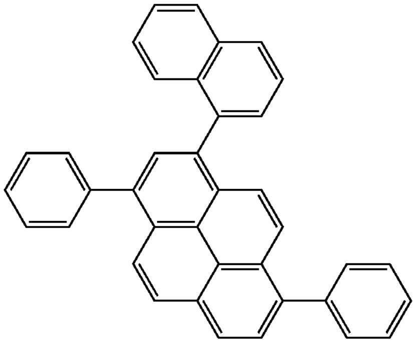
H30
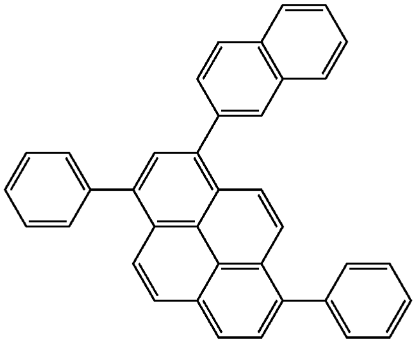
H31
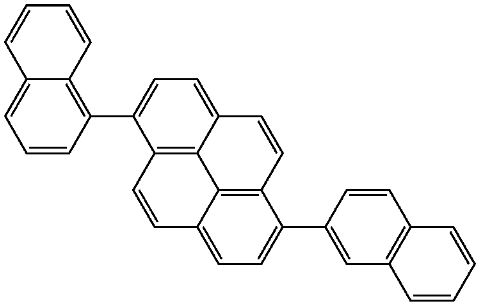
H32
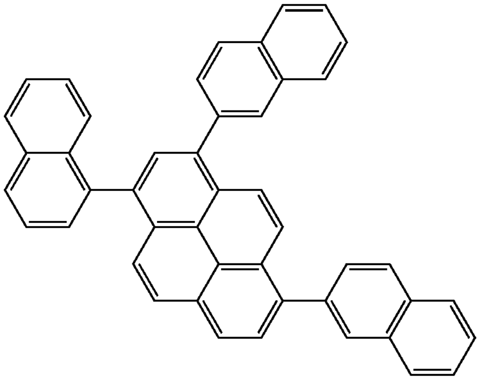
H33
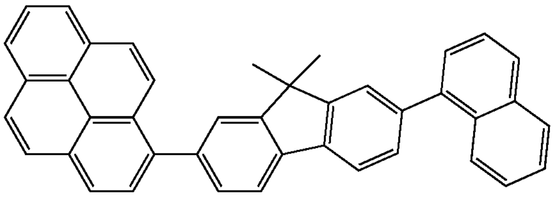
-continued
H34
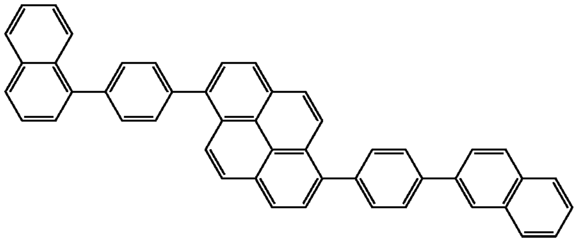
H35
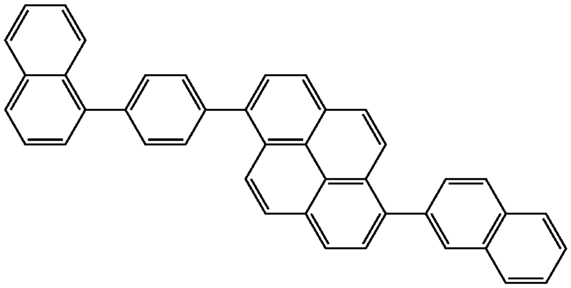
H36
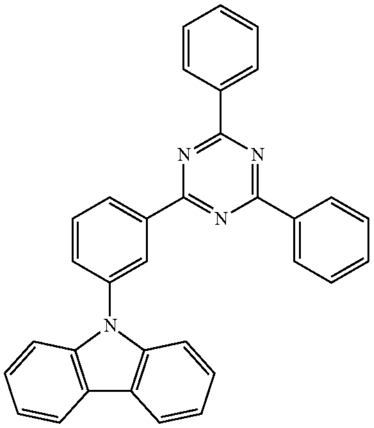
H37
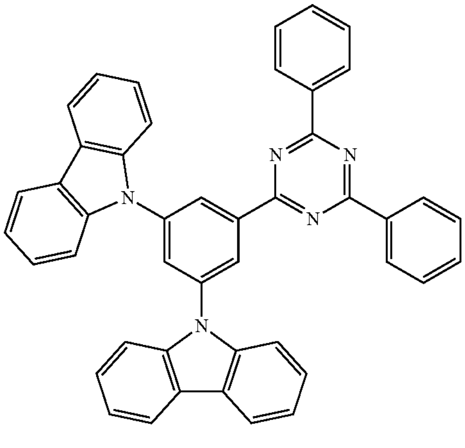

-continued
H38
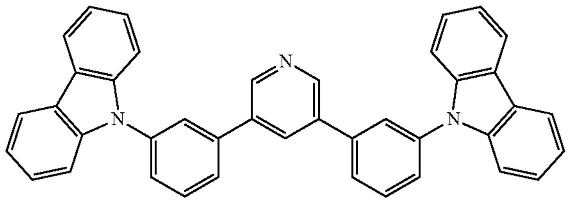
H39
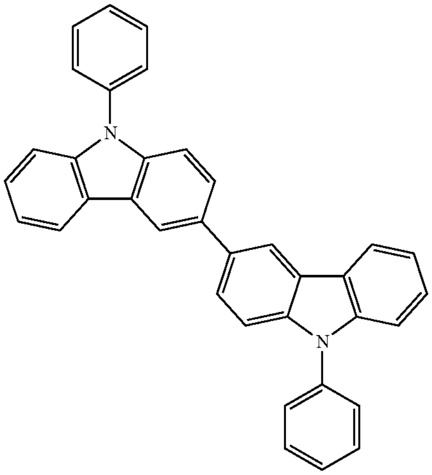
H40
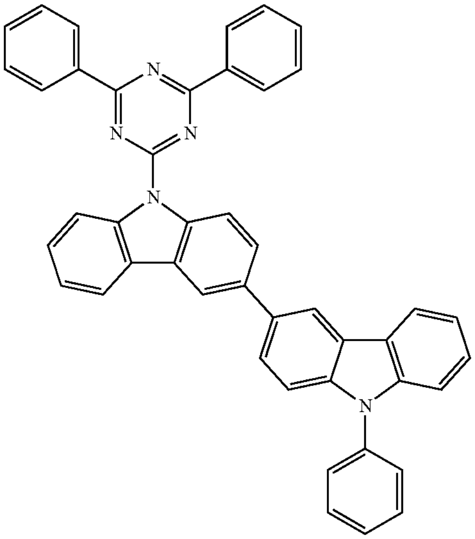
-continued
H41
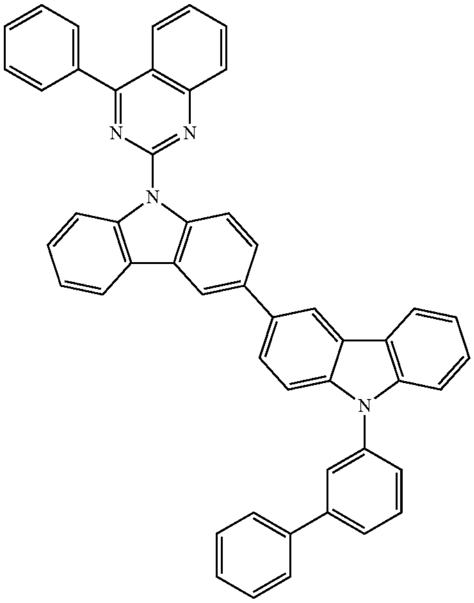
H42
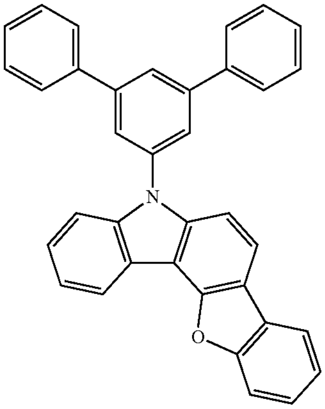
H43
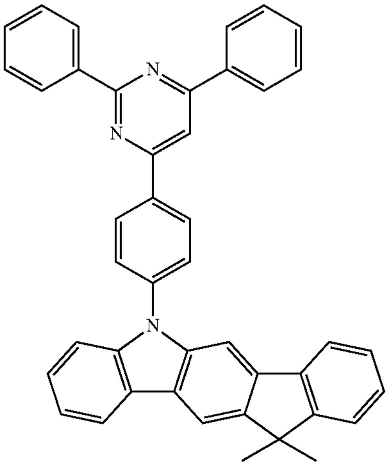

-continued
H44
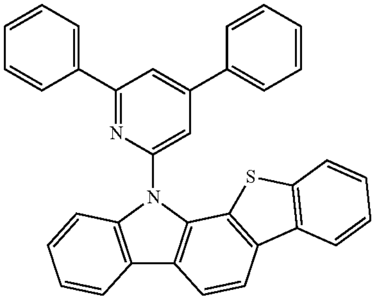
H45
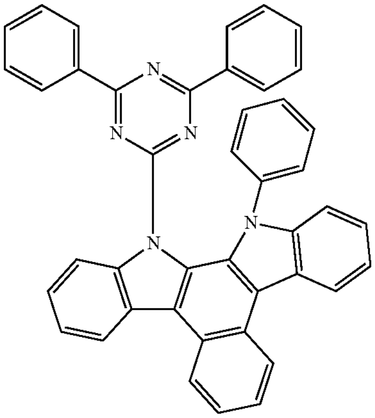
H46
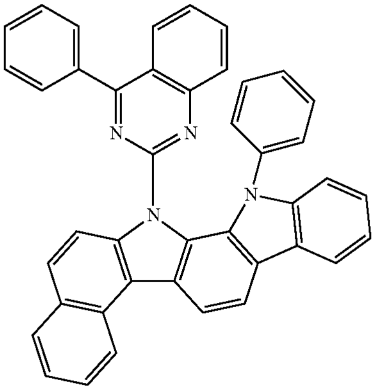
H47
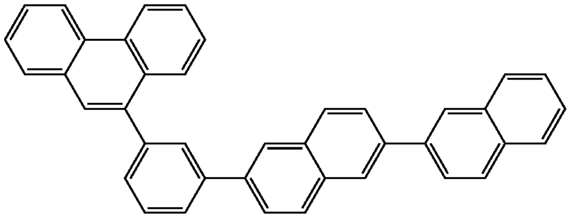
H48
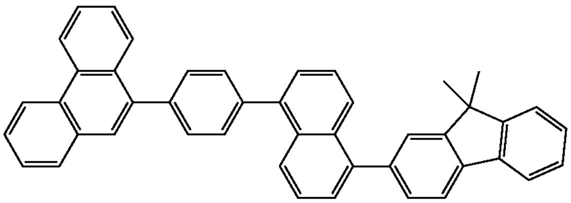
-continued
H49
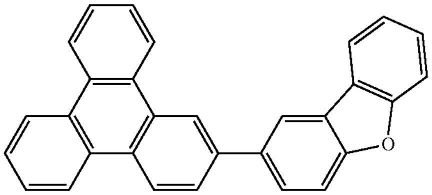
H50
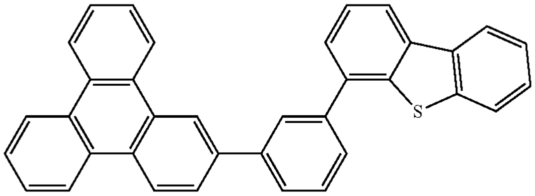
H51
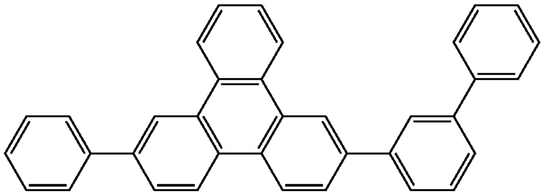
H52
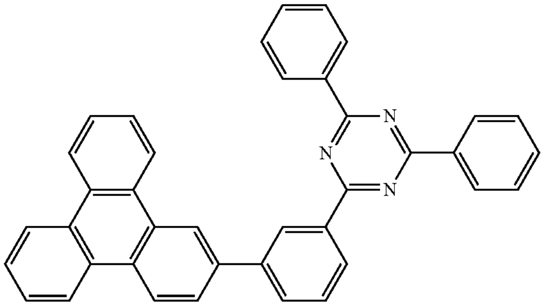
H53
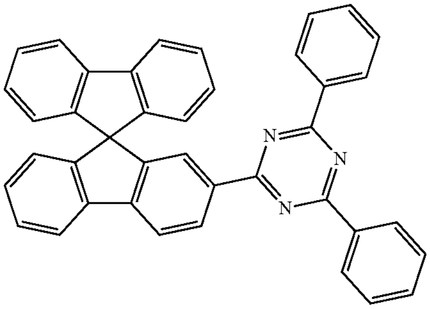

-continued
H54
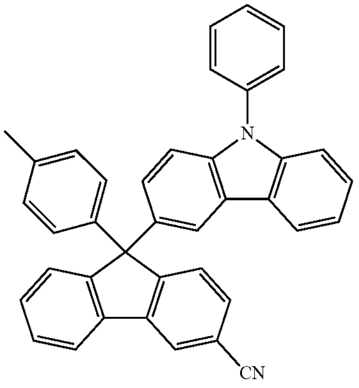
H55
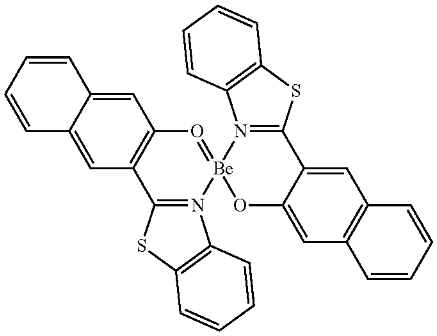
H56
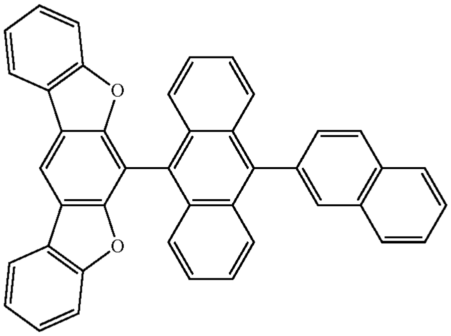
H57
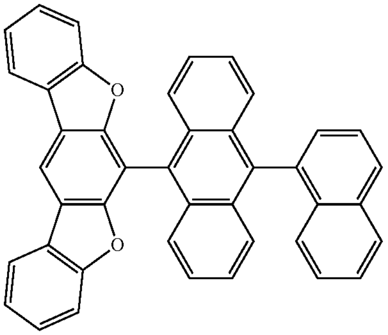
-continued
H58
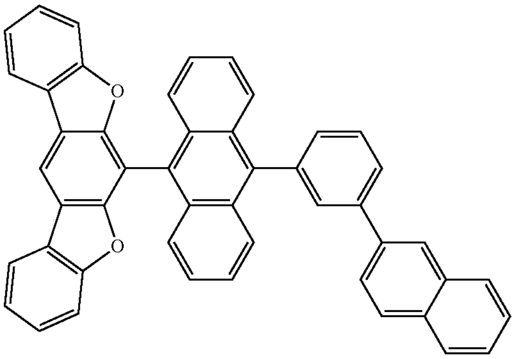
H59
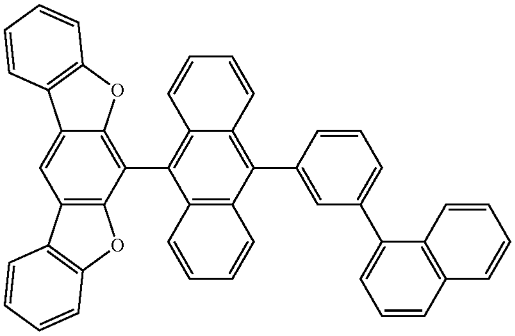
H60
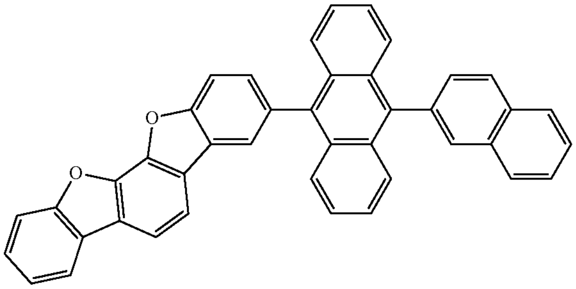
H61
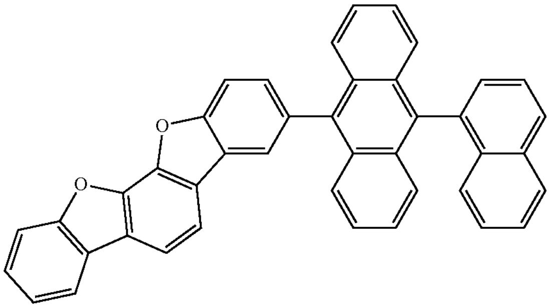

-continued
H62
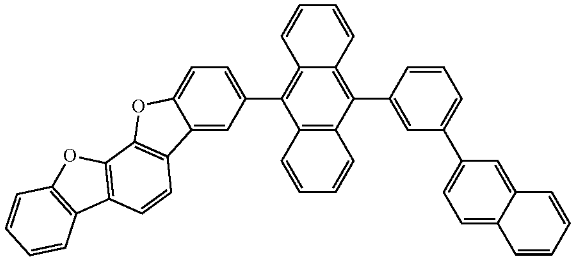
H63
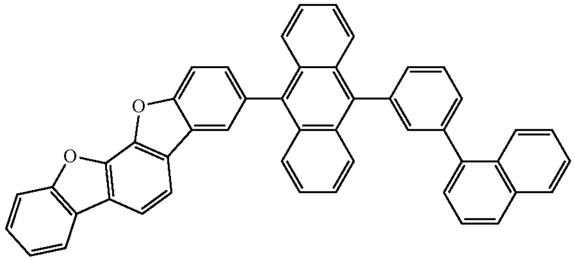
H64
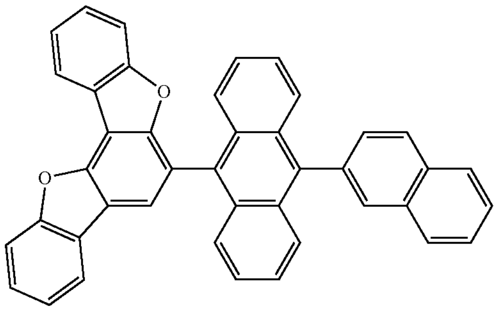
H65
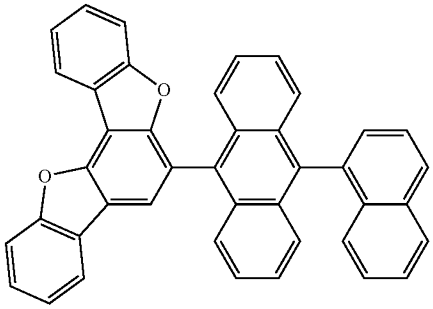
H66
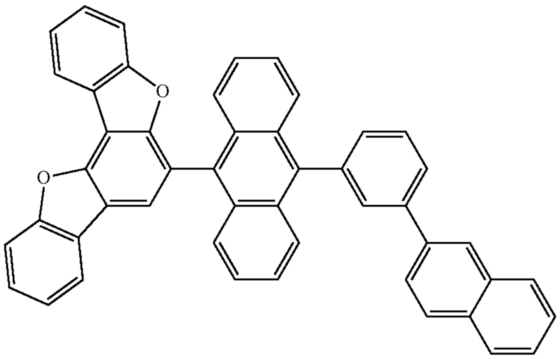
-continued
H67
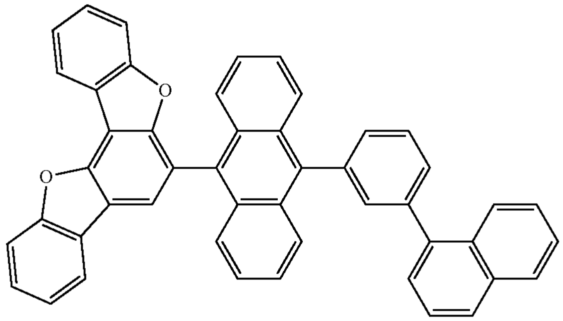
H68
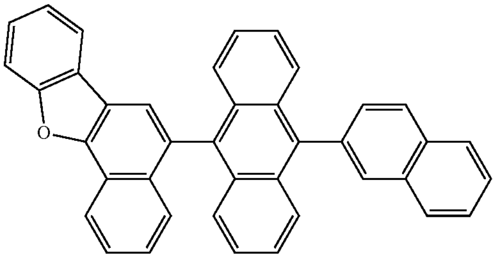
H69
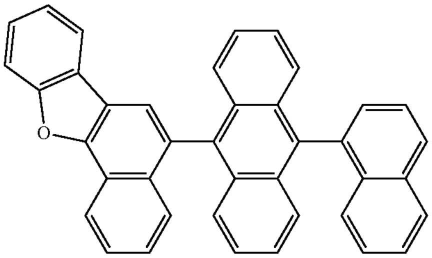
H70
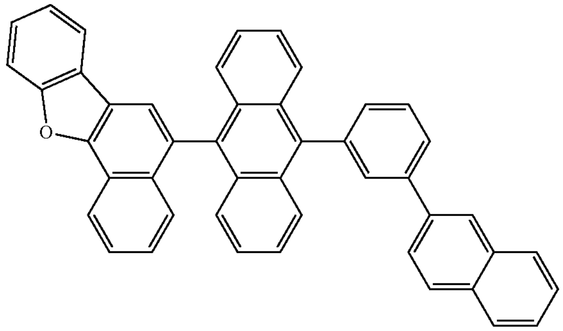
H71
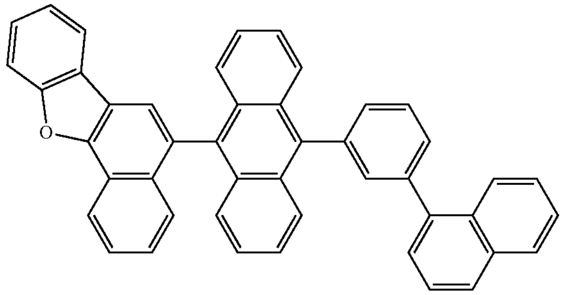

-continued
H72
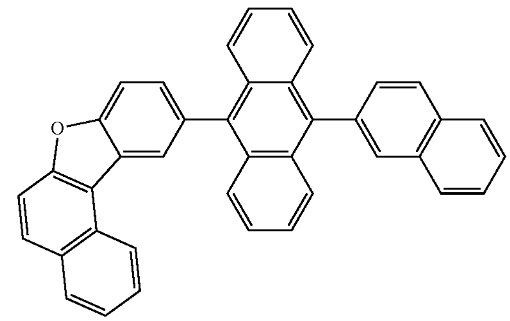
H73
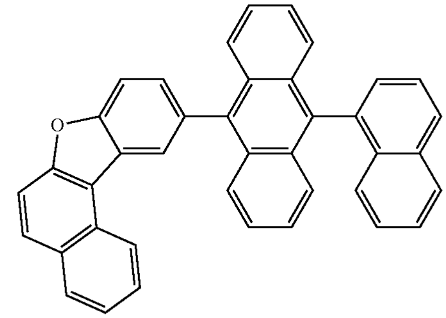
H74
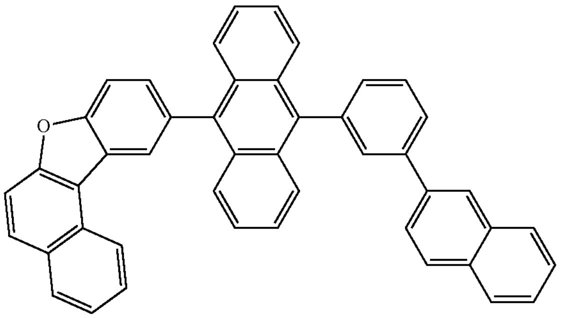
H75
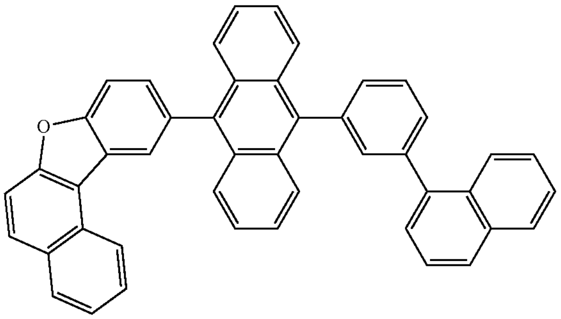
H76
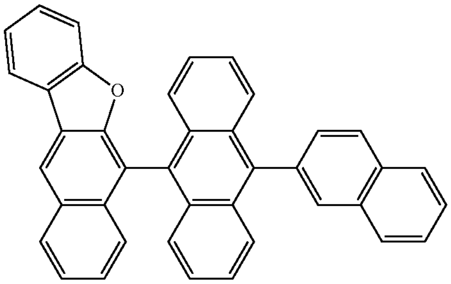
-continued
H77
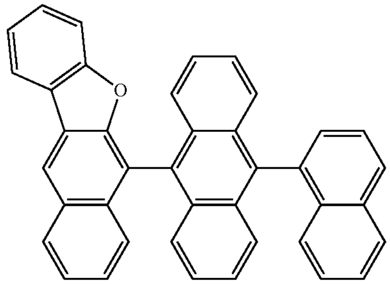
H78
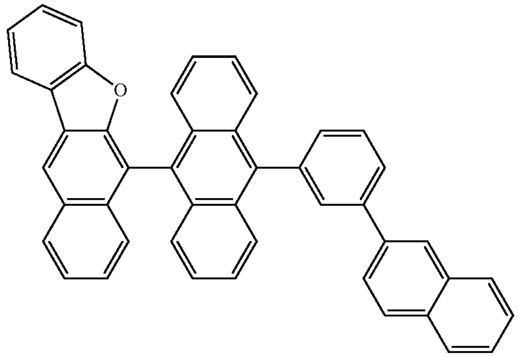
H79
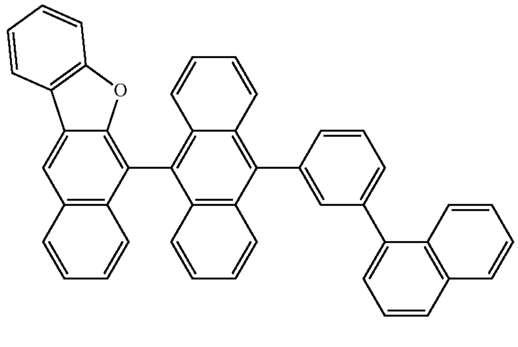
H80
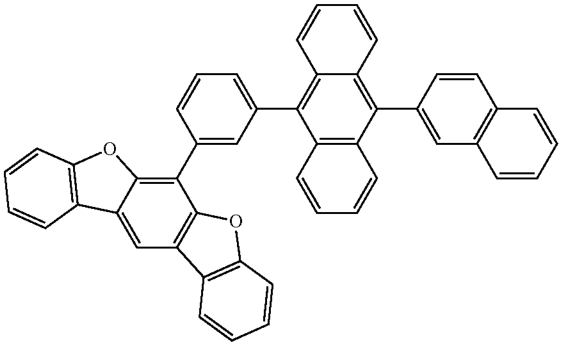

-continued
H81
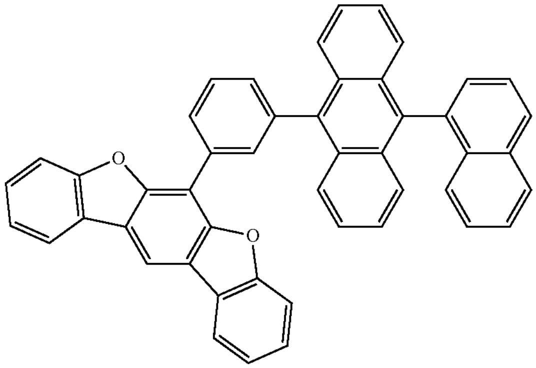
H82
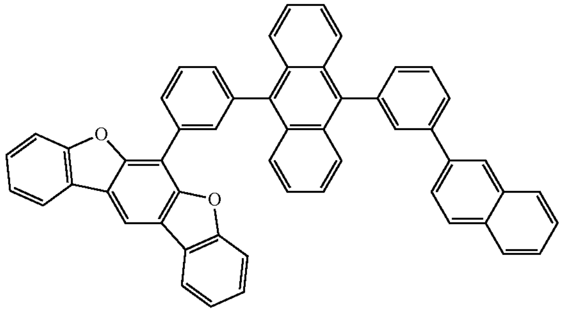
H83
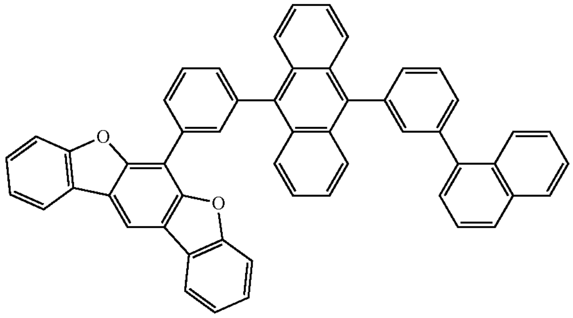
H84
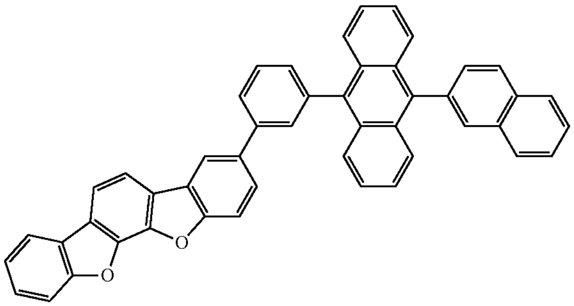
-continued
H85
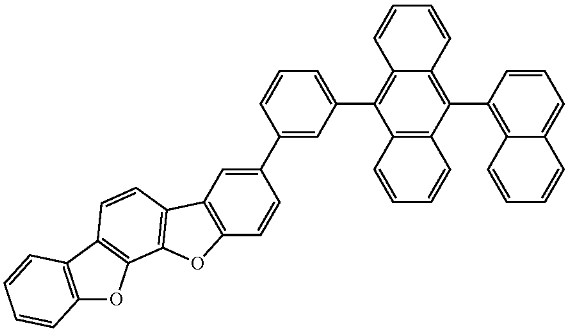
H86
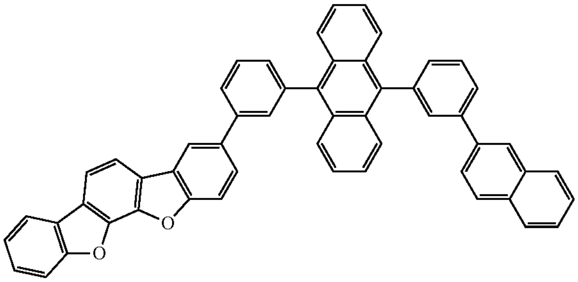
H87
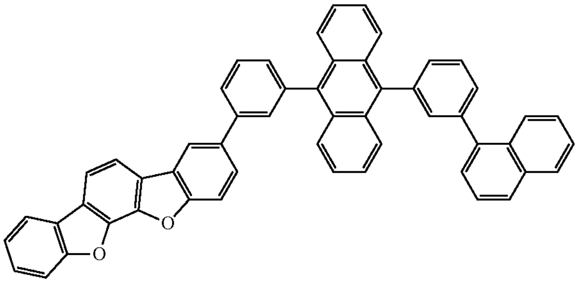
H88
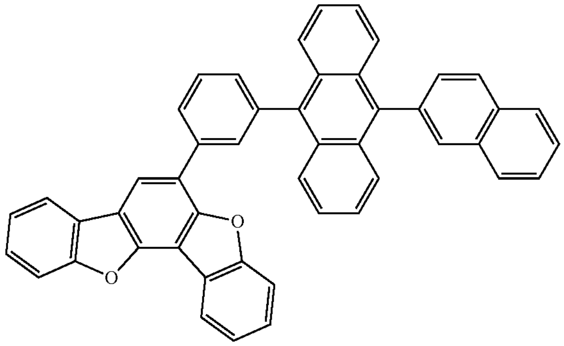

-continued
H89
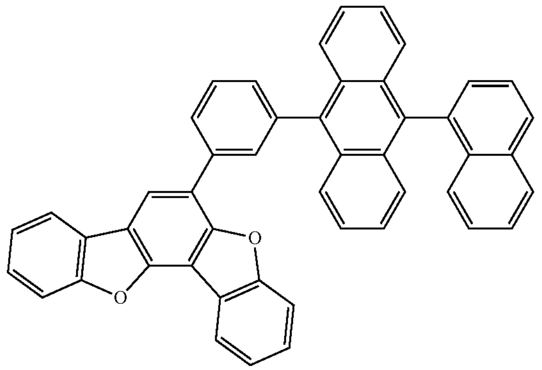
H90
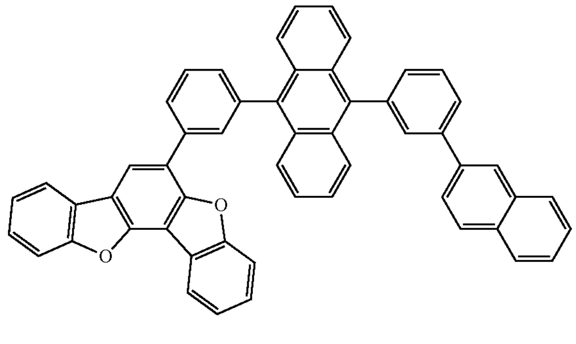
H91
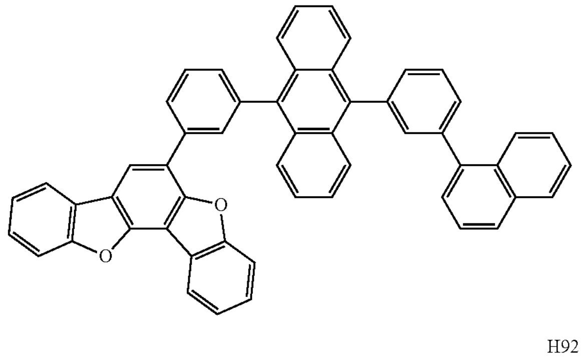
H92
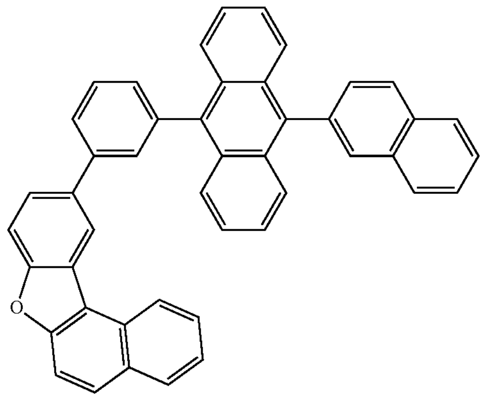
-continued
H93
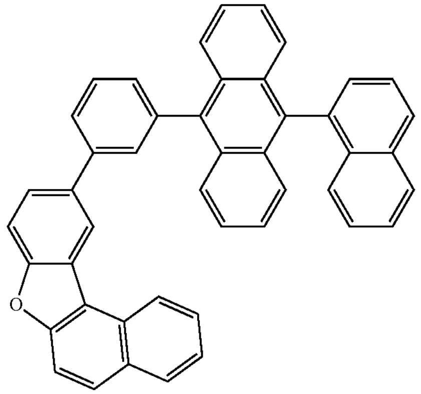
H94
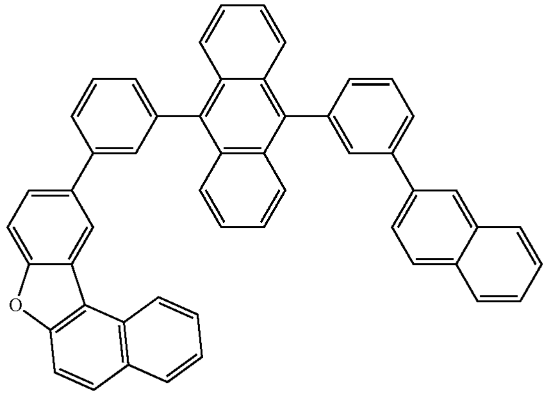
H95
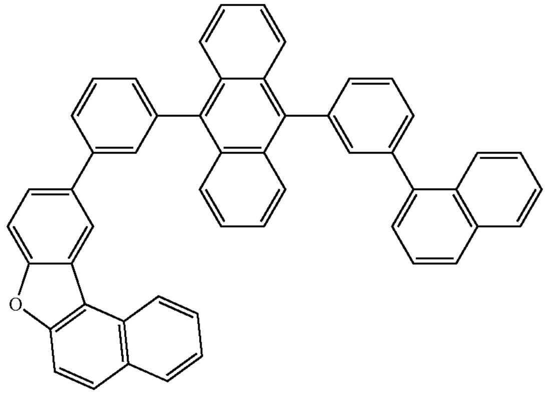
H96
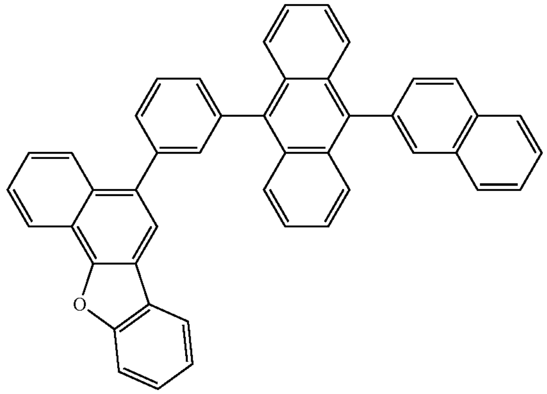

-continued
H97
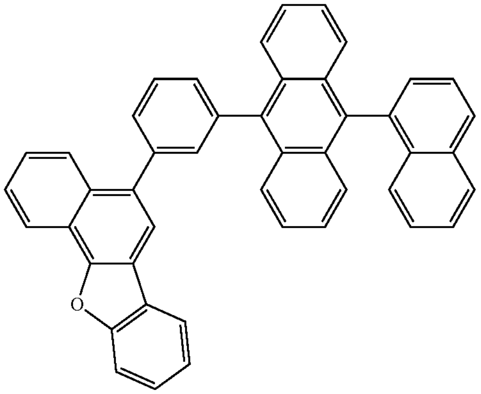
H98
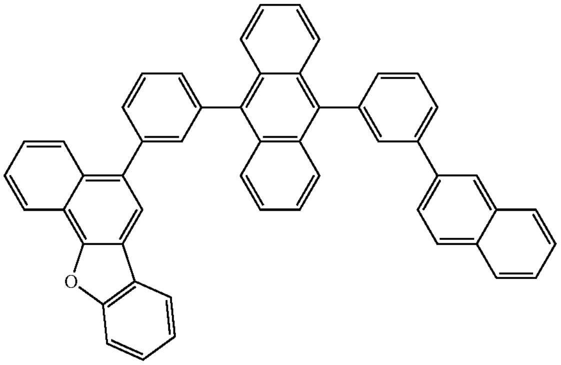
H99
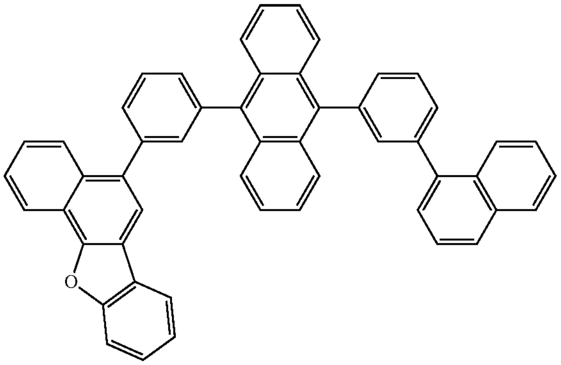
H100
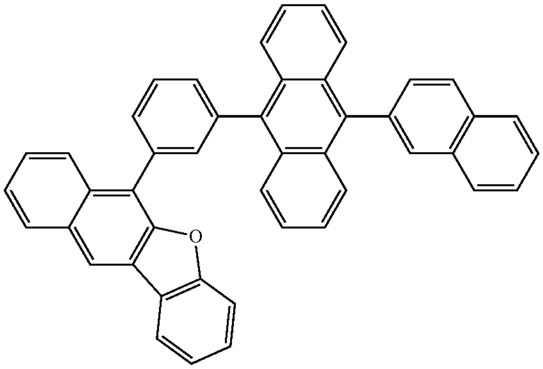
-continued
H101
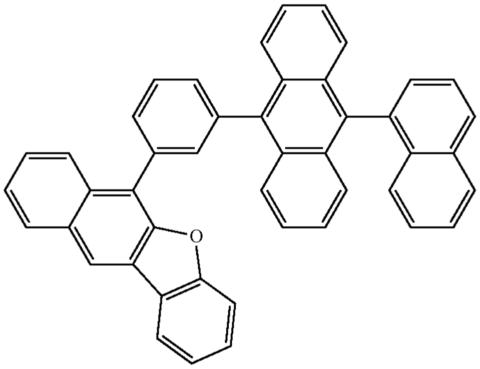
H102
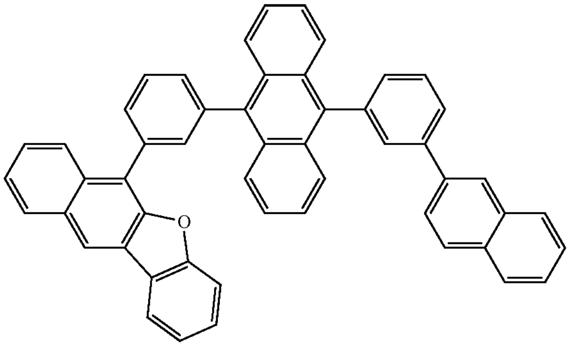
H103
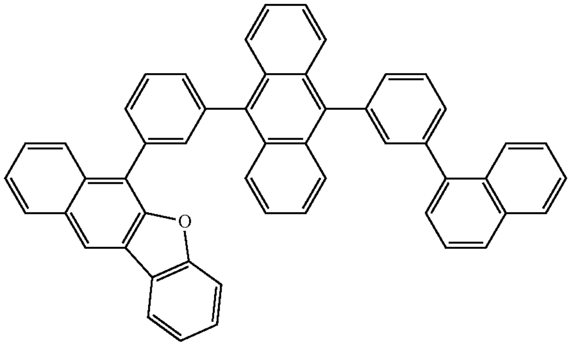
H104
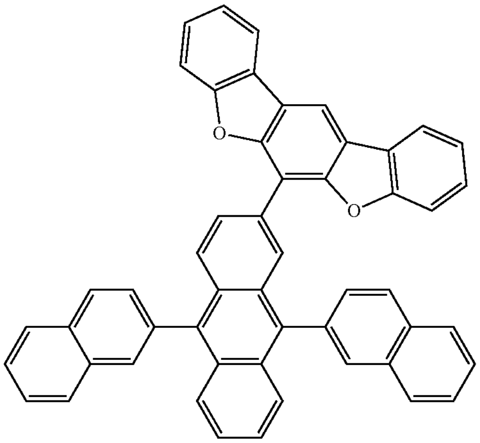

-continued
H105
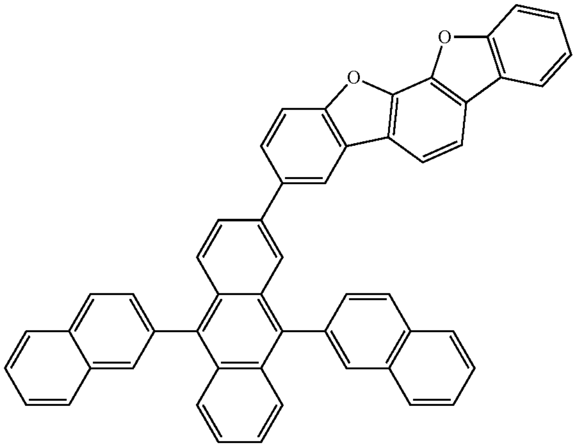
H106
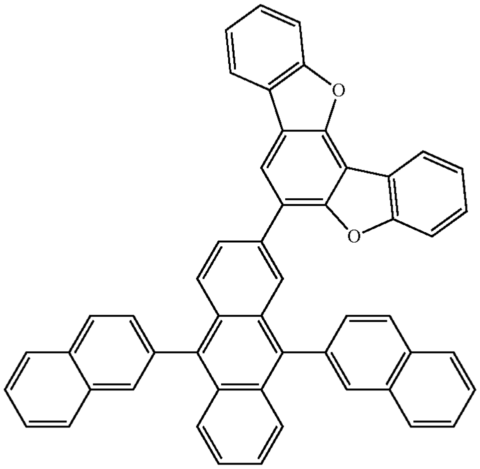
H107
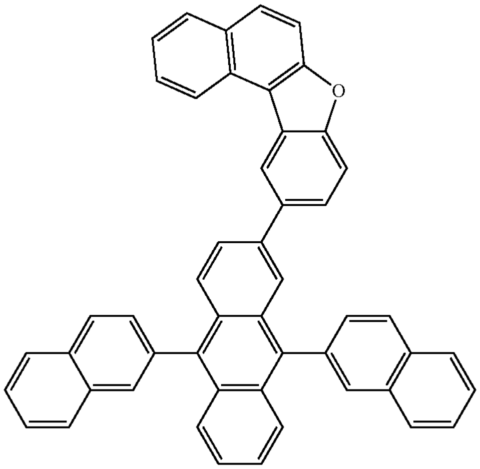
-continued
H108
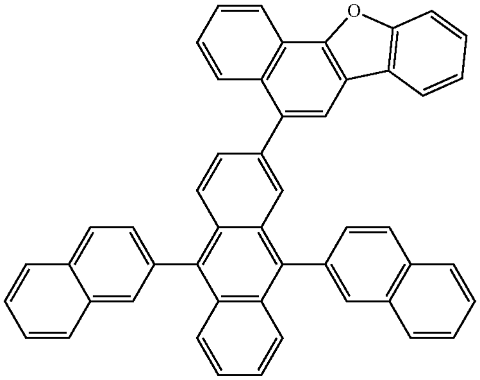
H109
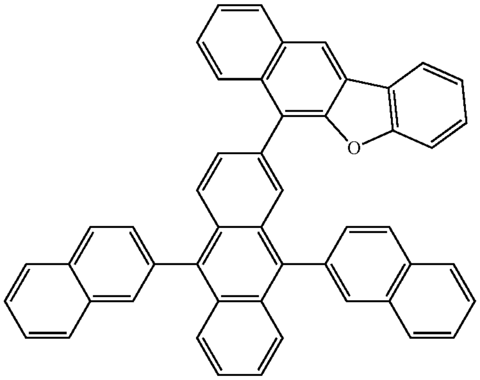
H110
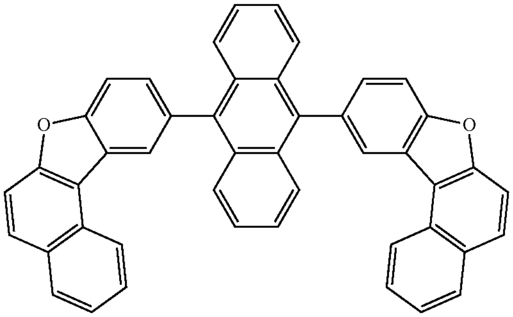
H111
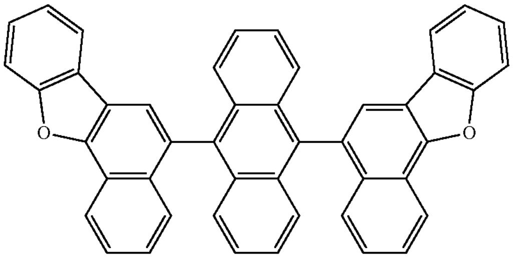

-continued
H112
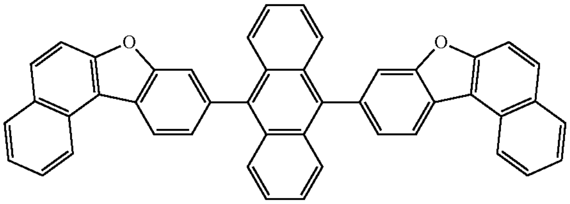
H113
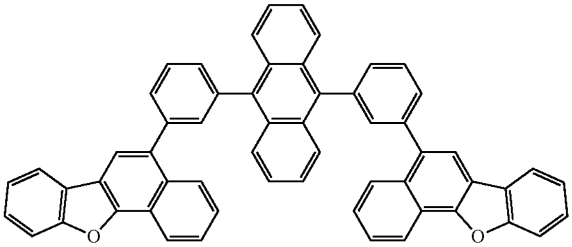
H114
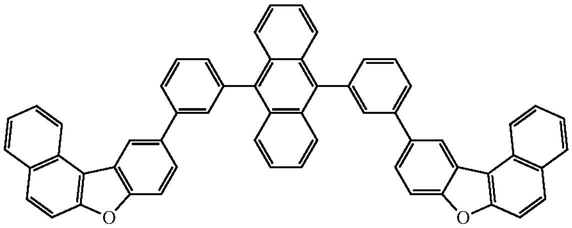
H115
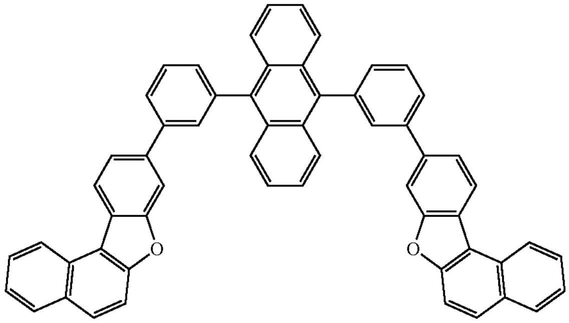
H116
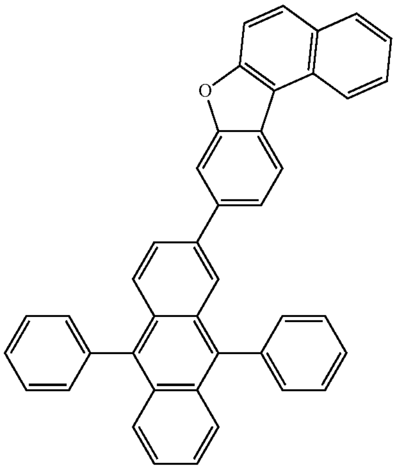
-continued
H117
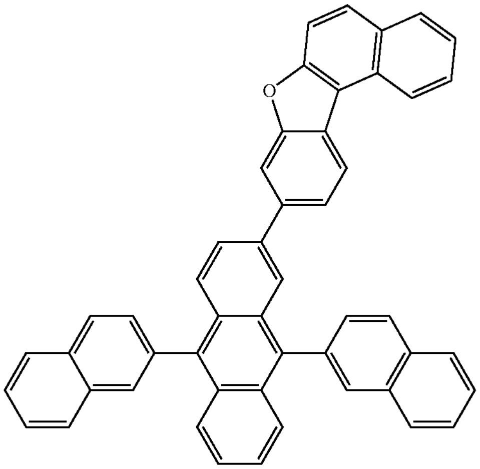
H118
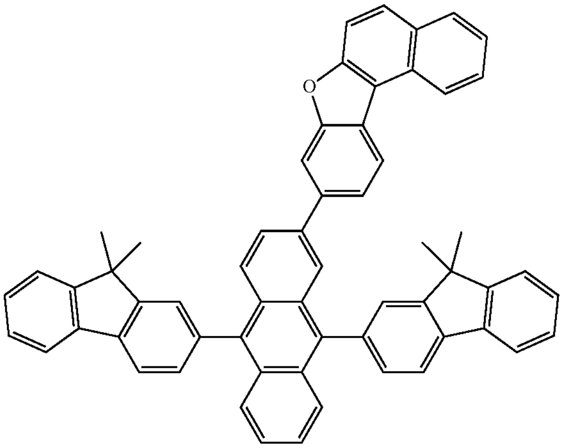
H119
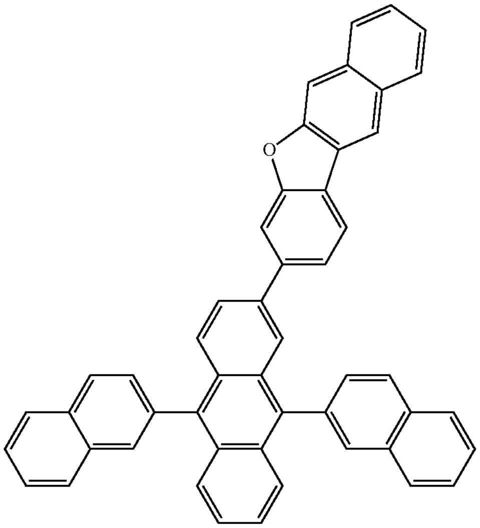

-continued
H120
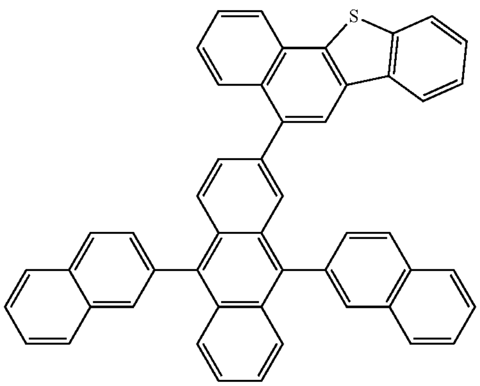
H121
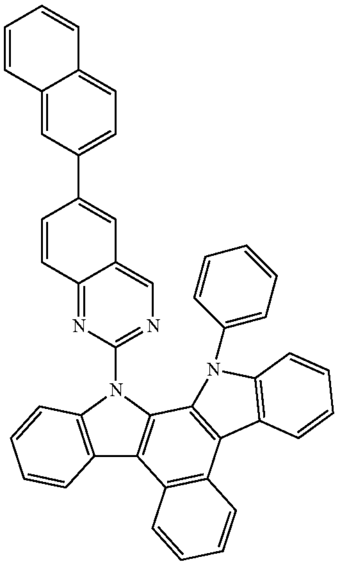
H122
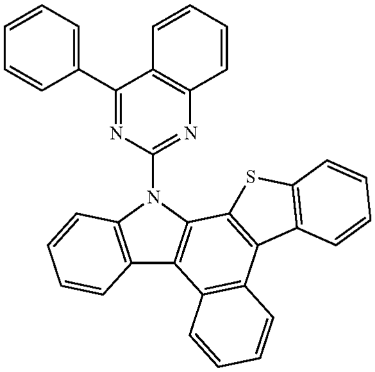
-continued
H123
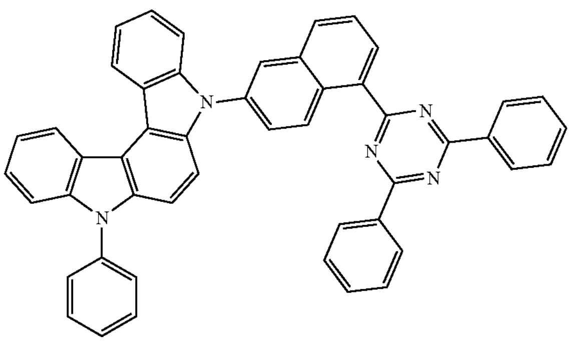
H124
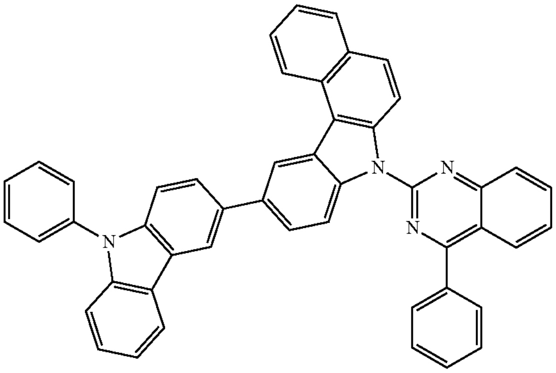
H125
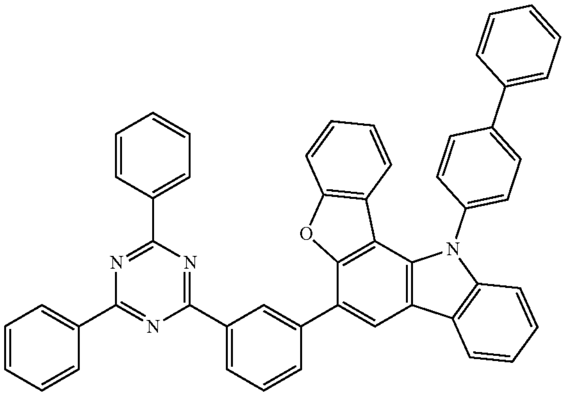
H126
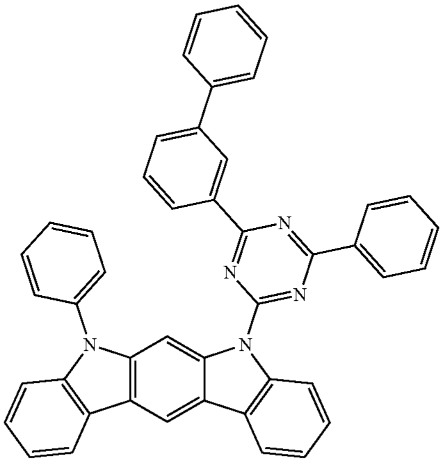

-continued

H127

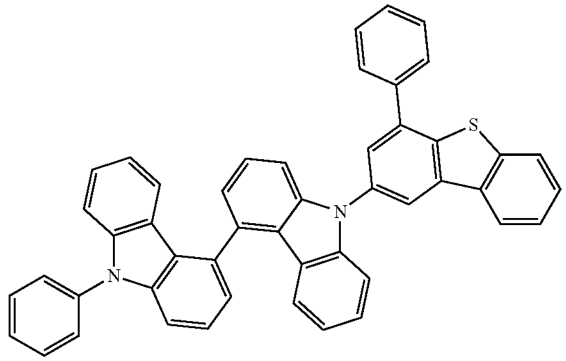

H128

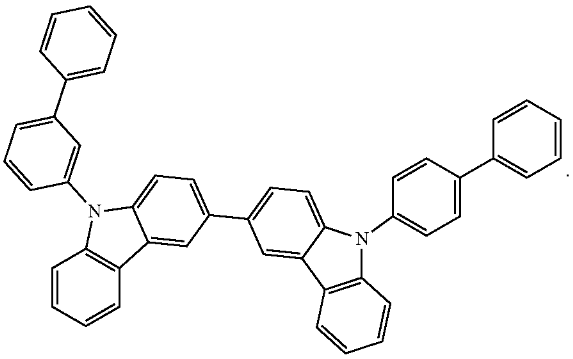

[Phosphorescent Dopant (Phosphorescent Emitter)]

The interlayer may 130 further include one or more phosphorescent dopants.

The phosphorescent dopant may include at least one transition metal as a central metal.

The phosphorescent dopant may include a monodentate ligand, a bidentate ligand, a tridentate ligand, a tetradentate ligand, a pentadentate ligand, a hexadentate ligand, or any combination thereof.

The phosphorescent dopant may be electrically neutral.

For example, the phosphorescent dopant may include an organometallic compound represented by Formula 401:

Formula 401

$$M(L401)_{xc1}(L402)_{xc2}$$

Formula 402

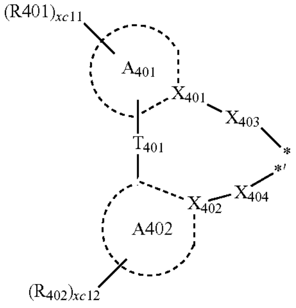

wherein, in Formulae 401 and 402,

M may be a transition metal (for example, iridium (Ir), platinum (Pt), palladium (Pd), osmium (Os), titanium (Ti), gold (Au), hafnium (Hf), europium (Eu), terbium (Tb), rhodium (Rh), rhenium (Re), or thulium (Tm)), $L_{401}$ may be a ligand represented by Formula 402, and xc1 is 1, 2, or 3, wherein, when xc1 is 2 or more, two or more of $L_{401}$ may be identical to or different from each other, $L_{402}$ may be an organic ligand, and xc2 may be 0, 1, 2, 3, or 4, wherein, when xc2 is 2 or more, two or more of $L_{402}$ may be identical to or different from each other, $X_{401}$ and $X_{402}$ may each independently be nitrogen or carbon, rings $A_{401}$ and $A_{402}$ may each independently be a $C_3$-$C_{60}$ carbocyclic group or a $C_1$-$C_{60}$ heterocyclic group, $T_{401}$ may be a single bond, *—O—*', *—S—*', *—C(=O)—*', *—N($Q_{411}$)-*', *—C($Q_{411}$)($Q_{412}$)-*', *—C($Q_{411}$)=C($Q_{412}$)-*', *—C($Q_{411}$)=*', or *=C($Q_{411}$)=*', $X_{403}$ and $X_{404}$ may each independently be a chemical bond (for example, a covalent bond or a coordination bond), O, S, N($Q_{413}$), B($Q_{413}$), P($Q_{413}$), C($Q_{413}$)($Q_{414}$), or Si($Q_{413}$)($Q_{414}$), $Q_{411}$ to $Q_{414}$ may each be the same as described in connection with $Q_1$, $R_{401}$ and $R_{402}$ may each independently be hydrogen, deuterium, —F, —Cl, —Br, —I, a hydroxyl group, a cyano group, a nitro group, a $C_1$-$C_{20}$ alkyl group unsubstituted or substituted with at least one $R_{10a}$, a $C_1$-$C_{20}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), or —P(=O)($Q_{401}$)($Q_{402}$), $Q_{401}$ to $Q_{403}$ may each be the same as described in connection with $Q_1$, xc11 and xc12 may each independently be an integer of 0 to 10, and

* and *' in Formula 402 each indicate a binding site to M in Formula 401.

For example, in Formula 402, i) $X_{401}$ may be nitrogen and $X_{402}$ may be carbon, or ii) each of $X_{401}$ and $X_{402}$ may be nitrogen.

When xc1 in Formula 401 is 2 or more, in two or more of $L_{401}$, two ring $A_{401}$(s) may optionally be bonded to each other via $T_{402}$, which is a linking group, and two ring $A_{402}$(s) may optionally be bonded to each other via $T_{403}$, which is a linking group. $T_{402}$ and $T_{403}$ may each be the same as described in connection with $T_{401}$.

In Formula 401, $L_{402}$ may be an organic ligand. For example, $L_{402}$ may include a halogen group, a diketone group (for example, an acetylacetonate group), a carboxylic acid group (for example, a picolinate group), —C(=O), an isonitrile group, a —CN group, a phosphorus group (for example, a phosphine group, a phosphite group, etc.), or any combination thereof.

The phosphorescent dopant may include, for example, one of Compounds PD1 to PD39, or any combination thereof:

-continued
PD1
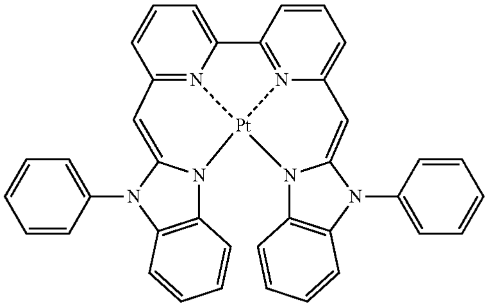
PD2
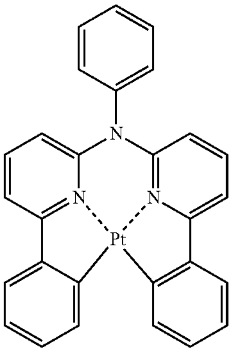
PD3
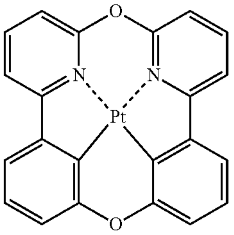
PD4
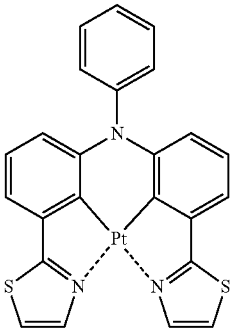
PD5
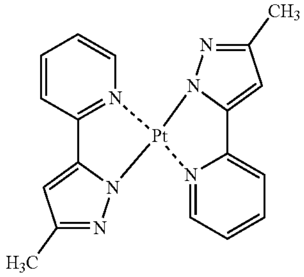
PD6
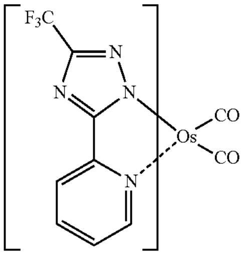
PD7
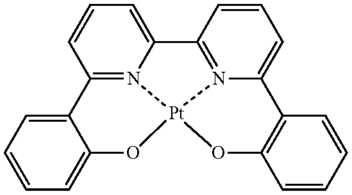
PD8
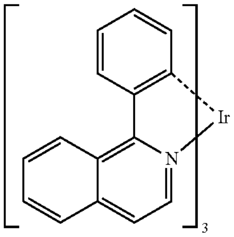
PD9
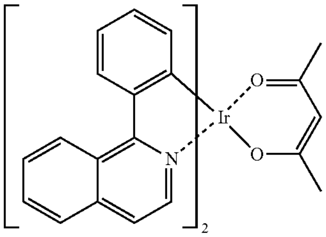
PD10
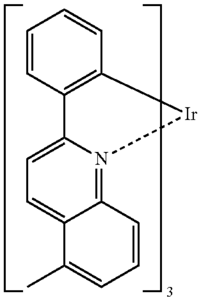
PD11
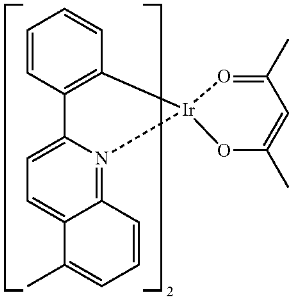

-continued
PD12
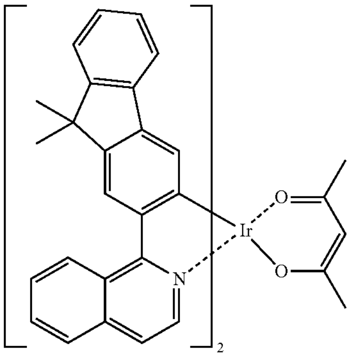
PD13
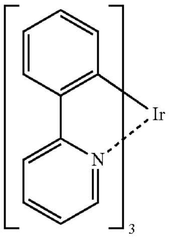
PD14
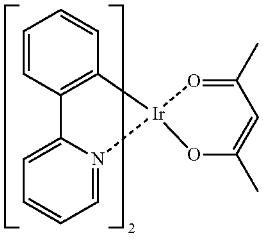
PD15
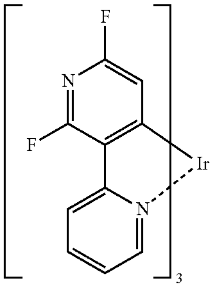
PD16
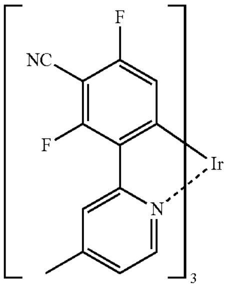
-continued
PD17
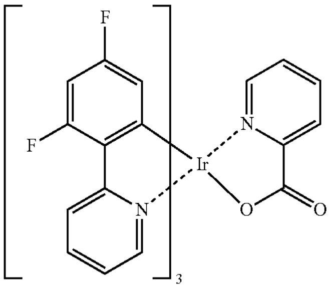
PD18
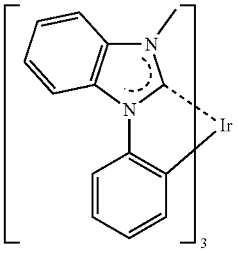
PD19
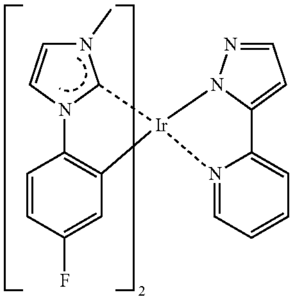
PD20
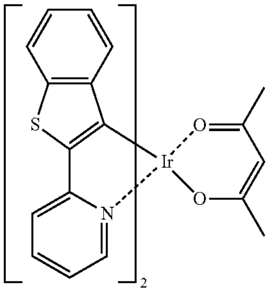
PD21
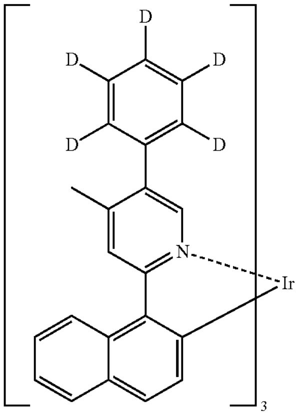

PD22
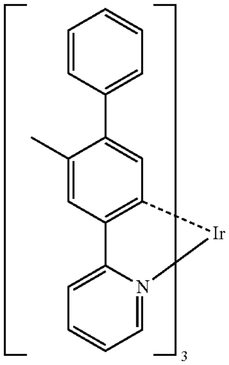
PD23
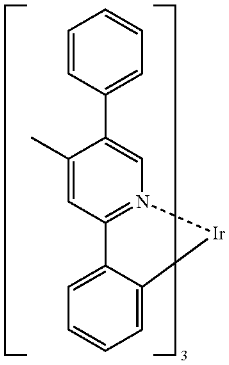
PD24
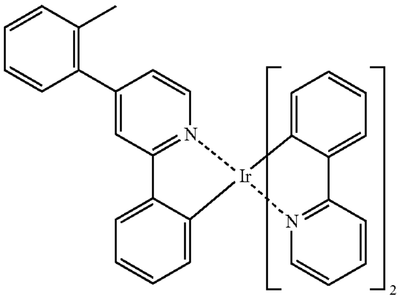
PD25
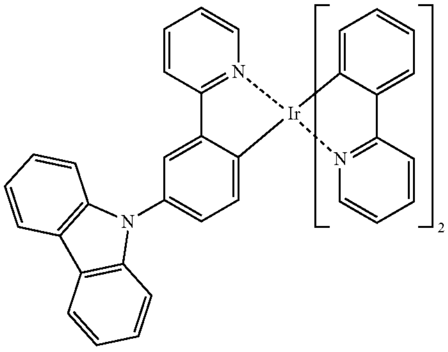
PD26
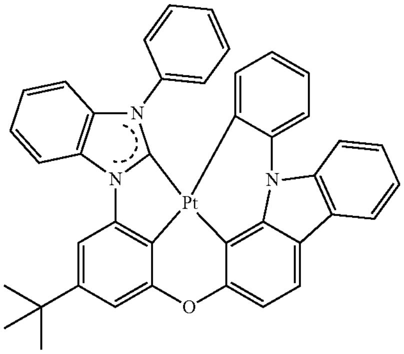
PD27
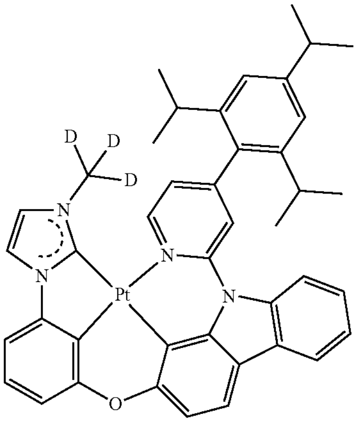
PD28
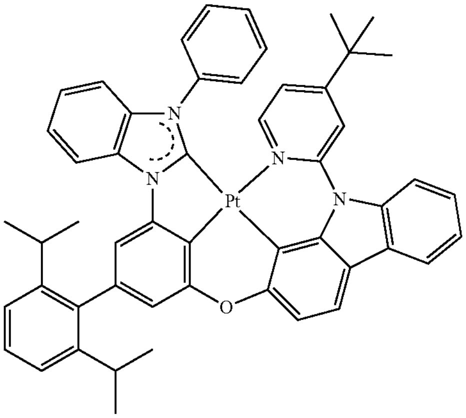
PD29
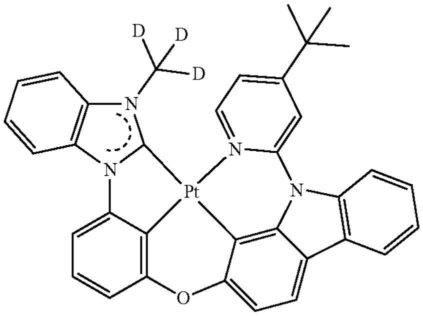

-continued
PD30
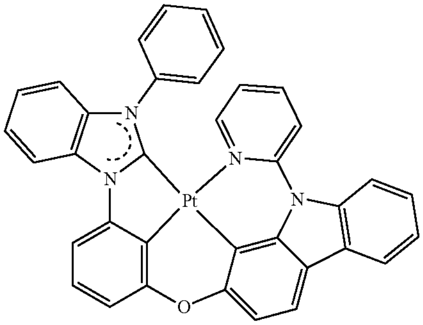
PD31
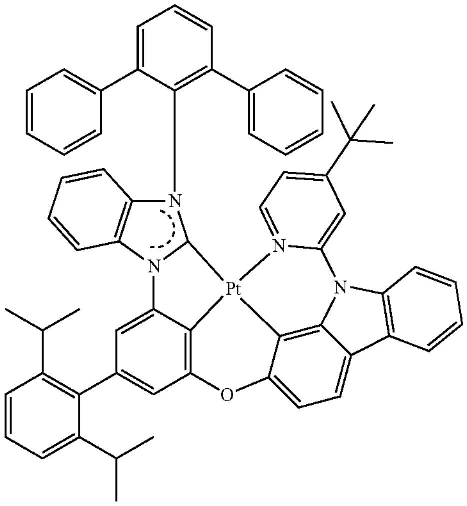
PD32
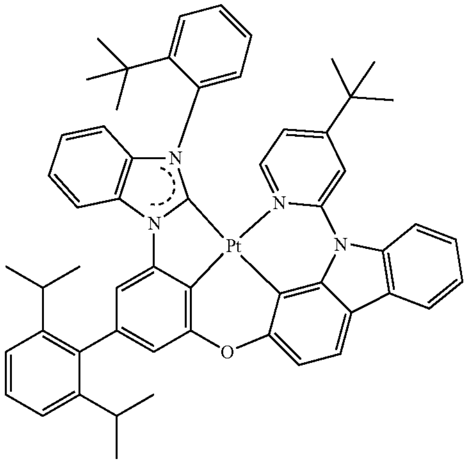
-continued
PD33
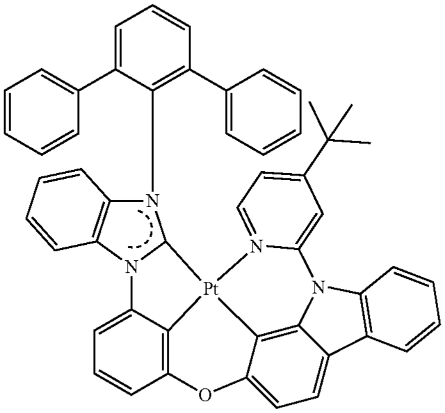
PD34
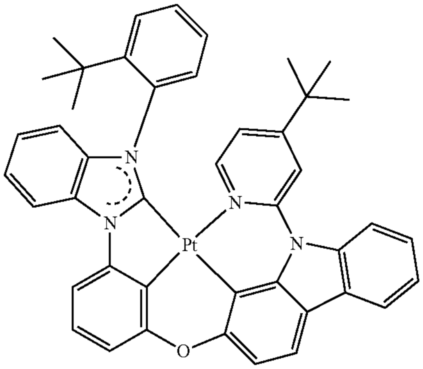
PD35
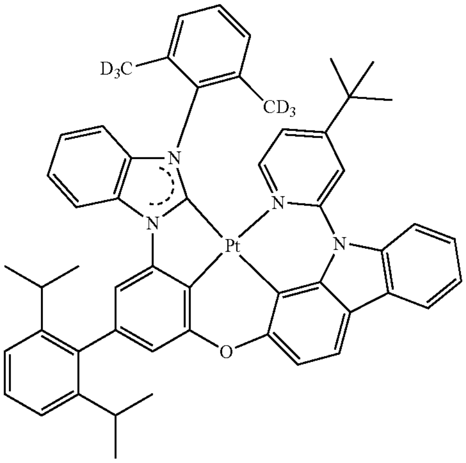

-continued

PD36

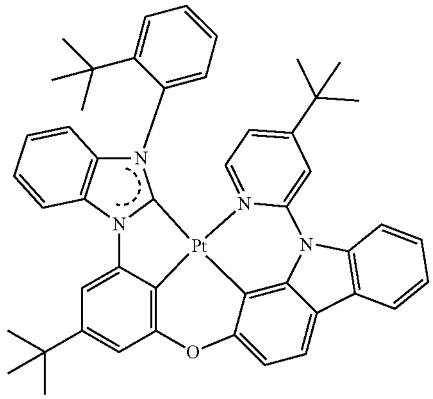

PD37

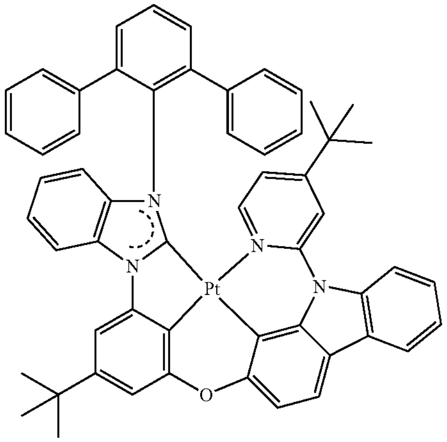

PD38

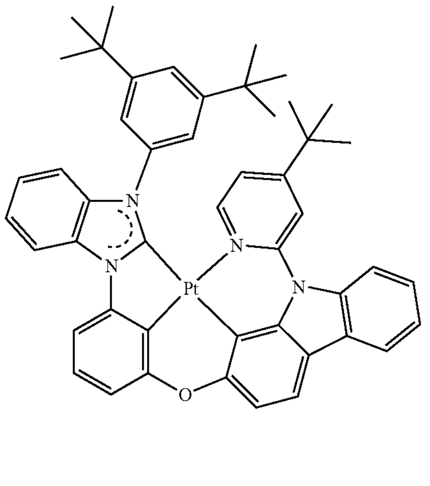

-continued

PD39

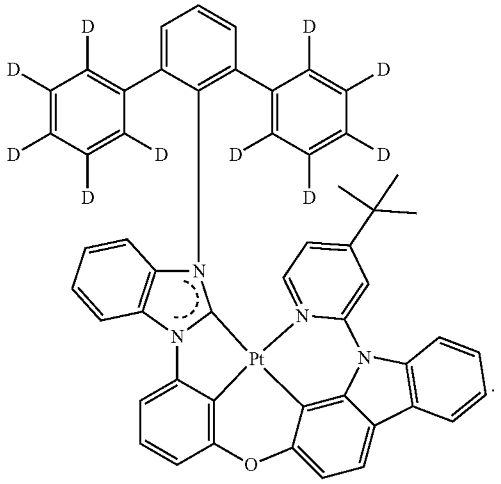

[Fluorescent Dopant (Fluorescent Emitter)]

The emission layer may include the organic molecule according to the invention as a fluorescent dopant.

The interlayer may 130 further include one or more Fluorescent dopants other than the organic molecule according to the invention.

The fluorescent dopant may include an amine group-containing compound, a styryl group-containing compound, or any combination thereof.

For example, the fluorescent dopant may include a compound represented by Formula 501:

Formula 501

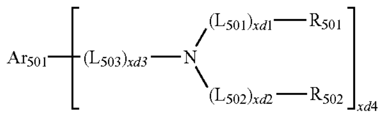

wherein, in Formula 501, $Ar_{501}$, $L_{501}$ to $L_{503}$, $R_{501}$, and $R_{502}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, xd1 to xd3 may each independently be 0, 1, 2, or 3, and xd4 may be 1, 2, 3, 4, 5, or 6.

In an embodiment, $Ar_{501}$ in Formula 501 may be a condensed cyclic group (for example, an anthracene group, a chrysene group, a pyrene group, etc.) in which three or more monocyclic groups are condensed together.

In an embodiment, xd4 in Formula 501 may be 2.

In an embodiment, the fluorescent dopant may include: one of Compounds FD1 to FD37; DPVBi; DPAVBi; or any combination thereof:

FD1
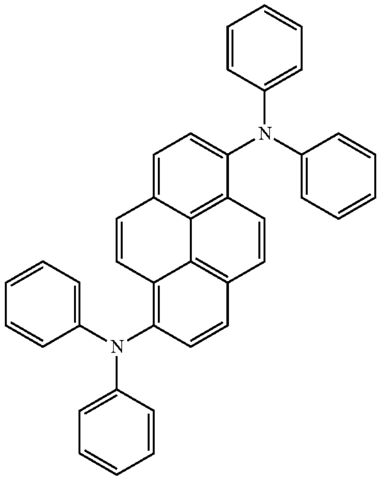
FD2
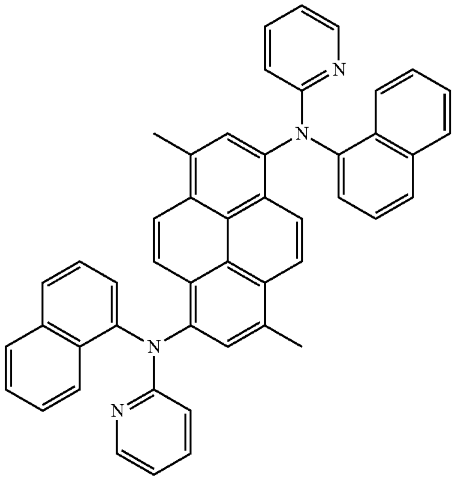
FD3
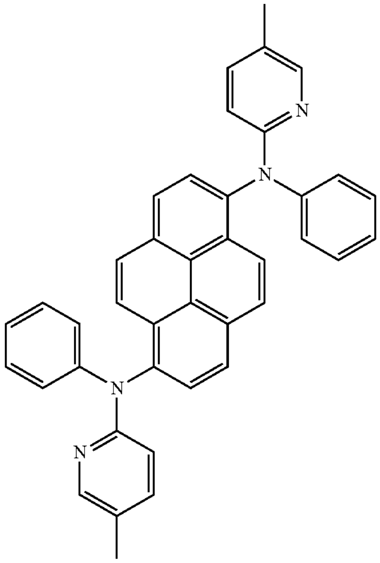
FD4
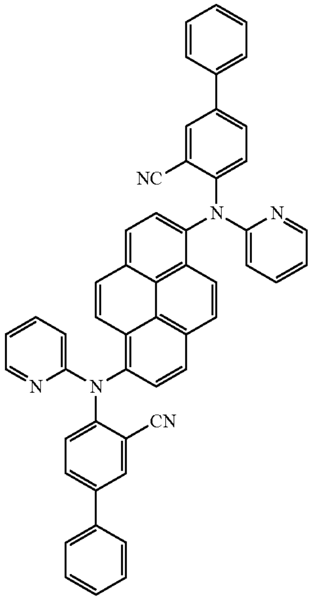
FD5
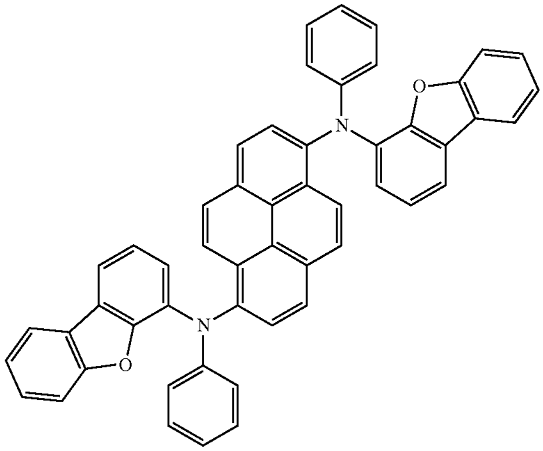
FD6
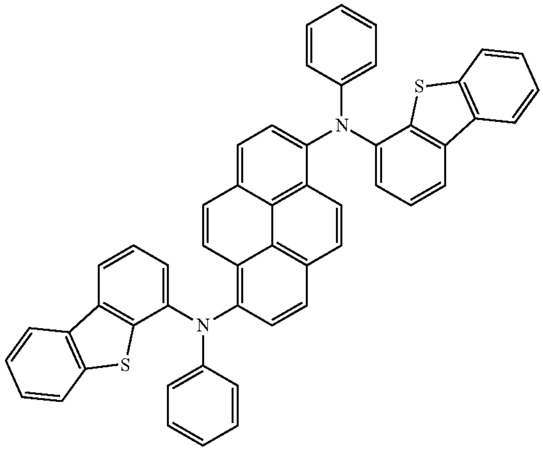

-continued
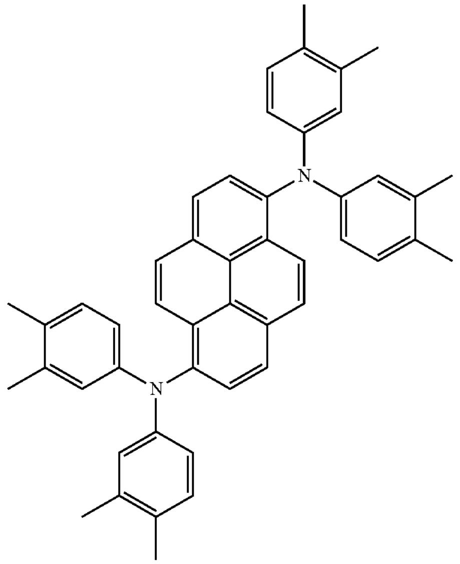
FD7
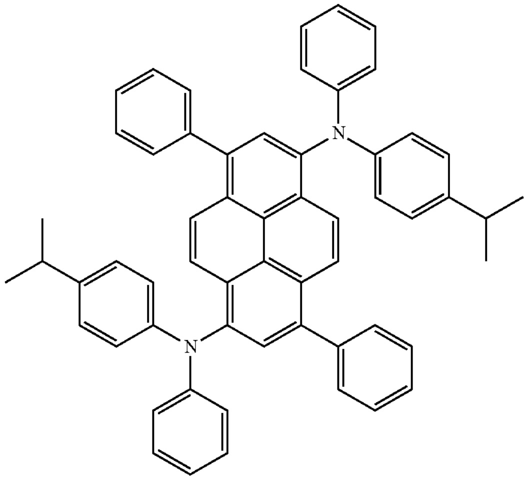
FD8
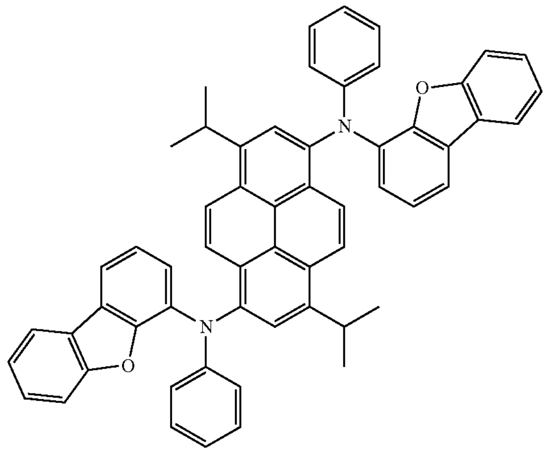
FD9
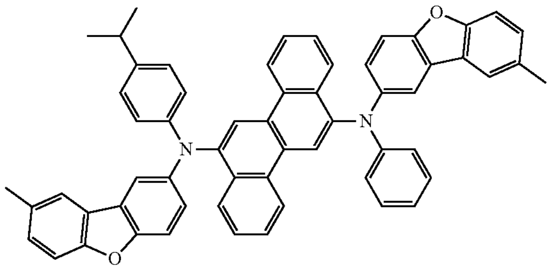
FD10
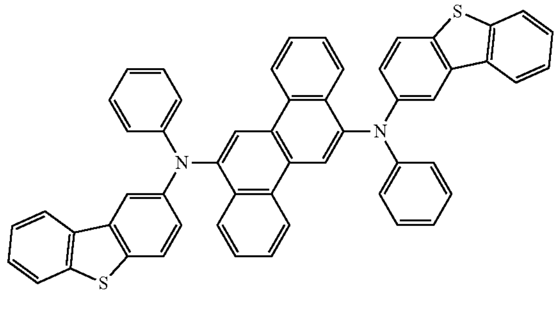
FD11
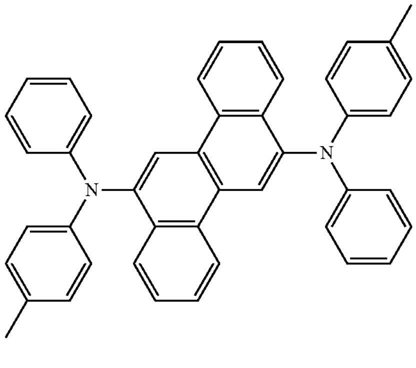
FD12

-continued
FD13
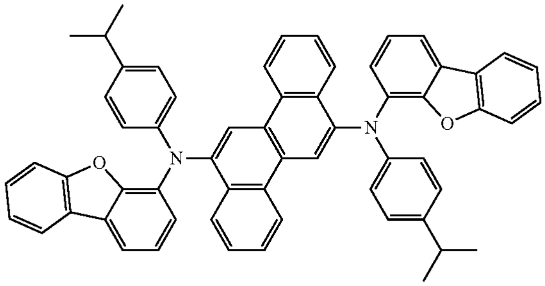
FD14
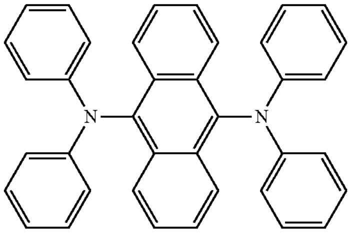
FD15
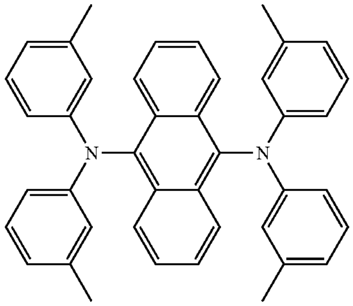
FD16
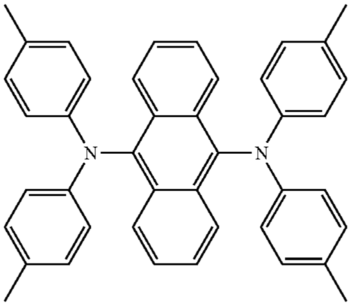
FD17
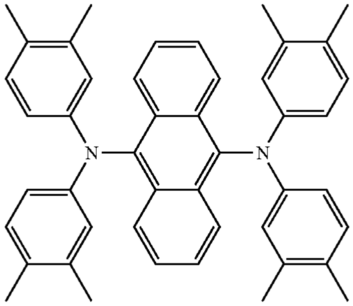
FD18
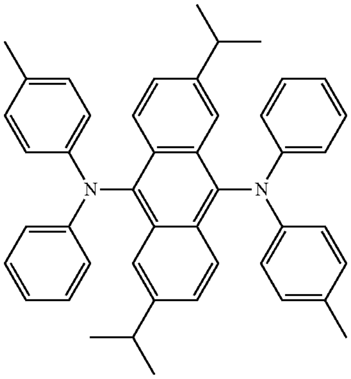
FD19
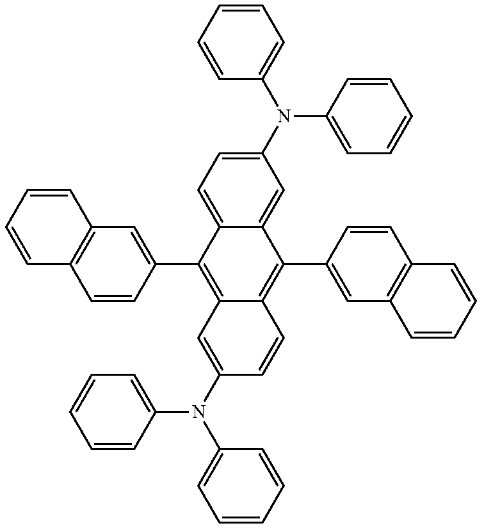
FD20
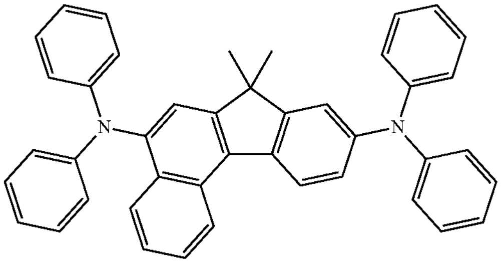

-continued
FD21
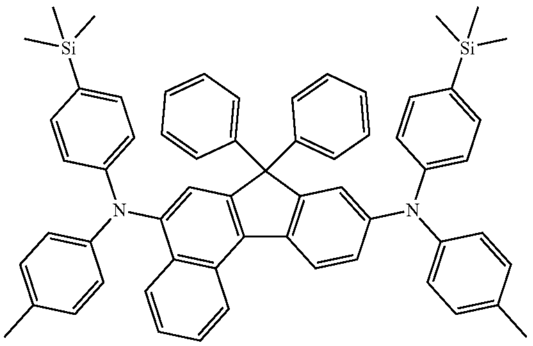
FD22
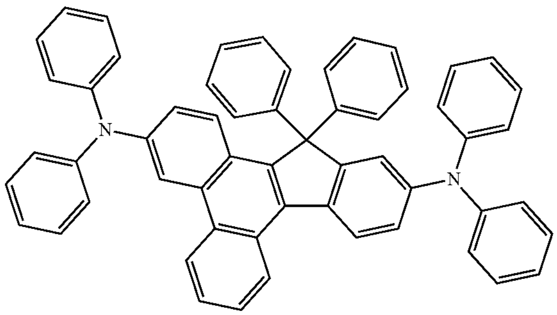
FD23
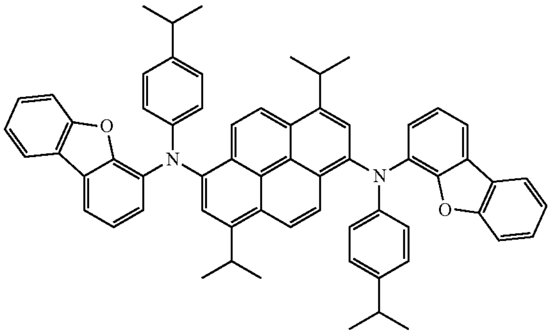
FD24
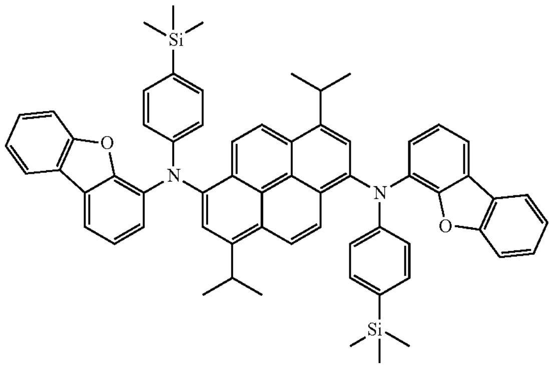
FD25
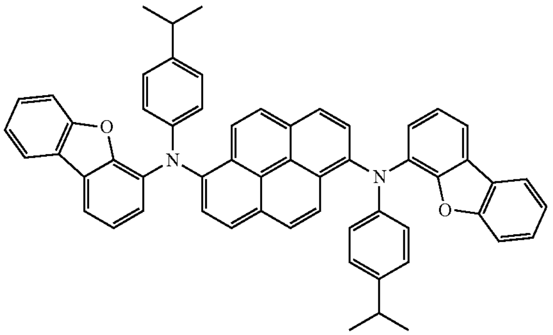
FD26
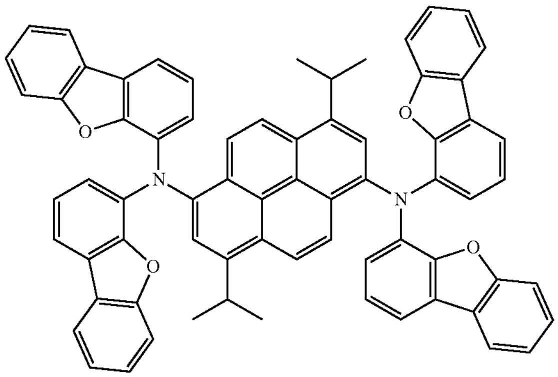
FD27
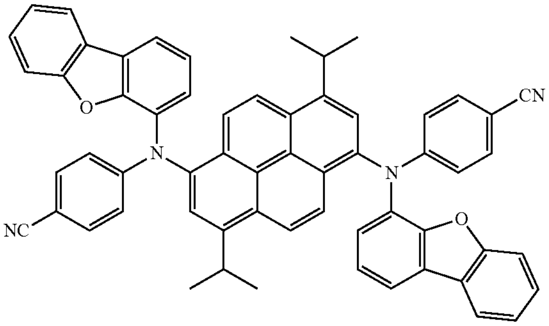
FD28
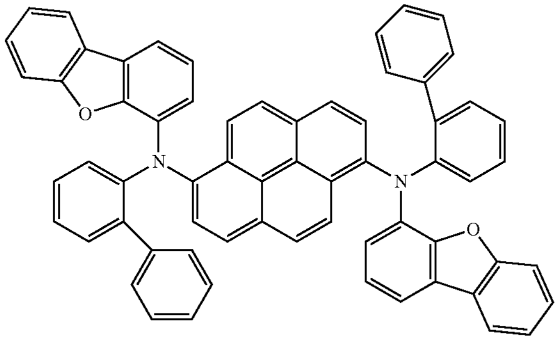

-continued
FD29
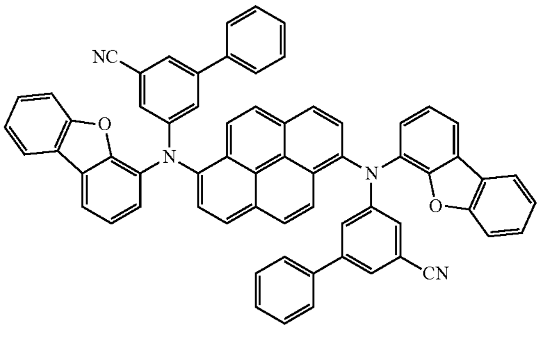
FD30
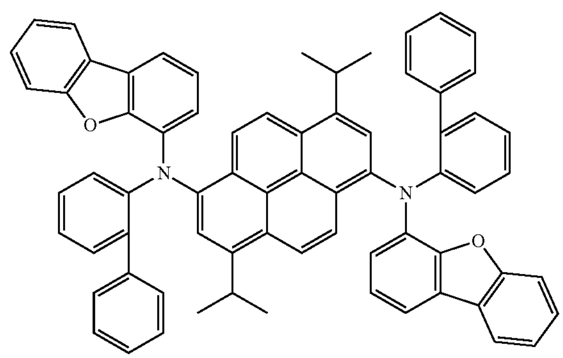
FD31
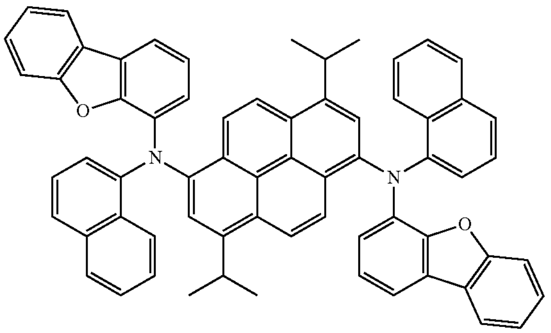
FD32
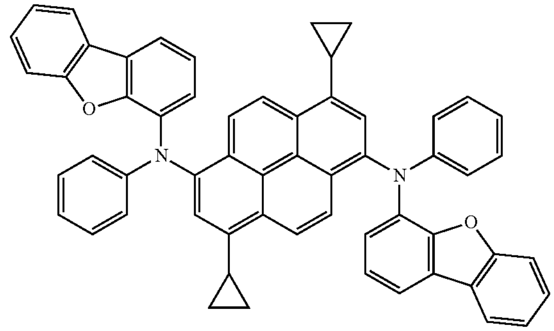
FD33
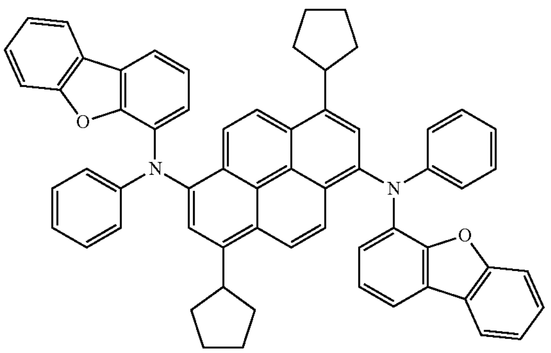
FD34
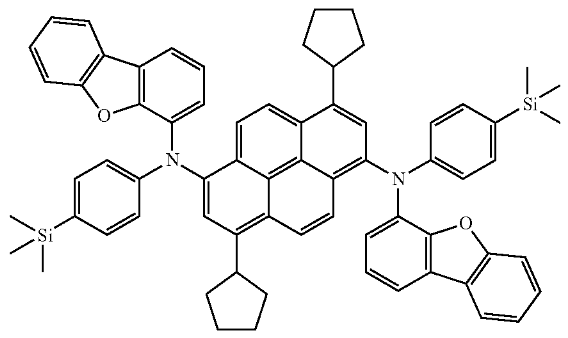
FD35
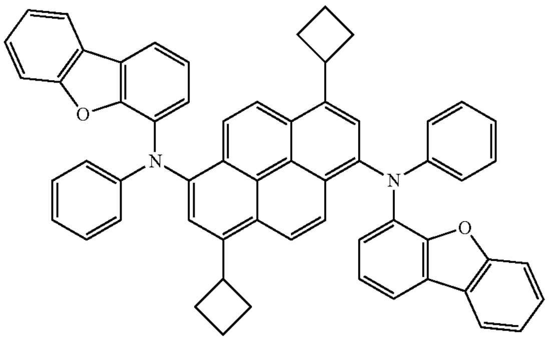
FD36
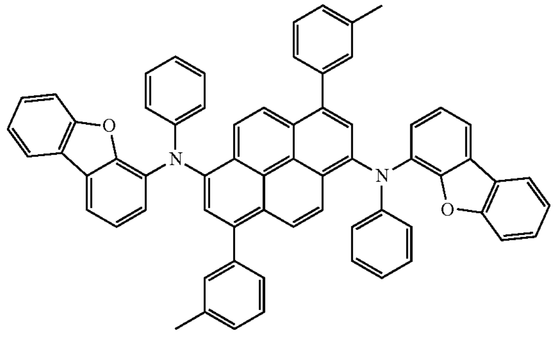

-continued

FD37

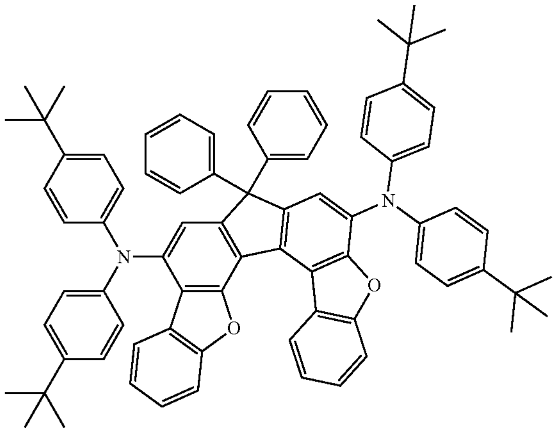

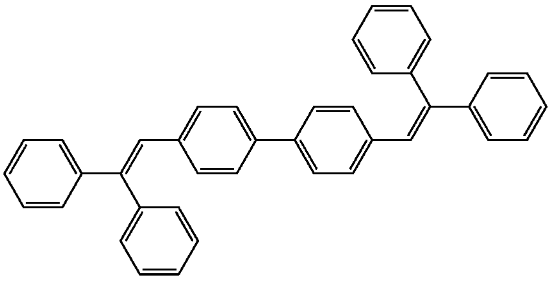

DPVBi

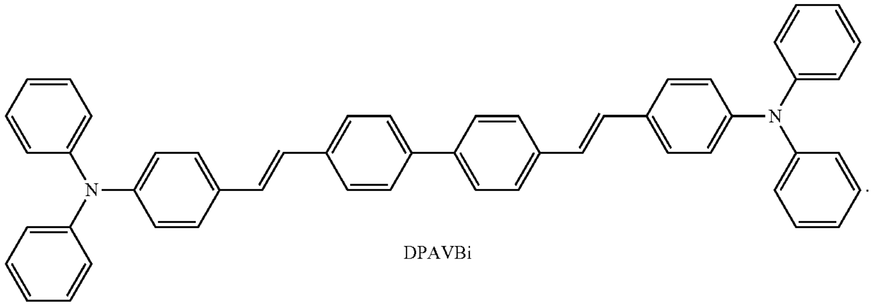

DPAVBi

[Delayed Fluorescence Material]

The emission layer may include the organic molecule according to the invention as thermally-activated delayed fluorescence (TADF) emitter materials.

The emission layer may include one or more delayed fluorescence materials other than the organic molecule according to the invention.

In the present specification, the delayed fluorescence material may be selected from compounds capable of emitting delayed fluorescence based on a delayed fluorescence emission mechanism.

The delayed fluorescence material included in the emission layer may act as a host or a dopant depending on the type of other materials included in the emission layer.

In an embodiment, a difference between a triplet energy level (eV) of the delayed fluorescence material and the singlet energy level (eV) of the delayed fluorescence material may be 0 eV or more and 0.5 eV or less. When the difference between the triplet energy level (eV) of the delayed fluorescence material and the singlet energy level (eV) of the delayed fluorescence material is satisfied within the range above, up-conversion from the triplet state to the singlet state of the delayed fluorescence materials may effectively occur, and thus, the light-emitting device 10 may have improved luminescence efficiency.

For example, the delayed fluorescence material may include: i) a material including at least one electron donor (for example, a π electron-rich $C_3$-$C_{60}$ cyclic group and the like, such as a carbazole group) and at least one electron acceptor (for example, a sulfoxide group, a cyano group, a π electron-deficient nitrogen-containing $C_1$-$C_{60}$ cyclic group, and the like), ii) a material including a $C_8$-$C_{60}$ polycyclic group including at least two cyclic groups condensed to each other while sharing boron (B), and the like.

Examples of the delayed fluorescence material may include at least one of Compounds DF1 to DF14:

DF1

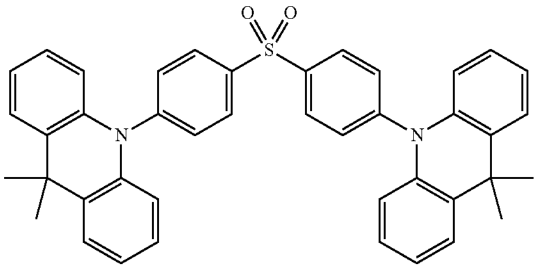

(DMAC-DPS)

DF2

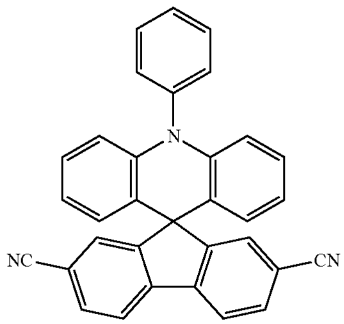

(ACRFLCN)

-continued
DF3
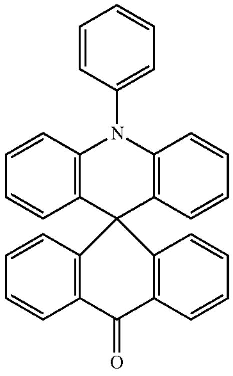
(ACRSA)
DF4
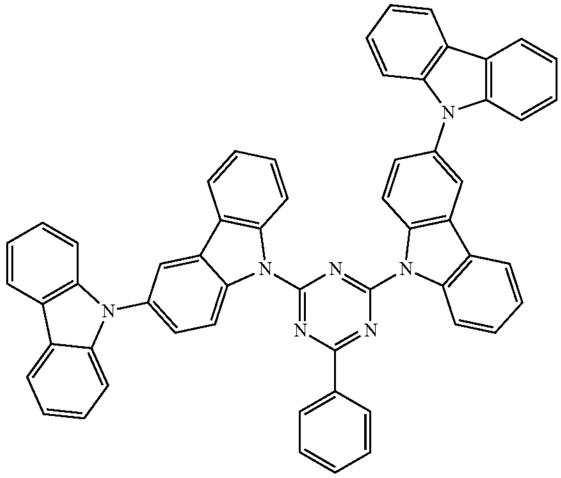
(CC2TA)
DF5
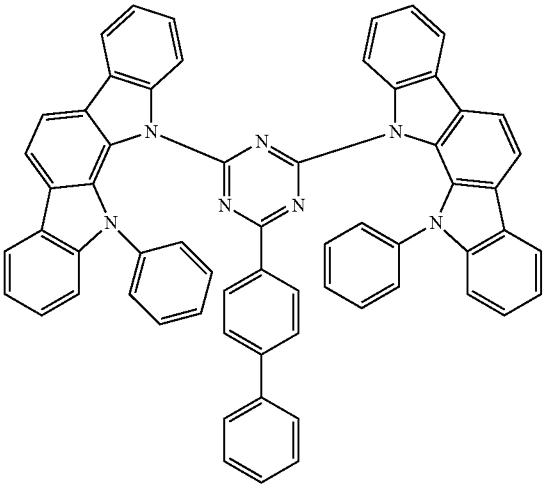
(PIC-TRZ)
-continued
DF6
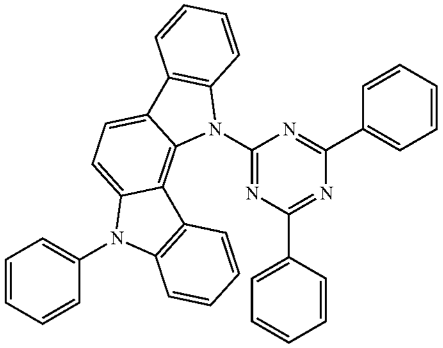
(PIC-TRZ2)
DF7
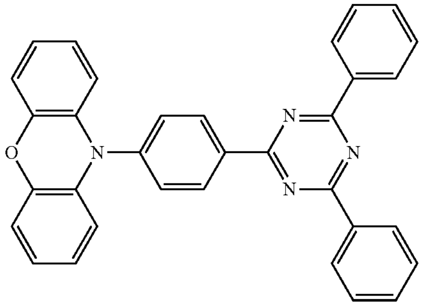
(PXZ-TRZ)
DF8
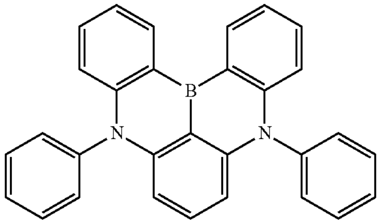
(DABNA-1)
DF9
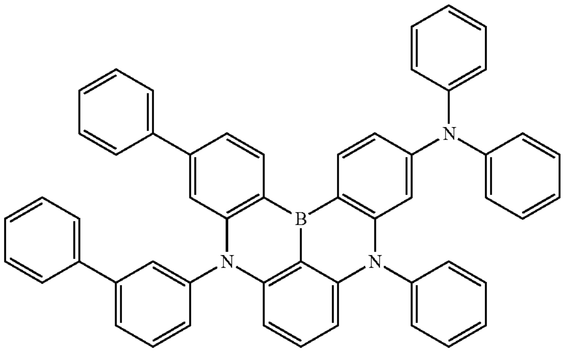
(DABNA-2)
DF10
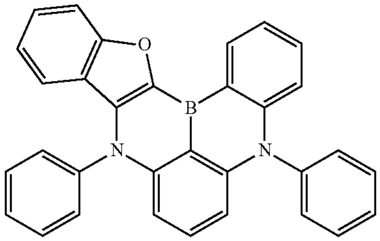

-continued

DF11

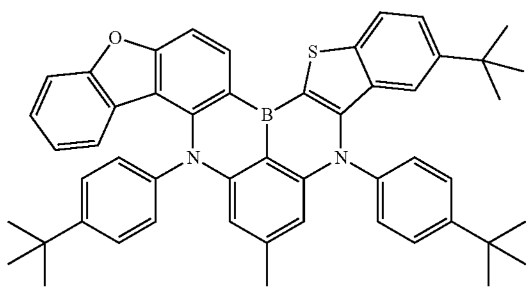

DF12

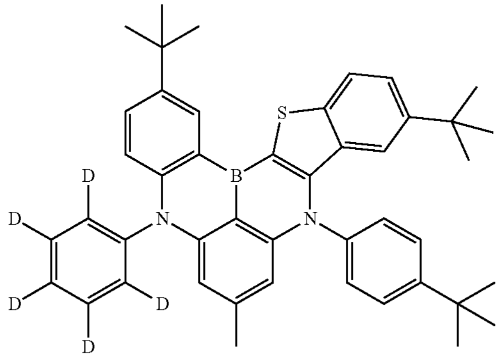

DF13

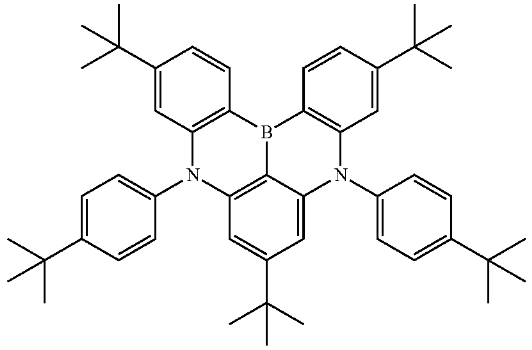

DF14

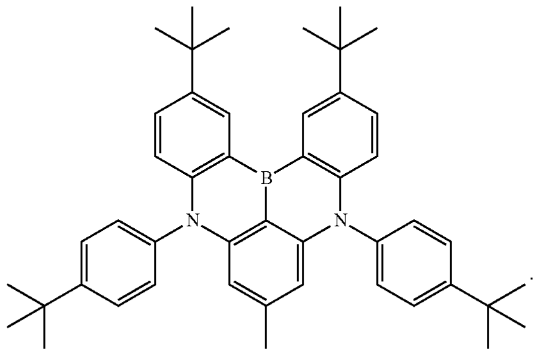

[Quantum Dot]

The emission layer may include one or more quantum dots.

The term "quantum dot" as used herein refers to a crystal of a semiconductor compound, and may include any material capable of emitting light of various emission wavelengths according to the size of the crystal.

A diameter of the quantum dot may be, for example, in a range of about 1 nm to about 10 nm.

The quantum dot may be synthesized by a wet chemical process, a metal organic chemical vapor deposition process, a molecular beam epitaxy process, or any process similar thereto. The wet chemical process is a method including mixing a precursor material with an organic solvent and then growing quantum dot particle crystals. When the crystal grows, the organic solvent naturally acts as a dispersant coordinated on the surface of the quantum dot crystal and controls the growth of the crystal so that the growth of quantum dot particles can be controlled through a process which costs lower, and is easier than vapor deposition methods, such as metal organic chemical vapor deposition (MOCVD) or molecular beam epitaxy (MBE).

The quantum dot may include: a Group II-VI semiconductor compound; a Group III-V semiconductor compound; a Group III-VI semiconductor compound; a Group I-III-VI semiconductor compound; a Group IV-VI semiconductor compound; a Group IV element or compound; or any combination thereof.

Examples of the Group II-VI semiconductor compound are: a binary compound, such as CdS, CdSe, CdTe, ZnS, ZnSe, ZnTe, ZnO, HgS, HgSe, HgTe, MgSe, MgS, and the like; a ternary compound, such as CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, MgZnS, and the like; a quaternary compound, such as CdZnSeS, CdZnSeTe, CdZnSTe, CdHgSeS, CdHgSeTe, CdHgSTe, HgZnSeS, HgZnSeTe, HgZnSTe, and the like; or any combination thereof.

Examples of the Group III-V semiconductor compound are: a binary compound, such as GaN, GaP, GaAs, GaSb, AlN, AlP, AlAs, AlSb, InN, InP, InAs, InSb, and the like; a ternary compound, such as GaNP, GaNAs, GaNSb, GaPAs, GaPSb, AlNP, AlNAs, AlNSb, AlPAs, AlPSb, InGaP, InNP, InAlP, InNAs, InNSb, InPAs, InPSb, and the like; a quaternary compound, such as GaAlNP, GaAlNAs, GaAlNSb, GaAlPAs, GaAlPSb, GaInNP, GaInNAs, GaInNSb, GaInPAs, GaInPSb, InAlNP, InAlNAs, InAlNSb, InAlPAs, InAlPSb, and the like; or any combination thereof. In an embodiment, the Group III-V semiconductor compound may further include a Group element. Examples of the Group III-V semiconductor compound further including the Group element are InZnP, InGaZnP, InAlZnP, and the like.

Examples of the Group III-VI semiconductor compound are: a binary compound, such as GaS, GaSe, $Ga_2Se_3$, GaTe, InS, InSe, $In_2S_3$, $In_2Se_3$, InTe, and the like; a ternary compound, such as $InGaS_3$, $InGaSe_3$, and the like; or any combination thereof.

Examples of the Group I-III-VI semiconductor compound are: a ternary compound, such as AgInS, $AgInS_2$, CuInS, $CuInS_2$, $CuGaO_2$, $AgGaO_2$, $AgAlO_2$, and the like; or any combination thereof.

Examples of the Group IV-VI semiconductor compound are: a binary compound, such as SnS, SnSe, SnTe, PbS, PbSe, PbTe, and the like; a ternary compound, such as SnSeS, SnSeTe, SnSTe, PbSeS, PbSeTe, PbSTe, SnPbS, SnPbSe, SnPbTe, and the like; a quaternary compound, such as SnPbSSe, SnPbSeTe, SnPbSTe, and the like; or any combination thereof. Examples of the Group IV element or compound are: a single element compound, such as Si, Ge, and the like; a binary compound, such as SiC, SiGe, and the like; or any combination thereof.

Each element included in a multi-element compound, such as the binary compound, the ternary compound, and the quaternary compound, may be present at a uniform concentration or non-uniform concentration in a particle.

In an embodiment, the quantum dot may have a single structure in which the concentration of each element in the quantum dot is uniform, or may have a core-shell dual structure. For example, a material included in the core and a material included in the shell may be different from each other.

The shell of the quantum dot may act as a protective layer which prevents chemical denaturation of the core to maintain semiconductor characteristics, and/or as a charging layer which impart electrophoretic characteristics to the quantum dot. The shell may be a single layer or a multi-layer. The interface between the core and the shell may have a concentration gradient in which the concentration of an element existing in the shell decreases toward the center of the core.

Examples of the shell of the quantum dot are an oxide of metal, metalloid, or non-metal, a semiconductor compound, or a combination thereof. Examples of the oxide of metal, metalloid, or non-metal are: a binary compound, such as $SiO_2$, $Al_2O_3$, $TiO_2$, ZnO, MnO, $Mn_2O_3$, $Mn_3O_4$, CuO, FeO, $Fe_2O_3$, $Fe_3O_4$, CoO, $Co_3O_4$, NiO, and the like; a ternary compound, such as $MgAl_2O_4$, $CoFe_2O_4$, $NiFe_2O_4$, $CoMn_2O_4$, and the like; or any combination thereof. Examples of the semiconductor compound are: as described herein, a Group II-VI semiconductor compound; a Group III-V semiconductor compound; a Group III-VI semiconductor compound; a Group I-III-VI semiconductor compound; a Group IV-VI semiconductor compound; or any combination thereof. Examples of the semiconductor compound are CdS, CdSe, CdTe, ZnS, ZnSe, ZnTe, ZnSeS, ZnTeS, GaAs, GaP, GaSb, HgS, HgSe, HgTe, InAs, InP, InGaP, InSb, AlAs, AlP, AlSb, or any combination thereof.

The quantum dot may have a full width of half maximum (FWHM) of the emission wavelength spectrum of about 45 nm or less, about 40 nm or less, or for example, about 30 nm or less. When the FWHM of the quantum dot is within these ranges, the quantum dot may have improved color purity or color reproducibility. In addition, since light emitted through the quantum dot is emitted in all directions, the wide viewing angle may be improved.

In addition, the quantum dot may be in the form of spherical, pyramidal, multi-arm, or cubic nanoparticles, nanotubes, nanowires, nanofibers, or nanoplate particles.

Since the energy band gap may be adjusted by controlling the size of the quantum dot, light having various wavelength bands may be obtained from the quantum dot emission layer. Accordingly, by using quantum dot of different sizes, a light-emitting device that emits light of various wavelengths may be implemented. In an embodiment, the size of the quantum dot may be selected to emit red, green and/or blue light. In addition, the size of the quantum dot may be configured to emit white light by combination of light of various colors.

[Electron Transport Region in Interlayer 130]

The electron transport region may have: i) a single layer structure consisting of a single layer consisting of a single material, ii) a single layer structure consisting of a single layer consisting of a plurality of different materials, or iii) a multi-layer structure including a plurality of layers including different materials.

The electron transport region may include a buffer layer, a hole blocking layer, an electron control layer, an electron transport layer, an electron injection layer, or any combination thereof. For example, the electron transport region may have an electron transport layer/electron injection layer structure, a hole blocking layer/electron transport layer/electron injection layer structure, an electron control layer/electron transport layer/electron injection layer structure, or a buffer layer/electron transport layer/electron injection layer structure, wherein constituent layers of each structure are sequentially stacked from the emission layer.

In an embodiment, the electron transport region (for example, the buffer layer, the hole blocking layer, the electron control layer, or the electron transport layer in the electron transport region) may include a metal-free compound including at least one π electron-deficient nitrogen-containing $C_1$-$C_{60}$ cyclic group.

For example, the electron transport region may include at least one of the third compound and the fourth compound.

In one or more embodiments, the electron transport region may include a compound represented by Formula 601:

Formula 601

$$[Ar_{601}]_{xe11}-[(L_{601})_{xe1}-R_{601}]_{xe21}$$

wherein, in Formula 601, $Ar_{601}$ and $L_{601}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, xe11 may be 1, 2, or 3, xe1 may be 0, 1, 2, 3, 4, or 5, $R_{601}$ may be a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, $-Si(Q_{601})(Q_{602})(Q_{603})$, $-C(=O)(Q_{601})$, $-S(=O)_2(Q_{601})$, or $-P(=O)(Q_{601})(Q_{602})$, $Q_{601}$ to $Q_{603}$ may each be the same as described in connection with $Q_1$, xe21 may be 1, 2, 3, 4, or 5, and at least one of $Ar_{601}$, $L_{601}$, and $R_{601}$ may each independently be a π electron-deficient nitrogen-containing $C_1$-$C_{60}$ cyclic group unsubstituted or substituted with at least one $R_{10a}$.

For example, when xe11 in Formula 601 is 2 or more, two or more of $Ar_{601}$ may be bonded to each other via a single bond.

In an embodiment, $Ar_{601}$ in Formula 601 may be a substituted or unsubstituted anthracene group.

In one or more embodiments, the electron transport region may include a compound represented by Formula 601-1:

Formula 601-1

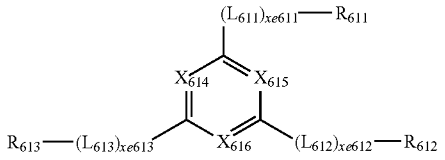

wherein, in Formula 601-1, $X_{614}$ may be N or $C(R_{614})$, $X_{615}$ may be N or $C(R_{615})$, $X_{616}$ may be N or $C(R_{616})$, and at least one of $X_{614}$ to $X_{616}$ may be N, $L_{611}$ to $L_{613}$ may each be the same as described in connection with $L_{601}$, xe611 to xe613 may each be the same as described in connection with xe1, $R_{611}$ to $R_{613}$ may each be the same as described in connection with $R_{601}$, and $R_{614}$ to $R_{616}$ may each independently be hydrogen, deuterium, —F, —Cl, —Br, —I, a hydroxyl group, a cyano group, a nitro group, a $C_1$-$C_{20}$ alkyl group, a $C_1$-$C_{20}$ alkoxy group, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$.

For example, xe1 and xe611 to xe613 in Formulae 601 and 601-1 may each independently be 0, 1, or 2.

The electron transport region may include one of Compounds ET1 to ET45, 2,9-dimethyl-4,7-diphenyl-1,10-phenanthroline (BCP), 4,7-diphenyl-1,10-phenanthroline (Bphen), $Alq_3$, BAlq, TAZ, NTAZ, or any combination thereof:

ET1

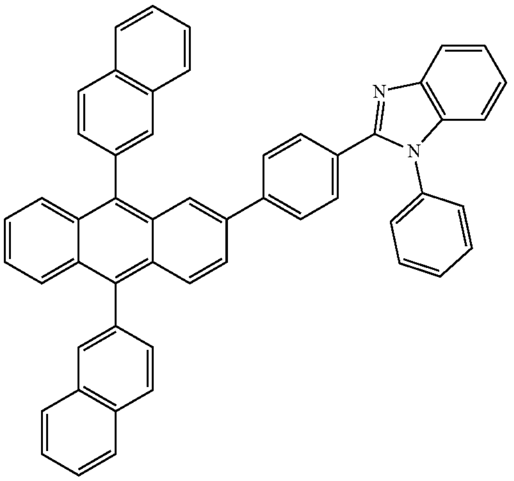

ET2

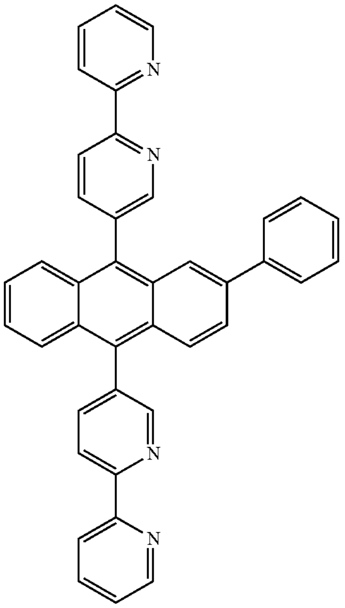

-continued

ET3

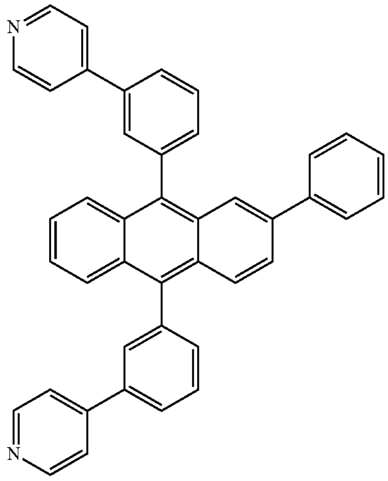

ET4

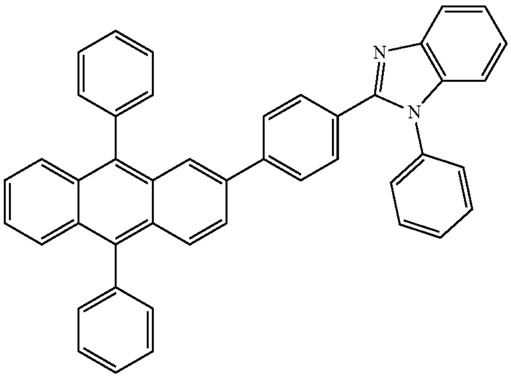

ET5

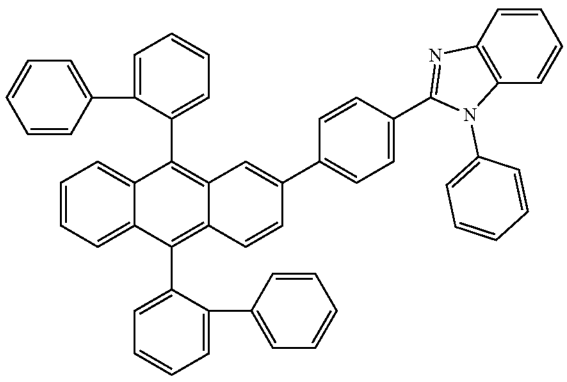

-continued
ET6
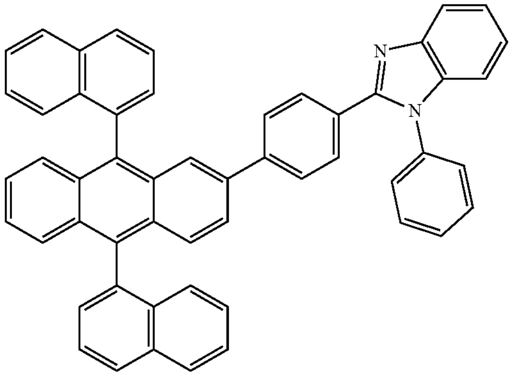
ET7
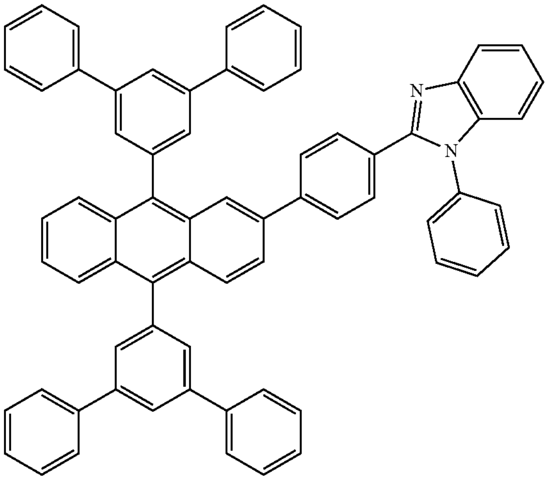
ET8
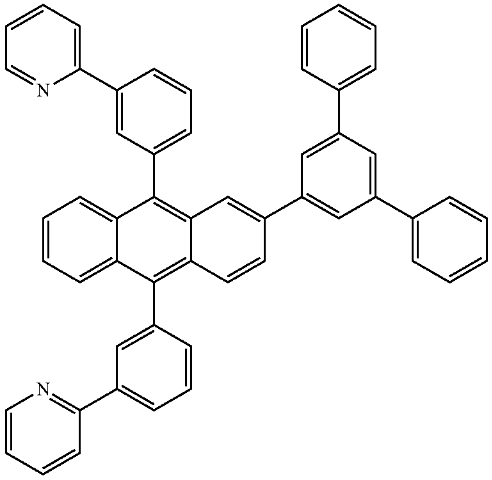
-continued
ET9
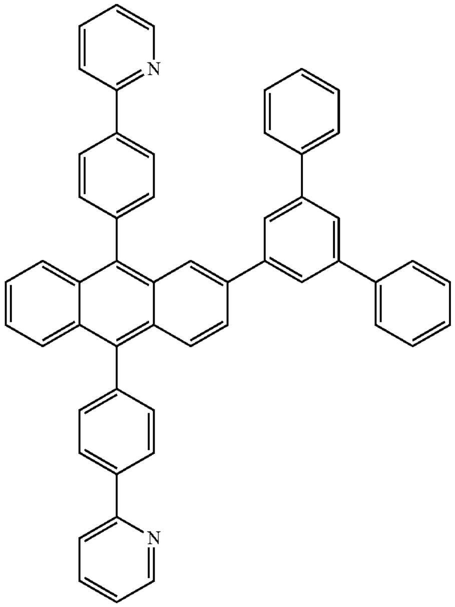
ET10
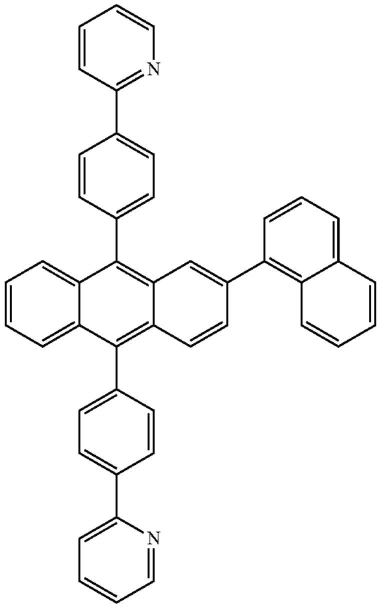

-continued
ET11
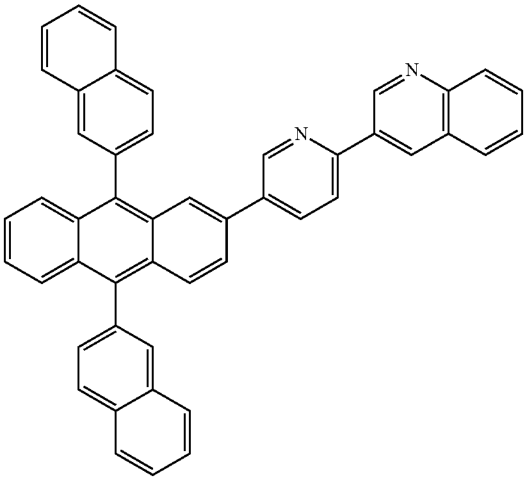
ET12
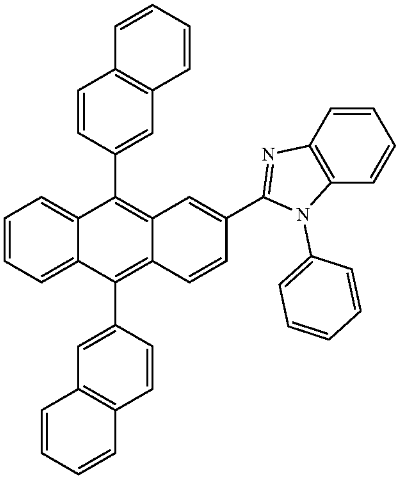
ET13
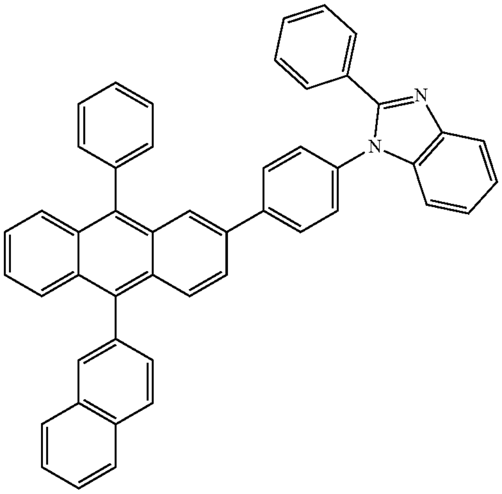
-continued
ET14
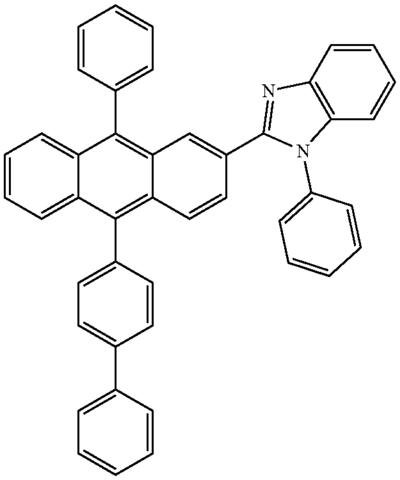
ET15
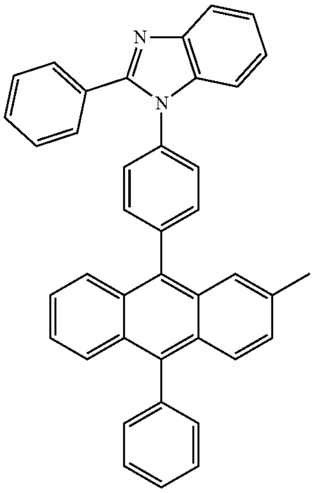
ET16
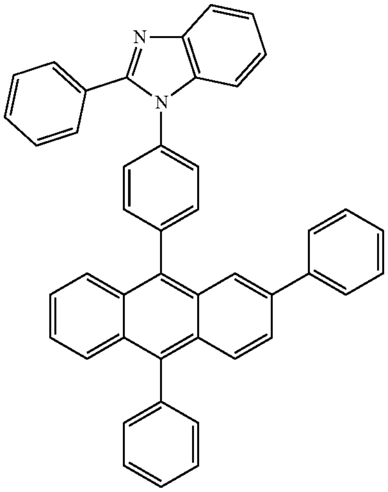

-continued
ET17
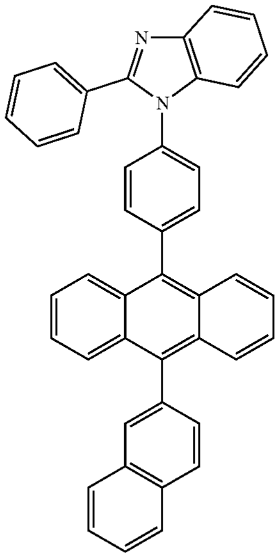
ET18
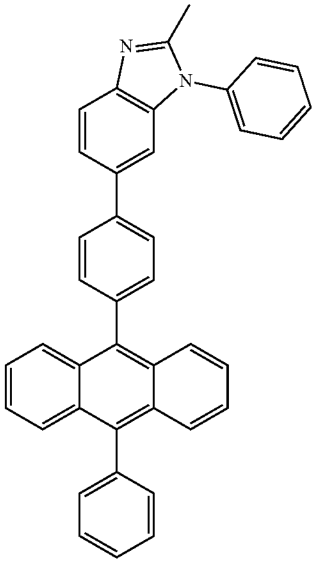
ET19
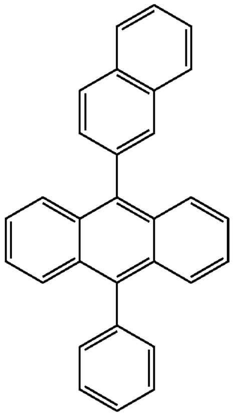
-continued
ET20
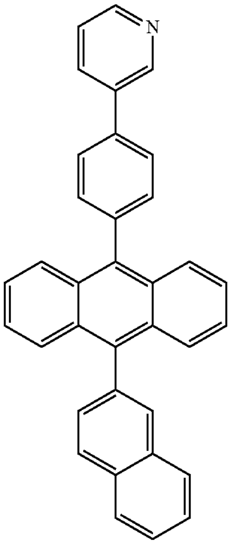
ET21
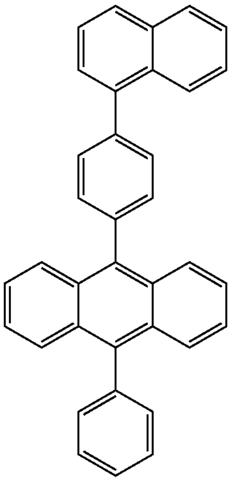
ET22
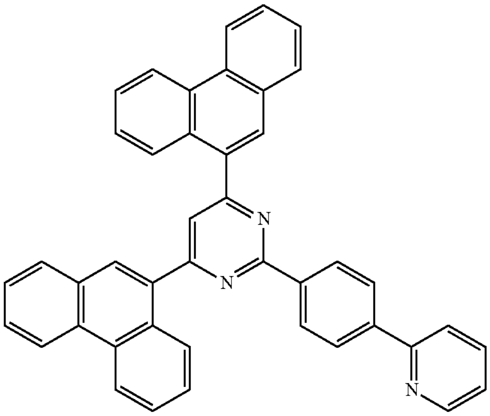

-continued
ET23
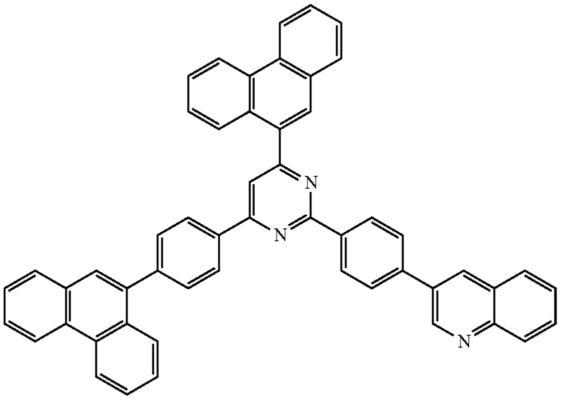
ET24
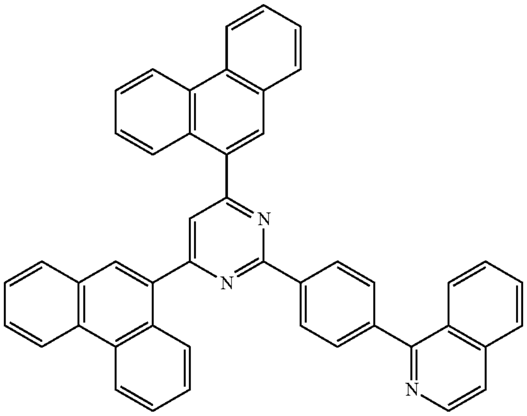
ET25
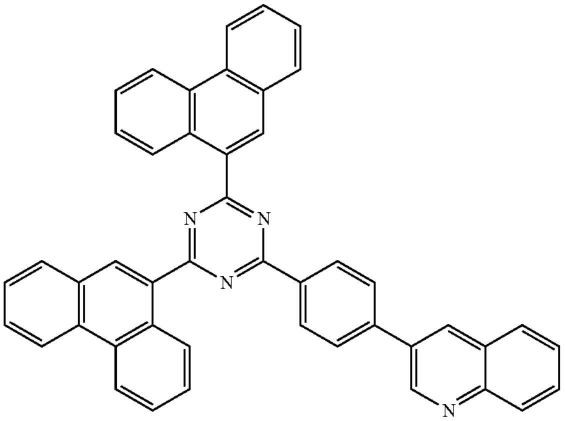
-continued
ET26
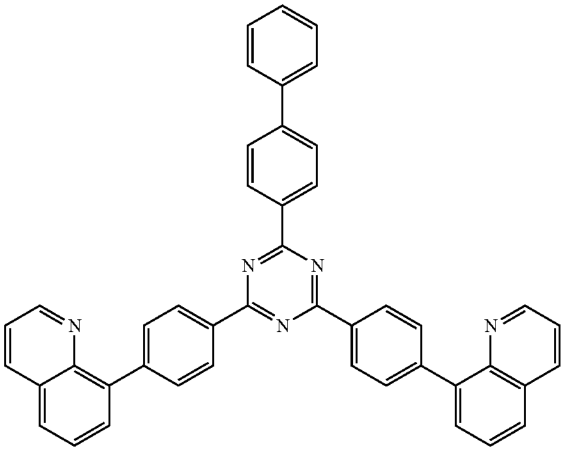
ET27
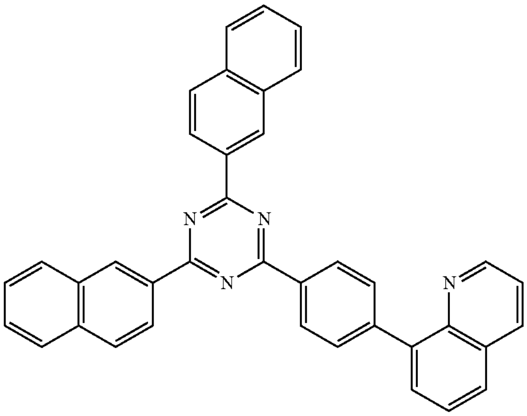
ET28
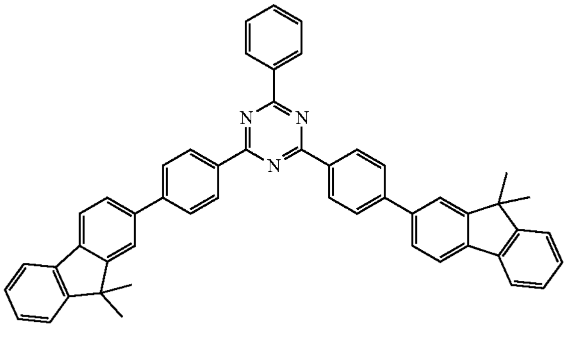

-continued
ET29
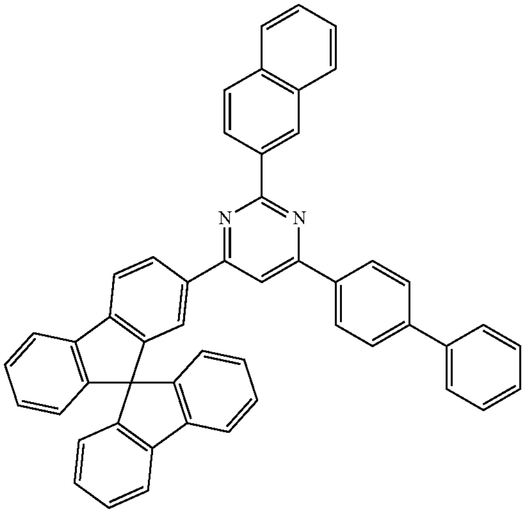
ET30
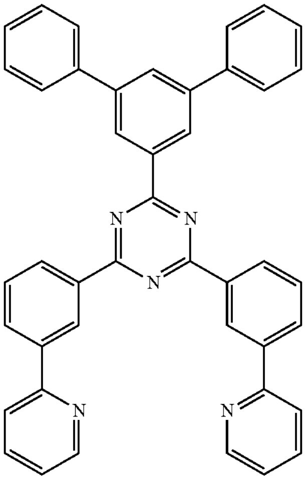
ET31
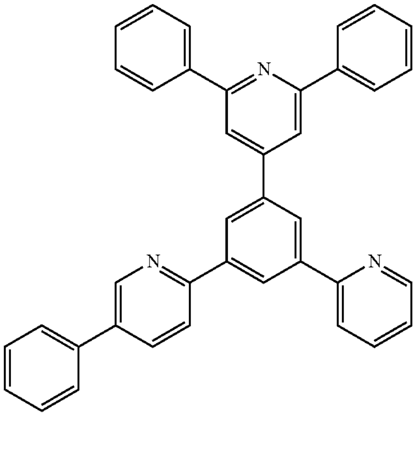
-continued
ET32
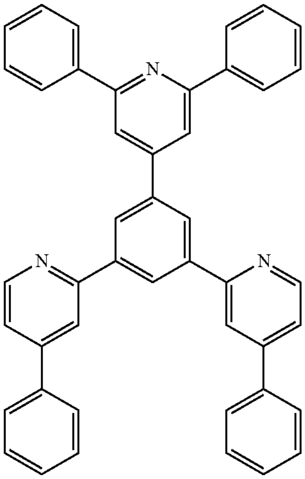
ET33
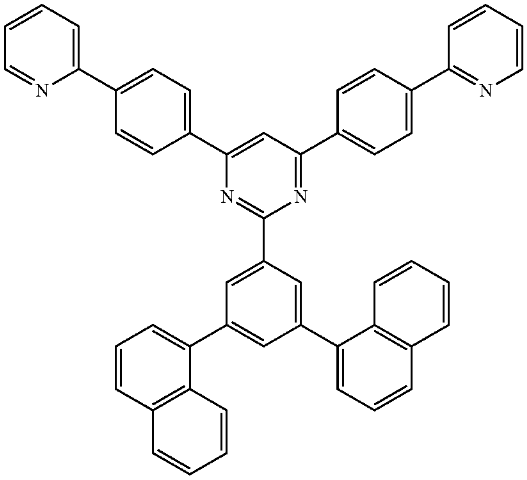
ET34
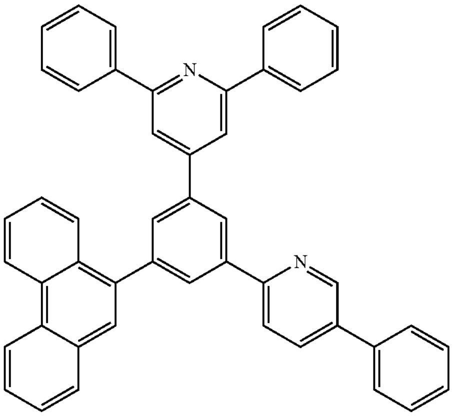

-continued
ET35
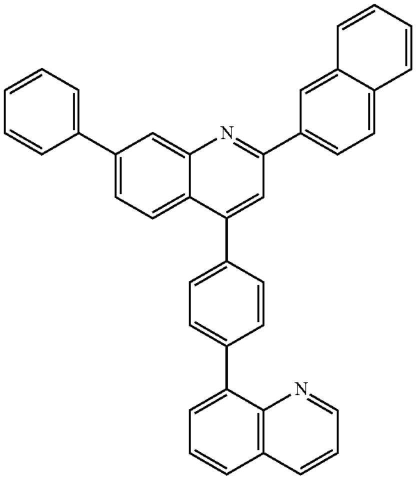
ET36
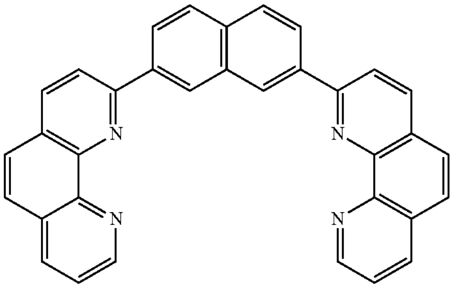
ET37
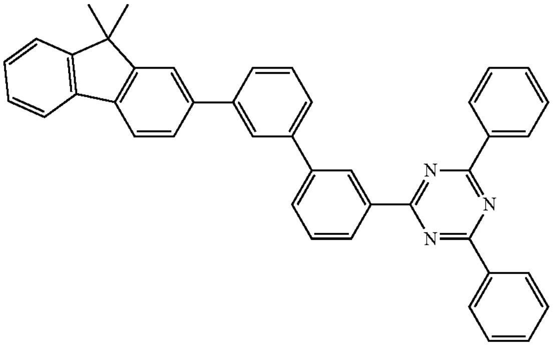
ET38
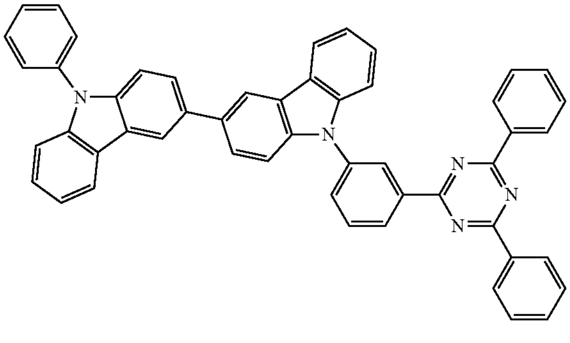
-continued
ET39
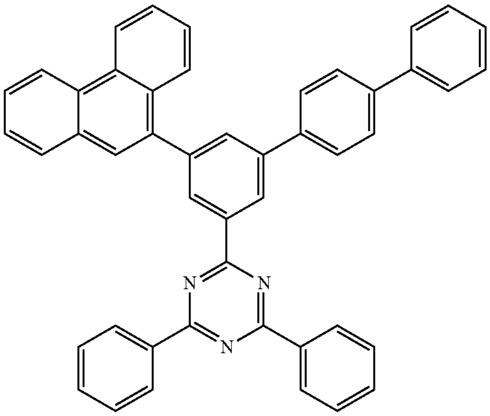
ET40
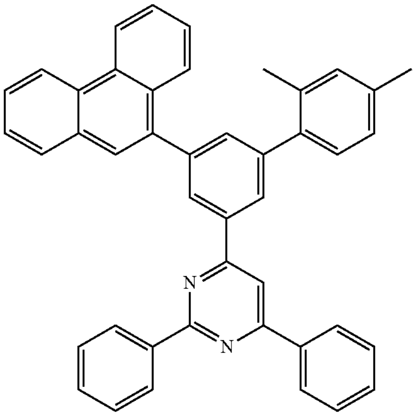
ET41
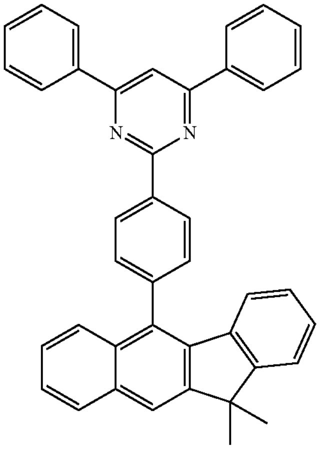

-continued

ET42

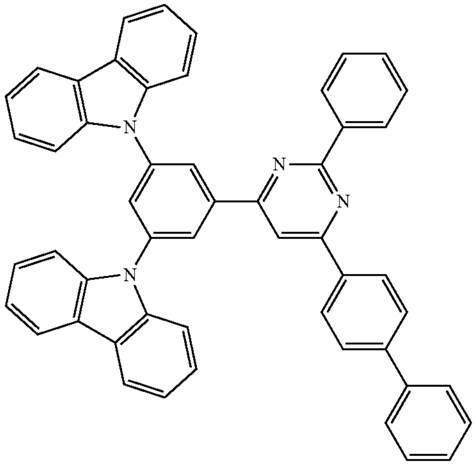

ET43

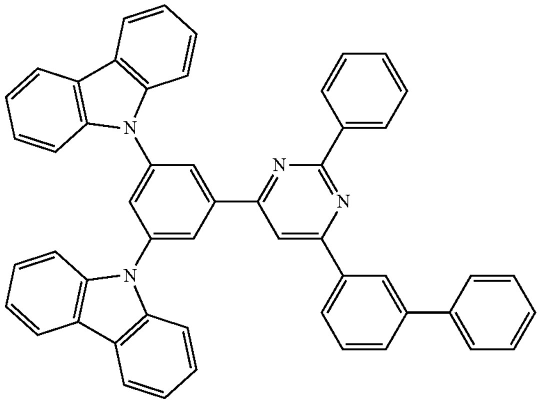

ET44

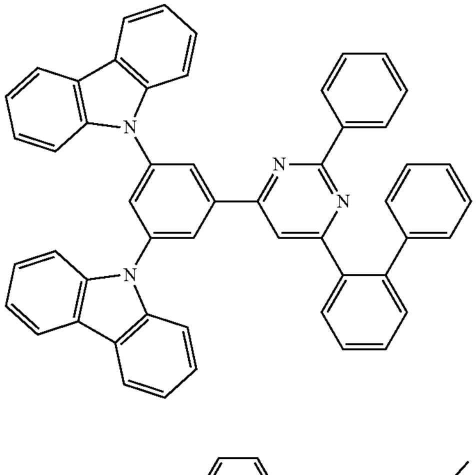

ET45

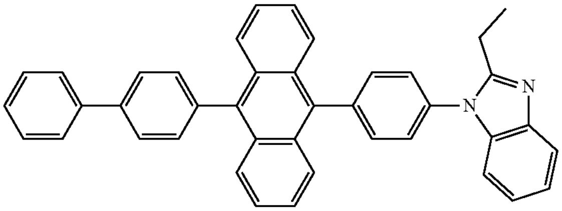

-continued

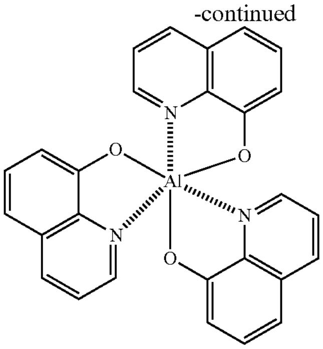

Alq3

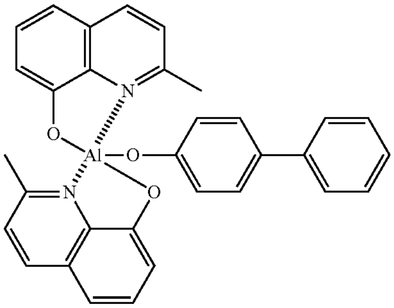

BAlq

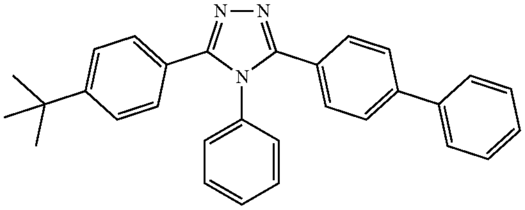

TAZ

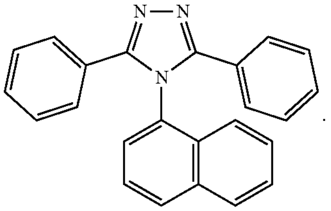

NTAZ

A thickness of the electron transport region may be in a range of about 100 Å to about 5,000 Å, for example, about 160 Å to about 4,000 Å. When the electron transport region includes a buffer layer, a hole blocking layer, an electron control layer, an electron transport layer, or any combination thereof, a thickness of the buffer layer, the hole blocking layer, or the electron control layer may be in a range of about 20 Å to about 1,000 Å, for example, about 30 Å to about 300 Å, and a thickness of the electron transport layer may be in a range of about 100 Å to about 1,000 Å, for example, about 150 Å to about 500 Å. When the thicknesses of the buffer layer, the hole blocking layer, the electron control layer, the electron transport layer, and/or the electron transport region are within these ranges, satisfactory electron transporting characteristics may be obtained without a substantial increase in driving voltage.

The electron transport region (for example, the electron transport layer in the electron transport region) may further include, in addition to the materials described above, a metal-containing material.

The metal-containing material may include an alkali metal complex, an alkaline earth metal complex, or any combination thereof. The metal ion of an alkali metal complex may be a Li ion, a Na ion, a K ion, a Rb ion, or a Cs ion, and the metal ion of an alkaline earth metal complex may be a Be ion, a Mg ion, a Ca ion, a Sr ion, or a Ba ion. A ligand coordinated with the metal ion of the alkali metal complex or the alkaline earth-metal complex may include hydroxyquinoline, hydroxyisoquinoline, hydroxybenzoquinoline, hydroxyacridine, hydroxyphenanthridine, hydroxyphenyloxazole, hydroxyphenylthiazole, hydroxyphenyloxadiazole, hydroxyphenylthiadiazole, hydroxyphenylpyridine, hydroxyphenylbenzimidazole, hydroxyphenylbenzothiazole, bipyridine, phenanthroline, cyclopentadiene, or any combination thereof.

For example, the metal-containing material may include a Li complex. The Li complex may include, for example, Compound ET-D1 (LiQ) or ET-D2:

ET-D1

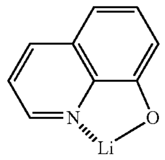

ET-D2

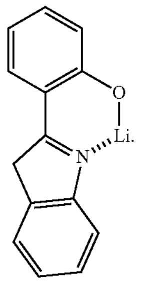

The electron transport region may include an electron injection layer that facilitates the injection of electrons from the second electrode 150. The electron injection layer may directly contact the second electrode 150.

The electron injection layer may have: i) a single-layer structure consisting of a single layer consisting of a single material, ii) a single-layer structure consisting of a single layer consisting of multiple materials that are different from each other, or iii) a multi-layer structure including multiple layers including multiple different materials that are different from each other.

The electron injection layer may include an alkali metal, alkaline earth metal, a rare earth metal, an alkali metal-containing compound, alkaline earth metal-containing compound, a rare earth metal-containing compound, an alkali metal complex, an alkaline earth metal complex, a rare earth metal complex, or any combination thereof.

The alkali metal may include Li, Na, K, Rb, Cs, or any combination thereof. The alkaline earth metal may include Mg, Ca, Sr, Ba, or any combination thereof. The rare earth metal may include Sc, Y, Ce, Tb, Yb, Gd, or any combination thereof.

The alkali metal-containing compound, the alkaline earth metal-containing compound, and the rare earth metal-containing compound may be oxides, halides (for example, fluorides, chlorides, bromides, iodides, etc.), or tellurides of the alkali metal, the alkaline earth metal, and the rare earth metal, or any combination thereof.

The alkali metal-containing compound may include: an alkali metal oxide, such as $Li_2O$, $Cs_2O$, $K_2O$, and the like; alkali metal halides, such as LiF, NaF, CsF, KF, LiI, NaI, CsI, KI, and the like; or any combination thereof. The alkaline earth metal-containing compound may include an alkaline earth metal compound, such as BaO, SrO, CaO, $Ba_xSr_{1-x}O$ (wherein x is a real number satisfying $0<x<1$), $Ba_xCa_{1-x}O$ (wherein x is a real number satisfying $0<x<1$), and the like. The rare earth metal-containing compound may include $YbF_3$, $ScF_3$, $Sc_2O_3$, $Y_2O_3$, $Ce_2O_3$, $GdF_3$, $TbF_3$, $YbI_3$, $ScI_3$, $TbI_3$, or any combination thereof. In an embodiment, the rare earth metal-containing compound may include lanthanide metal telluride. Examples of the lanthanide metal telluride are LaTe, CeTe, PrTe, NdTe, PmTe, SmTe, EuTe, GdTe, TbTe, DyTe, HoTe, ErTe, TmTe, YbTe, LuTe, $La_2Te_3$, $Ce_2Te_3$, $Pr_2Te_3$, $Nd_2Te_3$, $Pm_2Te_3$, $Sm_2Te_3$, $Eu_2Te_3$, $Gd_2Te_3$, $Tb_2Te_3$, $Dy_2Te_3$, $Ho_2Te_3$, $Er_2Te_3$, $Tm_2Te_3$, $Yb_2Te_3$, $Lu_2Te_3$, and the like.

The alkali metal complex, the alkaline earth-metal complex, and the rare earth metal complex may include i) one of ions of the alkali metal, the alkaline earth metal, and the rare earth metal and ii), as a ligand bonded to the metal ion, for example, hydroxyquinoline, hydroxyisoquinoline, hydroxybenzoquinoline, hydroxyacridine, hydroxyphenanthridine, hydroxyphenyloxazole, hydroxyphenylthiazole, hydroxyphenyloxadiazole, hydroxyphenylthiadiazole, hydroxyphenylpyridine, hydroxyphenyl benzimidazole, hydroxyphenylbenzothiazole, bipyridine, phenanthroline, cyclopentadiene, or any combination thereof.

In an embodiment, the electron injection layer may consist of an alkali metal, an alkaline earth metal, a rare earth metal, an alkali metal-containing compound, an alkaline earth metal-containing compound, a rare earth metal-containing compound, an alkali metal complex, an alkaline earth metal complex, a rare earth metal complex, or any combination thereof, as described above. In one or more embodiments, the electron injection layer may further include an organic material (for example, a compound represented by Formula 601).

In an embodiment, the electron injection layer may consist of i) an alkali metal-containing compound (for example, alkali metal halide), ii) a) an alkali metal-containing compound (for example, alkali metal halide); and b) an alkali metal, an alkaline earth metal, a rare earth metal, or any combination thereof. For example, the electron injection layer may be a KI:Yb co-deposited layer, an RbI:Yb co-deposited layer, a LiF:Yb co-deposited layer, and the like.

When the electron injection layer further includes an organic material, an alkali metal, an alkaline earth metal, a rare earth metal, an alkali metal-containing compound, an alkaline earth metal-containing compound, a rare earth metal-containing compound, an alkali metal complex, an alkaline earth-metal complex, a rare earth metal complex, or any combination thereof may be uniformly or non-uniformly dispersed in a matrix including the organic material.

A thickness of the electron injection layer may be in a range of about 1 Å to about 100 Å, and, for example, about 3 Å to about 90 Å. When the thickness of the electron injection layer is within the ranges above, satisfactory electron injection characteristics may be obtained without a substantial increase in driving voltage.

Adjacent to the emission layer EML an electron transport layer (ETL) may be located. Herein, any electron transporter may be used. Exemplarily, electron-poor compounds such as, e.g., benzimidazoles, pyridines, triazoles, oxadiazoles (e.g., 1,3,4-oxadiazole), phosphinoxides and sulfone, may be used. An electron transporter may also be a star-shaped heterocycle such as 1,3,5-tri(1-phenyl-1H-benzo[d]imidazol-2-yl)phenyl (TPBi). The ETL may comprise NBphen (2,9-bis(naphthalen-2-yl)-4,7-diphenyl-1,10-phenanthroline), $Alq_3$ (Aluminum-tris(8-hydroxyquinoline)), TSPO1 (diphenyl-4-triphenylsilylphenyl-phosphinoxide), BPyTP2 (2,7-di(2,2'-bipyridin-5-yl)triphenyle), Sif87 (dibenzo[b,d]thiophen-2-yltriphenylsilane), Sif88 (dibenzo[b,d]thiophen-2-yl)diphenylsilane), BmPyPhB (1,3-bis[3,5-di(pyridin-3-yl)phenyl]benzene) and/or BTB (4,4'-bis-[2-(4,6-diphenyl-1,3,5-triazinyl)]-1,1'-biphenyl). Optionally, the ETL may be doped with materials such as Liq. The electron transport layer (ETL) may also block holes or a holeblocking layer (HBL) is introduced.

The HBL may exemplarily comprise BCP (2,9-dimethyl-4,7-diphenyl-1,10-phenanthroline=Bathocuproine), BAlq (bis(8-hydroxy-2-methylquinoline)-(4-phenylphenoxy)aluminum), NBphen (2,9-bis(naphthalen-2-yl)-4,7-diphenyl-1,10-phenanthroline), $Alq_3$ (Aluminum-tris(8-hydroxyquinoline)), TSPO1 (diphenyl-4-triphenylsilylphenyl-phosphinoxide), T2T (2,4,6-tris(biphenyl-3-yl)-1,3,5-triazine), T3T (2,4,6-tris(triphenyl-3-yl)-1,3,5-triazine), TST (2,4,6-tris(9,9'-spirobifluorene-2-yl)-1,3,5-triazine), and/or TCB/TCP (1,3,5-tris(N-carbazolyl)benzol/1,3,5-tris (carbazol)-9-yl) benzene).

[Second Electrode 150]

The second electrode 150 may be arranged on the interlayer 130 having a structure as described above. The second electrode 150 may be a cathode, which is an electron injection electrode, and as a material for forming the second electrode 150, a metal, an alloy, an electrically conductive compound, or any combination thereof, each having a low-work function, may be used.

The second electrode 150 may include lithium (Li), silver (Ag), magnesium (Mg), aluminum (Al), aluminum-lithium (Al—Li), calcium (Ca), magnesium-indium (Mg—In), magnesium-silver (Mg—Ag), ytterbium (Yb), silver-ytterbium (Ag—Yb), ITO, IZO, or any combination thereof. The second electrode 150 may be a transmissive electrode, a semi-transmissive electrode, or a reflective electrode.

The second electrode 150 may have a single layer structure or a multi-layer structure including a plurality of layers.

Adjacent to the electron transport layer (ETL), a second electrode 150 may be located. Exemplarily, the second electrode 150 may comprise or may consist of a metal (e.g., Al, Au, Ag, Pt, Cu, Zn, Ni, Fe, Pb, LiF, Ca, Ba, Mg, In, W, or Pd) or a metal alloy. For practical reasons, the second electrode may also consist of (essentially) intransparent metals such as Mg, Ca or Al. Alternatively or additionally, the second electrode 150 may also comprise graphite and or carbon nanotubes (CNTs). Alternatively, the second electrode 150 may also consist of nanoscalic silver wires.

An OLED may further, optionally, comprise a protection layer between the electron transport layer (ETL) and the second electrode (which may be designated as electron injection layer (EIL)). This layer may comprise lithium fluoride, cesium fluoride, silver, Liq (8-hydroxyquinolinolatolithium), $Li_2O$, $BaF_2$, MgO and/or NaF.

Optionally, also the electron transport layer (ETL) and/or a hole blocking layer (HBL) may comprise one or more host compounds H.

[Capping Layer]

A first capping layer may be arranged outside the first electrode 110, and/or a second capping layer may be arranged outside the second electrode 150. In particular, the light-emitting device may have a structure in which the first capping layer, the first electrode 110, the interlayer 130, and the second electrode 150 are sequentially stacked in the stated order, a structure in which the first electrode 110, the interlayer 130, the second electrode 150, and the second capping layer are sequentially stacked in the stated order, or a structure in which the first capping layer, the first electrode 110, the interlayer 130, the second electrode 150, and the second capping layer are sequentially stacked in the stated order.

Light generated in an emission layer of the interlayer 130 of the light-emitting device 10 may be extracted toward the outside through the first electrode 110 which is a semi-transmissive electrode or a transmissive electrode, and the first capping layer. Light generated in an emission layer of the interlayer 130 of the light-emitting device 10 may be extracted toward the outside through the second electrode 150 which is a semi-transmissive electrode or a transmissive electrode, and the second capping layer.

The first capping layer and the second capping layer may increase external emission efficiency according to the principle of constructive interference. Accordingly, the light extraction efficiency of the light-emitting device 10 is increased, so that the luminescence efficiency of the light-emitting device 10 may be improved.

Each of the first capping layer and the second capping layer may include a material having a refractive index of greater than or equal to 1.6 (at 589 nm).

The first capping layer and the second capping layer may each independently be an organic capping layer including an organic material, an inorganic capping layer including an inorganic material, or an organic-inorganic composite capping layer including an organic material and an inorganic material.

At least one of the first capping layer and the second capping layer may each independently include a carbocyclic compound, a heterocyclic compound, an amine group-containing compound, a porphine derivative, a phthalocyanine derivative, a naphthalocyanine derivative, an alkali metal complex, an alkaline earth metal complex, or any combination thereof. The carbocyclic compound, the heterocyclic compound, and the amine group-containing compound may optionally be substituted with a substituent including O, N, S, Se, Si, F, Cl, Br, I, or any combination thereof. In an embodiment, at least one of the first capping layer and the second capping layer may each independently include an amine group-containing compound.

In one or more embodiments, at least one of the first capping layer and the second capping layer may each independently include a compound represented by Formula 201, a compound represented by Formula 202, or any combination thereof.

In one or more embodiments, at least one of the first capping layer and the second capping layer may each independently include: one of Compounds HT28 to HT33; one of Compounds CP1 to CP6; β-NPB; or any combination thereof:

CP1

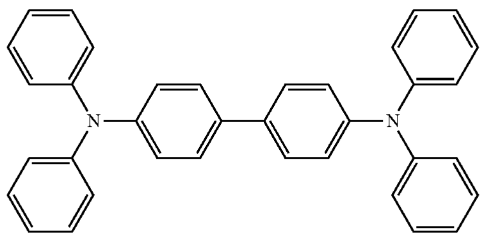

-continued

CP2

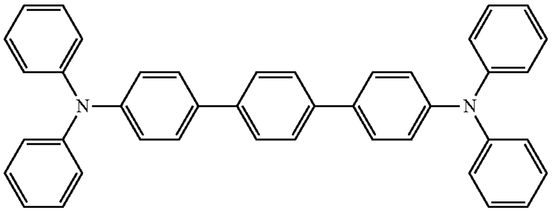

CP3

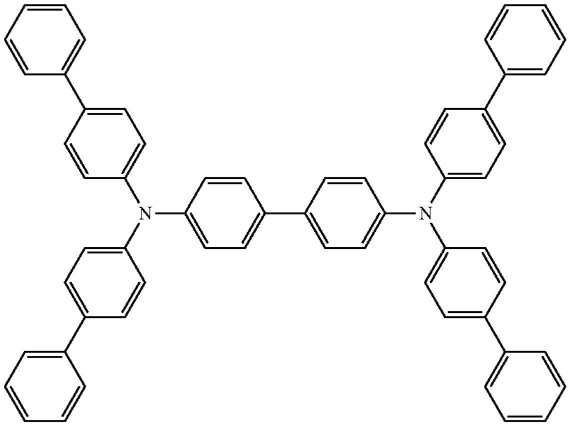

CP4

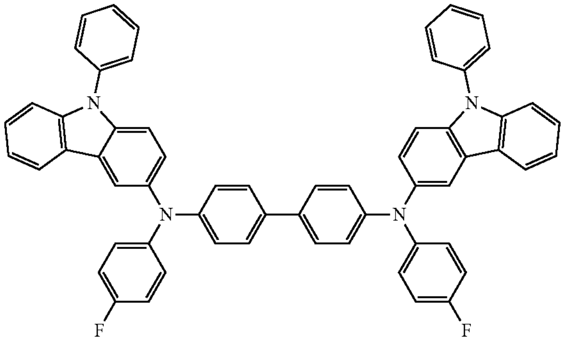

CP5

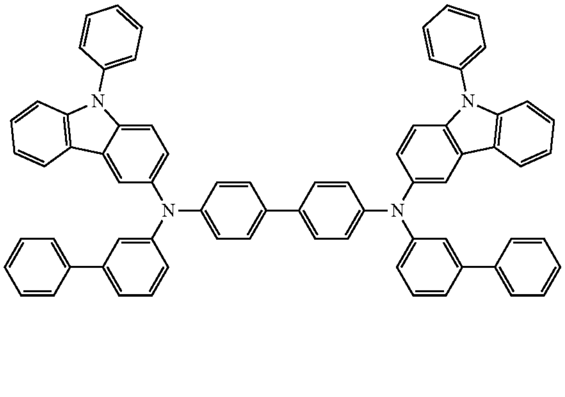

-continued

CP6

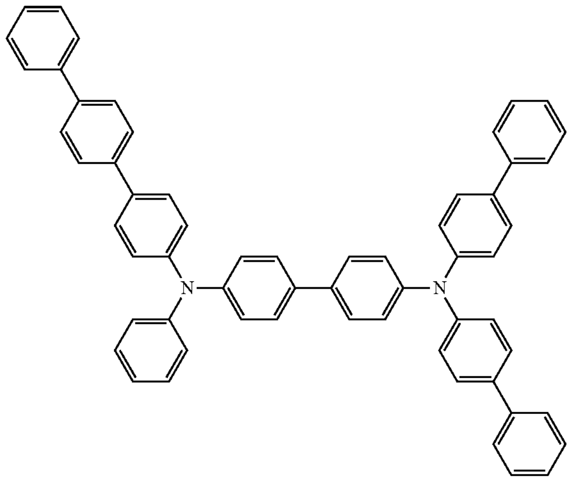

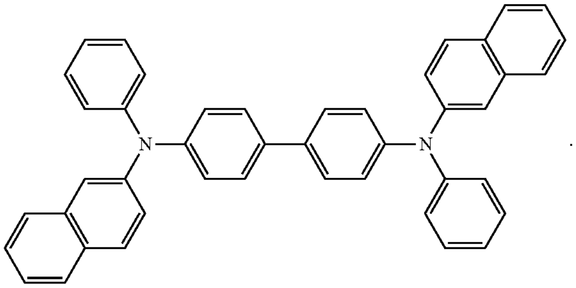

β-NPB

[Film]

The organic molecule represented by Formula I may be included in various films. According to one or more embodiments, a film including an organic molecule represented by Formula I may be provided. The film may be, for example, an optical member (or a light control means) (for example, a color filter, a color conversion member, a capping layer, a light extraction efficiency enhancement layer, a selective light absorbing layer, a polarizing layer, a quantum dot-containing layer, or like), a light-blocking member (for example, a light reflective layer, a light absorbing layer, or the like), a protective member (for example, an insulating layer, a dielectric layer, or the like).

[Electronic Apparatus]

The light-emitting device may be included in various electronic apparatuses. For example, the electronic apparatus including the light-emitting device may be a light-emitting apparatus, an authentication apparatus, and the like.

The electronic apparatus (for example, a light-emitting apparatus) may further include, in addition to the light-emitting device, i) a color filter, ii) a color conversion layer, or iii) a color filter and a color conversion layer. The color filter and/or the color conversion layer may be arranged in at least one traveling direction of light emitted from the light-emitting device. For example, the light emitted from the light-emitting device may be blue light or white light. The light-emitting device may be the same as described herein. In an embodiment, the color conversion layer may include a quantum dot. The quantum dot may be, for example, the quantum dot as described herein.

The electronic apparatus may include a first substrate. The first substrate may include a plurality of subpixel areas, the color filter may include a plurality of color filter areas respectively corresponding to the subpixel areas, and the color conversion layer may include a plurality of color conversion areas respectively corresponding to the subpixel areas.

A pixel-defining film may be arranged among the subpixel areas to define each of the subpixel areas.

The color filter may further include a plurality of color filter areas and light-shielding patterns arranged among the color filter areas, and the color conversion layer may further include a plurality of color conversion areas and light-shielding patterns arranged among the color conversion areas.

The plurality of color filter areas (or the plurality of color conversion areas) may include a first area emitting first color light, a second area emitting second color light, and/or a third area emitting third color light, wherein the first color light, the second color light, and/or the third color light may have different maximum emission wavelengths from one another. For example, the first color light may be red light, the second color light may be green light, and the third color light may be blue light. For example, the plurality of color filter areas (or the plurality of color conversion areas) may include quantum dots. In particular, the first area may include a red quantum dot, the second area may include a green quantum dot, and the third area may not include a quantum dot. The quantum dot may be the same as described herein. The first area, the second area, and/or the third area may each include a scatter.

For example, the light-emitting device may emit first light, the first area may absorb the first light to emit first-first color light, the second area may absorb the first light to emit second-first color light, and the third area may absorb the first light to emit third-first color light. Here, the first-first color light, the second-first color light, and the third-first color light may have different maximum emission wavelengths. In particular, the first light may be blue light, the first-first color light may be red light, the second-first color light may be green light, and the third-first color light may be blue light.

The electronic apparatus may further include a thin-film transistor, in addition to the light-emitting device as described above. The thin-film transistor may include a source electrode, a drain electrode, and an activation layer, wherein any one of the source electrode and the drain electrode may be electrically connected to any one of the first electrode and the second electrode of the light-emitting device.

The thin-film transistor may further include a gate electrode, a gate insulating film, or the like. The activation layer may include crystalline silicon, amorphous silicon, an organic semiconductor, an oxide semiconductor, or the like.

The electronic apparatus may further include a sealing portion for sealing the light-emitting device. The sealing portion may be arranged between the color filter and/or the color conversion layer and the light-emitting device. The sealing portion allows light from the light-emitting device to be extracted to the outside, and simultaneously prevents ambient air and moisture from penetrating into the light-emitting device. The sealing portion may be a sealing substrate including a transparent glass substrate or a plastic substrate. The sealing portion may be a thin-film encapsulation layer including at least one layer of an organic layer and/or an inorganic layer. When the sealing portion is a thin film encapsulation layer, the electronic apparatus may be flexible.

Various functional layers may be arranged on the sealing portion according to the use of the electronic device in addition to the color filter and/or the color conversion layer. Examples of the functional layers may include a touch screen layer, a polarizing layer, and the like. The touch screen layer may be a pressure-sensitive touch screen layer, a capacitive touch screen layer, or an infrared touch screen layer. The authentication apparatus may be, for example, a biometric authentication apparatus that authenticates an individual by using biometric information of a living body (for example, fingertips, pupils, etc.).

The authentication apparatus may further include, in addition to the light-emitting device as described above, a biometric information collector.

The electronic apparatus may be applied to various displays, light sources, lighting, personal computers (for example, a mobile personal computer), mobile phones, digital cameras, electronic organizers, electronic dictionaries, electronic game machines, medical instruments (for example, electronic thermometers, sphygmomanometers, blood glucose meters, pulse measurement devices, pulse wave measurement devices, electrocardiogram displays, ultrasonic diagnostic devices, or endoscope displays), fish finders, various measuring instruments, meters (for example, meters for a vehicle, an aircraft, and a vessel), projectors, and the like.

[Electronic Equipment]

The light-emitting device may be included in various electronic equipment.

For example, the electronic equipment including the light-emitting device may be a flat panel display, a curved display, a computer monitor, a medical monitor, a television, a billboard, a light for indoor or outdoor lighting and/or signaling, a head-up display, a fully or partially transparent display, a flexible display, a rollable display, a foldable display, a stretchable display, a laser printer, a telephone, a mobile phone, a tablet, a phablet, a personal digital assistant (PDA), a wearable device, a laptop computer, a digital camera, a camcorder, a viewfinder, a micro display, a 3D display, a virtual or augmented-reality display, a vehicle, a video wall including multiple displays tiled together, a theater or stadium screen, a phototherapy device, and a signboard.

The light-emitting device may have excellent effects in terms of luminescence efficiency long lifespan, and thus the electronic equipment including the light-emitting device may have characteristics, such as high luminance, high resolution, and low power consumption.

Figure 5:
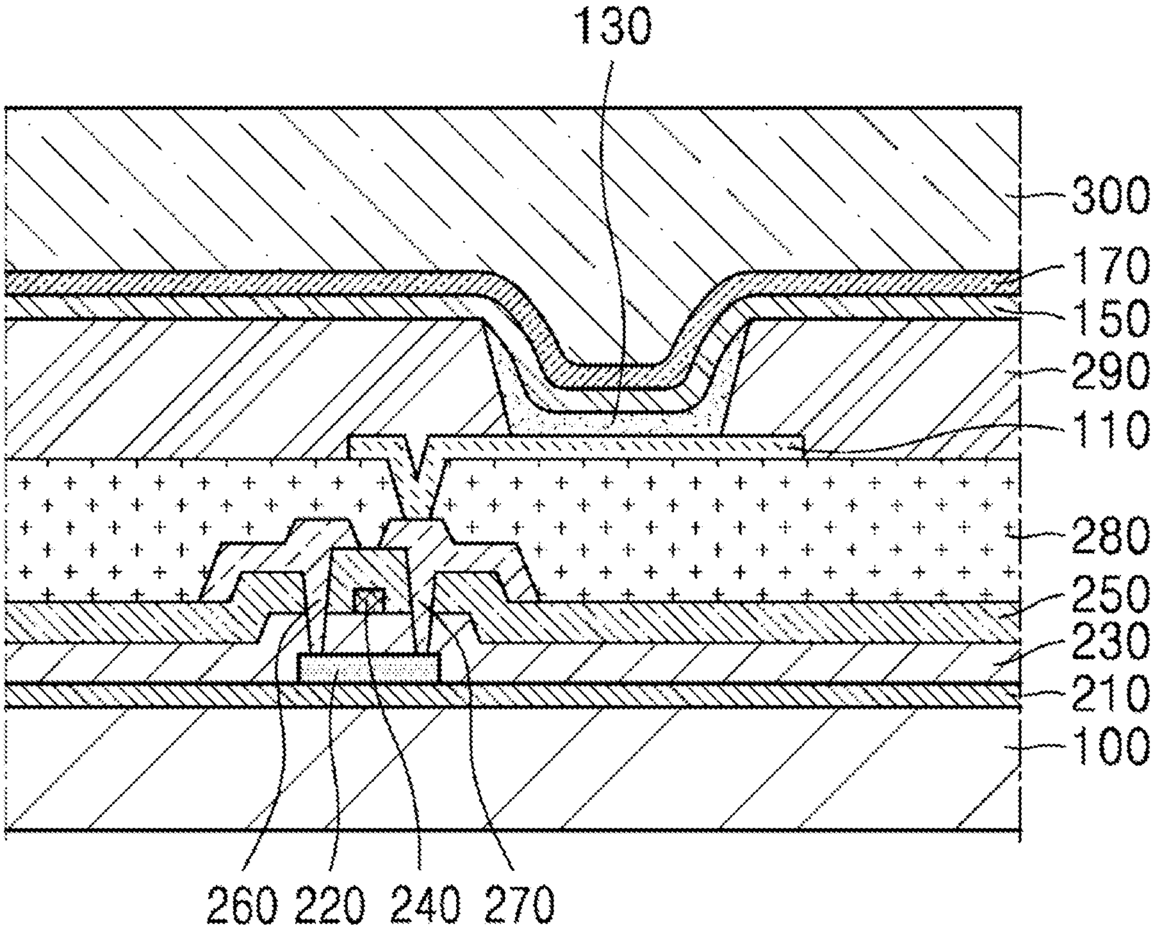
FIG. 5 is a cross-sectional view showing a light-emitting apparatus according to an embodiment of the present disclosure.
Figure 6:
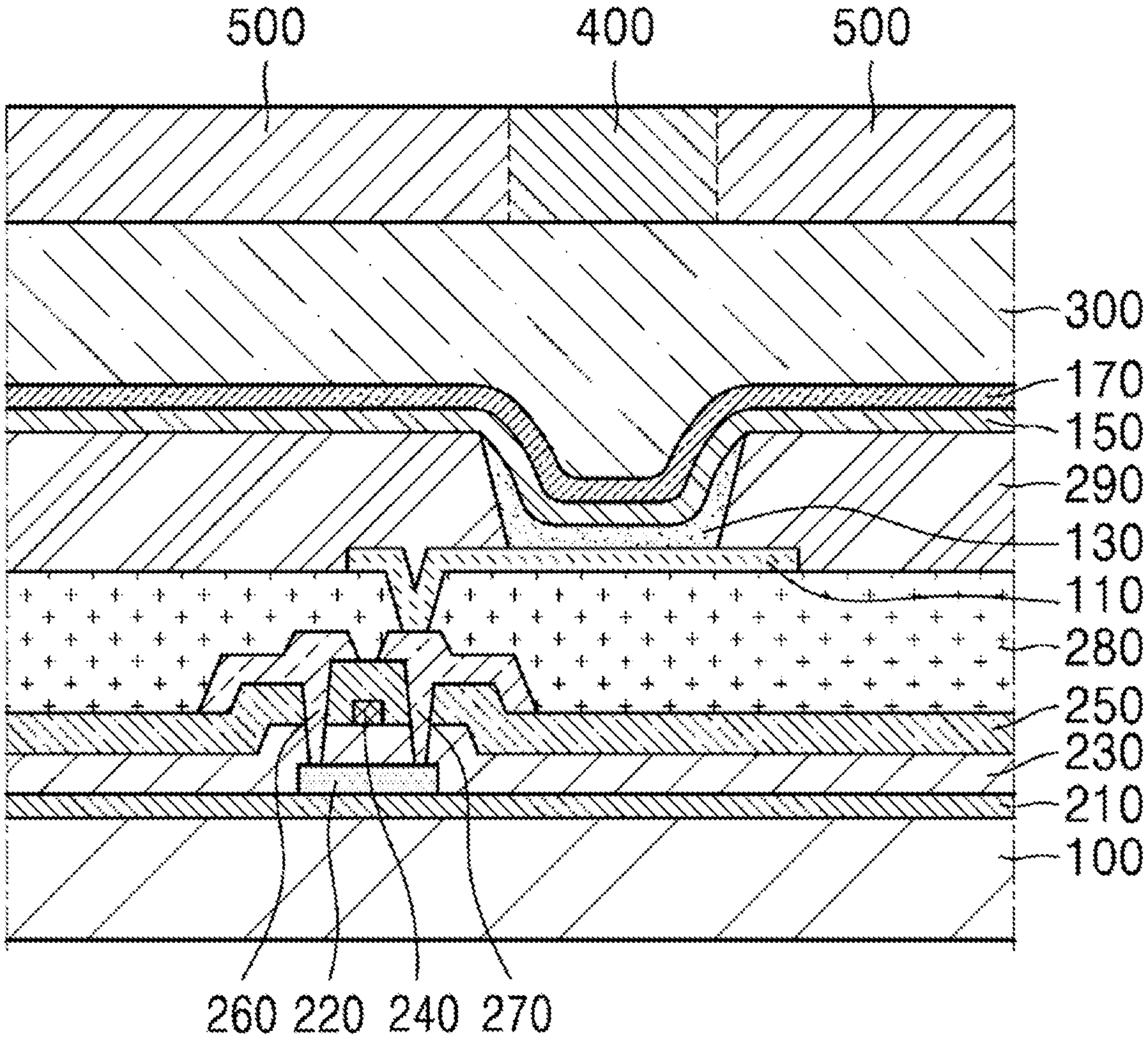
FIG. 6 shows a cross-sectional view showing a light-emitting apparatus according to another embodiment of the present disclosure.

Description of FIGS. 5 and 6

FIG. 5 is a cross-sectional view showing a light-emitting apparatus according to an embodiment of the present disclosure.

The light-emitting apparatus of FIG. 5 includes a substrate 100, a thin-film transistor (TFT), a light-emitting device, and an encapsulation portion 300 that seals the light-emitting device. The substrate 100 may be a flexible substrate, a glass substrate, or a metal substrate. A buffer layer 210 may be arranged on the substrate 100. The buffer layer 210 may prevent penetration of impurities through the substrate 100 and may provide a flat surface on the substrate 100. A TFT may be arranged on the buffer layer 210. The TFT may include an activation layer 220, a gate electrode 240, a source electrode 260, and a drain electrode 270.

The activation layer 220 may include an inorganic semiconductor such as silicon or polysilicon, an organic semiconductor, or an oxide semiconductor, and may include a source region, a drain region, and a channel region.

A gate insulating film 230 for insulating the activation layer 220 from the gate electrode 240 may be arranged on the activation layer 220, and the gate electrode 240 may be arranged on the gate insulating film 230.

An interlayer insulating film 250 may be arranged on the gate electrode 240. The interlayer insulating film 250 may be arranged between the gate electrode 240 and the source electrode 260 and between the gate electrode 240 and the drain electrode 270, to insulate from one another.

The source electrode 260 and the drain electrode 270 may be arranged on the interlayer insulating film 250. The interlayer insulating film 250 and the gate insulating film 230 may be formed to expose the source region and the drain region of the activation layer 220, and the source electrode 260 and the drain electrode 270 may be arranged in contact with the exposed portions of the source region and the drain region of the activation layer 220.

The TFT may be electrically connected to a light-emitting device to drive the light-emitting device, and may be covered and protected by a passivation layer 280. The passivation layer 280 may include an inorganic insulating film, an organic insulating film, or any combination thereof. A light-emitting device may be provided on the passivation layer 280. The light-emitting device may include a first electrode 110, an interlayer 130, and a second electrode 150.

The first electrode 110 may be arranged on the passivation layer 280. The passivation layer 280 may be arranged to expose a portion of the drain electrode 270, not fully covering the drain electrode 270, and the first electrode 110 may be arranged to be connected to the exposed portion of the drain electrode 270.

A pixel defining layer 290 including an insulating material may be arranged on the first electrode 110. The pixel defining layer 290 may expose a certain region of the first electrode 110, and an interlayer 130 may be formed in the exposed region of the first electrode 110. The pixel defining layer 290 may be a polyimide or polyacrylic organic film. Although not shown in FIG. 5, at least some layers of the interlayer 130 may extend beyond the upper portion of the pixel defining layer 290 to be arranged in the form of a common layer.

The second electrode 150 may be arranged on the interlayer 130, and a capping layer 170 may be additionally formed on the second electrode 150. The capping layer 170 may be formed to cover the second electrode 150.

The encapsulation portion 300 may be arranged on the capping layer 170. The encapsulation portion 300 may be arranged on a light-emitting device to protect the light-emitting device from moisture or oxygen. The encapsulation portion 300 may include: an inorganic film including silicon nitride (SiNx), silicon oxide (SiOx), indium tin oxide, indium zinc oxide, or any combination thereof; an organic film including polyethylene terephthalate, polyethylene naphthalate, polycarbonate, polyimide, polyethylene sulfonate, polyoxymethylene, polyarylate, hexamethyldisiloxane, an acrylic resin (for example, polymethyl methacrylate, polyacrylic acid, or the like), an epoxy-based resin (for example, aliphatic glycidyl ether (AGE), or the like), or any combination thereof; or any combination of the inorganic films and the organic films. FIG. 6 shows a cross-sectional view showing a light-emitting apparatus according to another embodiment of the present disclosure.

The light-emitting apparatus of FIG. 6 is the same as the light-emitting apparatus of FIG. 5, except that a light-shielding pattern 500 and a functional region 400 are additionally arranged on the encapsulation portion 300. The functional region 400 may be i) a color filter area, ii) a color conversion area, or iii) a combination of the color filter area and the color conversion area. In an embodiment, the light-emitting device included in the light-emitting apparatus of FIG. 6 may be a tandem light-emitting device.

Figure 7:
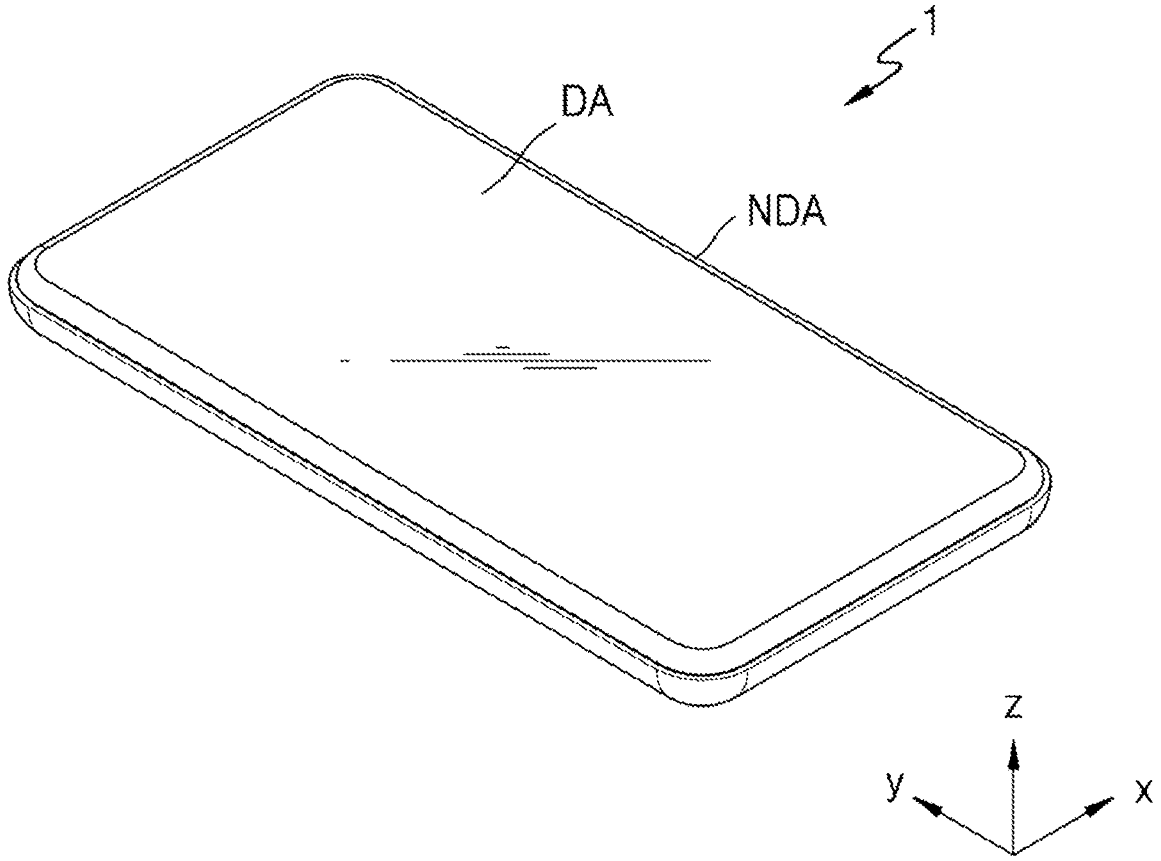
FIG. 7 is a schematic perspective view of electronic device 1 including a light-emitting device according to an embodiment.

FIG. 7 is a schematic perspective view of electronic device 1 including a light-emitting device according to an embodiment. The electronic equipment 1 may be, as a device apparatus, that displays a moving image or still image, a portable electronic equipment, such as a mobile phone, a smart phone, a tablet personal computer (PC), a mobile communication terminal, an electronic notebook, an electronic book, a portable multimedia player (PMP), a navigation, or an ultra mobile PC (UMPC) as well as various products, such as a television, a laptop, a monitor, a billboards or an Internet of things (IOT). The electronic equipment 1 may be such a product above or a part thereof. In addition, the electronic equipment 1 may be a wearable device, such as a smart watch, a watch phone, a glasses-type display, or a head mounted display (HMD), or a part of the wearable device. However, embodiments of the present disclosure are not limited thereto. For example, the electron equipment 1 may include a dashboard of a vehicle, a center fascia of a vehicle, a center information display arranged on a dashboard of a vehicle, a room mirror display replacing a side mirror of a vehicle, an entertainment display for the rear seat of a vehicle or a display arranged on the back of the front seat, or a head up display (HUD) installed in the front of a vehicle or projected on a front window glass, a computer-generated hologram augmented-reality head up display (CGH AR HUD). FIG. 7 illustrates a case in which the electronic equipment 1 is a smartphone for convenience of explanation.

The electronic equipment 1 may include a display area DA and a non-display area NDA outside the display area DA. A display device may implement an image through an array of a plurality of pixels that are two-dimensionally arranged in the display area DA.

The non-display area NDA is an area that does not display an image, and may entirely surround the display area DA. On the non-display area NDA, a driver for providing electrical signals or power to display devices arranged on the display area DA may be arranged. On the non-display area NDA, a pad, which is an area to which an electronic element or a printing circuit board may be electrically connected, may be arranged.

In the electronic equipment 1, a length in the x-axis direction and a length in the y-axis direction may be different from each other. For example, as shown in FIG. 7, the length in the x-axis direction may be shorter than the length in the y-axis direction. In one or more embodiments, the length in the x-axis direction may be the same as the length in the y-axis direction. In one or more embodiments, the length in the x-axis direction may be longer than the length in the y-axis direction.

Accordingly, a further aspect of the present invention relates to an OLED, which exhibits an external quantum efficiency at 1000 cd/$m^2$ of more than 8%, more preferably of more than 10%, more preferably of more than 13%, even more preferably of more than 15% or even more than 20% and/or exhibits an emission maximum between 420 nm and 500 nm, preferably between 430 nm and 490 nm, more preferably between 440 nm and 480 nm, even more preferably between 450 nm and 470 nm and/or exhibits a LT80 value at 500 cd/$m^2$ of more than 100 h, preferably more than 200 h, more preferably more than 400 h, even more preferably more than 750 h or even more than 1000 h. Accordingly, a further aspect of the present invention relates to an OLED, whose emission exhibits a CIEy color coordinate of less than 0.45, preferably less than 0.30, more preferably less than 0.20 or even more preferably less than 0.15 or even less than 0.10.

A further aspect of the present invention relates to an OLED, which emits light at a distinct color point. According to the present invention, the OLED emits light with a narrow emission band (small full width at half maximum (FWHM)). In one aspect, the OLED according to the invention emits light with a FWHM of the main emission peak of less than 0.50 eV, preferably less than 0.48 eV, more preferably less than 0.45 eV, even more preferably less than 0.43 eV or even less than 0.40 eV.

A further aspect of the present invention relates to an OLED, which emits light with CIEx and CIEy color coordinates close to the CIEx (=0.131) and CIEy (=0.046) color coordinates of the primary color blue (CIEx=0.131 and CIEy=0.046) as defined by ITU-R Recommendation BT.2020 (Rec. 2020) and thus is suited for the use in Ultra High Definition (UHD) displays, e.g. UHD-TVs. Accordingly, a further aspect of the present invention relates to an OLED, whose emission exhibits a CIEx color coordinate of between 0.02 and 0.30, preferably between 0.03 and 0.25, more preferably between 0.05 and 0.20 or even more preferably between 0.08 and 0.18 or even between 0.10 and 0.15 and/or a a CIEy color coordinate of between 0.00 and 0.45, preferably between 0.01 and 0.30, more preferably between 0.02 and 0.20 or even more preferably between 0.03 and 0.15 or even between 0.04 and 0.10.

Descriptions of FIGS. 8 and 9A to 9C

Figure 8:
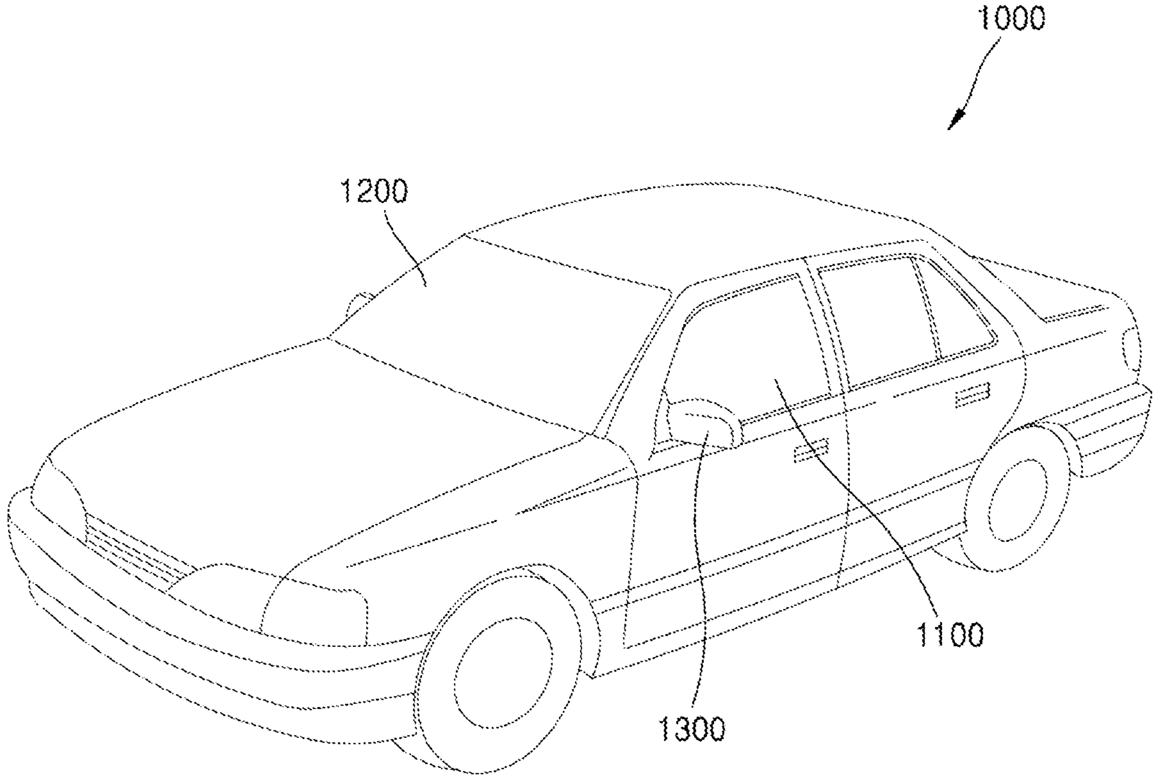
FIG. 8 is a diagram illustrating the exterior of a vehicle 1000 as an electronic device including a light-emitting device according to an embodiment.
Figure 9A:
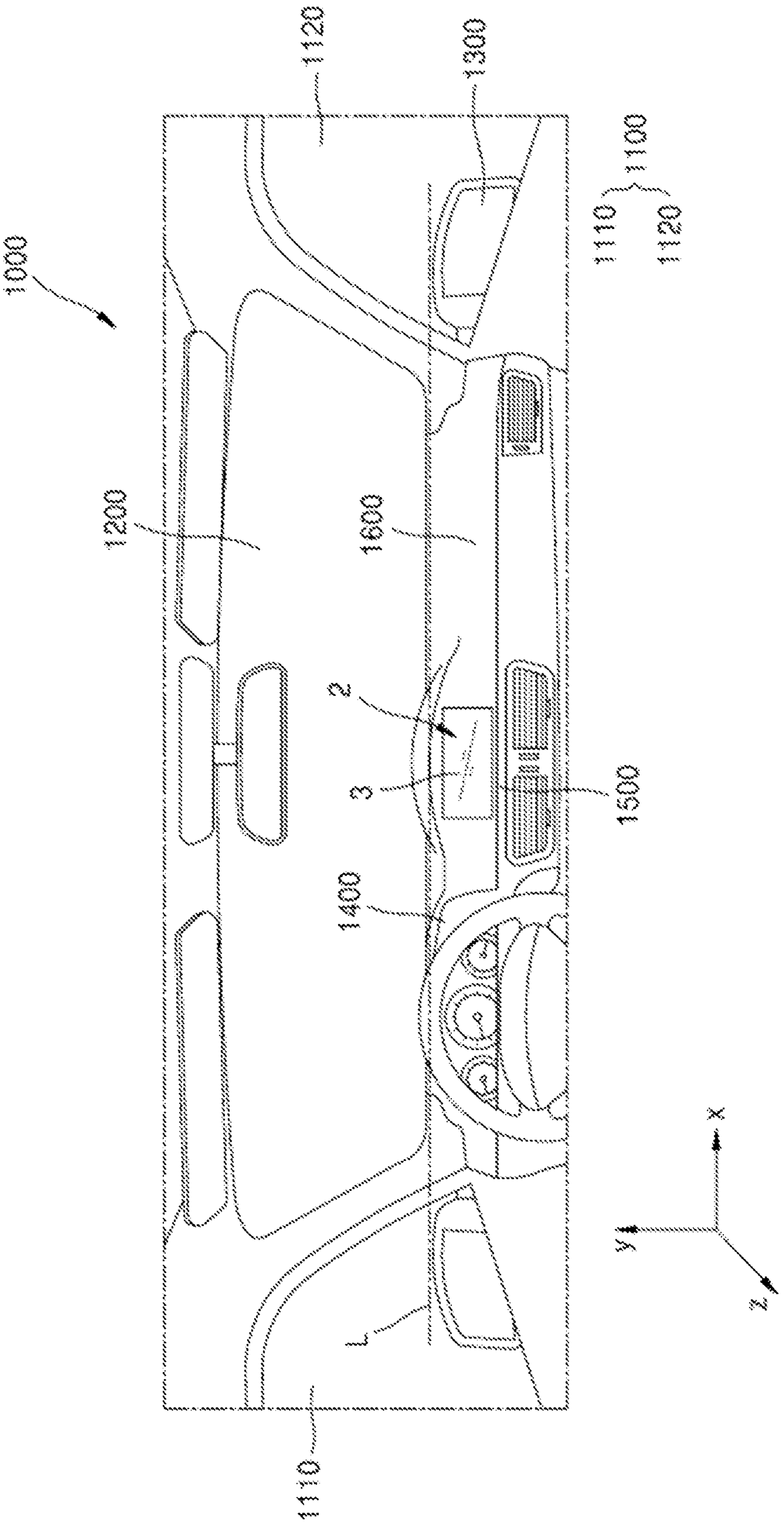
FIGS. 9A to 9C are each a diagram schematically illustrating the interior of a vehicle 1000 according to various embodiments of the present disclosure.
Figure 9B:
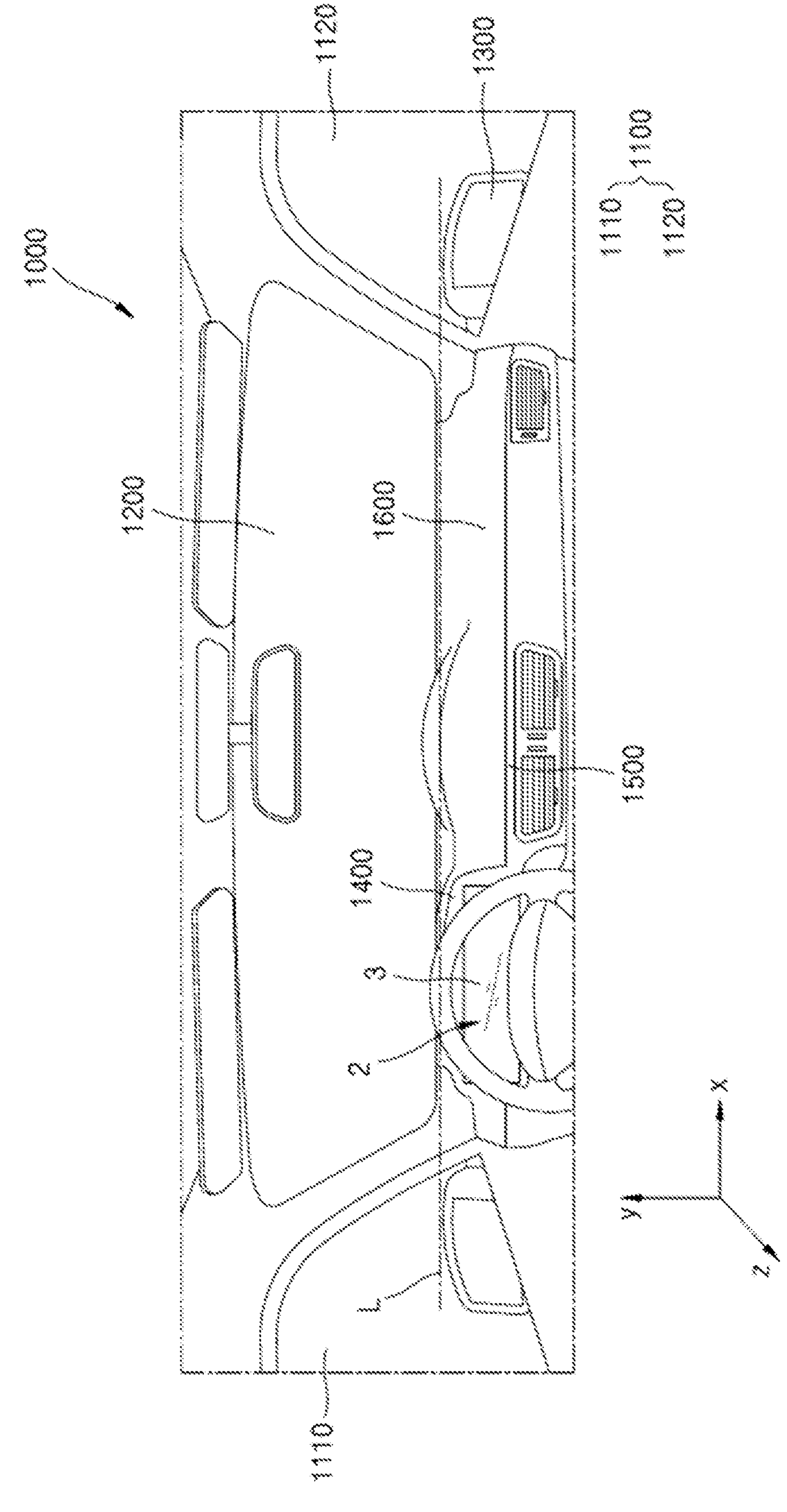
Figure 9C:
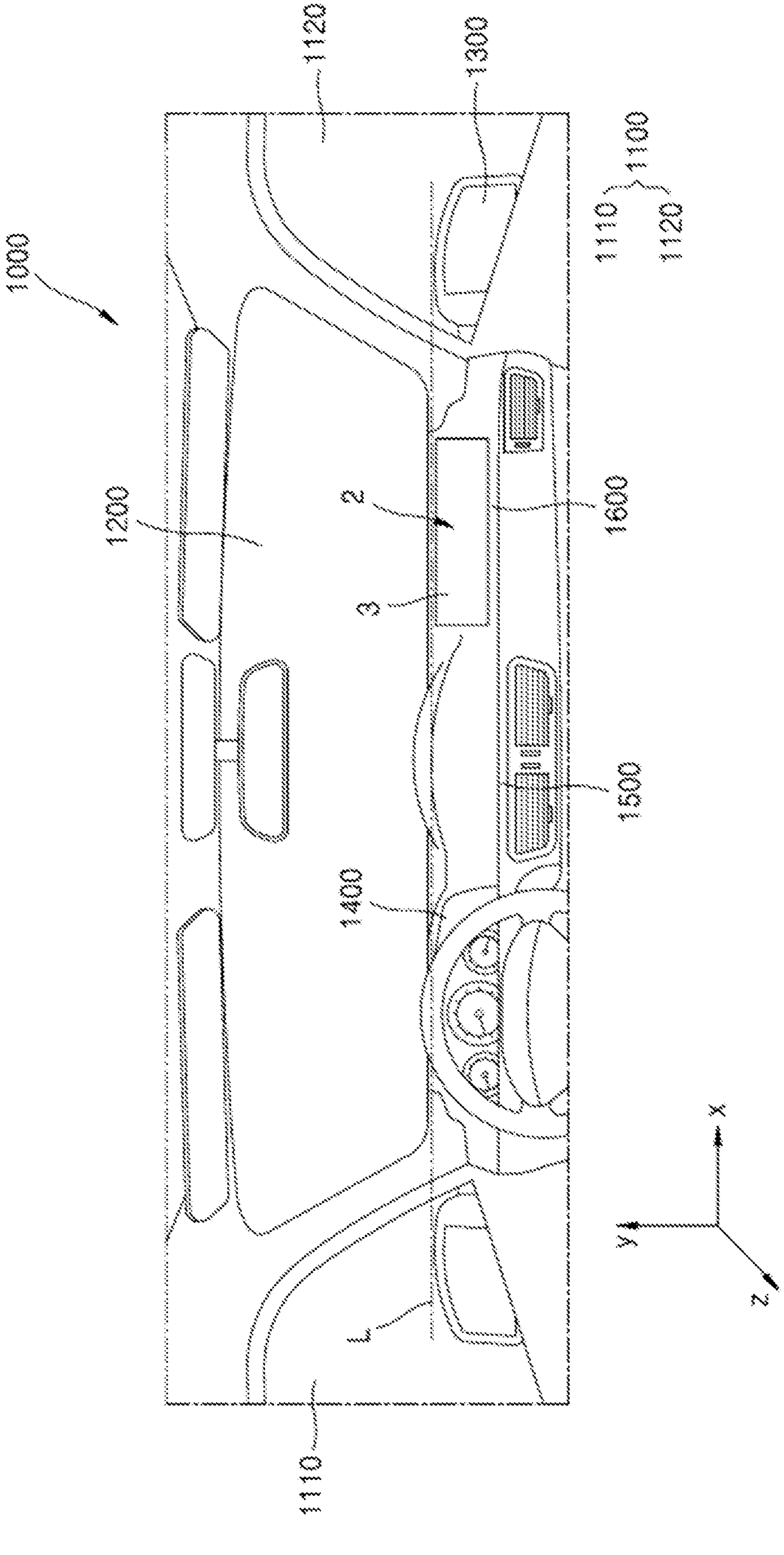

FIG. 8 is a diagram illustrating the exterior of a vehicle 1000 as an electronic device including a light-emitting device according to an embodiment. FIGS. 9A to 9C are each a diagram schematically illustrating the interior of a vehicle 1000 according to various embodiments of the present disclosure.

Referring to FIGS. 8, 9A, 9B, and 9C, the vehicle 1000 may refer to various apparatuses for moving a subject object to be transported, such as a human, an object, or an animal, from a departure point to a destination. The vehicle 1000 may include a vehicle traveling on a road or track, a vessel moving over a sea or river, an airplane flying in the sky using the action of air, and the like.

The vehicle 1000 may travel on a road or a track. The vehicle 1000 may move in a predetermined direction according to the rotation of at least one wheel. For example, the vehicle 1000 may include a three-wheeled or four-wheeled vehicle, a construction machine, a two-wheeled vehicle, a prime mover device, a bicycle, and a train running on a track.

The vehicle 1000 may include a body having an interior and an exterior, and a chassis in which mechanical apparatuses necessary for driving are installed as other parts except for the body. The exterior of the vehicle body may include a front panel, a bonnet, a roof panel, a rear panel, a trunk, a filler provided at a boundary between doors, and the like. The chassis of the vehicle 1000 may include a power generating device, a power transmitting device, a driving device, a steering device, a braking device, a suspension device, a transmission device, a fuel device, front and rear wheels, left and right wheels, and the like.

The vehicle 1000 may include a side window glass 1100, a front window glass 1200, a side mirror 1300, a cluster 1400, a center fascia 1500, a passenger seat dashboard 1600, and a display device 2.

The side window glass 1100 and the front window glass 1200 may be partitioned by a filler arranged between the side window glass 1100 and the front window glass 1200.

The side window glass 1100 may be installed on the side of the vehicle 1000. In an embodiment, the side window glass 1100 may be installed on a door of the vehicle 1000. A plurality of side window glasses 1100 may be provided and may face each other. In an embodiment, the side window glass 1100 may include a first side window glass 1110 and a second side window glass 1120. In an embodiment, the first side window glass 1110 may be arranged adjacent to the cluster 1400. The second side window glass 1120 may be arranged adjacent to the passenger seat dashboard 1600.

In an embodiment, the side window glasses 1100 may be spaced apart from each other in the x-direction or the −x-direction. For example, the first side window glass 1110 and the second side window glass 1120 may be spaced apart from each other in the x direction or the −x direction. In other words, an imaginary straight line L connecting the side window glasses 1100 may extend in the x-direction or the −x-direction. For example, an imaginary straight line L connecting the first side window glass 1110 and the second side window glass 1120 to each other may extend in the x direction or the −x direction.

The front window glass 1200 may be installed in the front of the vehicle 1000. The front window glass 1200 may be arranged between the side window glasses 1100 facing each other.

The side mirror 1300 may provide a rear view of the vehicle 1000. The side mirror 1300 may be installed on the exterior of the vehicle body. In one embodiment, a plurality of side mirrors 1300 may be provided. Any one of the plurality of side mirrors 1300 may be arranged outside the first side window glass 1110. The other one of the plurality of side mirrors 1300 may be arranged outside the second side window glass 1120.

The cluster 1400 may be arranged in front of the steering wheel. The cluster 1400 may include a tachometer, a speedometer, a coolant thermometer, a fuel gauge turn indicator, a high beam indicator, a warning lamp, a seat belt warning lamp, an odometer, an hodometer, an automatic shift selector indicator lamp, a door open warning lamp, an engine oil warning lamp, and/or a low fuel warning light.

The center fascia 1500 may include a control panel on which a plurality of buttons for adjusting an audio device, an air conditioning device, and a heater of a seat are disposed. The center fascia 1500 may be arranged on one side of the cluster 1400.

A passenger seat dashboard 1600 may be spaced apart from the cluster 1400 with the center fascia 1500 arranged therebetween. In an embodiment, the cluster 1400 may be arranged to correspond to a driver seat (not shown), and the passenger seat dashboard 1600 may be disposed to correspond to a passenger seat (not shown). In an embodiment, the cluster 1400 may be adjacent to the first side window glass 1110, and the passenger seat dashboard 1600 may be adjacent to the second side window glass 1120.

In an embodiment, the display device 2 may include a display panel 3, and the display panel 3 may display an image. The display device 2 may be arranged inside the vehicle 1000. In an embodiment, the display device 2 may be arranged between the side window glasses 1100 facing each other. The display device 2 may be arranged on at least one of the cluster 1400, the center fascia 1500, and the passenger seat dashboard 1600.

The display device 2 may include an organic light-emitting display device, an inorganic electroluminescent (EL) display device, a quantum dot display device, and the like. Hereinafter, as the display device 2 according to an embodiment of the present disclosure, an organic light-emitting display device display including the light-emitting device according to the present disclosure will be described as an example, but various types of display devices as described above may be used in embodiments of the present disclosure.

Referring to FIG. 9A, the display device 2 may be arranged on the center fascia 1500. In an embodiment, the display device 2 may display navigation information. In an embodiment, the display device 2 may display audio, video, or information regarding vehicle settings.

Referring to FIG. 9B, the display device 2 may be arranged on the cluster 1400. When the display device 2 is arranged on the cluster 1400, the cluster 1400 may display driving information and the like through the display device 2. That is, the cluster 1400 may be implemented digitally. The digital cluster 1400 may display vehicle information and driving information as images. For example, a needle and a gauge of a tachometer and various warning light icons may be displayed by a digital signal.

Referring to FIG. 9C, the display device 2 may be arranged on the dashboard 1600 of the passenger seat. The display device 2 may be embedded in the passenger seat dashboard 1600 or arranged on the passenger seat dashboard 1600. In an embodiment, the display device 2 arranged on the dashboard 1600 for the passenger seat may display an image related to information displayed on the cluster 1400 and/or information displayed on the center fascia 1500. In one or more embodiments, the display device 2 arranged on the passenger seat dashboard 1600 may display information different from information displayed on the cluster 1400 and/or information displayed on the center fascia 1500.

[Manufacturing Method]

Respective layers included in the hole transport region, the emission layer, and respective layers included in the electron transport region may be formed in a certain region by using one or more suitable methods selected from vacuum deposition, spin coating, casting, Langmuir-Blodgett (LB) deposition, ink-jet printing, laser-printing, laser-induced thermal imaging, and the like.

When respective layers included in the hole transport region, the emission layer, and respective layers included in the electron transport region are formed by vacuum deposition, the deposition may be performed at a deposition temperature of about 100° C. to about 500° C., a vacuum degree of about $10^{-8}$ torr to about $10^{-3}$ torr, and a deposition speed of about 0.01 Å/sec to about 100 Å/sec, depending on a material to be included in a layer to be formed and the structure of a layer to be formed.

Definition of Terms

The term "$C_3$-$C_{60}$ carbocyclic group" as used herein refers to a cyclic group consisting of carbon only as a ring-forming atom and having three to sixty carbon atoms, and the term "$C_1$-$C_{60}$ heterocyclic group" as used herein refers to a cyclic group that has one to sixty carbon atoms and further has, in addition to carbon, a heteroatom as a ring-forming atom. The $C_3$-$C_{60}$ carbocyclic group and the $C_1$-$C_{60}$ heterocyclic group may each be a monocyclic group consisting of one ring or a polycyclic group in which two or more rings are condensed with each other. For example, the number of ring-forming atoms of the $C_1$-$C_{60}$ heterocyclic group may be from 3 to 61.

The "cyclic group" as used herein may include both the $C_3$-$C_{60}$ carbocyclic group and the $C_1$-$C_{60}$ heterocyclic group.

The term "π electron-rich $C_3$-$C_{60}$ cyclic group" as used herein refers to a cyclic group that has three to sixty carbon atoms and does not include *—N=*' as a ring-forming moiety, and the term "π electron-deficient nitrogen-containing $C_1$-$C_{60}$ cyclic group" as used herein refers to a heterocyclic group that has one to sixty carbon atoms and includes *—N=*' as a ring-forming moiety.

For example, the $C_3$-$C_{60}$ carbocyclic group may be i) a T1 group or ii) a condensed cyclic group in which two or more T1 groups are condensed with each other (for example, a cyclopentadiene group, an adamantane group, a norbornane group, a benzene group, a pentalene group, a naphthalene group, an azulene group, an indacene group, an acenaphthylene group, a phenalene group, a phenanthrene group, an anthracene group, a fluoranthene group, a triphenylene group, a pyrene group, a chrysene group, a perylene group, a pentaphene group, a heptalene group, a naphthacene group, a picene group, a hexacene group, a pentacene group, a rubicene group, a coronene group, an ovalene group, an indene group, a fluorene group, a spiro-bifluorene group, a benzofluorene group, an indenophenanthrene group, or an indenoanthracene group), the $C_1$-$C_{60}$ heterocyclic group may be i) a T2 group, ii) a condensed cyclic group in which at least two T2 groups are condensed with each other, or iii) a condensed cyclic group in which at least one T2 group and at least one T1 group are condensed with each other (for example, a pyrrole group, a thiophene group, a furan group, an indole group, a benzoindole group, a naphthoindole group, an isoindole group, a benzoisoindole group, a naphthoisoindole group, a benzosilole group, a benzothiophene group, a benzofuran group, a carbazole group, a dibenzosilole group, a dibenzothiophene group, a dibenzofuran group, an indenocarbazole group, an indolocarbazole group, a benzofurocarbazole group, a benzothienocarbazole group, a benzosilolocarbazole group, a benzoindolocarbazole group, a benzocarbazole group, a benzonaphthofuran group, a benzonaphthothiophene group, a benzonaphthosilole group, a benzofurodibenzofuran group, a benzofurodibenzothiophene group, a benzothienodibenzothiophene group, a pyrazole group, an imidazole group, a triazole group, an oxazole group, an isoxazole group, an oxadiazole group, a thiazole group, an isothiazole group, a thiadiazole group, a benzopyrazole group, a benzimidazole group, a benzoxazole group, a benzoisoxazole group, a benzothiazole group, a benzoisothiazole group, a pyridine group, a pyrimidine group, a pyrazine group, a pyridazine group, a triazine group, a quinoline group, an isoquinoline group, a benzoquinoline group, a benzoisoquinoline group, a quinoxaline group, a benzoquinoxaline group, a quinazoline group, a benzoquinazoline group, a phenanthroline group, a cinnoline group, a phthalazine group, a naphthyridine group, an imidazopyridine group, an imidazopyrimidine group, an imidazotriazine group, an imidazopyrazine group, an imidazopyridazine group, an azacarbazole group, an azafluorene group, an azadibenzosilole group, an azadibenzothiophene group, an azadibenzofuran group, or the like.), the π electron-rich $C_3$-$C_{60}$ cyclic group may be i) a T1 group, ii) a condensed cyclic group in which at least two T1 groups are condensed with each other, iii) a T3 group, iv) a condensed cyclic group in which at least two T3 groups are condensed with each other, or v) a condensed cyclic group in which at least one T3 group and at least one T1 group are condensed with each other (for example, the $C_3$-$C_{60}$ carbocyclic group, a 1H-pyrrole group, a silole group, a borole group, a 2H-pyrrole group, a 3H-pyrrole group, a thiophene group, a furan group, an indole group, a benzoindole group, a naphthoindole group, an isoindole group, a benzoisoindole group, a naphthoisoindole group, a benzosilole group, a benzothiophene group, a benzofuran group, a carbazole group, a dibenzosilole group, a dibenzothiophene group, a dibenzofuran group, an indenocarbazole group, an indolocarbazole group, a benzofurocarbazole group, a benzothienocarbazole group, a benzosilolocarbazole group, a benzoindolocarbazole group, a benzocarbazole group, a benzonaphthofuran group, a benzonaphthothiophene group, a benzonaphthosilole group, a benzofurodibenzofuran group, a benzofurodibenzothiophene group, a benzothienodibenzothiophene group, or the like.), the π electron-deficient nitrogen-containing $C_1$-$C_{60}$ cyclic group may be i) a T4 group, ii) a condensed cyclic group in which at least two T4 groups are condensed with each other, iii) a condensed cyclic group in which at least one T4 group and at least one T1 group are condensed with each other, iv) a condensed cyclic group in which at least one T4 group and at least one T3 group are condensed with each other, or v) a condensed cyclic group in which at least one T4 group, at least one T1 group, and at least one T3 group are condensed with one another (for example, a pyrazole group, an imidazole group, a triazole group, an oxazole group, an isoxazole group, an oxadiazole group, a thiazole group, an isothiazole group, a thiadiazole group, a benzopyrazole group, a benzimidazole group, a benzoxazole group, a benzoisoxazole group, a benzothiazole group, a benzoisothiazole group, a pyridine group, a pyrimidine group, a pyrazine group, a pyridazine group, a triazine group, a quinoline group, an isoquinoline group, a benzoquinoline group, a benzoisoquinoline group, a quinoxaline group, a benzoquinoxaline group, a quinazoline group, a benzoquinazoline group, a phenanthroline group, a cinnoline group, a phthalazine group, a naphthyridine group, an imidazopyridine group, an imidazopyrimidine group, an imidazotriazine group, an imidazopyrazine group, an imidazopyridazine group, an azacarbazole group, an azafluorene group, an azadibenzosilole group, an azadibenzothiophene group, an azadibenzofuran group, and the like), the T1 group may be a cyclopropane group, a cyclobutane group, a cyclopentane group, a cyclohexane group, a cycloheptane group, a cyclooctane group, a cyclobutene group, a cyclopentene group, a cyclopentadiene group, a cyclohexene group, a cyclohexadiene group, a cycloheptene group, an adamantane group, a norbornane (or bicyclo[2.2.1]heptane) group, a norbornene group, a bicyclo[1.1.1]pentane group, a bicyclo[2.1.1]hexane group, a bicyclo[2.2.2]octane group, or a benzene group, the T2 group may be a furan group, a thiophene group, a 1H-pyrrole group, a silole group, a borole group, a 2H-pyrrole group, a 3H-pyrrole group, an imidazole group, a pyrazole group, a triazole group, a tetrazole group, an oxazole group, an isoxazole group, an oxadiazole group, a thiazole group, an isothiazole group, a thiadiazole group, an azasilole group, an azaborole group, a pyridine group, a pyrimidine group, a pyrazine group, a pyridazine group, a triazine group, a tetrazine group, a pyrrolidine group, an imidazolidine group, a dihydropyrrole group, a piperidine group, a tetrahydropyridine group, a dihydropyridine group, a hexahydropyrimidine group, a tetrahydropyrimidine group, a dihydropyrimidine group, a piperazine group, a tetrahydropyrazine group, a dihydropyrazine group, a tetrahydropyridazine group, or a dihydropyridazine group, the T3 group may be a furan group, a thiophene group, a 1H-pyrrole group, a silole group, or a borole group, and the T4 group may be a 2H-pyrrole group, a 3H-pyrrole group, an imidazole group, a pyrazole group, a triazole group, a tetrazole group, an oxazole group, an isoxazole group, an oxadiazole group, a thiazole group, an isothiazole group, a thiadiazole group, an azasilole group, an azaborole group, a pyridine group, a pyrimidine group, a pyrazine group, a pyridazine group, a triazine group, or a tetrazine group.

The terms "the cyclic group, the $C_3$-$C_{60}$ carbocyclic group, the $C_1$-$C_{10}$ heterocyclic group, the π electron-rich $C_3$-$C_{60}$ cyclic group, or the π electron-deficient nitrogen-containing $C_1$-$C_{60}$ cyclic group" as used herein refer to a group condensed to any cyclic group, a monovalent group, or a polyvalent group (for example, a divalent group, a trivalent group, a tetravalent group, etc.) according to the structure of a formula for which the corresponding term is used. For example, the "benzene group" may be a benzo group, a phenyl group, a phenylene group, or the like, which may be easily understood by one of ordinary skill in the art according to the structure of a formula including the "benzene group."

Examples of the monovalent $C_3$-$C_{60}$ carbocyclic group and the monovalent $C_1$-$C_{60}$ heterocyclic group are a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{10}$ aryl group, a $C_1$-$C_{60}$ heteroaryl group, a monovalent non-aromatic condensed polycyclic group, and a monovalent non-aromatic condensed heteropolycyclic group. Examples of the divalent $C_3$-$C_{60}$ carbocyclic group and the monovalent $C_1$-$C_{60}$ heterocyclic group are a $C_3$-$C_{10}$ cycloalkylene group, a $C_1$-$C_{10}$ heterocycloalkylene group, a $C_3$-$C_{10}$ cycloalkenylene group, a $C_1$-$C_{10}$ heterocycloalkenylene group, a $C_6$-$C_{60}$ arylene group, a $C_1$-$C_{60}$ heteroarylene group, a divalent non-aromatic condensed polycyclic group, and a substituted or unsubstituted divalent non-aromatic condensed heteropolycyclic group.

The term "$C_1$-$C_{60}$ alkyl group" as used herein refers to a linear or branched aliphatic hydrocarbon monovalent group that has one to sixty carbon atoms, and specific examples thereof are a methyl group, an ethyl group, an n-propyl group, an isopropyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, and a tert-decyl group. The term "$C_1$-$C_{60}$ alkylene group" as used herein refers to a divalent group having the same structure as the $C_1$-$C_{60}$ alkyl group.

The term "$C_2$-$C_{60}$ alkenyl group" as used herein refers to a monovalent hydrocarbon group having at least one carbon-carbon double bond in the middle or at the terminus of the $C_2$-$C_{60}$ alkyl group, and examples thereof are an ethenyl group, a propenyl group, a butenyl group, and the like. The term "$C_2$-$C_{60}$ alkenylene group" as used herein refers to a divalent group having the same structure as the $C_2$-$C_{60}$ alkenyl group.

The term "$C_2$-$C_{60}$ alkynyl group" as used herein refers to a monovalent hydrocarbon group having at least one carbon-carbon triple bond in the middle or at the terminus of the $C_2$-$C_{60}$ alkyl group, and examples thereof are an ethynyl group, a propynyl group, and the like. The term "$C_2$-$C_{60}$ alkynylene group" as used herein refers to a divalent group having the same structure as the $C_2$-$C_{60}$ alkynyl group.

The term "$C_1$-$C_{60}$ alkoxy group" as used herein refers to a monovalent group represented by —$OA_{101}$ (wherein $A_{101}$ is the $C_1$-$C_{60}$ alkyl group), and examples thereof are a methoxy group, an ethoxy group, an isopropyloxy group, and the like.

The term "$C_3$-$C_{10}$ cycloalkyl group" as used herein refers to a monovalent saturated hydrocarbon cyclic group having 3 to 10 carbon atoms, and examples thereof are a cyclopropyl group, a cyclobutyl group, a cyclopentyl group, a cyclohexyl group, a cycloheptyl group, a cyclooctyl group, an adamantanyl group, a norbornanyl group (or bicyclo[2.2.1]heptyl group), a bicyclo[1.1.1]pentyl group, a bicyclo[2.1.1]hexyl group, a bicyclo[2.2.2]octyl group, and the like. The term "$C_3$-$C_{10}$ cycloalkylene group" as used herein refers to a divalent group having the same structure as the $C_3$-$C_{10}$ cycloalkyl group.

The term "$C_1$-$C_{10}$ heterocycloalkyl group" as used herein refers to a monovalent cyclic group of 1 to 10 carbon atoms, further including, in addition to carbon atoms, at least one heteroatom, as ring-forming atoms, and examples thereof are a 1,2,3,4-oxatriazolidinyl group, a tetrahydrofuranyl group, a tetrahydrothiophenyl group, and the like. The term "$C_1$-$C_{10}$ heterocycloalkylene group" as used herein refers to a divalent group having the same structure as the $C_1$-$C_{10}$ heterocycloalkyl group.

The term "$C_3$-$C_{10}$ cycloalkenyl group" as used herein refers to a monovalent cyclic group that has three to ten carbon atoms and at least one carbon-carbon double bond in the ring thereof and no aromaticity, and examples thereof are a cyclopentenyl group, a cyclohexenyl group, a cycloheptenyl group, and the like. The term "$C_3$-$C_1$ cycloalkenylene group" as used herein refers to a divalent group having the same structure as the $C_3$-$C_{10}$ cycloalkenyl group.

The term "$C_1$-$C_{10}$ heterocycloalkenyl group" as used herein refers to a monovalent cyclic group of 1 to 10 carbon atoms, further including, in addition to carbon atoms, at least one heteroatom, as ring-forming atoms, and having at least one carbon-carbon double bond in the cyclic structure thereof. Examples of the $C_1$-$C_{10}$ heterocycloalkenyl group are a 4,5-dihydro-1,2,3,4-oxatriazolyl group, a 2,3-dihydrofuranyl group, a 2,3-dihydrothiophenyl group, and the like. The term "$C_1$-$C_{10}$ heterocycloalkenylene group" as used herein refers to a divalent group having the same structure as the $C_1$-$C_{10}$ heterocycloalkenyl group.

The term "$C_6$-$C_{60}$ aryl group" as used herein refers to a monovalent group having a carbocyclic aromatic system of 6 to 60 carbon atoms, and the term "$C_6$-$C_{60}$ arylene group" as used herein refers to a divalent group having a carbocyclic aromatic system of 6 to 60 carbon atoms. Examples of the $C_6$-$C_{60}$ aryl group are a phenyl group, a pentalenyl group, a naphthyl group, an azulenyl group, an indacenyl group, an acenaphthyl group, a phenalenyl group, a phenanthrenyl group, an anthracenyl group, a fluoranthenyl group, a triphenylenyl group, a pyrenyl group, a chrysenyl group, a perylenyl group, a pentaphenyl group, a heptalenyl group, a naphthacenyl group, a picenyl group, a hexacenyl group, a pentacenyl group, a rubicenyl group, a coronenyl group, an ovalenyl group, and the like. When the $C_6$-$C_{60}$ aryl group and the $C_6$-$C_{60}$ arylene group each include two or more rings, the rings may be condensed with each other.

The term "$C_1$-$C_6$ heteroaryl group" as used herein refers to a monovalent group having a heterocyclic aromatic system of 1 to 60 carbon atoms, further including, in addition to carbon atoms, at least one heteroatom, as ring-forming atoms. The term "$C_1$-$C_6$ heteroarylene group" as used herein refers to a divalent group having a heterocyclic aromatic system of 1 to 60 carbon atoms, further including, in addition to carbon atoms, at least one heteroatom, as ring-forming atoms. Examples of the $C_1$-$C_{60}$ heteroaryl group are a pyridinyl group, a pyrimidinyl group, a pyrazinyl group, a pyridazinyl group, a triazinyl group, a quinolinyl group, a benzoquinolinyl group, an isoquinolinyl group, a benzoisoquinolinyl group, a quinoxalinyl group, a benzoquinoxalinyl group, a quinazolinyl group, a benzoquinazolinyl group, a cinnolinyl group, a phenanthrolinyl group, a phthalazinyl group, and a naphthyridinyl group. When the $C_1$-$C_{60}$ heteroaryl group and the $C_1$-$C_{60}$ heteroarylene group each include two or more rings, the rings may be condensed with each other.

The term "monovalent non-aromatic condensed polycyclic group" as used herein refers to a monovalent group (for example, having 8 to 60 carbon atoms) having two or more rings condensed to each other, only carbon atoms as ring-forming atoms, and no aromaticity in its entire molecular structure. Examples of the monovalent non-aromatic condensed polycyclic group are an indenyl group, a fluorenyl group, a spiro-bifluorenyl group, a benzofluorenyl group, an indenophenanthrenyl group, an indeno anthracenyl group, and the like. The term "divalent non-aromatic condensed polycyclic group" as used herein refers to a divalent group having the same structure as the monovalent non-aromatic condensed polycyclic group described above.

The term "monovalent non-aromatic condensed heteropolycyclic group" as used herein refers to a monovalent group (for example, having 1 to 60 carbon atoms) having two or more rings condensed to each other, further including, in addition to carbon atoms, at least one heteroatom, as ring-forming atoms, and having non-aromaticity in its entire molecular structure. Examples of the monovalent non-aromatic condensed heteropolycyclic group are a pyrrolyl group, a thiophenyl group, a furanyl group, an indolyl group, a benzoindolyl group, a naphthoindolyl group, an isoindolyl group, a benzoisoindolyl group, a naphthoisoindolyl group, a benzosilolyl group, a benzothiophenyl group, a benzofuranyl group, a carbazolyl group, a dibenzosilolyl group, a dibenzothiophenyl group, a dibenzofuranyl group, an azacarbazolyl group, an azafluorenyl group, an azadibenzosilolyl group, an azadibenzothiophenyl group, an azadibenzofuranyl group, a pyrazolyl group, an imidazolyl group, a triazolyl group, a tetrazolyl group, an oxazolyl group, an isoxazolyl group, a thiazolyl group, an isothiazolyl group, an oxadiazolyl group, a thiadiazolyl group, a benzopyrazolyl group, a benzimidazolyl group, a benzoxazolyl group, a benzothiazolyl group, a benzoxadiazolyl group, a benzothiadiazolyl group, an imidazopyridinyl group, an imidazopyrimidinyl group, an imidazotriazinyl group, an imidazopyrazinyl group, an imidazopyridazinyl group, an indeno carbazolyl group, an indolocarbazolyl group, a benzofurocarbazolyl group, a benzothienocarbazolyl group, a benzosilolocarbazolyl group, a benzoindolocarbazolyl group, a benzocarbazolyl group, a benzonaphthofuranyl group, a benzonaphthothiophenyl group, a benzonaphtho silolyl group, a benzofurodibenzofuranyl group, a benzofurodibenzothiophenyl group, and a benzothienodibenzothiophenyl group. The term "divalent non-aromatic condensed heteropolycyclic group" as used herein refers to a divalent group having the same structure as the monovalent non-aromatic condensed heteropolycyclic group described above.

The term "$C_6$-$C_{60}$ aryloxy group" as used herein indicates —$OA_{102}$ (wherein $A_{102}$ is the $C_6$-$C_{60}$ aryl group), and the term "$C_6$-$C_{60}$ arylthio group" as used herein indicates —$SA_{103}$ (wherein $A_{103}$ is the $C_6$-$C_{60}$ aryl group).

The term "$C_7$-$C_{60}$ arylalkyl group" as used herein refers to -$A_{104}A_{105}$ (wherein $A_{104}$ is a $C_1$-$C_{54}$ alkylene group, and $A_{105}$ is a $C_6$-$C_{59}$ aryl group), and the term "$C_2$-$C_{60}$ heteroarylalkyl group" as used herein refers to -$A_{106}A_{107}$ (wherein $A_{106}$ is a $C_1$-$C_{59}$ alkylene group, and $A_{107}$ is a $C_1$-$C_{59}$ heteroaryl group).

The term "$R_{10a}$" as used herein may be:

deuterium, —F, —Cl, —Br, —I, a hydroxyl group, a cyano group, or a nitro group; a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ arylalkyl group, a $C_2$-$C_{60}$ heteroarylalkyl group, —$Si(Q_{11})(Q_{12})(Q_{13})$, —$N(Q_{11})(Q_{12})$, —$B(Q_{11})(Q_{12})$, —$C(=O)(Q_{11})$, —$S(=O)_2(Q_{11})$, —$P(=O)(Q_{11})(Q_{12})$, or any combination thereof;

a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, or a $C_2$-$C_{60}$ heteroaryl alkyl group, each unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —$Si(Q_{21})(Q_{22})(Q_{23})$, —$N(Q_{21})(Q_{22})$, —$B(Q_{21})(Q_{22})$, —$C(=O)(Q_{21})$, —$S(=O)_2(Q_{21})$, —$P(=O)(Q_{21})(Q_{22})$, or any combination thereof; or —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, or —$P(=O)(Q_{31})(Q_{32})$.

In the present specification, $Q_1$ to $Q_3$, $Q_{11}$ to $Q_{13}$, $O_{21}$ to $Q_{23}$, and $Q_{31}$ to $Q_{33}$ may each independently be: hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof; a $C_7$-$C_{60}$ aryl alkyl group; or a $C_2$-$C_{60}$ heteroaryl alkyl group.

The term "heteroatom" as used herein refers to any atom other than a carbon atom. Examples of the heteroatom are O, S, N, P, Si, B, Ge, Se, or any combination thereof.

"Ph" as used herein refers to a phenyl group, "Me" as used herein refers to a methyl group, "Et" as used herein refers to an ethyl group, "tert-Bu" or "$Bu^t$" as used herein refers to a tert-butyl group, and "OMe" as used herein refers to a methoxy group.

The term "biphenyl group" as used herein refers to "a phenyl group substituted with a phenyl group." In other words, the "biphenyl group" is a substituted phenyl group having a $C_6$-$C_{60}$ aryl group as a substituent.

The term "terphenyl group" as used herein refers to "a phenyl group substituted with a biphenyl group." In other words, the "terphenyl group" is a substituted phenyl group having, as a substituent, a $C_6$-$C_{60}$ aryl group substituted with a $C_6$-$C_{60}$ aryl group.

* and *' as used herein, unless defined otherwise, each refer to a binding site to a neighboring atom in a corresponding formula or moiety.

In the present specification, the x-axis, y-axis, and z-axis are not limited to three axes in an orthogonal coordinate system, and may be interpreted in a broad sense including these axes. For example, the x-axis, y-axis, and z-axis may refer to those orthogonal to each other, or may refer to those in different directions that are not orthogonal to each other.

In a further aspect, the invention relates to a method for producing an optoelectronic component. In this case an organic molecule of the invention is used.

The organic light-emitting device, in particular the OLED according to the present invention can be fabricated by any means of vapor deposition and/or liquid processing. Accordingly, at least one layer is prepared by means of a sublimation process, prepared by means of an organic vapor phase deposition process, prepared by means of a carrier gas sublimation process, solution processed or printed.

The methods used to fabricate the organic light-emitting device, in particular the OLED according to the present invention are known in the art. The different layers are individually and successively deposited on a suitable substrate by means of subsequent deposition processes. The individual layers may be deposited using the same or differing deposition methods.

Vapor deposition processes exemplarily comprise thermal (co)evaporation, chemical vapor deposition and physical vapor deposition. For active matrix OLED display, an AMOLED backplane is used as substrate. The individual layer may be processed from solutions or dispersions employing adequate solvents. Solution deposition process exemplarily comprise spin coating, dip coating and jet printing. Liquid processing may optionally be carried out in an inert atmosphere (e.g., in a nitrogen atmosphere) and the solvent may optionally be completely or partially removed by means known in the state of the art.

EXAMPLES

General synthesis scheme I

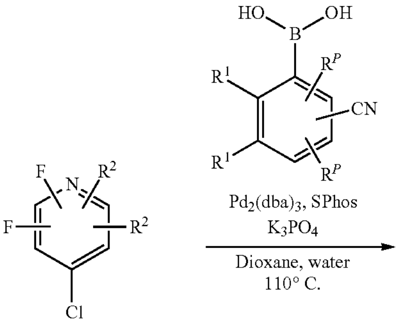

-continued

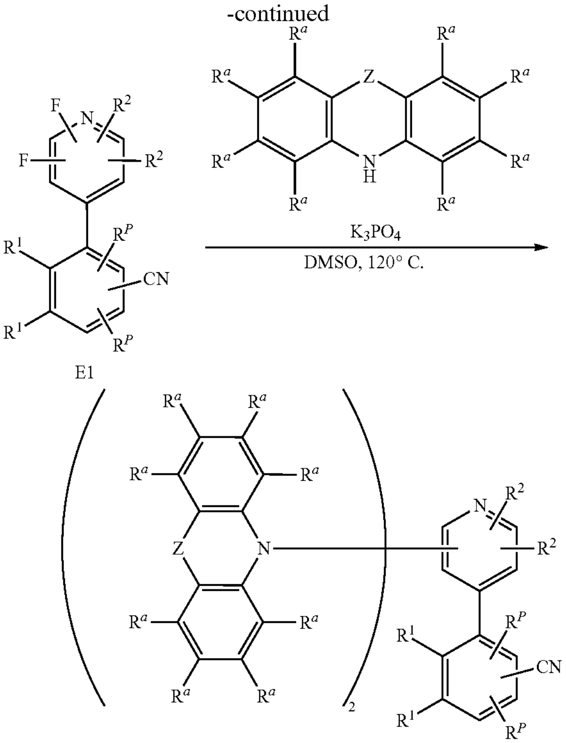

E1

General Synthesis Scheme AAV1-1:

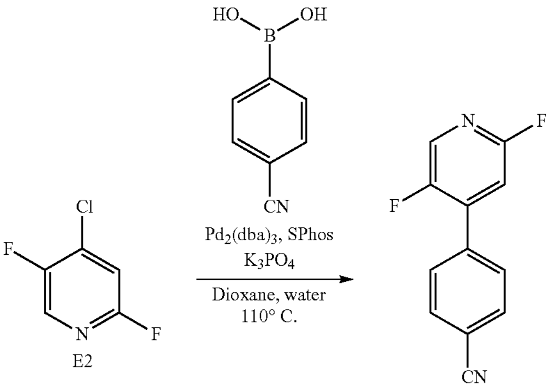

E2
Z1

4-chloro-2,5-difluoropyridine E2 (1.00 equivalents), 4-cyano-phenylboronic acid (1.20 equivalents), $Pd_2(dba)_3$ (0.02 equivalent), 2-dicyclohexylphosphino-2',6'-dimethoxybiphenyl (SPhos) (0.08 equivalents) and tribasic potassium phosphate (2.50 equivalents) are stirred under nitrogen atmosphere in a dioxane/water mixture (ratio of 10:1) at 110° C. for 20 h. To the reaction mixture Celite and active carbon are added and stirred at 110° C. for 15 min. Subsequently the reaction mixture is hot filtered and the residue washed with dioxane. The reaction mixture is poured into 200 mL of a saturated sodium chloride solution and extracted with ethyl acetate. The combined organic phases are washed with saturated sodium chloride solution, dried over $MgSO_4$ and the solvent is evaporated under reduced pressure. The crude product obtained is purified by recrystallization in cyclohexane and the product obtained as solid.

Instead of a boronic acid a corresponding boronic acid ester may be used.

General Procedure for Synthesis AAV1-2:

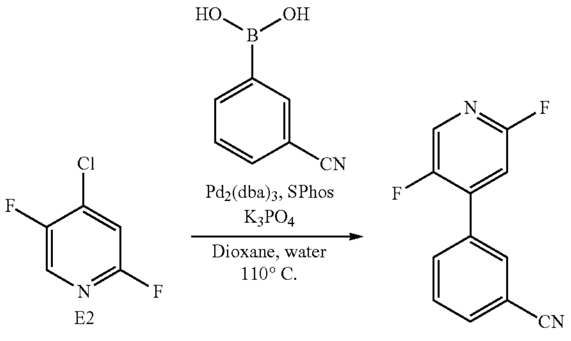

E2
Z2

The synthesis of Z2 is carried out according to AAV1-1, wherein 4-chloro-2,5-difluoropyridine E2 reacts with 3-cyano-phenylboronic acid.

General Procedure for Synthesis AAV1-3:

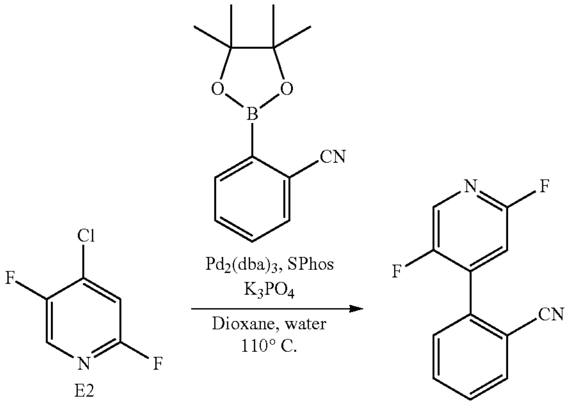

E2
Z3

The synthesis of Z3 is carried out according to AAV1-1, wherein 4-chloro-2,5-difluoropyridine E2 reacts with 3-cyano-phenylboronic acid ester.

General Procedure for Synthesis AAV2-1:

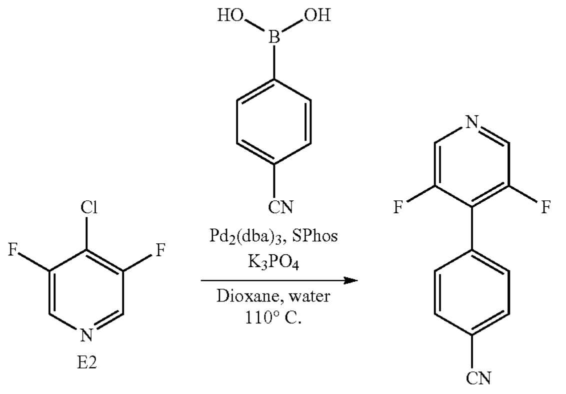

E2
Z4

The synthesis of Z4 is carried out according to AAV1-1, wherein 4-chloro-3,5-difluoropyridine E2 reacts with 4-cyano-phenylboronic acid.

General Procedure for Synthesis AAV2-2:

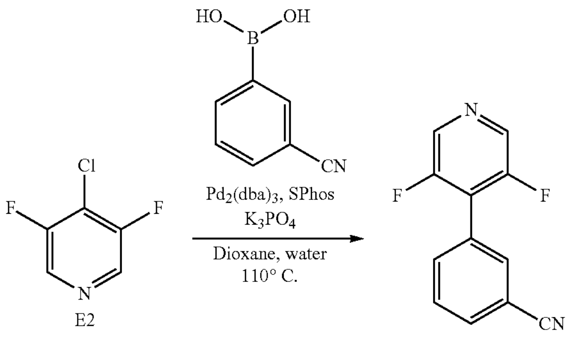

E2 Z5

The synthesis of Z5 is carried out according to AAV1-1, wherein 4-chloro-3,5-difluoropyridine E2 reacts with 3-cyano-phenylboronic acid.

General Procedure for Synthesis AAV2-3:

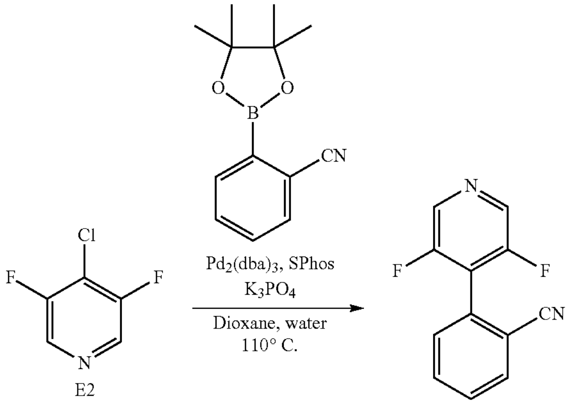

E2 Z6

The synthesis of Z6 is carried out according to AAV1-1, wherein 4-chloro-3,5-difluoropyridine E2 reacts with 2-cyano-phenylboronic acid ester.

General Procedure for Synthesis AAV3-1:

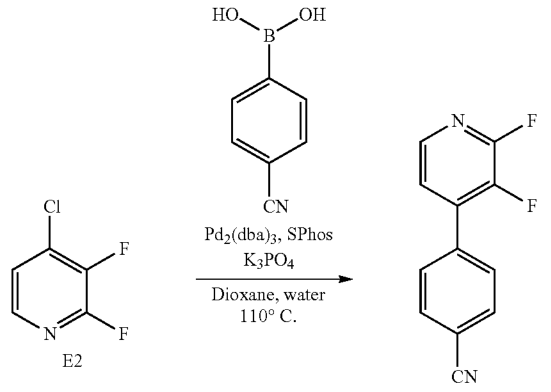

E2 Z7

The synthesis of Z7 is carried out according to AAV1-1, wherein 4-chloro-2,3-difluoropyridine E2 reacts with 4-cyano-phenylboronic acid.

General Procedure for Synthesis AAV3-2:

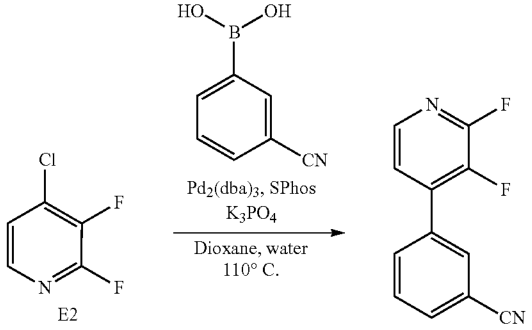

E2 Z8

The synthesis of Z8 is carried out according to AAV1-1, wherein 4-chloro-2,3-difluoropyridine E2 reacts with 3-cyano-phenylboronic acid.

General Procedure for Synthesis AAV3-3:

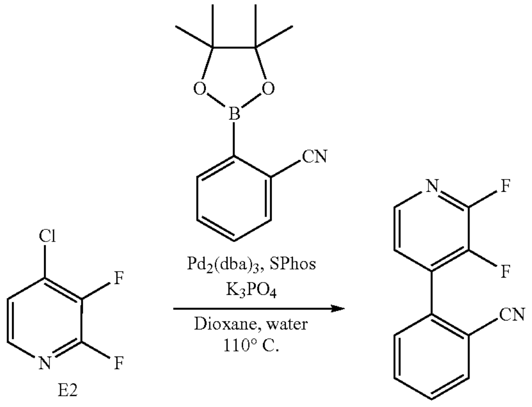

E2 Z9

The synthesis of Z9 is carried out according to AAV1-1, wherein 4-chloro-2,3-difluoropyridine E2 reacts with 2-cyano-phenylboronic acid ester.
General Procedure for Synthesis AAV7:
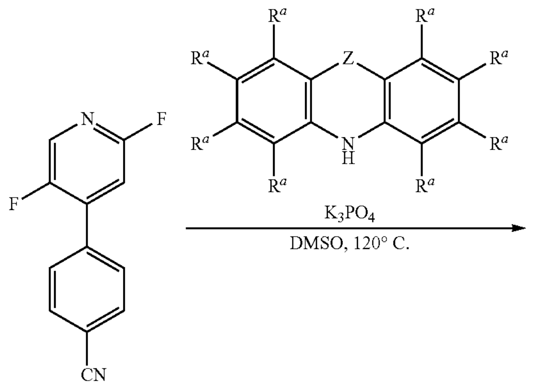
Z1
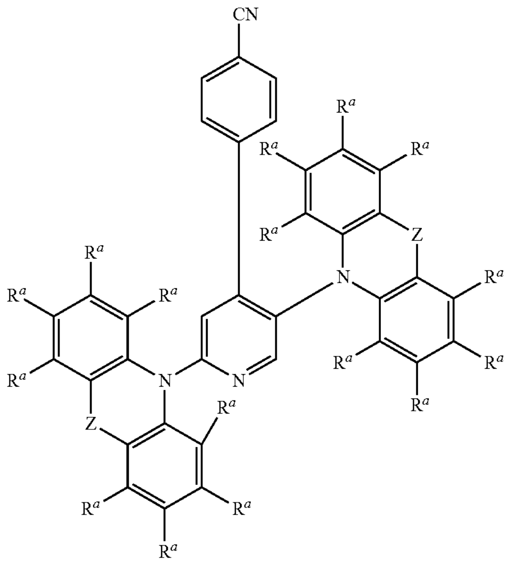
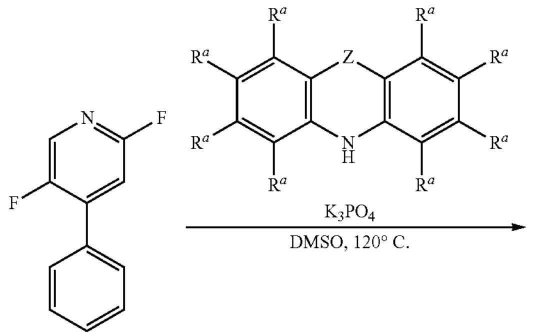
Z2
-continued
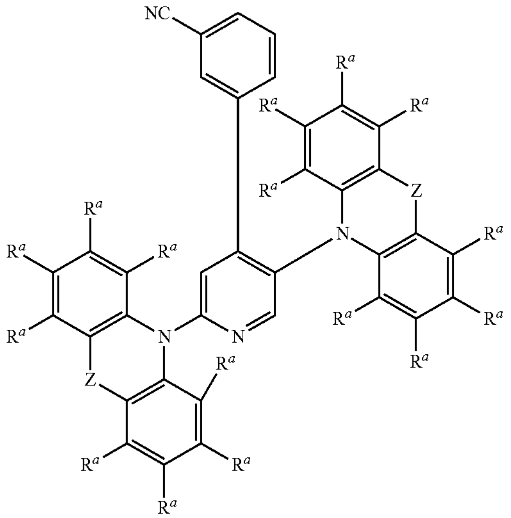
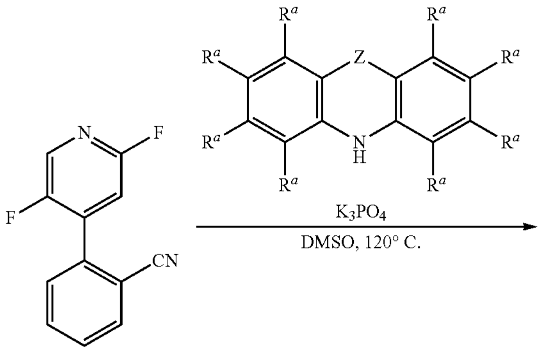
Z3
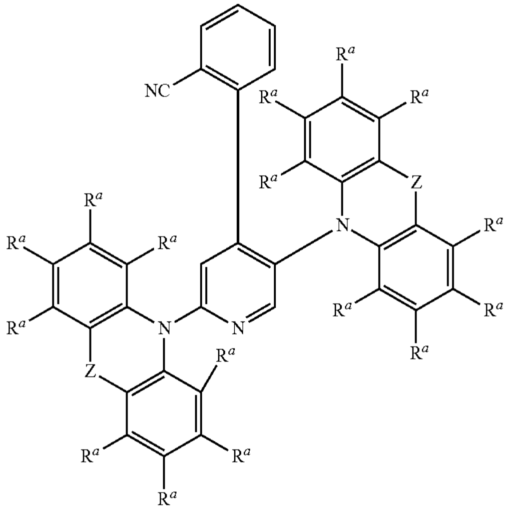

-continued
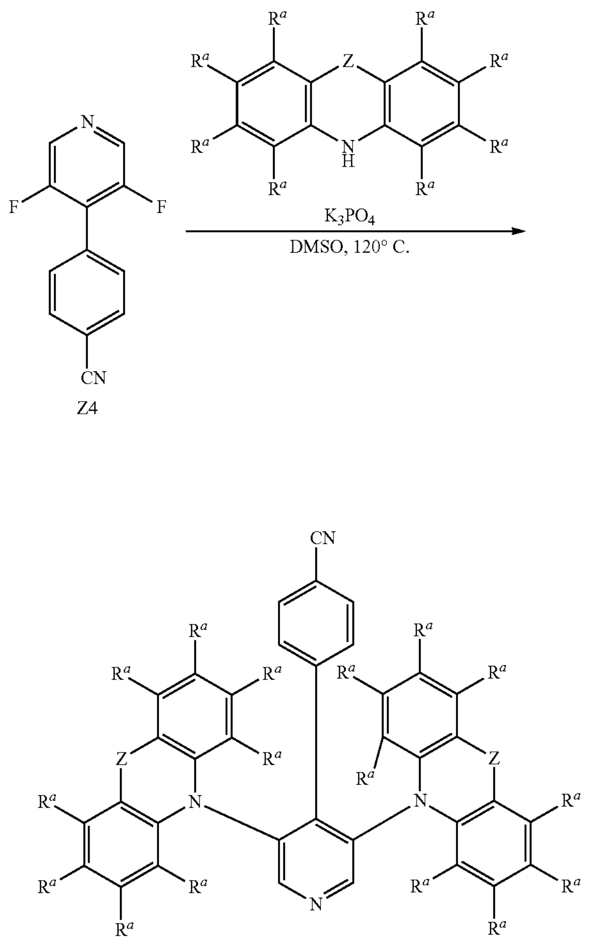
Z4
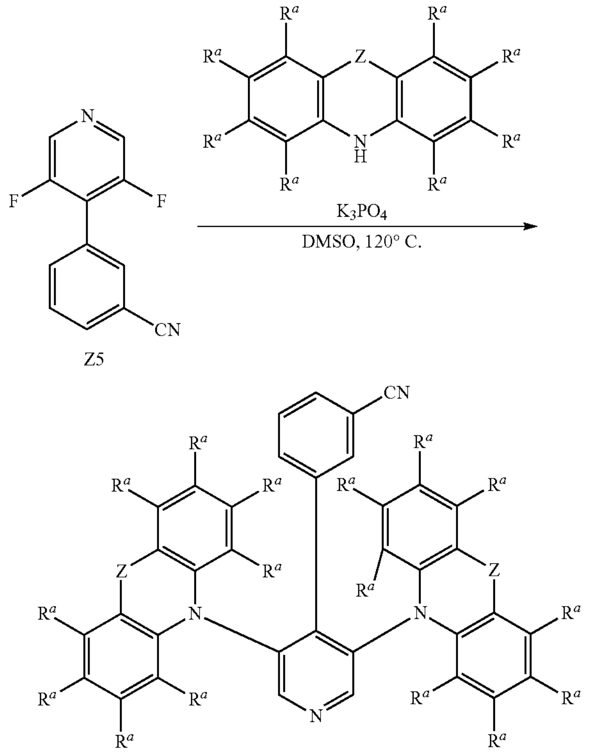
Z5
-continued
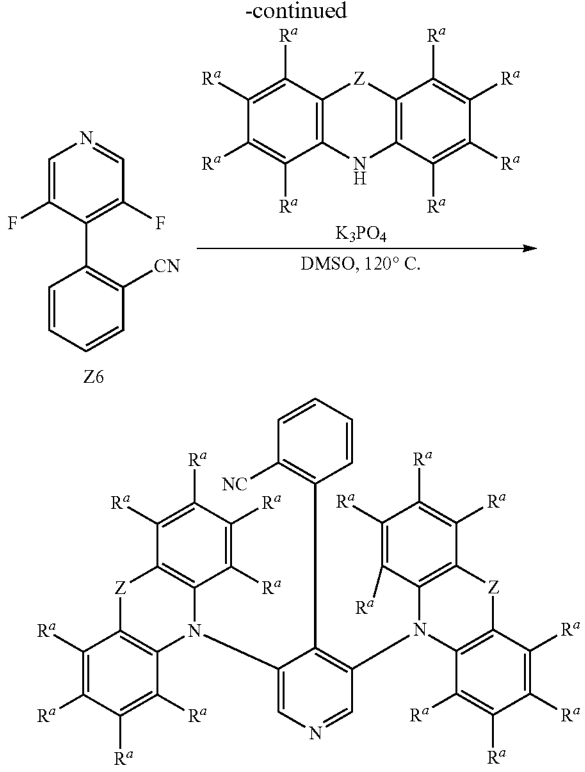
Z6
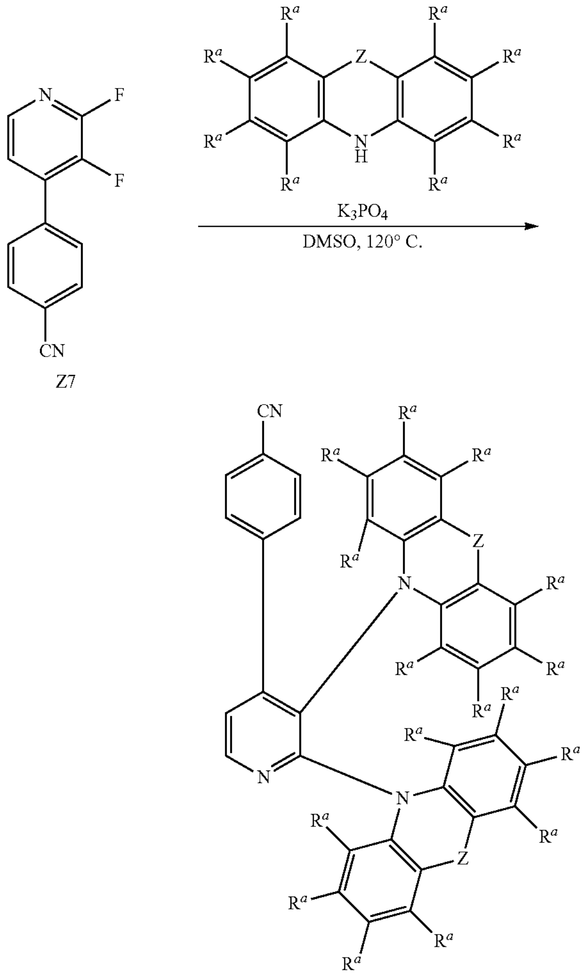
Z7

-continued

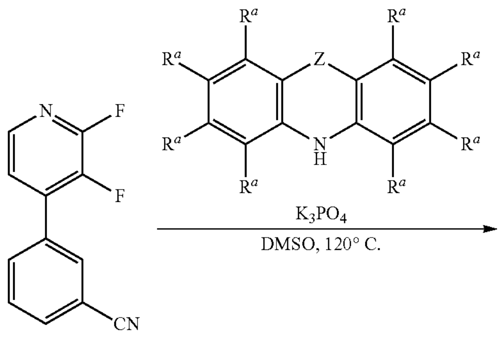

Z8

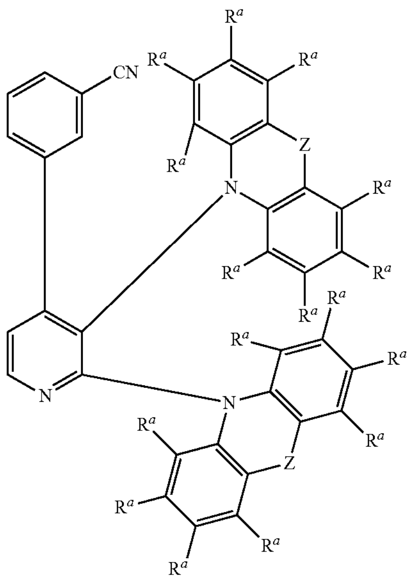

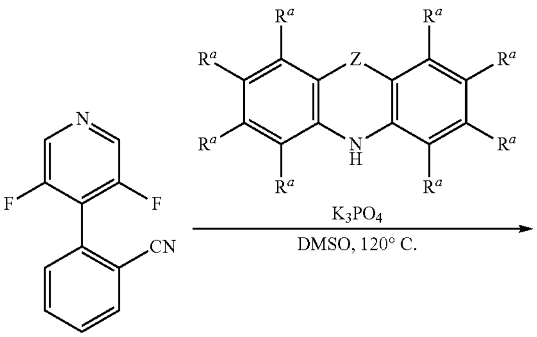

Z9

-continued

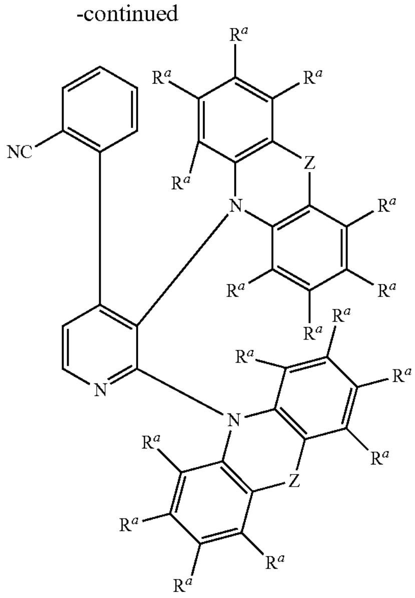

Z1, Z2, Z3, Z4, Z5, Z6, Z7, Z8, or Z9 (1 equivalent each), the corresponding donor molecule D-H (2.00 equivalents) and tribasic potassium phosphate (5.00 equivalents) are suspended under nitrogen atmosphere in DMSO and stirred at 120° C. (16 h). Subsequently the reaction mixture is poured into a saturated sodium chloride solution and extracted three times with dichloromethane. The combined organic phases are washed twice with saturated sodium chloride solution, dried over $MgSO_4$ and the solvent evaporated under reduced pressure. The crude product is purified by recrystallization out of ethanol or by flash chromatography. The product is obtained as a solid.

In particular, the donor molecule D-H is a 3,6-substituted carbazole (e.g., 3,6-dimethylcarbazole, 3,6-diphenylcarbazole, 3,6-di-tert-butylcarbazole), a 2,7-substituted carbazole (e.g., 2,7-dimethylcarbazole, 2,7-diphenylcarbazole, 2,7-di-tert-butylcarbazole), a 1,8-substituted carbazole (e.g., 1,8-dimethylcarbazole, 1,8-diphenylcarbazole, 1,8-di-tert-butylcarbazole), a 1-substituted carbazole (e.g., 1-methylcarbazole, 1-phenylcarbazole, 1-tert-butylcarbazole), a 2-substituted carbazole (e.g., 2-methylcarbazole, 2-phenylcarbazole, 2-tert-butylcarbazole), or a 3-substituted carbazole (e.g., 3-methylcarbazole, 3-phenylcarbazole, 3-tert-butylcarbazole).

Exemplarily a halogen-substituted carbazole, particularly 3-bromocarbazole, can be used as D-H.

In a subsequent reaction a boronic acid ester functional group or boronic acid functional group may be exemplarily introduced at the position of the one or more halogen substituents, which was introduced via D-H, to yield the corresponding carbazol-3-ylboronic acid ester or carbazol-3-ylboronic acid, e.g., via the reaction with bis(pinacolato) diboron (CAS No. 73183-34-3). Subsequently, one or more substituents $R^a$ may be introduced in place of the boronic acid ester group or the boronic acid group via a coupling reaction with the corresponding halogenated reactant $R^a$-Hal, preferably $R^a$—Cl and $R^a$—Br.

Alternatively, one or more substituents $R^a$ may be introduced at the position of the one or more halogen substituents, which was introduced via D-H, via the reaction with a boronic acid of the substituent $R^a$ [$R^a$—$B(OH)_2$] or a corresponding boronic acid ester.

Cyclic Voltammetry

Cyclic voltammograms are measured from solutions having concentration of $10^3$ mol/L of the organic molecules in dichloromethane or a suitable solvent and a suitable supporting electrolyte (e.g. 0.1 mol/L of tetrabutylammonium hexafluorophosphate). The measurements are conducted at room temperature under nitrogen atmosphere with a three-electrode assembly (Working and counter electrodes: Pt wire, reference electrode: Pt wire) and calibrated using $FeCp_2/FeCp_2^+$ as internal standard. The HOMO data was corrected using ferrocene as internal standard against SCE.

Density Functional Theory Calculation

Molecular structures are optimized employing the BP86 functional and the resolution of identity approach (RI). Excitation energies are calculated using the (BP86) optimized structures employing Time-Dependent DFT (TD-DFT) methods. Orbital and excited state energies are calculated with the B3LYP functional. Def2-SVP basis sets (and a m4-grid for numerical integration are used. The Turbomole program package is used for all calculations.

Photophysical Measurements

Sample pretreatment: Spin-coating

Apparatus: Spin150, SPS euro.

The sample concentration is 10 mg/ml, dissolved in a suitable solvent.

Program: $1)_3$ s at 400 U/min; 20 s at 1000 U/min at 1000 Upm/s. 3) 10 s at 4000 U/min at 1000 Upm/s. After coating, the films are tried at 70° C. for 1 min.

Photoluminescence spectroscopy and TCSPC (Time-correlated single-photon counting) Steady-state emission spectroscopy is measured by a Horiba Scientific, Modell FluoroMax-4 equipped with a 150 W Xenon-Arc lamp, excitation- and emissions monochromators and a Hamamatsu R928 photomultiplier and a time-correlated single-photon counting option.

Emissions and excitation spectra are corrected using standard correction fits.

Excited state lifetimes are determined employing the same system using the TCSPC method with FM-2013 equipment and a Horiba Yvon TCSPC hub.

Excitation Sources:

NanoLED 370 (wavelength: 371 nm, pulse duration: 1.1 ns)

NanoLED 290 (wavelength: 294 nm, pulse duration: <1 ns)

SpectraLED 310 (wavelength: 314 nm)

SpectraLED 355 (wavelength: 355 nm).

Data analysis (exponential fit) is done using the software suite DataStation and DAS6 analysis software. The fit is specified using the chi-squared-test.

Photoluminescence Quantum Yield Measurements

For photoluminescence quantum yield (PLQY) measurements an Absolute PL Quantum Yield Measurement C9920-03G system (Hamamatsu Photonics) is used. Quantum yields and CIE coordinates are determined using the software U6039-05 version 3.6.0.

Emission maxima are given in nm, quantum yields Φ in % and CIE coordinates as x,y values. PLQY is determined using the following protocol:

1) Quality assurance: Anthracene in ethanol (known concentration) is used as reference 2) Excitation wavelength: the absorption maximum of the organic molecule is determined and the molecule is excited using this wavelength 3) Measurement Quantum yields are measured for sample of solutions or films under nitrogen atmosphere. The yield is calculated using the equation:

$$\Phi_{PL} = \frac{n_{photon},\ \text{emited}}{n_{photon},\ \text{absorbed}} = \frac{\int \frac{\lambda}{hc}\left[Int_{emitted}^{sample}(\lambda) - Int_{absorbed}^{sample}(\lambda)\right]d\lambda}{\int \frac{\lambda}{hc}\left[Int_{emitted}^{reference}(\lambda) - Int_{absorbed}^{reference}(\lambda)\right]d\lambda}$$

wherein $n_{photon}$ denotes the photon count and Int. the intensity.

Production and Characterization of Organic Electroluminescence Devices

OLED devices comprising organic molecules according to the invention can be produced via vacuum-deposition methods. If a layer contains more than one compound, the weight-percentage of one or more compounds is given in %. The total weight-percentage values amount to 100%, thus if a value is not given, the fraction of this compound equals to the difference between the given values and 100%.

The not fully optimized OLEDs are characterized using standard methods and measuring electroluminescence spectra, the external quantum efficiency (in %) in dependency on the intensity, calculated using the light detected by the photodiode, and the current. The OLED device lifetime is extracted from the change of the luminance during operation at constant current density. The LT50 value corresponds to the time, where the measured luminance decreased to 50% of the initial luminance, analogously LT80 corresponds to the time point, at which the measured luminance decreased to 80% of the initial luminance, LT 95 to the time point, at which the measured luminance decreased to 95% of the initial luminance etc. Accelerated lifetime measurements are performed (e.g. applying increased current densities). Exemplarily LT80 values at 500 cd/m$^2$ are determined using the following equation:

$$LT80\left(500\frac{\text{cd}^2}{\text{m}^2}\right) = LT80(L_0)\left(\frac{L_0}{500\frac{\text{cd}^2}{\text{m}^2}}\right)^{1.6}$$

wherein $L_0$ denotes the initial luminance at the applied current density.

The values correspond to the average of several pixels (typically two to eight), the standard deviation between these pixels is given. Figures show the data series for one OLED pixel.

Example 1

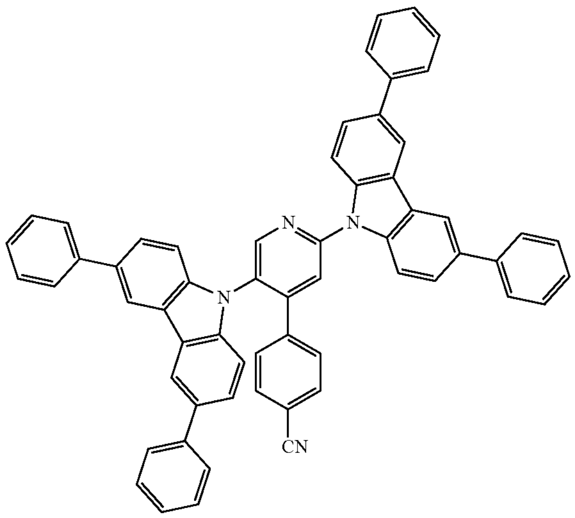 [SMILES: N#Cc1ccc(-c2cc(-n3c4ccc(-c5ccccc5)cc4c4cc(-c5ccccc5)ccc43)ncc2-n2c3ccc(-c4ccccc4)cc3c3cc(-c4ccccc4)ccc32)cc1]

Example 1 was synthesized according to AAV1-1 (52% yield) and AAV7 (50% yield).

| Molecular Formula | Retention Time | m/z calculated | m/z found |
|---|---|---|---|
| $C_{60}H_{38}N_4$ | 10.99 min | 814.31 | 814.45 |

FIG. 1 depicts the emission spectrum of example 1 (10% by weight in PMMA). The emission maximum is at 471 nm. The photoluminescence quantum yield (PLQY) is 83% and the full width at half maximum is 0.41 eV.

Example 2

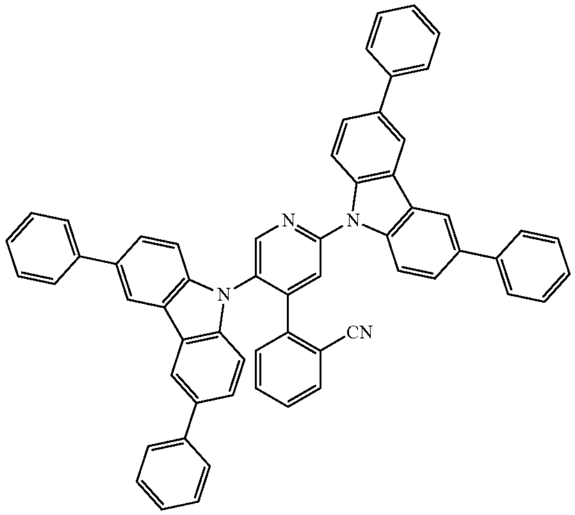 [SMILES: N#Cc1ccccc1-c1cc(-n2c3ccc(-c4ccccc4)cc3c3cc(-c4ccccc4)ccc32)ncc1-n1c2ccc(-c3ccccc3)cc2c2cc(-c3ccccc3)ccc21]

Example 2 was synthesized according to AAV1-3 (42% yield) and AAV7 (39% yield). MS (HPLC-MS):

| Molecular Formula | Retention Time | m/z calculated | m/z found |
|---|---|---|---|
| $C_{60}H_{38}N_4$ | 10.92 min | 814.31 | 814.43 |

Figure 2:
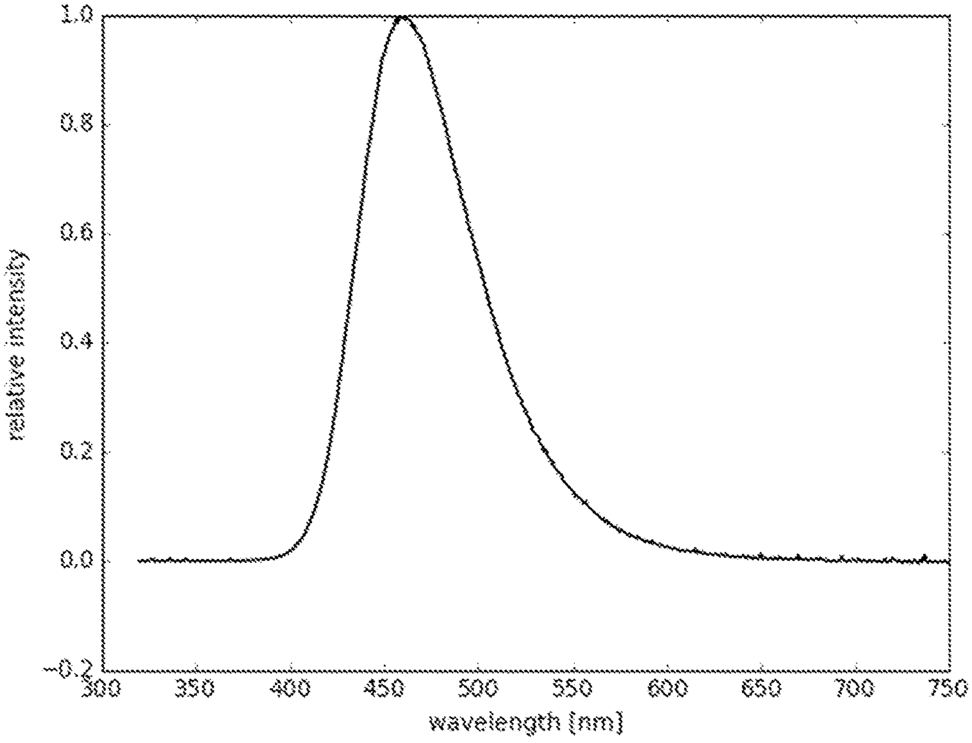
FIG. 2 is an emission spectrum of example 2 (10%) by weight) in PMMA.

FIG. 2 depicts the emission spectrum of example 2 (10% by weight in PMMA). The emission maximum is at 461 nm. The photoluminescence quantum yield (PLQY) is 78% and the full width at half maximum is 0.40 eV.

Example 3

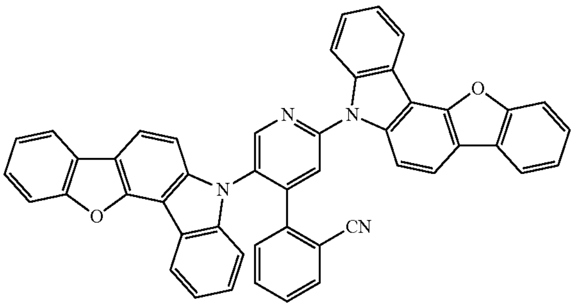 [SMILES: N#Cc1ccccc1-c1cc(-n2c3ccccc3c3c4oc5ccccc5c4ccc32)ncc1-n1c2ccccc2c2c3oc4ccccc4c3ccc21]

Example 3 was synthesized according to AAV1-3 (73% yield) and AAV7 (32% yield).

| Molecular Formula | Retention Time | m/z calculated | m/z found |
|---|---|---|---|
| $C_{48}H_{26}N_4O_2$ | 9.86 min | 690.76 | 690.36 |

Figure 3:
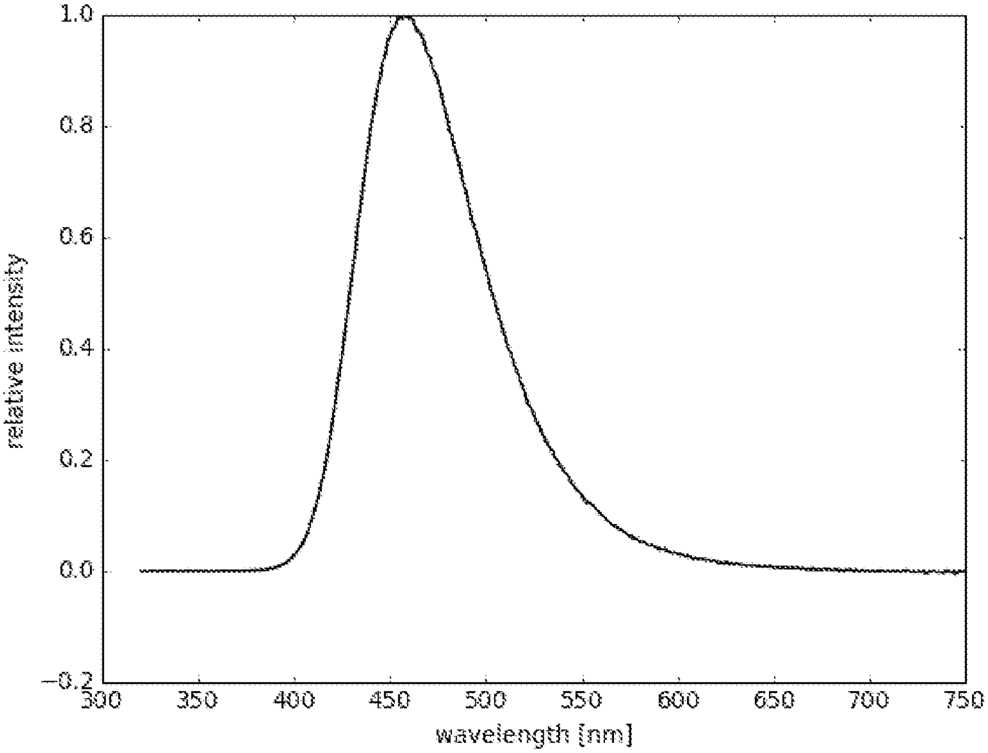
FIG. 3 is an emission spectrum of example 3 (10%) by weight) in PMMA.

FIG. 3 depicts the emission spectrum of example 3 (10% by weight in PMMA). The emission maximum is at 458 nm. The photoluminescence quantum yield (PLQY) is 79% and the full width at half maximum is 0.43 eV.

Example D1

Example 2 was tested in the OLED D1, which was fabricated with the following layer structure:

| Layer No. | Thickness | Compound |
|---|---|---|
| 8 | 100 nm | Al |
| 7 | 2 nm | Liq |
| 6 | 25 nm | NBPhen |
| 5 | 50 nm | Example 2 (10%): mCBP (70%): T2T (20%) |
| 4 | 10 nm | mCBP |
| 3 | 10 nm | TCTA |
| 2 | 95 nm | NPB |
| 1 | 130 nm | ITO |
| Substrate | | glass |

Device D1 yielded an external quantum efficiency (EQE) at 1000 cd/m$^2$ of 6.0%. The emission maximum is at 461 nm with a FWHM of 59 nm at 7 V. The corresponding CIEx value is 0.15 and CIEy is 0.15.

Example D2

Example 2 was tested in the OLED D2, which was fabricated with the following layer structure:

| Layer No. | Thickness | Compound |
|---|---|---|
| 8 | 100 nm | Al |
| 7 | 2 nm | Liq |
| 6 | 30 nm | NBPhen |
| 5 | 50 nm | Example 2 (20%): mCBP (80%) |
| 4 | 10 nm | mCBP |
| 3 | 10 nm | TCTA |
| 2 | 100 nm | NPB |
| 1 | 130 nm | ITO |
| Substrate | | glass |

Device D2 yielded an external quantum efficiency (EQE) at 1000 cd/$m^2$ of 5.9%. The emission maximum is at 468 nm with a FWHM of 64 nm at 10 V. The corresponding CIEx value is 0.14 and CIEy is 0.17.

Example D3

Example 3 was tested in the OLED D3, which was fabricated with the following layer structure:

| Layer No. | Thickness | Compound |
|---|---|---|
| 9 | 100 nm | Al |
| 8 | 2 nm | Liq |
| 7 | 20 nm | NBPhen |
| 6 | 10 nm | T2T |
| 5 | 50 nm | Example 3 (10%): mCBP (90%) |
| 4 | 10 nm | mCBP |
| 3 | 10 nm | TCTA |
| 2 | 100 nm | NPB |
| 1 | 130 nm | ITO |
| Substrate | | glass |

Device D3 yielded an external quantum efficiency (EQE) at 1000 cd/$m^2$ of 4.9%. The emission maximum is at 457 nm with a FWHM of 68 nm at 10 V. The corresponding CIEx value is 0.15 and CIEy is 0.14.

Additional Examples of Organic Molecules of the Invention

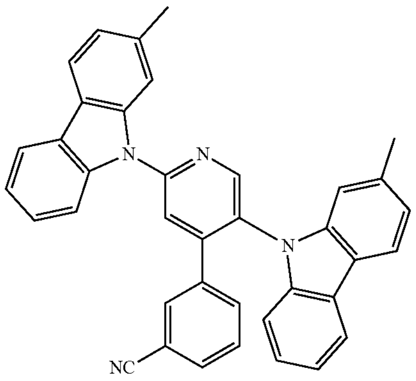

-continued

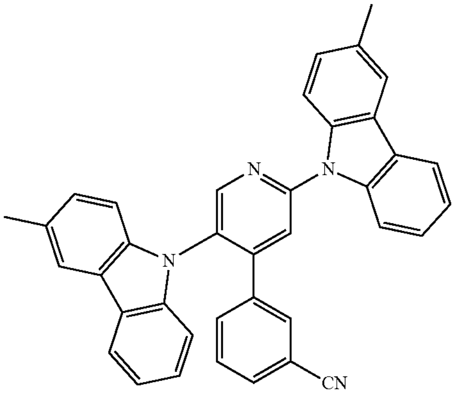

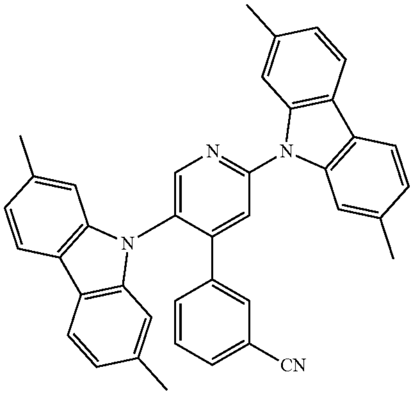

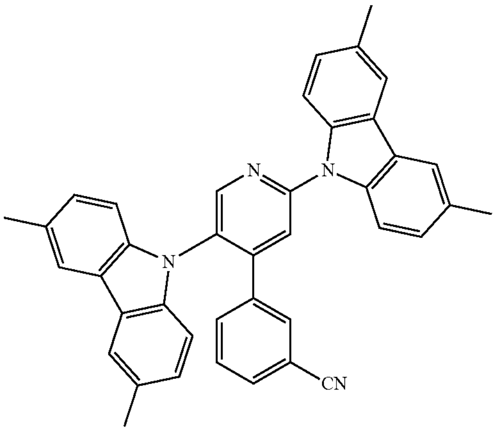

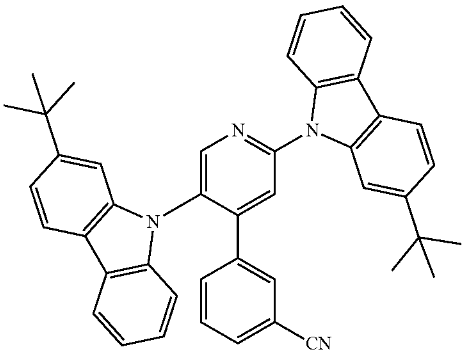

-continued
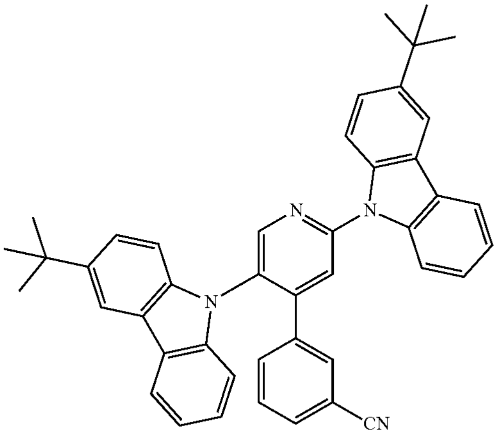
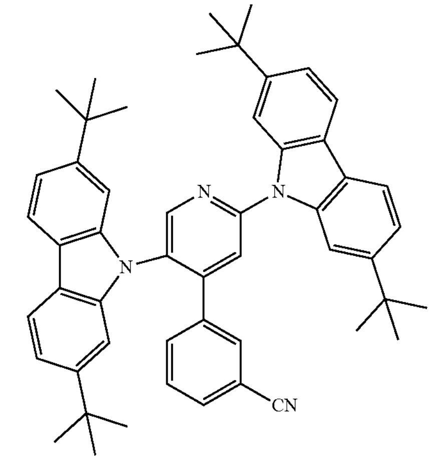
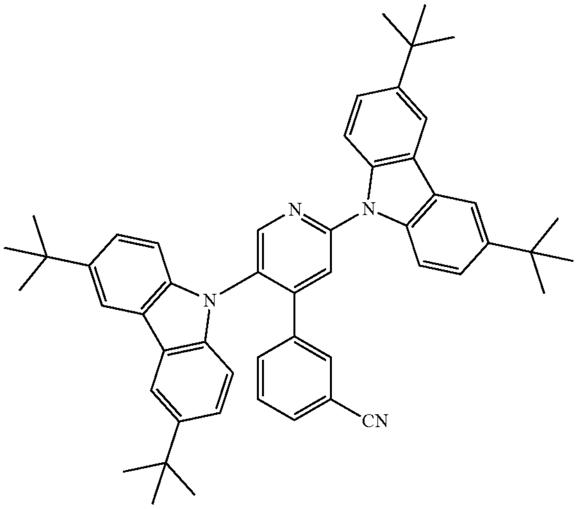
-continued
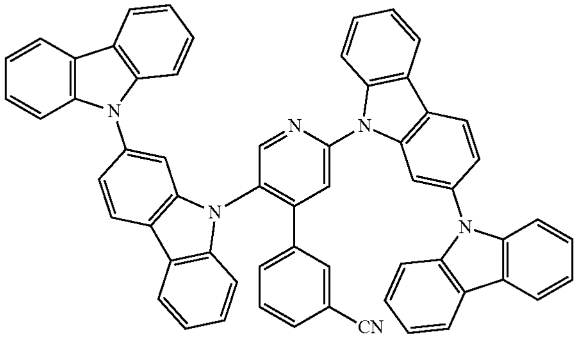
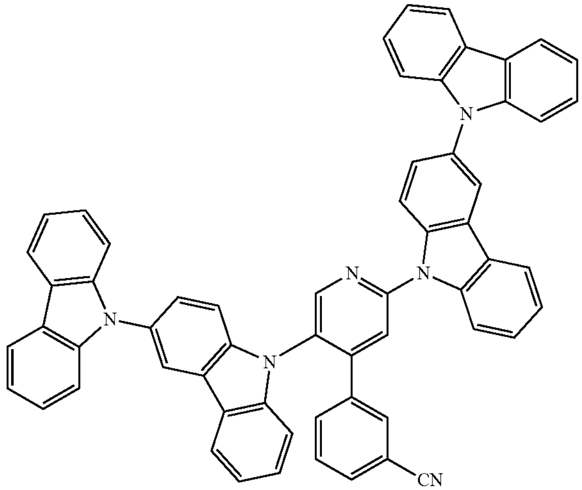
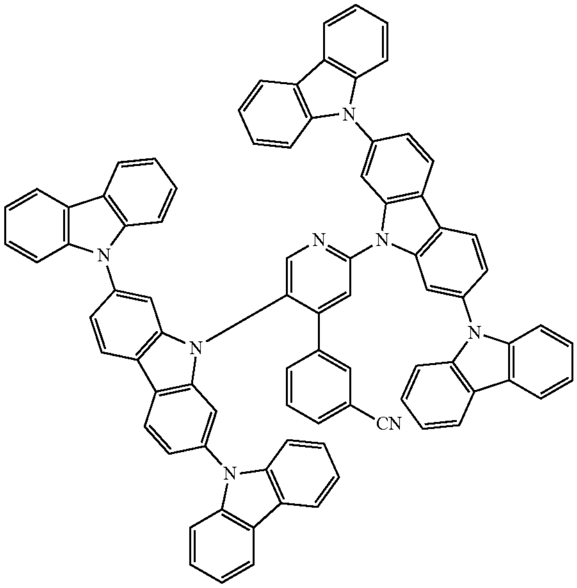

-continued
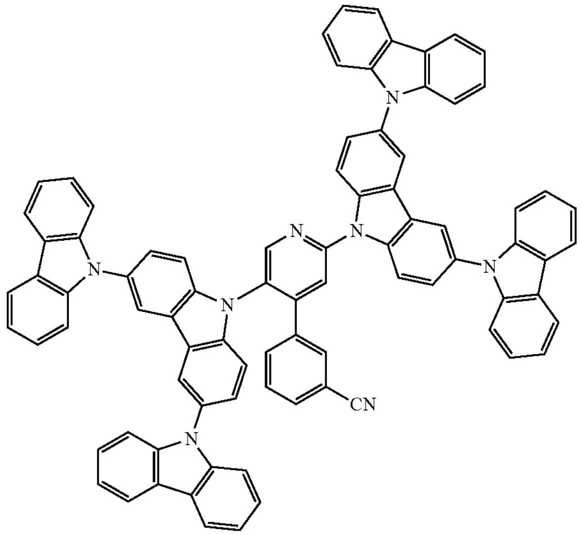
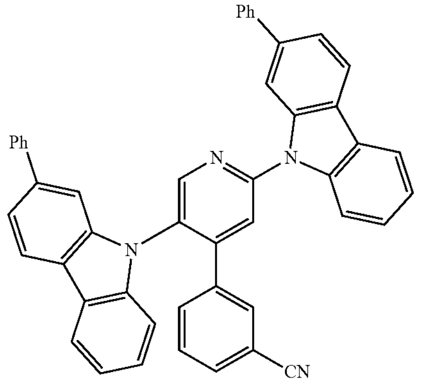
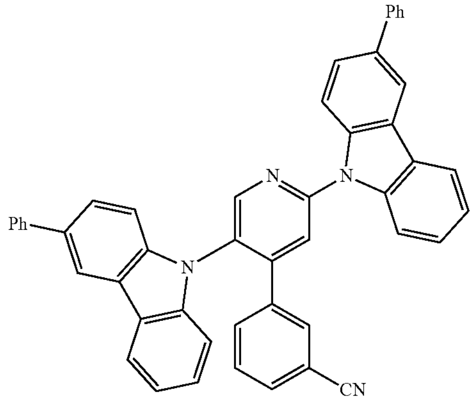
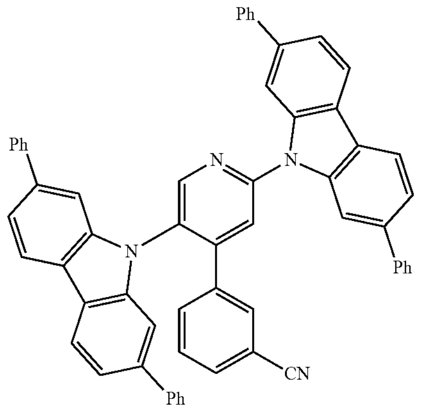
-continued
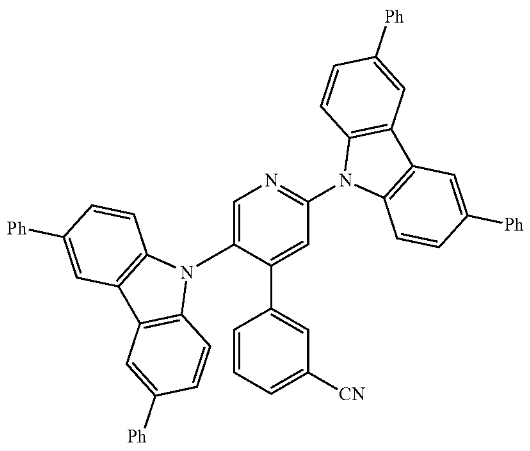
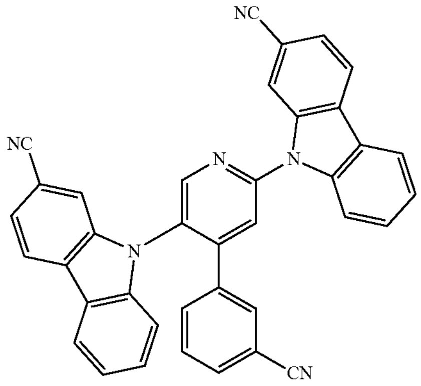
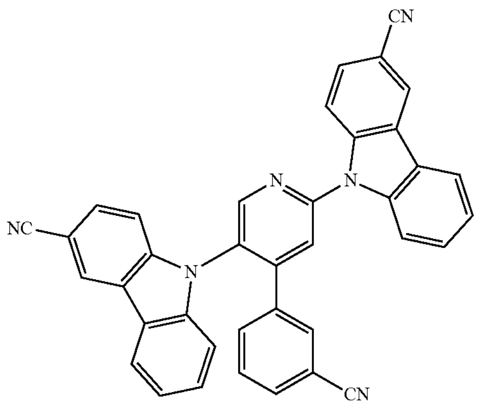
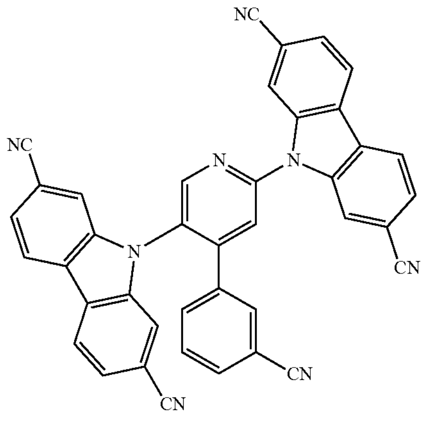

-continued
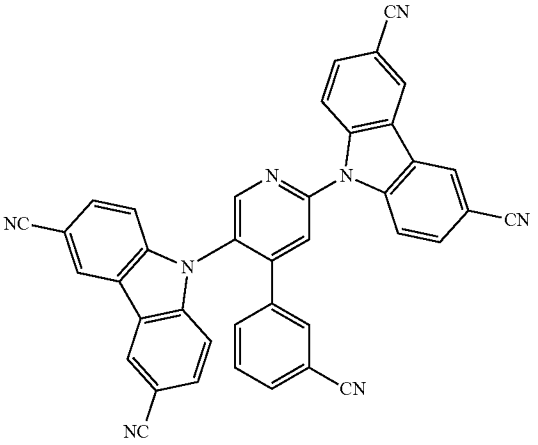
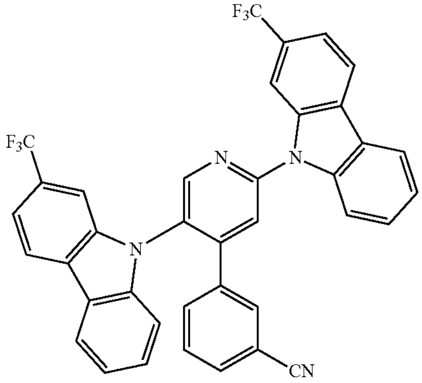
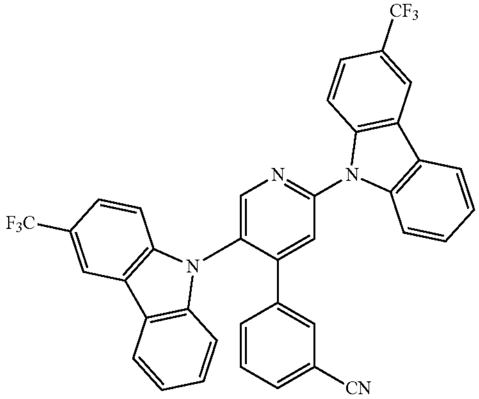
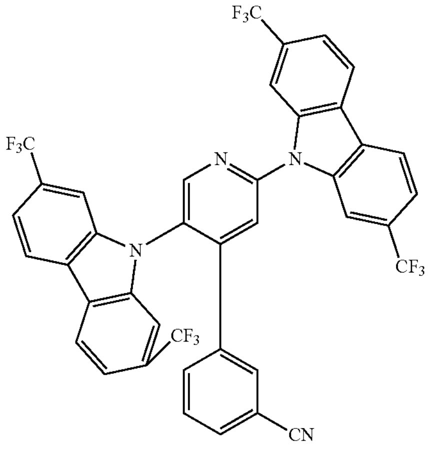
-continued
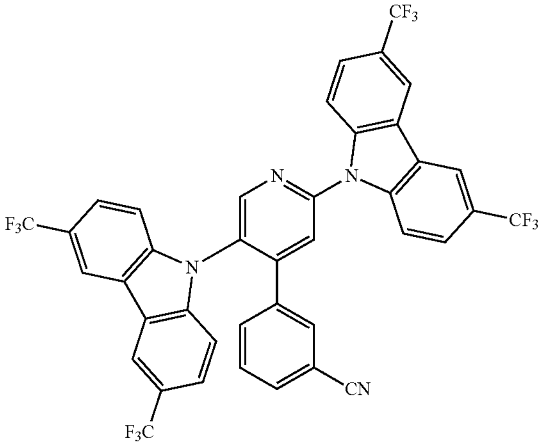
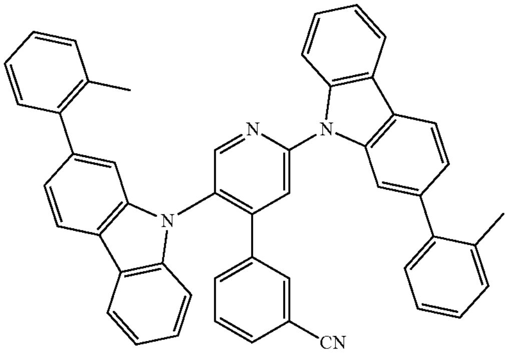
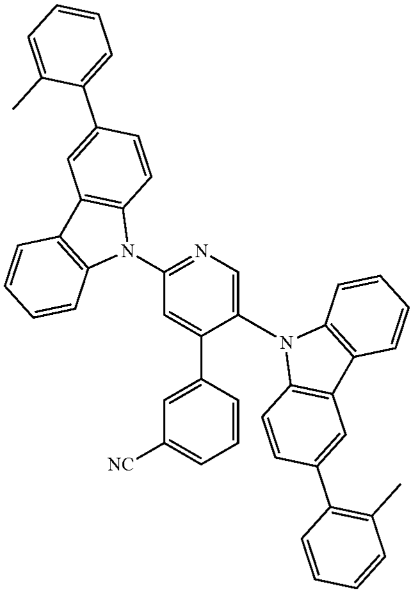

-continued
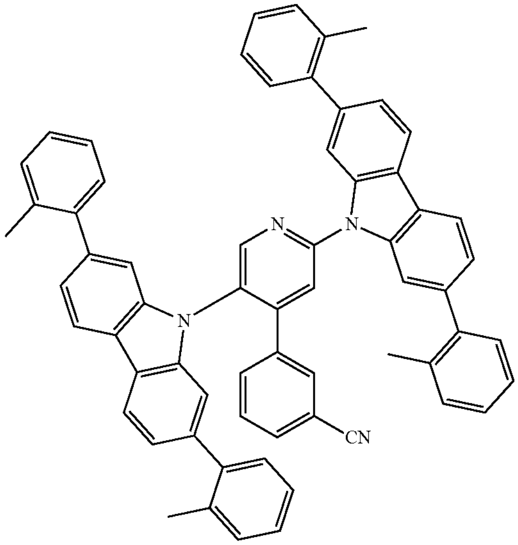
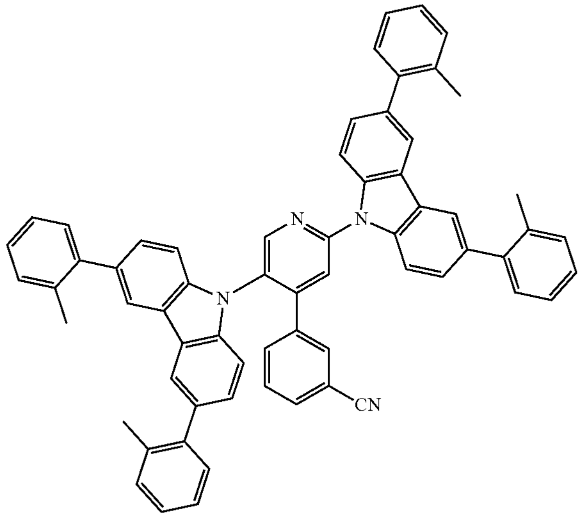
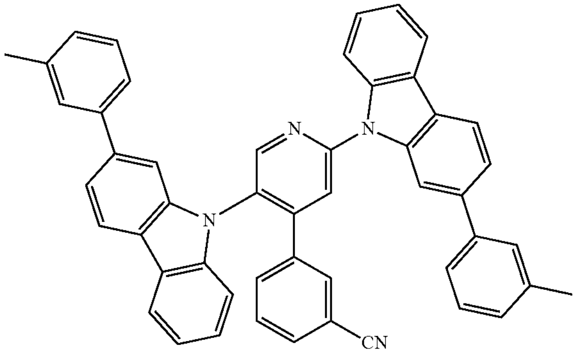
-continued
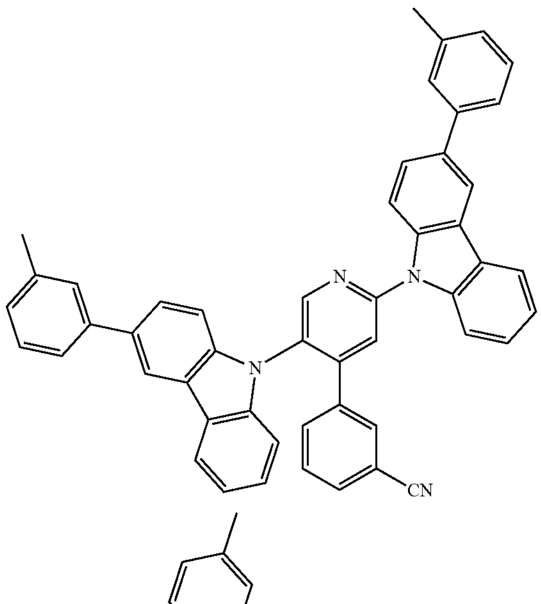
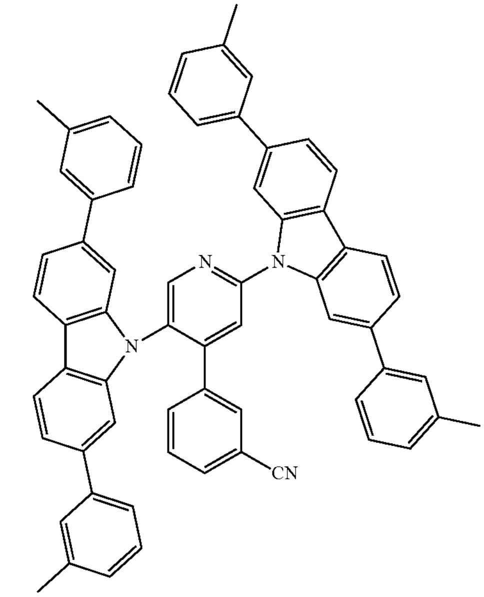
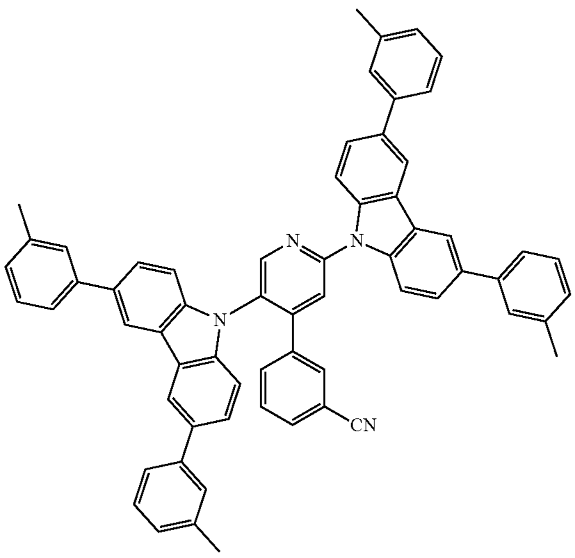

-continued
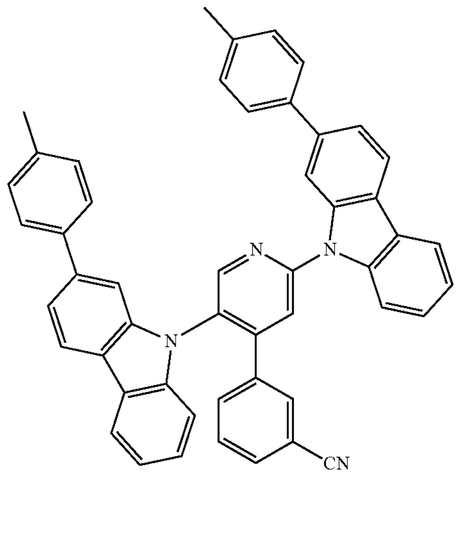
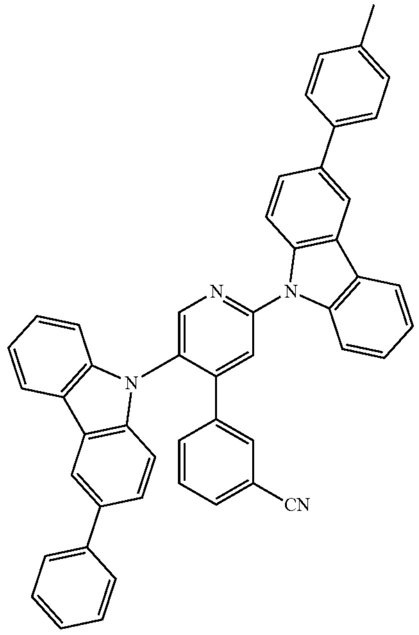
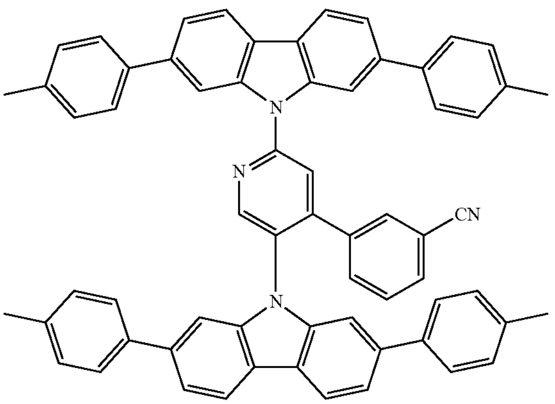
-continued
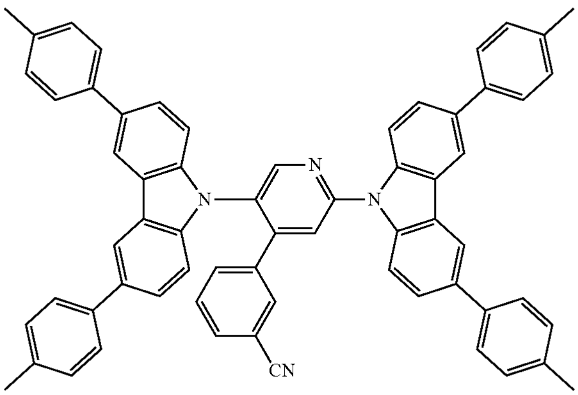
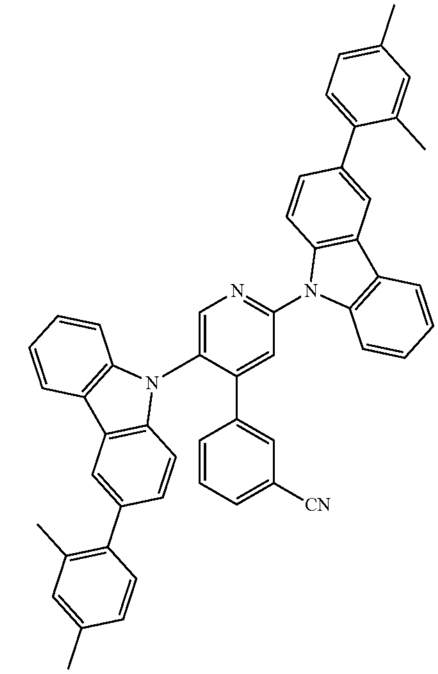
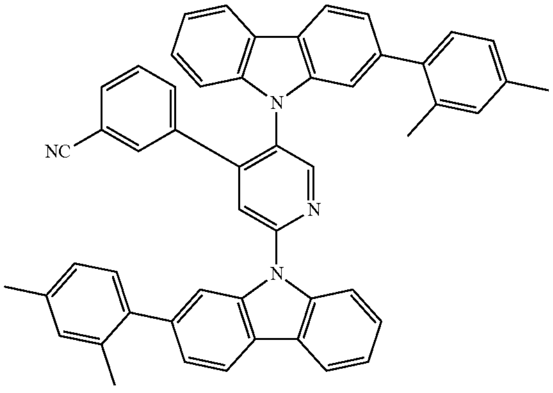

-continued
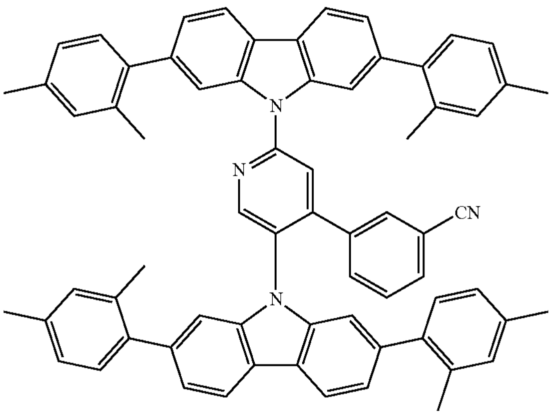
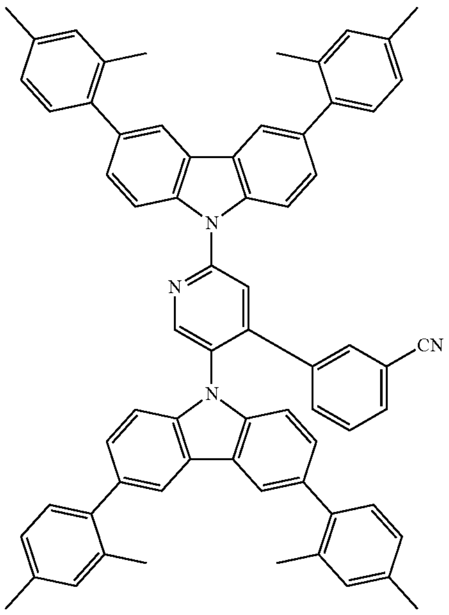
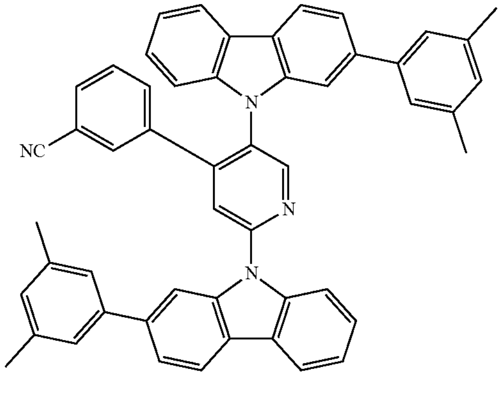
-continued
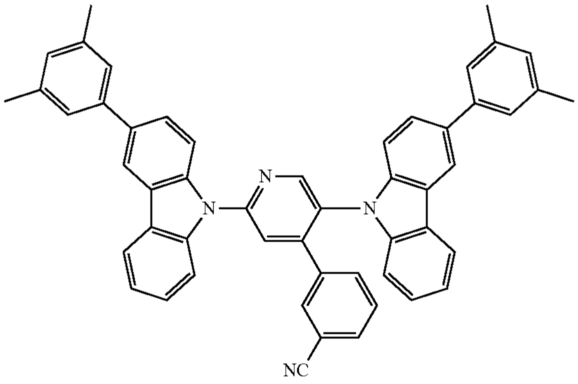
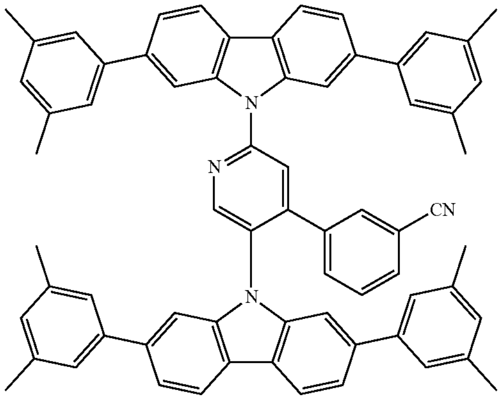
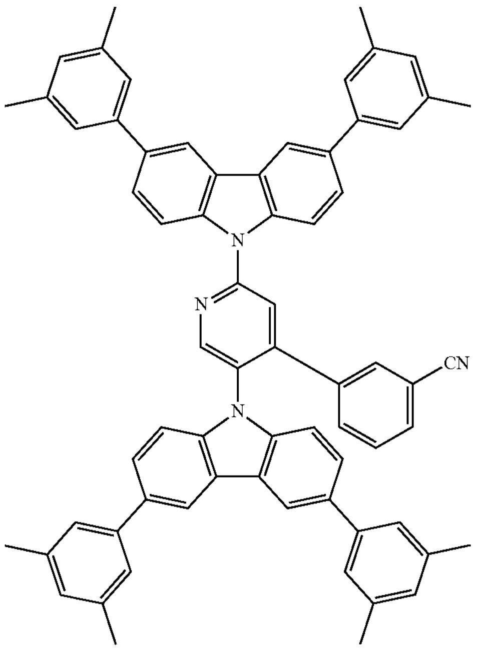

-continued
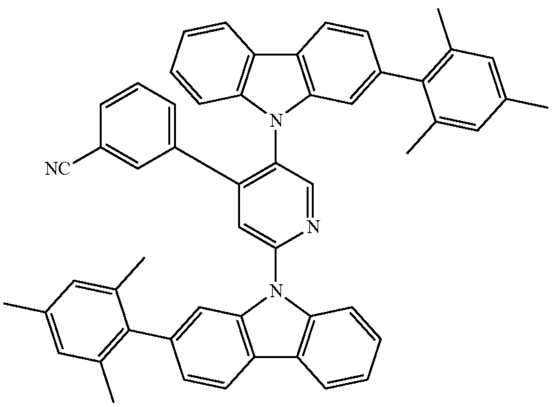
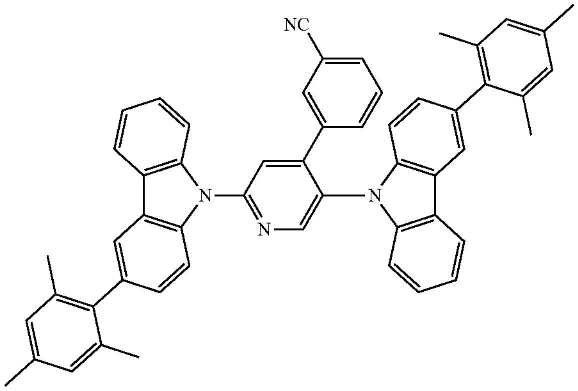
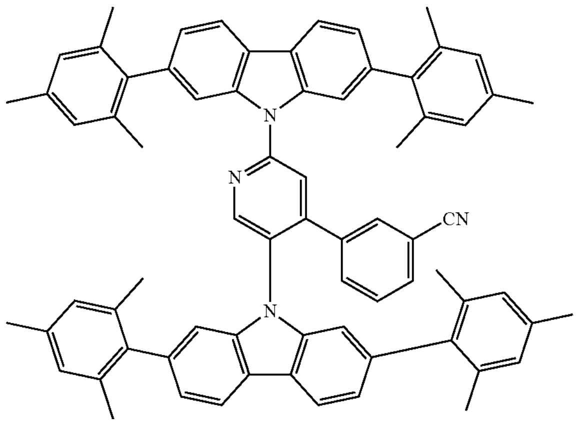
-continued
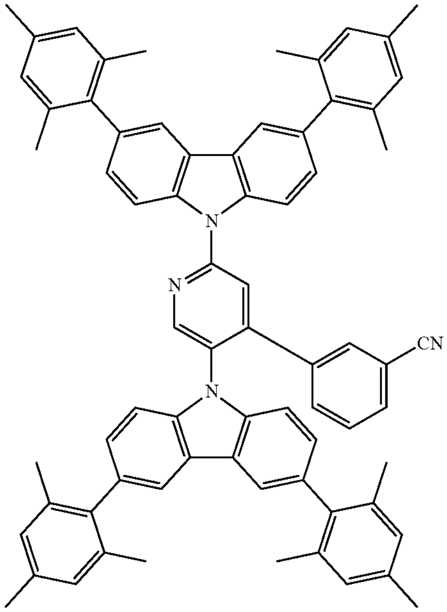
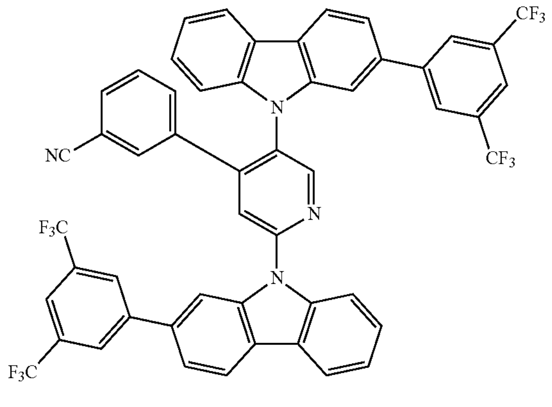
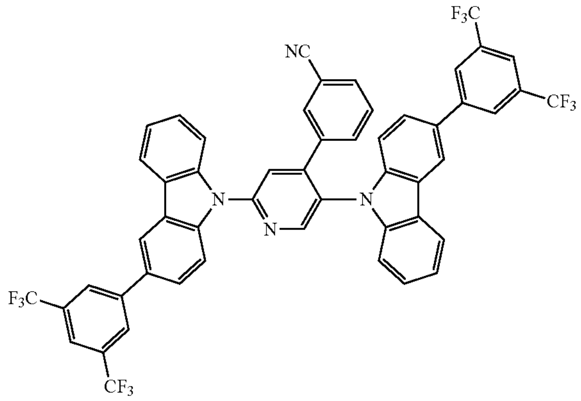

-continued
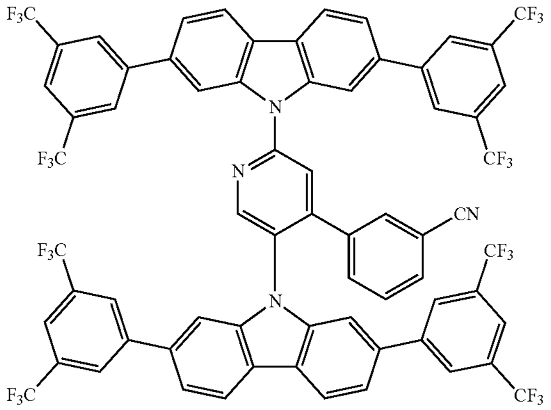
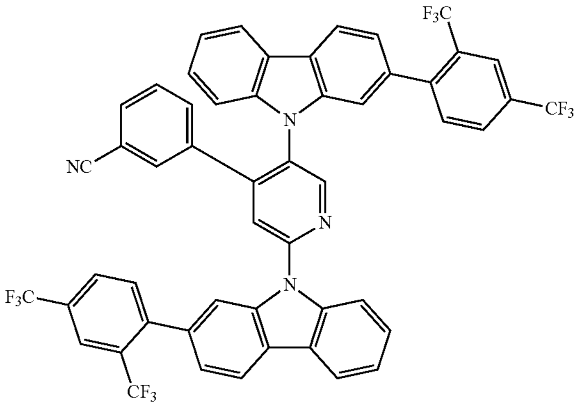
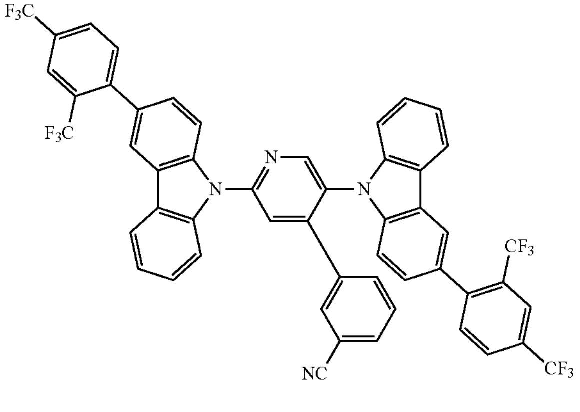
-continued
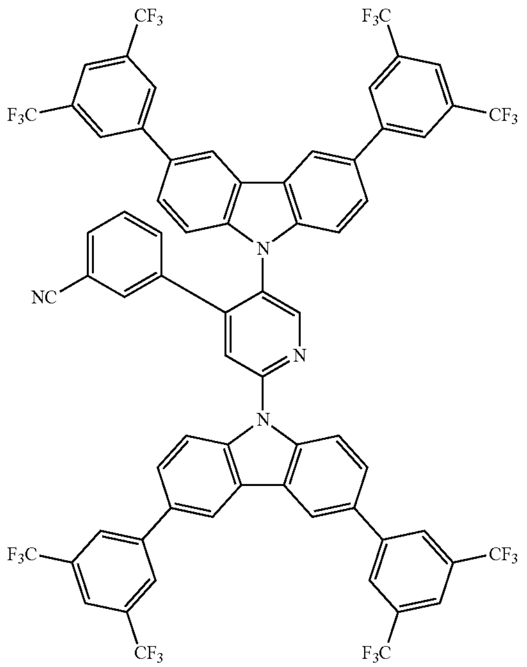
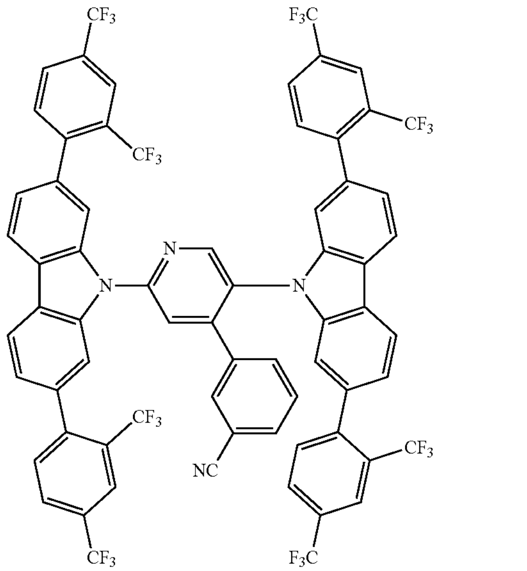

-continued
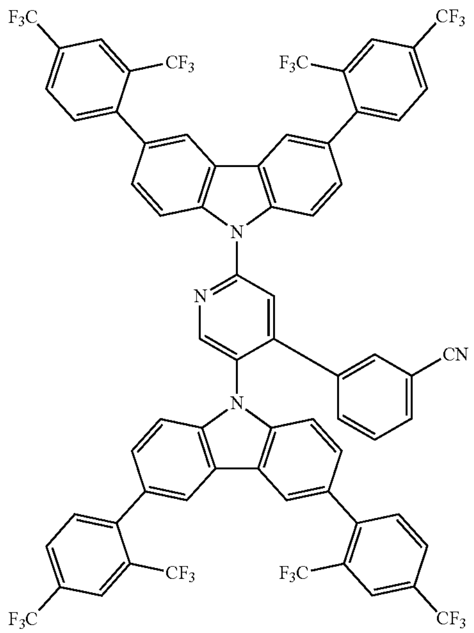
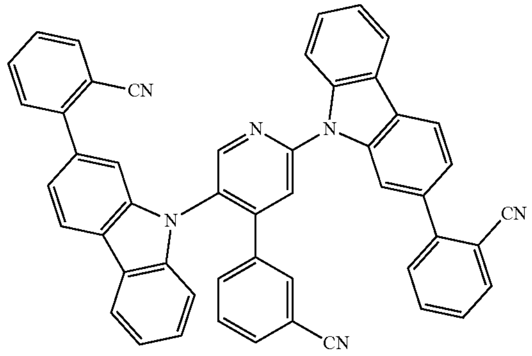
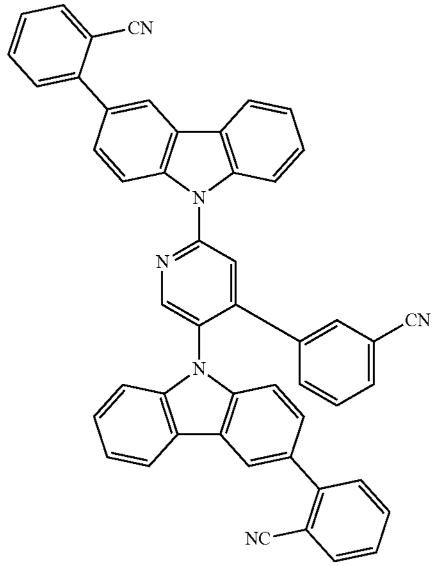
-continued
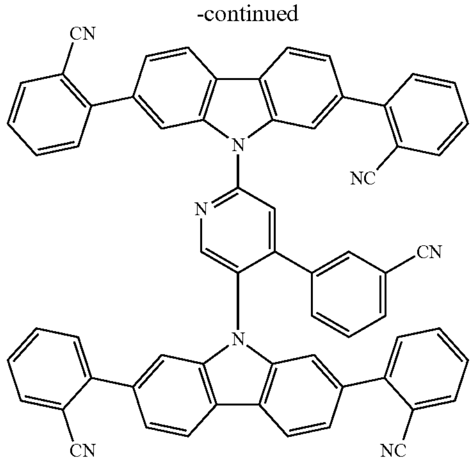
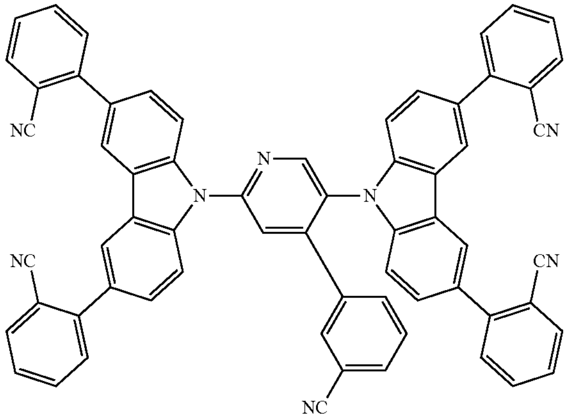
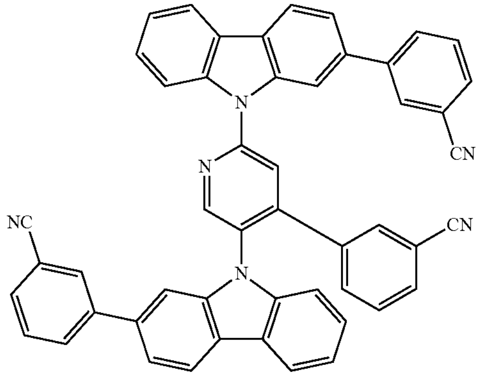
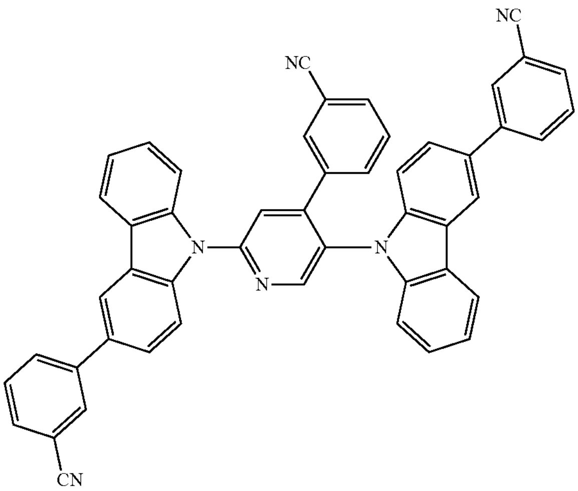

-continued
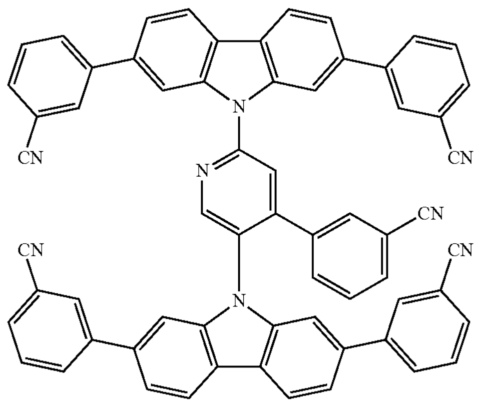
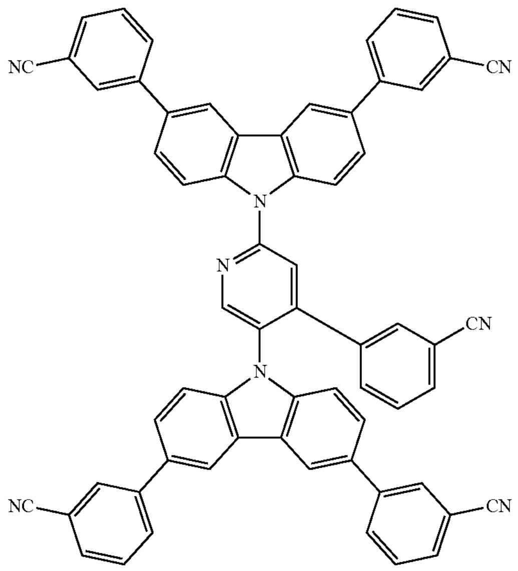
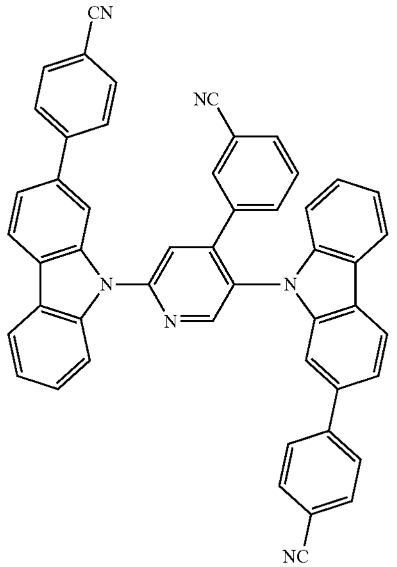
-continued
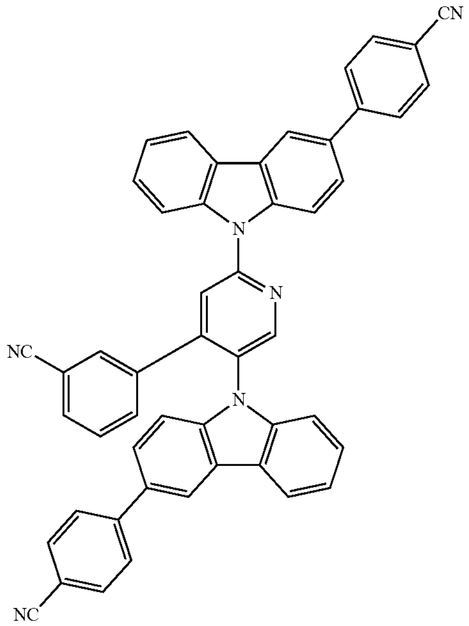
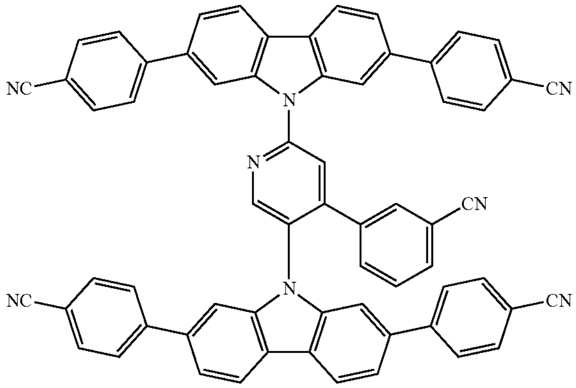
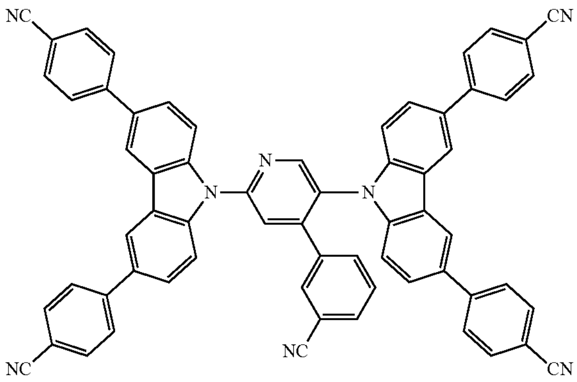

-continued
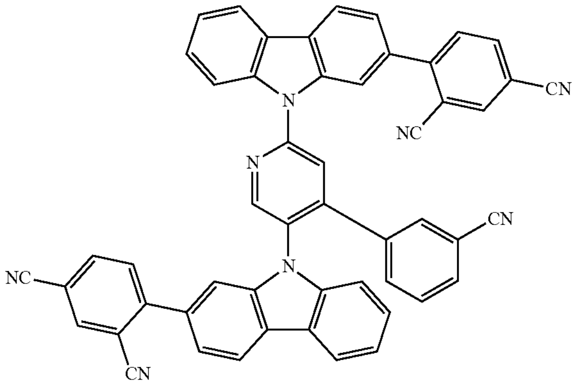
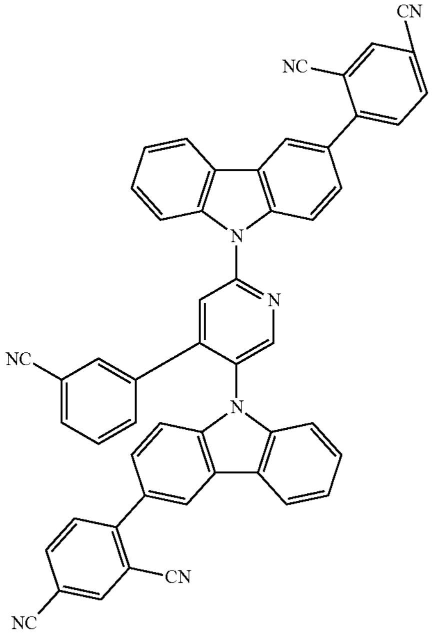
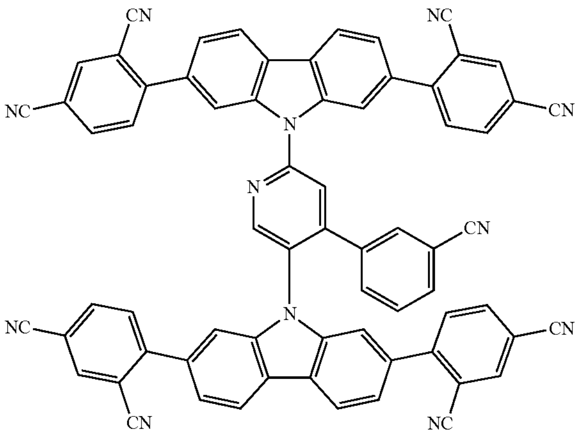
-continued
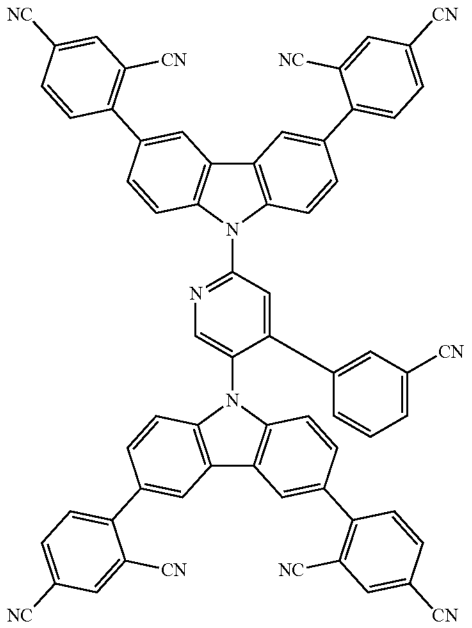
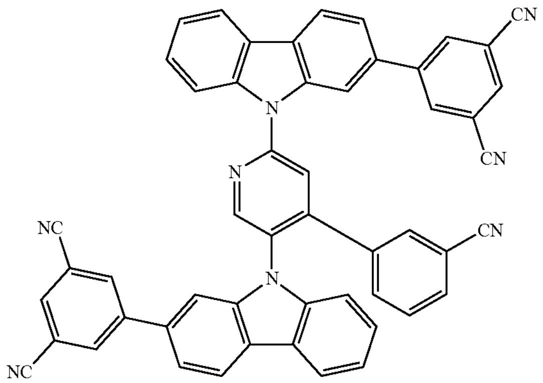
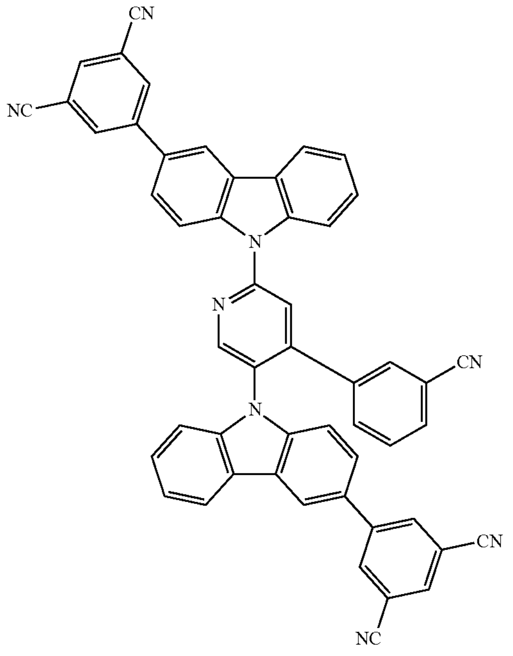

-continued
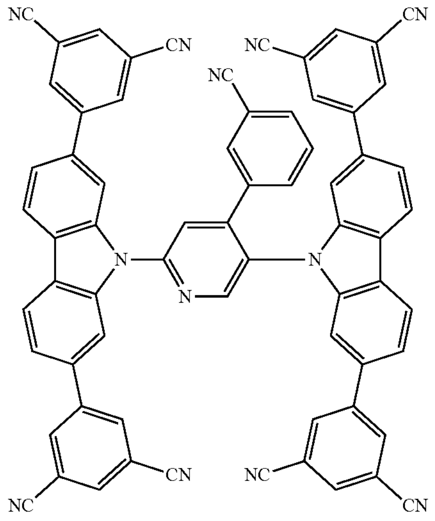
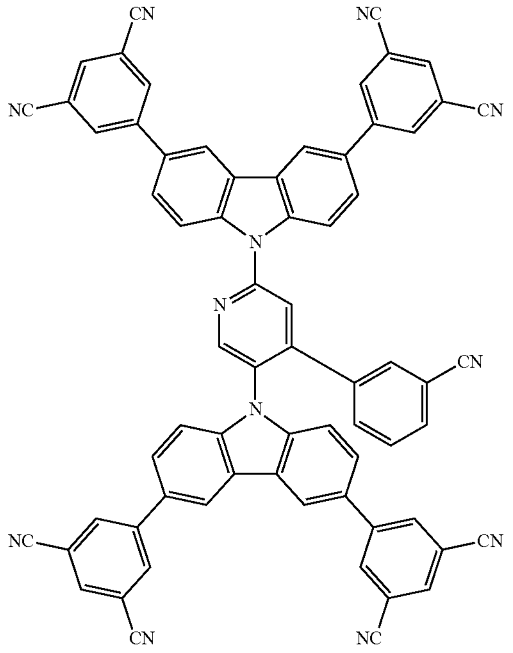
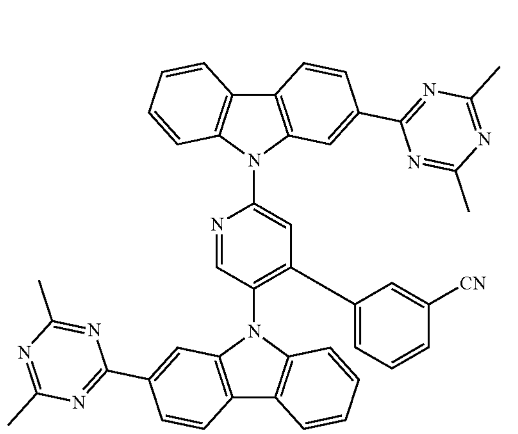
-continued
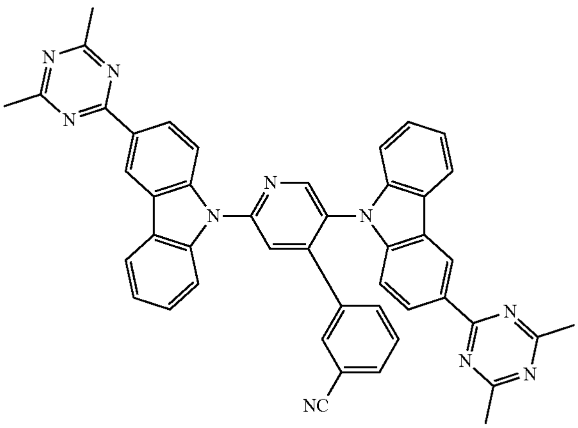
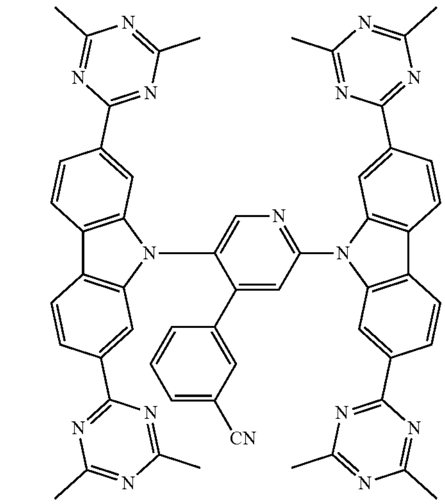
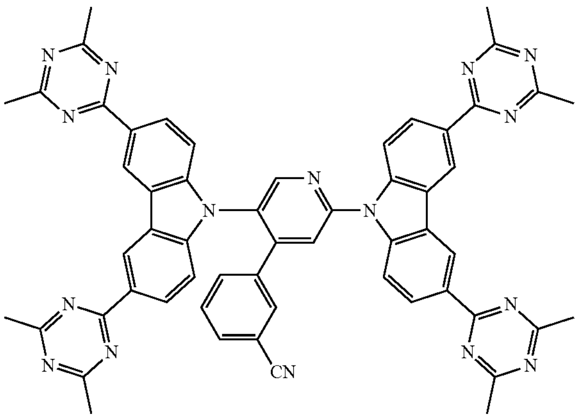

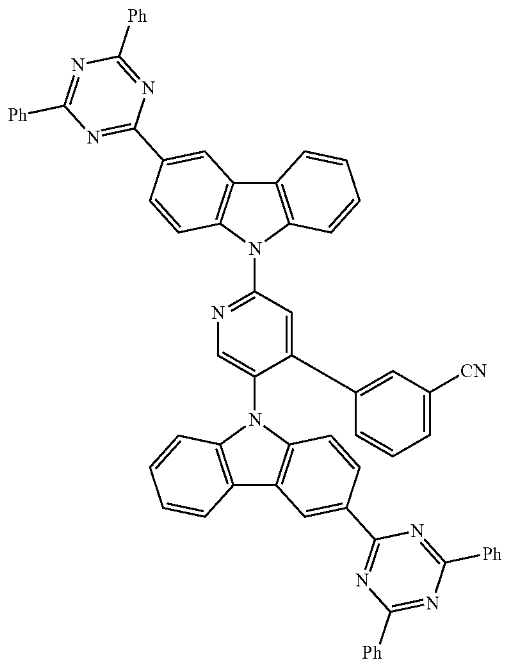
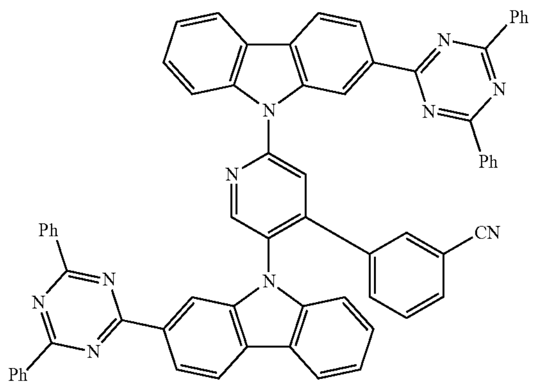
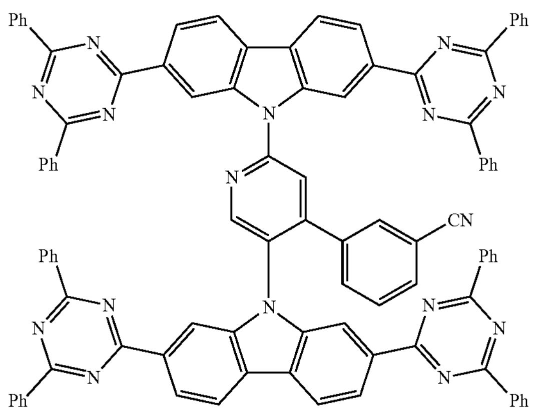
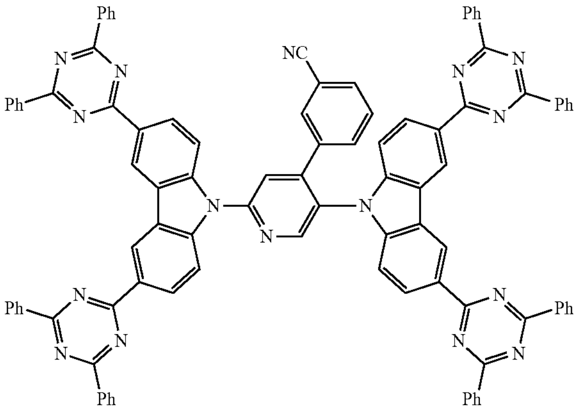
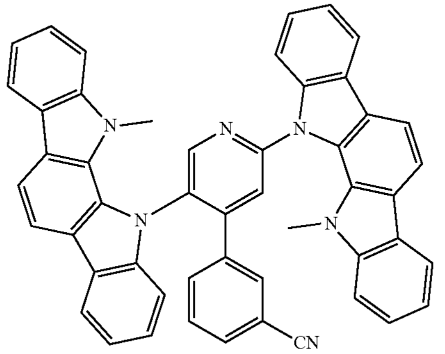
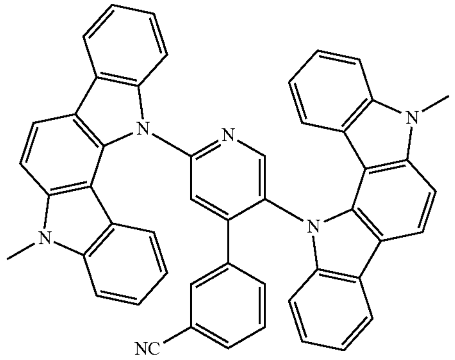
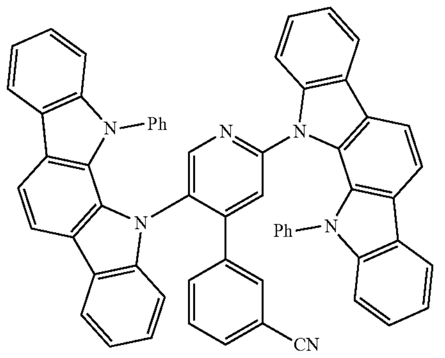

-continued
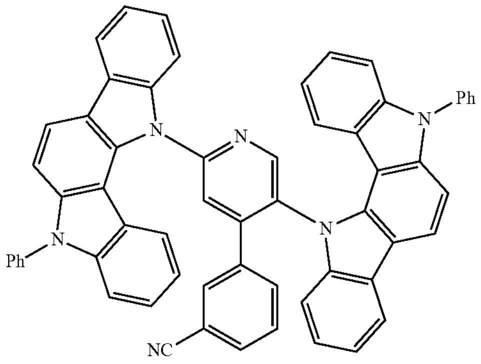
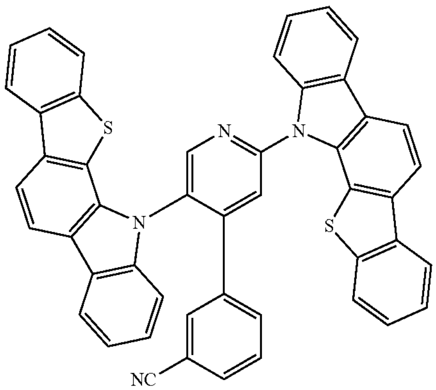
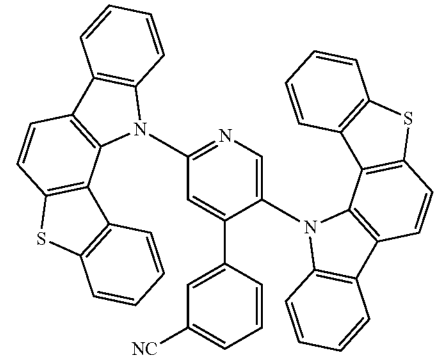
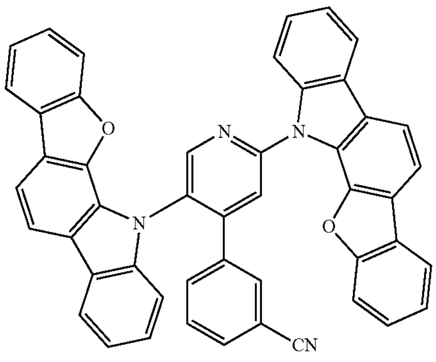
-continued
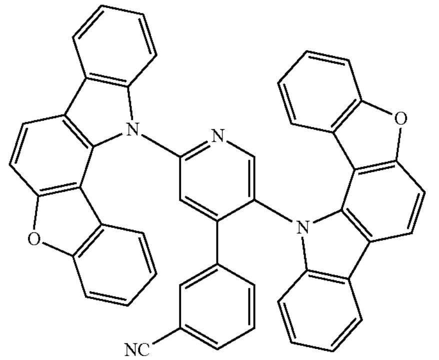
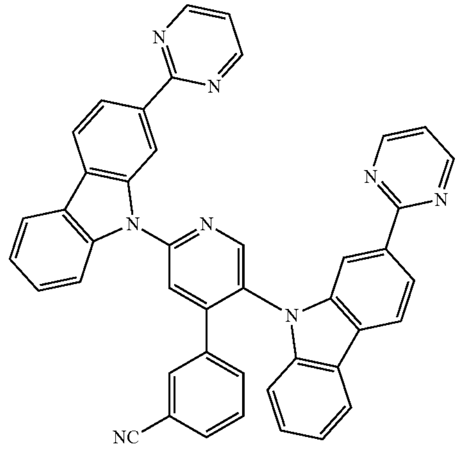
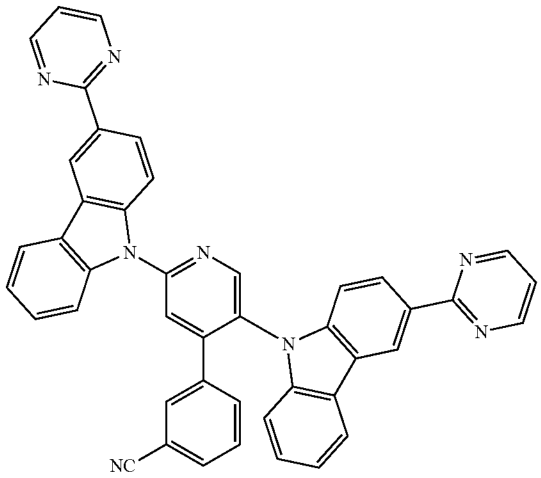

-continued
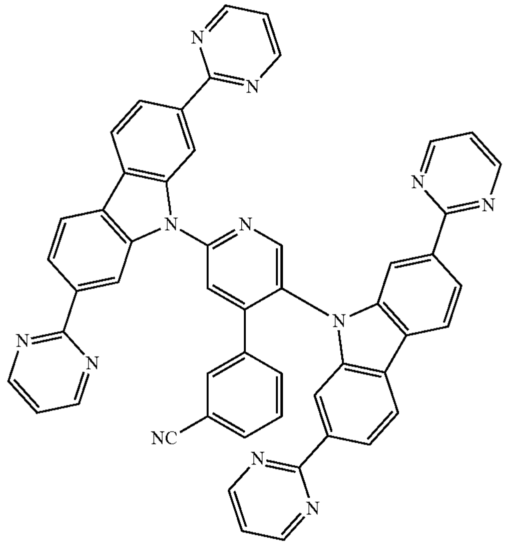
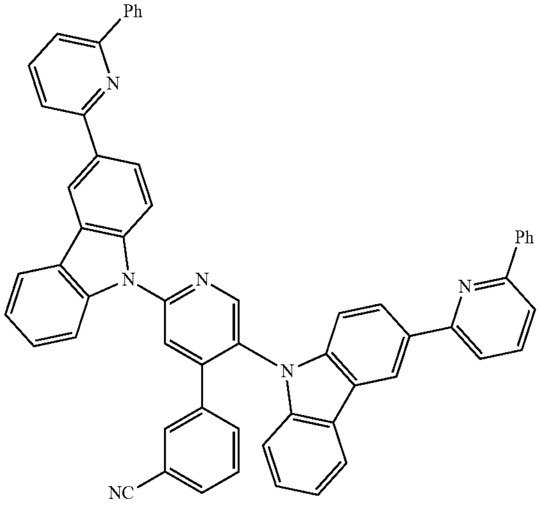
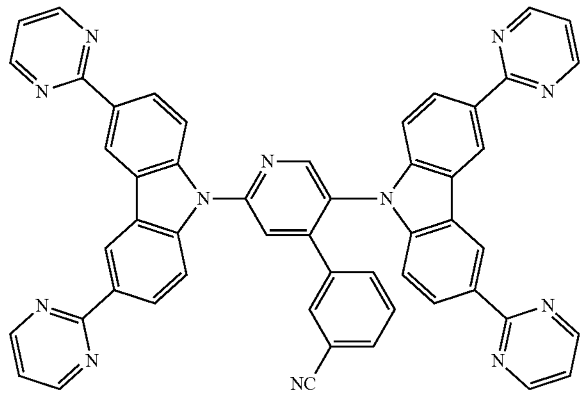
-continued
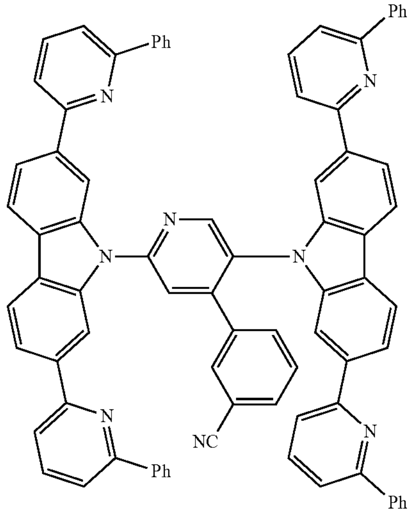
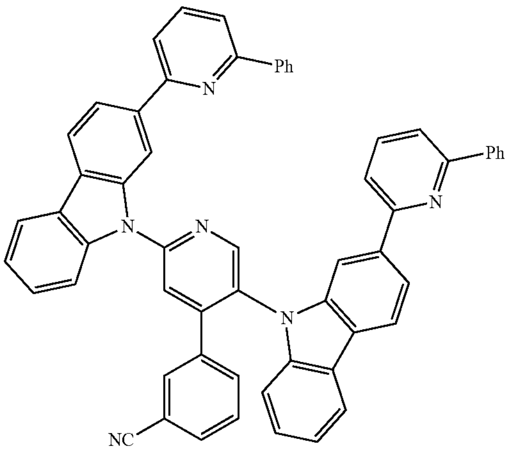
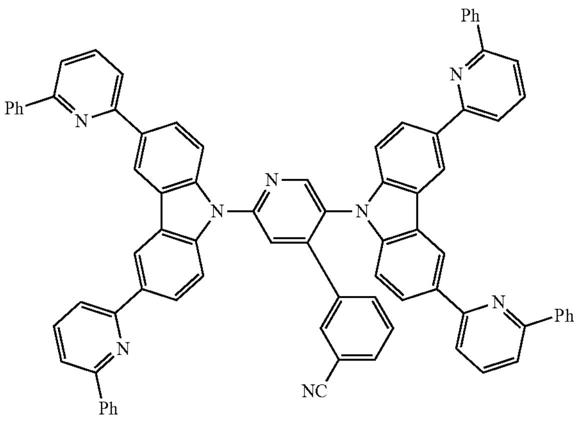

-continued
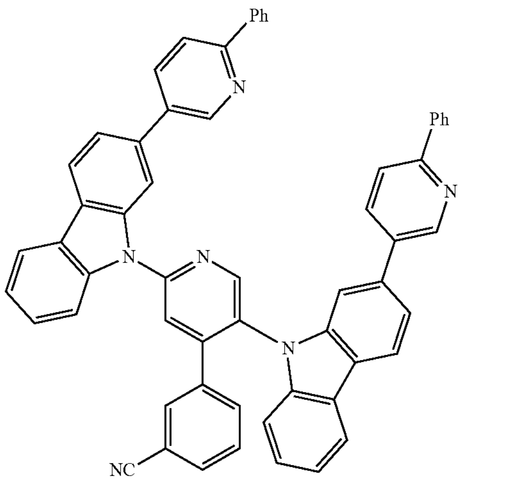
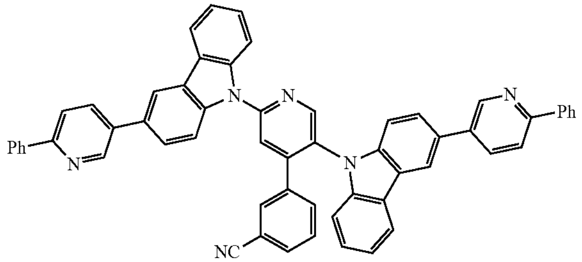
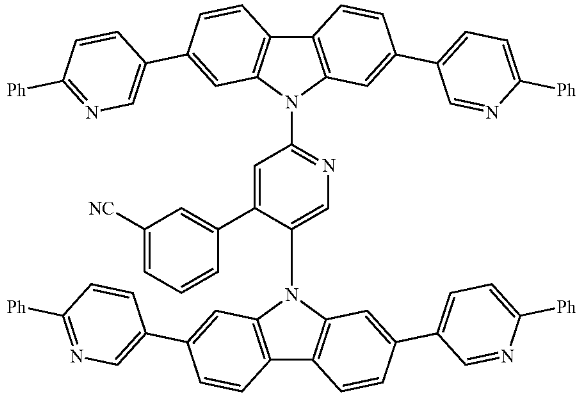
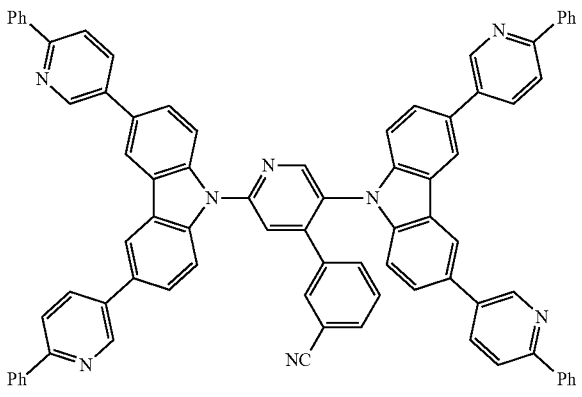
-continued
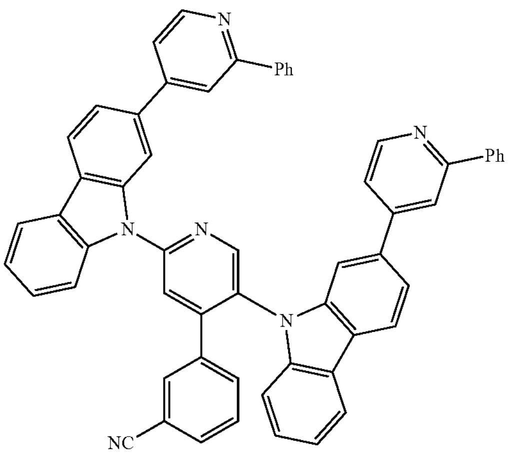
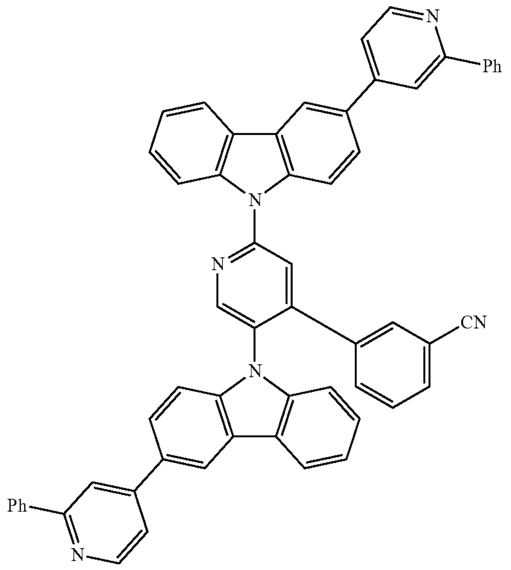
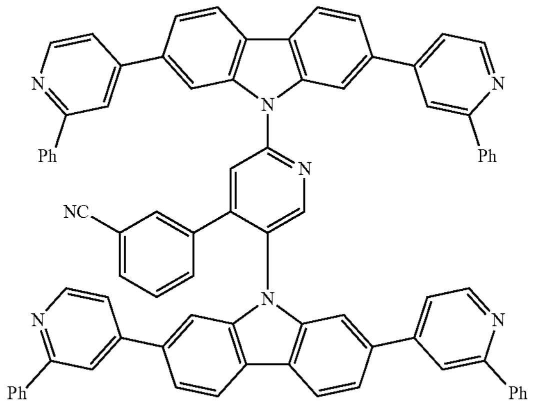

-continued
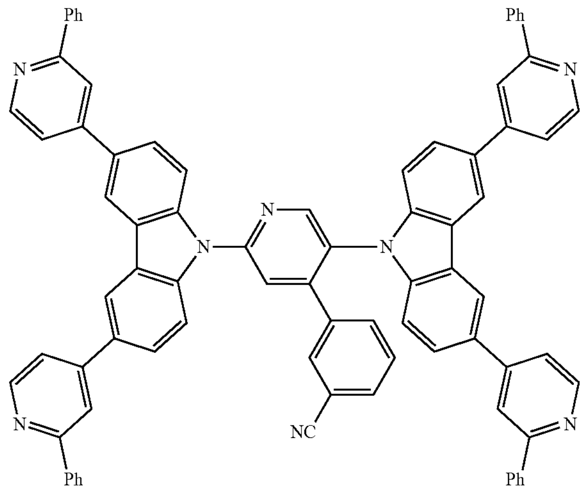
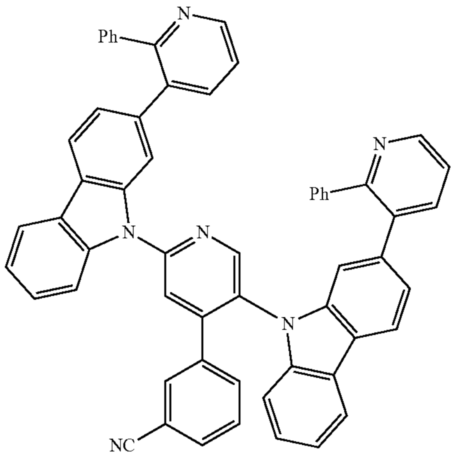
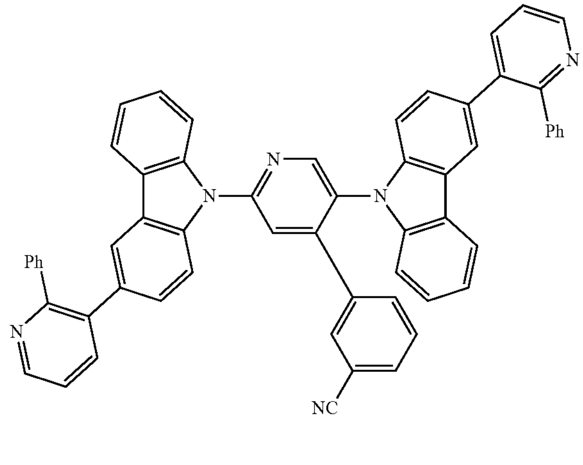
-continued
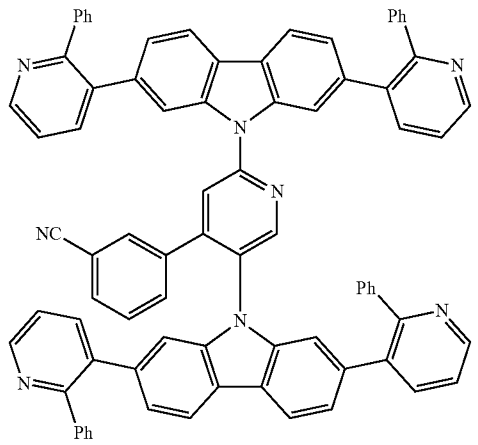
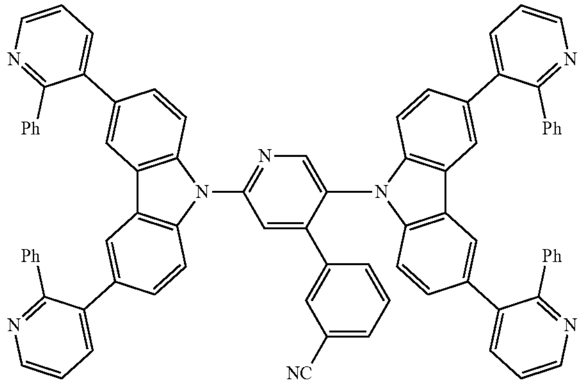
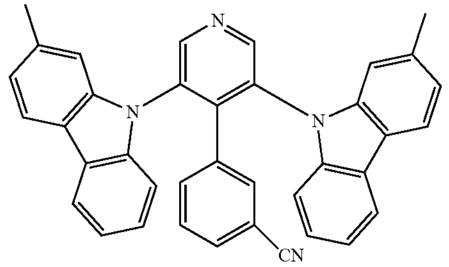
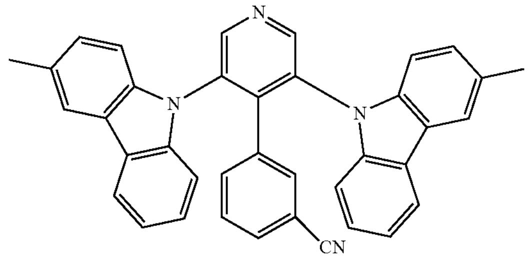
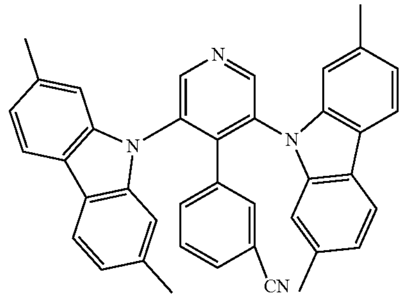

-continued
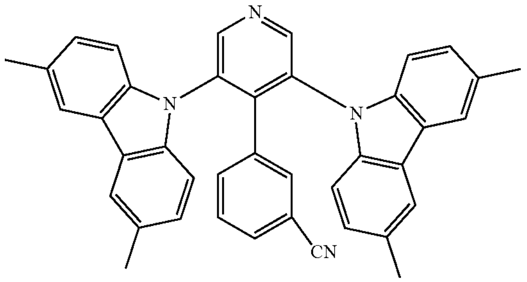
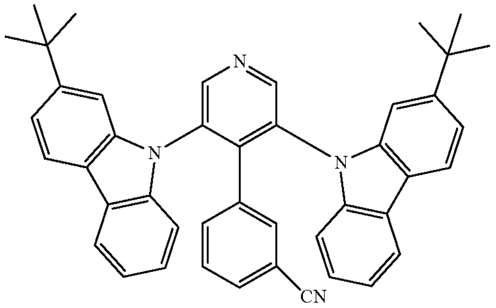
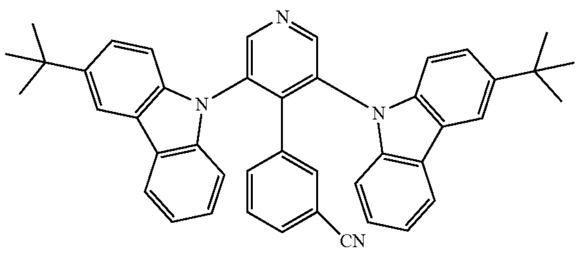
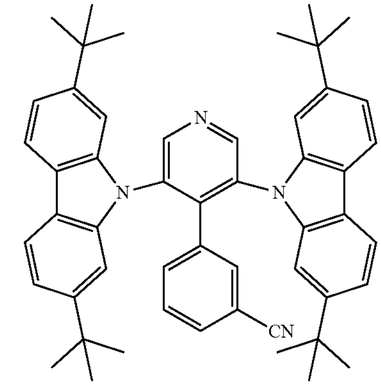
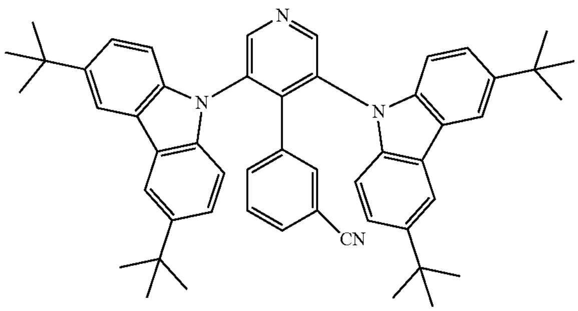
-continued
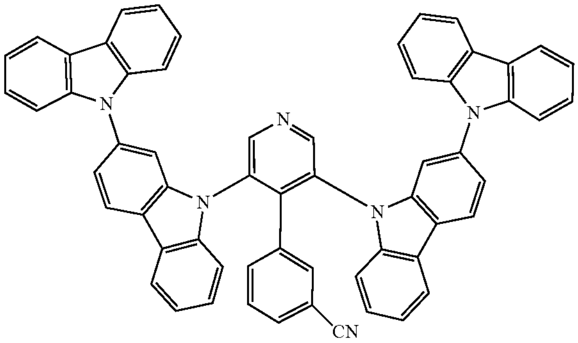
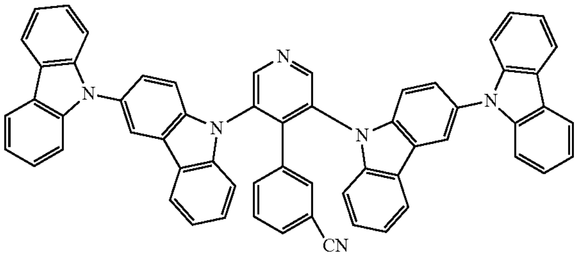
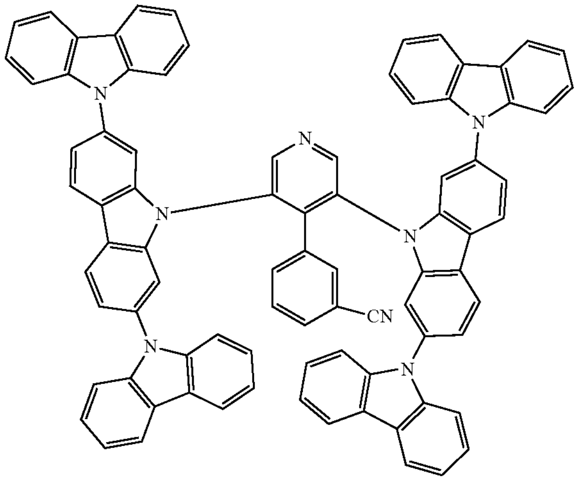
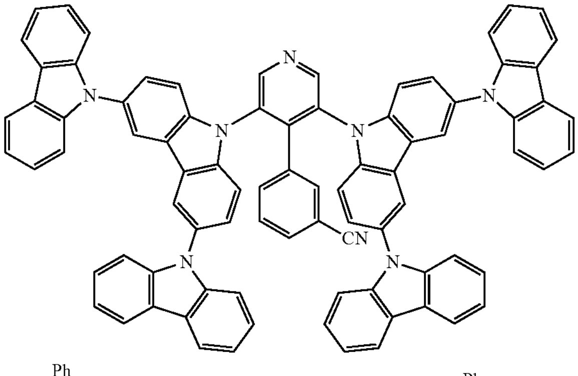
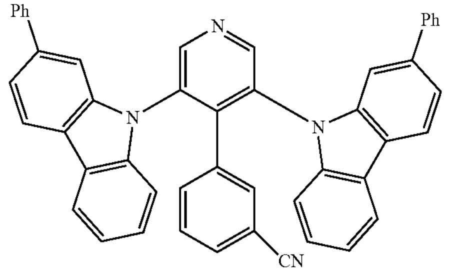

-continued
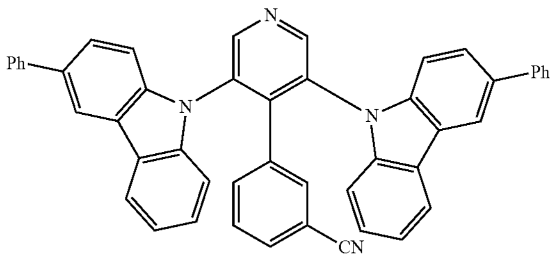
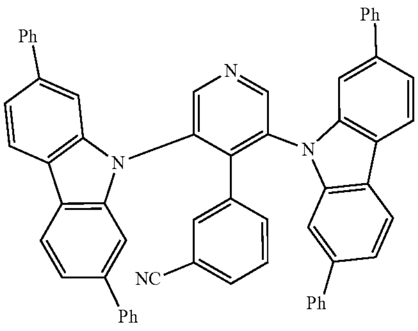
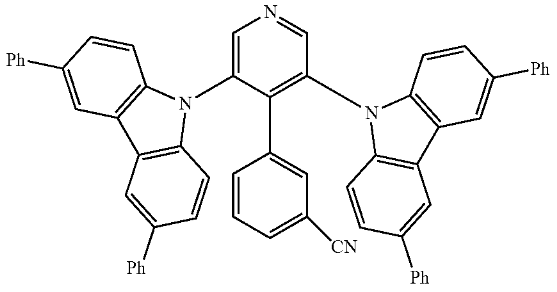
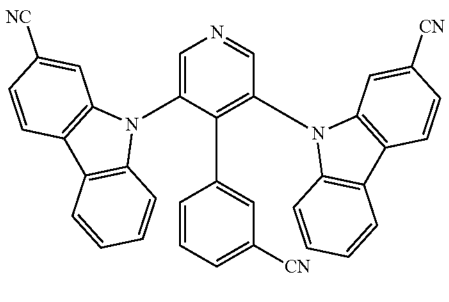
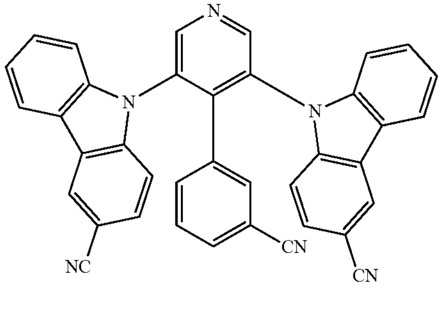
-continued
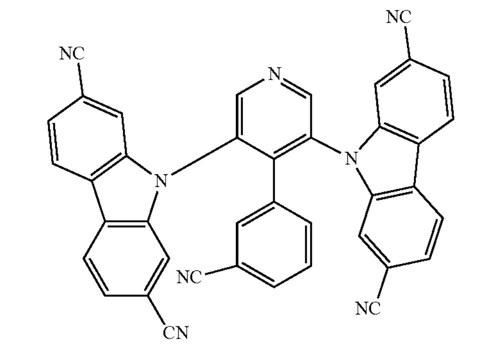
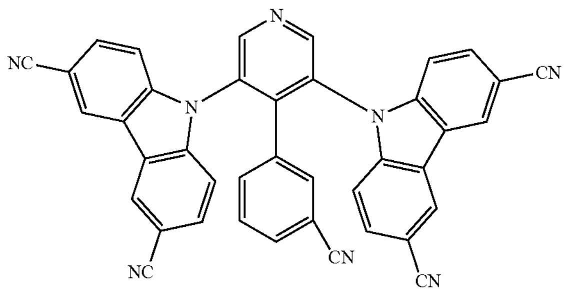
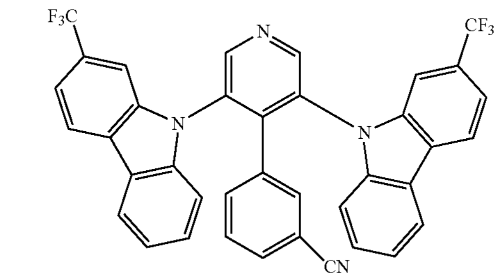
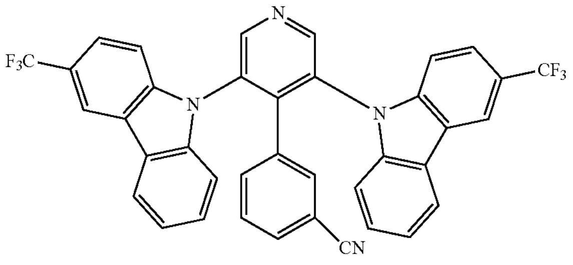
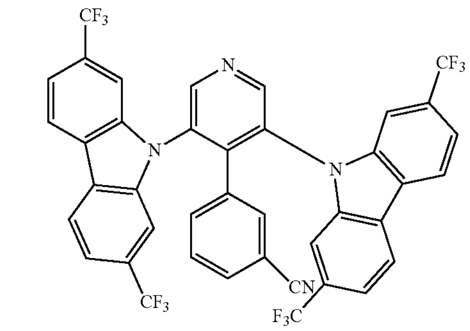

-continued
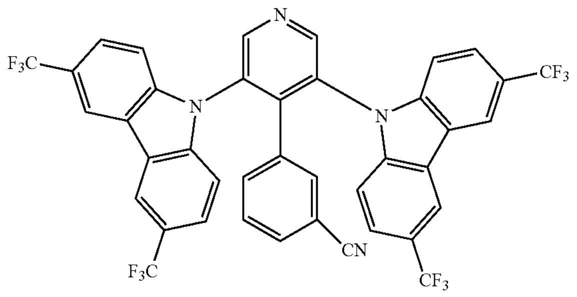
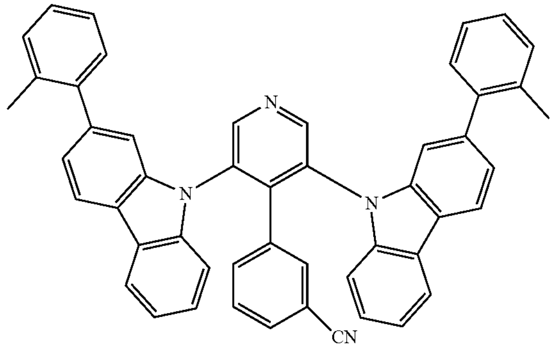
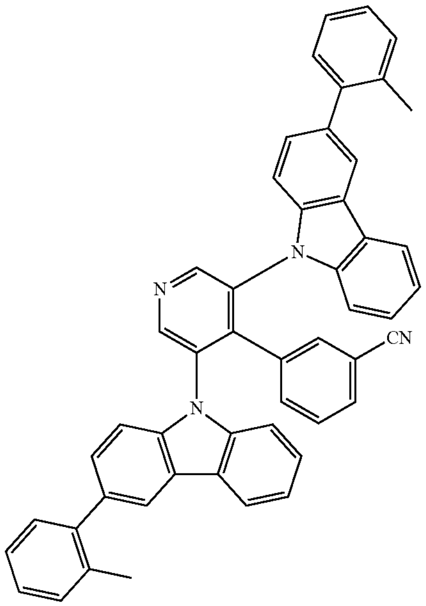
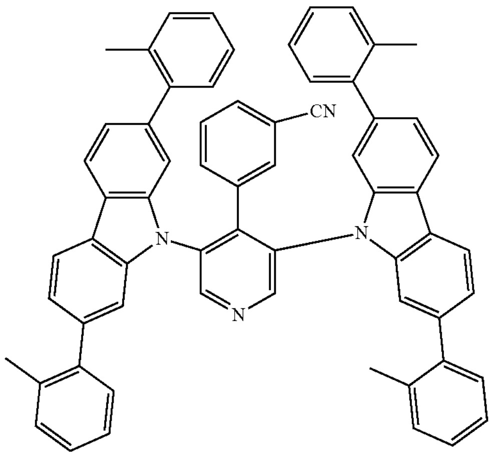
-continued
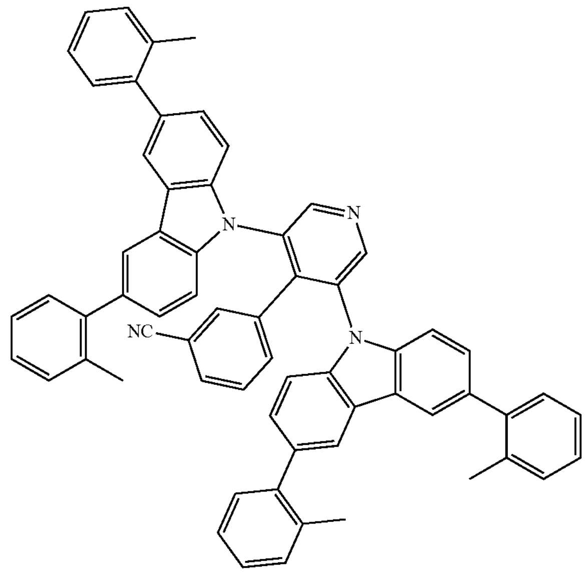
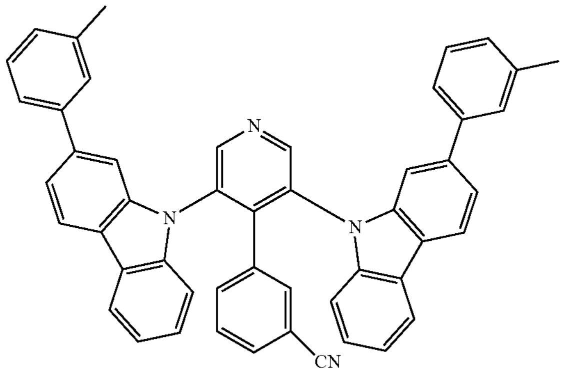
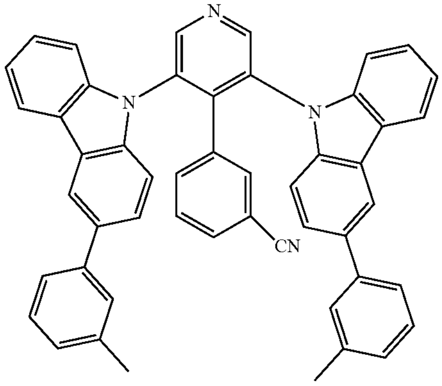

-continued
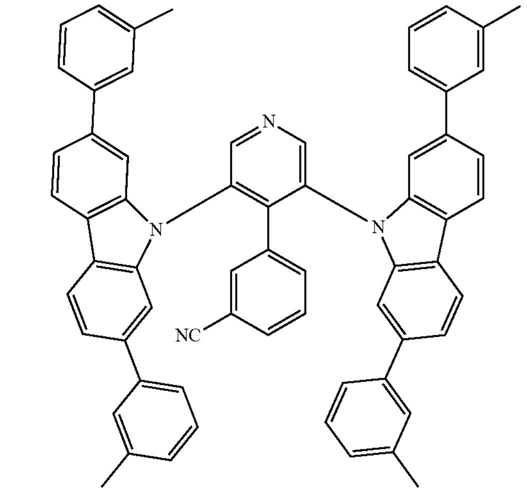
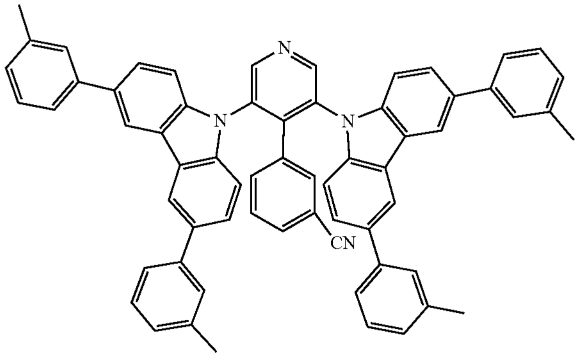
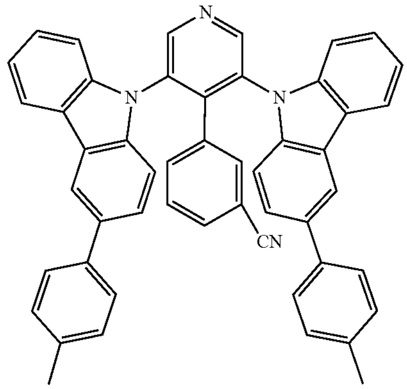
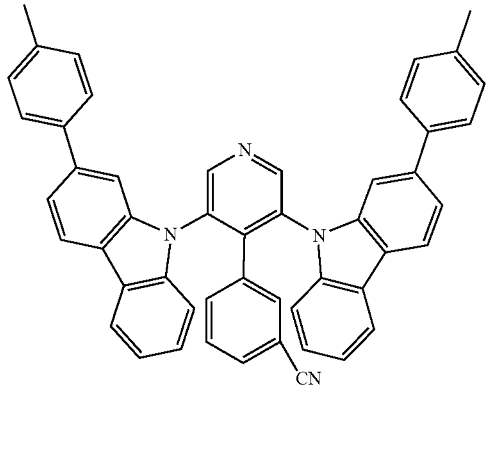
-continued
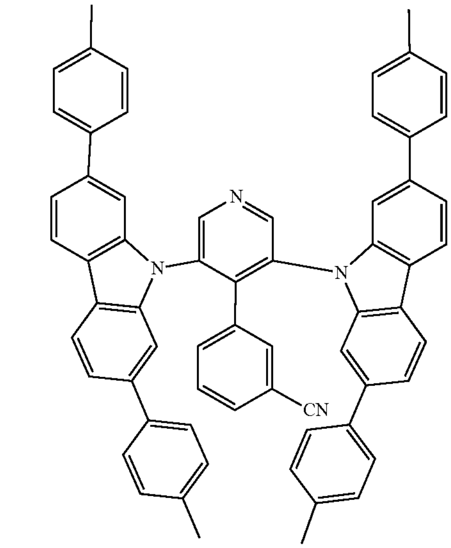
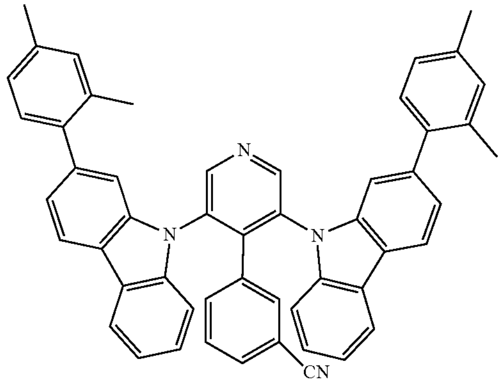
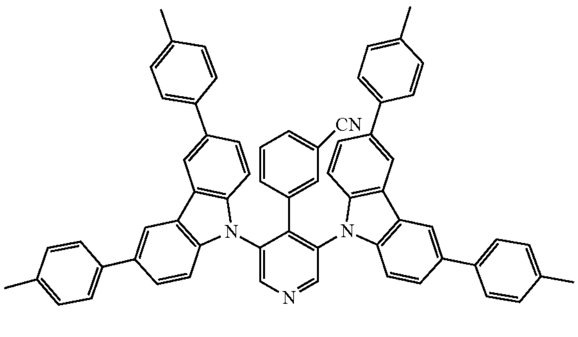

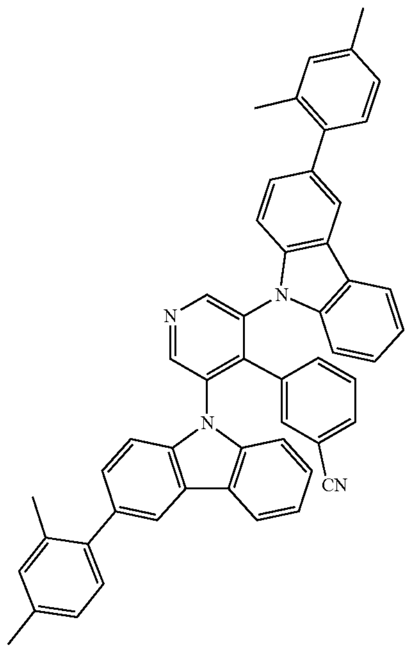
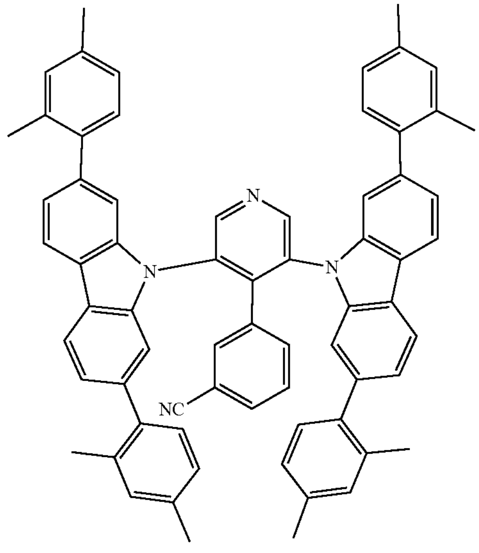
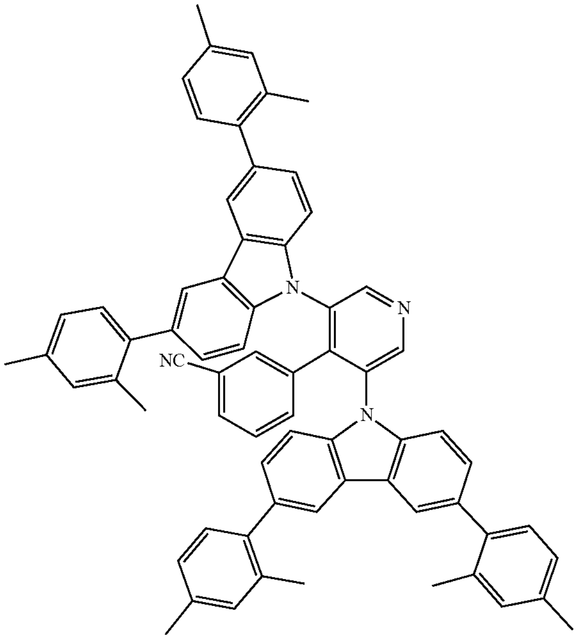
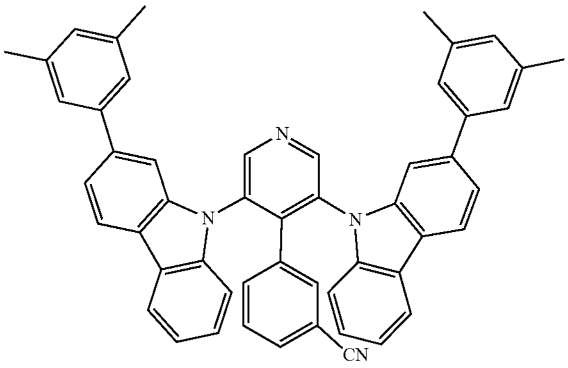
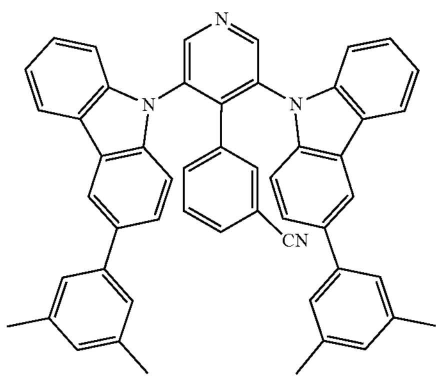

-continued
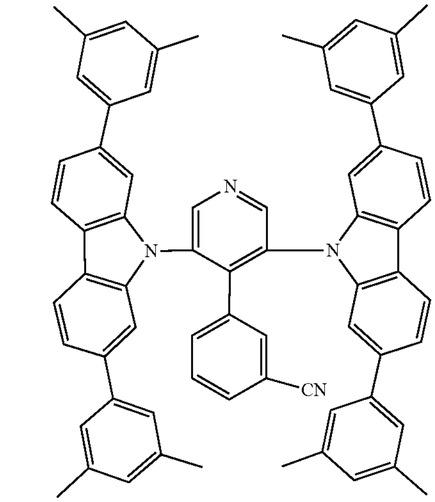
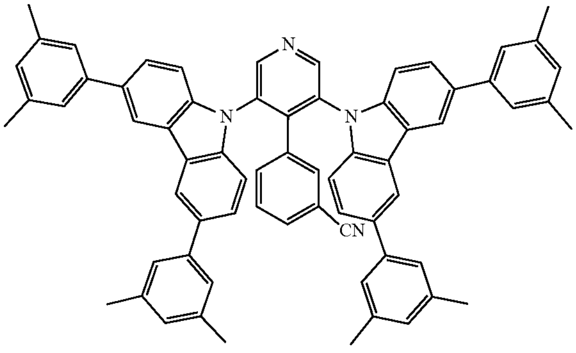
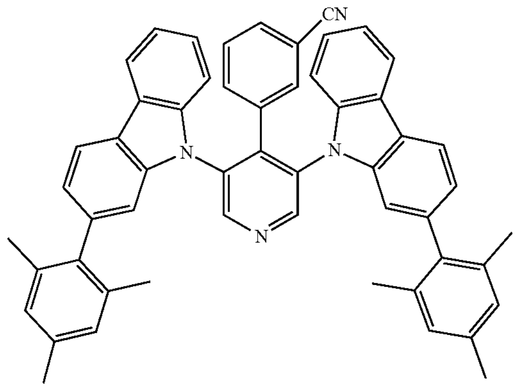
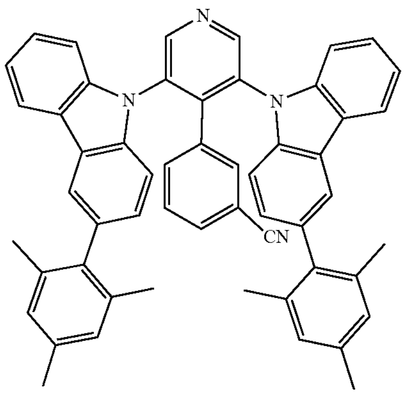
-continued
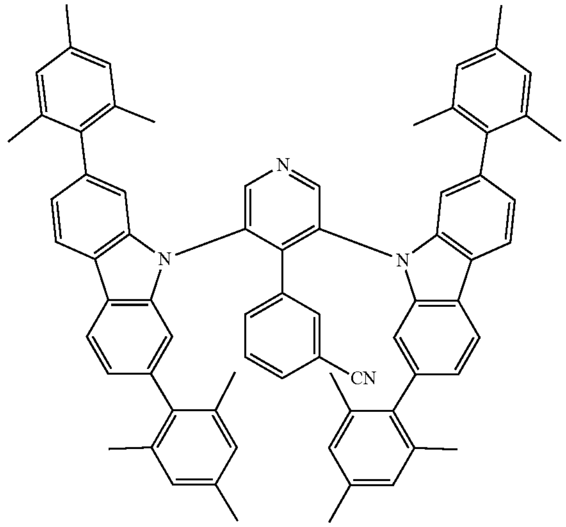
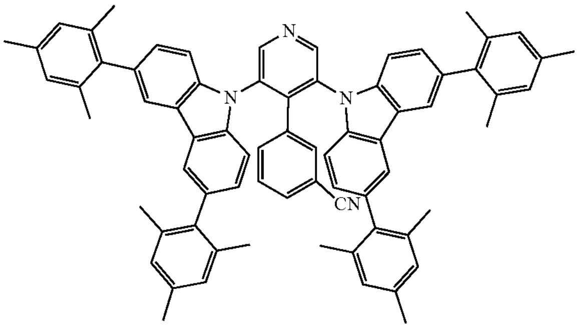
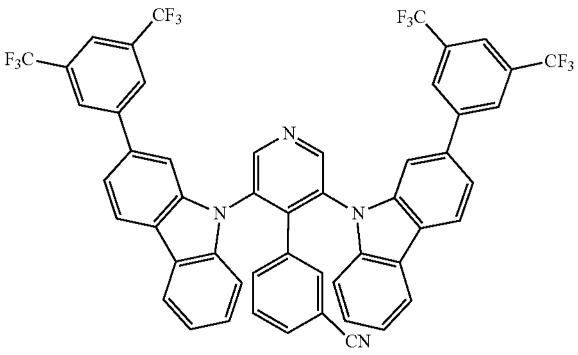
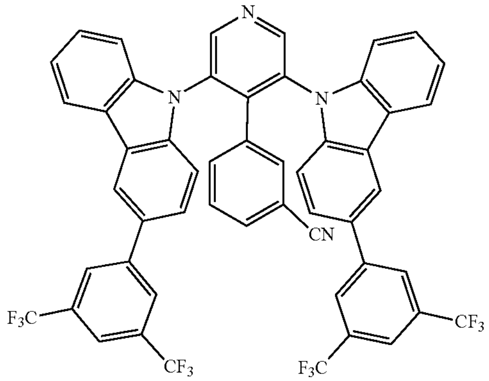

-continued
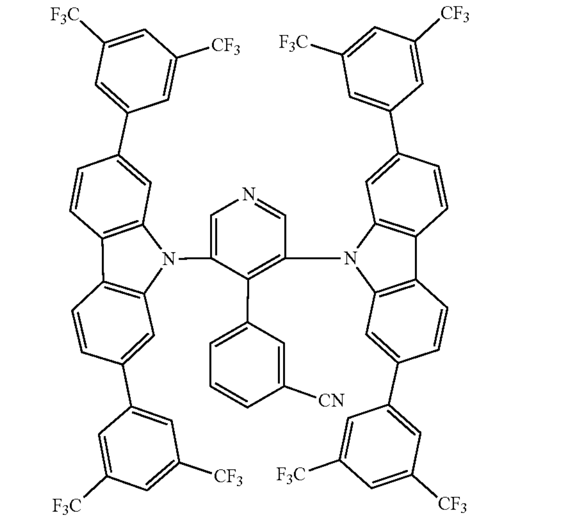
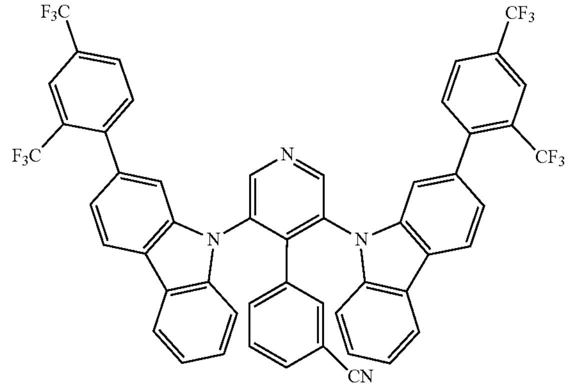
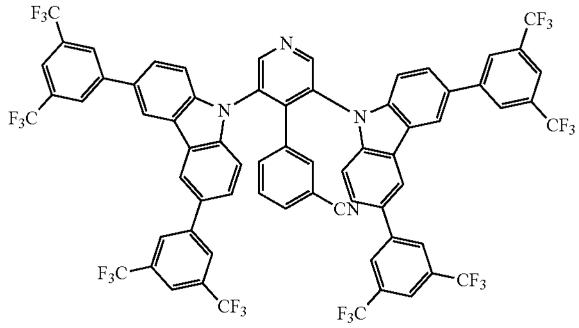
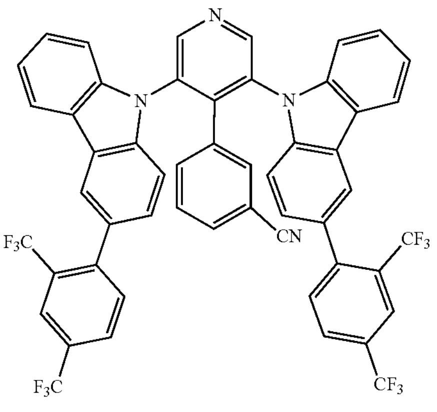
-continued
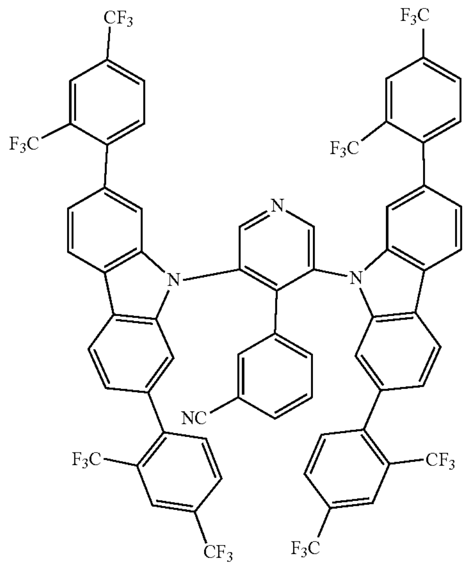
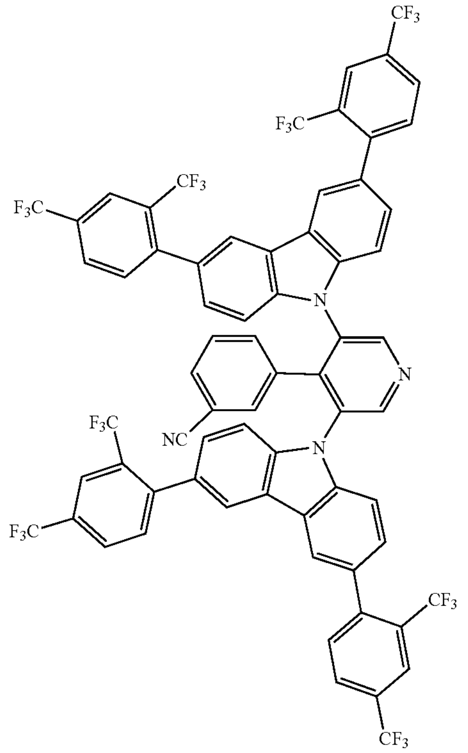
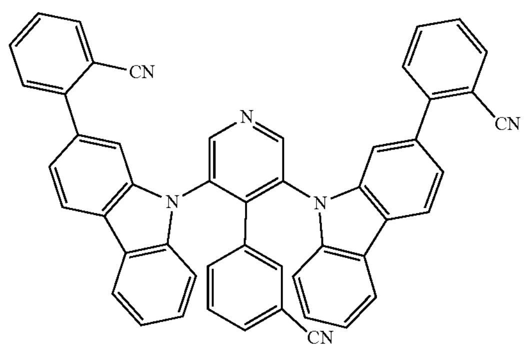

-continued
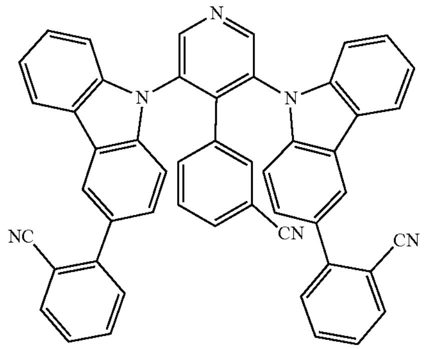
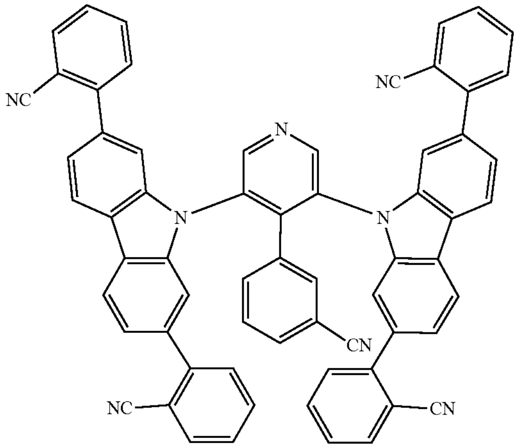
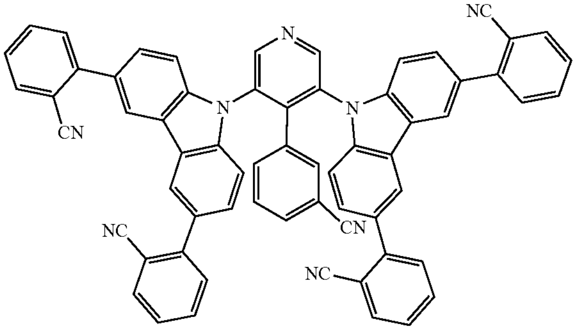
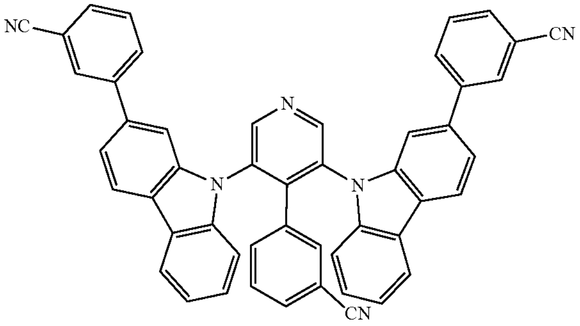
-continued
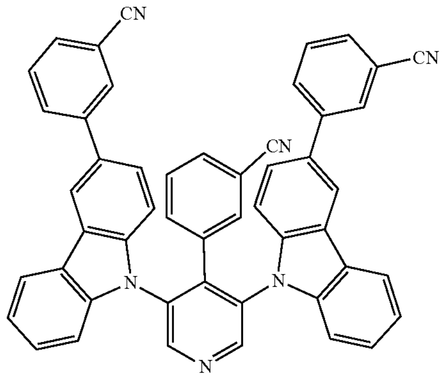
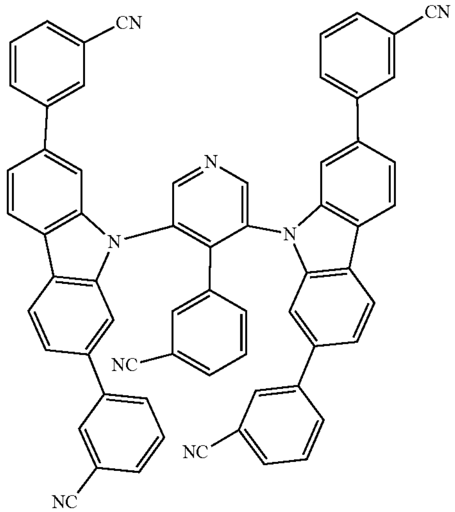
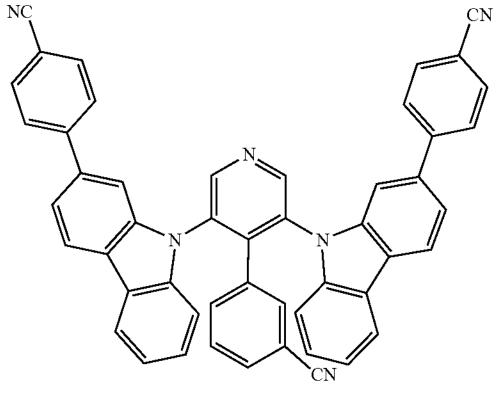

-continued
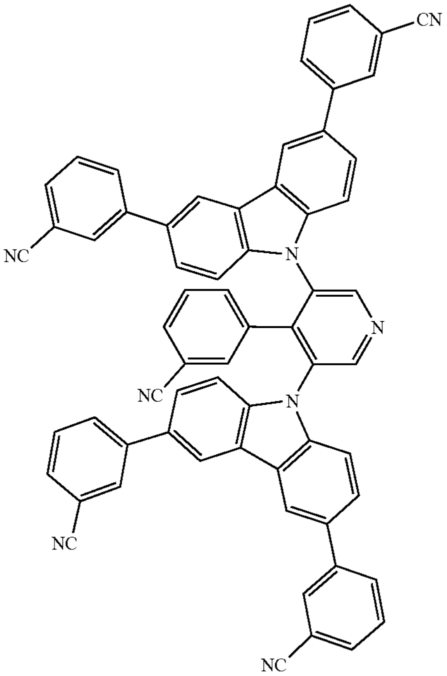
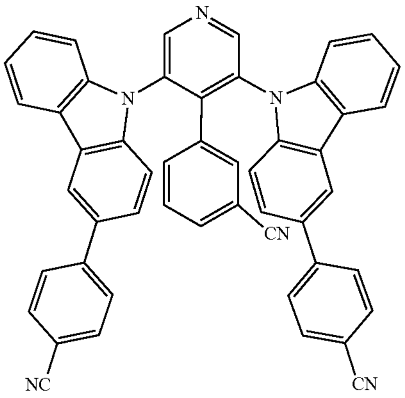
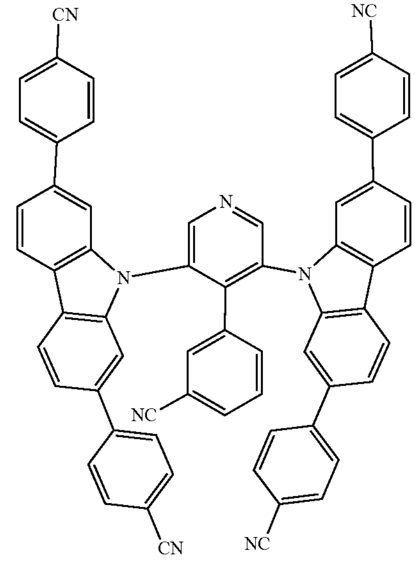
-continued
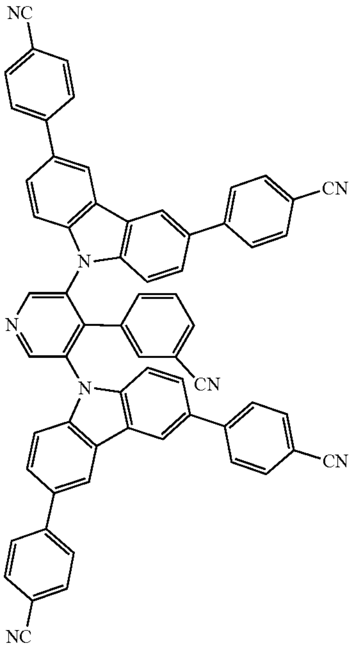
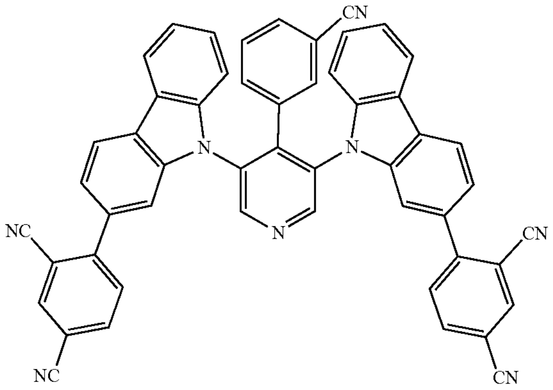
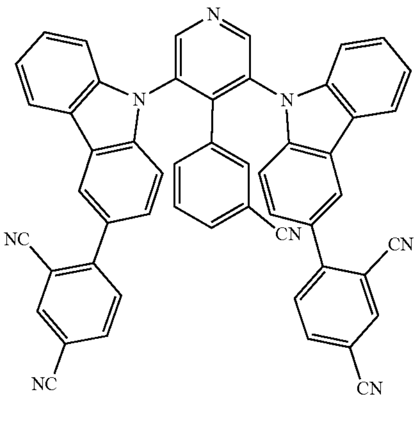

-continued
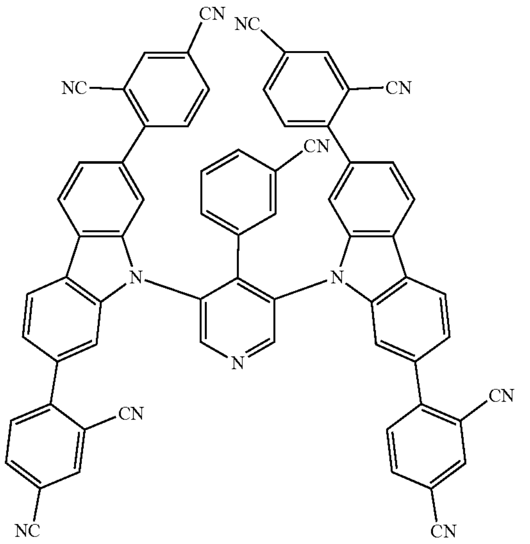
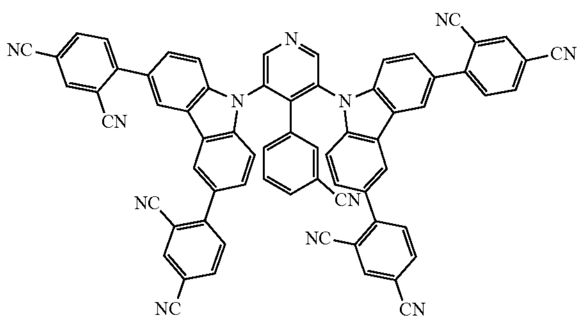
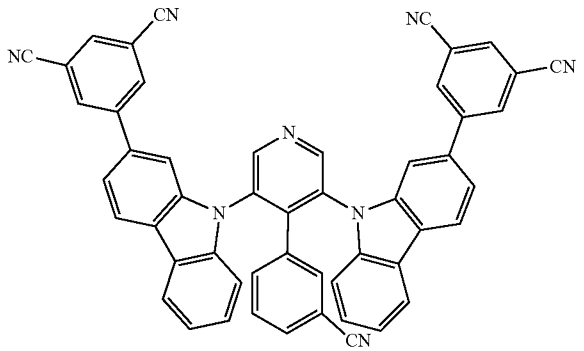
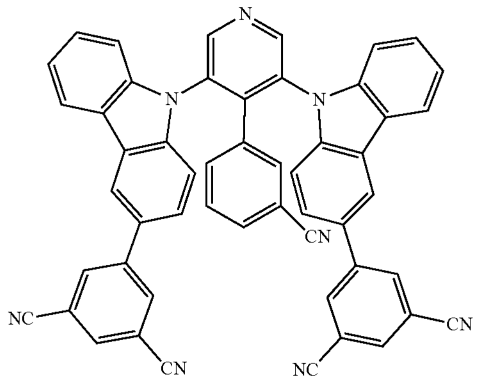
-continued
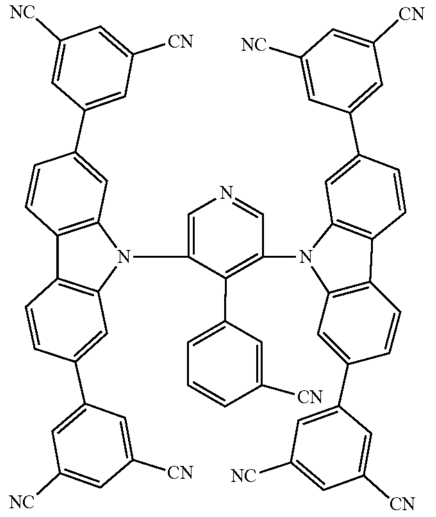
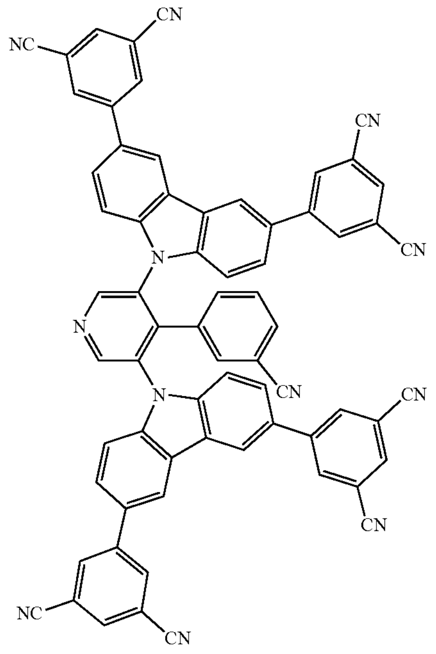
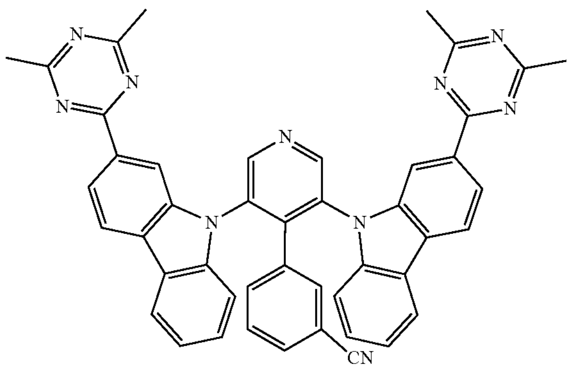

-continued
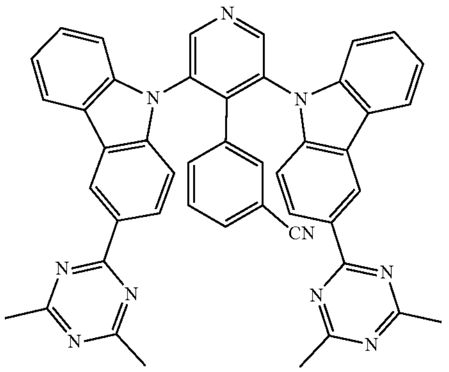
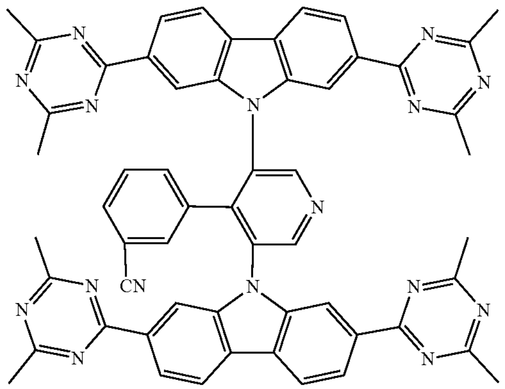
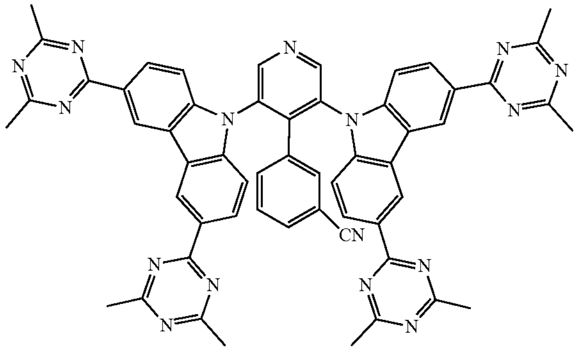
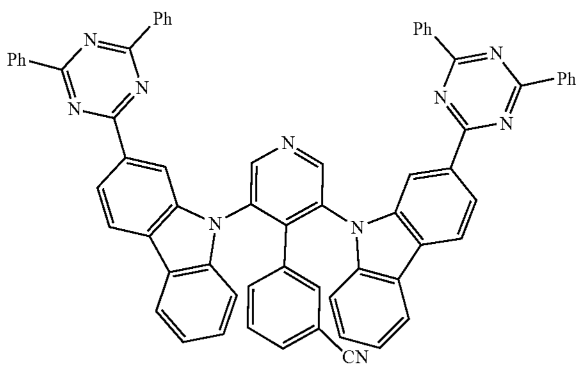
-continued
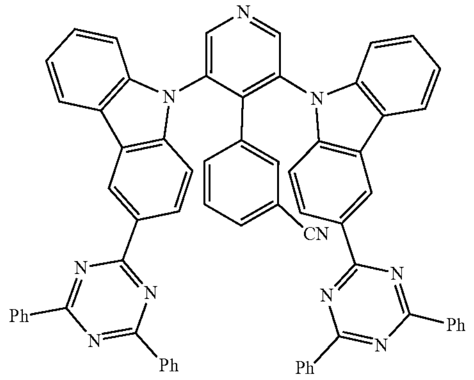
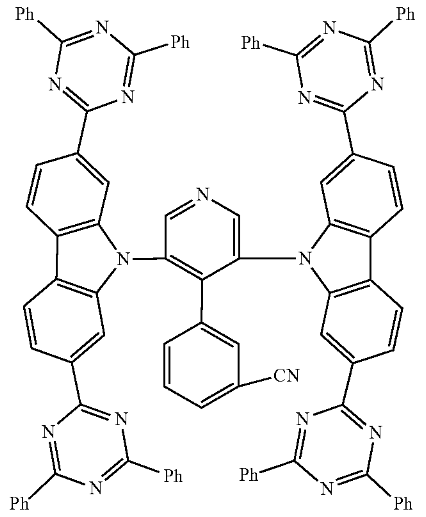
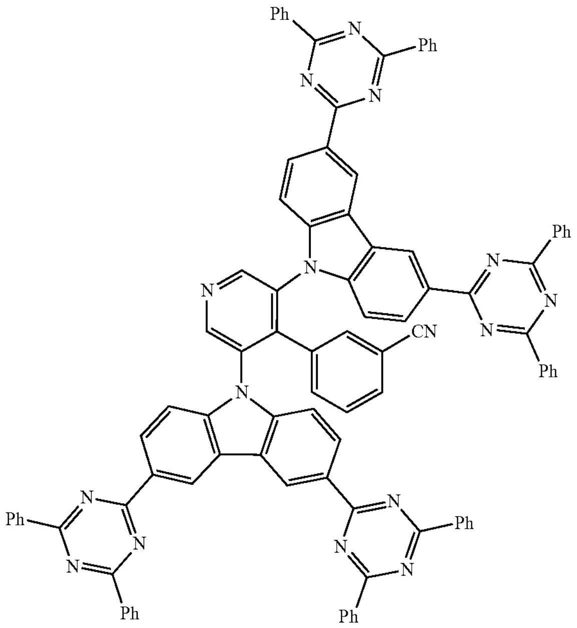

-continued
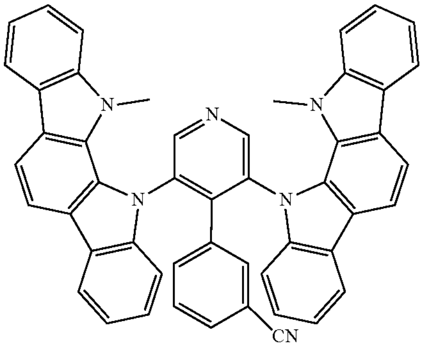
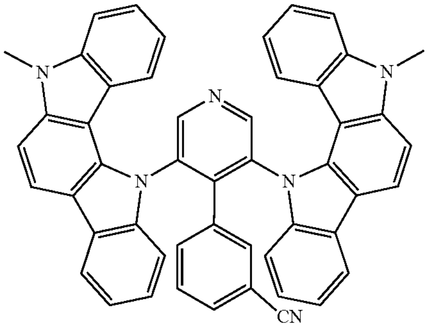
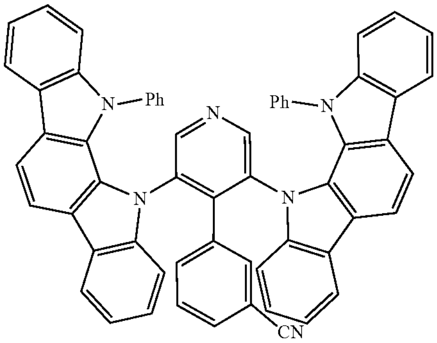
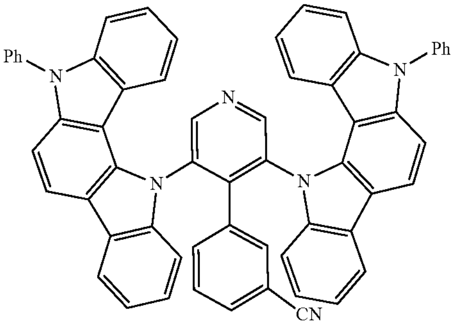
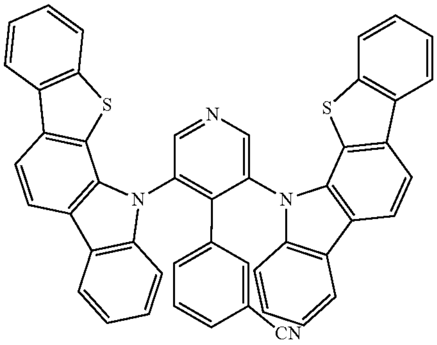
-continued
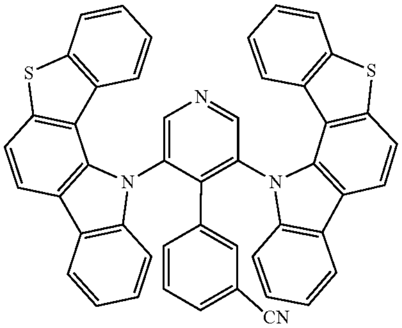
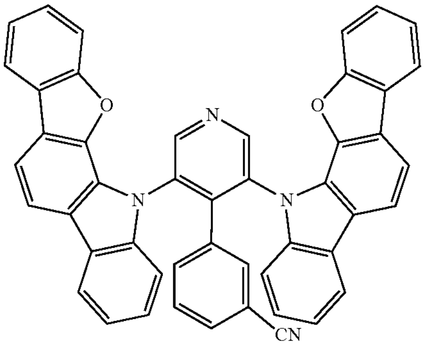
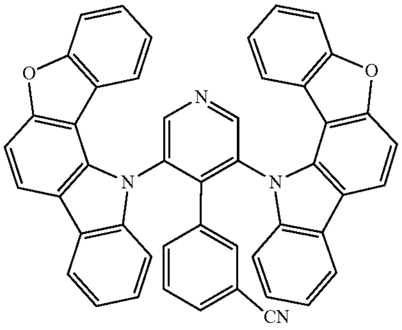
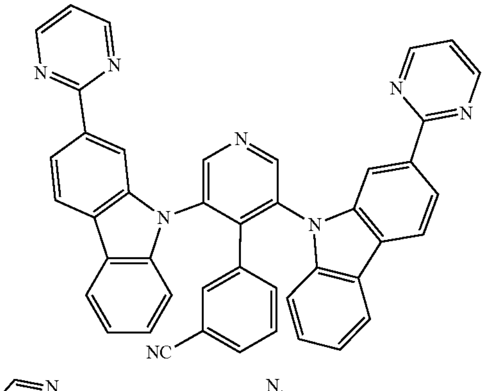
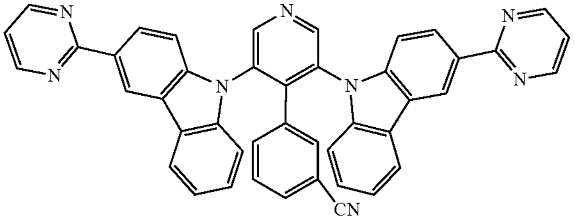

-continued
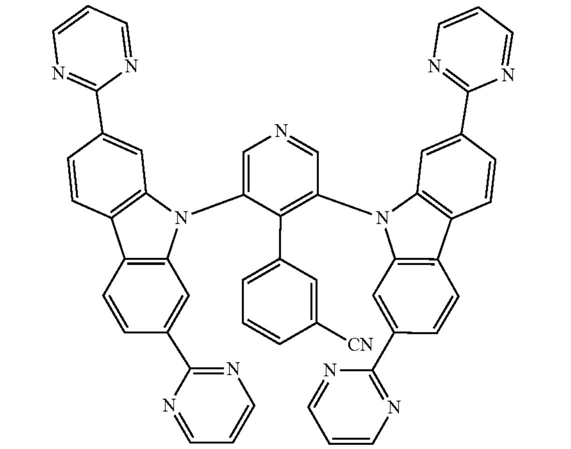
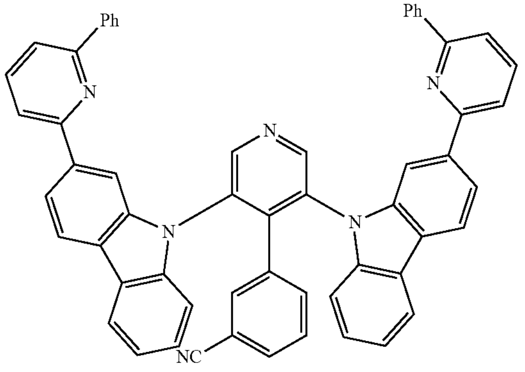
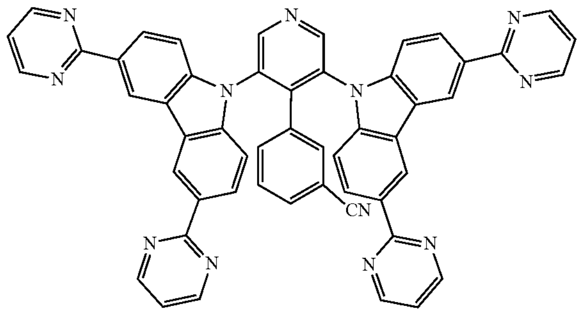
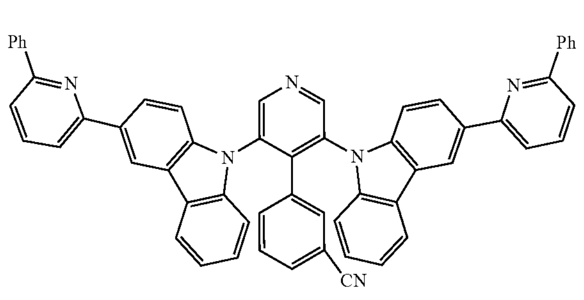
-continued
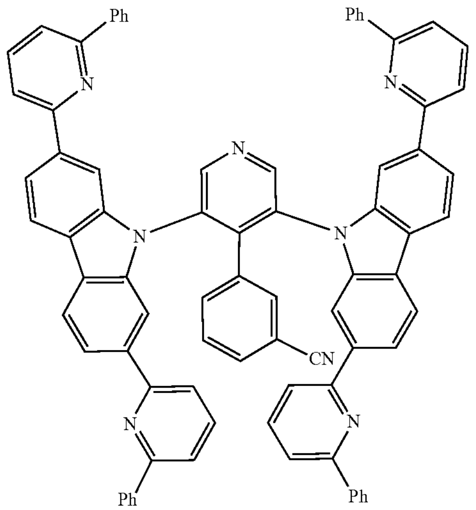
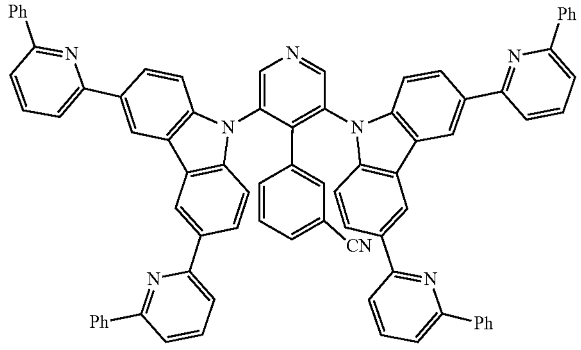
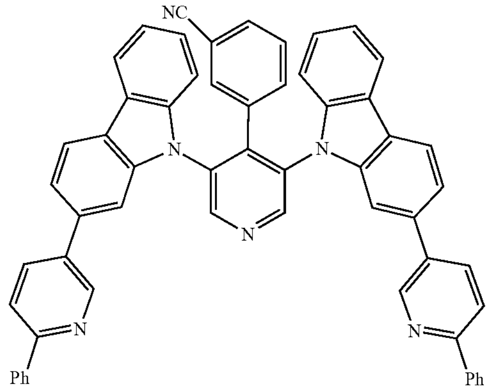
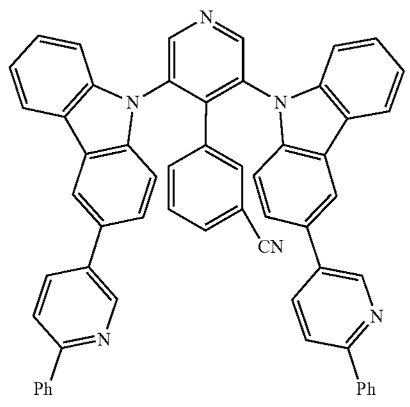

-continued
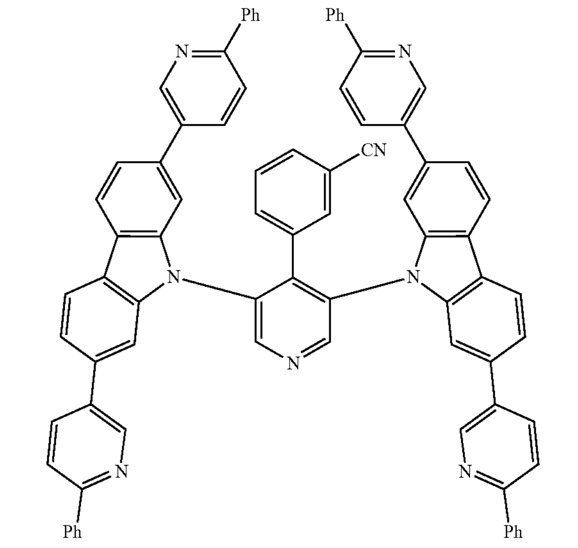
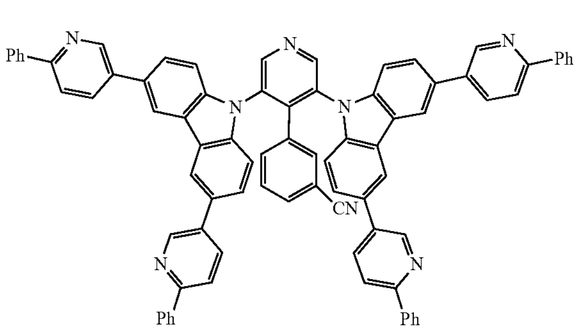
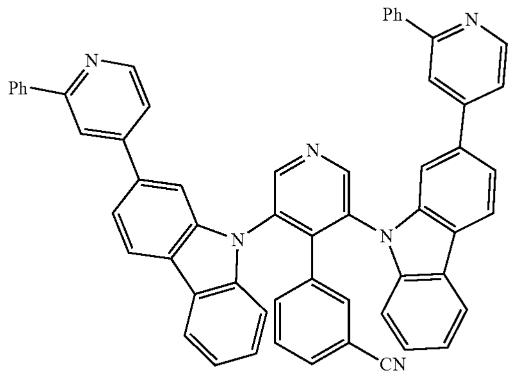
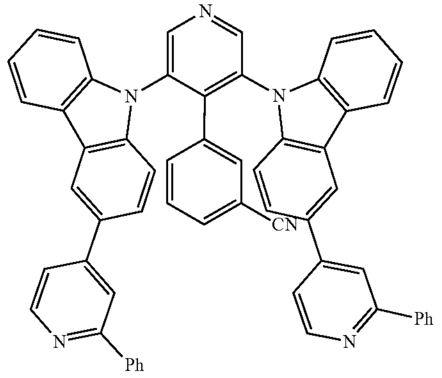
-continued
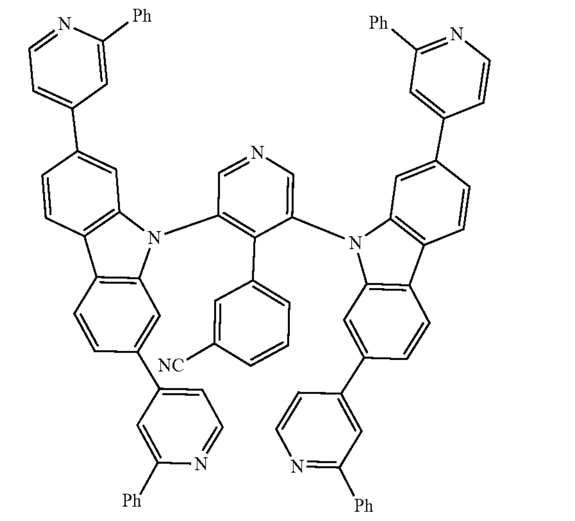
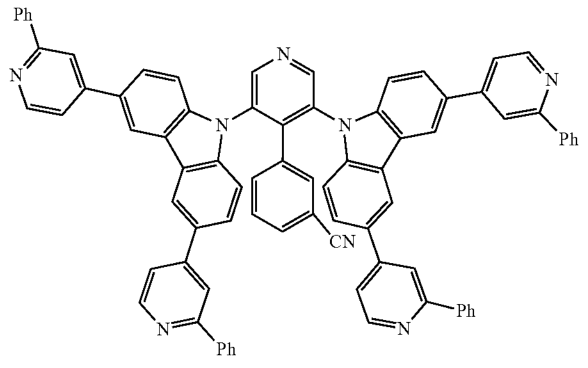
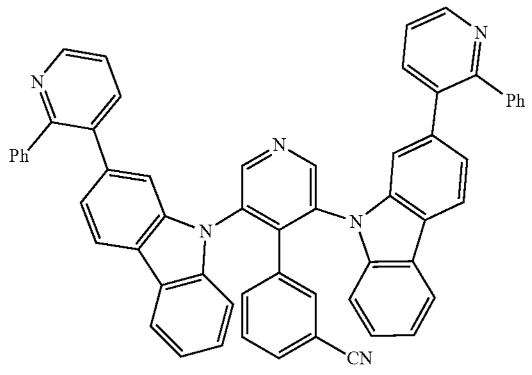
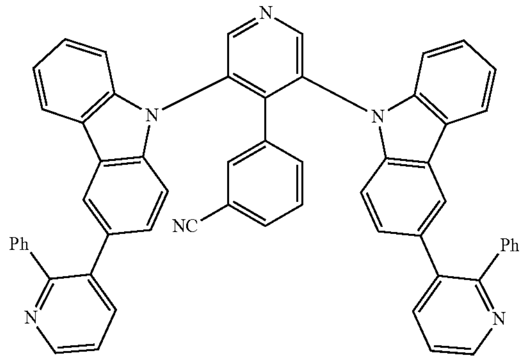

-continued
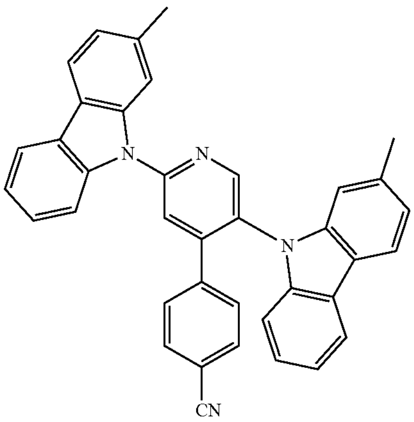
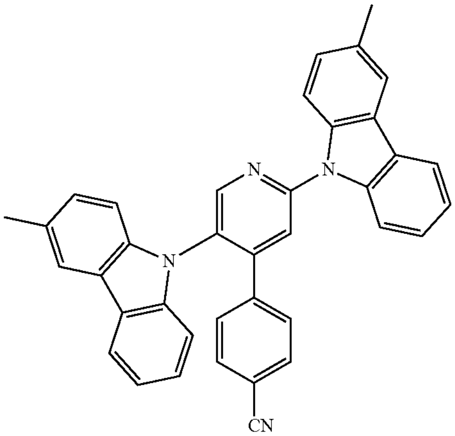
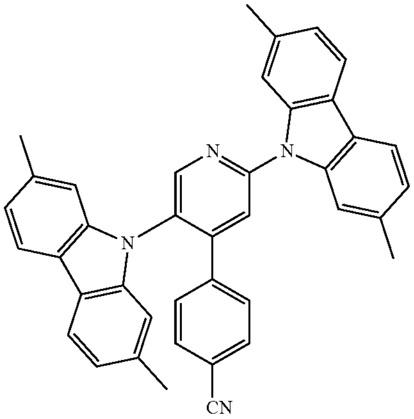
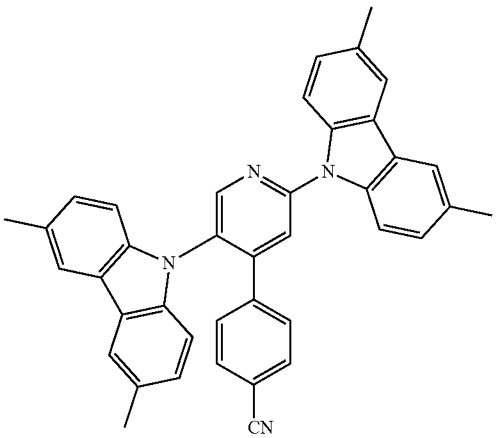
-continued
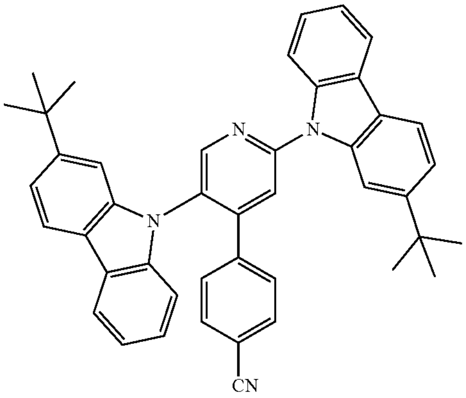
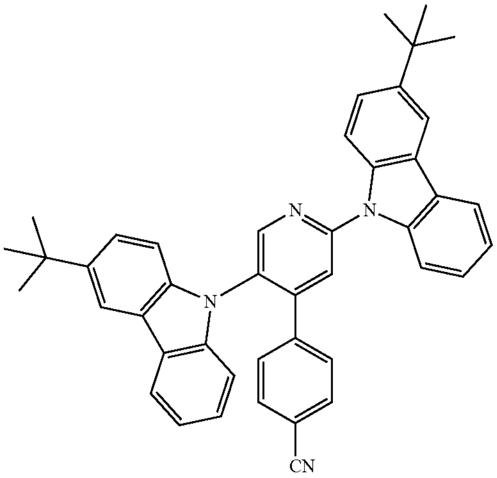
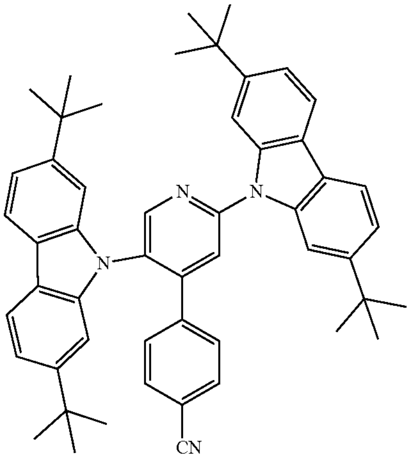

-continued
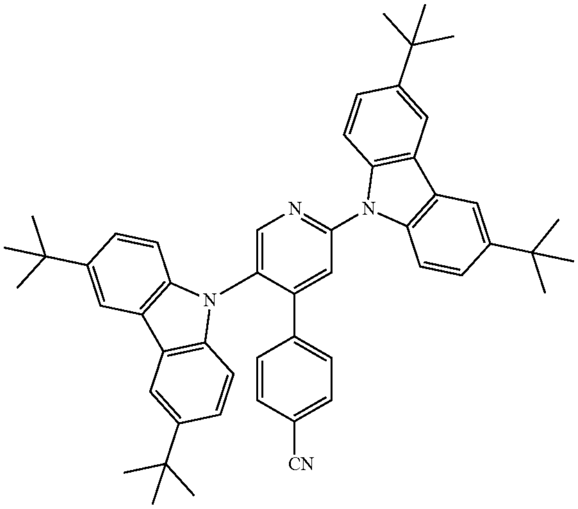
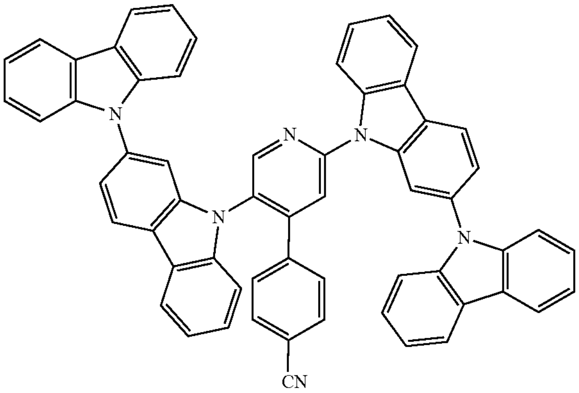
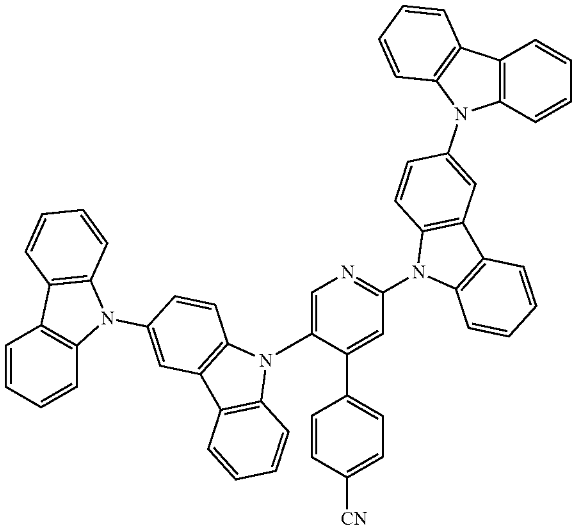
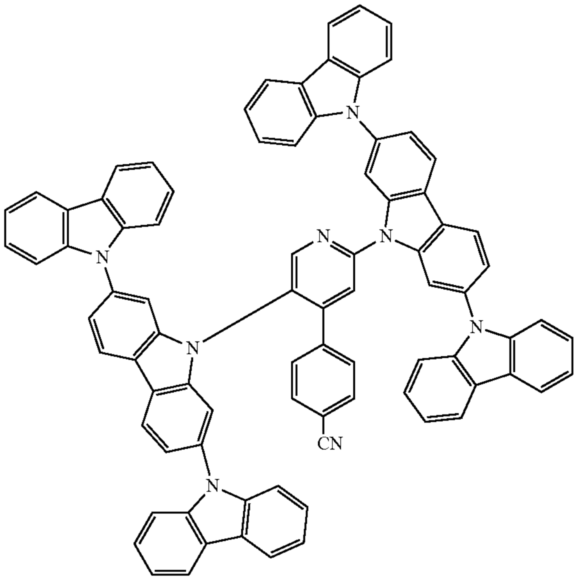
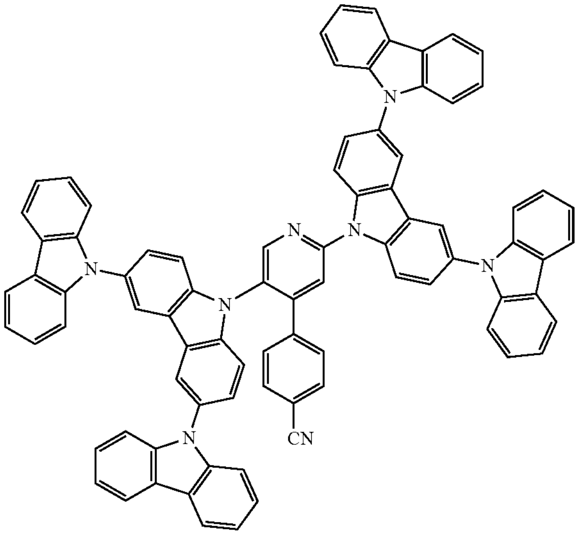
-continued
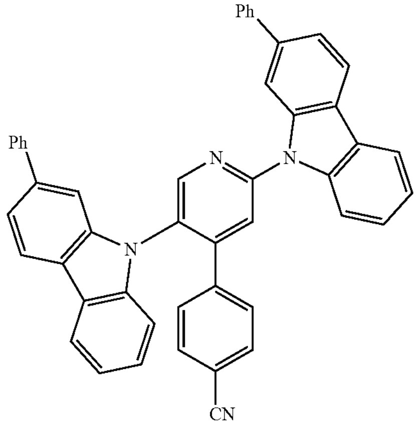

-continued
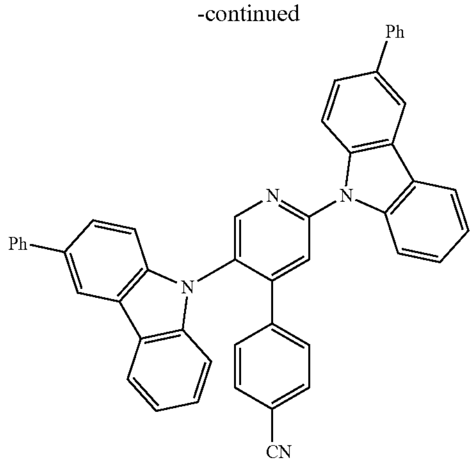
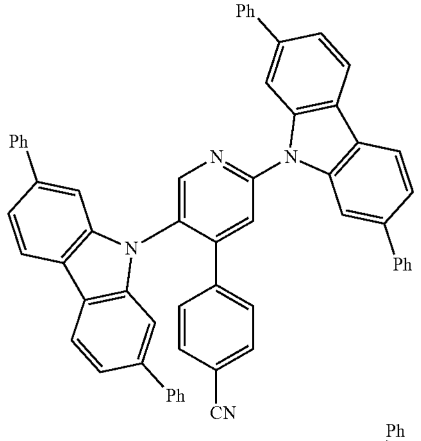
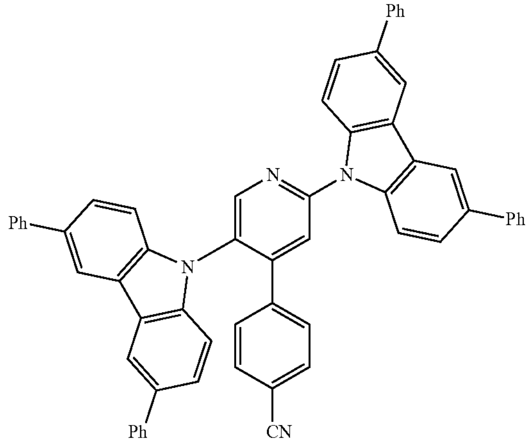
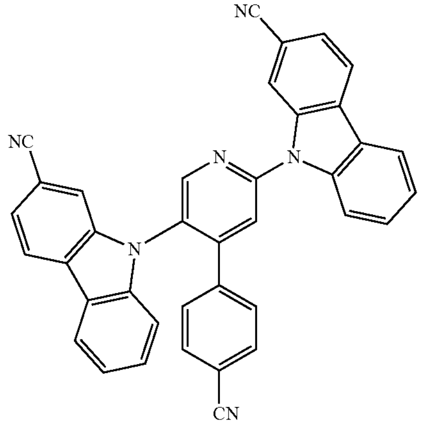
-continued
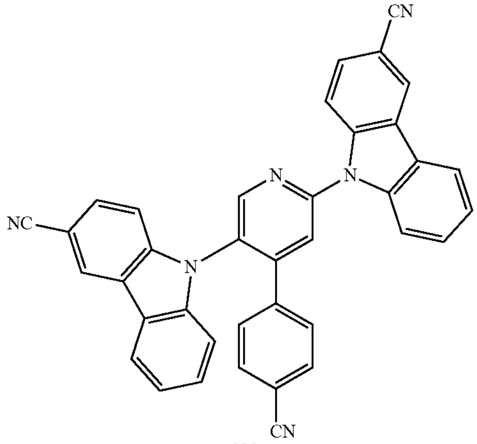
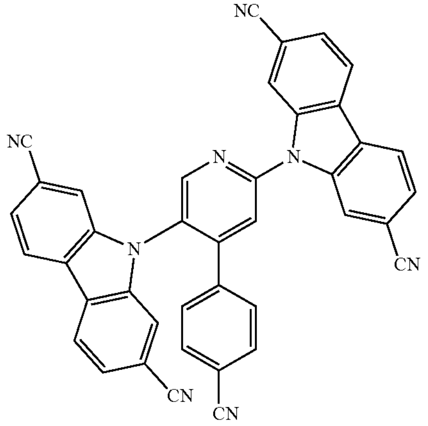
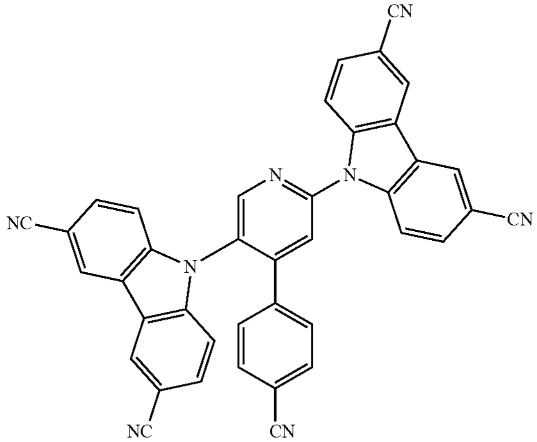
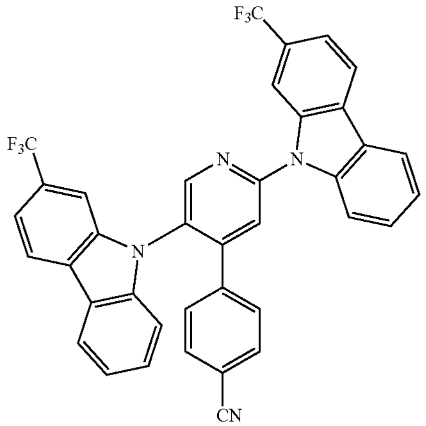

-continued
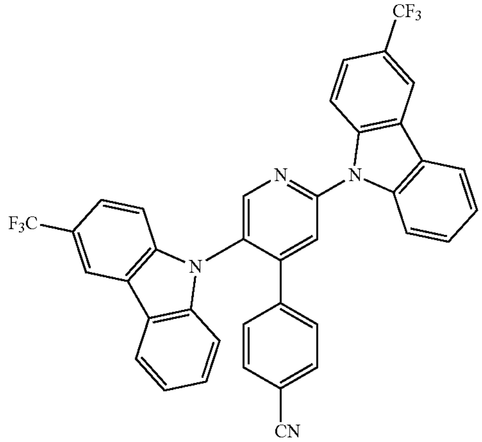
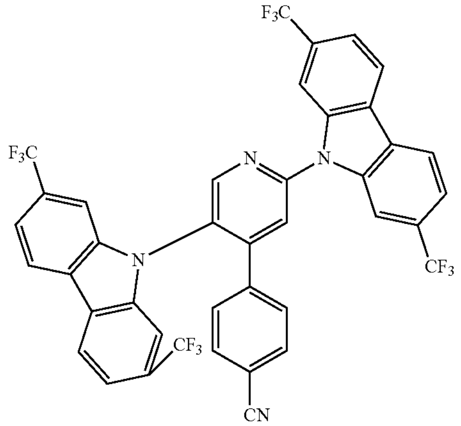
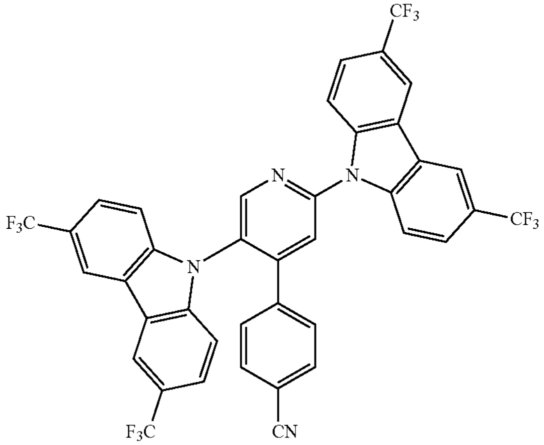
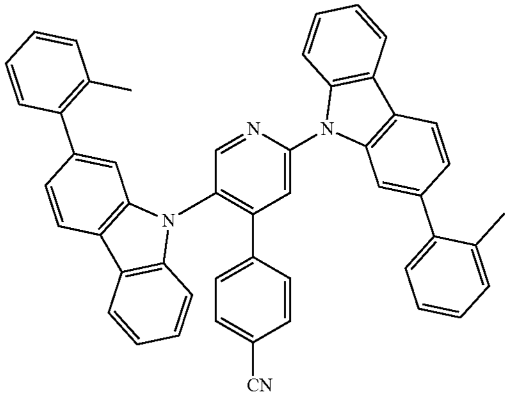
-continued
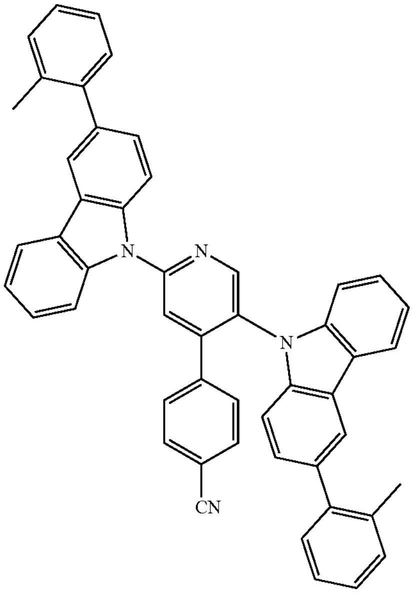
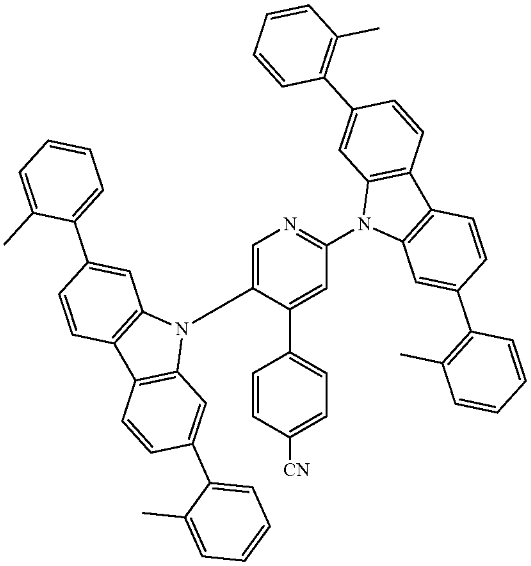
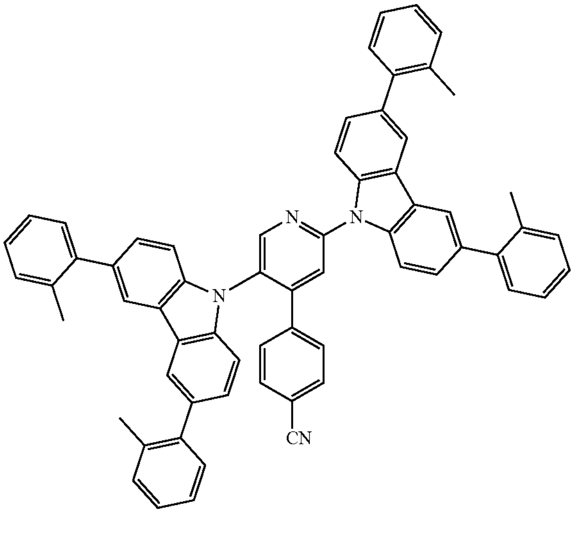

-continued
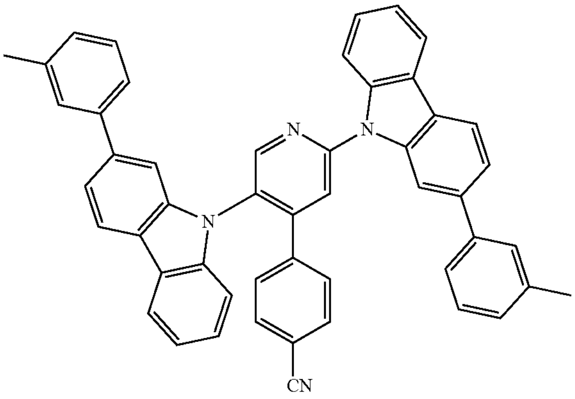
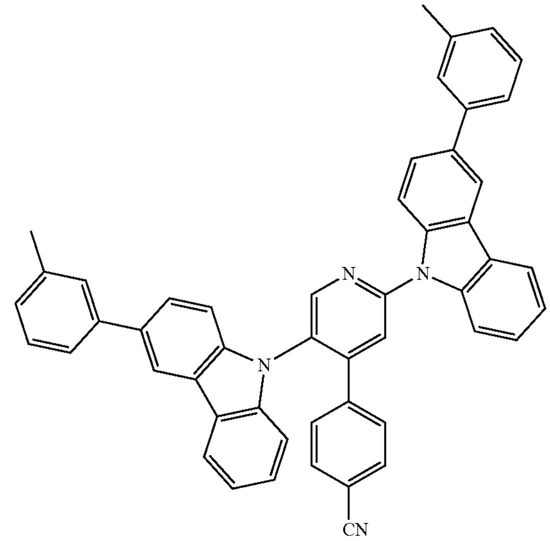
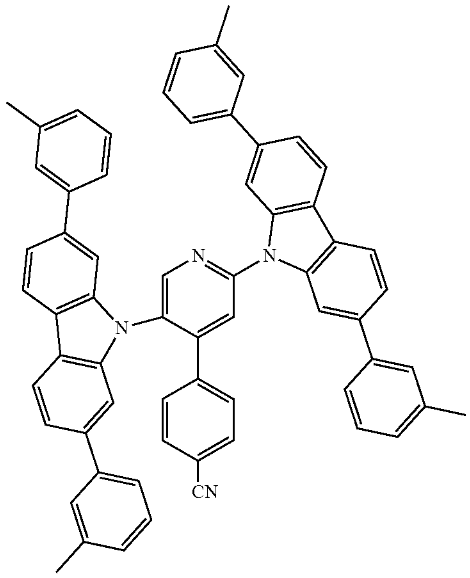
-continued
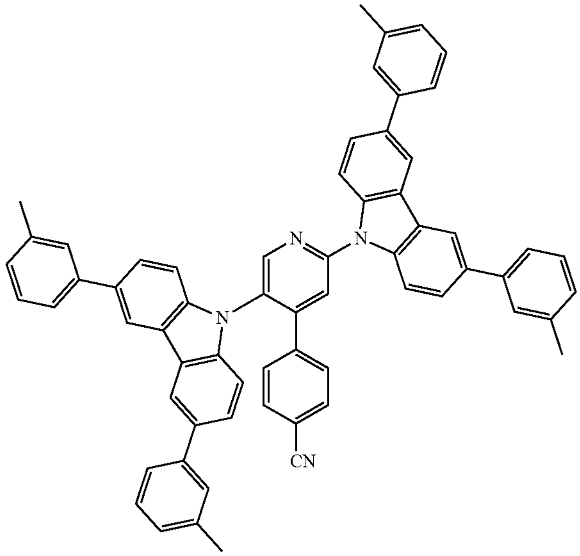
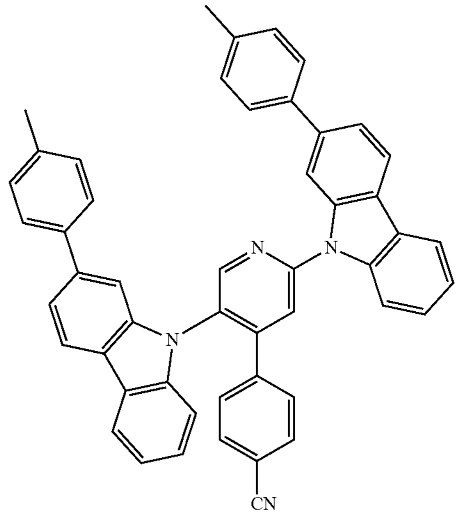
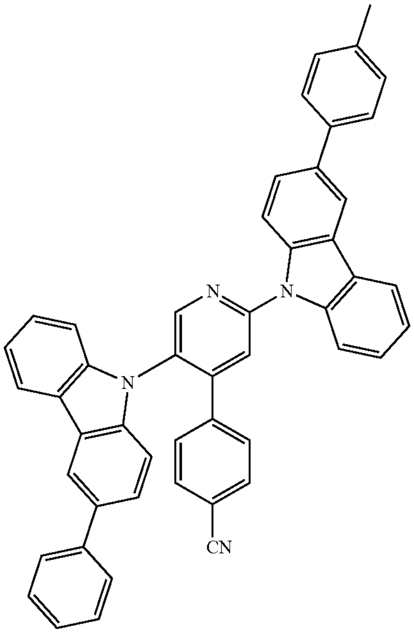

-continued
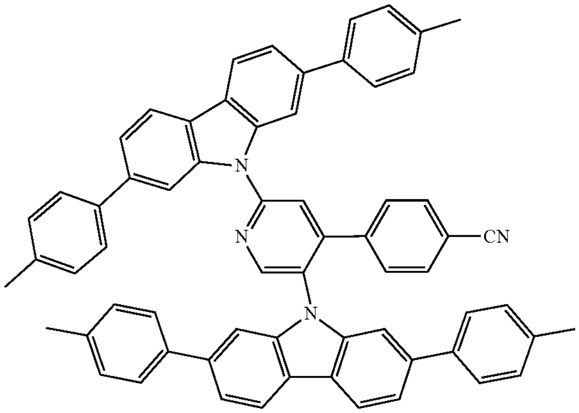
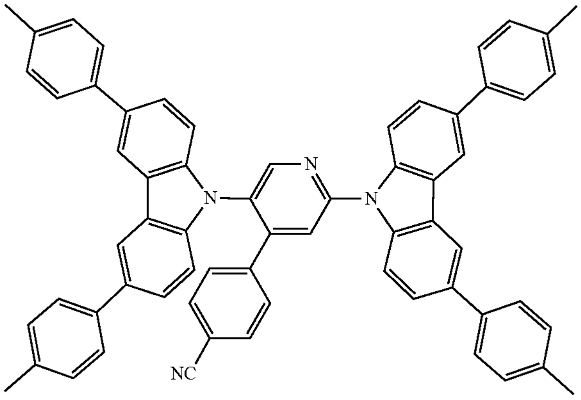
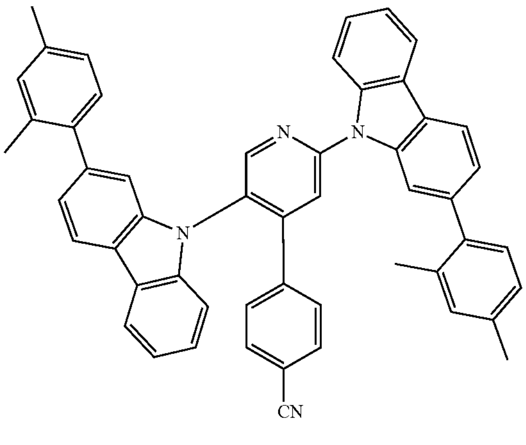
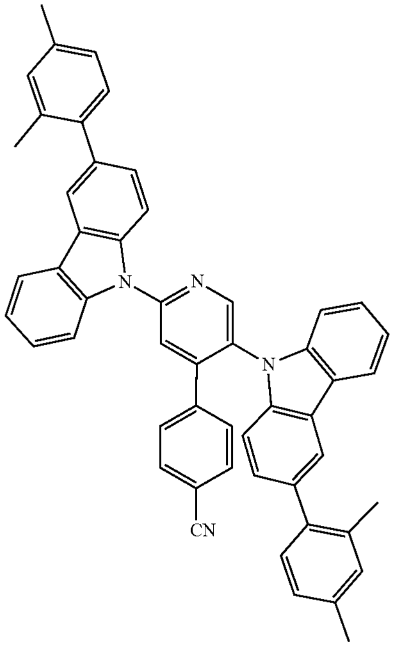
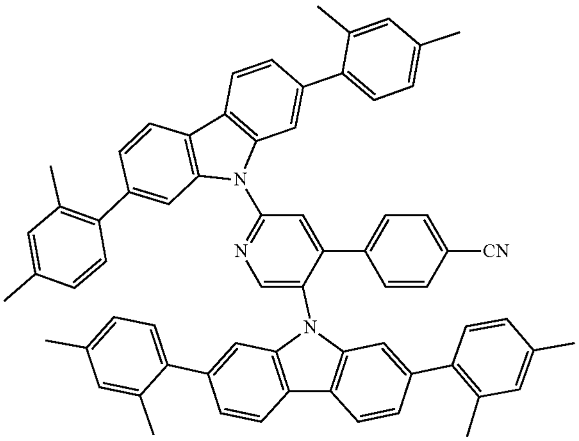
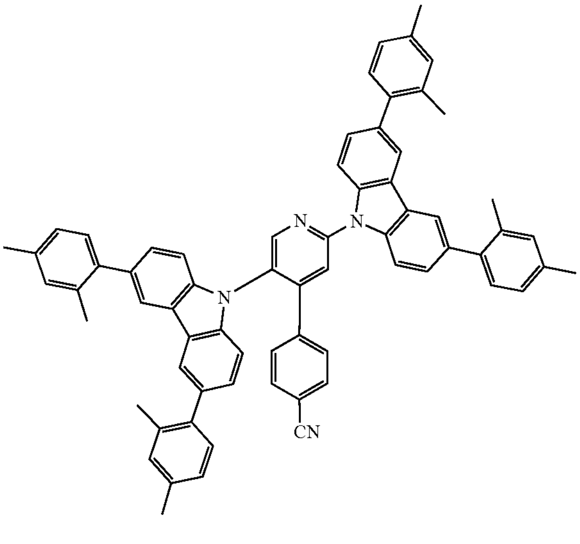

-continued
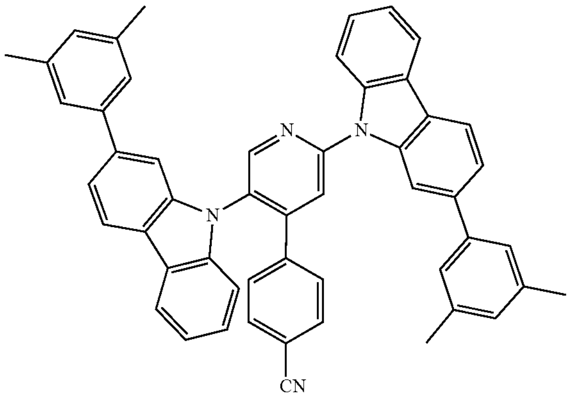
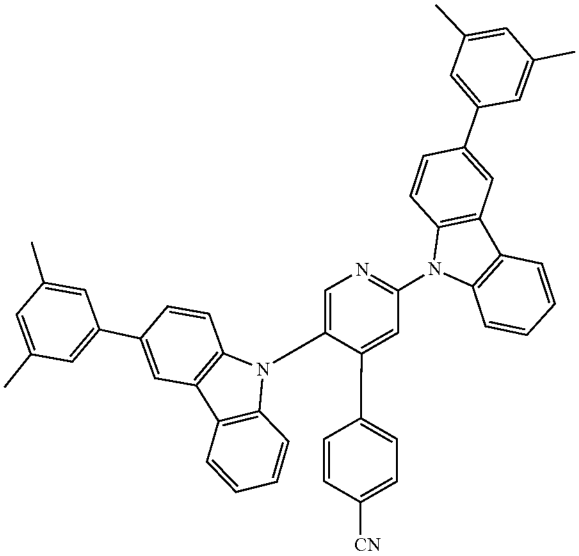
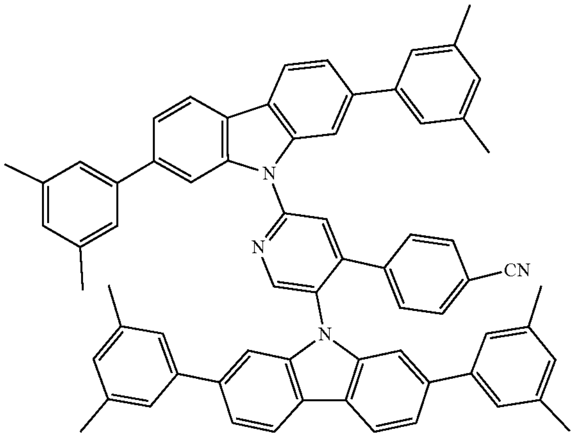
-continued
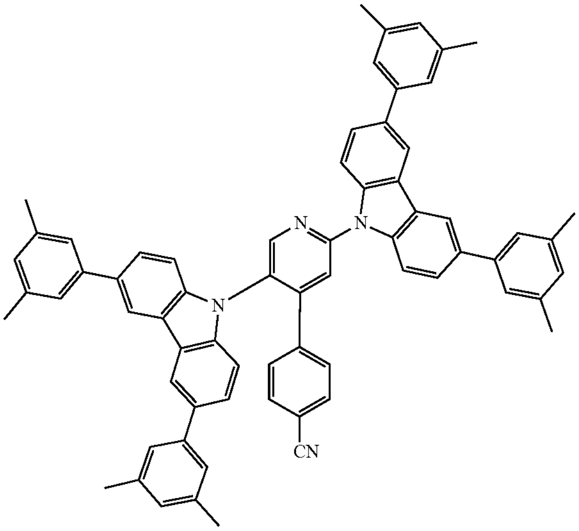
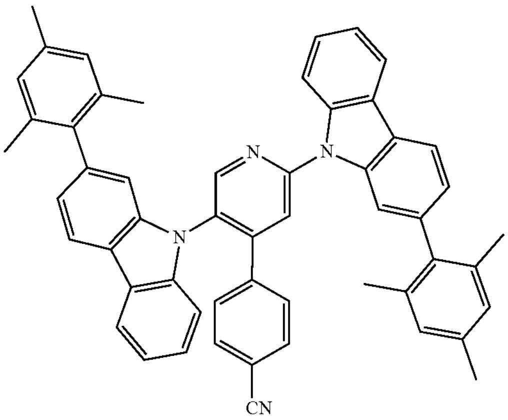
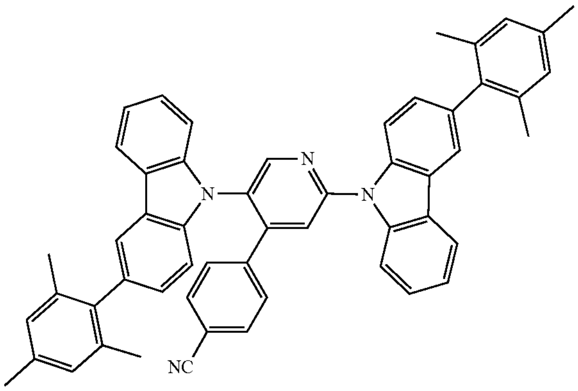

-continued
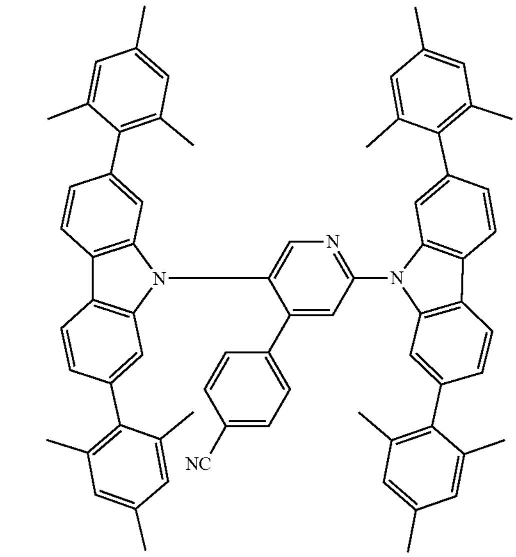
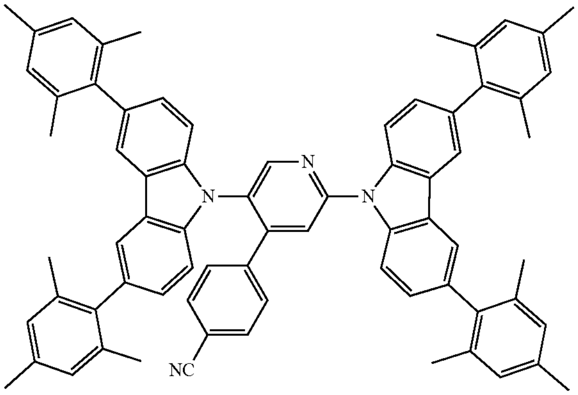
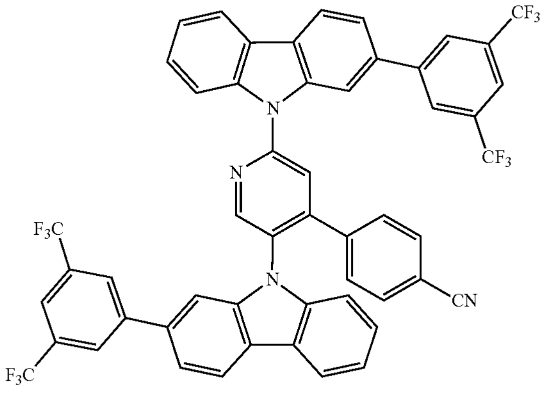
-continued
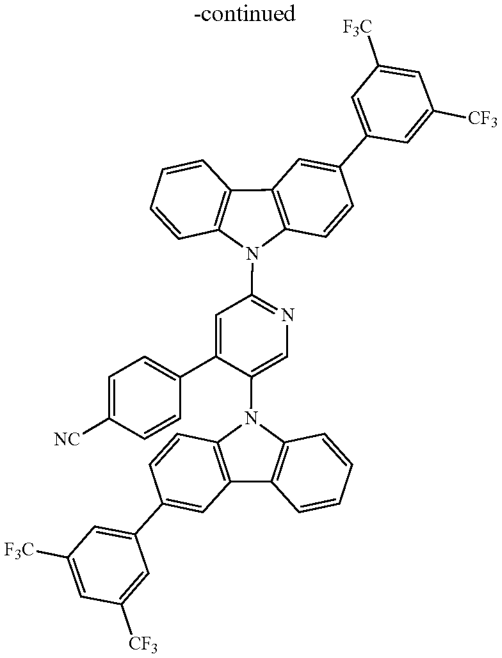
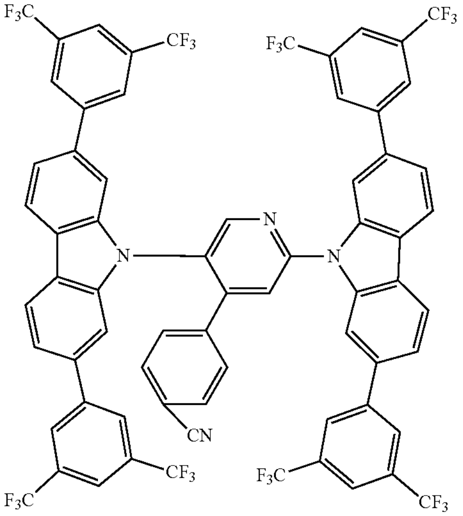
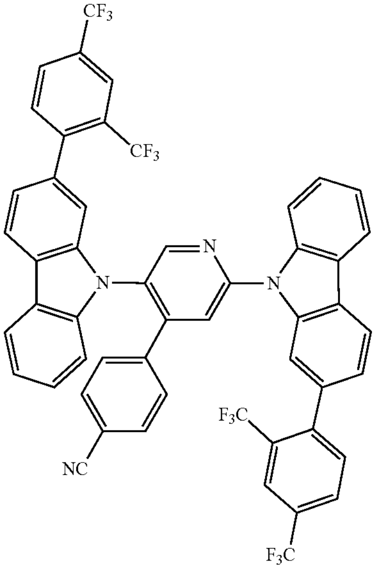

-continued
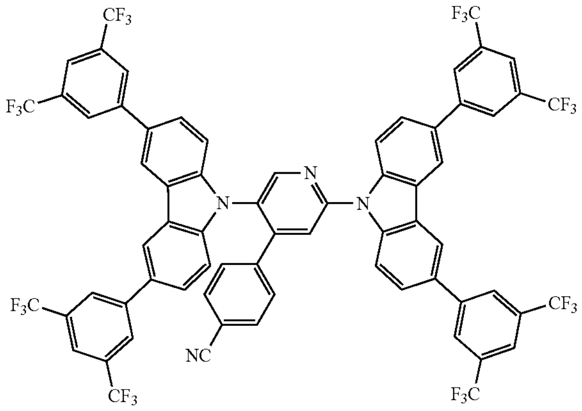
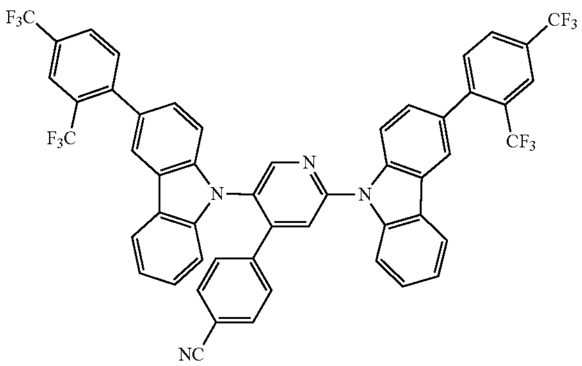
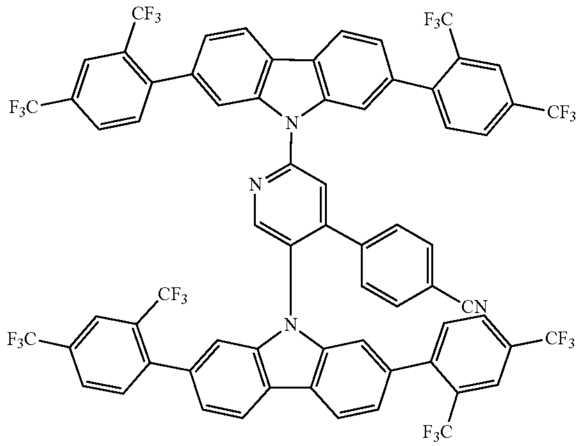
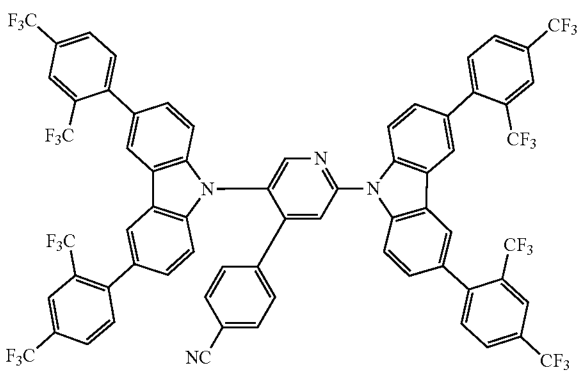
-continued
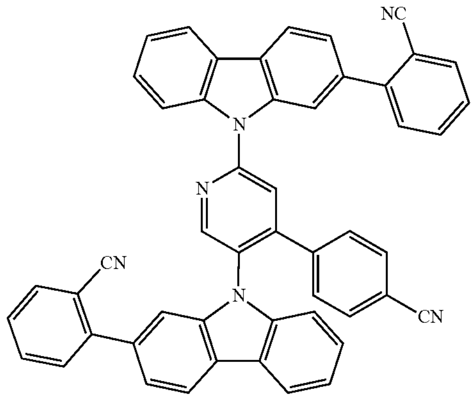
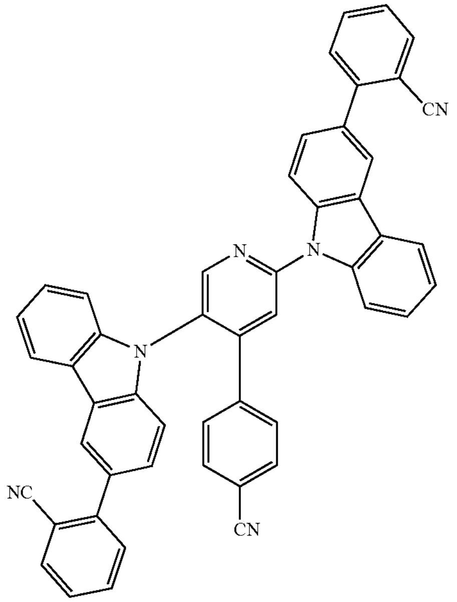
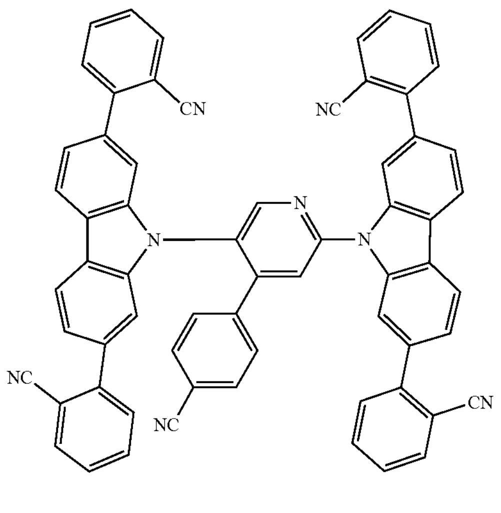

-continued
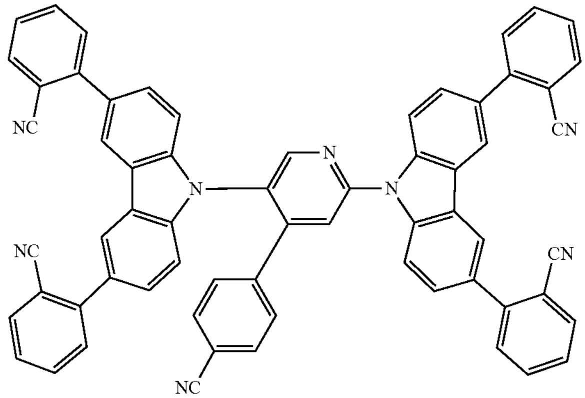
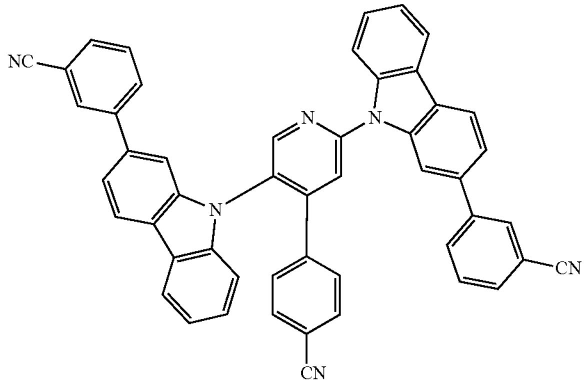
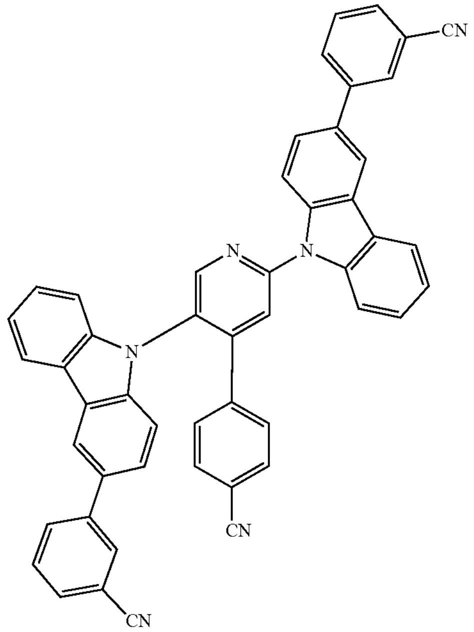
-continued
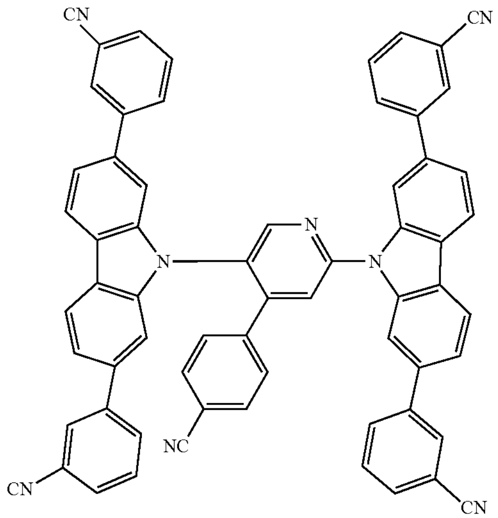
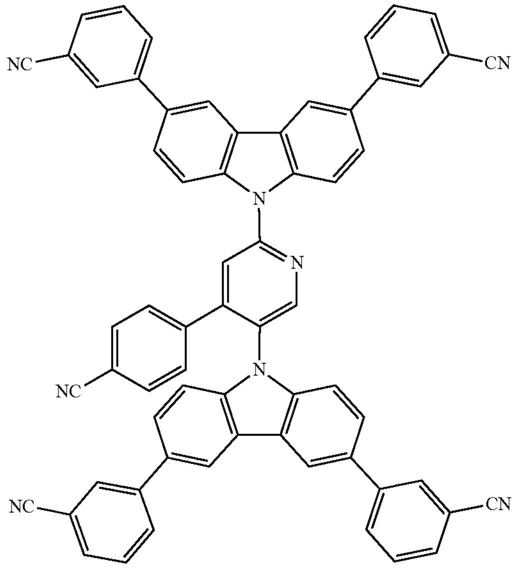
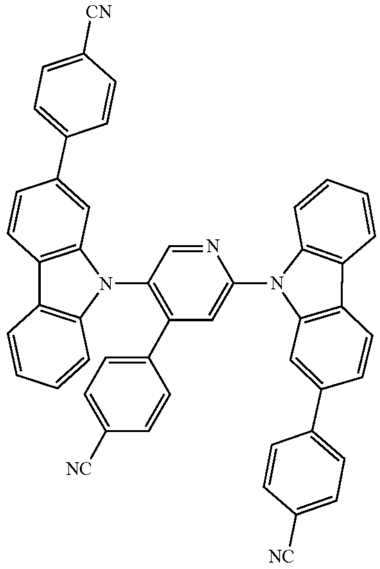

-continued
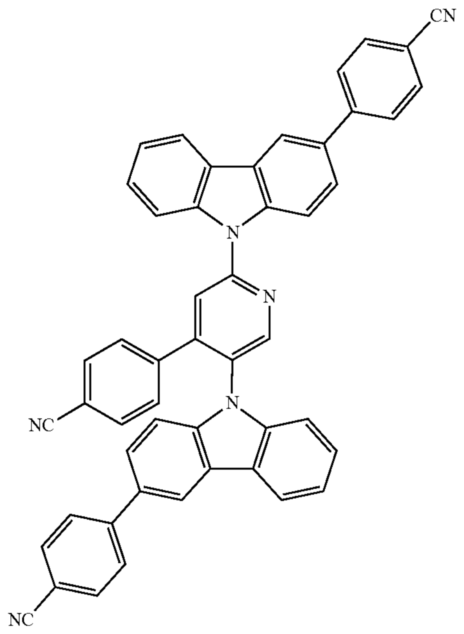
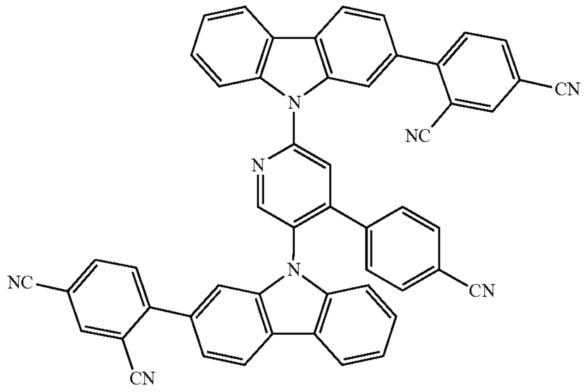
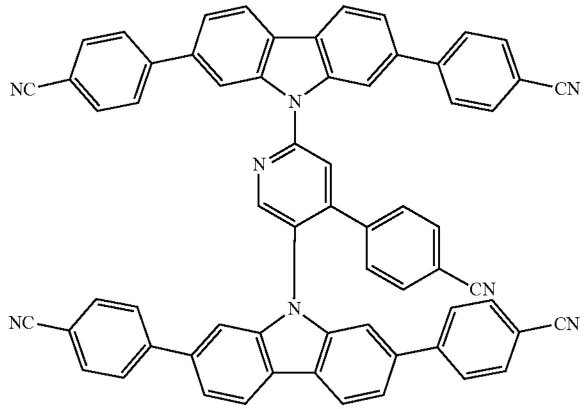
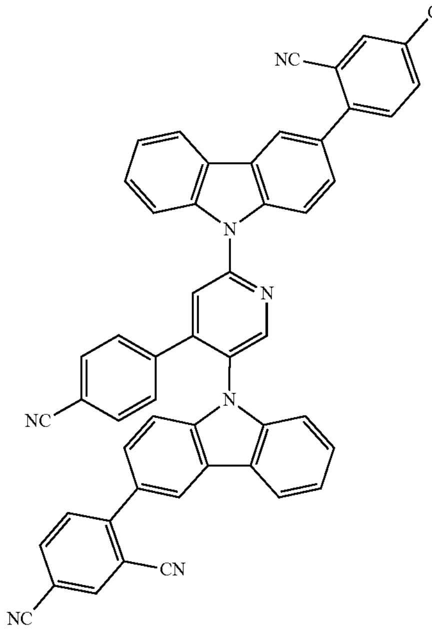
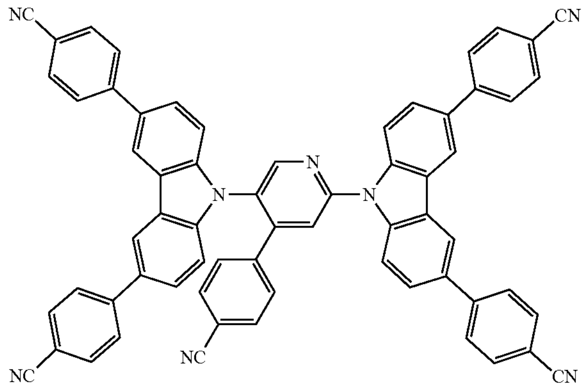
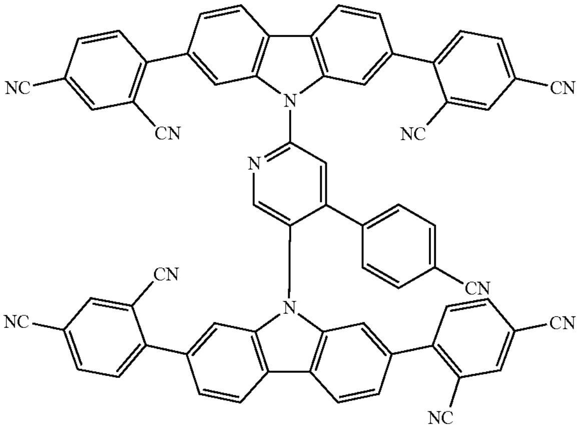
-continued -continued
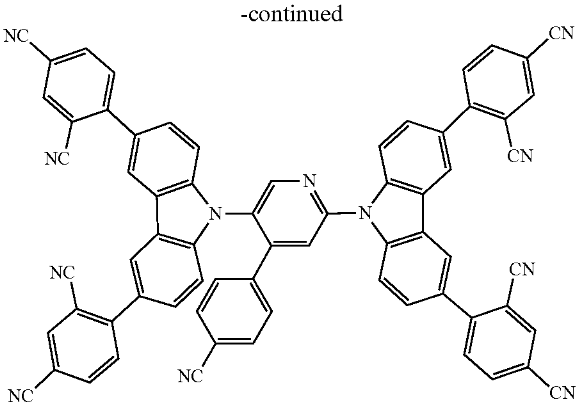
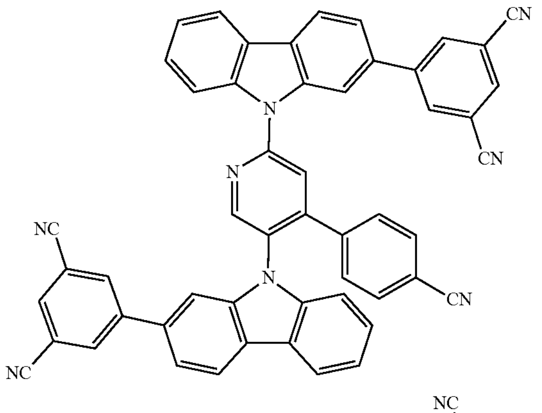
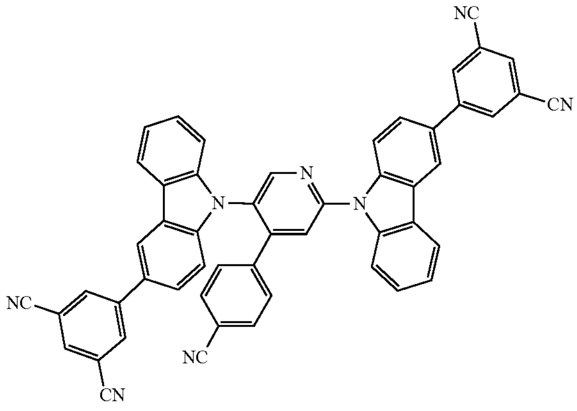
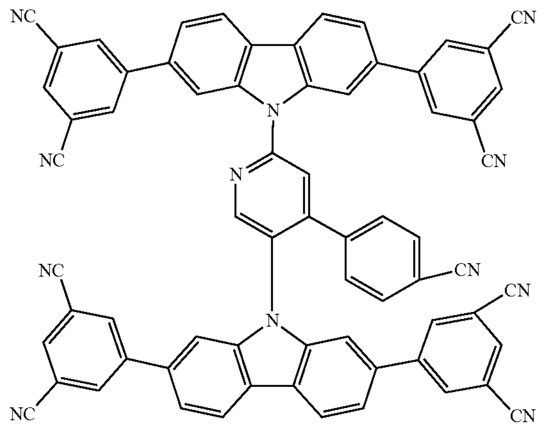
-continued
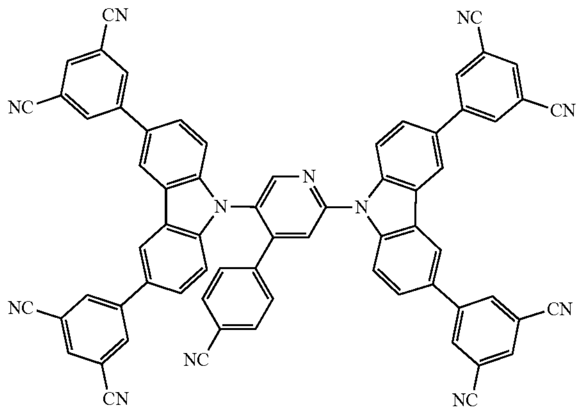
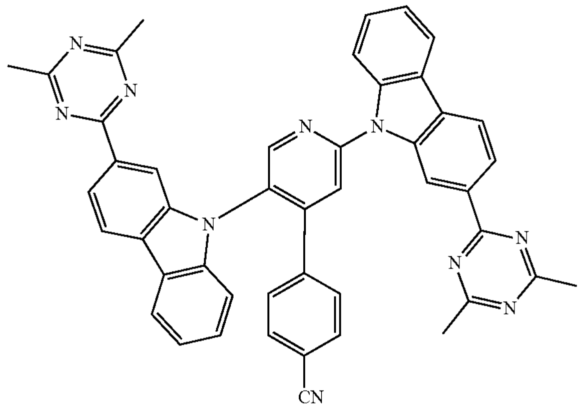
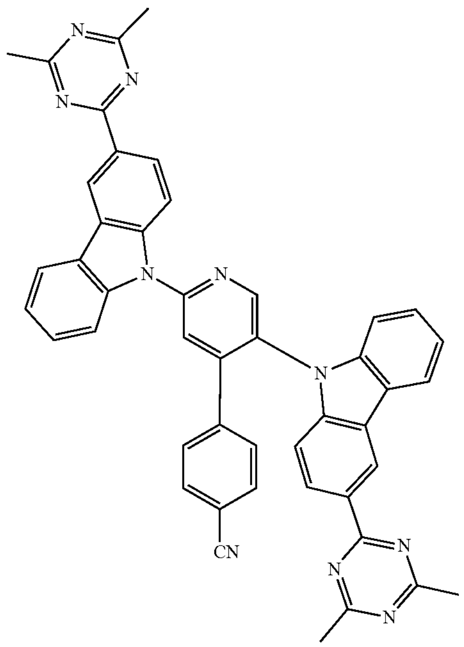

-continued
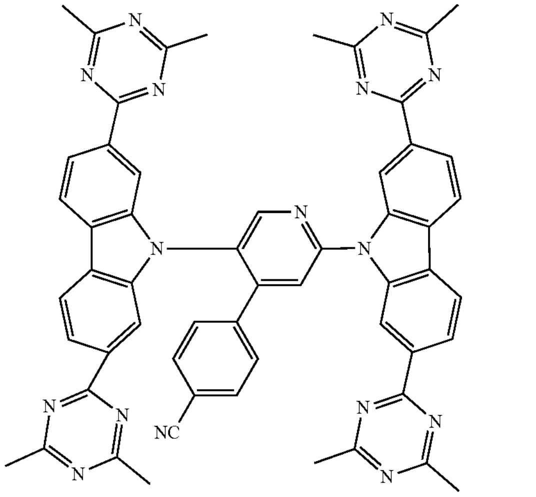
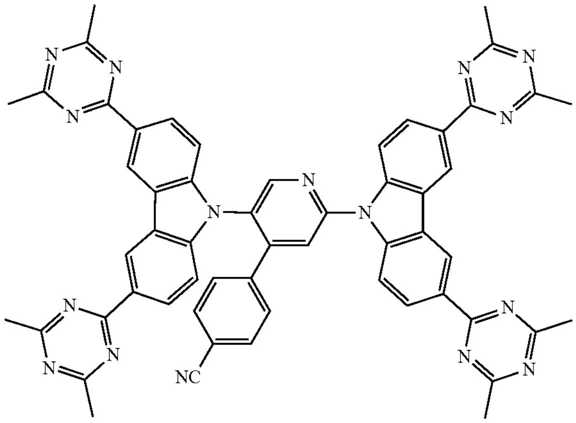
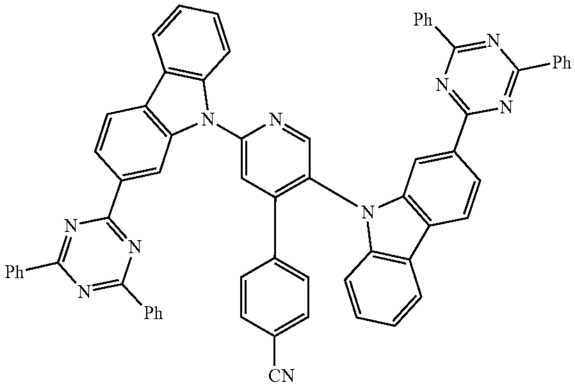
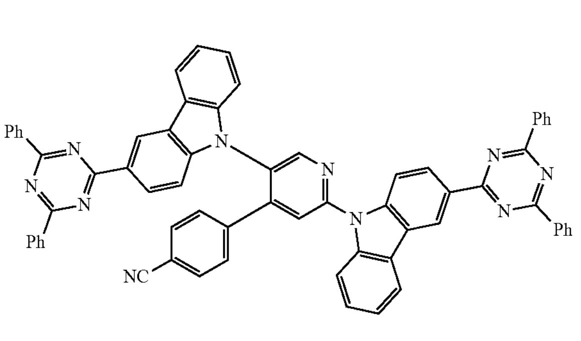
-continued
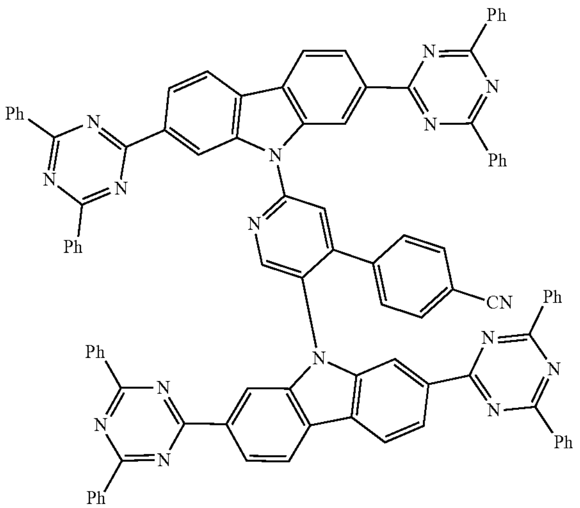
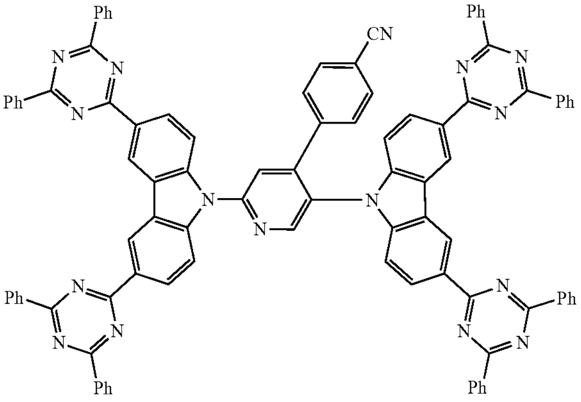
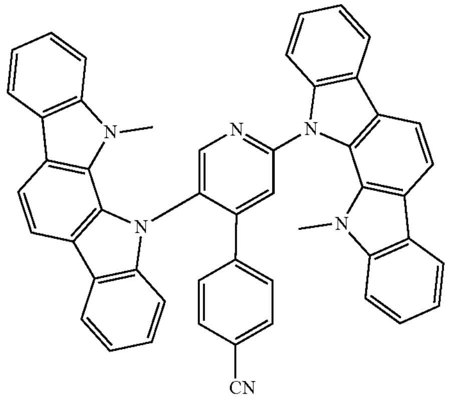
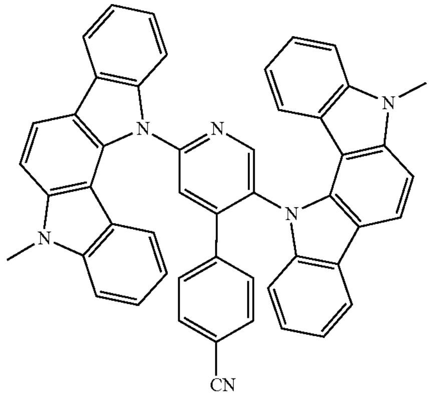

-continued
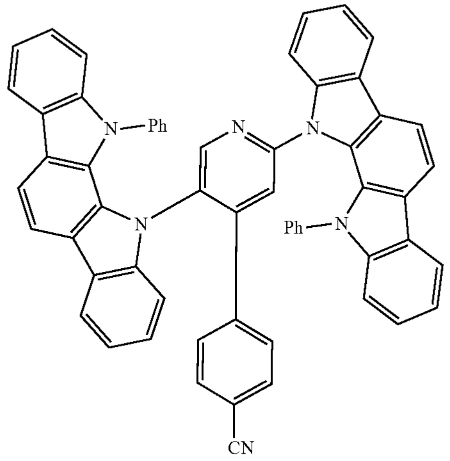
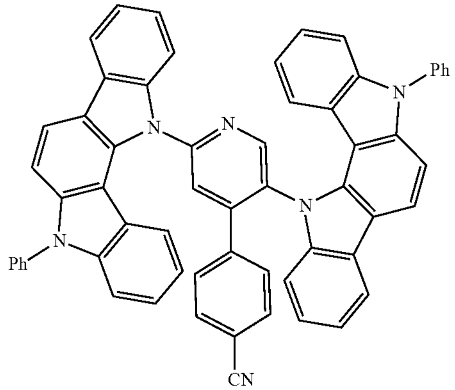
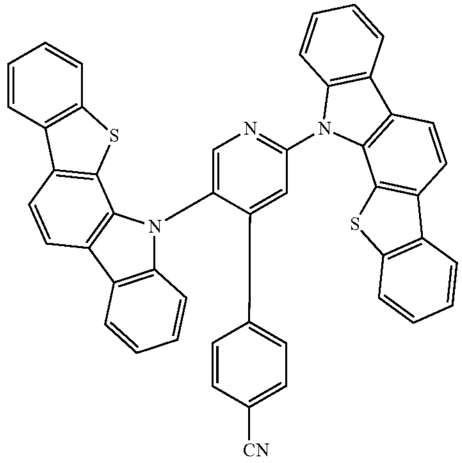
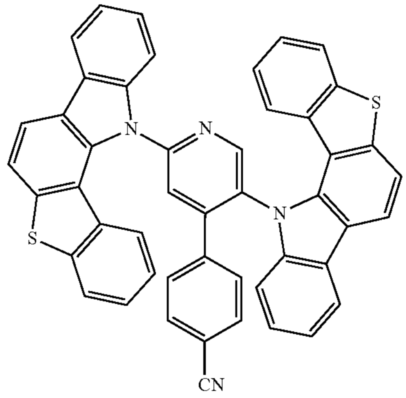
-continued
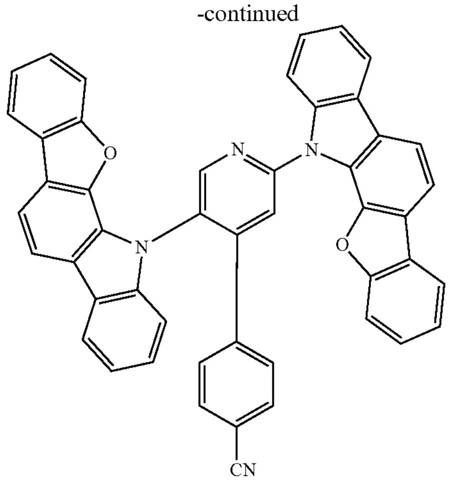
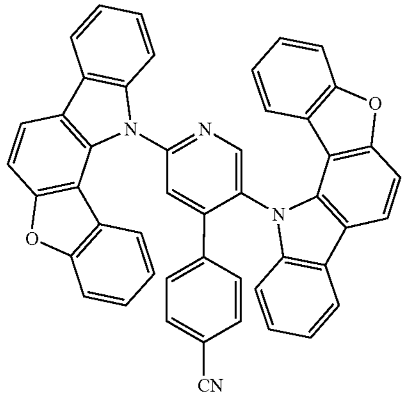
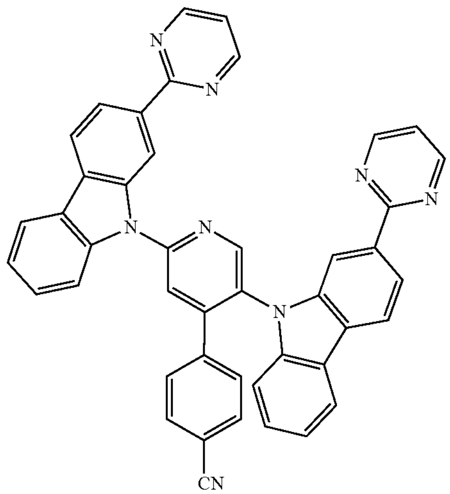

-continued
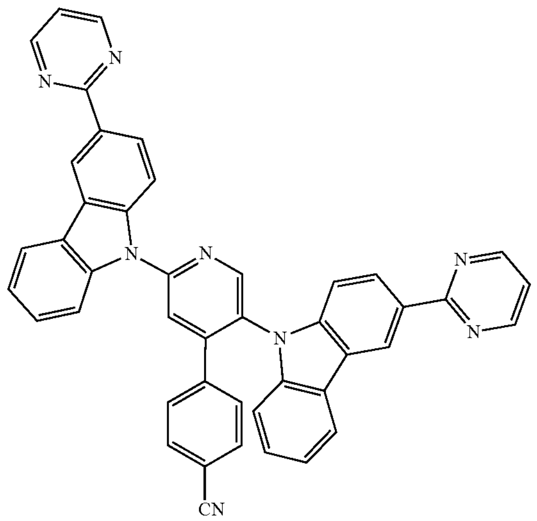
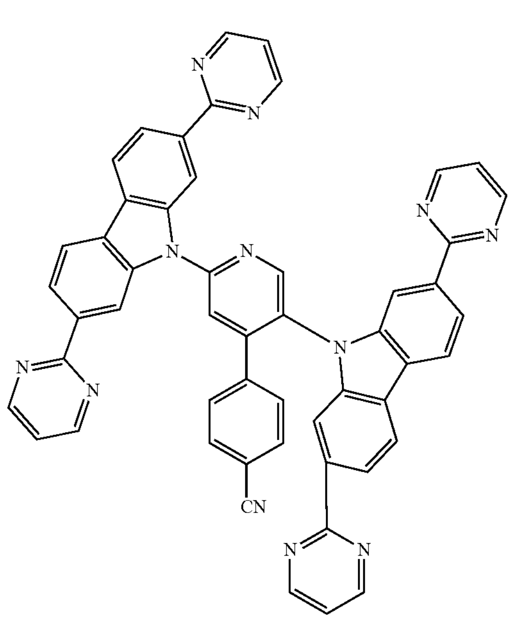
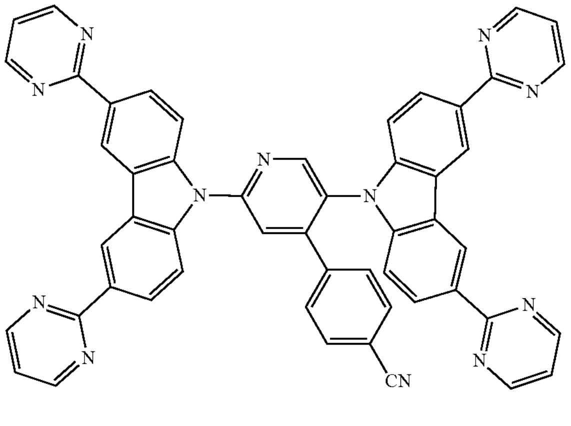
-continued
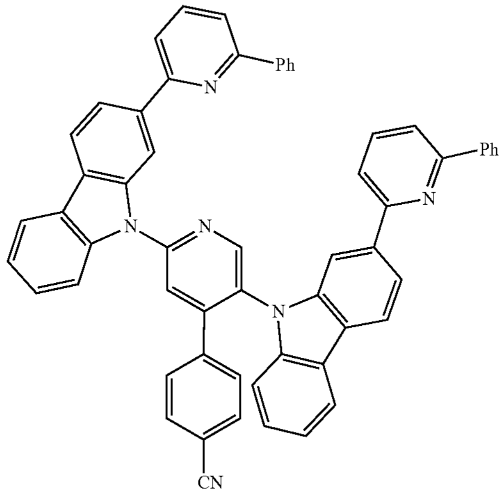
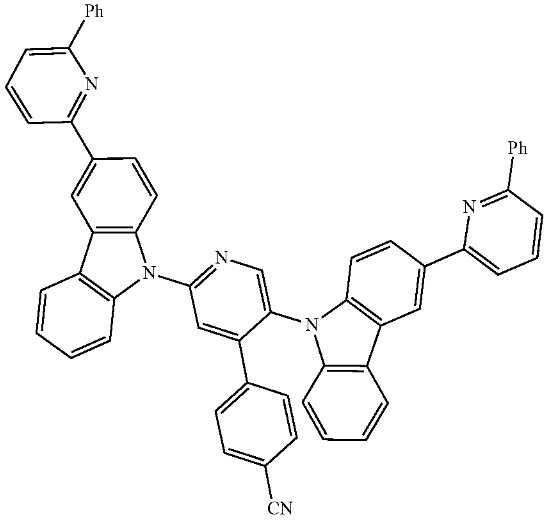
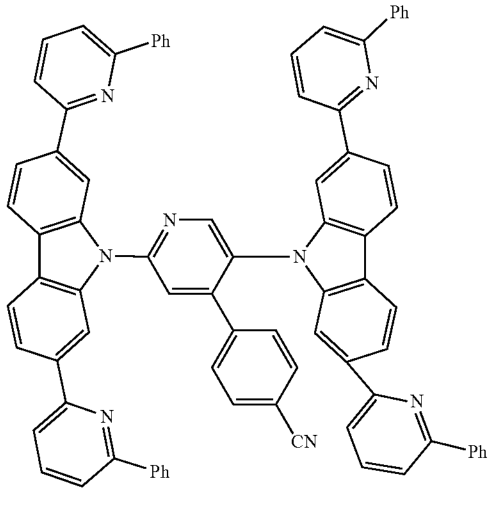

-continued
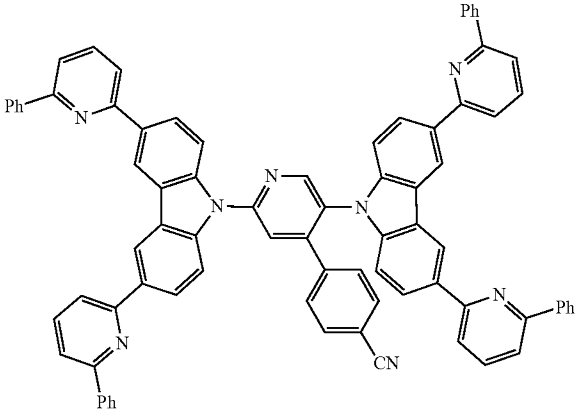
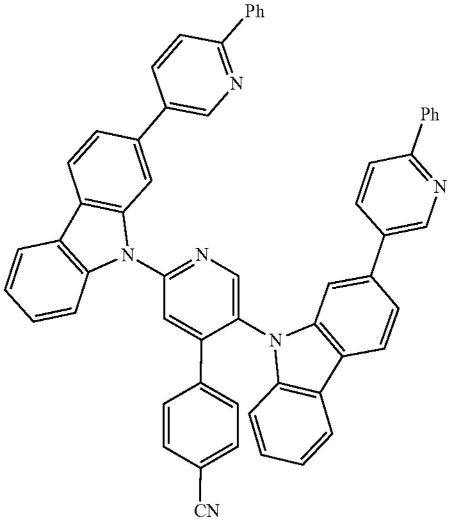
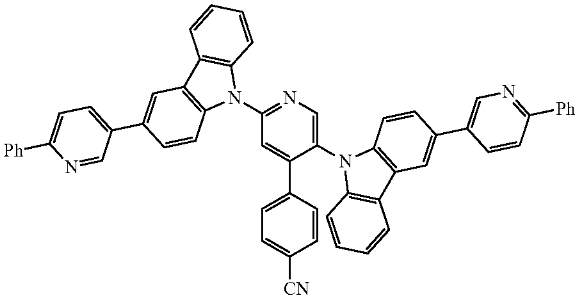
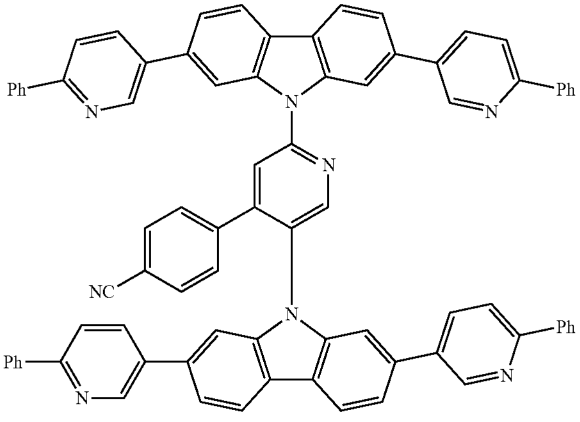
-continued
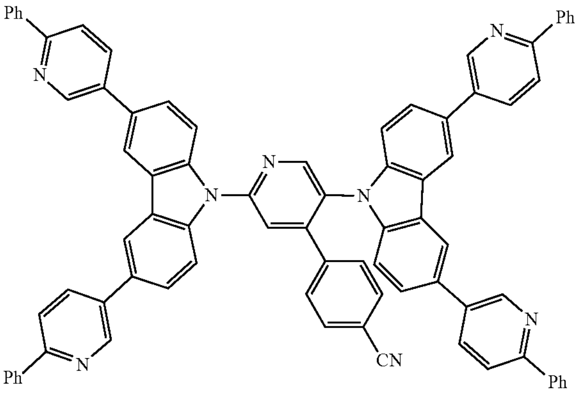
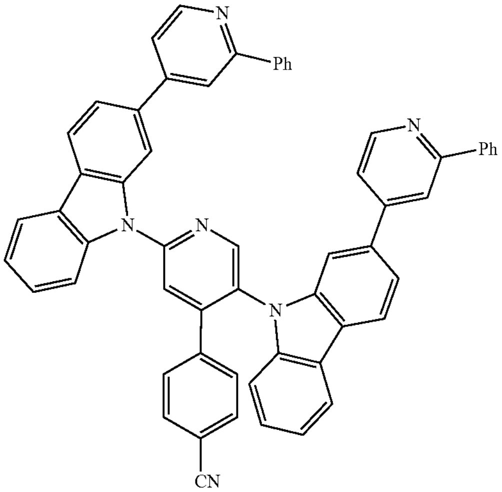
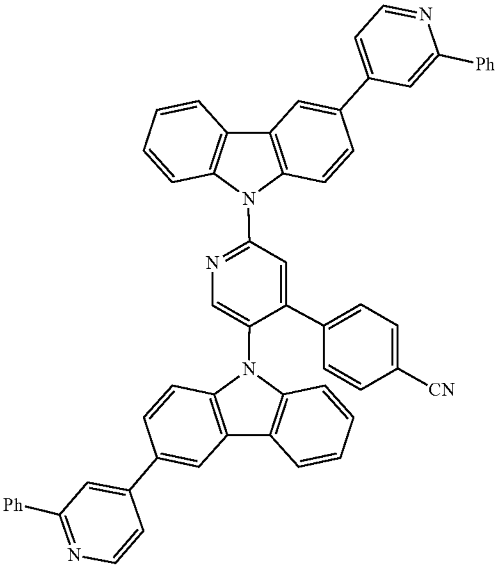

-continued
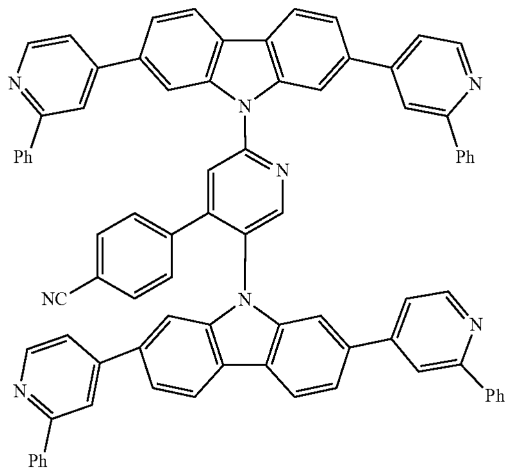
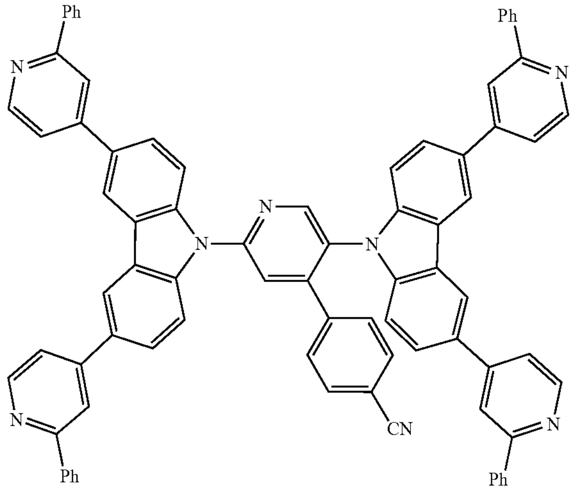
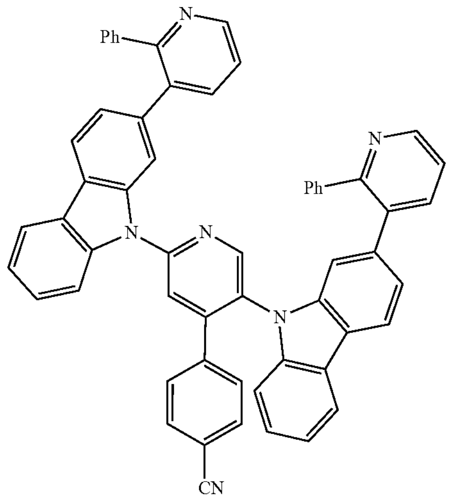
-continued
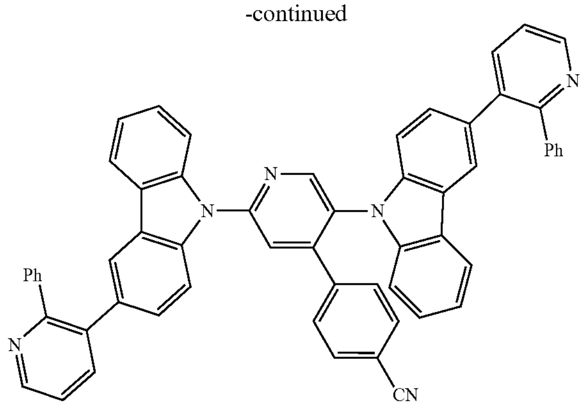
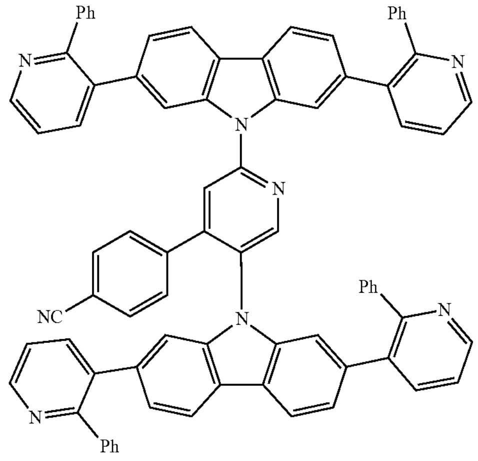
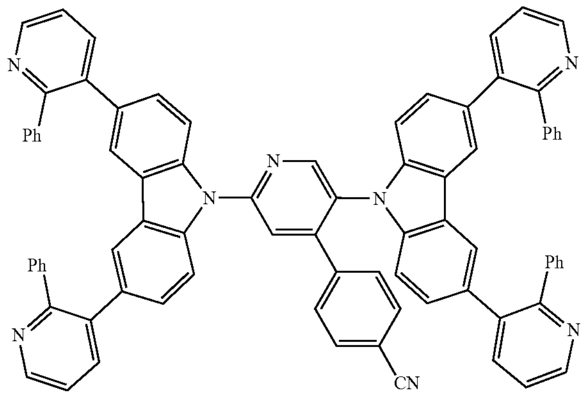
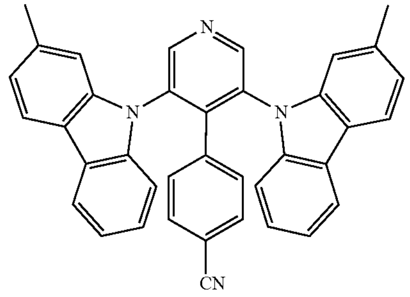

-continued
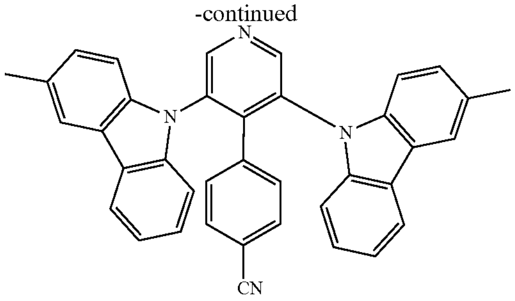
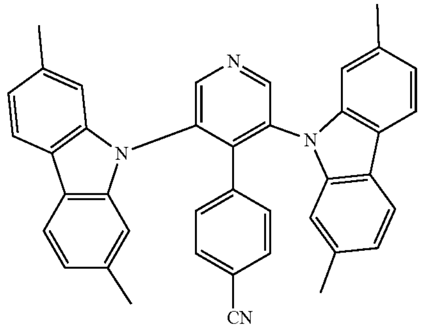
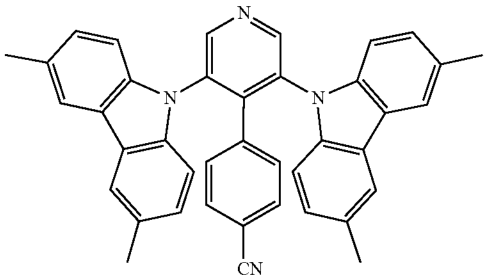
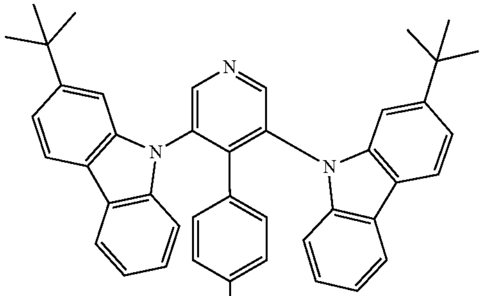
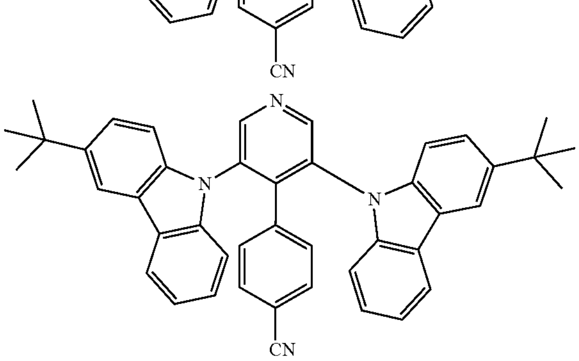
-continued
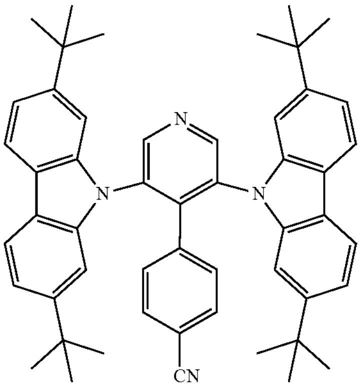
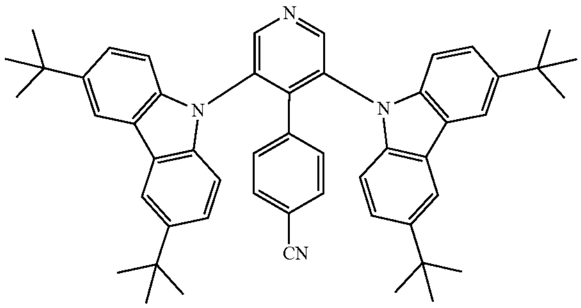
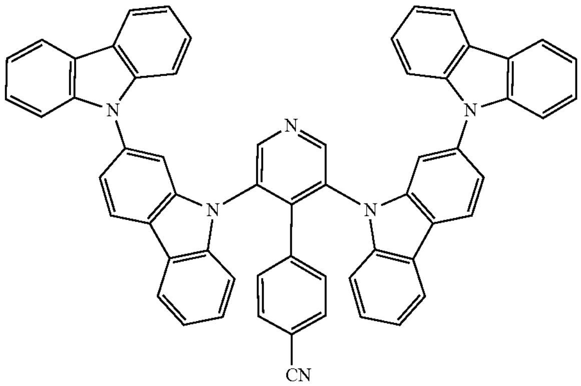
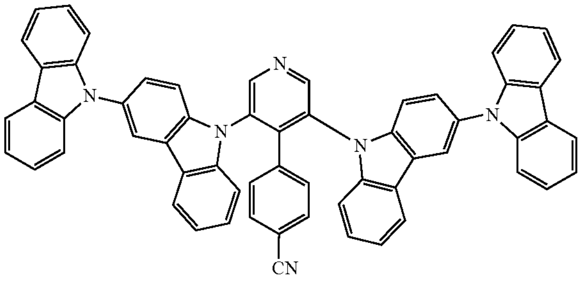

-continued
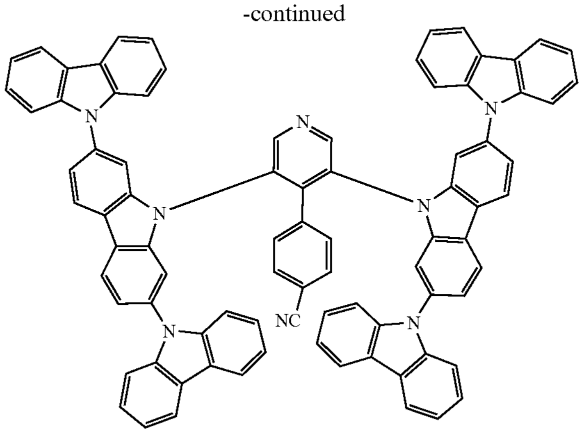
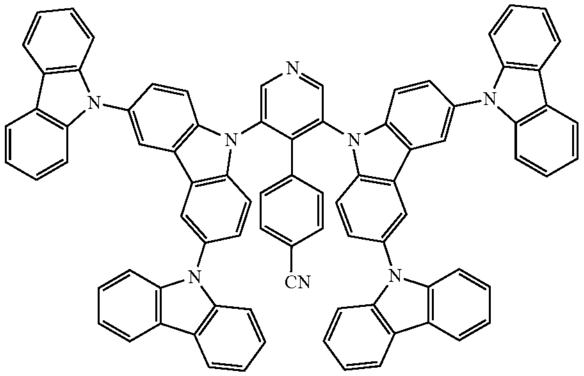
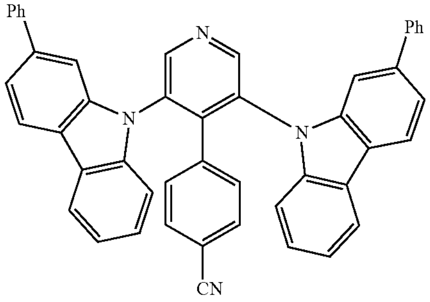
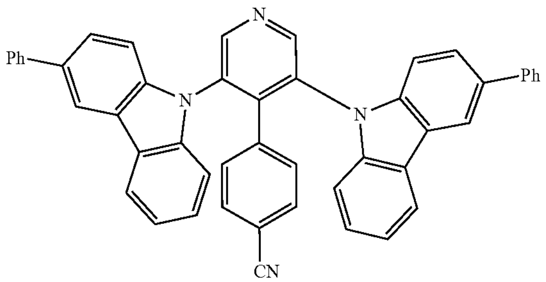
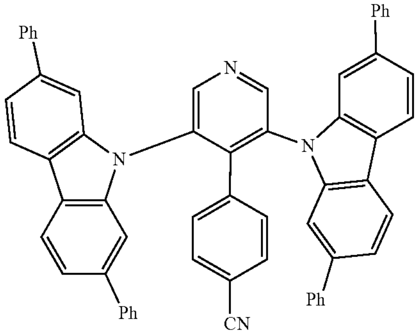
-continued
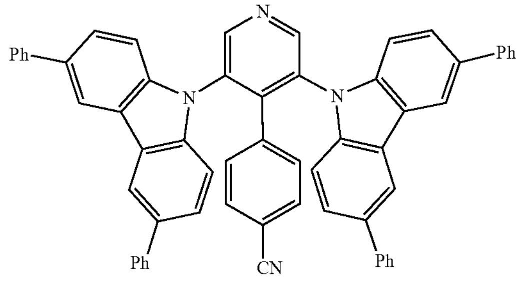
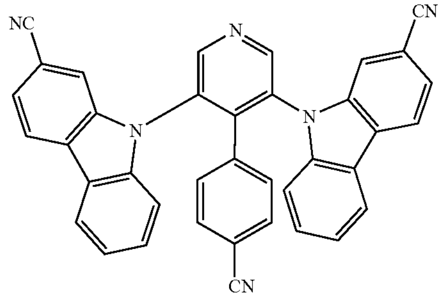
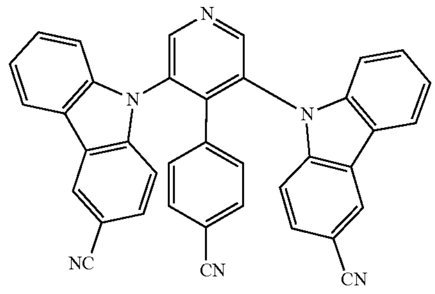
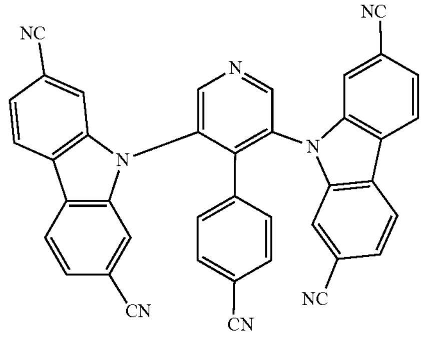
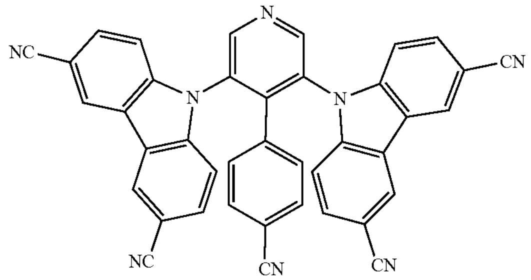

-continued
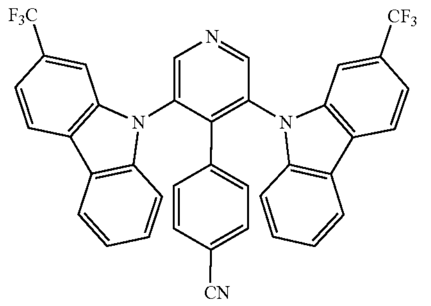
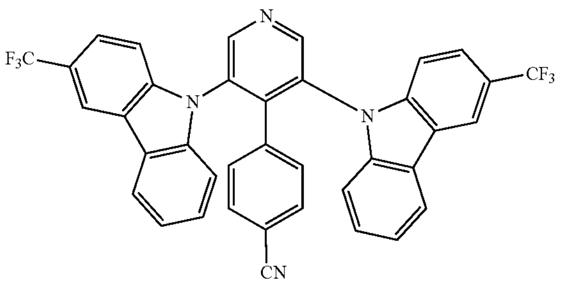
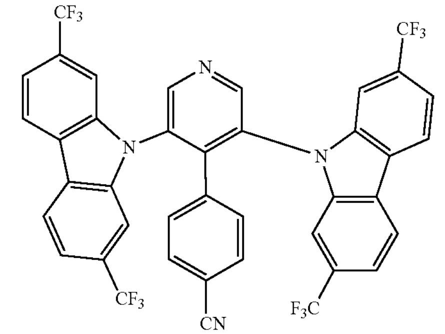
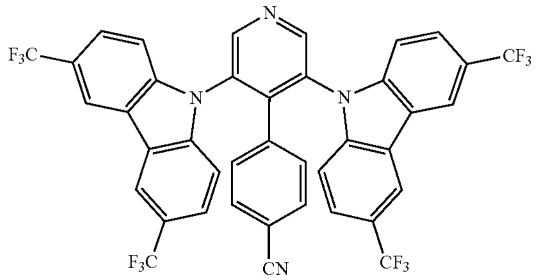
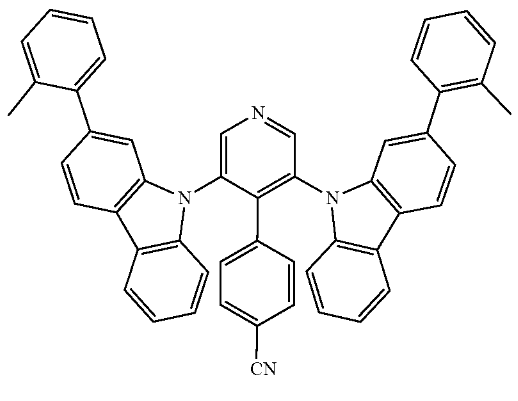
-continued
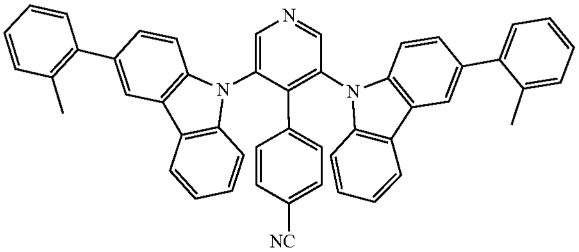
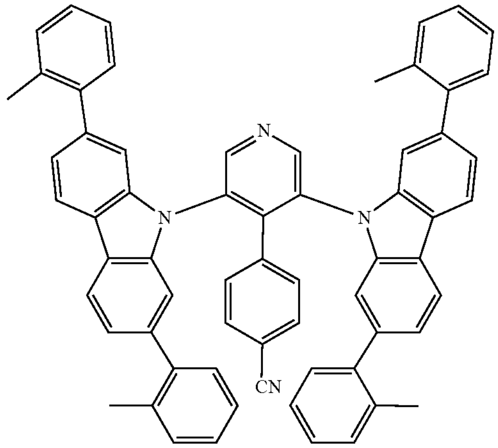
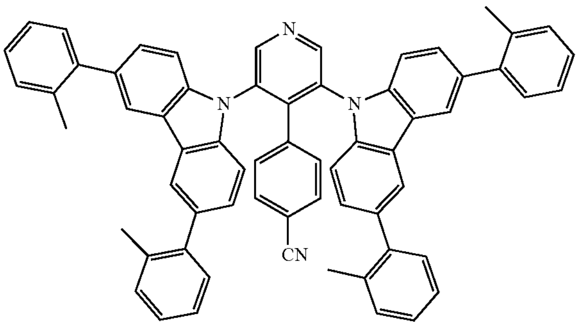
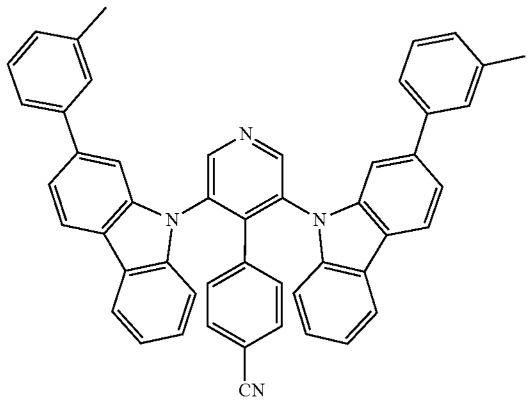

-continued
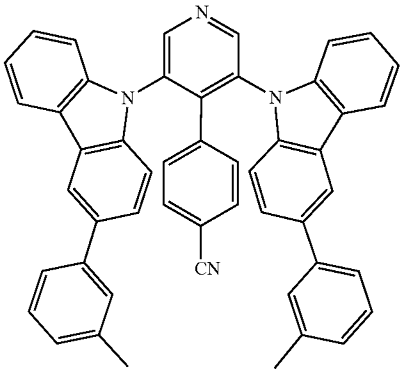
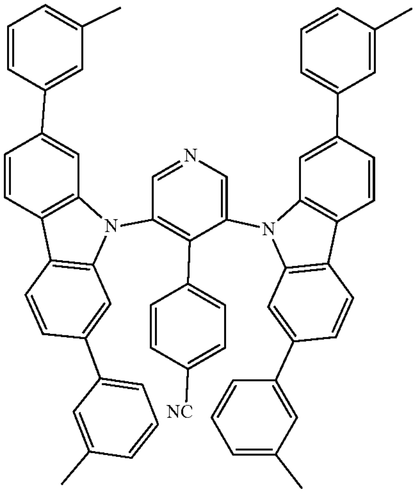
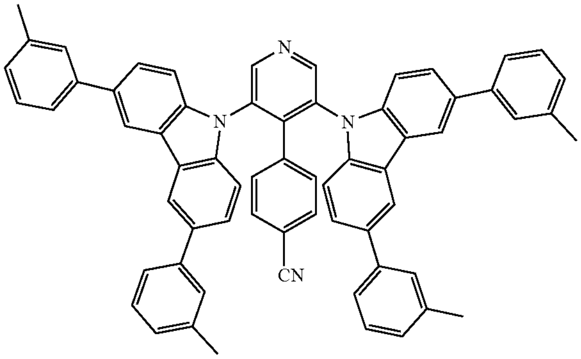
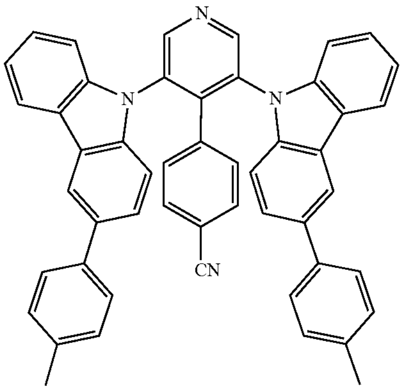
-continued
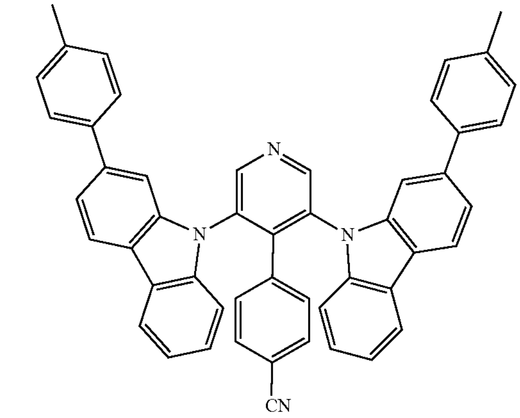
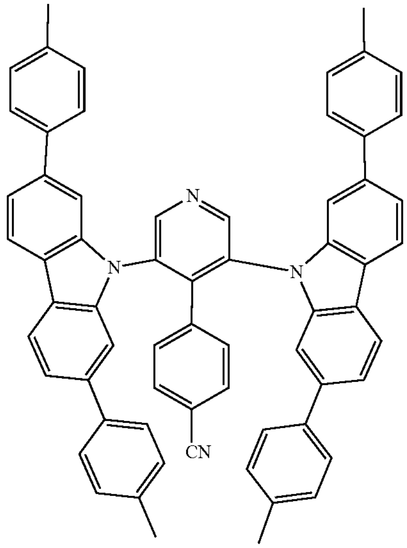
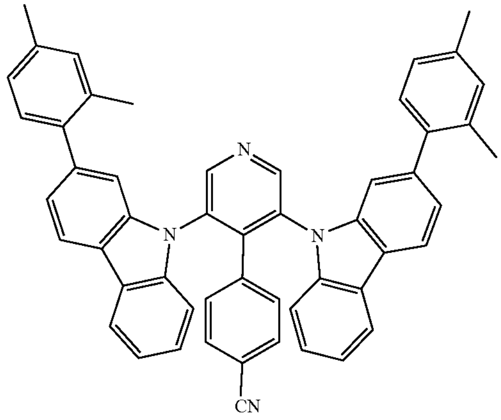
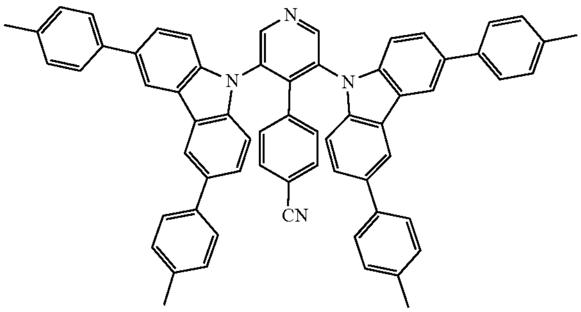

-continued
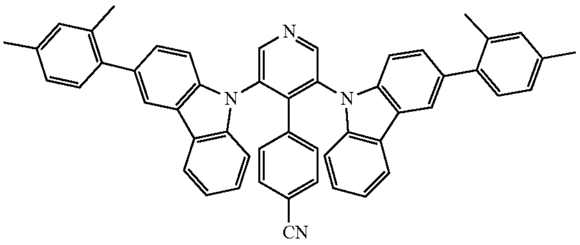
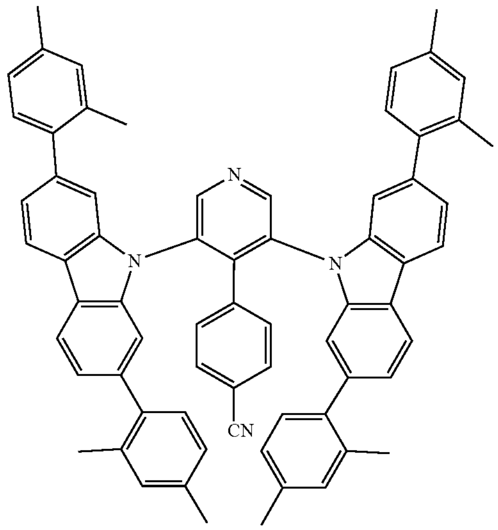
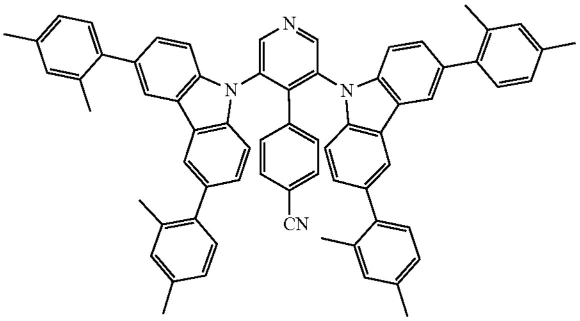
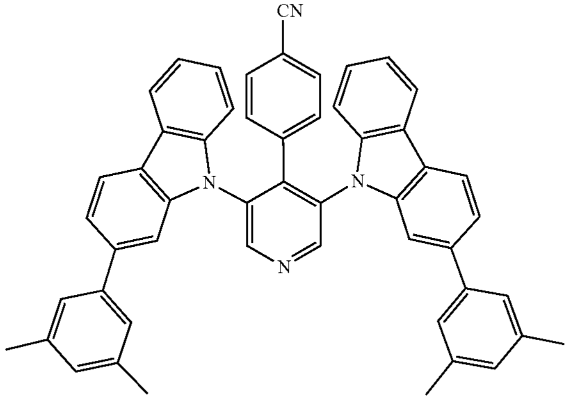
-continued
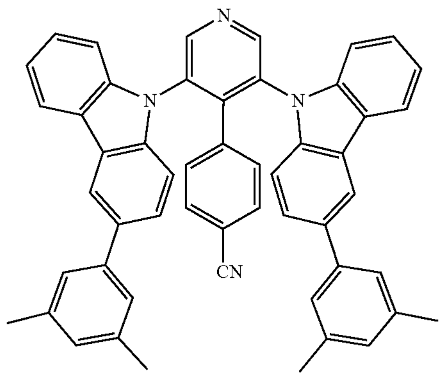
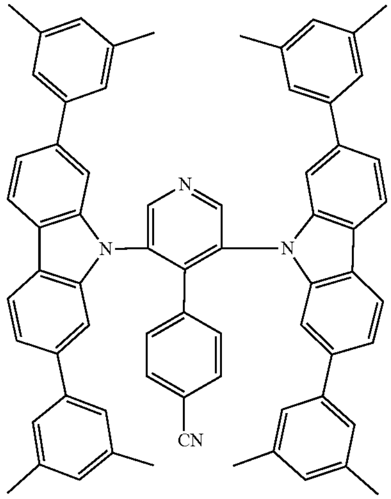
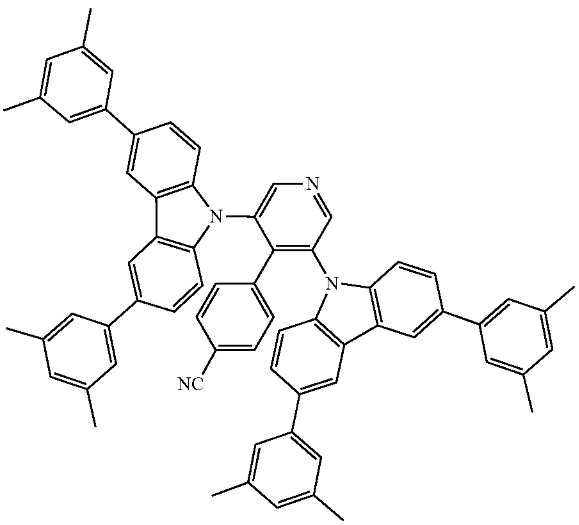

-continued
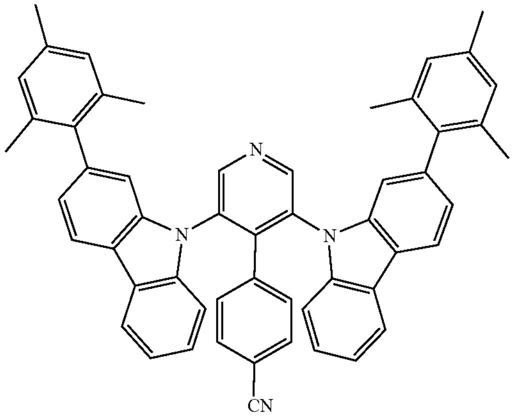
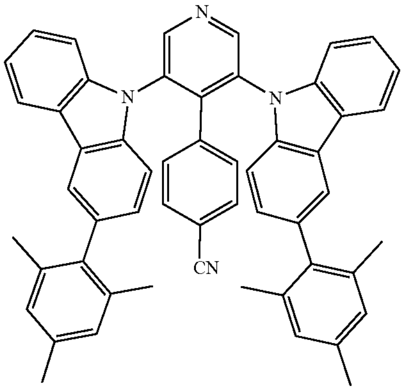
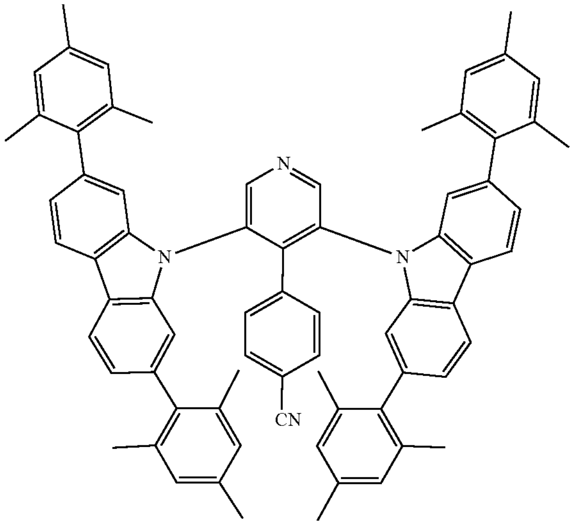
-continued
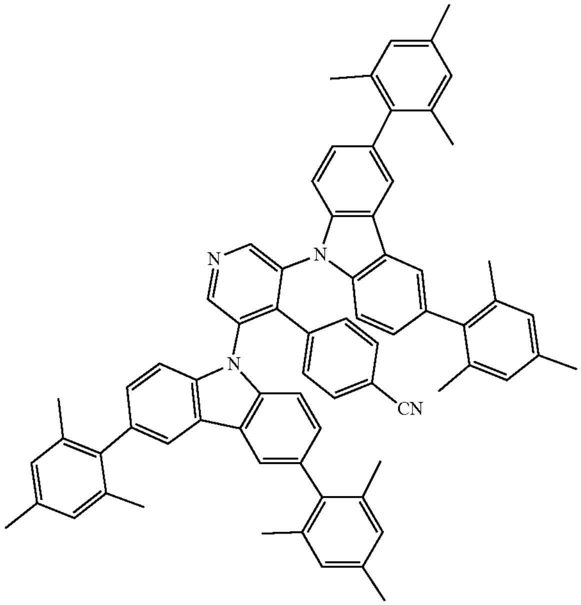
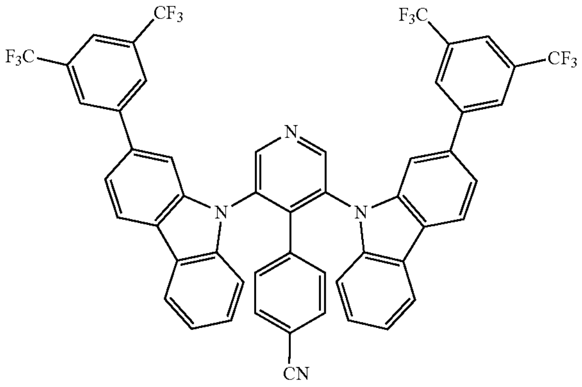
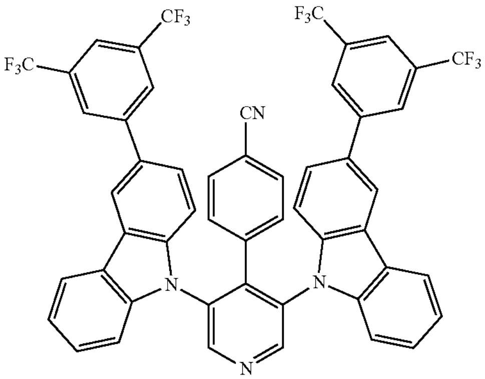

-continued
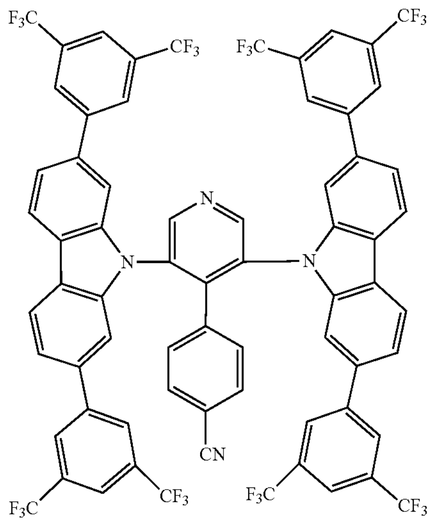
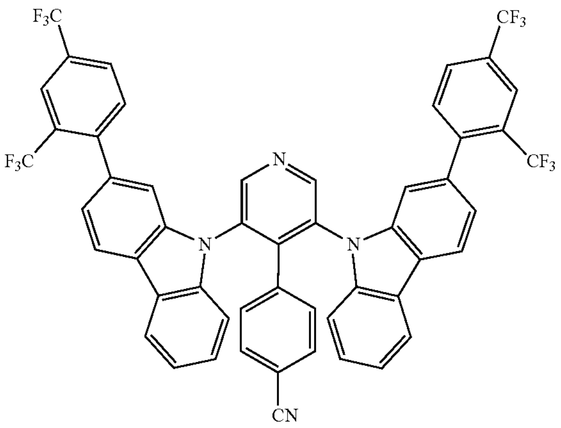
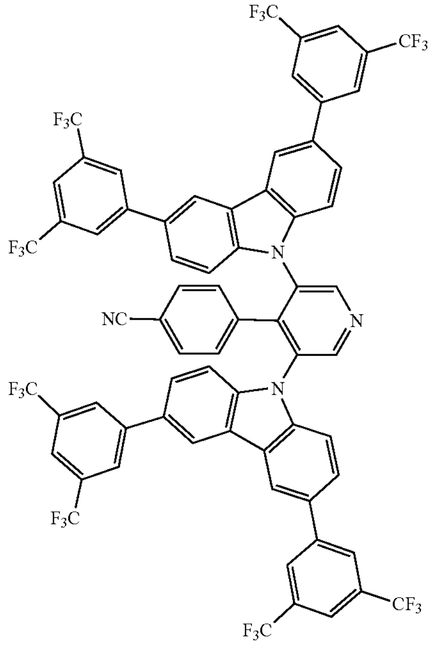
-continued
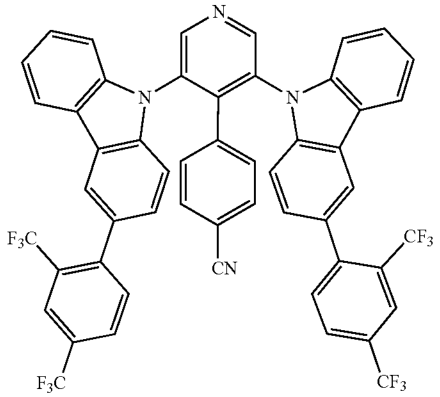
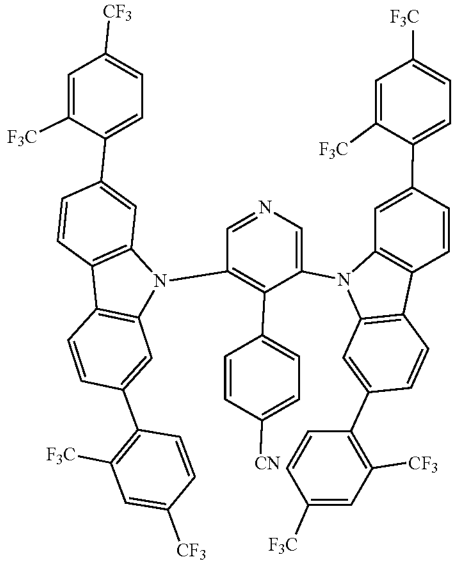
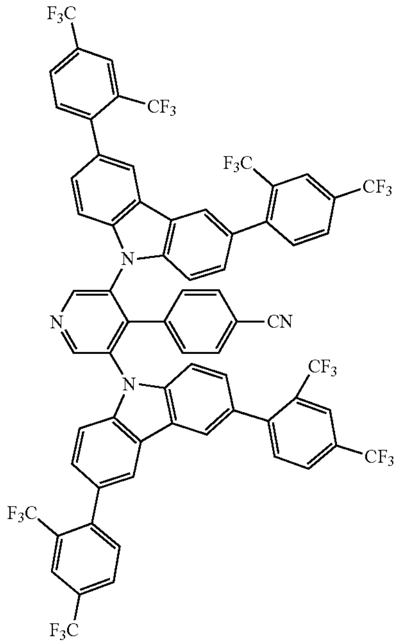

-continued
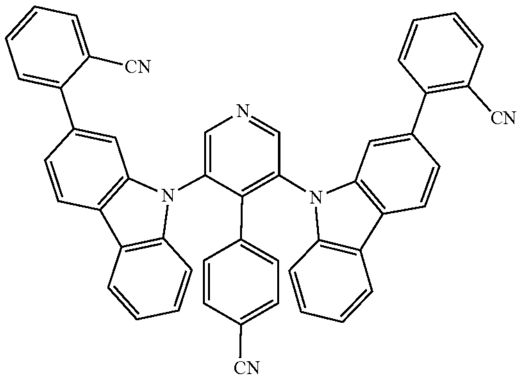
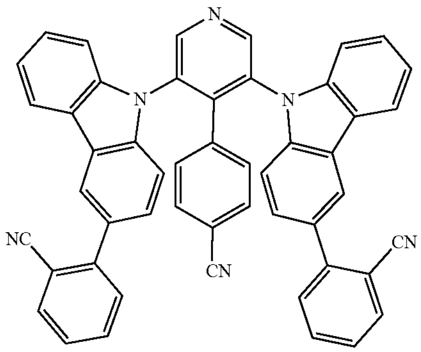
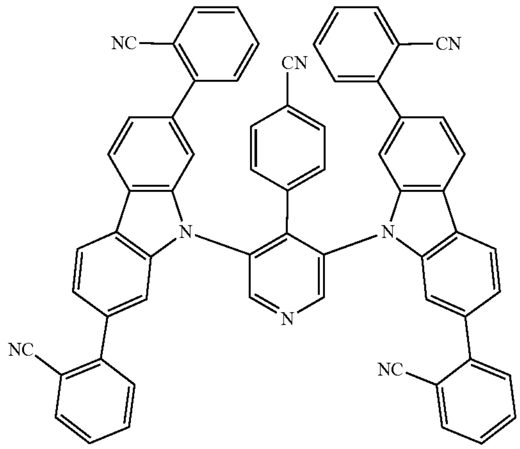
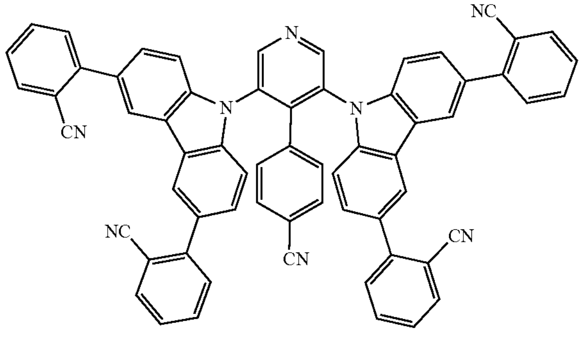
-continued
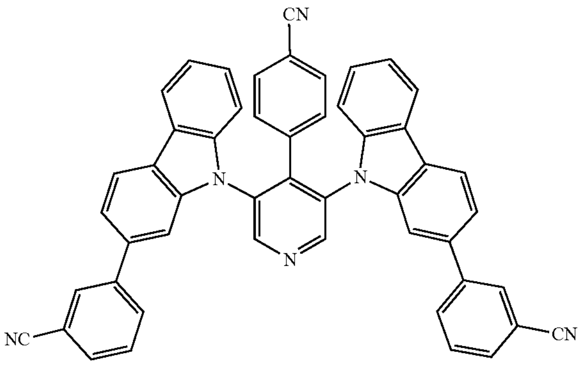
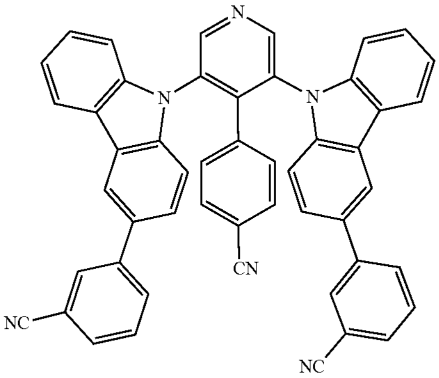
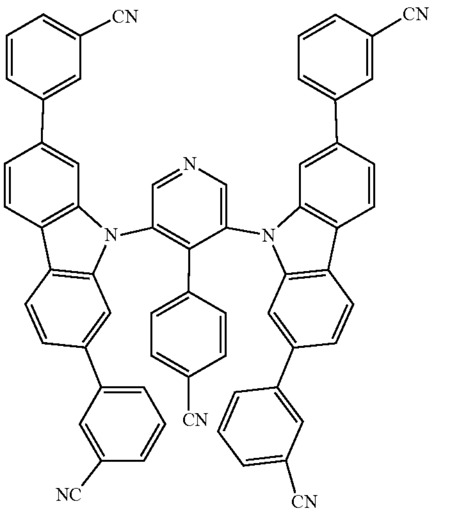
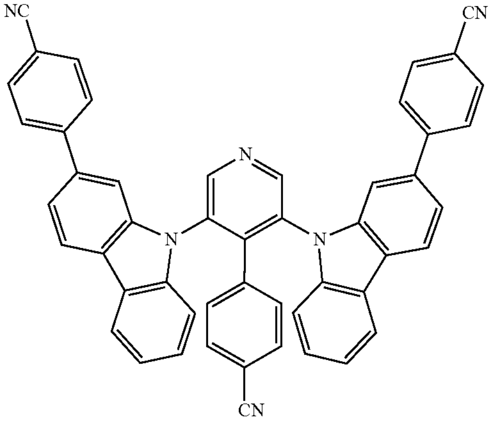

-continued
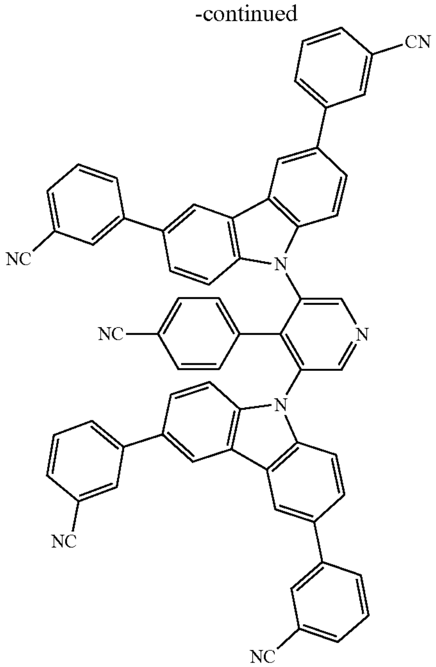
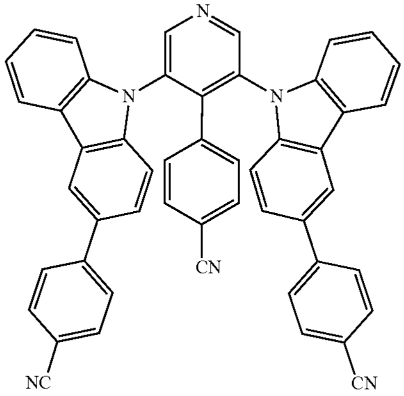
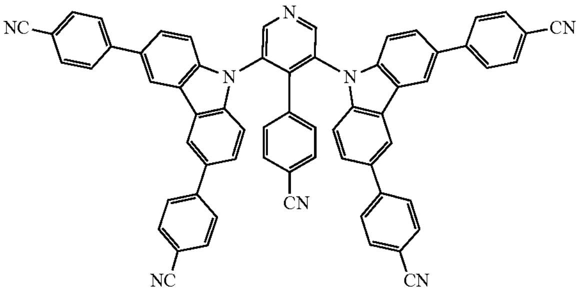
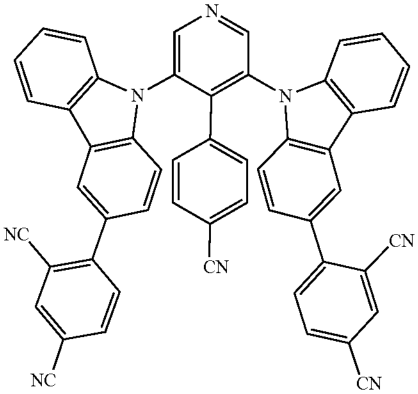
-continued
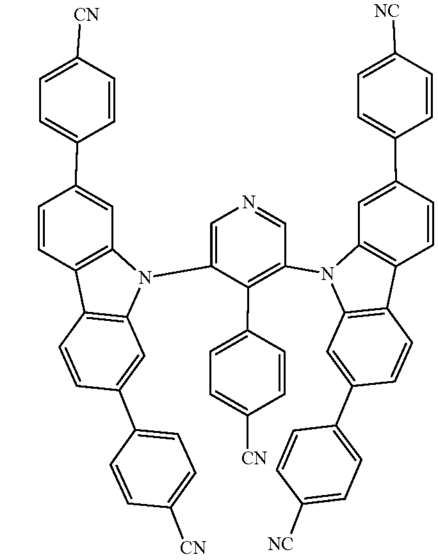
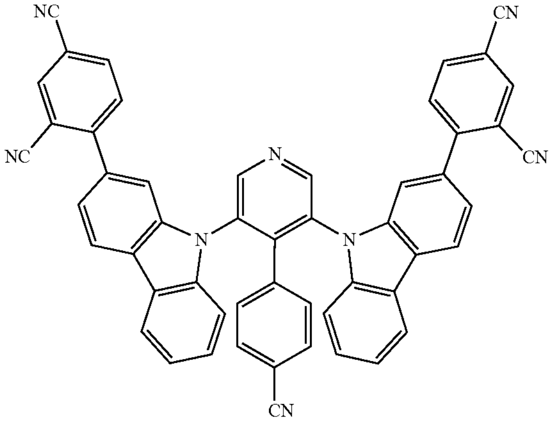
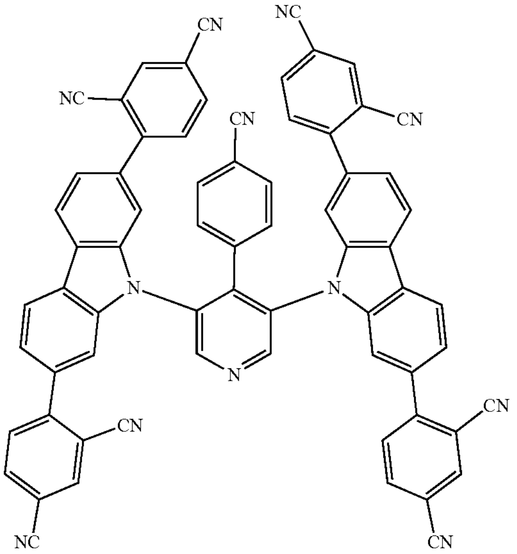

-continued
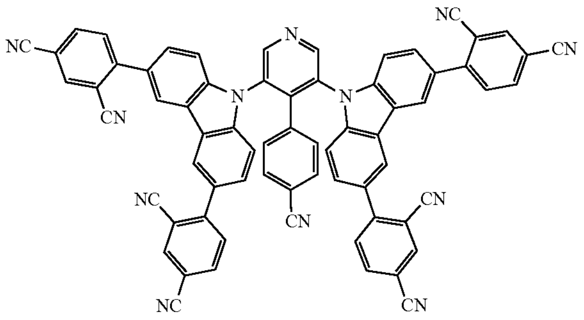
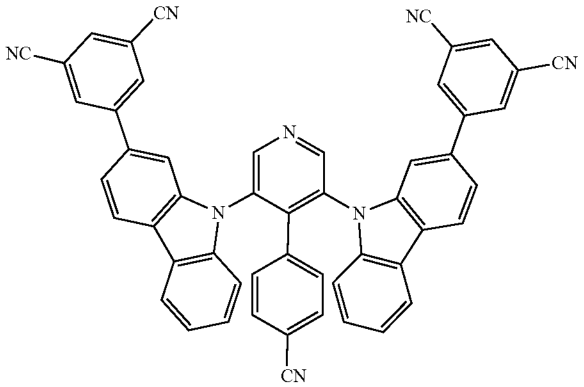
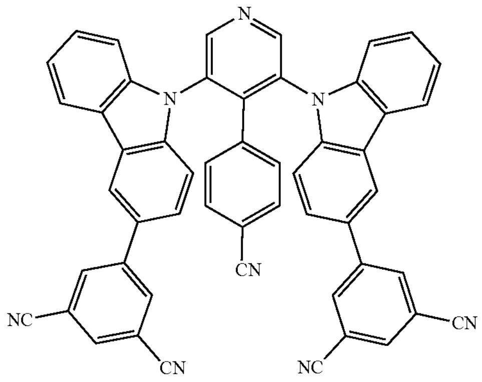
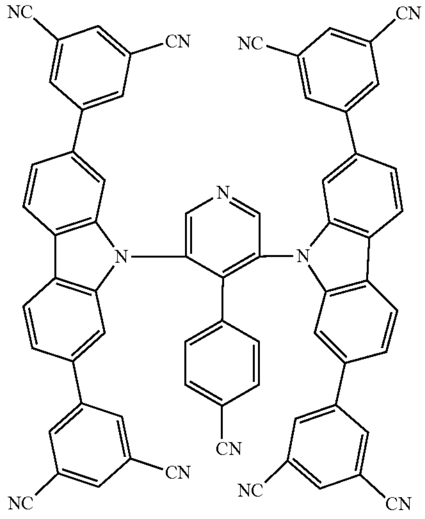
-continued
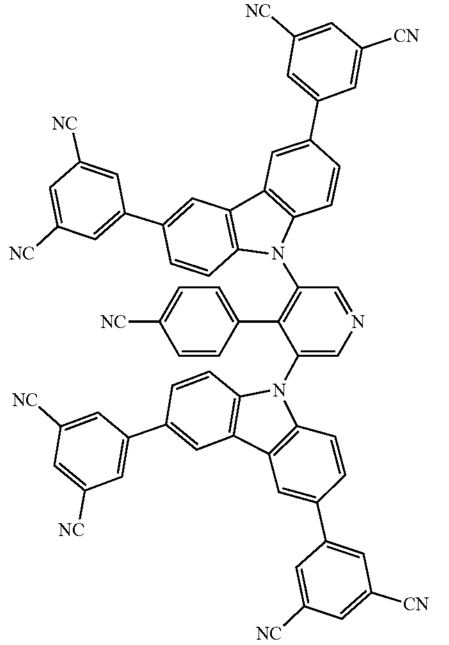
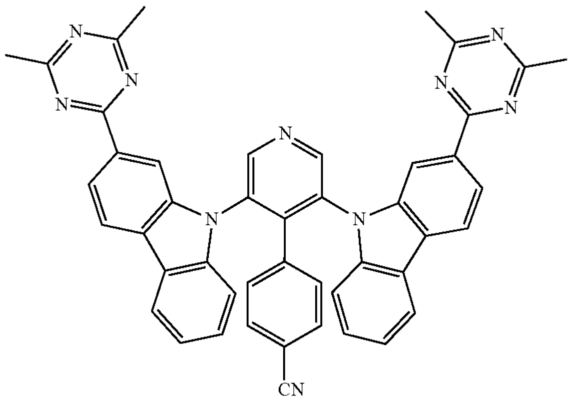
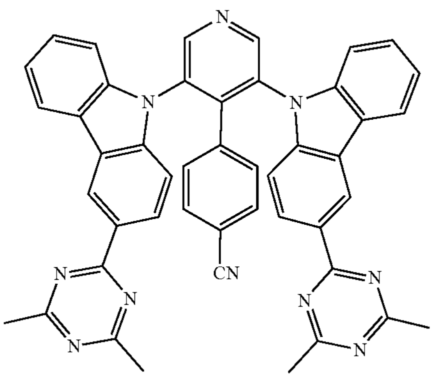

-continued
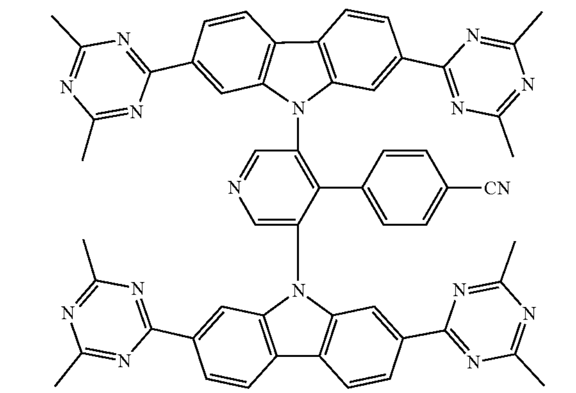
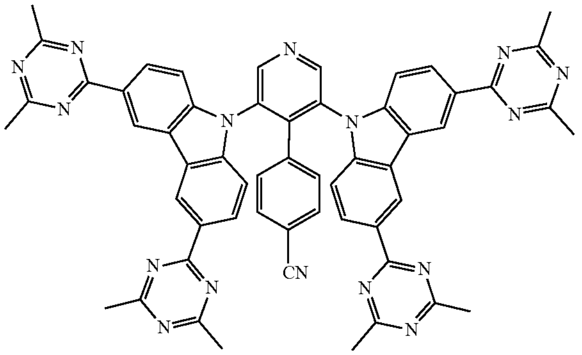
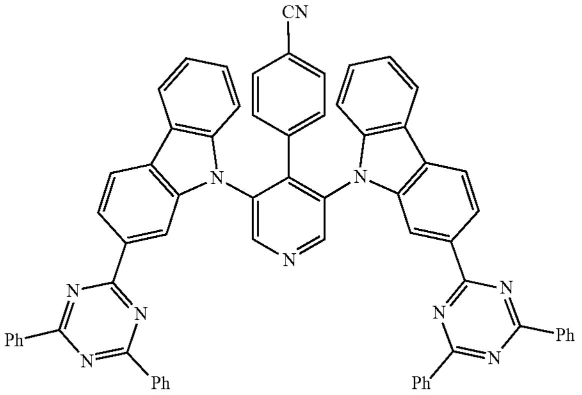
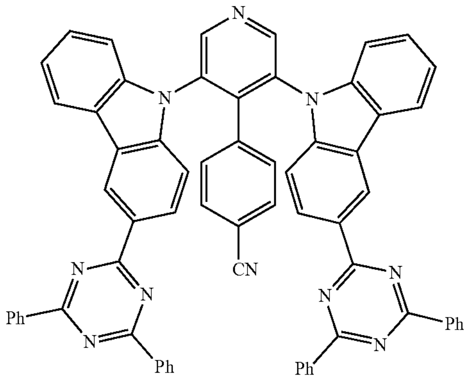
-continued
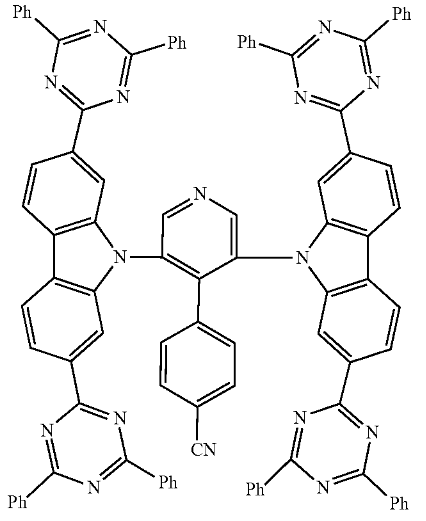
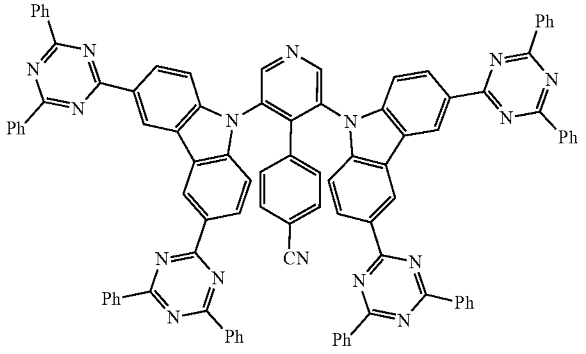
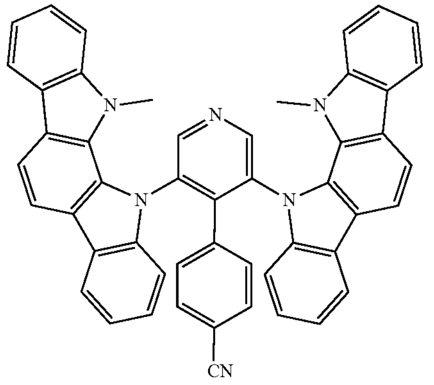
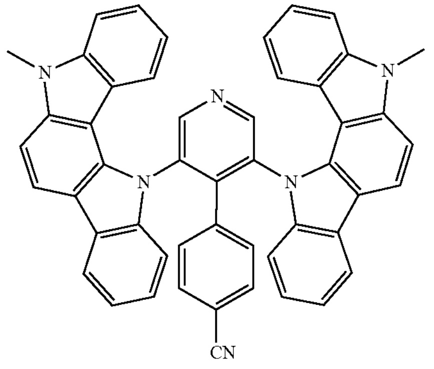

-continued
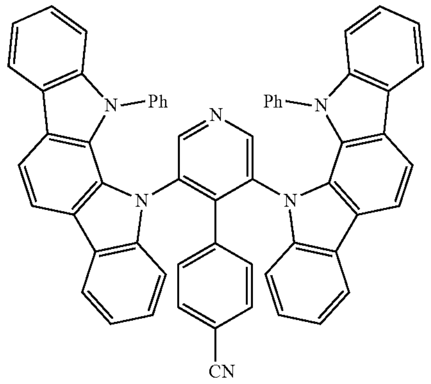
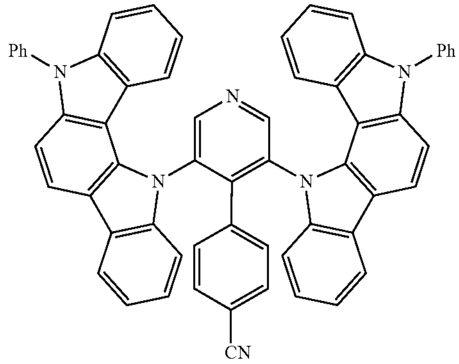
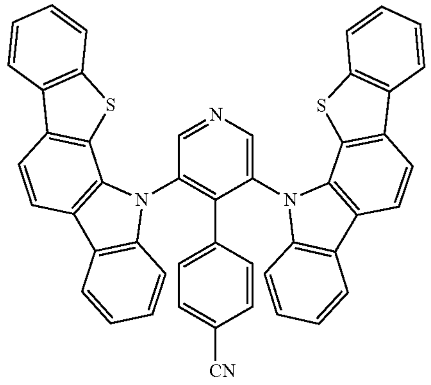
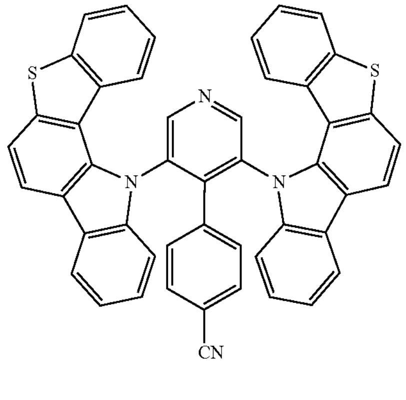
-continued
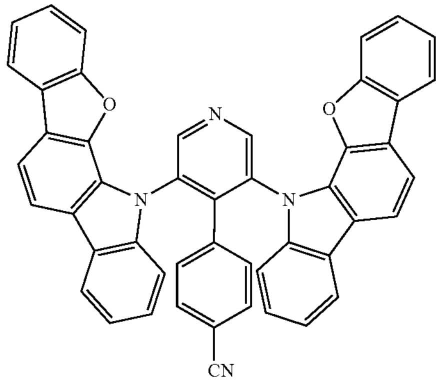
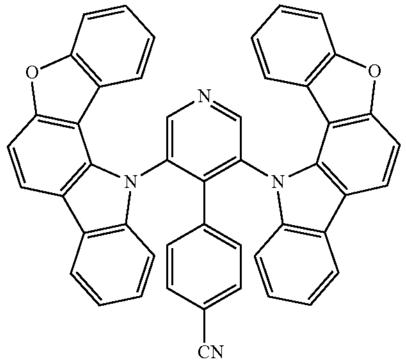
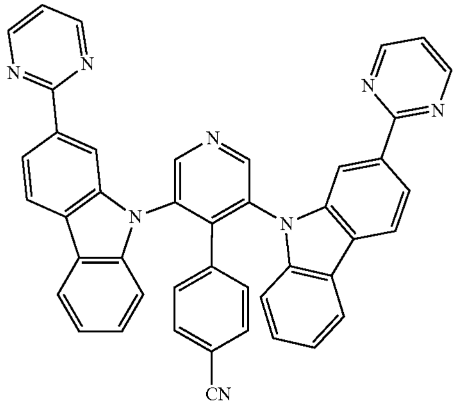
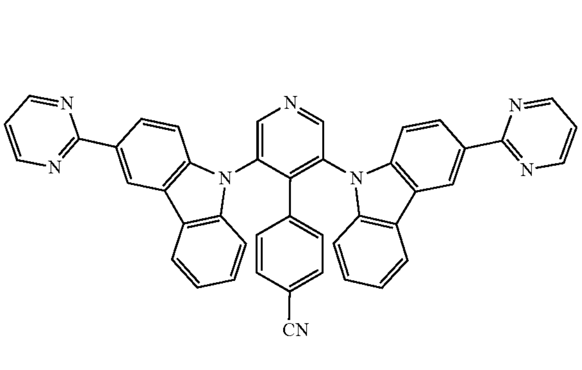

-continued
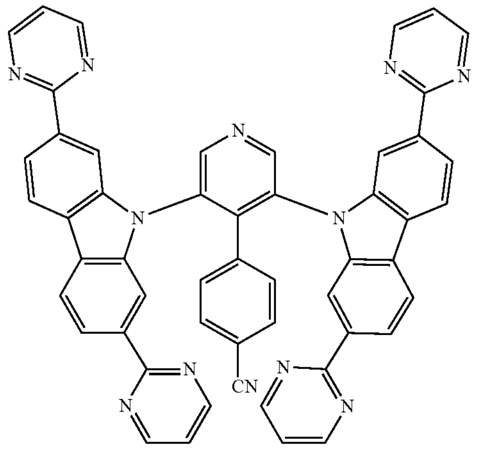
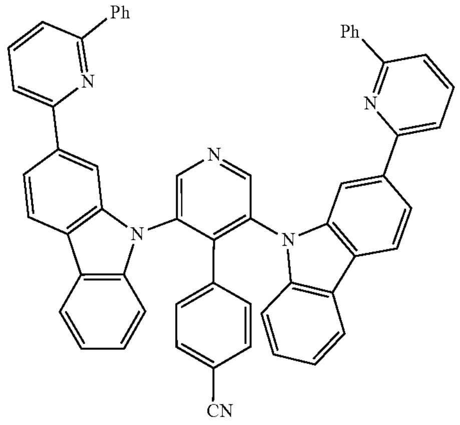
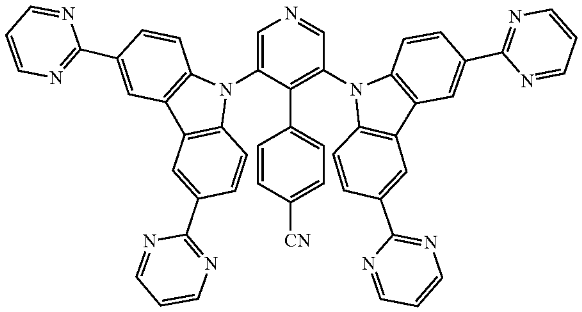
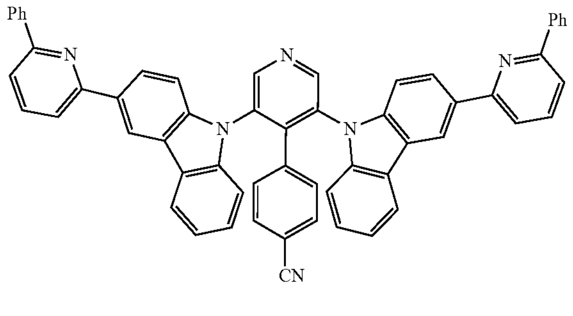
-continued
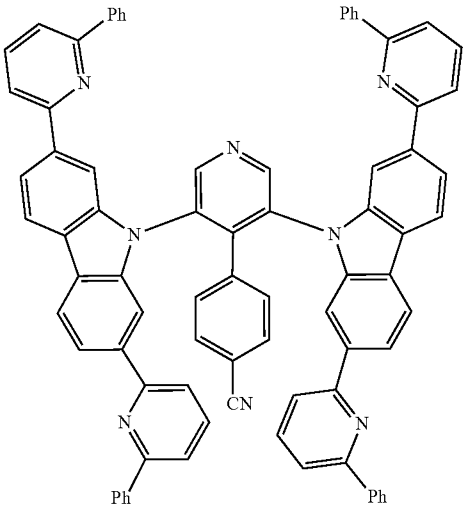
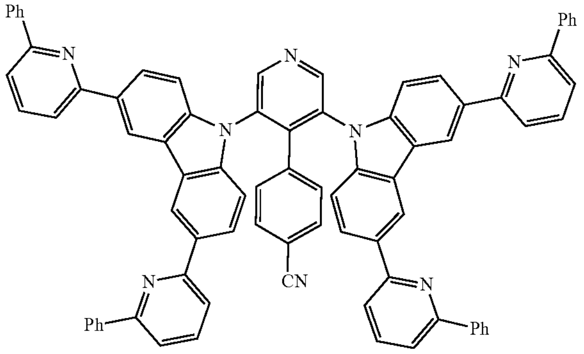
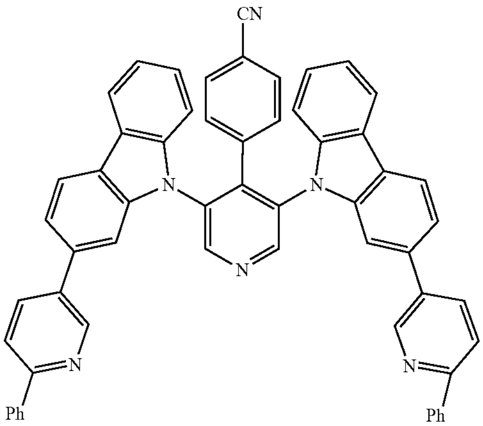
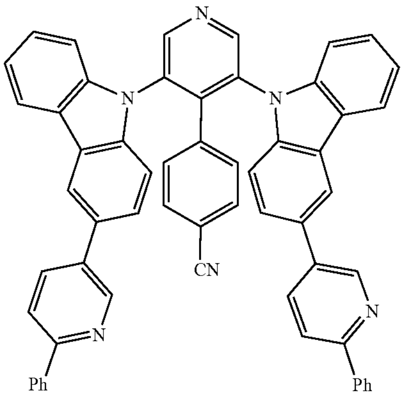

-continued
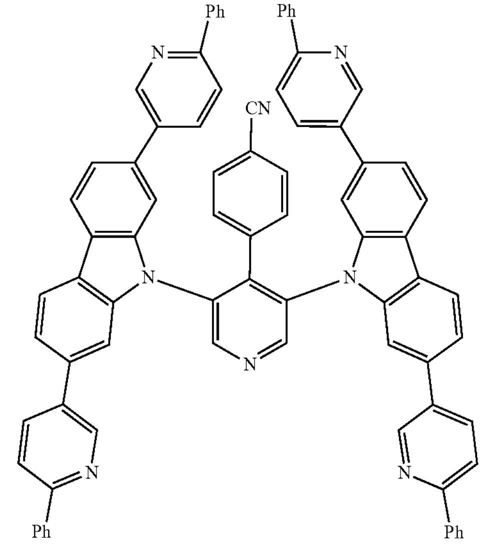
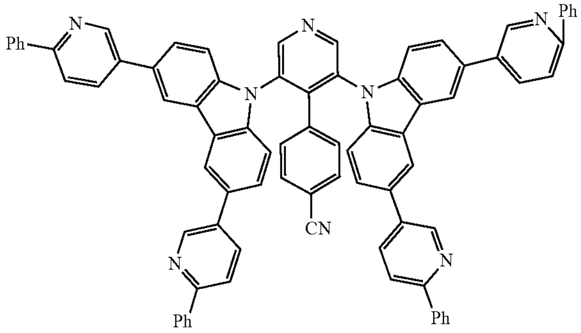
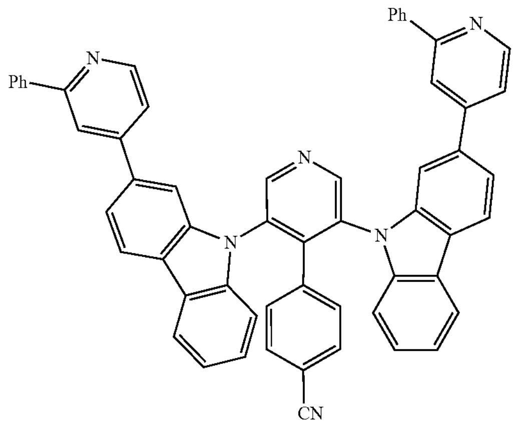
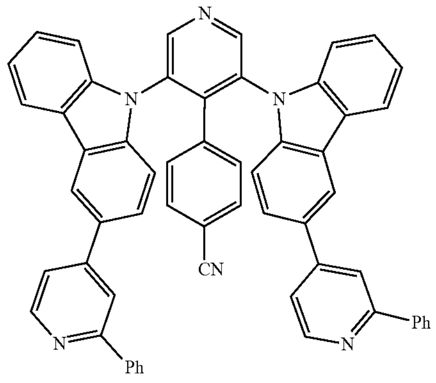
-continued
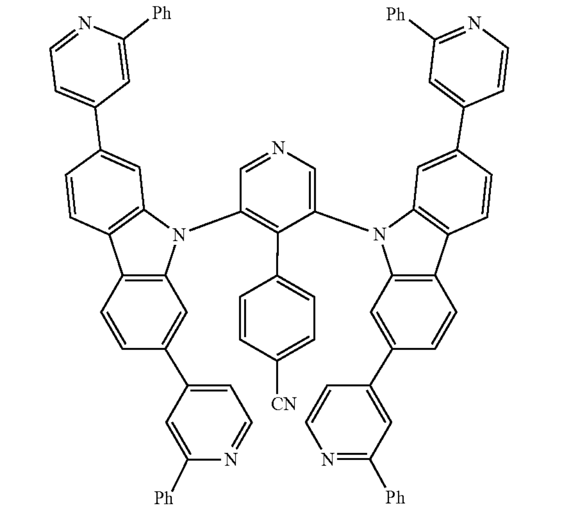
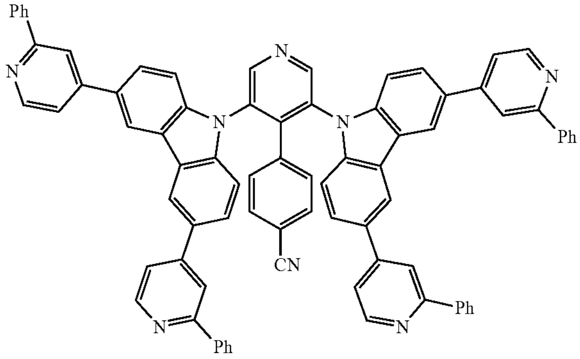
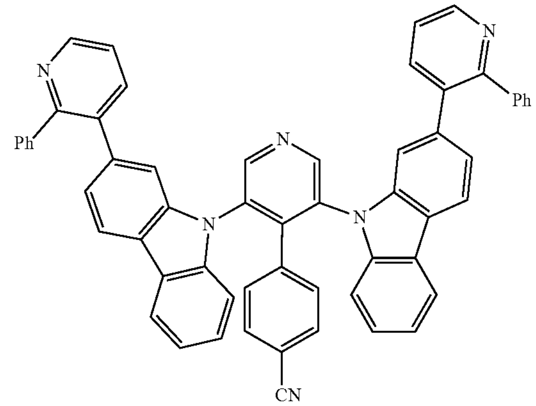
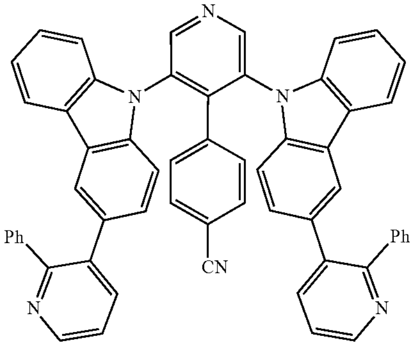

-continued
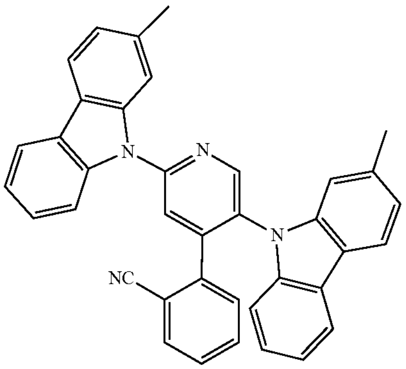
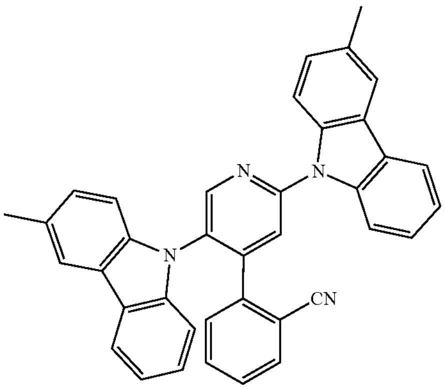
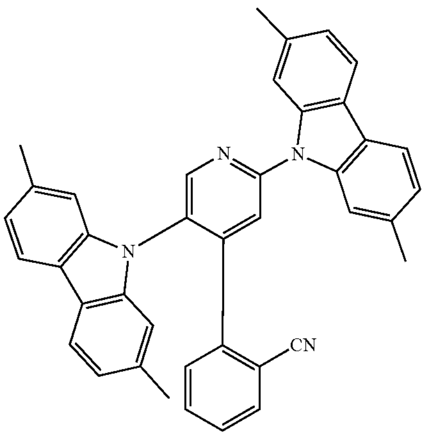
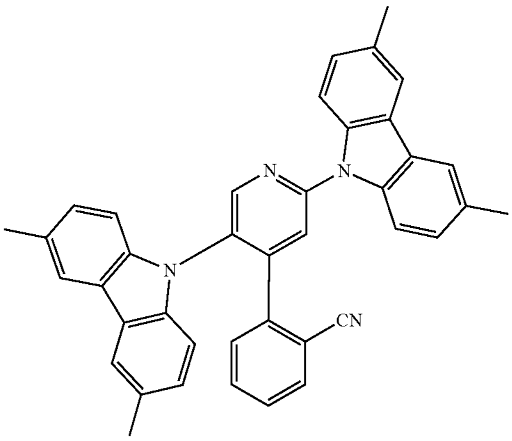
-continued
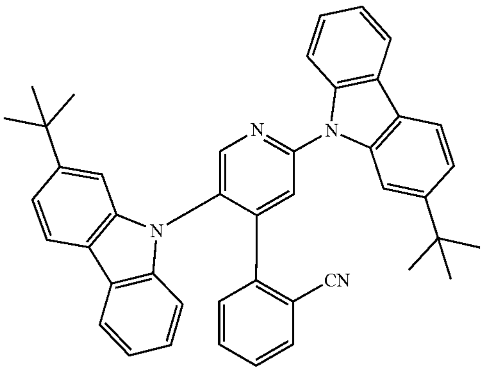
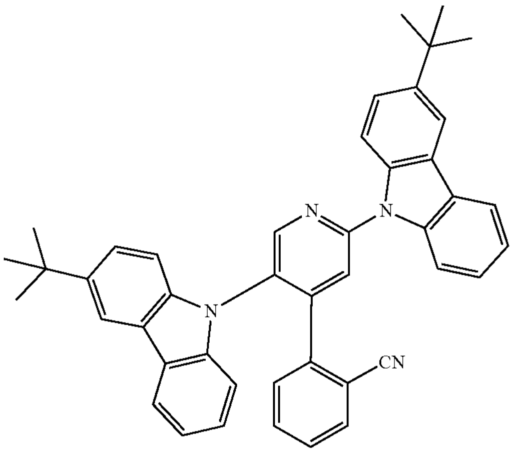
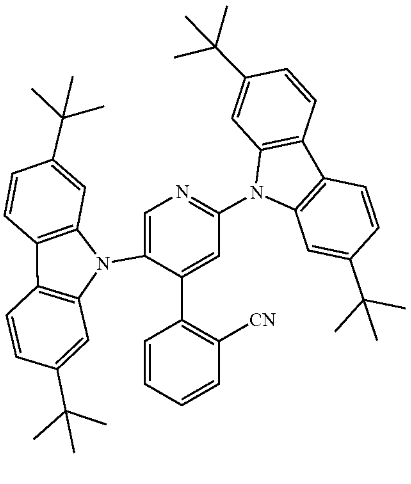

-continued
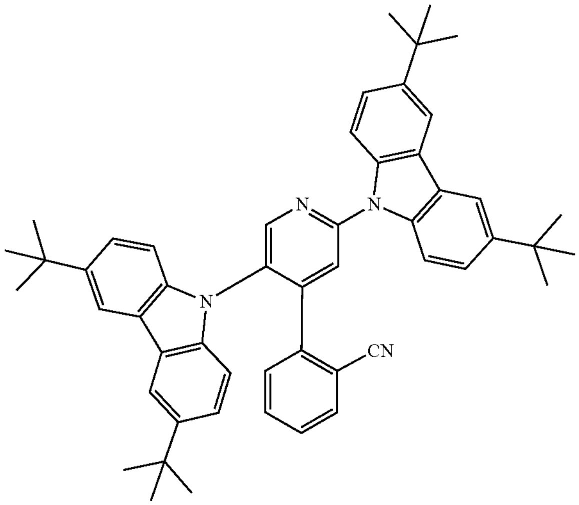
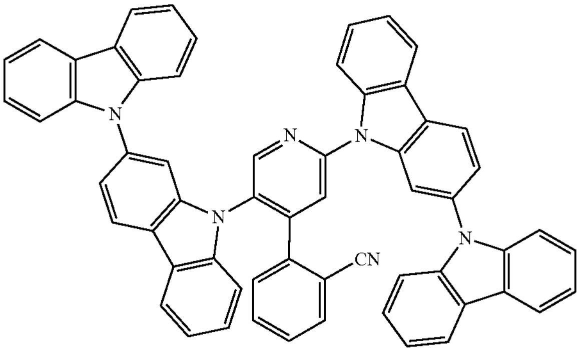
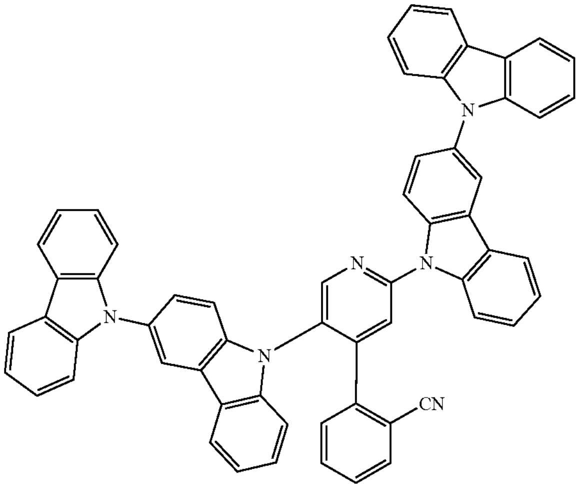
-continued
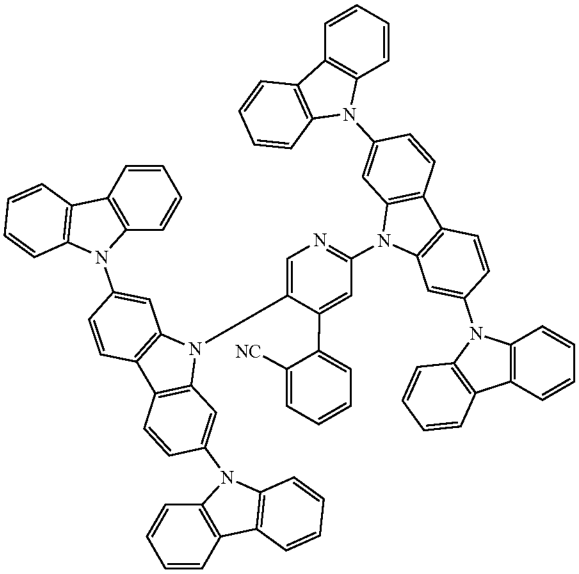
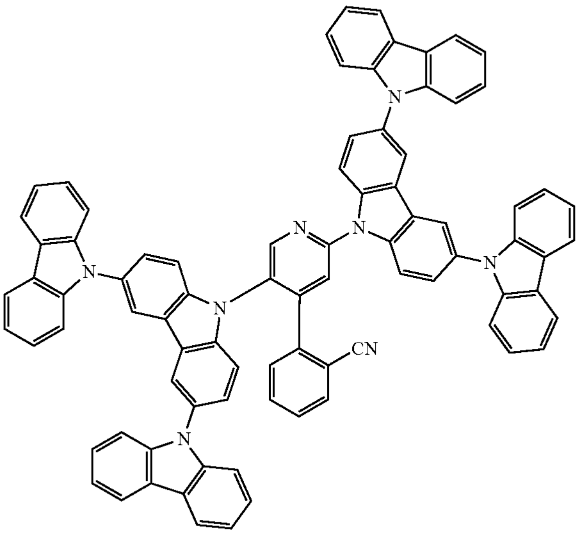
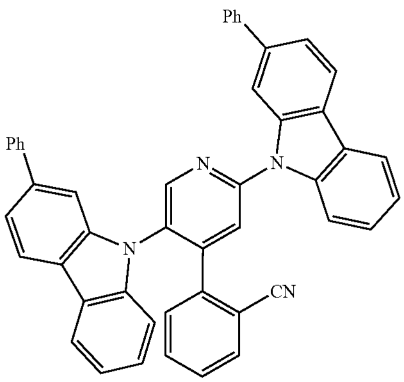

-continued
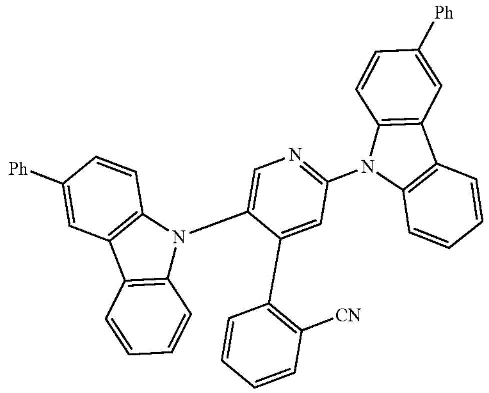
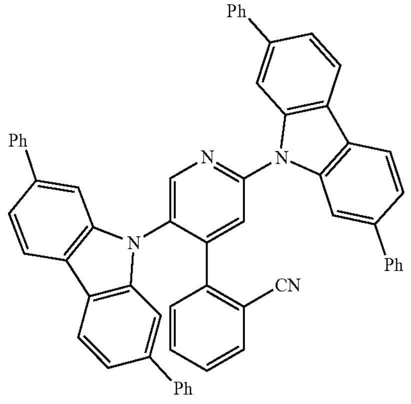
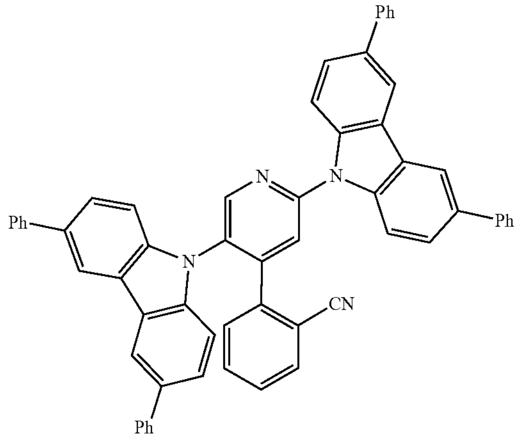
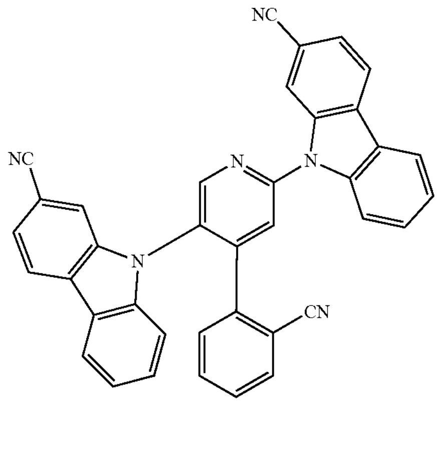
-continued
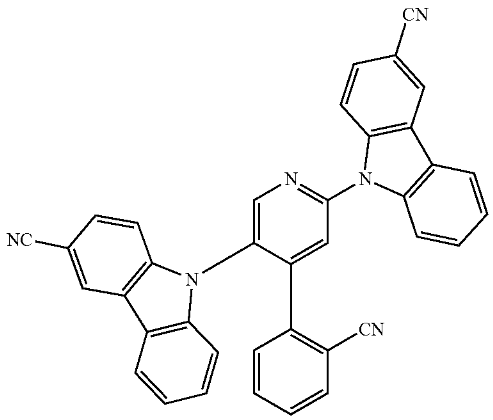
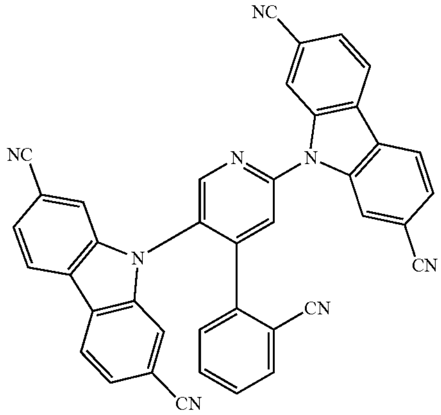
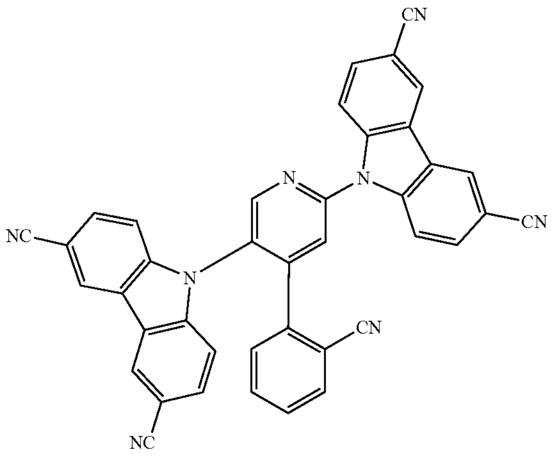
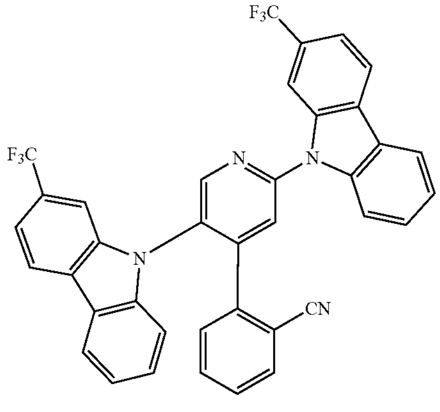

-continued
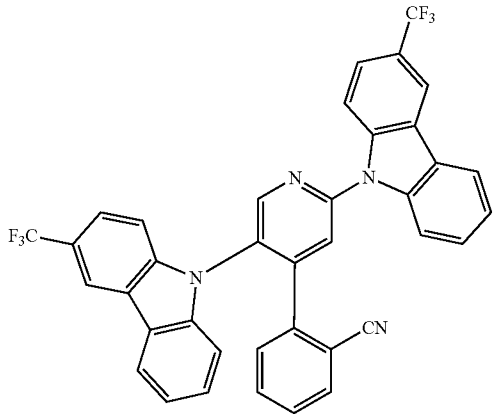
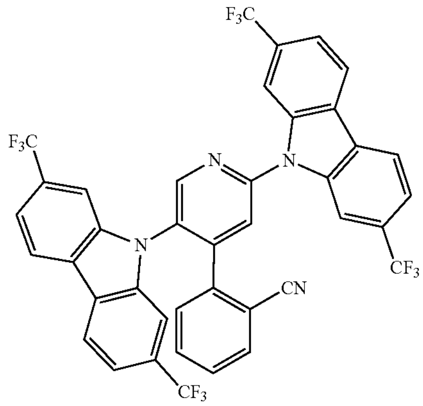
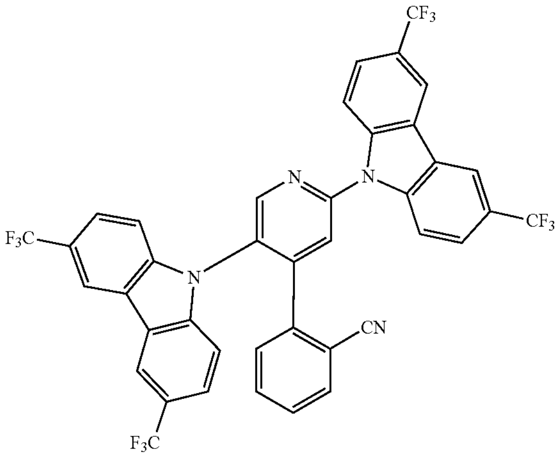
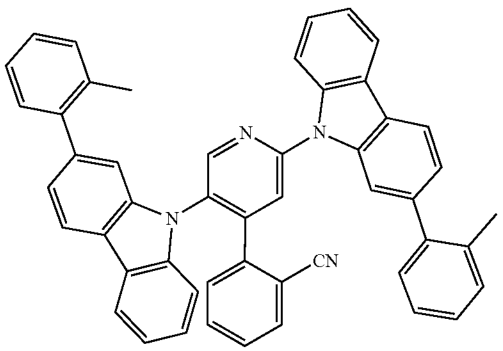
-continued
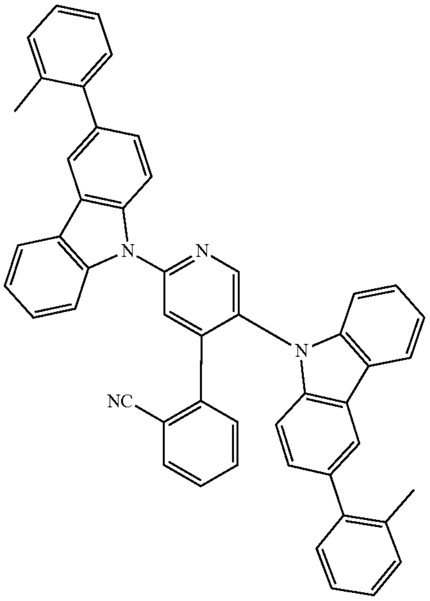
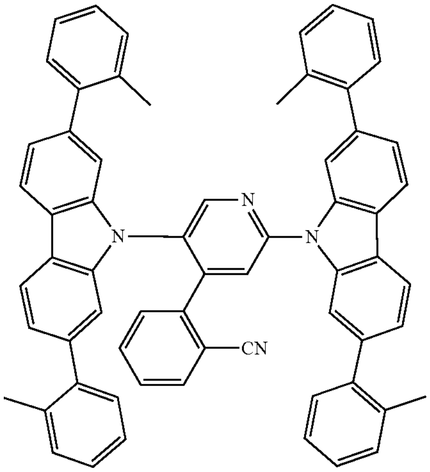
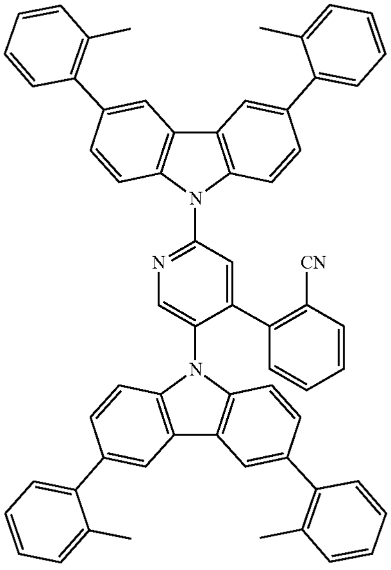

-continued
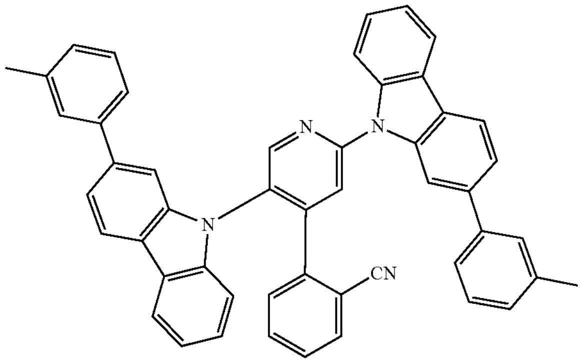
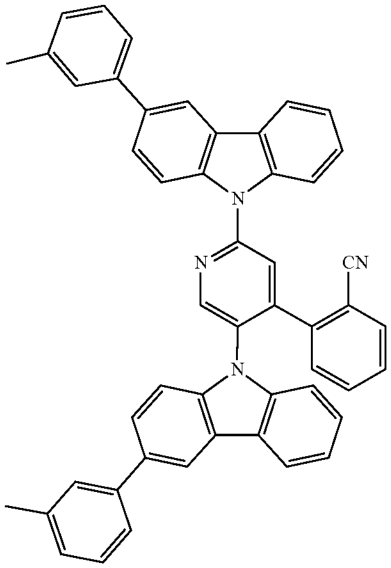
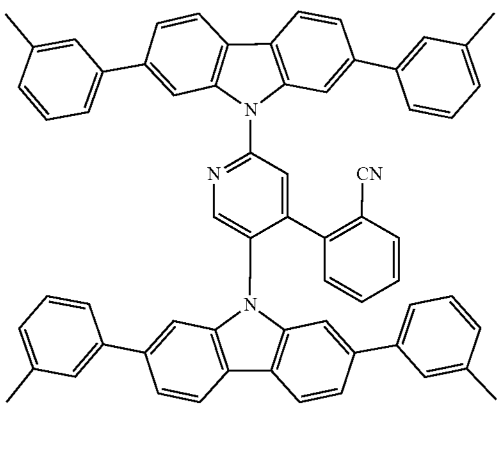
-continued
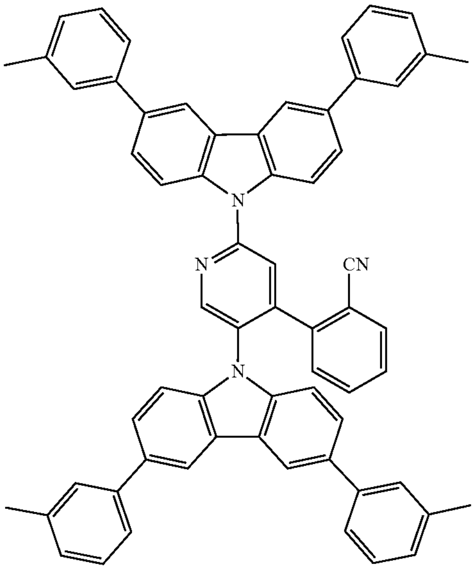
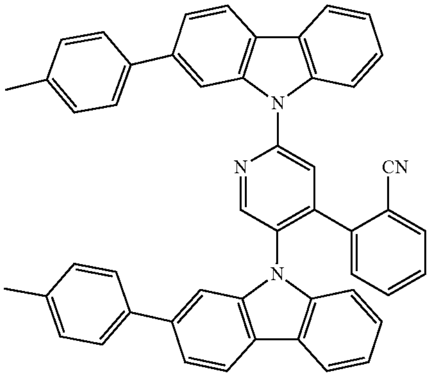
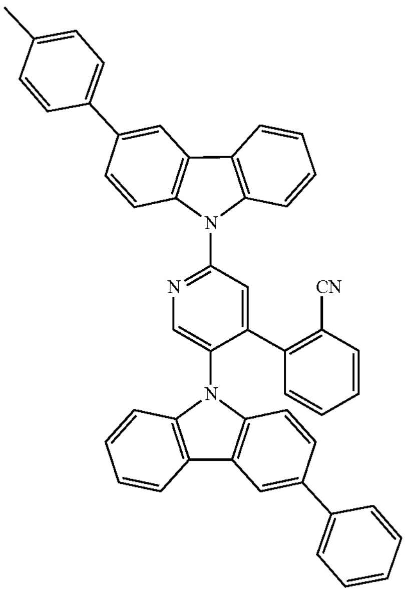

-continued
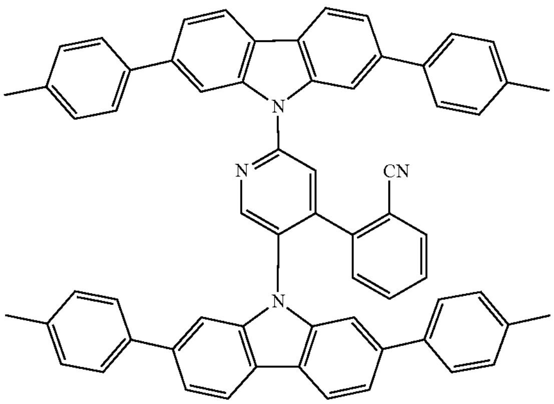
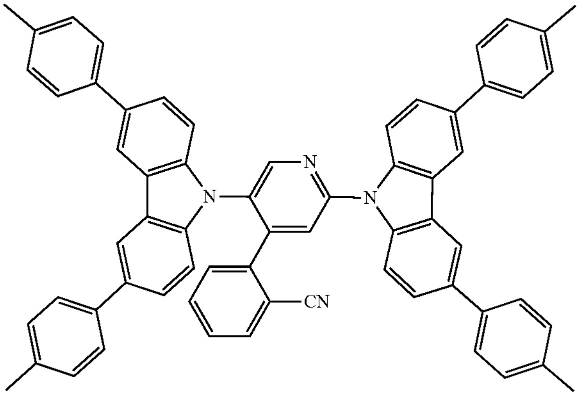
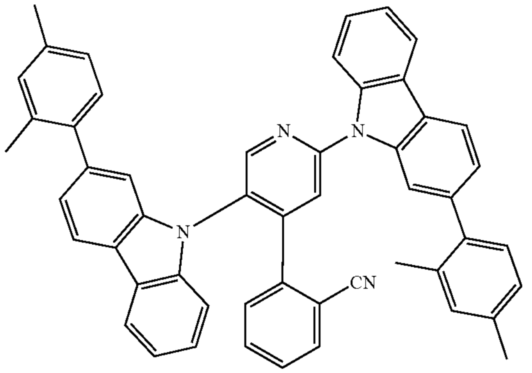
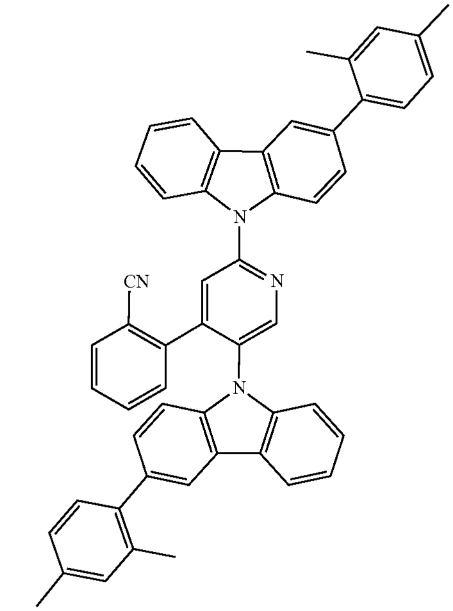
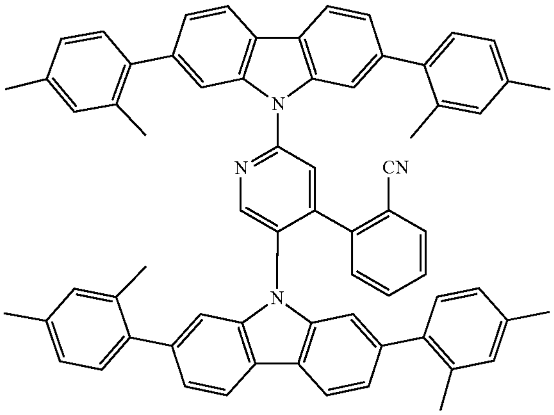
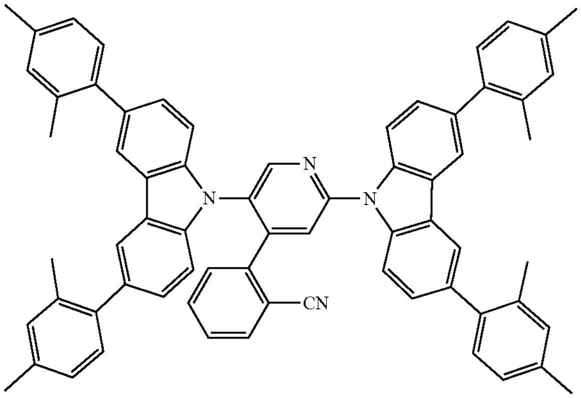
-continued -continued
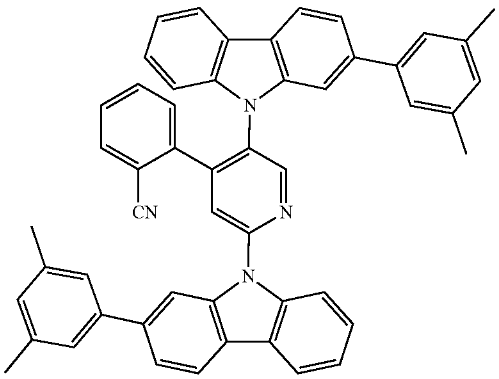
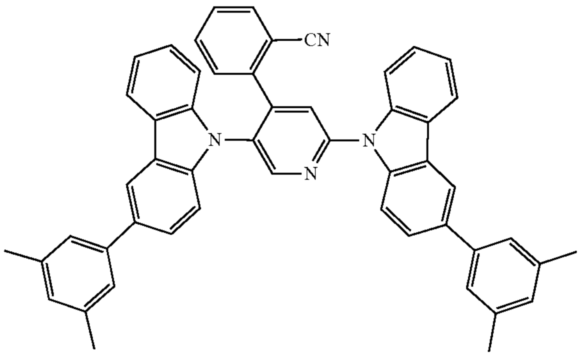
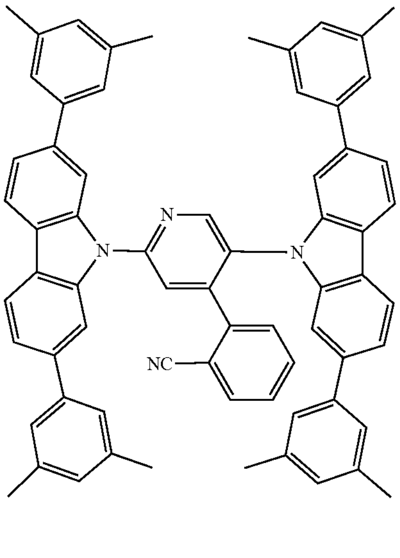
-continued
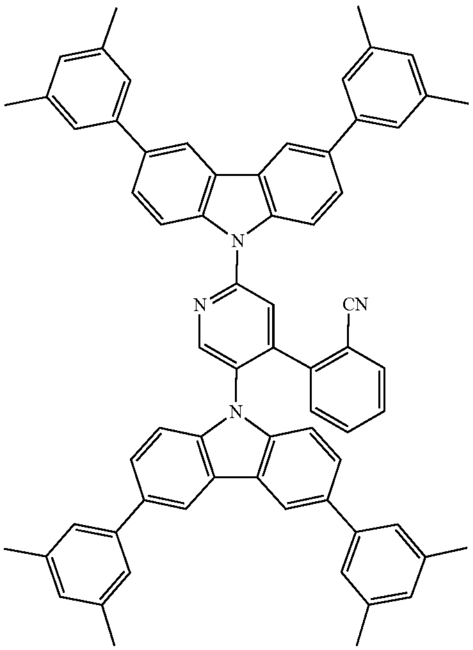
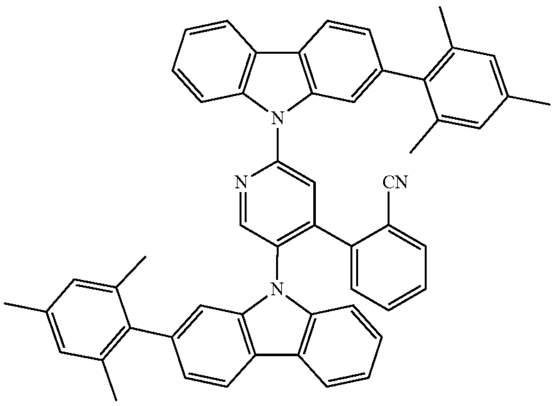
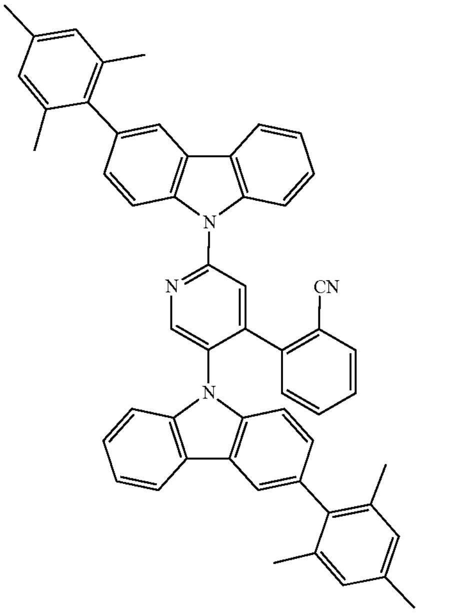

-continued
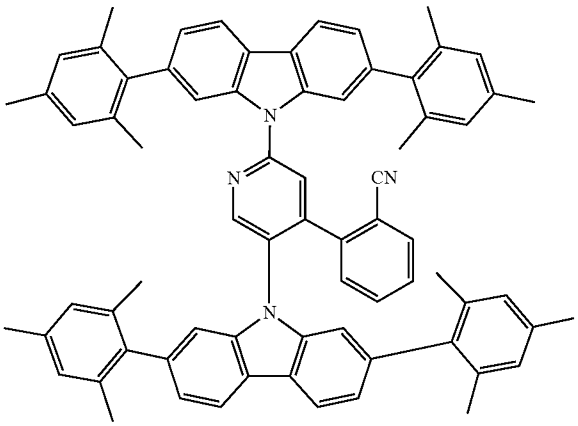
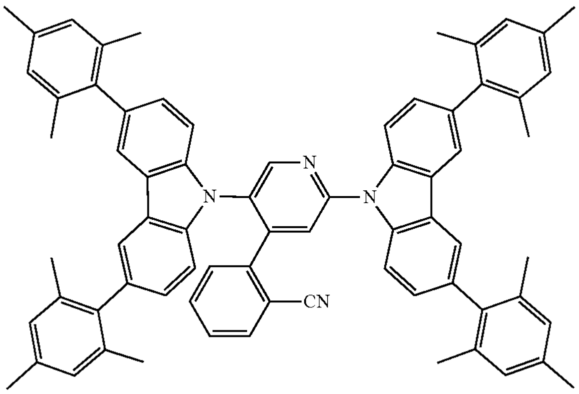
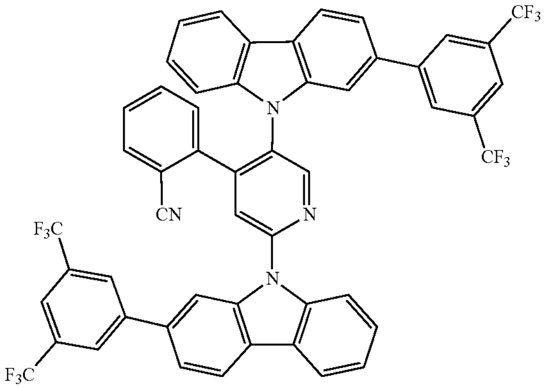
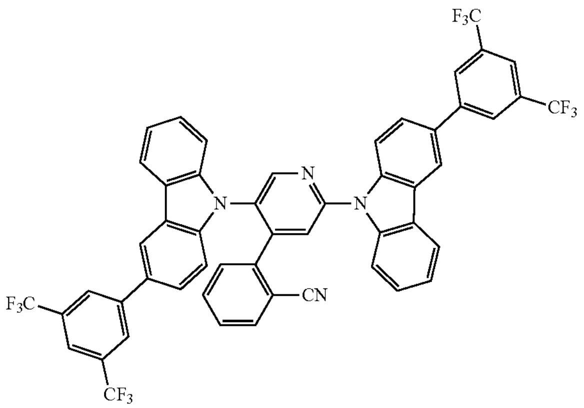
-continued
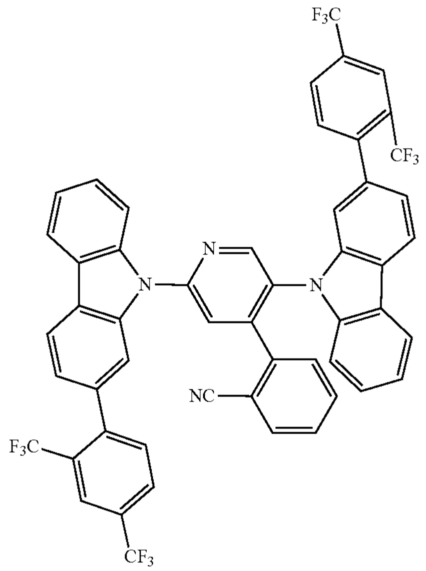
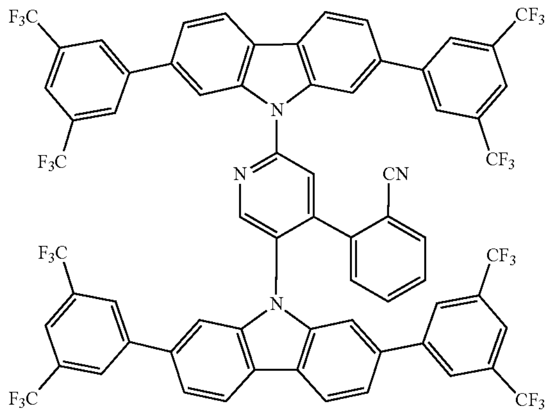
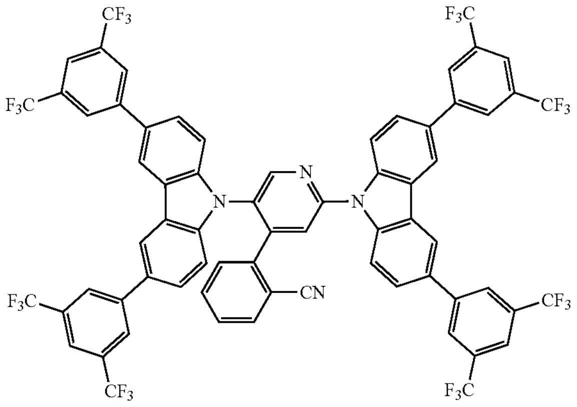

-continued
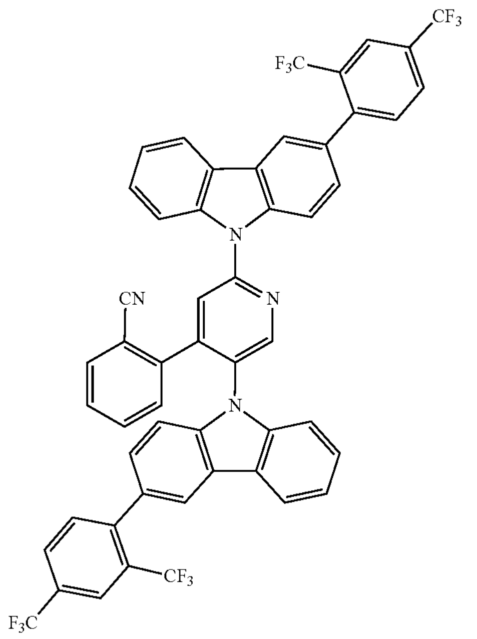
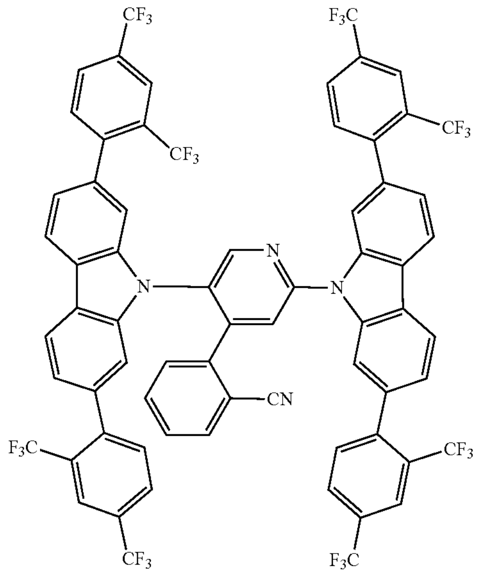
-continued
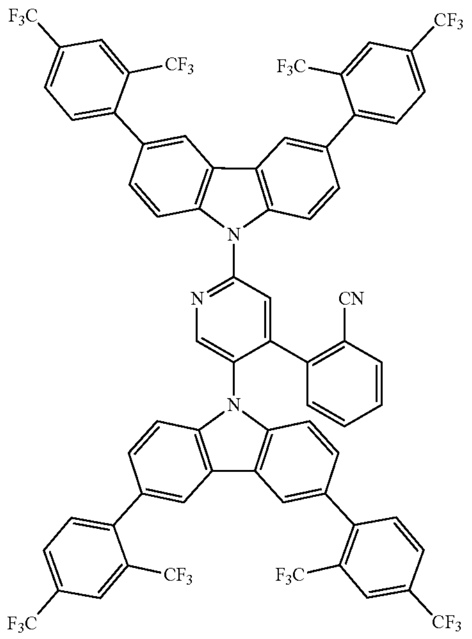 [SMILES: N#Cc1ccccc1-c1cc(-n2c3ccc(-c4ccc(C(F)(F)F)cc4C(F)(F)F)cc3c3cc(-c4ccc(C(F)(F)F)cc4C(F)(F)F)ccc32)ncc1-n1c2ccc(-c3ccc(C(F)(F)F)cc3C(F)(F)F)cc2c2cc(-c3ccc(C(F)(F)F)cc3C(F)(F)F)ccc21]
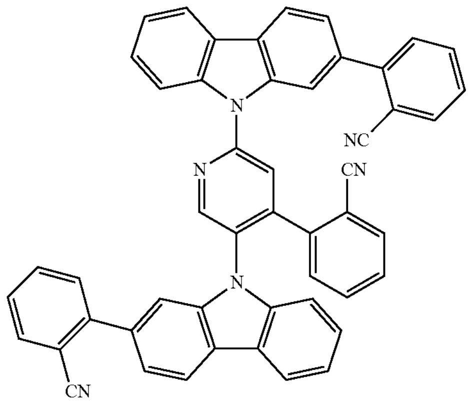
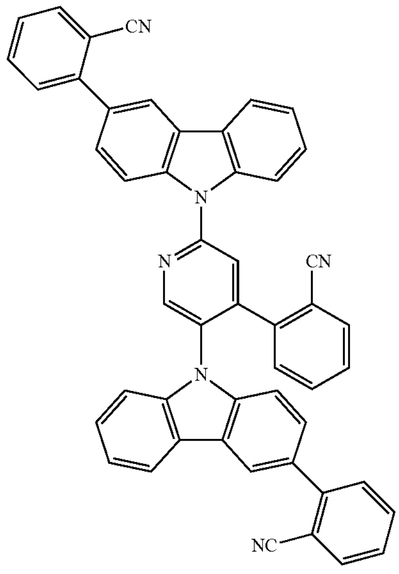

-continued
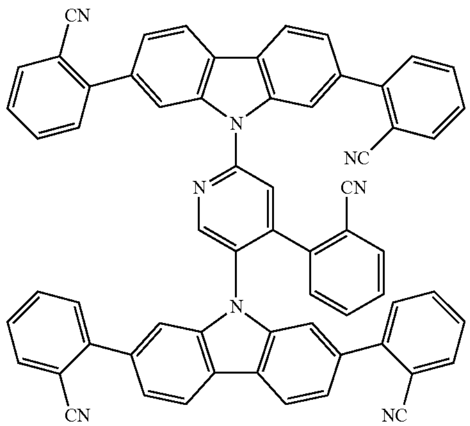
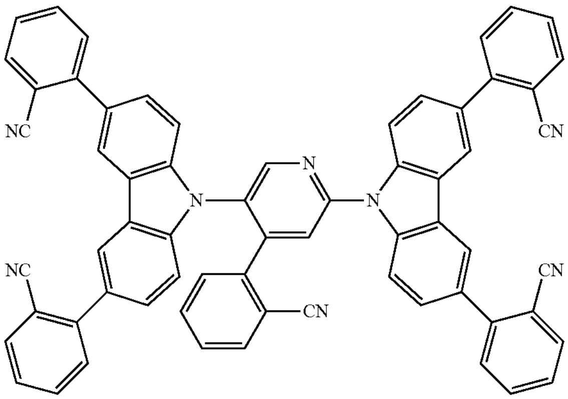
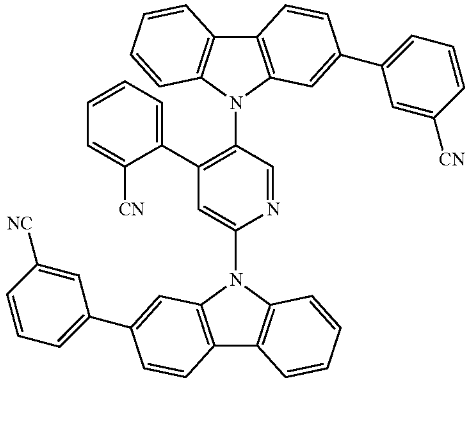
-continued
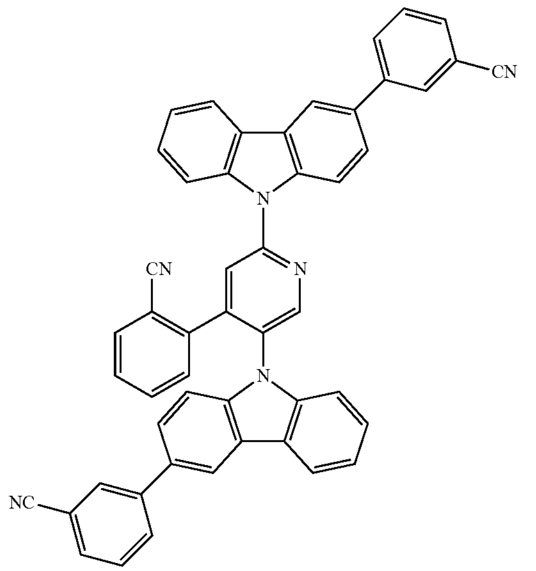
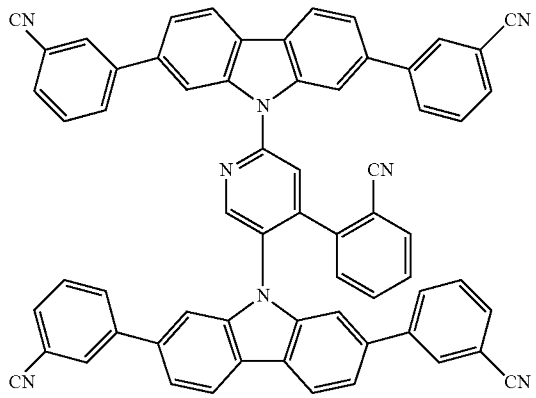
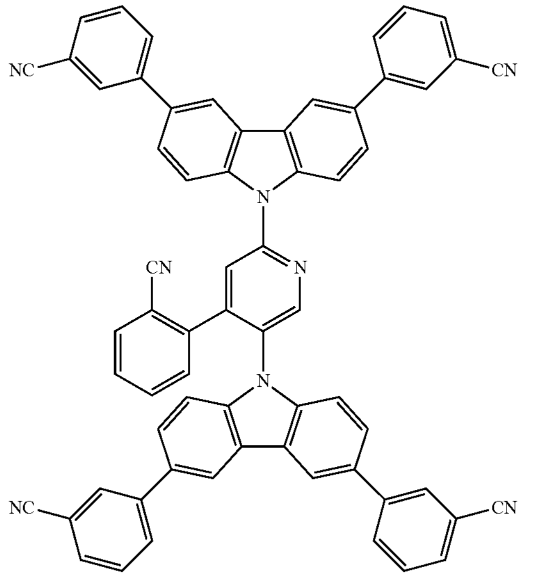

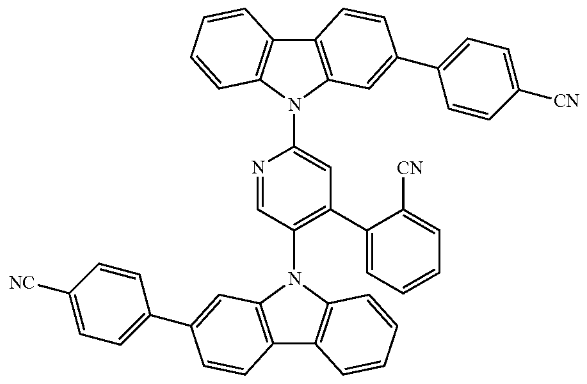
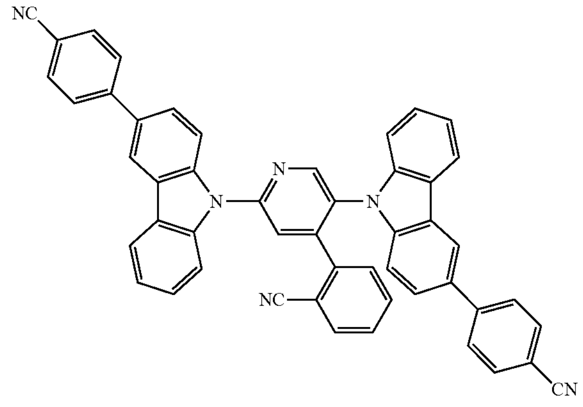
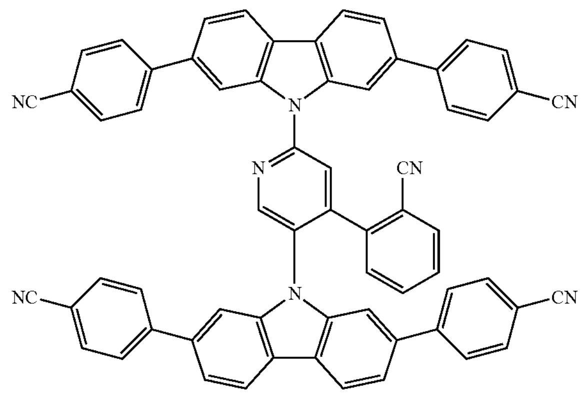
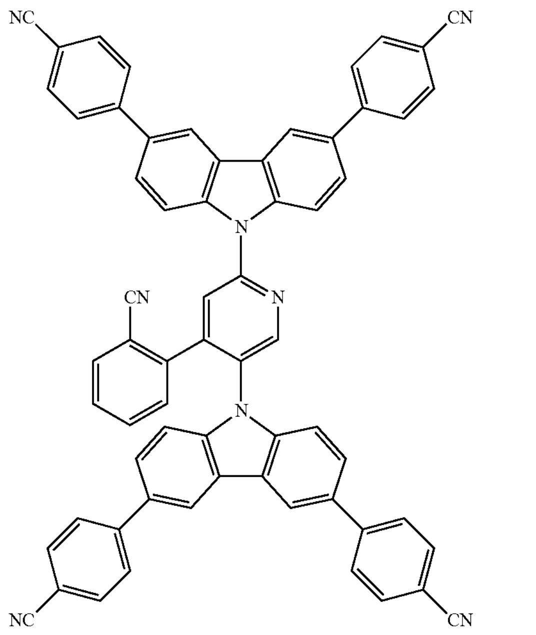
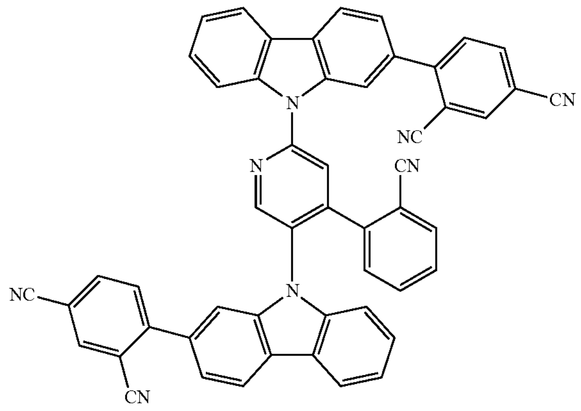
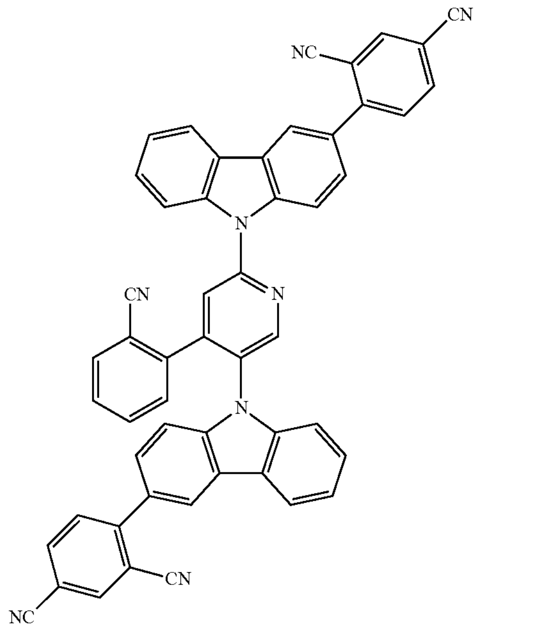

-continued
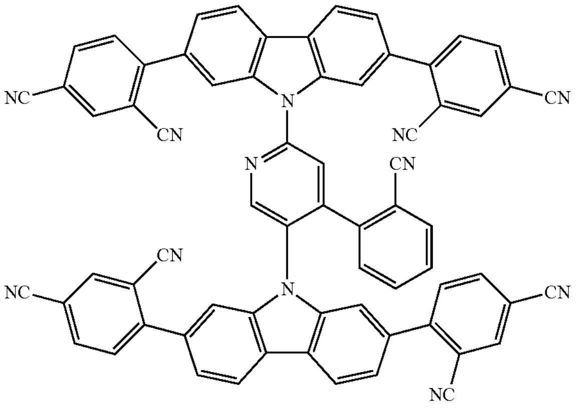
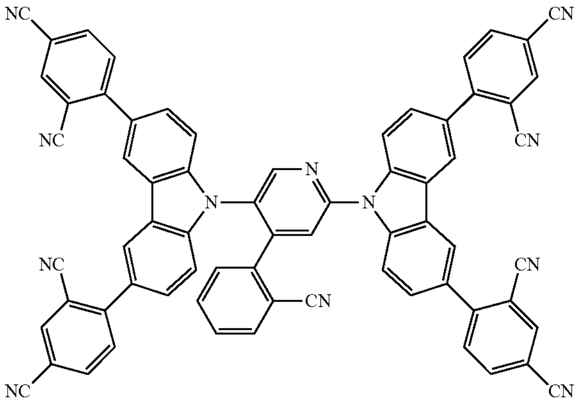
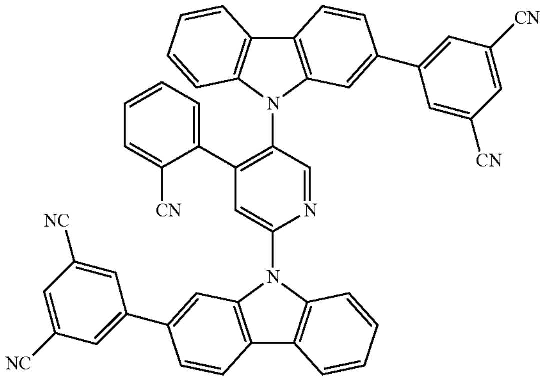
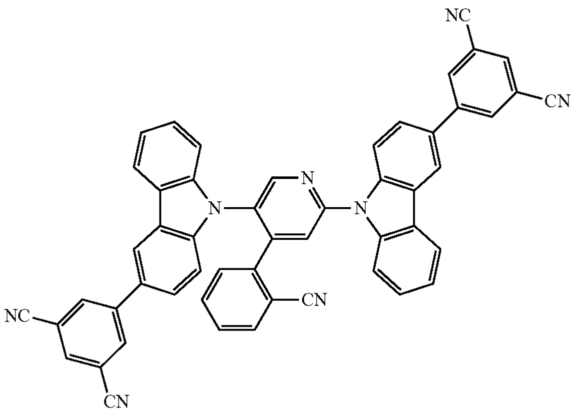
-continued
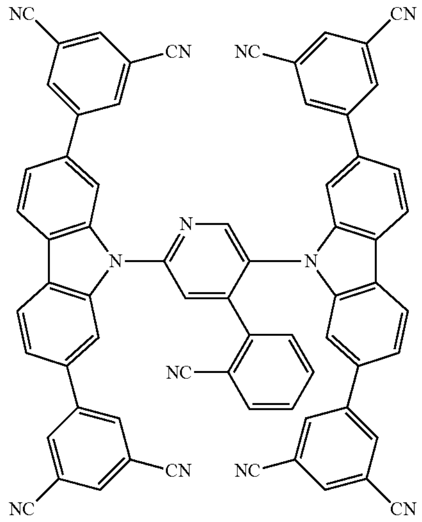
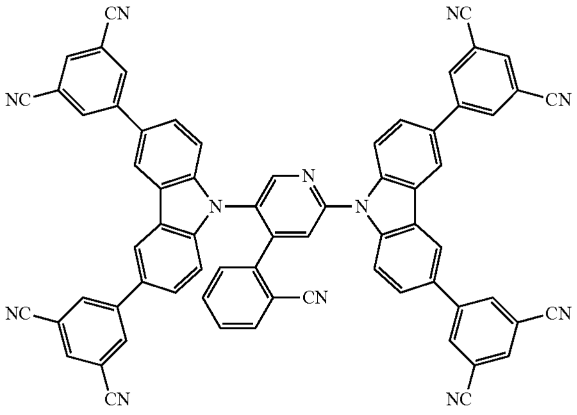
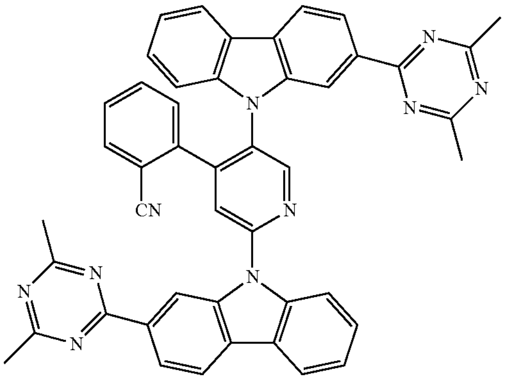

-continued
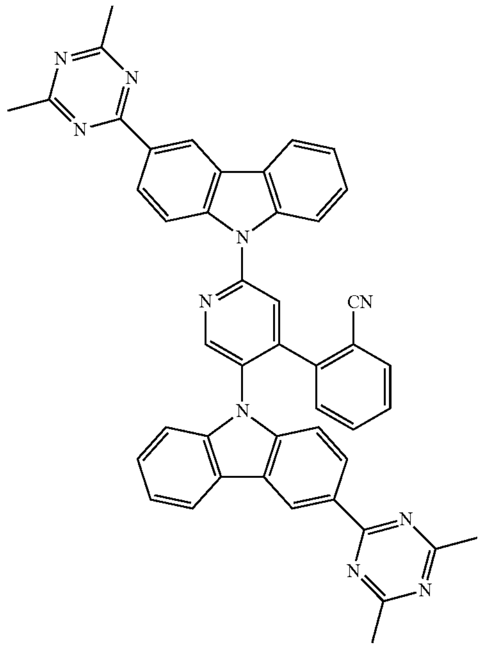
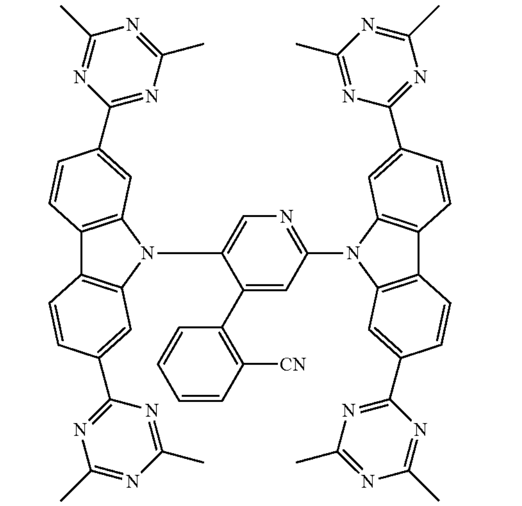
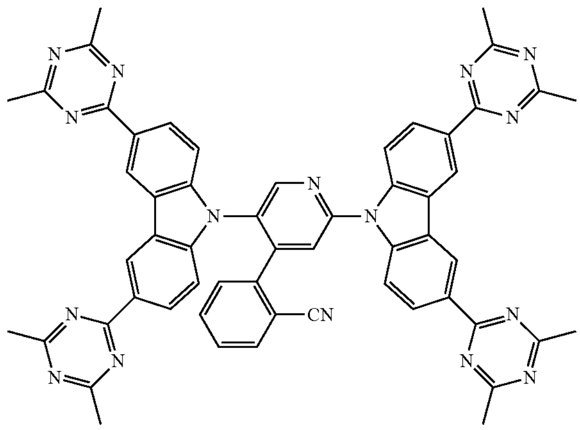
-continued
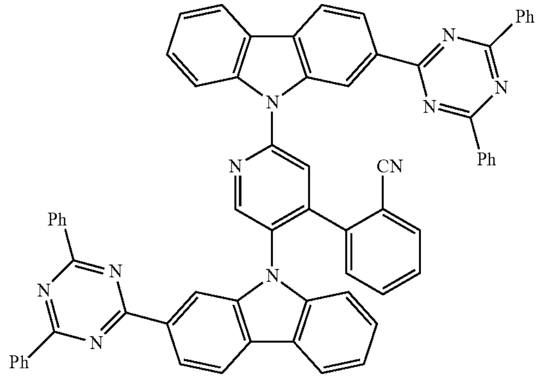
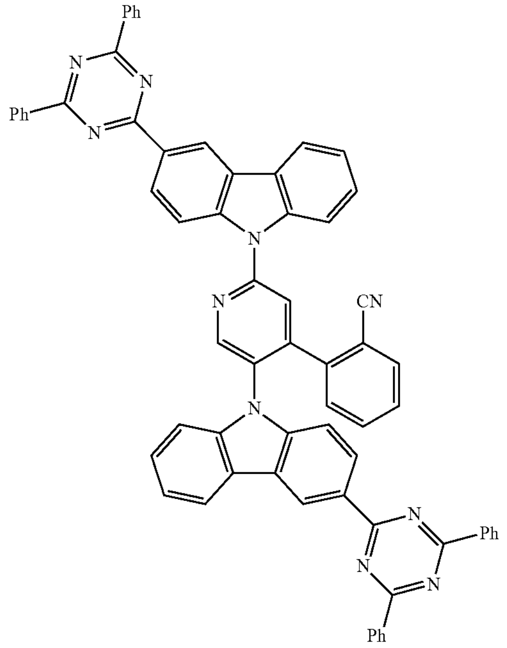
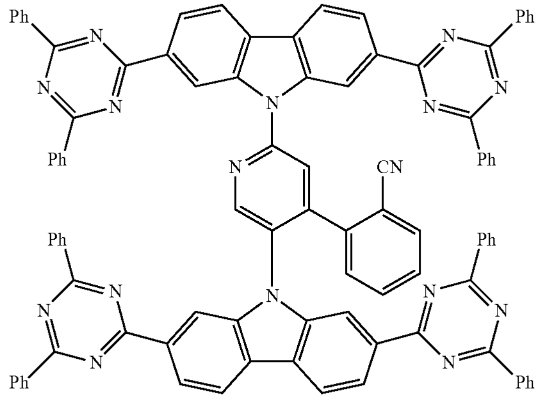

-continued
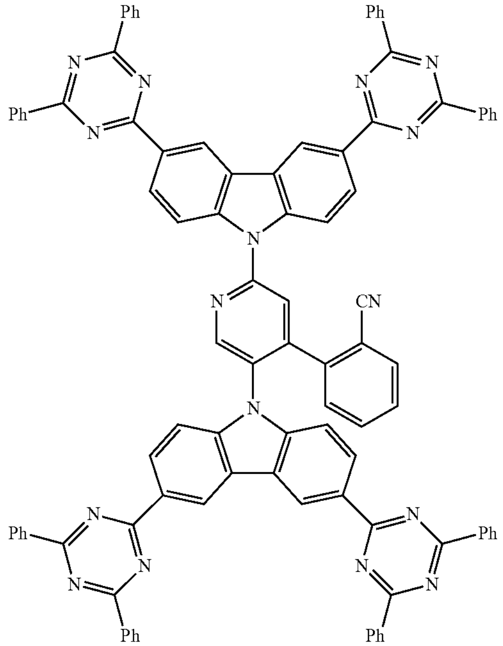
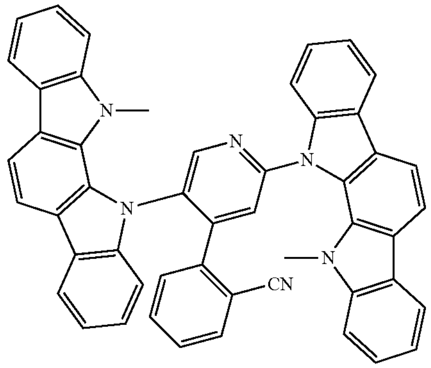
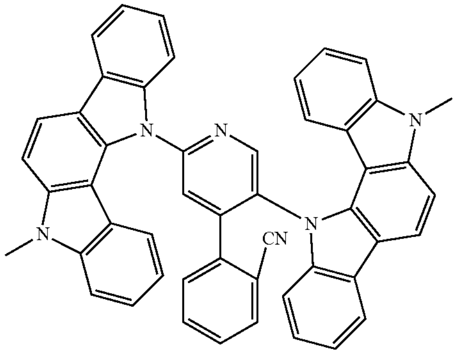
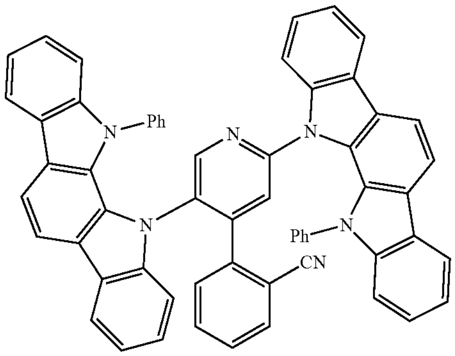
-continued
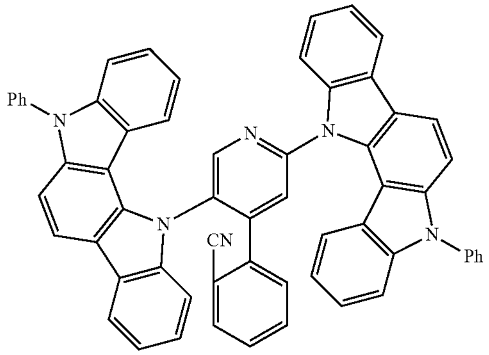
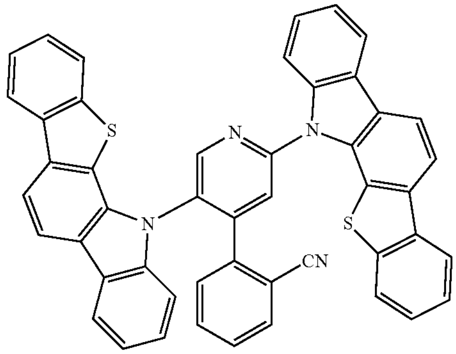
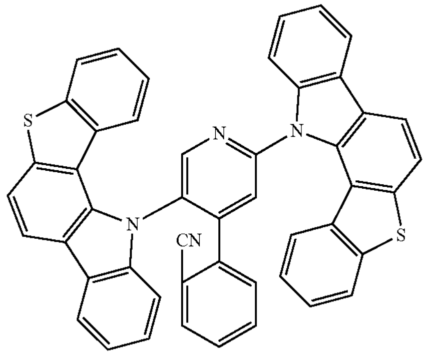
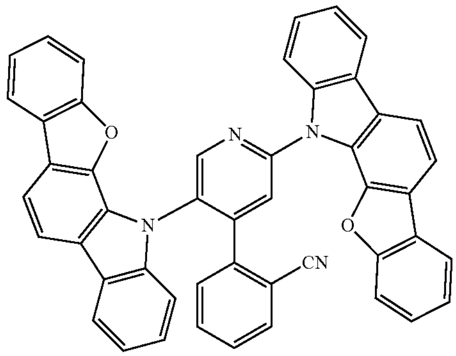

-continued
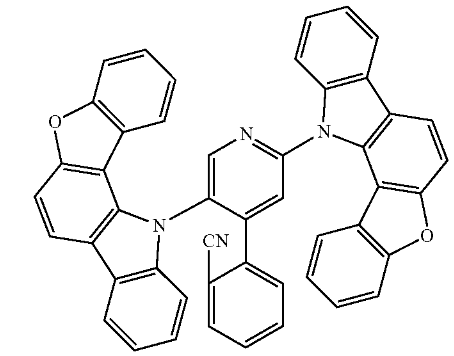
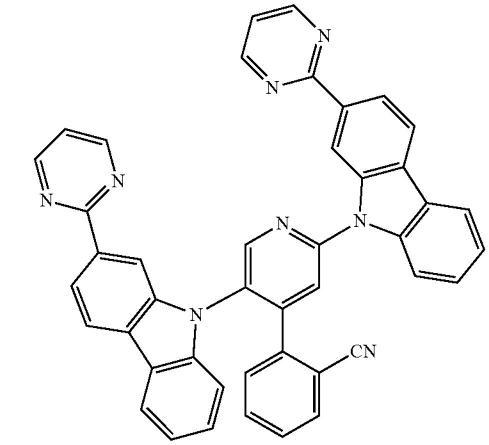
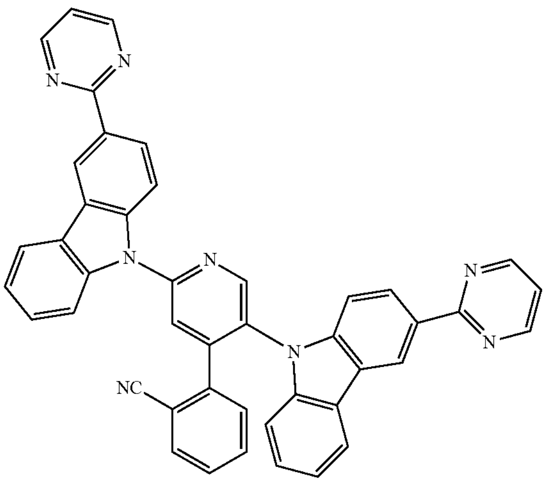
-continued
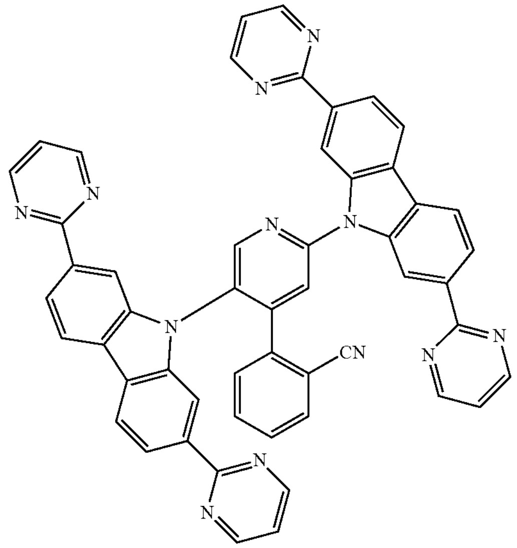
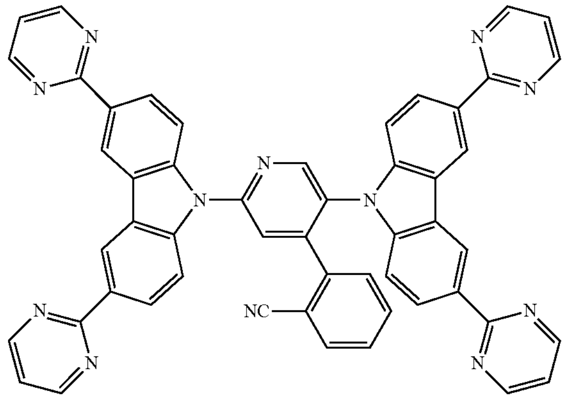
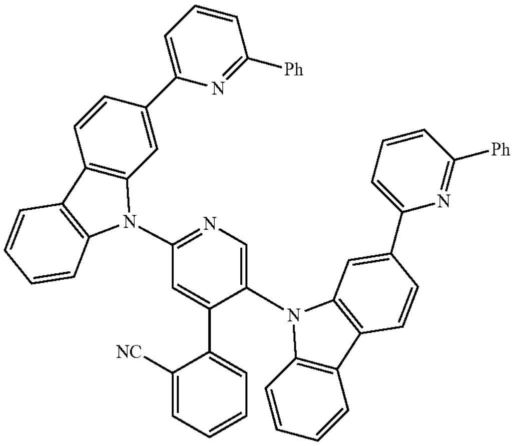

-continued
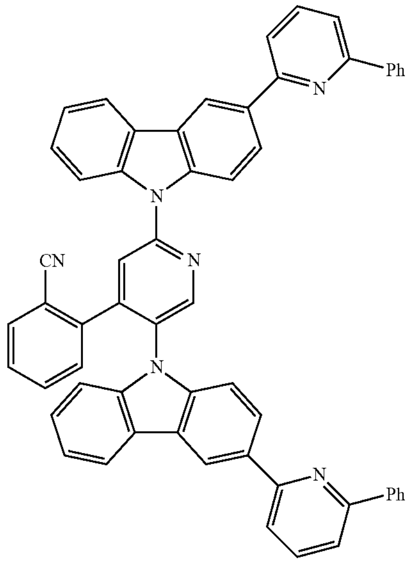
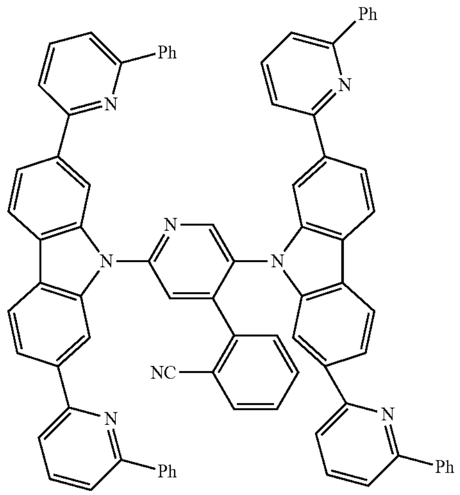
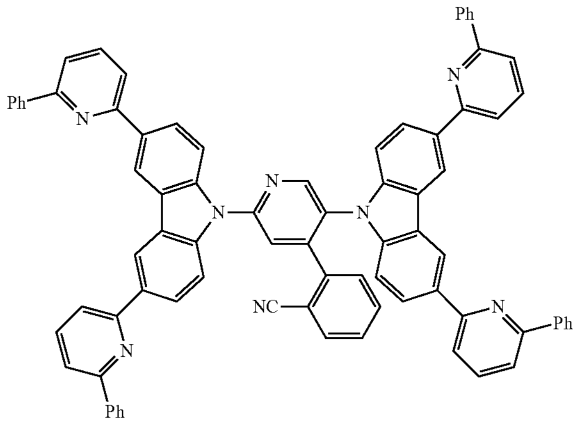
-continued
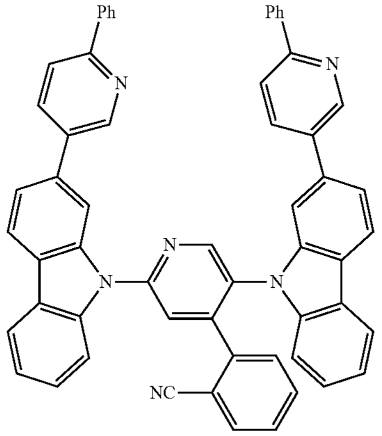
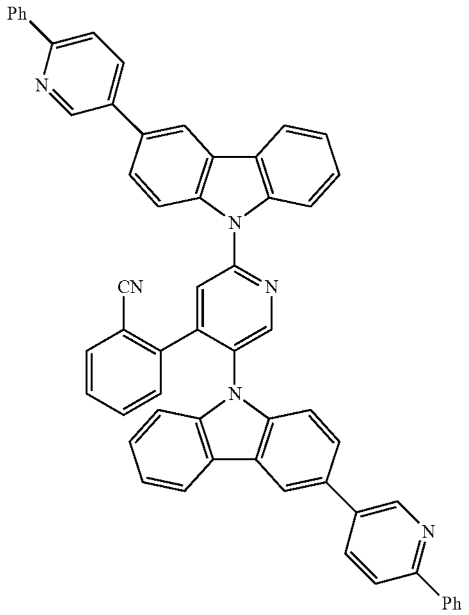
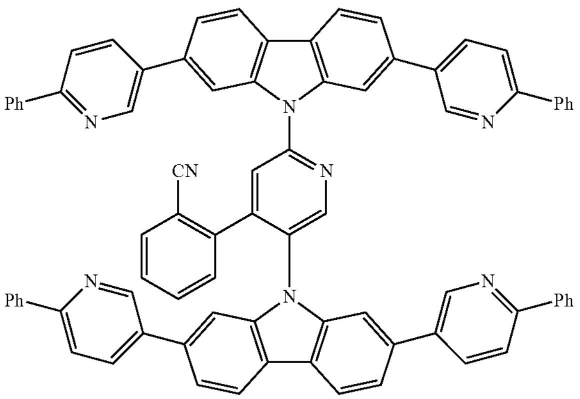

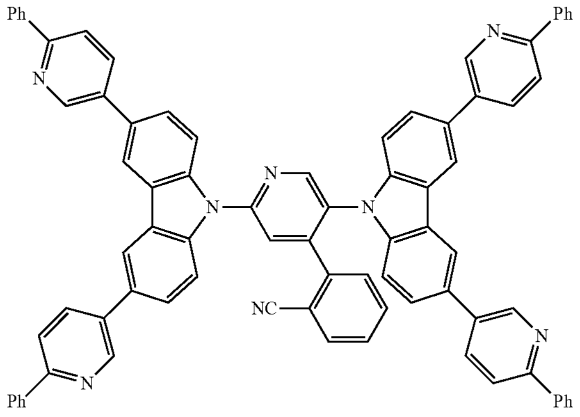
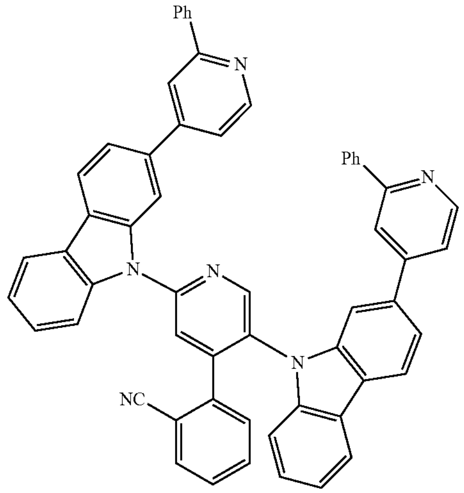
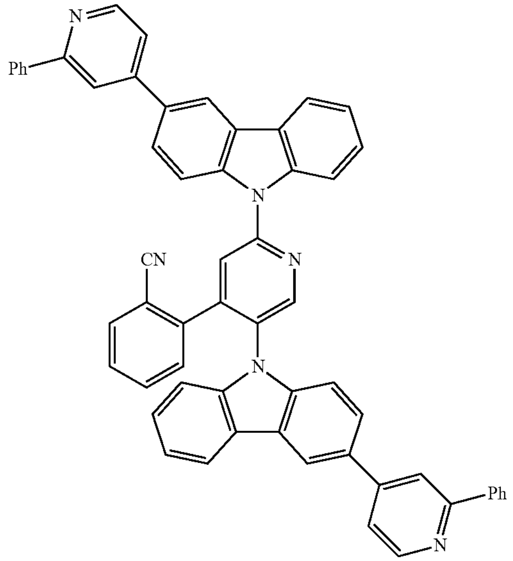
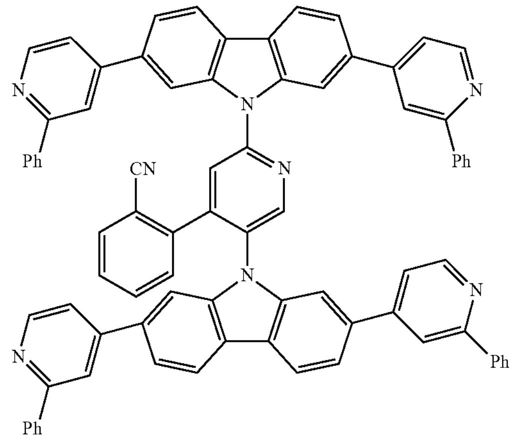
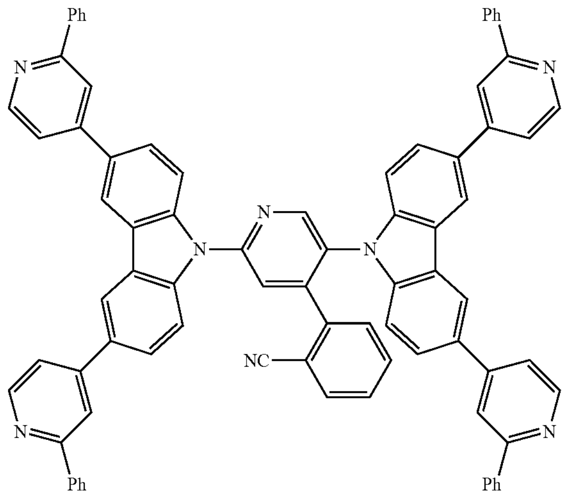
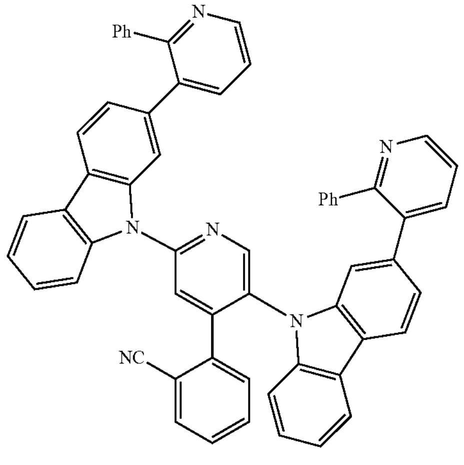

-continued
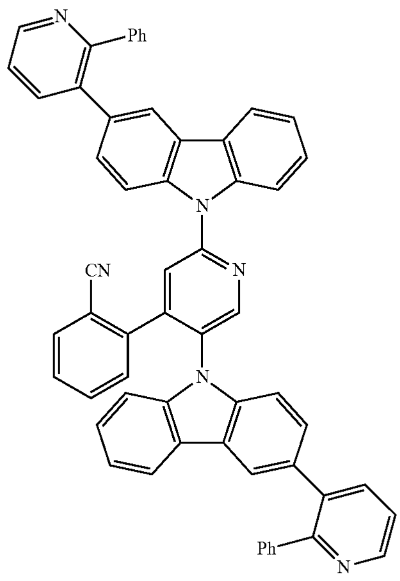
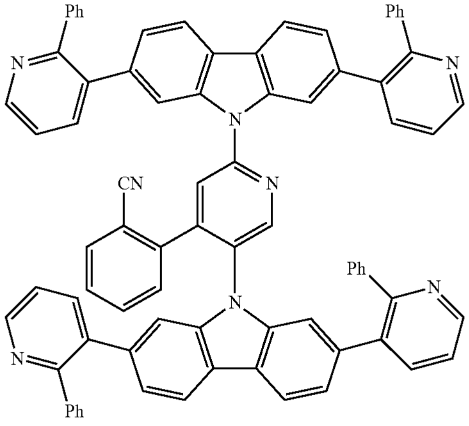
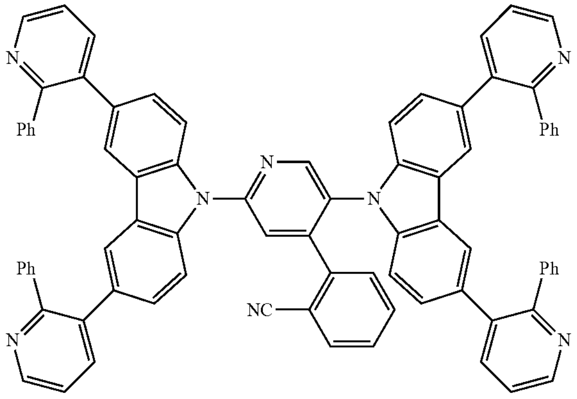
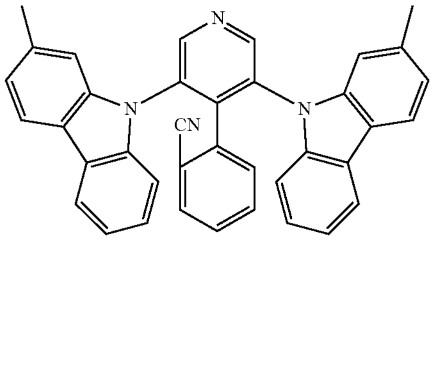
-continued
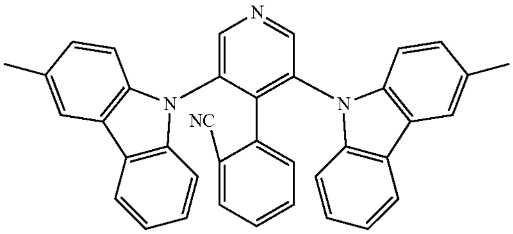
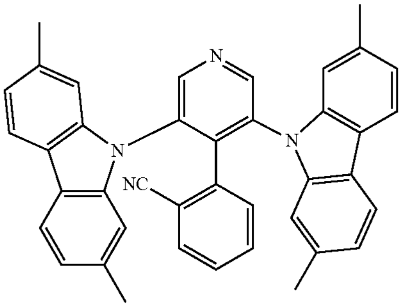
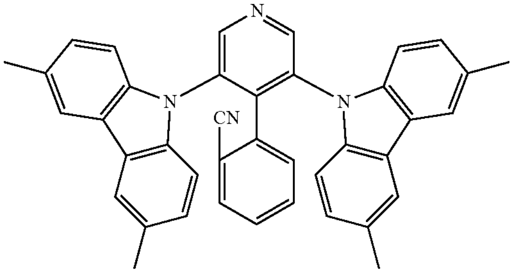
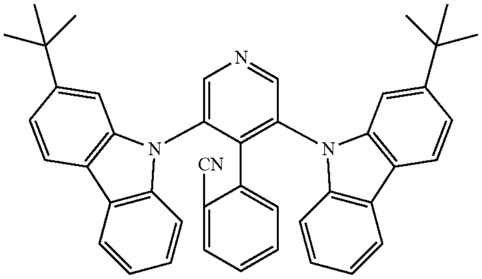
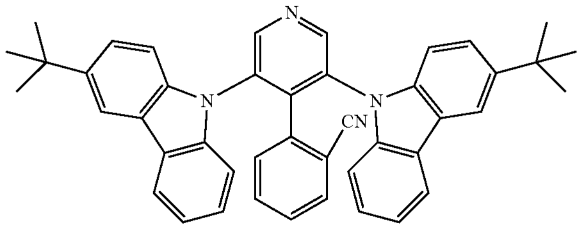
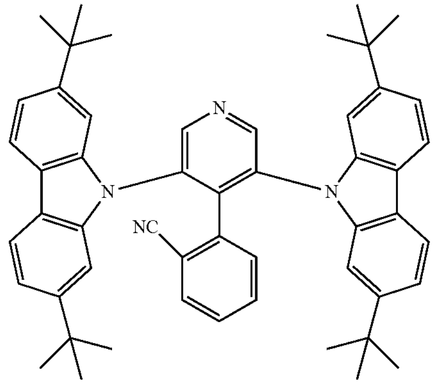

-continued
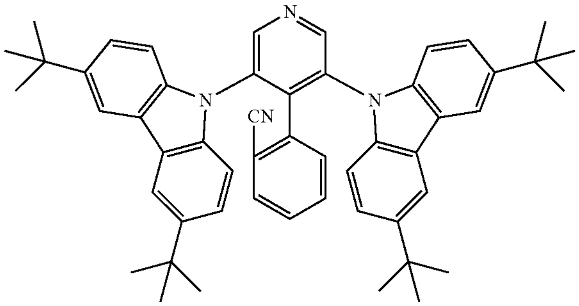
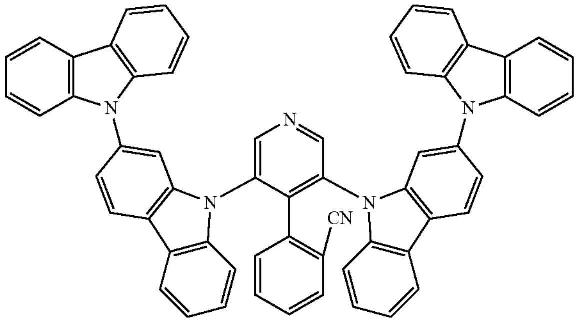
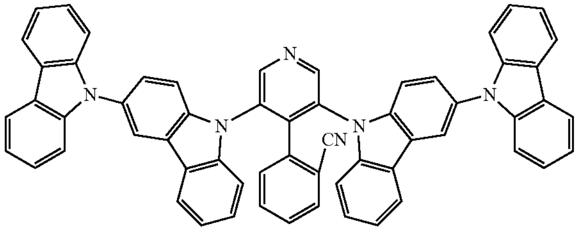
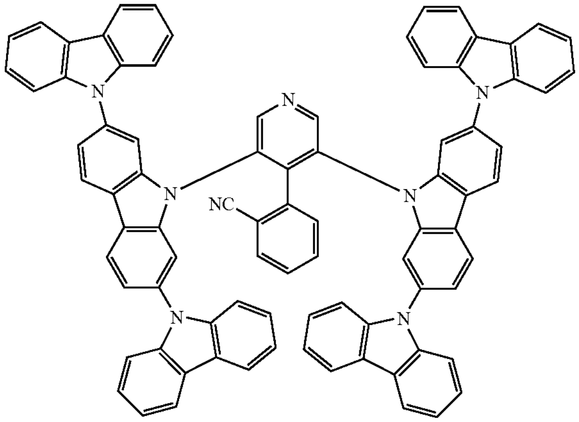
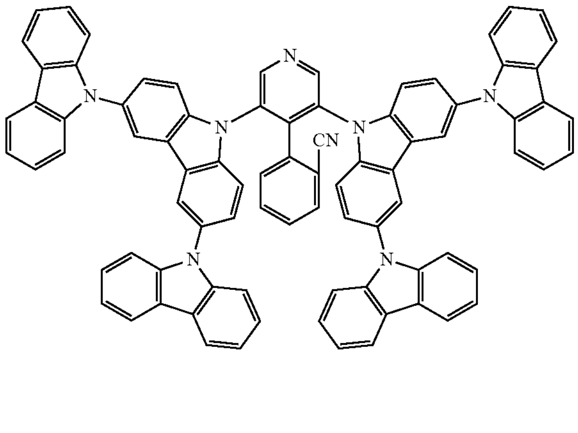
-continued
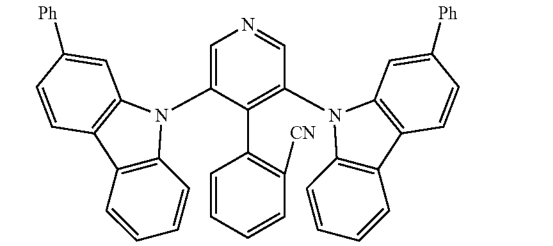
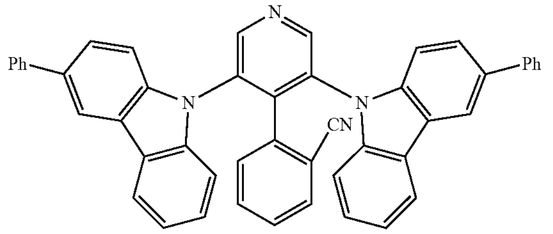
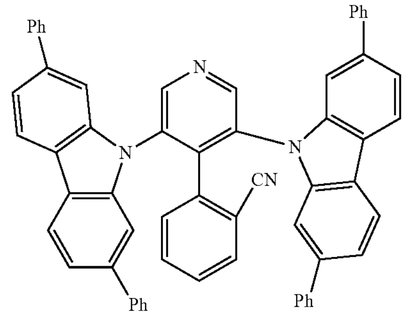
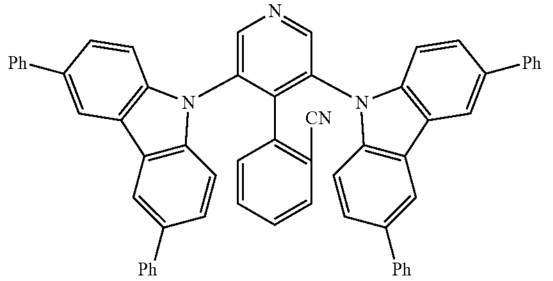
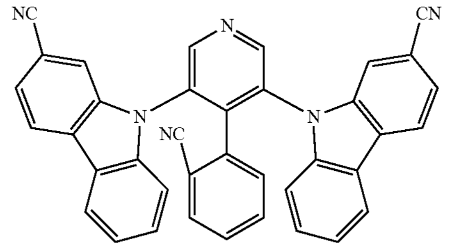
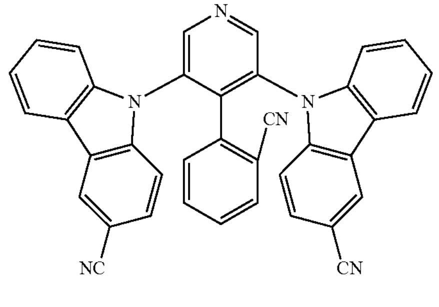

-continued
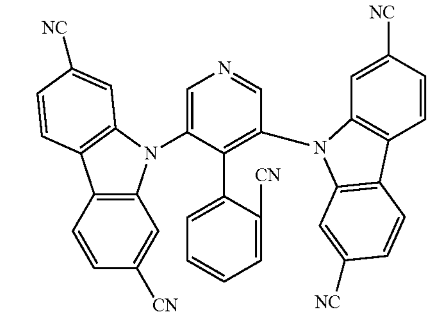
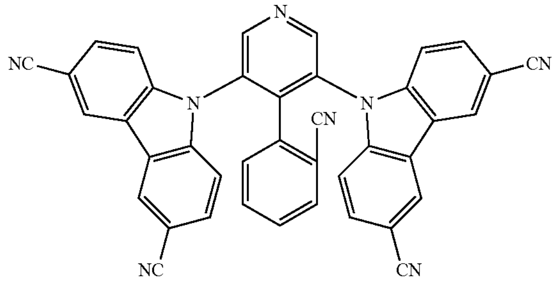
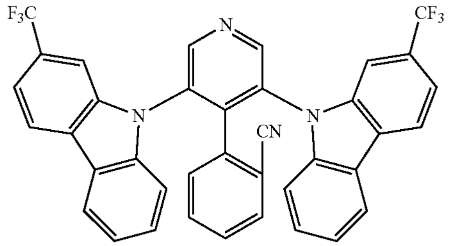
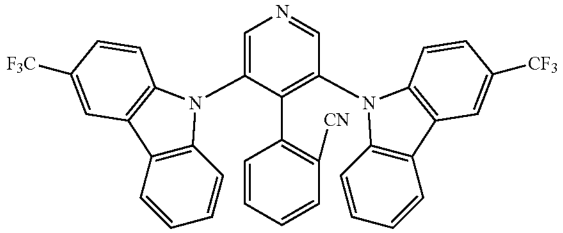
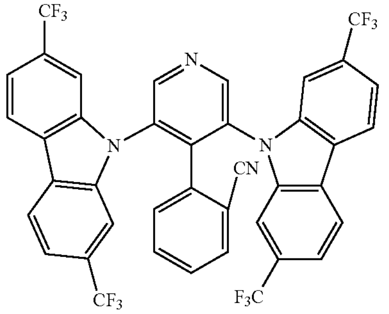
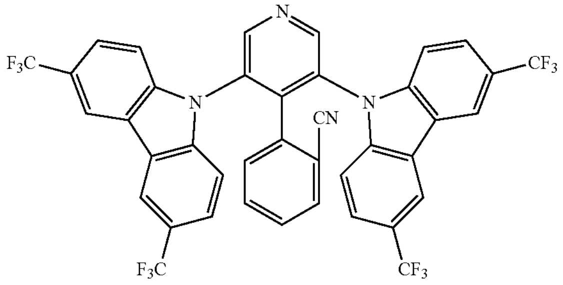
-continued
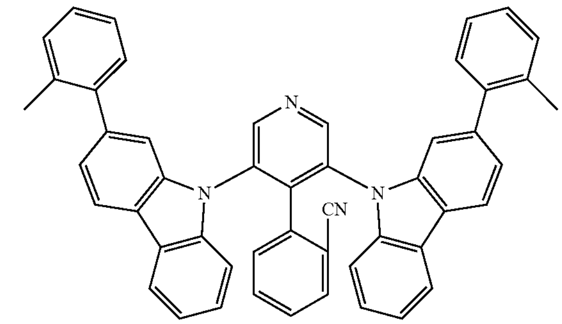
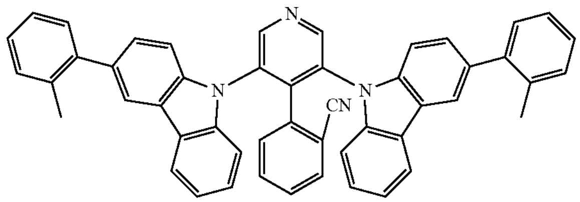
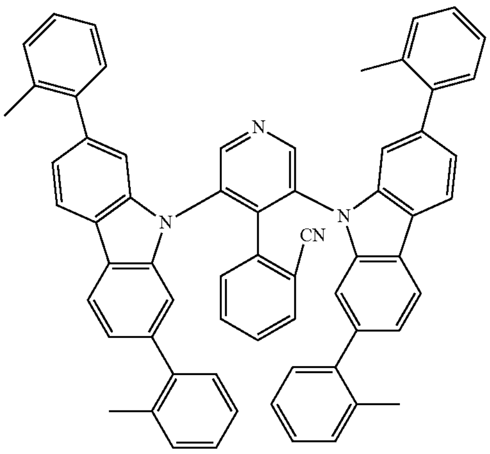
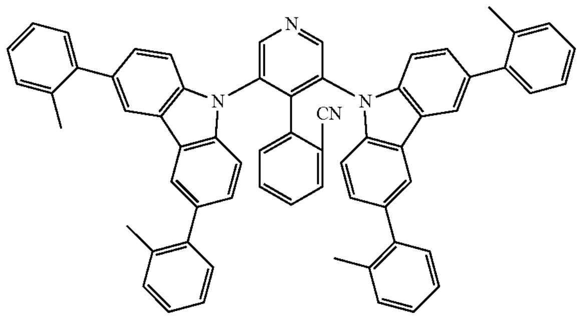
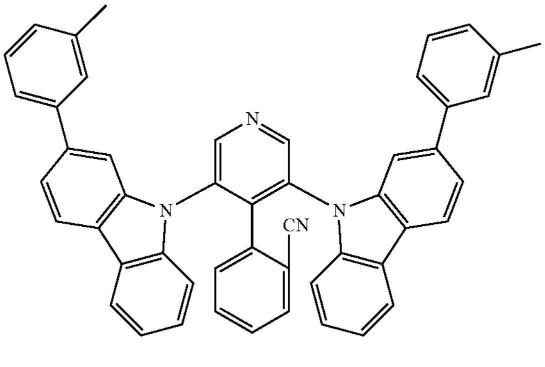

-continued
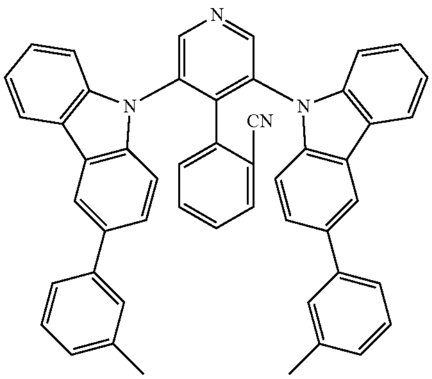
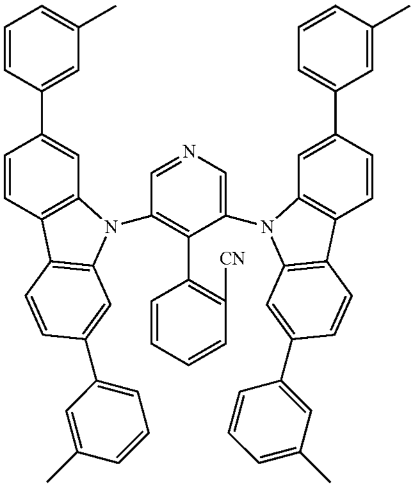
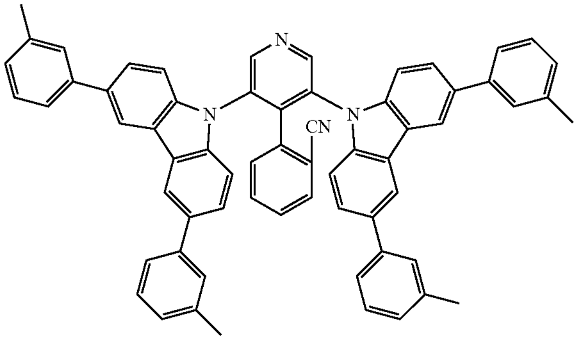
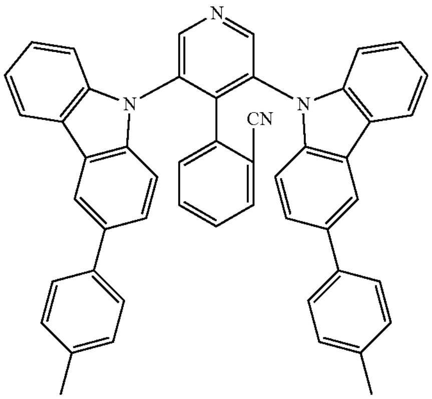
-continued
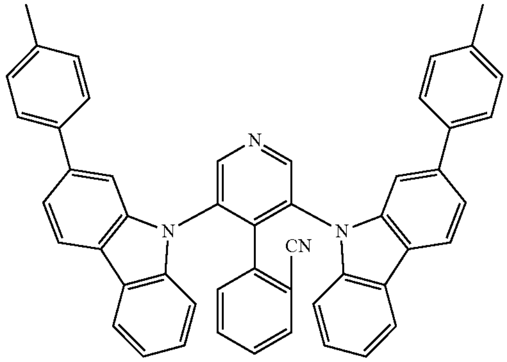
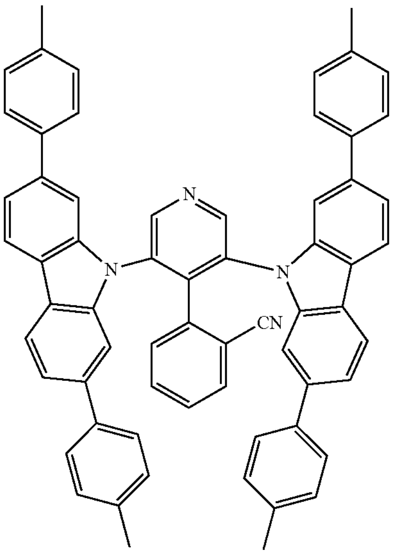
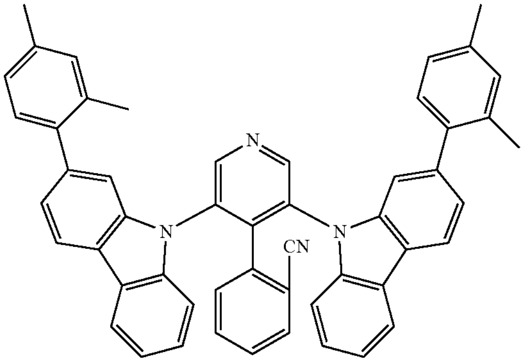
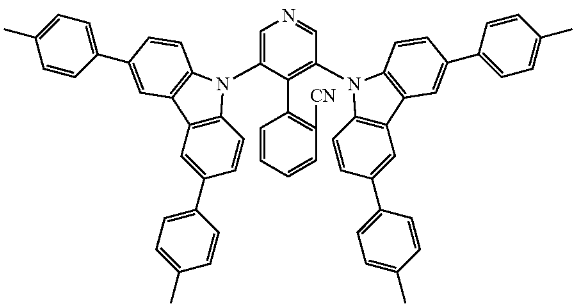

-continued
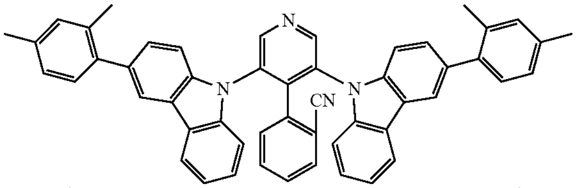
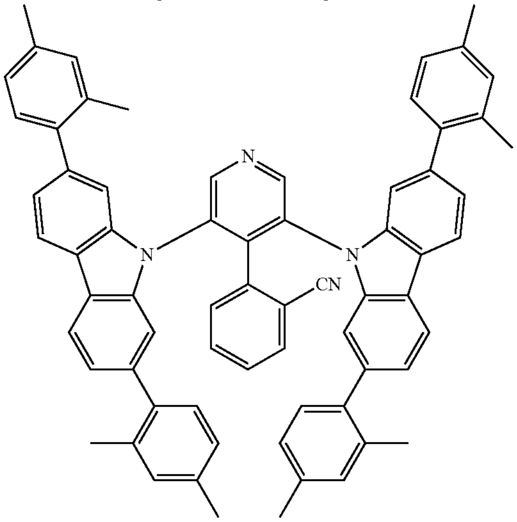
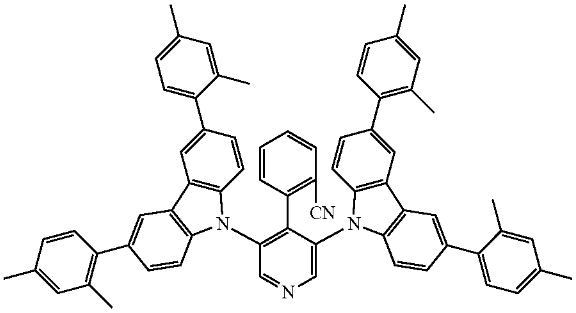
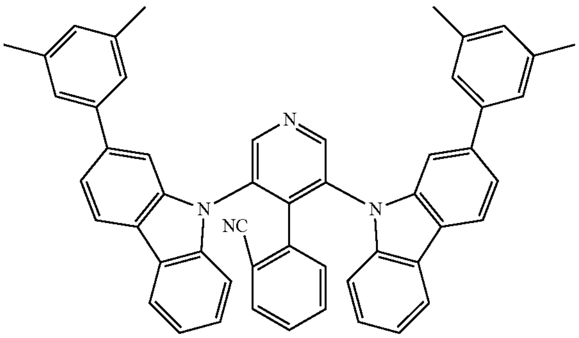
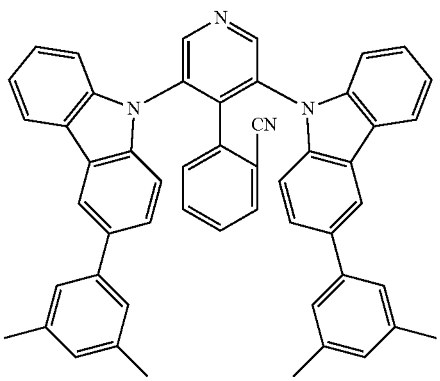
-continued
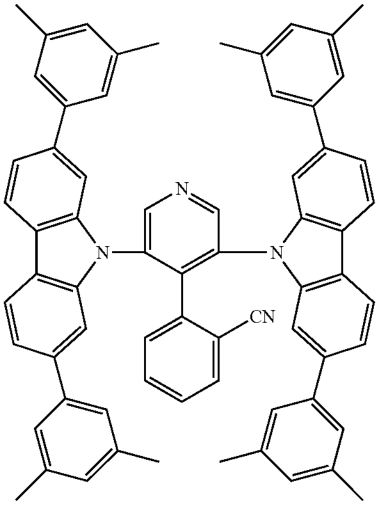
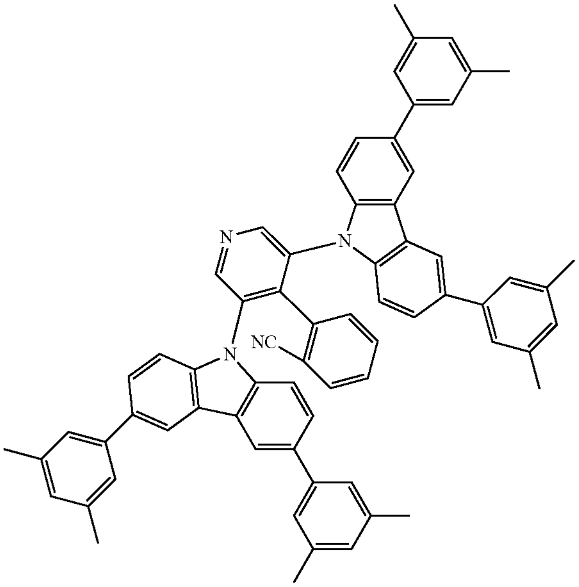
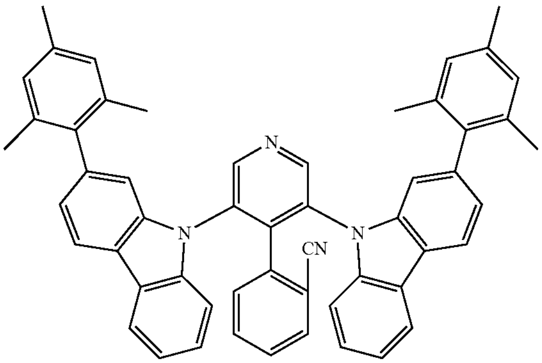

-continued
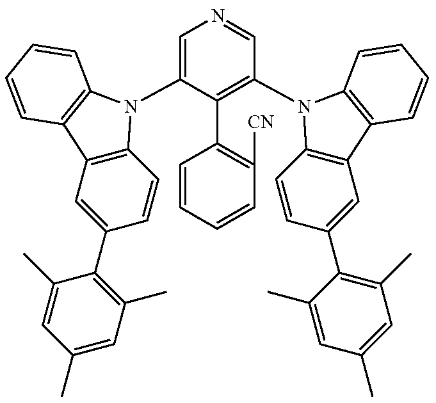
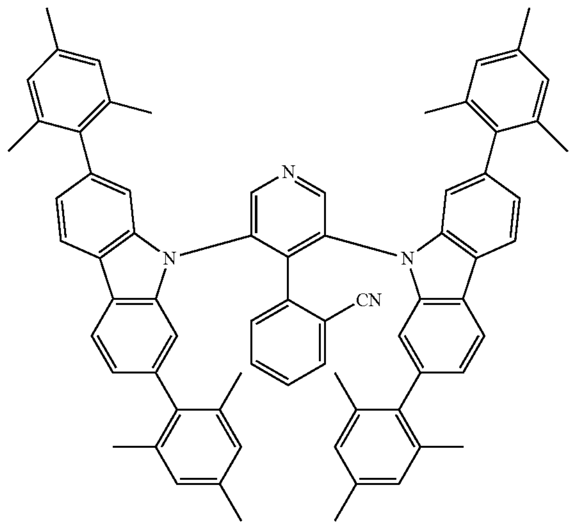
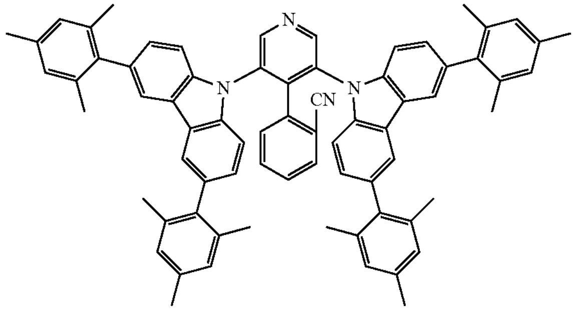
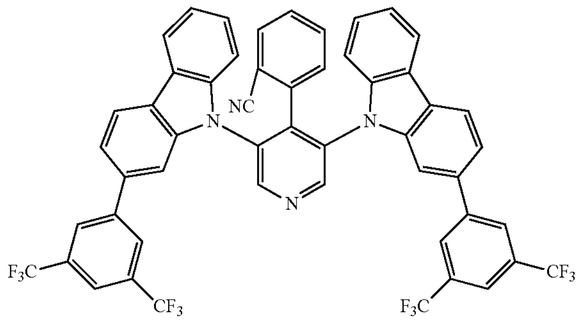
-continued
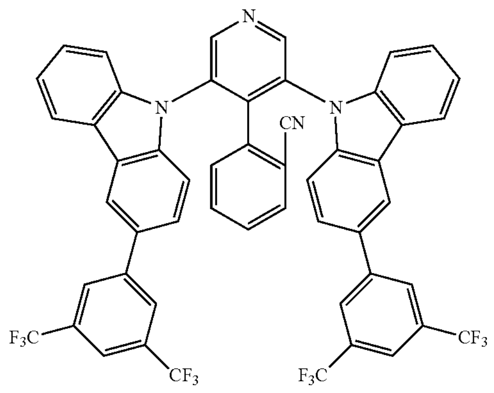
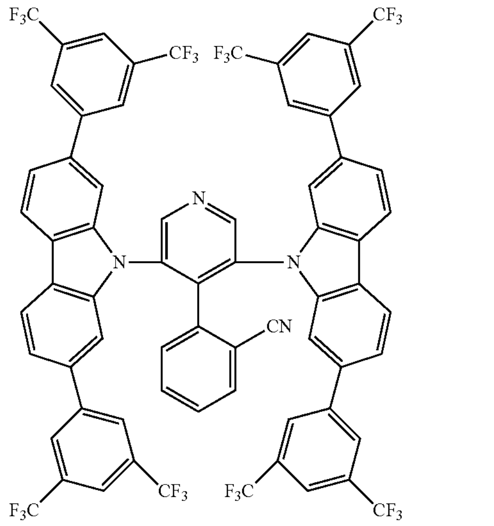
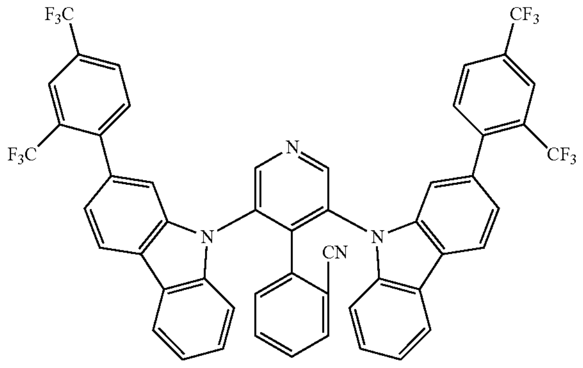
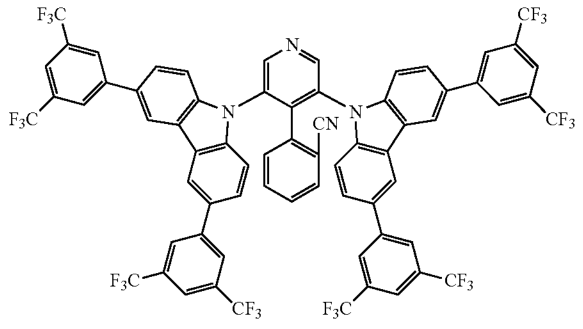

-continued
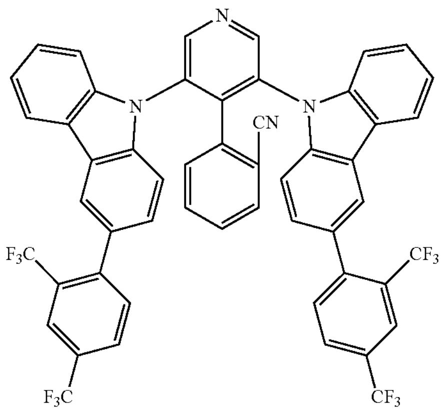
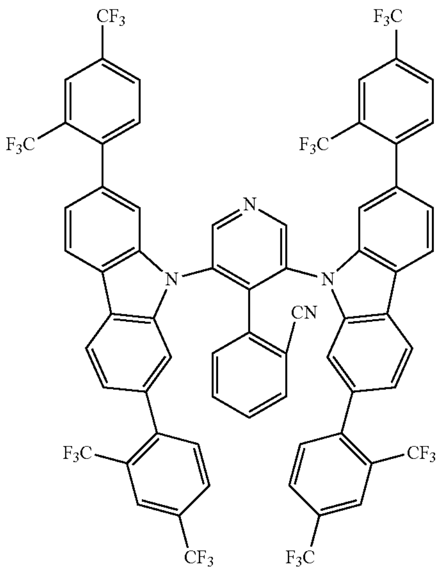
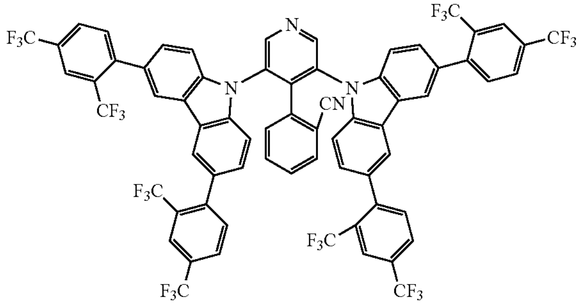
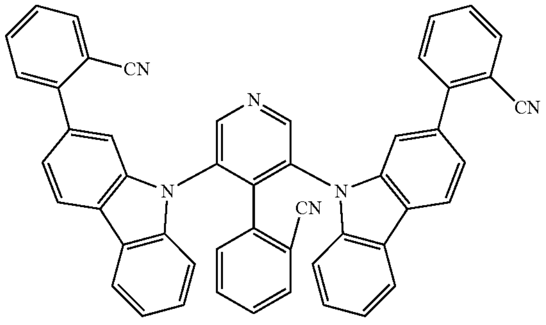
-continued
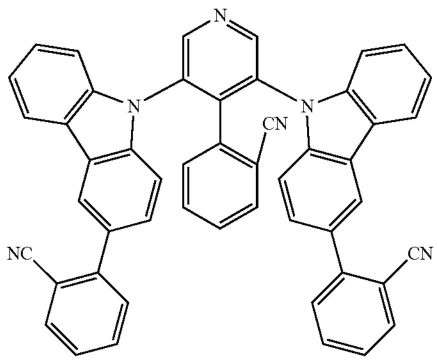
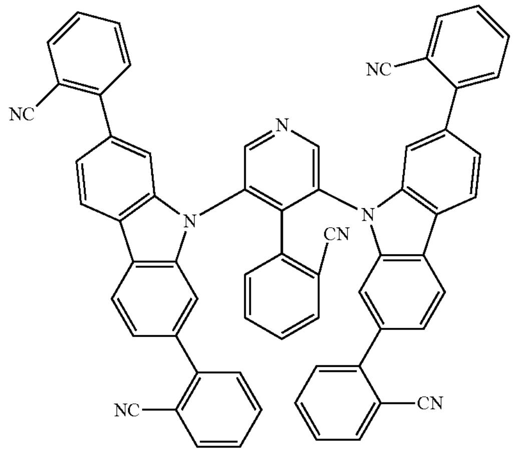
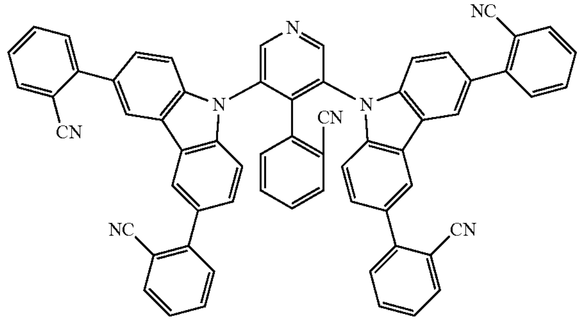
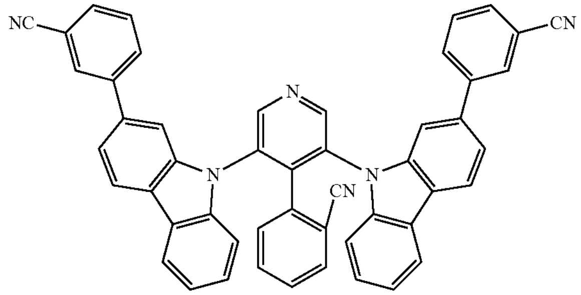

-continued
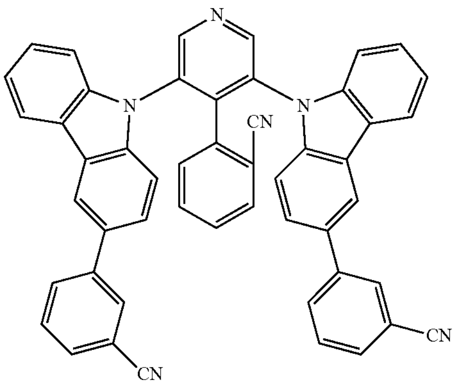
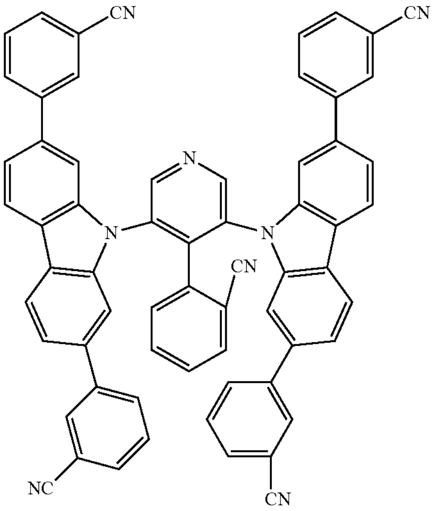
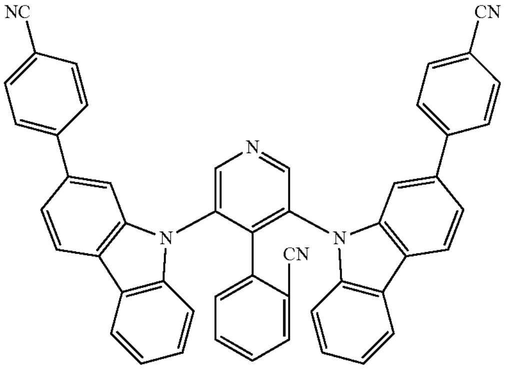
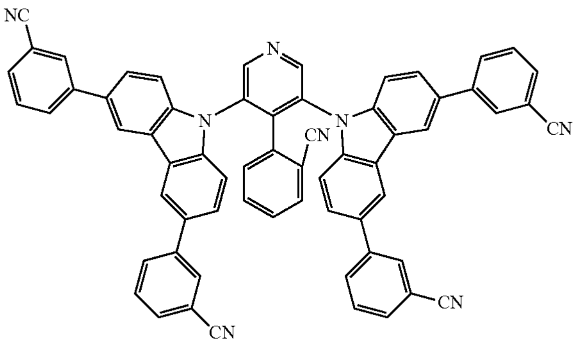
-continued
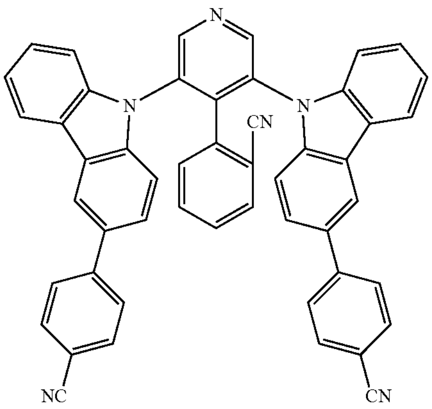
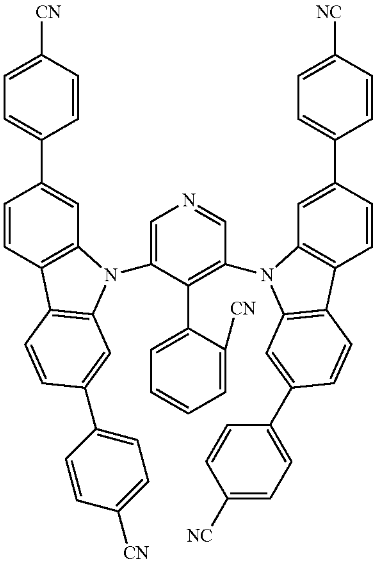
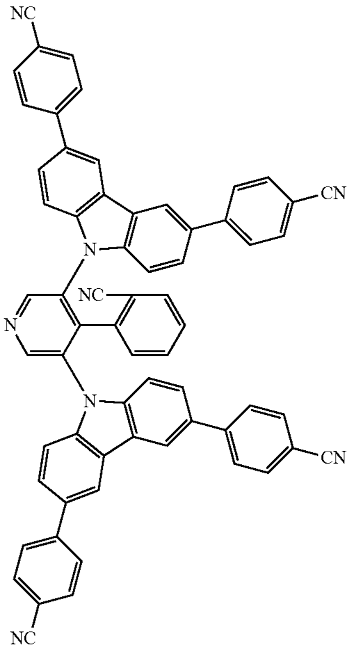

-continued
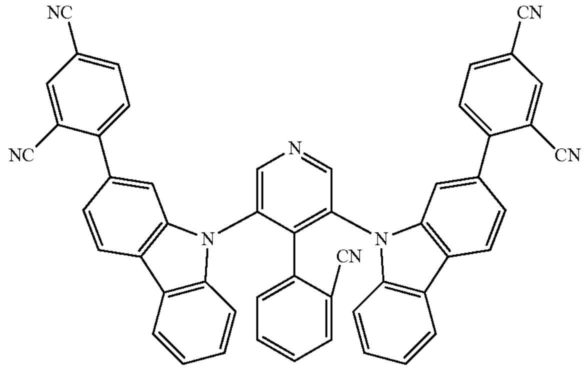
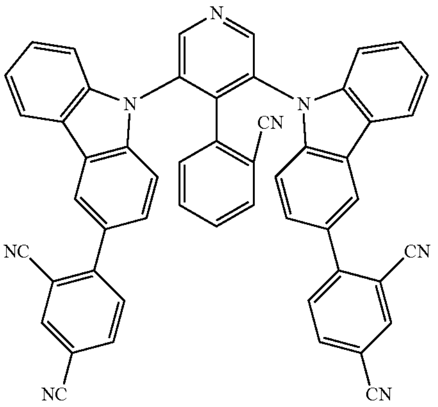
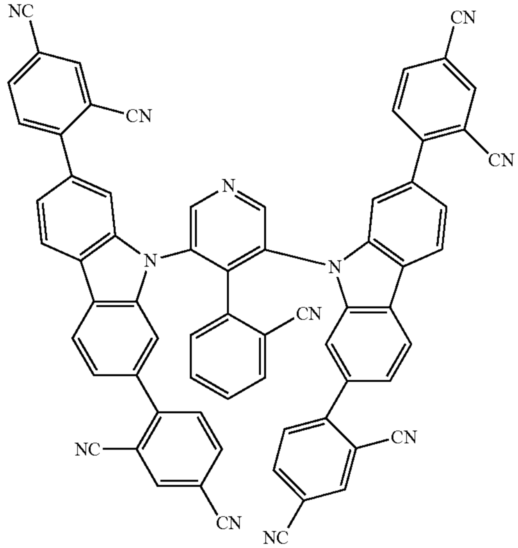
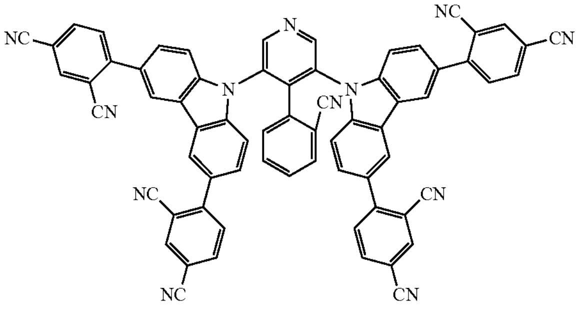
-continued
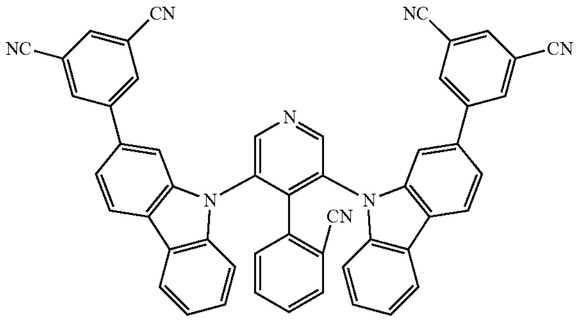
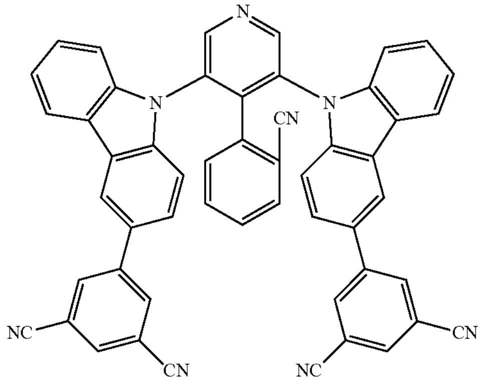
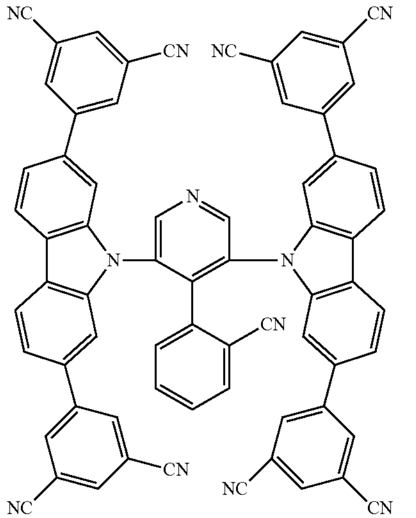
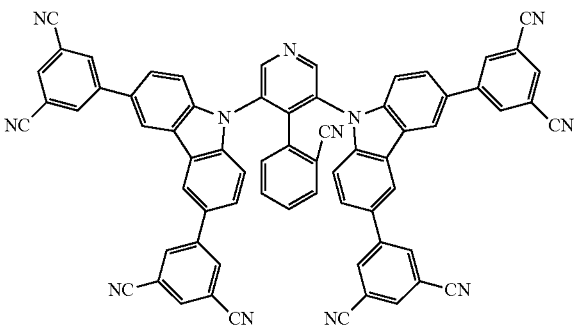

-continued
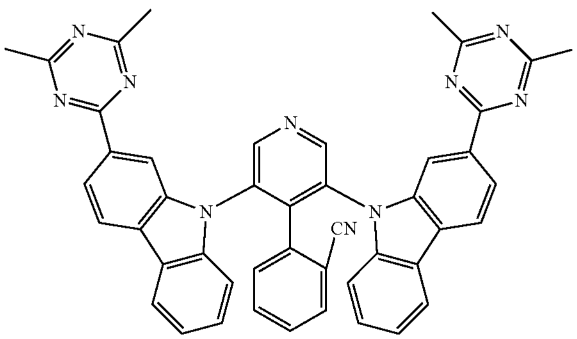
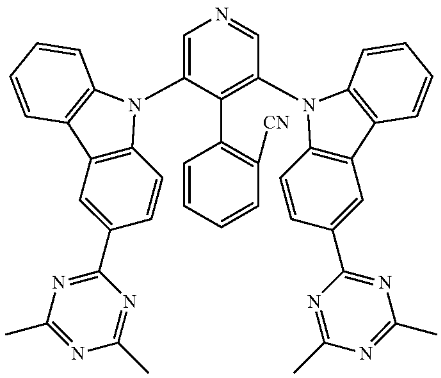
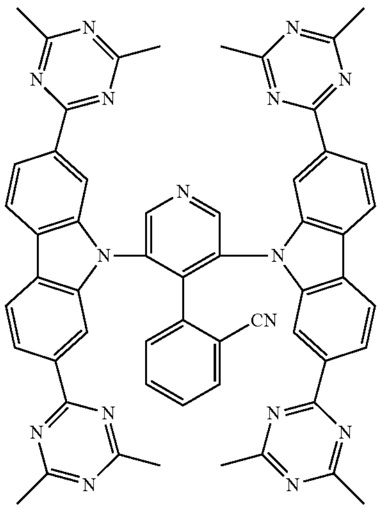
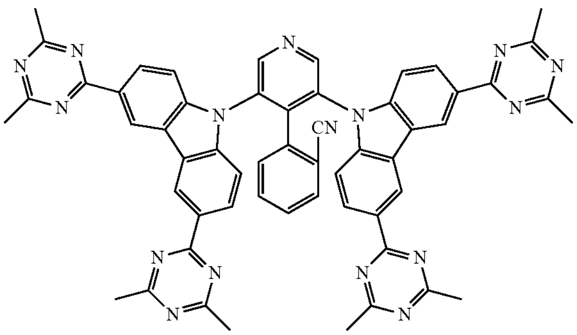
-continued
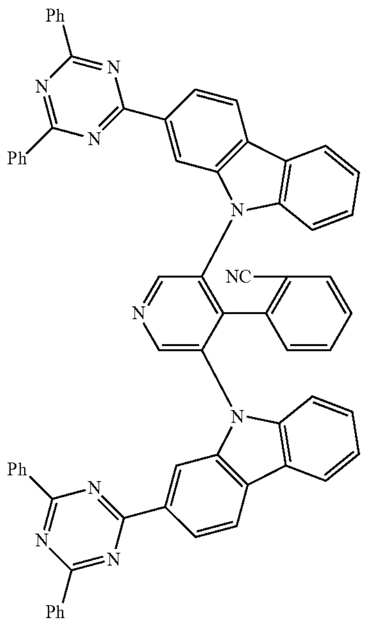
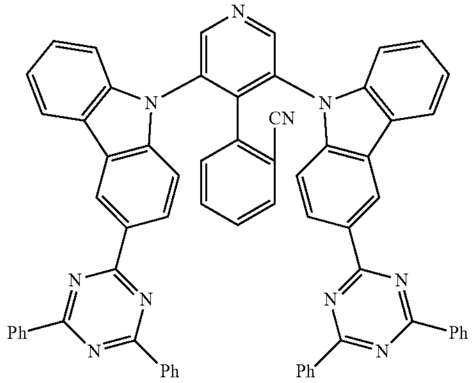
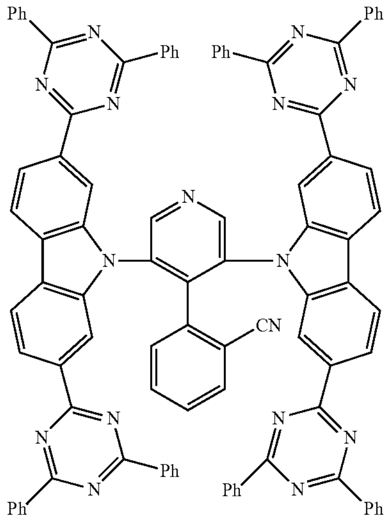

-continued
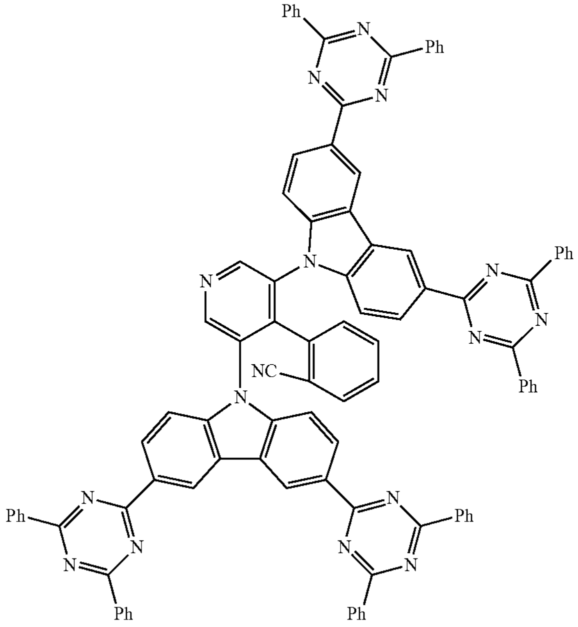
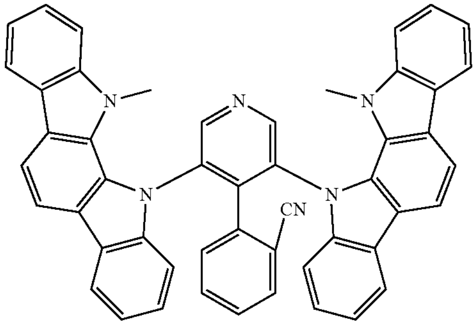
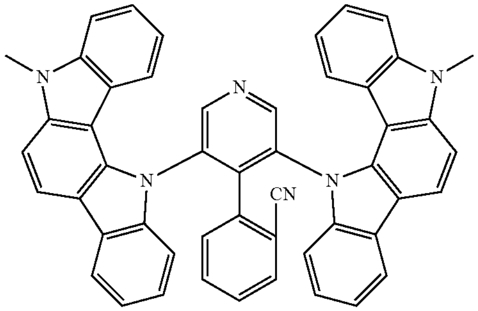
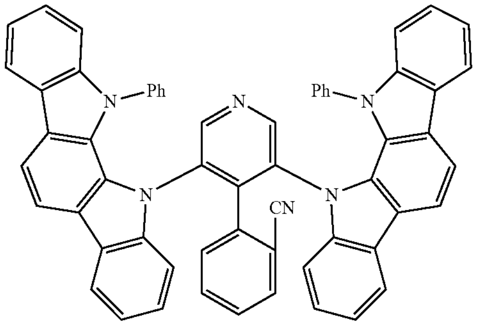
-continued
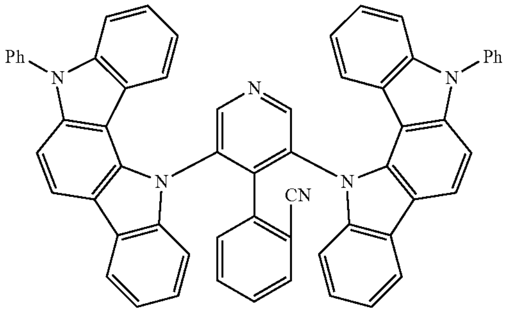
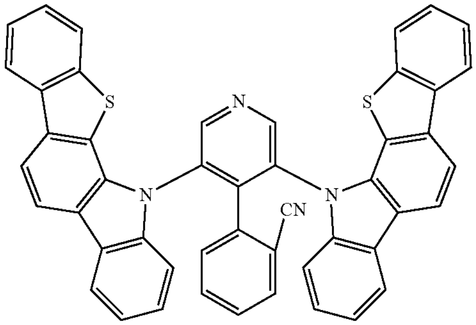
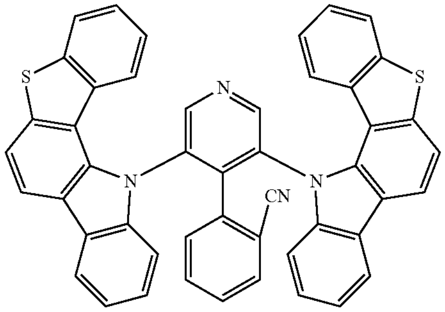
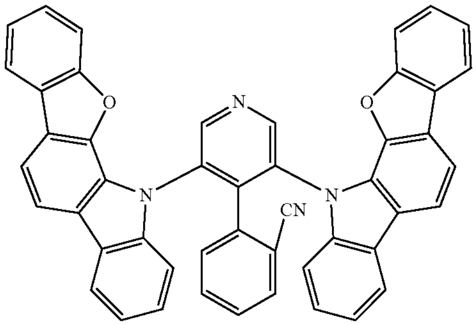
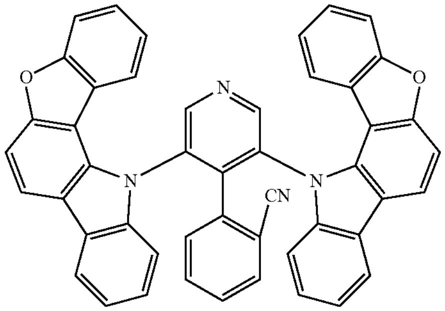

-continued
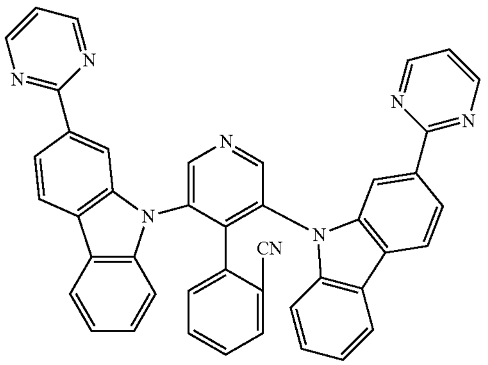
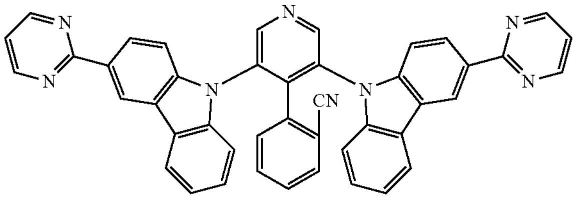
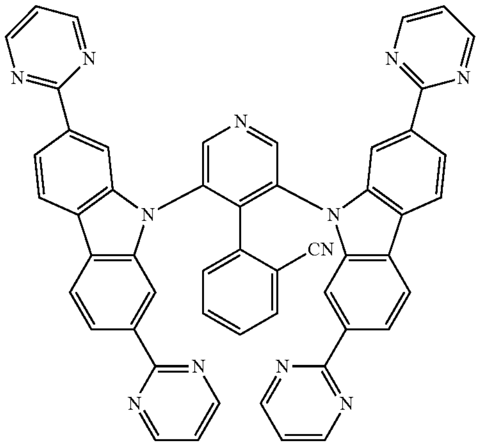
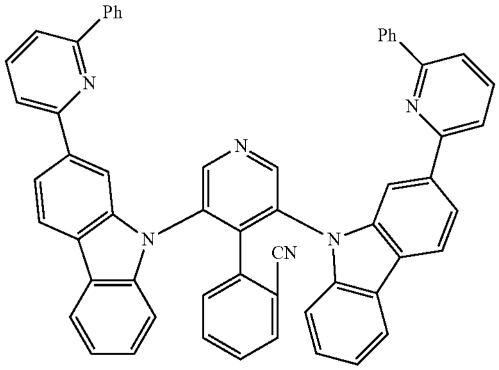
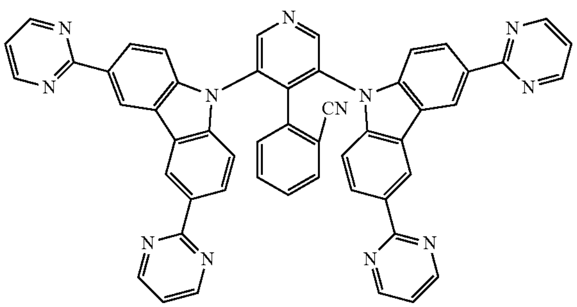
-continued
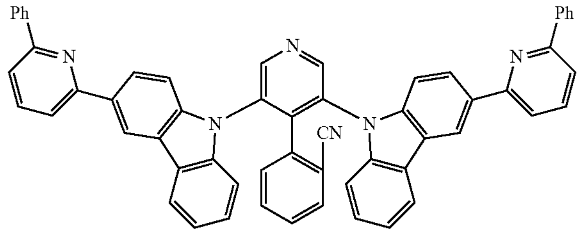
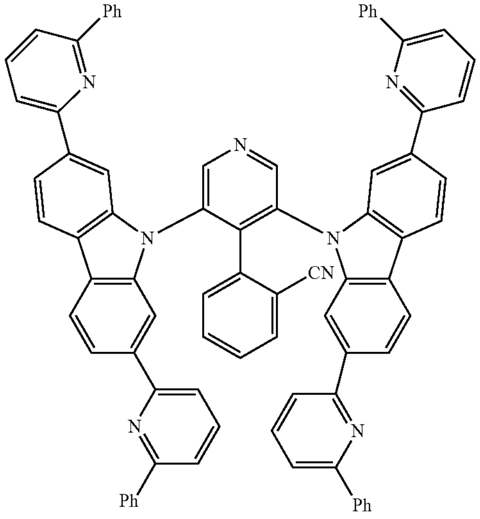
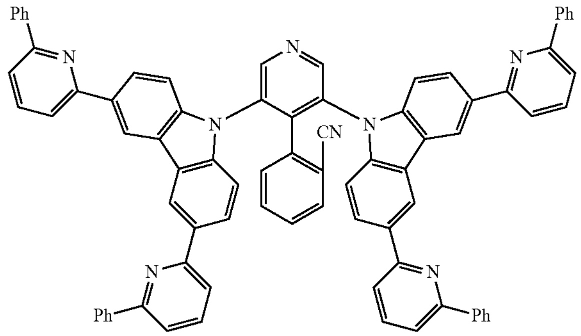
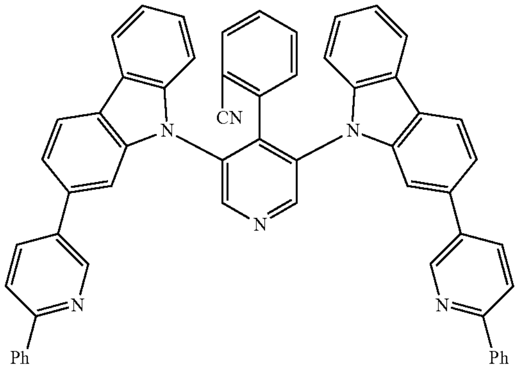

-continued
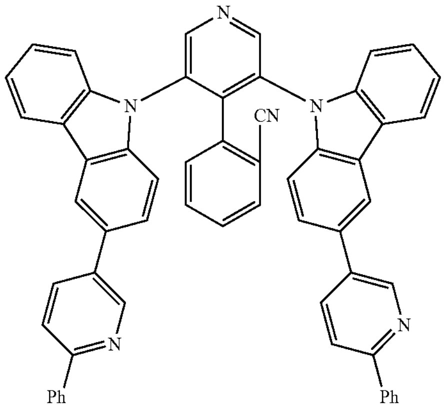
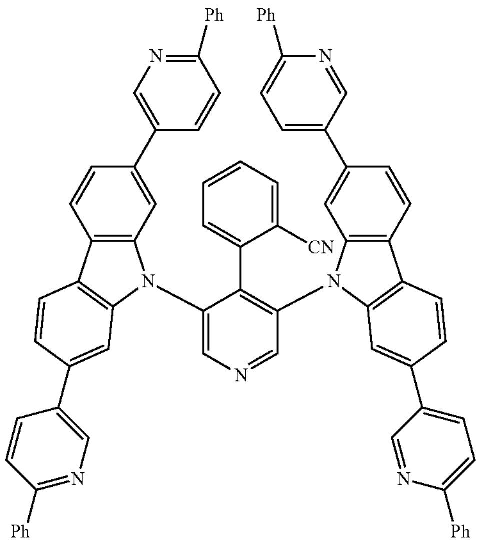
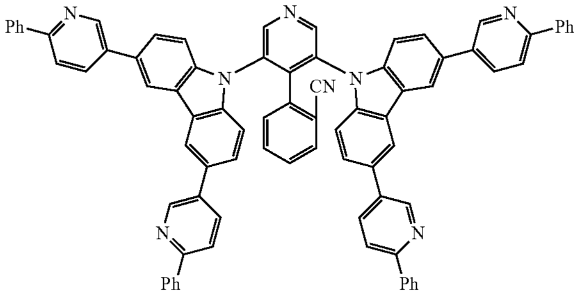
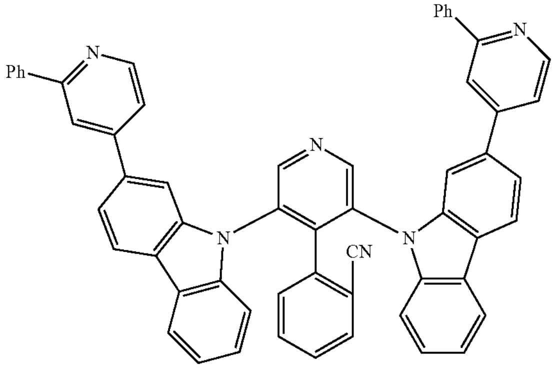
-continued
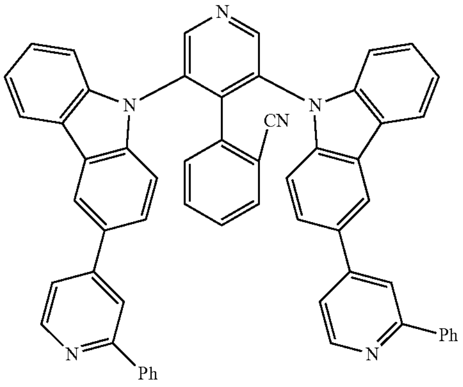
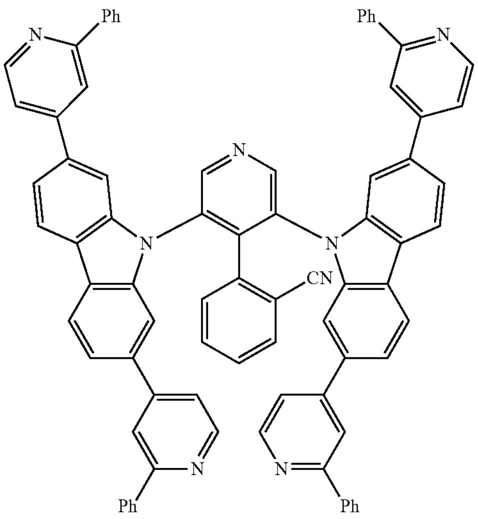
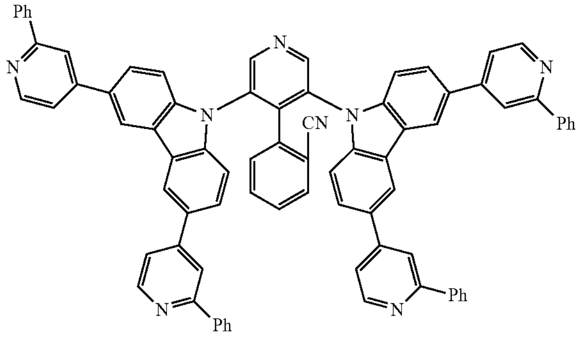
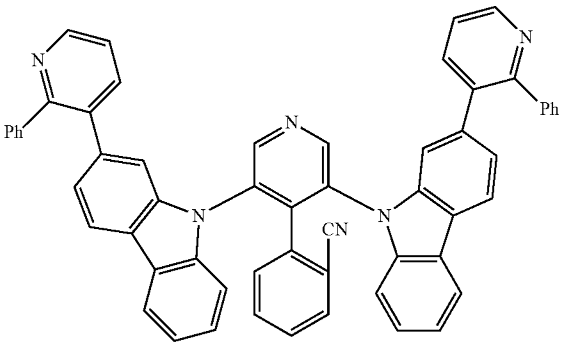

-continued
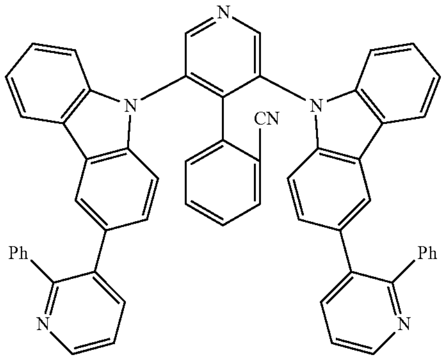
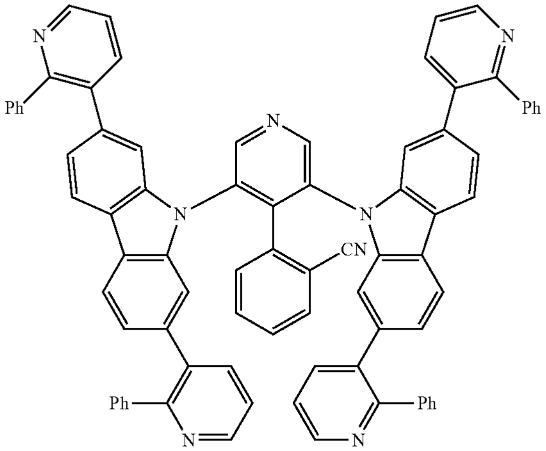
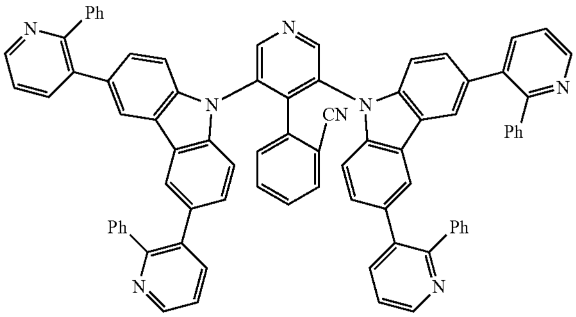
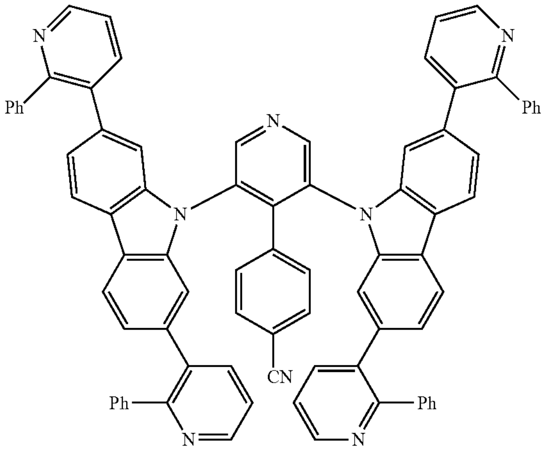
-continued
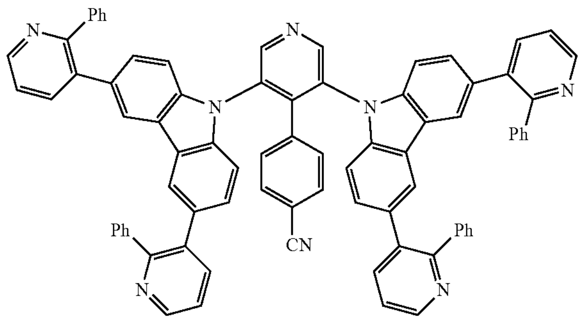
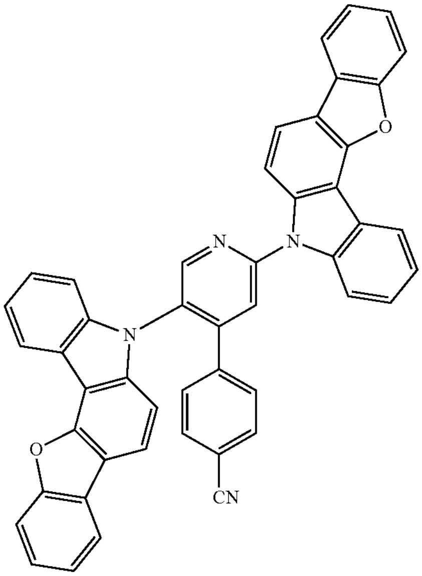
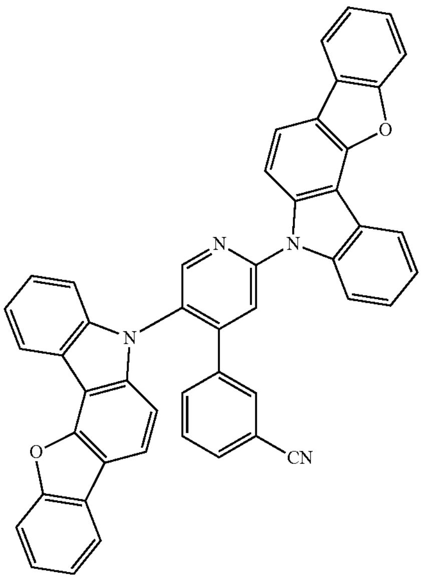

-continued
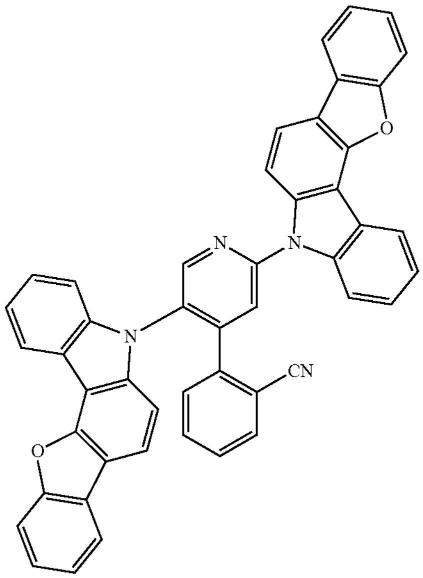
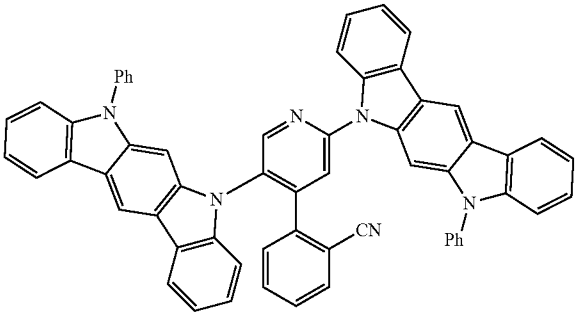
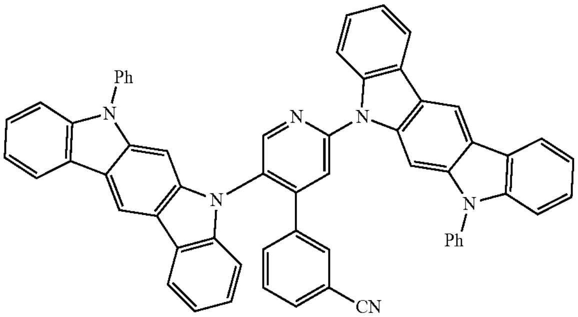
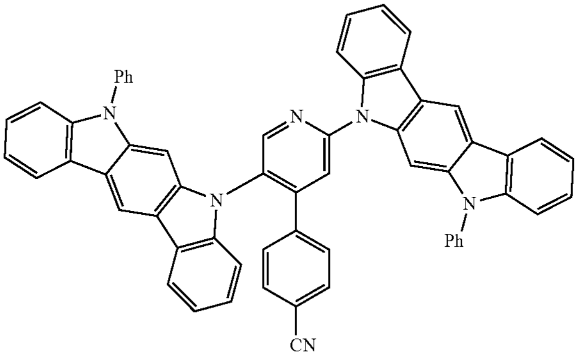
-continued
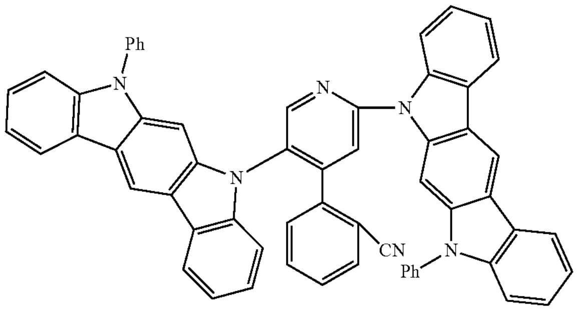
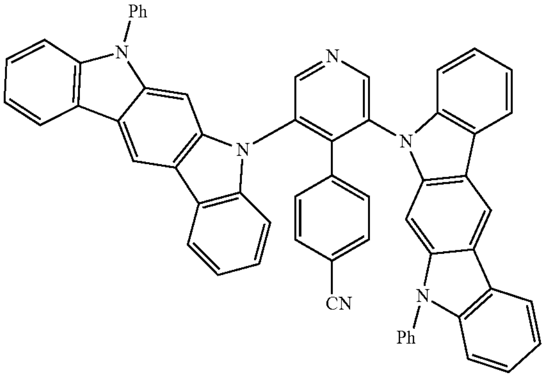
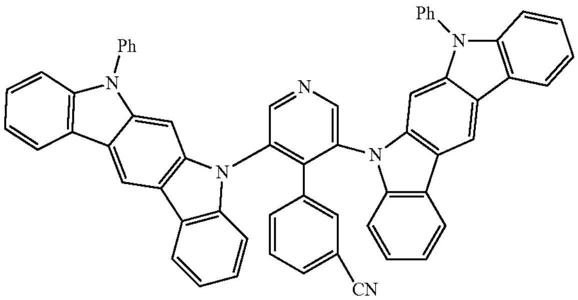
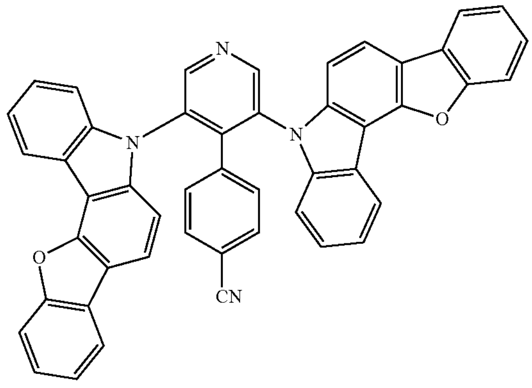

-continued
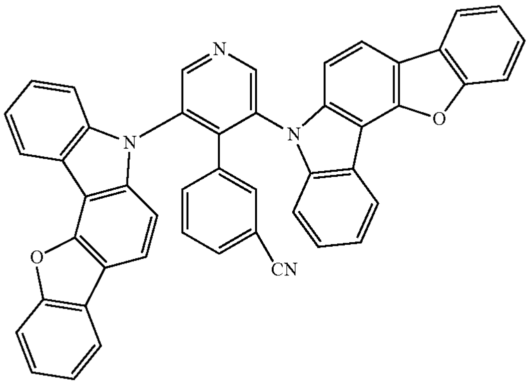
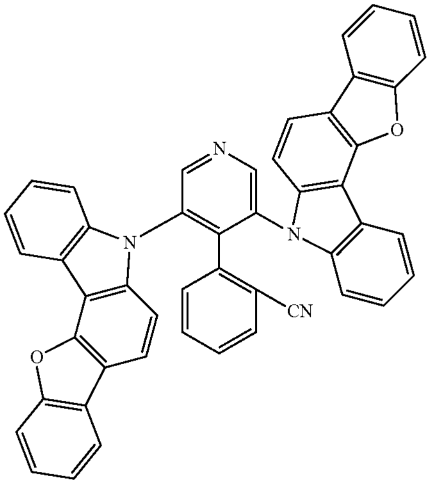
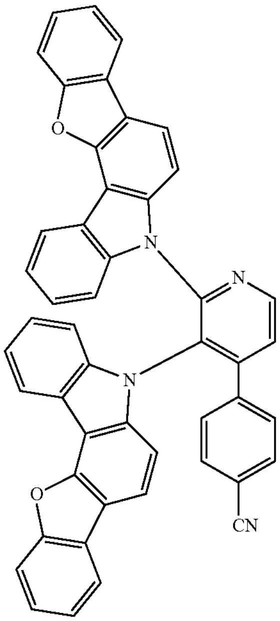
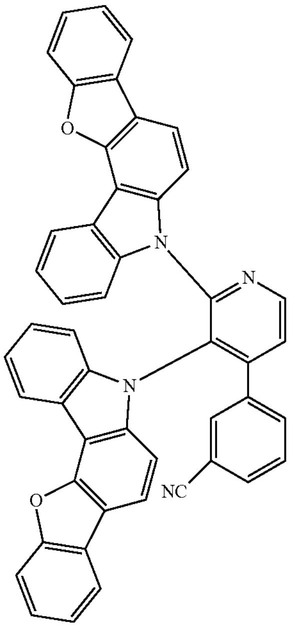
-continued
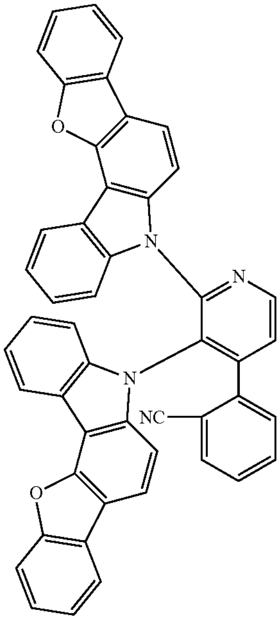

-continued

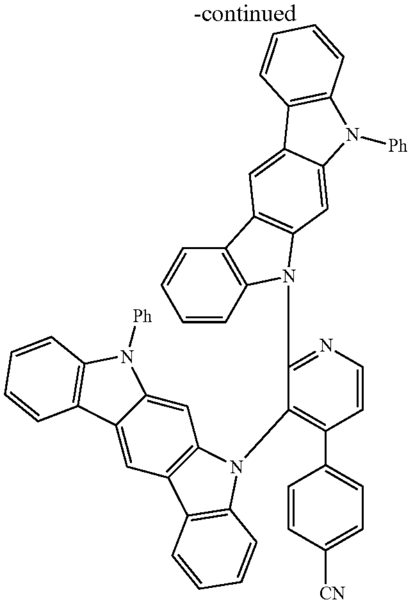

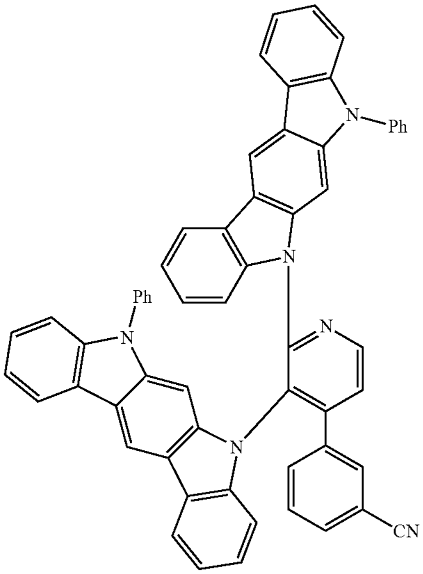

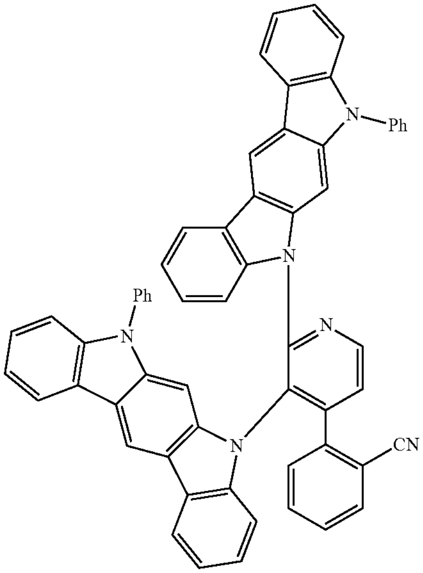

-continued

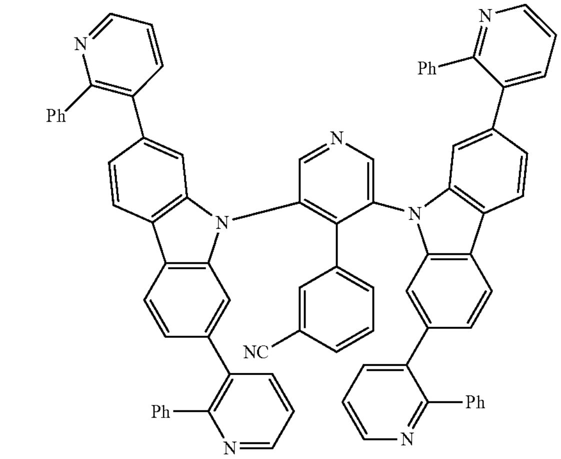

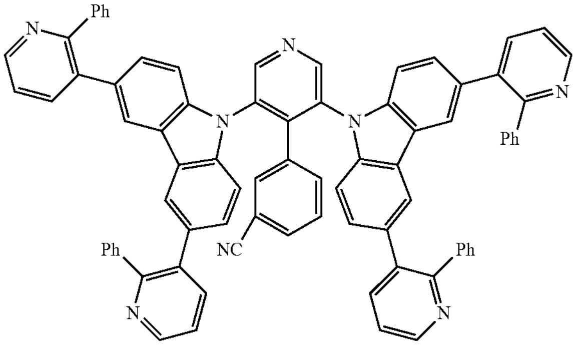

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

The invention claimed is:

1. An organic molecule comprising:

a first chemical moiety comprising a structure of Formula I,

Formula I

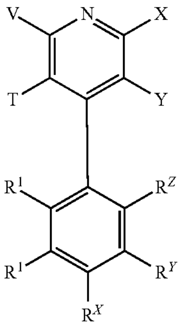

and two second chemical moieties, each independently from another comprising or consisting of a structure of Formula II, Formula II

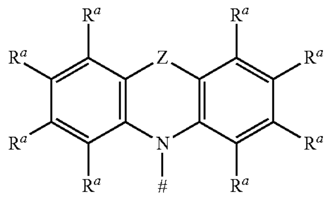

wherein the first chemical moiety is linked to each of the two second chemical moieties via a single bond;

wherein

T is the binding site of a single bond linking the first chemical moiety to one of the two second chemical moieties or is $R^2$;

V is $R^2$;

X is the binding site of a single bond linking the first chemical moiety to one of the two second chemical moieties or is $R^2$;

Y is the binding site of a single bond linking the first chemical moiety to one of the two second chemical moieties or is $R^2$;

#represents the binding site of a single bond linking the second chemical moieties to the first chemical moiety;

Z is at each occurrence independently from another selected from the group consisting of a direct bond, $CR^3R^4$, $C{=}CR^3R^4$, $C{=}O$, $C{=}NR^3$, $NR^3$, O, $SIR^3R^4$, S, S(O) and $S(O)_2$;

$R^X$ is selected from the group consisting of CN and $R^P$;

$R^Y$ is selected from the group consisting of CN and $R^P$;

$R^Z$ is selected from the group consisting of CN and $R^P$;

$R^1$ is at each occurrence independently from another selected from the group consisting of hydrogen, deuterium, $C_1$-$C_5$-alkyl,
 wherein one or more hydrogen atoms are optionally substituted by deuterium;

$C_2$-$C_8$-alkenyl,
 wherein one or more hydrogen atoms are optionally substituted by deuterium;

$C_2$-$C_8$-alkynyl,
 wherein one or more hydrogen atoms are optionally substituted by deuterium; and $C_6$-$C_{18}$-aryl,
 which is optionally substituted with one or more substituents $R^6$;

$R^2$ is at each occurrence independently from another selected from the group consisting of hydrogen, deuterium, $C_1$-$C_5$-alkyl,
 wherein one or more hydrogen atoms are optionally substituted by deuterium;

$C_2$-$C_8$-alkenyl,
 wherein one or more hydrogen atoms are optionally substituted by deuterium;

$C_2$-$C_8$-alkynyl,
 wherein one or more hydrogen atoms are optionally substituted by deuterium; and $C_6$-$C_{18}$-aryl,
 which is optionally substituted with one or more substituents $R^6$;

$R^P$ is at each occurrence independently from another selected from the group consisting of hydrogen, deuterium, $C_1$-$C_5$-alkyl,
 wherein one or more hydrogen atoms are optionally substituted by deuterium;

$C_2$-$C_8$-alkenyl,
 wherein one or more hydrogen atoms are optionally substituted by deuterium;

$C_2$-$C_8$-alkynyl,
 wherein one or more hydrogen atoms are optionally substituted by deuterium; and $C_6$-$C_{18}$-aryl,
 which is optionally substituted with one or more substituents $R^6$;

$R^a$, $R^3$ and $R^4$ is at each occurrence independently from another selected from the group consisting of hydrogen, deuterium, $N(R^5)_2$, $OR^5$, $Si(R^5)_3$, $B(OR^5)_2$, $OSO_2R^5$, $CF_3$, CN, F, Br, I, $C_1$-$C_{40}$-alkyl,
 which is optionally substituted with one or more substituents $R^5$ and
 wherein one or more non-adjacent CH2-groups are optionally substituted by $R^5C{=}CR^5$, C≡C, $Si(R^5)_2$, $Ge(R^5)_2$, $Sn(R^5)_2$, C=O, C=S, C=Se, $C{=}NR^5$, $P({=}O)(R^5)$, SO, $SO_2$, $NR^5$, O, S or $CONR^5$;

$C_1$-$C_{40}$-alkoxy,
 which is optionally substituted with one or more substituents $R^5$ and
 wherein one or more non-adjacent $CH_2$-groups are optionally substituted by $R^5C{=}CR^5$, C≡C, $Si(R^5)_2$, $Ge(R^5)_2$, $Sn(R^5)_2$, C=O, C=S, C=Se, $C{=}NR^5$, $P({=}O)(R^5)$, SO, $SO_2$, $NR^5$, O, S or $CONR^5$;

$C_1$-$C_{40}$-thioalkoxy,
 which is optionally substituted with one or more substituents $R^5$ and wherein one or more non-adjacent $CH_2$-groups are optionally substituted by $R^5C{=}CR^5$, C≡C, $Si(R^5)_2$, $Ge(R^5)_2$, $Sn(R^5)_2$, C=O, C=S, C=Se, $C{=}NR^5$, $P({=}O)(R^5)$, SO, $SO_2$, $NR^5$, O, S or $CONR^5$;

$C_2$-$C_{40}$-alkenyl,
 which is optionally substituted with one or more substituents $R^5$ and
 wherein one or more non-adjacent $CH_2$-groups are optionally substituted by $R^5C{=}CR^5$, C≡C, $Si(R^5)_2$, $Ge(R^5)_2$, $Sn(R^5)_2$, C=O, C=S, C=Se, $C{=}NR^5$, $P({=}O)(R^5)$, SO, $SO_2$, $NR^5$, O, S or $CONR^5$;

$C_2$-$C_{40}$-alkynyl,
 which is optionally substituted with one or more substituents $R^5$ and
 wherein one or more non-adjacent $CH_2$-groups are optionally substituted by $R^5C{=}CR^5$, C≡C, $Si(R^5)_2$, $Ge(R^5)_2$, $Sn(R^5)_2$, C=O, C=S, C=Se, $C{=}NR^5$, $P({=}O)(R^5)$, SO, $SO_2$, $NR^5$, O, S or $CONR^5$;

$C_6$-$C_{60}$-aryl,
 which is optionally substituted with one or more substituents $R^5$; and $C_3$-$C_{57}$-heteroaryl,
 which is optionally substituted with one or more substituents $R^5$;

$R^5$ is at each occurrence independently from another selected from the group consisting of hydrogen, deuterium, $N(R^6)_2$, $OR^6$, $Si(R^6)_3$, $B(OR^6)_2R^6$, $CF_3$, CN, F, Br, I, $C_1$-$C_{40}$-alkyl,
 which is optionally substituted with one or more substituents $R^6$ and
 wherein one or more non-adjacent $CH_2$-groups are optionally substituted by $R^5C{=}CR^6$, C≡C, $Si(R^6)_2$, Ge($R^6$)$_2$, Sn($R^6$)$_2$, C═O, C═S, C═Se, C═$NR^6$, P(═O)($R^6$), SO, $SO_2$, $NR^6$, O, S or $CONR^6$;

$C_1$-$C_{40}$-alkoxy, which is optionally substituted with one or more substituents $R^6$ and wherein one or more non-adjacent $CH_2$-groups are optionally substituted by $R^5C$═$CR^6$, C≡C, Si($R^6$)$_2$, Ge($R^6$)$_2$, Sn($R^6$)$_2$, C═O, C═S, C═Se, C═$NR^6$, P(═O)($R^6$), SO, $SO_2$, $NR^6$, O, S or $CONR^6$;

$C_1$-$C_{40}$-thioalkoxy, which is optionally substituted with one or more substituents $R^6$ and wherein one or more non-adjacent $CH_2$-groups are optionally substituted by $R^6C$═$CR^6$, C≡C, Si($R^6$)$_2$, Ge($R^6$)$_2$, Sn($R^6$)$_2$, C═O, C═S, C═Se, C═$NR^6$, P(═O)($R^6$), SO, $SO_2$, $NR^6$, O, S or $CONR^6$;

$C_2$-$C_{40}$-alkenyl, which is optionally substituted with one or more substituents $R^6$ and wherein one or more non-adjacent $CH_2$-groups are optionally substituted by $R^6C$═$CR^6$, C≡C, Si($R^6$)$_2$, Ge($R^6$)$_2$, Sn($R^6$)$_2$, C═O, C═S, C═Se, C═$NR^6$, P(═O)($R^6$), SO, $SO_2$, $NR^6$, O, S or $CONR^6$;

$C_2$-$C_{40}$-alkynyl, which is optionally substituted with one or more substituents $R^6$ and wherein one or more non-adjacent $CH_2$-groups are optionally substituted by $R^6C$═$CR^6$, C≡C, Si($R^6$)$_2$, Ge($R^6$)$_2$, Sn($R^6$)$_2$, C═O, C═S, C═Se, C═$NR^6$, P(═O)($R^6$), SO, $SO_2$, $NR^6$, O, S or $CONR^6$;

$C_6$-$C_{60}$-aryl, which is optionally substituted with one or more substituents $R^6$; and $C_3$-$C_{57}$-heteroaryl, which is optionally substituted with one or more substituents $R^6$;

$R^6$ is at each occurrence independently from another selected from the group consisting of hydrogen, deuterium, OPh, $CF_3$, CN, F, $C_1$-$C_5$-alkyl, wherein one or more hydrogen atoms are optionally, independently from each other substituted by deuterium, CN, $CF_3$, or F;

$C_1$-$C_5$-alkoxy, wherein one or more hydrogen atoms are optionally, independently from each other substituted by deuterium, CN, $CF_3$, or F;

$C_1$-$C_5$-thioalkoxy, wherein one or more hydrogen atoms are optionally, independently from each other substituted by deuterium, CN, $CF_3$, or F;

$C_2$-$C_5$-alkenyl, wherein one or more hydrogen atoms are optionally, independently from each other substituted by deuterium, CN, $CF_3$, or F;

$C_2$-$C_5$-alkynyl, wherein one or more hydrogen atoms are optionally, independently from each other substituted by deuterium, CN, $CF_3$, or F;

$C_6$-$C_{18}$-aryl, which is optionally substituted with one or more $C_1$-$C_5$-alkyl substituents;

$C_3$-$C_{17}$-heteroaryl, which is optionally substituted with one or more $C_1$-$C_5$-alkyl substituents;

N ($C_6$-$C_{18}$-aryl)$_2$;

N ($C_3$-$C_{17}$-heteroaryl)$_2$, and N ($C_3$-$C_{17}$-heteroaryl) ($C_6$-$C_{18}$-aryl);

wherein the substituents $R^a$, $R^3$, $R^4$ or $R^5$ independently from each other optionally form a mono- or polycyclic, aliphatic, aromatic and/or benzo-fused ring system with one or more substituents $R^a$, $R^3$, $R^4$ or $R^5$;

wherein exactly one substituent selected from the group consisting of $R^X$, $R^Y$ and $R^Z$ is CN, and exactly two substituents selected from the group consisting of T, X and Y represent the binding sites of a single bond linking the first chemical moiety and one of the two second chemical moieties.

2. The organic molecule according to claim 1, wherein the first chemical moiety comprises a structure of Formula Ia:

Formula Ia

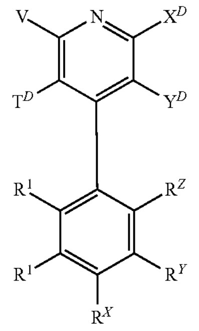

wherein $T^D$ is the binding site of a single bond linking the first chemical moiety to one of the two second chemical moieties;

$X^D$ is the binding site of a single bond linking the first chemical moiety to one of the two second chemical moieties; and $Y^D$ is $R^2$.

3. The organic molecule according to claim 1, wherein $R^1$, $R^2$ and $R^P$ is independently from each other at each occurrence independently from another selected from the group consisting of H, methyl and phenyl.

4. The organic molecule according to claim 1, wherein $R^X$ is CN.

5. The organic molecule according to claim 1, wherein the two second chemical moieties, each at each occurrence independently from another, comprise a structure of Formula IIa:

Formula IIa

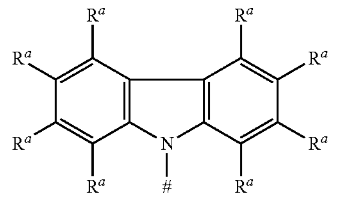

wherein # and $R^a$ are defined as in claim 1.

6. The organic molecule according to claim 1, wherein the two second chemical moieties, each at each occurrence independently from another, comprise a structure of Formula IIb:

Formula IIb

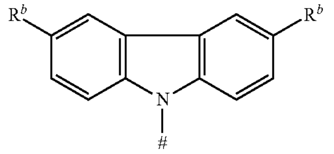

wherein $R^b$ is at each occurrence independently from another selected from the group consisting of hydrogen, deuterium, $N(R^5)_2$, $OR^5$, $Si(R^5)_3$, $B(OR^5)_2$, $OSO_2R^5$, $CF_3$, CN, F, Br, I, $C_1$-$C_{40}$-alkyl, which is optionally substituted with one or more substituents $R^5$ and wherein one or more non-adjacent $CH_2$-groups are optionally substituted by $R^5C{=}CR^5$, C≡C, $Si(R^5)_2$, $Ge(R^5)_2$, $Sn(R^5)_2$, C=O, C=S, C=Se, $C{=}NR^5$, $P({=}O)(R^5)$, SO, $SO_2$, $NR^5$, O, S or $CONR^5$;

$C_1$-$C_{40}$-alkoxy, which is optionally substituted with one or more substituents $R^5$ and wherein one or more non-adjacent $CH_2$-groups are optionally substituted by $R^5C{=}CR^5$, C≡C, $Si(R^5)_2$, $Ge(R^5)_2$, $Sn(R^5)_2$, C=O, C=S, C=Se, $C{=}NR^5$, $P({=}O)(R^5)$, SO, $SO_2$, $NR^5$, O, S or $CONR^5$;

$C_1$-$C_{40}$-thioalkoxy, which is optionally substituted with one or more substituents $R^5$ and wherein one or more non-adjacent $CH_2$-groups are optionally substituted by $R^5C{=}CR^5$, C≡C, $Si(R^5)_2$, $Ge(R^5)_2$, $Sn(R^5)_2$, C=O, C=S, C=Se, $C{=}NR^5$, $P({=}O)(R^5)$, SO, $SO_2$, $NR^5$, O, S or $CONR^5$;

$C_2$-$C_{40}$-alkenyl, which is optionally substituted with one or more substituents $R^5$ and wherein one or more non-adjacent $CH_2$-groups are optionally substituted by $R^5C{=}CR^5$, C≡C, $Si(R^5)_2$, $Ge(R^5)_2$, $Sn(R^5)_2$, C=O, C=S, C=Se, $C{=}NR^5$, $P({=}O)(R^5)$, SO, $SO_2$, $NR^5$, O, S or $CONR^5$;

$C_2$-$C_{40}$-alkynyl, which is optionally substituted with one or more substituents $R^5$ and wherein one or more non-adjacent $CH_2$-groups are optionally substituted by $R^5C{=}CR^5$, C≡C, $Si(R^5)_2$, $Ge(R^5)_2$, $Sn(R^5)_2$, C=O, C=S, C=Se, $C{=}NR^5$, $P({=}O)(R^5)$, SO, $SO_2$, $NR^5$, O, S or $CONR^5$;

$C_6$-$C_{60}$-aryl, which is optionally substituted with one or more substituents $R^5$; and $C_3$-$C_{57}$-heteroaryl, which is optionally substituted with one or more substituents $R^5$;

and wherein apart from that the definitions in claim 1 apply.

7. The organic molecule according to claim 1, wherein the two second chemical moieties, each at each occurrence independently from another, comprise a structure of Formula IIc:

Formula IIc

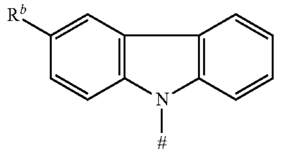

wherein $R^b$ is at each occurrence independently from another selected from the group consisting of hydrogen, deuterium, $N(R^5)_2$, $OR^5$, $Si(R^5)_3$, $B(OR^5)_2$, $OSO_2R^5$, $CF_3$, CN, F, Br, I, $C_1$-$C_{40}$-alkyl, which is optionally substituted with one or more substituents $R^5$ and wherein one or more non-adjacent $CH_2$-groups are optionally substituted by $R^5C{=}CR^5$, C≡C, $Si(R^5)_2$, $Ge(R^5)_2$, $Sn(R^5)_2$, C=O, C=S, C=Se, $C{=}NR^5$, $P({=}O)(R^5)$, SO, $SO_2$, $NR^5$, O, S or $CONR^5$;

$C_1$-$C_{40}$-alkoxy, which is optionally substituted with one or more substituents $R^5$ and wherein one or more non-adjacent $CH_2$-groups are optionally substituted by $R^5C{=}CR^5$, C≡C, $Si(R^5)_2$, $Ge(R^5)_2$, $Sn(R^5)_2$, C=O, C=S, C=Se, $C{=}NR^5$, $P({=}O)(R^5)$, SO, $SO_2$, $NR^5$, O, S or $CONR^5$;

$C_1$-$C_{40}$-thioalkoxy, which is optionally substituted with one or more substituents $R^5$ and wherein one or more non-adjacent $CH_2$-groups are optionally substituted by $R^5C{=}CR^5$, C≡C, $Si(R^5)_2$, $Ge(R^5)_2$, $Sn(R^5)_2$, C=O, C=S, C=Se, $C{=}NR^5$, $P({=}O)(R^5)$, SO, $SO_2$, $NR^5$, O, S or $CONR^5$;

$C_2$-$C_{40}$-alkenyl, which is optionally substituted with one or more substituents $R^5$ and wherein one or more non-adjacent $CH_2$-groups are optionally substituted by $R^5C{=}CR^5$, C≡C, $Si(R^5)_2$, $Ge(R^5)_2$, $Sn(R^5)_2$, C=O, C=S, C=Se, $C{=}NR^5$, $P({=}O)(R^5)$, SO, $SO_2$, $NR^5$, O, S or $CONR^5$;

$C_2$-$C_{40}$-alkynyl, which is optionally substituted with one or more substituents $R^5$ and wherein one or more non-adjacent $CH_2$-groups are optionally substituted by $R^5C{=}CR^5$, C≡C, $Si(R^5)_2$, $Ge(R^5)_2$, $Sn(R^5)_2$, C=O, C=S, C=Se, $C{=}NR^5$, $P({=}O)(R^5)$, SO, $SO_2$, $NR^5$, O, S or $CONR^5$;

$C_6$-$C_{60}$-aryl, which is optionally substituted with one or more substituents $R^5$; and $C_3$-$C_{57}$-heteroaryl, which is optionally substituted with one or more substituents $R^5$;

and wherein apart from that the definitions in claim 1 apply.

8. The organic molecule according to claim 6, wherein $R^b$ is at each occurrence independently from another selected from the group consisting of Me, iPr, $^t$Bu, CN, $CF_3$, Ph, which is optionally substituted with one or more substituents independently from each other selected from the group consisting of Me, $^i$Pr, $^t$Bu, CN, $CF_3$ and Ph;

pyridinyl, which is optionally substituted with one or more substituents independently from each other selected from the group consisting of Me, $^i$Pr, $^t$Bu, CN, $CF_3$ and Ph;

pyrimidinyl, which is optionally substituted with one or more substituents independently from each other selected from the group consisting of Me, $^{i}$Pr, $^{t}$Bu, CN, $CF_3$ and Ph;

carbazolyl, which is optionally substituted with one or more substituents independently from each other selected from the group consisting of Me, $^{i}$Pr, $^{t}$Bu, CN, $CF_3$ and Ph;

triazinyl, which is optionally substituted with one or more substituents independently from each other selected from the group consisting of Me, $^{i}$Pr, $^{t}$Bu, CN, $CF_3$, and Ph;

and

N $(Ph)_2$.

9. The organic molecule according to claim 1, wherein $R^a$ is at each occurrence independently from each other optionally form a mono- or polycyclic, aliphatic, aromatic and/or benzo-fused ring system with one or more neighboring substituents $R^a$.

10. The organic molecule according to claim 1 comprises a structure of Formula III:

Formula III

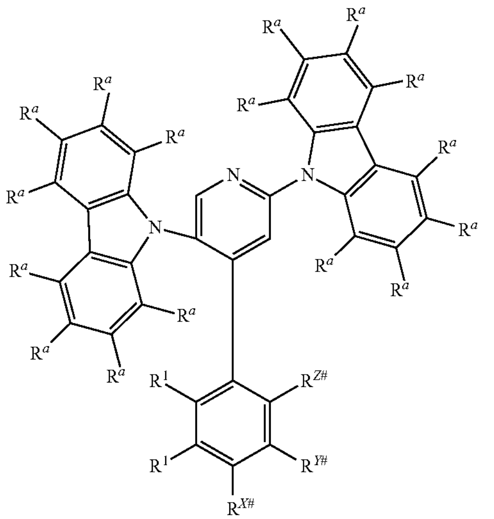

wherein, $R^{X\#}$, $R^{Y\#}$ and $R^{Z\#}$ is independently from each other selected from the group consisting of CN and $R^P$, and $R^a$ and $R^P$ are defined as in claim 1.

11. The organic molecule according to claim 1 comprises a structure of Formula IV:

Formula IV

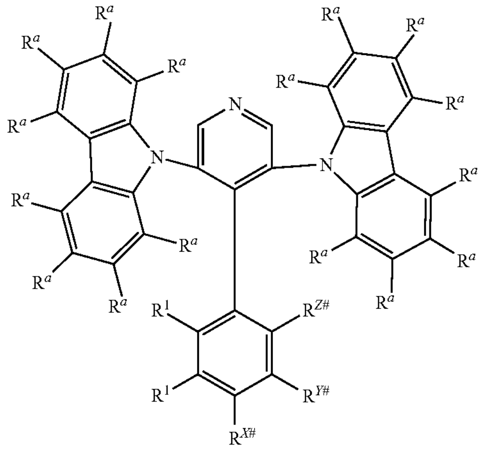

wherein, $R^{X\#}$, $R^{Y\#}$ and $R^{Z\#}$ is independently from each other selected from the group consisting of CN and $R^P$, and $R^a$ and $R^P$ are defined as in claim 1.

12. The organic molecule according to claim 1 comprises a structure of Formula V:

Formula V

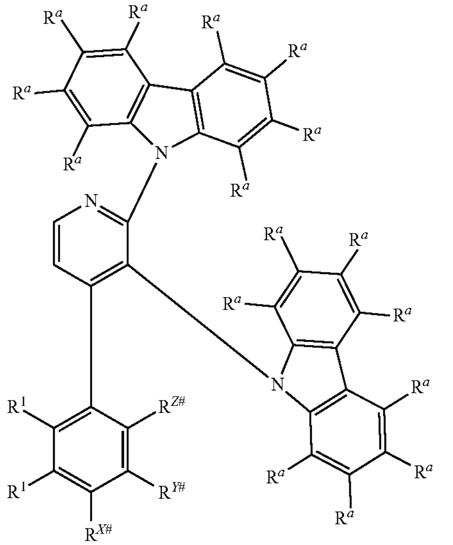

wherein, $R^{X\#}$, $R^{Y\#}$ and $R^{Z\#}$ is independently from each other selected from the group consisting of CN and $R^P$, and $R^a$ and $R^P$ are defined as in claim 1.

13. The organic molecule according to claim 1, wherein the organic molecule has an emission peak in a range of a wavelength of 380 nm to 800 nm.

14. The organic molecule according to claim 1, wherein the organic molecule emits light with a full width at half maximum of less than 0.5 eV.

15. A light-emitting device comprising the organic molecule according to claim 1.

16. The light-emitting device according to claim 15, comprising:

a substrate;

an anode;

a cathode, wherein the anode or the cathode is applied to the substrate; and at least one light-emitting layer disposed between the anode and the cathode and which comprises the organic molecule.

17. The light-emitting device according to claim 15, wherein the organic molecule is one of a luminescent emitter, a host material, and an electron transport material, a hole injection material or a hole blocking material in the light-emitting device.

18. The light-emitting device according to claim 17, wherein the host material has higher triplet ($T_1$) energy level than triplet ($T_1$) energy level of the organic molecule, and the host material has higher singlet ($S_1$) energy level than singlet ($S_1$) energy level of the organic molecule.

19. The optoelectronic device according to claim 17, wherein the host material (H) has a highest occupied molecular orbital HOMO(H) having an energy $E^{HOMO}$(H), and the organic molecule has a highest occupied molecular orbital HOMO(E) having an energy $E^{HOMO}$(E), wherein a difference between $E^{HOMO}$(E) and $E^{HOMO}$(H) is in a range of −0.5 eV to 0.5 eV.

20. The light-emitting device according to claim 15, wherein the light-emitting device is an organic light-emitting diode, light-emitting electrochemical cell, organic light-emitting sensor, an organic diode, an organic solar cell, an organic transistor, an organic field-effect transistor, an organic laser or a down-conversion element.

* * * * *